(12) United States Patent
Bernett et al.

(10) Patent No.: US 10,981,992 B2
(45) Date of Patent: Apr. 20, 2021

(54) BISPECIFIC IMMUNOMODULATORY ANTIBODIES THAT BIND COSTIMULATORY AND CHECKPOINT RECEPTORS

(71) Applicant: Xencor, Inc., Monrovia, CA (US)

(72) Inventors: Matthew Bernett, Monrovia, CA (US); Gregory Moore, Azusa, CA (US); John Desjarlais, Pasadena, CA (US); Michael Hedvat, Encino, CA (US); Christine Bonzon, Los Angeles, CA (US)

(73) Assignee: Xencor, Inc., Monrovia, CA (US)

( * ) Notice: Subject to any disclaimer, the term of this patent is extended or adjusted under 35 U.S.C. 154(b) by 246 days.

(21) Appl. No.: 16/184,929

(22) Filed: Nov. 8, 2018

(65) Prior Publication Data

US 2019/0270816 A1 Sep. 5, 2019

Related U.S. Application Data

(60) Provisional application No. 62/583,431, filed on Nov. 8, 2017, provisional application No. 62/614,271, filed on Jan. 5, 2018, provisional application No. 62/640,468, filed on Mar. 8, 2018, provisional application No. 62/683,554, filed on Jun. 11, 2018, provisional application No. 62/724,502, filed on Aug. 29, 2018.

(51) Int. Cl.
| C07K 16/28 | (2006.01) |
| A61K 39/395 | (2006.01) |
| A61P 35/00 | (2006.01) |
| A61P 37/06 | (2006.01) |
| A61K 39/00 | (2006.01) |

(52) U.S. Cl.
CPC .......... C07K 16/2818 (2013.01); A61P 35/00 (2018.01); A61P 37/06 (2018.01); C07K 16/2803 (2013.01); C07K 16/2827 (2013.01); A61K 2039/505 (2013.01); A61K 2039/507 (2013.01); C07K 2317/31 (2013.01); C07K 2317/33 (2013.01); C07K 2317/52 (2013.01); C07K 2317/55 (2013.01); C07K 2317/622 (2013.01); C07K 2317/64 (2013.01); C07K 2317/76 (2013.01); C07K 2317/92 (2013.01)

(58) Field of Classification Search
None
See application file for complete search history.

(56) References Cited

U.S. PATENT DOCUMENTS

| 3,773,919 A | 11/1973 | Boswell et al. |
| 4,169,888 A | 10/1979 | Hanka et al. |
| 4,179,337 A | 12/1979 | Davis et al. |
| 4,256,746 A | 3/1981 | Miyashita et al. |
| 4,294,757 A | 10/1981 | Asai |
| 4,301,144 A | 11/1981 | Iwashita et al. |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 5/1982 | Asai et al. |
| 4,362,663 A | 12/1982 | Kida et al. |
| 4,364,866 A | 12/1982 | Asai et al. |
| 4,364,935 A | 12/1982 | Kung et al. |
| 4,371,533 A | 2/1983 | Akimoto et al. |
| 4,424,219 A | 1/1984 | Hashimoto et al. |
| 4,450,254 A | 5/1984 | Isley et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,880,935 A | 11/1989 | Thorpe |
| 4,923,990 A | 5/1990 | Nakano et al. |
| 4,943,533 A | 7/1990 | Mendelsohn et al. |
| 4,970,198 A | 11/1990 | Lee et al. |
| 5,053,394 A | 10/1991 | Ellestad et al. |
| 5,070,092 A | 12/1991 | Kanda et al. |
| 5,084,468 A | 1/1992 | Saito et al. |
| 5,101,038 A | 3/1992 | Nakano et al. |
| 5,122,368 A | 6/1992 | Greenfield et al. |
| 5,187,186 A | 2/1993 | Kanda et al. |
| 5,208,020 A | 5/1993 | Chari et al. |
| 5,264,586 A | 11/1993 | Nicolaou et al. |
| 5,384,412 A | 1/1995 | Nicolaou et al. |
| 5,416,064 A | 5/1995 | Chari et al. |
| 5,475,092 A | 12/1995 | Chari et al. |
| 5,500,362 A | 3/1996 | Robinson et al. |
| 5,530,101 A | 6/1996 | Queen et al. |
| 5,541,087 A | 7/1996 | Lo et al. |

(Continued)

FOREIGN PATENT DOCUMENTS

| EP | 0425235 B1 | 9/1996 |
| EP | 1752471 | 2/2007 |

(Continued)

OTHER PUBLICATIONS

U.S. Appl. No. 12/631,508, filed Dec. 4, 2009, Chari et al.
(No Author Name) "A method for making multispecific antibodies having heteromultimeric and common components", Expert Opinion on Therapeutic Patents, Genentech, Inc. (1999) 9(6): 785-790, pp. 785-790.
"Polythene Glycol and Derivatives for Advanced PEGylation", Catalog 2005-2006, Nektar Therapeutics.

(Continued)

*Primary Examiner* — Ilia I Ouspenski
(74) *Attorney, Agent, or Firm* — Louis-Vu T. Nguyen; Robin M. Silva; Morgan, Lewis & Bockius, LLP

(57) ABSTRACT

The present invention is directed to bispecific, heterodimeric immunomodulatory antibodies.

6 Claims, 295 Drawing Sheets

Specification includes a Sequence Listing.

(56) References Cited

U.S. PATENT DOCUMENTS

| | | |
|---|---|---|
| 5,550,246 A | 8/1996 | Nicolaou et al. |
| 5,558,864 A | 9/1996 | Bendig et al. |
| 5,585,089 A | 12/1996 | Queen et al. |
| 5,585,097 A | 12/1996 | Bolt et al. |
| 5,585,499 A | 12/1996 | Chari et al. |
| 5,622,929 A | 4/1997 | Willner et al. |
| 5,635,483 A | 6/1997 | Pettit et al. |
| 5,641,780 A | 6/1997 | Amishiro et al. |
| 5,663,149 A | 9/1997 | Pettit et al. |
| 5,677,171 A | 10/1997 | Hudziak et al. |
| 5,693,761 A | 12/1997 | Queen et al. |
| 5,693,762 A | 12/1997 | Queen et al. |
| 5,703,080 A | 12/1997 | Nakakura et al. |
| 5,712,374 A | 1/1998 | Kuntsmann et al. |
| 5,714,586 A | 2/1998 | Kuntsmann et al. |
| 5,726,044 A | 3/1998 | Lo et al. |
| 5,731,168 A | 3/1998 | Carter et al. |
| 5,736,137 A | 4/1998 | Anderson et al. |
| 5,739,116 A | 4/1998 | Hamann et al. |
| 5,767,237 A | 6/1998 | Sakakibara et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,807,706 A | 9/1998 | Carter et al. |
| 5,821,333 A | 10/1998 | Carter et al. |
| 5,821,337 A | 10/1998 | Carter et al. |
| 5,824,805 A | 10/1998 | King et al. |
| 5,846,545 A | 12/1998 | Chari et al. |
| 5,859,205 A | 1/1999 | Adair et al. |
| 5,877,291 A | 3/1999 | Mezes et al. |
| 5,877,296 A | 3/1999 | Hamann et al. |
| 5,891,996 A | 4/1999 | Mateo de Acosta del Rio et al. |
| 5,892,020 A | 4/1999 | Mezes et al. |
| 5,945,311 A | 8/1999 | Lindhofer et al. |
| 5,968,509 A | 10/1999 | Gorman et al. |
| 6,054,297 A | 4/2000 | Carter et al. |
| 6,071,515 A | 6/2000 | Mezes et al. |
| 6,124,431 A | 9/2000 | Sakakibara et al. |
| 6,180,370 B1 | 1/2001 | Queen et al. |
| 6,214,345 B1 | 4/2001 | Firestone et al. |
| 6,235,883 B1 | 5/2001 | Jakobovits et al. |
| 6,329,507 B1 | 12/2001 | Mezes et al. |
| 6,407,213 B1 | 6/2002 | Carter et al. |
| 6,441,163 B1 | 8/2002 | Chari et al. |
| 6,455,677 B1 | 9/2002 | Park et al. |
| 6,506,883 B2 | 1/2003 | Meteo de Acosta del Rio et al. |
| 6,602,684 B1 | 8/2003 | Umana et al. |
| 6,632,927 B2 | 10/2003 | Adair et al. |
| 6,706,265 B1 | 3/2004 | Bolt et al. |
| 6,716,410 B1 | 4/2004 | Witztum |
| 6,723,538 B2 | 4/2004 | MacK et al. |
| 6,803,039 B2 * | 10/2004 | Tsuji ............... A61P 29/00 424/144.1 |
| 6,884,869 B2 | 4/2005 | Senter et al. |
| 6,989,452 B2 | 1/2006 | Ng et al. |
| 7,087,600 B2 | 8/2006 | Ng et al. |
| 7,112,324 B1 | 9/2006 | Dorken et al. |
| 7,129,261 B2 | 10/2006 | Ng et al. |
| 7,276,497 B2 | 10/2007 | Chari et al. |
| 7,303,749 B1 | 12/2007 | Chari |
| 7,368,565 B2 | 5/2008 | Chari et al. |
| 7,498,302 B2 | 3/2009 | Ng et al. |
| 7,507,420 B2 | 3/2009 | Ng et al. |
| 7,517,903 B2 | 4/2009 | Chen et al. |
| 7,601,354 B2 | 10/2009 | Chari |
| 7,642,228 B2 | 1/2010 | Carter et al. |
| 7,691,962 B2 | 4/2010 | Boyd et al. |
| 7,695,936 B2 | 4/2010 | Carter et al. |
| 7,696,338 B2 | 4/2010 | Neville, Jr. et al. |
| 7,728,114 B2 | 6/2010 | Mach et al. |
| 8,063,187 B2 | 11/2011 | Chu et al. |
| 8,114,967 B2 | 2/2012 | Bhatt et al. |
| 8,216,805 B2 | 7/2012 | Carter et al. |
| 8,236,308 B2 | 8/2012 | Kischel et al. |
| 8,309,690 B2 | 11/2012 | Allan et al. |
| 8,367,805 B2 | 2/2013 | Chamberlain et al. |
| 8,409,568 B2 | 4/2013 | Gao et al. |
| 8,592,562 B2 | 11/2013 | Kannan et al. |
| 8,637,641 B2 | 1/2014 | Dahiyat et al. |
| 8,946,387 B2 | 2/2015 | Koenig et al. |
| 9,822,181 B2 | 11/2017 | Bonvini et al. |
| 9,856,327 B2 | 1/2018 | Bernett et al. |
| 10,793,632 B2 * | 10/2020 | Bernett ............ C07K 16/2809 |
| 2001/0035606 A1 | 11/2001 | Schoen |
| 2002/0076406 A1 | 6/2002 | Leung |
| 2002/0103345 A1 | 8/2002 | Zhu |
| 2002/0131968 A1 | 9/2002 | Waldmann et al. |
| 2003/0003097 A1 | 1/2003 | Reff et al. |
| 2003/0017979 A1 | 1/2003 | Mack et al. |
| 2003/0091561 A1 | 5/2003 | Van de Winekl |
| 2003/0157108 A1 | 8/2003 | Presta |
| 2003/0223999 A1 | 12/2003 | Lindhofer |
| 2004/0018191 A1 | 1/2004 | Wang |
| 2004/0071696 A1 | 4/2004 | Adams et al. |
| 2004/0162411 A1 | 8/2004 | Lanzavecchia |
| 2004/0170626 A1 | 9/2004 | Schuurman |
| 2004/0242851 A1 | 12/2004 | Zhu |
| 2005/0114037 A1 | 5/2005 | Desjarlais et al. |
| 2005/0136050 A1 | 6/2005 | Kufer et al. |
| 2005/0142133 A1 | 6/2005 | Lazar et al. |
| 2005/0176028 A1 | 8/2005 | Hofmeiser et al. |
| 2005/0191702 A1 | 9/2005 | Mack et al. |
| 2005/0238648 A1 | 10/2005 | Jacobs |
| 2005/0238649 A1 | 10/2005 | Doronina |
| 2006/0008883 A1 | 1/2006 | Lazar |
| 2006/0018897 A1 | 1/2006 | Lee et al. |
| 2006/0024298 A1 | 2/2006 | Lazar et al. |
| 2006/0024317 A1 | 2/2006 | Boyd |
| 2006/0073142 A1 | 4/2006 | Chan et al. |
| 2006/0074008 A1 | 4/2006 | Senter |
| 2006/0115481 A1 | 6/2006 | Lindhofer et al. |
| 2006/0121032 A1 | 6/2006 | Dahiyat et al. |
| 2006/0134105 A1 | 6/2006 | Lazar et al. |
| 2006/0235208 A1 | 10/2006 | Lazar |
| 2007/0071675 A1 | 3/2007 | Wu et al. |
| 2007/0105199 A1 | 5/2007 | Yan et al. |
| 2007/0123479 A1 | 5/2007 | Kufer et al. |
| 2007/0148170 A1 | 6/2007 | Desjarlais |
| 2007/0287170 A1 | 12/2007 | Davis et al. |
| 2008/0044413 A1 | 2/2008 | Hammond et al. |
| 2008/0050370 A1 | 2/2008 | Glaser et al. |
| 2008/0138335 A1 | 6/2008 | Takahashi et al. |
| 2008/0213273 A1 | 9/2008 | Burge |
| 2008/0219974 A1 | 9/2008 | Bernett et al. |
| 2008/0242845 A1 | 10/2008 | Lazar et al. |
| 2009/0082213 A1 | 3/2009 | Horowitz et al. |
| 2009/0163699 A1 | 6/2009 | Desjarlais |
| 2009/0214539 A1 | 8/2009 | Grosmaire et al. |
| 2009/0252683 A1 | 10/2009 | Kischel et al. |
| 2009/0252729 A1 | 10/2009 | Farrington et al. |
| 2009/0274692 A1 | 11/2009 | Tan et al. |
| 2009/0311253 A1 | 12/2009 | Ghayur et al. |
| 2009/0317869 A1 | 12/2009 | Alley et al. |
| 2010/0004431 A1 | 1/2010 | Bernett et al. |
| 2010/0015133 A1 | 1/2010 | Igawa et al. |
| 2010/0080814 A1 | 4/2010 | Desjarlais et al. |
| 2010/0150918 A1 | 6/2010 | Kufer et al. |
| 2010/0174053 A1 | 7/2010 | Johnson et al. |
| 2010/0178298 A1 | 7/2010 | Lindhofer |
| 2010/0183554 A1 | 7/2010 | Mach et al. |
| 2010/0226925 A1 | 9/2010 | Dillon et al. |
| 2010/0239567 A1 | 9/2010 | Esue |
| 2010/0239582 A1 | 9/2010 | Humphreys et al. |
| 2010/0256339 A1 | 10/2010 | Bossenmaier et al. |
| 2010/0256340 A1 | 10/2010 | Brinkmann et al. |
| 2010/0298542 A1 | 11/2010 | Igawa et al. |
| 2010/0322933 A1 | 12/2010 | Lindhofer et al. |
| 2010/0330089 A1 | 12/2010 | Damle et al. |
| 2010/0331527 A1 | 12/2010 | Davis et al. |
| 2011/0054151 A1 | 3/2011 | Lazar et al. |
| 2011/0076275 A1 | 3/2011 | Igawa et al. |
| 2011/0177500 A1 | 7/2011 | Winther et al. |

(56) References Cited

U.S. PATENT DOCUMENTS

| | | |
|---|---|---|
| 2011/0189178 A1 | 8/2011 | Desjarlais et al. |
| 2011/0189209 A1 | 8/2011 | Neville, Jr. et al. |
| 2011/0201032 A1 | 8/2011 | Zeng et al. |
| 2011/0217302 A1 | 9/2011 | Odegard et al. |
| 2011/0262439 A1 | 10/2011 | Kufer et al. |
| 2011/0275787 A1 | 11/2011 | Kufer et al. |
| 2011/0293619 A1 | 12/2011 | Kufer et al. |
| 2012/0028304 A1 | 2/2012 | Dahiyat et al. |
| 2012/0034228 A1 | 2/2012 | Kufer et al. |
| 2012/0121597 A1 | 5/2012 | Ho et al. |
| 2012/0149876 A1 | 6/2012 | Von Kreudenstein et al. |
| 2012/0156207 A1 | 6/2012 | Chu et al. |
| 2012/0251531 A1 | 10/2012 | Baehner et al. |
| 2012/0251541 A1 | 10/2012 | Baurin et al. |
| 2013/0089541 A1 | 4/2013 | D'Angelo et al. |
| 2013/0095097 A1 | 4/2013 | Blakenship et al. |
| 2013/0101586 A1 | 4/2013 | Riegler et al. |
| 2013/0115208 A1 | 5/2013 | Ho et al. |
| 2013/0129723 A1 | 5/2013 | Blakenship et al. |
| 2013/0142793 A1 | 6/2013 | Ledbetter et al. |
| 2013/0171095 A1 | 7/2013 | Bernett et al. |
| 2013/0195849 A1 | 8/2013 | Von Kreudenstein et al. |
| 2013/0209355 A1 | 8/2013 | De Weers et al. |
| 2013/0267686 A1 | 10/2013 | Brinkmann |
| 2013/0336981 A1 | 12/2013 | de Kruif et al. |
| 2014/0024111 A1 | 1/2014 | Kannan et al. |
| 2014/0056879 A1 | 2/2014 | Lazar |
| 2014/0072581 A1 | 3/2014 | Dixit et al. |
| 2014/0086916 A1 | 3/2014 | Zha |
| 2014/0212435 A1 | 7/2014 | Moore et al. |
| 2014/0212436 A1 | 7/2014 | Moore et al. |
| 2014/0249297 A1 | 9/2014 | Lazar et al. |
| 2014/0288275 A1 | 9/2014 | Moore et al. |
| 2014/0294759 A1 | 10/2014 | Chu et al. |
| 2014/0294823 A1 | 10/2014 | Moore et al. |
| 2014/0294833 A1 | 10/2014 | Desjarlais et al. |
| 2014/0294835 A1 | 10/2014 | Moore et al. |
| 2014/0294836 A1 | 10/2014 | Chu et al. |
| 2014/0302064 A1 | 10/2014 | Moore |
| 2014/0322217 A1 | 10/2014 | Moore et al. |
| 2014/0356381 A1 | 12/2014 | Moore et al. |
| 2014/0363426 A1 | 12/2014 | Moore et al. |
| 2014/0370013 A1 | 12/2014 | Desjarlais et al. |
| 2014/0370020 A1 | 12/2014 | Kuramochi et al. |
| 2014/0377269 A1 | 12/2014 | Mabry et al. |
| 2014/0377270 A1 | 12/2014 | Moore et al. |
| 2015/0071948 A1 | 3/2015 | Lazar et al. |
| 2015/0307629 A1 | 10/2015 | Bernett et al. |
| 2016/0060360 A1 | 3/2016 | Moore et al. |
| 2016/0068588 A1 | 3/2016 | Bernett et al. |
| 2016/0176969 A1 | 6/2016 | Bernett et al. |
| 2016/0215063 A1 | 7/2016 | Bernett et al. |
| 2016/0229924 A1 | 8/2016 | Bernett et al. |
| 2017/0020963 A1 | 1/2017 | Qu et al. |
| 2018/0118828 A1 | 5/2018 | Bernett et al. |
| 2018/0127501 A1* | 5/2018 | Bernett .............. C07K 16/2809 |
| 2019/0263909 A1* | 8/2019 | Bernett ............ A61K 39/39541 |

FOREIGN PATENT DOCUMENTS

| | | |
|---|---|---|
| EP | 1829895 | 5/2007 |
| EP | 2006381 | 12/2008 |
| EP | 2009101 A1 | 12/2008 |
| EP | 2194066 | 6/2010 |
| EP | 2202245 A1 | 6/2010 |
| EP | 2522724 | 6/2011 |
| EP | 2155788 | 2/2014 |
| EP | 3252078 | 12/2017 |
| WO | WO8705330 | 9/1987 |
| WO | WO9211018 | 7/1992 |
| WO | WO9321232 | 10/1993 |
| WO | WO9413804 | 5/1994 |
| WO | WO9520045 | 1/1995 |
| WO | WO9640210 | 6/1996 |
| WO | WO96027011 | 9/1996 |
| WO | WO98050431 | 11/1998 |
| WO | WO199937791 | 7/1999 |
| WO | WO99054440 | 10/1999 |
| WO | WO99066951 | 12/1999 |
| WO | WO200061739 A1 | 10/2000 |
| WO | WO200124763 A2 | 4/2001 |
| WO | WO200129246 A1 | 4/2001 |
| WO | WO200162931 A1 | 8/2001 |
| WO | WO200188138 | 11/2001 |
| WO | WO2001083525 | 11/2001 |
| WO | WO2001090192 | 11/2001 |
| WO | WO200216368 | 2/2002 |
| WO | WO200230954 A1 | 4/2002 |
| WO | WO200231140 A1 | 4/2002 |
| WO | WO2002088172 A2 | 7/2002 |
| WO | WO2002062850 | 8/2002 |
| WO | WO2002083180 | 10/2002 |
| WO | WO2002098883 | 12/2002 |
| WO | WO2004010957 | 2/2004 |
| WO | WO2004043493 | 5/2004 |
| WO | WO2004103272 | 12/2004 |
| WO | WO2004106383 | 12/2004 |
| WO | WO2005063816 | 7/2005 |
| WO | WO2005112919 A2 | 12/2005 |
| WO | WO2005118635 | 12/2005 |
| WO | WO2006020258 | 2/2006 |
| WO | WO2006034488 | 3/2006 |
| WO | WO2006036834 | 4/2006 |
| WO | WO2006072620 | 7/2006 |
| WO | WO2006110476 A2 | 10/2006 |
| WO | WO2006106905 | 12/2006 |
| WO | WO2007005612 | 1/2007 |
| WO | WO2007018431 A2 | 2/2007 |
| WO | WO2007033230 | 3/2007 |
| WO | WO2007042261 | 4/2007 |
| WO | WO2007046006 | 4/2007 |
| WO | WO2007047829 | 4/2007 |
| WO | WO2007059404 A2 | 5/2007 |
| WO | WO2007062037 | 5/2007 |
| WO | WO2007084342 | 7/2007 |
| WO | WO2007089149 A2 | 8/2007 |
| WO | WO2007093630 | 8/2007 |
| WO | WO2007098934 | 9/2007 |
| WO | WO2007110205 | 10/2007 |
| WO | WO2007113648 | 10/2007 |
| WO | WO20070147901 | 12/2007 |
| WO | WO2008003103 | 1/2008 |
| WO | WO2008003115 | 1/2008 |
| WO | WO2008003116 | 1/2008 |
| WO | WO2008119096 | 10/2008 |
| WO | WO2008119566 | 10/2008 |
| WO | WO2008124858 | 10/2008 |
| WO | WO2008145142 | 12/2008 |
| WO | WO2008150494 | 12/2008 |
| WO | WO2009000006 | 12/2008 |
| WO | WO2009017394 A1 | 2/2009 |
| WO | WO2009017823 | 2/2009 |
| WO | WO2009030734 | 3/2009 |
| WO | WO2009032782 | 3/2009 |
| WO | WO2009086320 | 7/2009 |
| WO | WO2009089004 | 7/2009 |
| WO | WO2009106096 | 9/2009 |
| WO | WO2009106321 | 9/2009 |
| WO | WO2010028796 | 3/2010 |
| WO | WO2010033736 | 3/2010 |
| WO | WO2010034441 | 4/2010 |
| WO | WO2010037835 | 4/2010 |
| WO | WO2010042904 | 4/2010 |
| WO | WO2010062171 A2 | 6/2010 |
| WO | WO2010085682 | 7/2010 |
| WO | WO2010106180 | 9/2010 |
| WO | WO2010115551 | 10/2010 |
| WO | WO2010115552 | 10/2010 |
| WO | WO2010115553 | 10/2010 |
| WO | WO2010115589 | 10/2010 |
| WO | WO2010119119 | 10/2010 |
| WO | WO20100112193 | 10/2010 |
| WO | WO2010136172 | 12/2010 |
| WO | WO2010151792 | 12/2010 |

(56) References Cited

FOREIGN PATENT DOCUMENTS

| WO | WO2010151808 | 12/2010 |
|---|---|---|
| WO | WO2011005621 | 1/2011 |
| WO | WO2011028952 | 3/2011 |
| WO | WO2011036183 | 3/2011 |
| WO | WO2011066342 | 3/2011 |
| WO | WO2011051307 | 5/2011 |
| WO | WO2011063348 | 5/2011 |
| WO | WO2011066501 | 6/2011 |
| WO | WO2011121110 | 10/2011 |
| WO | WO2011131746 | 10/2011 |
| WO | WO2011133886 | 10/2011 |
| WO | WO2011143545 | 11/2011 |
| WO | WO2011159877 | 12/2011 |
| WO | WO2012016227 | 2/2012 |
| WO | WO2012018687 | 2/2012 |
| WO | WO2012032080 | 3/2012 |
| WO | WO2012058768 | 5/2012 |
| WO | WO2012062596 | 5/2012 |
| WO | WO2012107417 | 8/2012 |
| WO | WO2012116453 | 9/2012 |
| WO | WO2012125495 | 9/2012 |
| WO | WO2012125850 | 9/2012 |
| WO | WO2012131555 | 10/2012 |
| WO | WO2012146394 | 11/2012 |
| WO | WO2012146628 | 11/2012 |
| WO | WO2012162067 | 11/2012 |
| WO | WO2013006544 | 1/2013 |
| WO | WO2013016714 | 1/2013 |
| WO | WO2013022855 | 2/2013 |
| WO | WO2013026833 | 2/2013 |
| WO | WO2013033008 | 3/2013 |
| WO | WO2013047748 | 4/2013 |
| WO | WO2013055809 | 4/2013 |
| WO | WO2013063702 | 5/2013 |
| WO | WO2013096828 | 6/2013 |
| WO | WO2013125667 | 8/2013 |
| WO | WO2013164694 | 11/2013 |
| WO | WO2013180201 | 12/2013 |
| WO | WO2014004586 | 1/2014 |
| WO | WO2014012085 | 1/2014 |
| WO | WO2014047231 | 3/2014 |
| WO | WO2014056783 | 4/2014 |
| WO | WO2014079000 | 5/2014 |
| WO | WO2014110601 | 7/2014 |
| WO | WO2014113510 | 7/2014 |
| WO | WO2014145806 | 9/2014 |
| WO | WO2014145907 | 9/2014 |
| WO | WO2014164553 | 10/2014 |
| WO | WO2014207064 | 12/2014 |
| WO | WO2014209804 | 12/2014 |
| WO | WO2015018528 | 2/2015 |
| WO | WO2015026892 | 2/2015 |
| WO | WO2015063339 | 5/2015 |
| WO | WO2015095392 | 6/2015 |
| WO | WO2015095410 | 6/2015 |
| WO | WO2015095423 | 6/2015 |
| WO | WO2015103072 | 7/2015 |
| WO | WO2015143079 | 9/2015 |
| WO | WO2015149077 | 10/2015 |
| WO | WO2015168379 | 11/2015 |
| WO | WO2015184207 | 12/2015 |
| WO | WO2016014984 | 1/2016 |
| WO | WO2016028672 | 2/2016 |
| WO | WO2016028896 | 2/2016 |
| WO | WO2016079050 | 5/2016 |
| WO | WO2016086186 | 6/2016 |
| WO | WO2016086189 | 6/2016 |
| WO | WO2016086196 | 6/2016 |
| WO | WO2016105450 | 6/2016 |
| WO | WO2016110584 | 7/2016 |
| WO | WO2016115274 | 7/2016 |
| WO | WO2016120789 | 8/2016 |
| WO | WO2016141387 | 9/2016 |
| WO | WO2016182751 | 11/2016 |
| WO | WO2017019846 | 2/2017 |
| WO | WO2017112775 | 6/2017 |
| WO | WO2017210443 | 12/2017 |
| WO | WO2017210485 | 12/2017 |
| WO | WO2017214092 | 12/2017 |
| WO | WO2019050521 | 3/2019 |

OTHER PUBLICATIONS

"Xencor Provides Data Updates on XmaB Bispecific Antibody Program and Announces Presentations at Upcoming American Society of Hematology 2014 Annual Meeting", Nov. 6, 2014, XP055255549, retrieved from the internet: http://files.shareholder.com/downloads/AMDA-2B2V8N/0x0x792404/77590b72-837a-4085-bc55-78fa500638dc/XNCR_News_2014_11_6_General_Releases.pdf.

Abbott Laboratories, Strategies and Current Approaches for Improving Drug-Like-Properties During Biologics Drug Candidate Selection, AAPS Webinar—Nov. 10, 2011.

Adams, et al., Avidity-Mediated Enhancement of In vivo Tumor Targeting by Single-Chain Fv Dimers, Clin Cancer Res, 2006, vol. 12(5), pp. 1599-1605, doi:10.1158/1078-0432.CCR-05-2217.

Alberola-Ila et al., Stimulation Through the TCR/CD3 Complex Up-Regulates the CD2 Srface Expression on Human T Lymphocytes, Feb. 15, 1991.

Alibaud et al., A New Monoclonal Anti-CD3? Antibody Reactive on Paraffin Sections, Journal of Histochemistry & Cytochemistry, 2000, vol. 48, p. 1609.

An, et al., IgG2m4, an engineered antibody isotype with reduced Fc function, mAbs, 2009, vol. 1, Issue 6, pp. 572-579, www.landesbioscience.com/journals/mabs/article/10185.

Aplin et al., Preparation, properties, and applications of carbohydrate conjugates of proteins and lipids, 1981, CRC Crit. Rev. Biochem., pp. 259-306.

Arnett, et al., Crystal structure of a human CD3-$\epsilon/\delta$ dimer in complex with a UCHT1 single-chain antibody fragment, PNAS, 2004, vol. 101, No. 46, pp. 16268-16273.

Asano, et al., Cytotoxic enhancement of a bispecific diabody (Db) by format conversion to tandem single-chain variable fragment (taFv): The Case of the hEx3 Diabody, JBC Papers in Press, 2010, http://www.jbc.org/cgi/doi/10.1074/jbc.M110.172957.

Asano, et al., Highly Effective Recombinant Format of a Humanized IgG-like Bispecific Antibody for Cancer Immunotherapy with Retargeting of Lymphocytes to Tumor Cells, The Journal of Biological Chemistry, 2007, vol. 282, No. 38, pp. 27659-27665.

Atwell, et al., Stable Heterodimers from Remodeling the Domain Interface of a Homodimer using a Phage Display Library, J. Mol. Biol., 1997, vol. 270, pp. 26-35.

Baca et al., Antibody humanization using monovalent phage display, 1997, J. Biol. Chem. 272(16):10678-10684.

Baeuerle, et al., Response to Letter, "Correct TandAb protein," Molecular Immunology, 2007, vol. 44, p. 3084.

Baeuerle, et al., Review—Bispecific T-Cell Engaging Antibodies for Cancer Therapy, Cancer Res, 2009, vol. 69: (12), pp. 4941-4944.

Barbas, et al. In vitro evolution of a neutralizing human antibody to human immunodeficiency virus type 1 to enhance affinity and broaden strain cross-reactivity, 1994, Proc. Nat. Acad. Sci, USA 91.3809-3813.

Bargou et al., Tumor Regression in Cancer Patients by Very Low Doses of a T Cell-Engaging Antibody, Science, 2008, vol. 321, pp. 974-977.

Bernett et al., Multiple Bispecific Checkpoint Combinations Promote T cell activation., Nov. 11, 2016, retrieved from the internet: http://files.shareholder.com/downloads/AMDA-2B2V8N/0x0x916283/67AE1A8B-40E8-4316-9F79-384D06B2C395/XNCR_SITC_2016_PD1xCTLA4_Poster126_12Nov2016.pdf.

Bhatt, Sea Lane—DDD presentation, "Surrobodies™—A Novel Approach to Bispecifics . . . ," Aug. 8, 2012.

Bibollet-Ruche et al., The Quality of Chimpanzee T-Cell Activation and Simian Immunodeficiency Virus/Human Immunodeficiency Virus Susceptibility Achieved via Antibody-Mediated T-Cell Receptor/CD3 Stimulation Is a Function of the Anti-CD3 Antibody Isotype, Jul. 30, 2008.

(56) References Cited

OTHER PUBLICATIONS

Biochemica, Your apoptosis specialist, 1999, No. 2, pp. 34-37 (Roche Molecular Biochemicals).
Bird et al., Single-chain antigen-binding proteins, 1988, Science 242:423-426.
Bluemel, et al., Epitope distance to the target cell membrane and antigen size determine the potency of T cell-mediated lysis by BiTE antibodies specific for a large melanoma surface antigen, Cancer Immunol Immunother, 2010, vol. 59(8), pp. 1197-1209.
Borras, et al., Generic Approach for the Generation of Stable Humanized Single-chain Fv Fragments from Rabbit Monoclonal Antibodies, The Journal of Biological Chemistry, 2010, vol. 285, No. 12, pp. 9054-9066.
Bortoletto, Nicola et al., "Optimizing anti-CD3 affinity for effective T cell targeting against tumor cells.", Eur J Immunol. Nov. 2002;32(11):3102-7.
Boswell et al., Effects of Charge on Antibody Tissue Distribution and Pharmacokinetics, 2010, Bioconjugate Chem, 21(21):2153-2163.
Brandl, et al., Bispecific antibody fragments with CD20 3 CD28 specificity allow effective autologous and allogeneic T-cell activation against malignant cells in peripheral blood and bone marrow cultures from patients with B-cell lineage leukemia and lymphoma, Experimental Hematology, 1999, vol. 27, pp. 1264-1270.
Brinkmann, et al., presentation slideshow—"Roche Penzberg & Roche Glycart, Schlieren: Centers of Excellence for Recombinant Proteins".
Brinkmann, et al., A recombinant immunotoxin containing a disulfide-stabilized Fv fragment, Proc. Natl. Acad. Sci. USA, 1993, vol. 90, pp. 7538-7542.
Cao, et al., Oligomerization is required for the activity of recombinant soluble LOX-1., FEBS J. Sep. 2009;276(17):4909-20. doi: 10.1111/j.1742-4658.2009.07190.x. Epub Jul. 31, 2009.
Carpenter, et al., Non-Fc Receptor-Binding Humanized Anti-CD3 Antibodies Induce Apoptosis of Activated Human T Cells, J. Immunol., 2000, vol. 165, No. 11, pp. 6205-6213.
Carter et al., Antibody-drug conjugates for cancer therapy, 2008, Cancer J. 14(3):154-169.
Carter et al., Humanization of an anti-p185HER2 antibody for human cancer therapy, 1992, Proc Natl Acad Sci USA 89:4285-9.
Castoldi, et al., Molecular characterization of novel trispecific ErbB-cMet-IGF1R antibodies and their antigen-binding properties, Protein Engineering, Design & Selection, 2012, vol. 25, No. 10, pp. 551-559.
Cemerski, et al., Suppression of mast cell degranulation through a dual-targeting tandem IgE-IgG Fc domain biologic engineered to bind with high affinity to FcγRIIb., Immunol Lett. Mar. 30, 2012;143(1):34-43. doi: 10.1016/j.imlet.2012.01.008. Epub Jan. 25, 2012.
Chames et al., Bispecific antibodies for cancer therapy—The light at the end of the tunnel?, mAbs, 2009, vol. 1, Issue 6, pp. 1-9.
Chang, et al., Monoclonal antibodies against oxidized low-density lipoprotein bind to apoptotic cells and inhibit their phagocytosis by elicited macrophages: evidence that oxidation-specific epitopes mediate macrophage recognition., Proc Natl Acad Sci U S A. May 25, 1999;96(11):6353-8.
Chari et al., Immunoconjugates containing novel maytansinoids: promising anticancer drugs, 1992, Cancer Research 52: 127-131.
Chatal, 1989, Monoclonal Antibodies in Immunoscintigraphy, CRC Press (Book Abstract).
Chelius, et al., Structural and functional characterization of the trifunctional antibody catumaxomab, mAbs, 2010, vol. 2, Issue 3, pp. 309-319.
Chichili et al., A CD3xCD123 bispecific DART for redirecting host T cells to myelogenous leukemia: preclinical activity and safety in nonhuman primates., Sci Transl Med. May 27, 2015;7(289):289ra82. doi: 10.1126/scitranslmed.aaa5693.
Chichili et al., Co-targeting of PD-1 and CTLA-4 Inhibitory Pathways with Bispecific DART® and TRIDENT™ Molecules., Apr. 4, 2017, retrieved from the internet: http://files.shareholder.com/downloads/AMDA-278VRP/0x0x935572/8CC86417-40BA-41C0-935D-EF1B7DB0B5BB/AACR_2017_-_Co-targeting_PD-1_and_CTLA-4_Inhibitory_Pathways_with_DART_and_TRIDENT_Molecules.pdf.
Chothia et al., Canonical structures for the hypervariable regions of immunoglobulins, 1987, J. Mol. Biol. 196:901-917.
Chothia, et al., Structural Determinants in the Sequences of Immunoglobulin Variable Domain, J. Mol. Biol., 1998, vol. 278, pp. 457-479.
Chu et al., Immunotherapy with Long-Lived Anti-CD123 x Anti-CD3 Bispecific Antibodies Stimulates Potent T Cell Mediated Killing of Human AML Cell Lines and of CD123+ Cells In Monkeys: A Potential Therapy for Acute Myelogenous Leukemia, Blood 2014, 124:2316.
Chu et al., Immunotherapy with Long-Lived Anti-CD123 x Anti-CD3 Bispecific Antibodies Stimulates Potent T Cell-Mediated Killing of Human B Cell Lines and of Circulating and Lymphoid B Cells in Monkeys: A Potential Therapy for B Cell Lymphomas and Leukemias, Blood 2014, 124:3111.
Chu et al., Inhibition of B cell receptor-mediated activation of primary human B cells by coengagement of CD19 and FcgammaRIIb with Fc-engineered antibodies., Mol Immunol. Sep. 2008;45(15):3926-33. doi: 10.1016/j.molimm.2008.06.027. Epub Aug. 8, 2008.
Chu et al., Reduction of total IgE by targeted coengagement of IgE B-cell receptor and FcγRIIb with Fc-engineered antibody., J Allergy Clin Immunol. Apr. 2012;129(4):1102-15. doi: 10.1016/j.jaci.2011.11.029. Epub Jan. 16, 2012.
Conrad, et al., TCR and CD3 Antibody Cross-Reactivity in 44 Species, Cytometry Part A, 2007, vol. 71A, pp. 925-933.
Conrath, et al., Antigen Binding and Solubility Effects upon the Veneering of a Camel VHH in Framework-2 to Mimic a VH, J. Mol. Biol., 2005, vol. 350, pp. 112-125.
Counterman et al., "Volumes of Individual Amino Acid Residues in Gas-Phase Peptide Ions.", J. Am. Chem. Soc., 1999, 121 (16), pp. 4031-4039.
Cuesta, et al., Multivalent antibodies: when design surpasses evolution, Trends in Biotechnology, 2010, vol. 28, No. 7, pp. 355-362, doi:10.1016/j.tibtech.2010.03.007.
D'Argouges, et al., Combination of rituximab with blinatumomab (MT103/MEDI-538), a T cell-engaging CD19-/CD3-bispecific antibody, for highly efficient lysis of human B lymphoma cells, Leukemia Research, 2009, vol. 33, pp. 465-473.
Davies et al., Expression of GnTIII in recombinant anti-CD20 CHO production cell line: expression of antibodies with altered glycoforms leads to an increase in ADCC through higher affinity for FCγRIII, 2001, Biotechnol Bioeng 74:288-294.
Davila, et al., Efficacy and Toxicity Management of 19-28z CAR T Cell Therapy in B Cell Acute Lymphoblastic Leukemia, Sci. Transl. Med., 2014, vol. 6, Issue 224, pp. 1-10, 224ra25.
Davis, et al., SEEDbodies: fusion proteins based on strand-exchange engineered domain (SEED) $C_H3$ heterodimers in an Fc analogue platform for asymmetric binders or immunofusions and bispecific antibodies, Protein Engineering, Design & Selection, 2010, vol. 23, No. 4 pp. 195-202.
De Groot et al., De-Immunization Of Therapeutic Proteins By T-Cell Epitope Modification, 2005, Dev. In Biologicals, 2005, 122:171-194.
De Pascalis et al., Grafting of "abbreviated" complementarity-determining regions containing specificity-determining residues essential for ligand contact to engineer a less immunogenic humanized monoclonal antibody, 2002, J. Immunol. 169:3076-3084.
Del Nagro et al., A critical role for complement C3d and the B cell coreceptor (CD19/CD21) complex in the initiation of inflammatory arthritis., J. Immunol. Oct. 15, 2005;175(8):5379-89.
Demarest et al., Antibody therapeutics, antibody engineering, and the merits of protein stability, Current Opinin in Drug Discovery & Development, 2008 11(5): 675-587, Sep. 11, 2008.
Deyev, et al., Multivalency: the hallmark of antibodies used for optimization of tumor targeting by design, BioEssays, 2008, vol. 30, pp. 904-918.
DiGiammarino et al., Ligand association rates to the inner-variable-domain of a dual-variable-domain immunoglobulin are significantly

(56) References Cited

OTHER PUBLICATIONS impacted by linker design, mAbs3:5, 1-8; Sep.-Oct.; 3(5):487-94, Landes Bioscience, Sep. 1, 2011.
DiGiandomenico et al., A multifuncitonal bispecific antibody protects against Pseudomonas aeruginosa., Sci Transl Med. Nov. 12, 2014;6(262):262ra155.doi: 10.1126/scitranslmed.3009655.
Dixon, et al., Activation of Human T Lymphocytes by Crosslinking of Anti-CD3 Monoclonal Antibodies, Journal of Leukocyte Biology, 1989, vol. 46, pp. 214-220.
Dong et al., A stable IgG-like bispecific antibody targeting the epidermal growth factor receptor and the type I insulin-like growth factor receptor demonstrates superior anti-tumor activity, mAbs 3:3, May-Jun. 2011: 273-288, May 1, 2011.
Doronina, Development of potent monoclonal antibody auristatin conjugates for cancer therapy, 2003, Nat Biotechnol 21(7):778-784.
Dreier, et al., Extremely Potent, Rapid and Costimulation-Independent Cytotoxic T-cell Response Against Lymphoma Cells Catalyzed by a Single-Chain Bispecific Antibody, Int. J. Cancer, 2002, vol. 100, pp. 690-697.
Dreier, et al., T Cell Costimulus-Independent and Very Efficacious Inhibition of Tumor Growth in Mice Bearing Subcutaneous or Leukemic Human B Cell Lymphoma Xenografts by a CD19-/CD3-Bispecific Single-Chain Antibody Construct, The Journal of Immunology, 2003, vol. 170, pp. 4397-4402.
Dubowchik et al., Receptor-mediated and enzyme-dependent targeting of cytotoxic anticancer drugs, 1999, Pharm. Therapeutics 83:67-123.
Ducry et al., Antibody-drug conjugates: linking cytotoxic payloads to monoclonal antibodies, 2010, Bioconjugate Chem. 21:5-13.
Dudgeon, et al., General strategy for the generation of human antibody variable domains with increased aggregation resistance, PNAS Early Edition, 2012, pp. 10879-10884, www.pnas.org/cgi/doi/10.1073/pnas.1202866109 & Supporting Information.
Duke, et al., Measurement of apoptosis and other forms of cell death, 2004, Curr protocols immunol. 3.17.1-3.17.16.
DukSin et al., Relationship of the structure and biological activity of the natural homologues of tunicamycin, 1982, J. Biol. Chem. 257:3105.
Duval, et al., A Bispecific Antibody Composed of a Nonneutralizing Antibody to the gp41 Immunodominant Region and an Anti-CD89 Antibody Directs Broad Human Immunodeficiency Virus Destruction by Neutrophils, Journal of Virology, 2008, pp. 4671-4674, doi:10.1128/JVI.02499-07.
Edge et al., Deglycosylation of glycoproteins by trifluoromethanesulfonic acid, 1981, Anal. Biochem. 118:131.
Elliott, et al., Antiparallel Conformation of Knob and Hole Aglycosylated Half-Antibody Homodimers Is Mediated by a CH2—CH3 Hydrophobic Interaction, Journal of Molecular Biology, 2014, vol. 426, Issue 9, pp. 1947-1957.
Feldmann et al., Novel Humanized and Highly Efficient Bispecific Antibodies Mediate Killing of Prostate Stem Cell Antigen-Expressing Tumor Cells by CD8+ and CD4+ T cells, Aug. 8, 2012.
Feldmann et al., Retargeting of T Cells to Prostate Stem Cell Antigen Expressing Tumor Cells: Comparison of Different Antibody Formats, Dec. 28, 2010.
Fernandes, et al., T Cell Receptors are Structures Capable of Initiating Signaling in the Absence of Large Conformational Rearrangements, The Journal of Biological Chemistry, 2012, vol. 287, No. 16, pp. 13324-13335.
Fischer, Nicolas et al., "Bispecifc antibodies: molecules that enable novel therapeutic strategies", 2007, vol. 74, pp. 3-14.
Foreman, et al., ErbB3 Inhibitory Surrobodies Inhibit Tumor Cell Proliferation In Vitro and In Vivo, Mol Cancer Ther, 2012, vol. 11(7), pp. 1411-1420.
Foreman, et al., PEGS poster, "ErbB3 Inhibitory Surrobodies Inhibit Tumor Cell Proliferation In Vitro and In Vivo," 2012.
Fraker et al., Crystal structure of peptide cyclo-(D-VAL-L-PRO-L-VAL-D-PRO)$_3$, 1978, Biochem. Biophys. Res. Commun. 80(4):849-57.

Francois, et al., Construction of a Bispecific Antibody Reacting with the α- and β-Chains of the Human IL-2 Receptor, The Journal of Immunology, May 15, 1993, vol. 150, No. 10, pp. 4610-4619.
F-star Modular Antibodies Fact Sheet, Apr. 2008, "Modular Antibody Technology" (w/ reference to Ruker WO 2006/072620 A1).
F-star Modular Antibodies Press Release, Mar. 28, 2008, "Antibody Engineering Company F-Star Buys Back Royalty Obligations. TVM Capital Joins Investor Syndicate."
Fudenberg, et al., Serologic Demonstration of Dual Specificity of Rabbit Bivalent Hybrid Antibody, The Journal of Experimental Medicine, 1964, vol. 119(1), pp. 151-166.
Ganesan, et al., FcγRllb on Liver Sinusoidal Endothelium Clears Small Immune Complexes, The Journal of Immunology, Nov. 15, 2012, vol. 189 No. 10, pp. 4981-4988.
GenBank AAA38124.1, immunoglobulin heavy-chain VJ region [Mus musculus] Protein/NCBI.
GenBank AAA39180.1, immunoglobulin light-chain VJ region [Mus musculus] Protein/NCBI.
Ghendler et al., One of the CD3ε Subunits within a T Cell Receptor Complex Lies in Close Proximity to the Cβ FG Loop, J. Exp. Med., 1998, vol. 187, No. 9. pp. 1529-1536.
Ghetie et al., Multiple roles for the major histocompatibility complex Class I-related receptor FcRn, 2000, Annu Rev Immunol 18:739-766.
Gilliland, et al., Universal bispecific antibody for targeting tumor cells for destruction by cytotoxic T cells, Proc. Natl. Acad. Sci. USA, 1988, vol. 85, pp. 7719-7723.
Gorman et al., Reshaping a therapeutic CD4 antibody, Proc. Natl. Acad. Sci. USA 88:4181-4185.
Grodzki & Bernstein, "Antibody Purification: Ion-Exchange Chromatography.", Methods Mol Biol 2010 ;588:27-32.
Gunasekaran et al., Enhancing Antibody Fc Heterodimer Formation through Electrostatic Steering Effects, Journal of Biological Chemistry, vol. 285, No. 25, pp. 19637-10946, Apr. 16, 2010 & Supplementary Tables.
Haagen, et al., The Efficacy of CD3 x CD19 Bispecific Monoclonal Antibody (BsAb) in a Clonogenic Assay: The Effect of Repeated Addition of BsAb, and Interleukin-2, Blood, 1995, vol. 85, No. 11, pp. 3208-3212.
Hakimuddin et al., A chemical method for the deglycosylation of proteins, 1987, Arch. Biochem. Biophys. 259:52.
Hamel, et al., The Role of the $V_L$- and $V_H$-Segments in the Preferential Reassociation of Immunoglobulin Subunits, Molecular Immunology, 1986, vol. 23, No. 5, pp. 503-510.
HAwkins et al, Selection of phage antibodies by binding affinity mimicking affinity maturation, 1992, J. Mol. Biol. 226:889-896.
Hayden-Ledbetter, et al., CD20-Directed Small Modular Immunopharmaceutical, TRU-015, Depletes Normal and Malignant B Cells, Clin Cancer Res, 2009, vol. 15(8), pp. 2739-2746.
He et al., Humanization and pharmacokinetics of a monoclonal antibody with specificity for both E- and P-selectin, 1998, J. Immunol. 160:1029-1035.
Hedvat et al., Dual Blockade of PD-1 and CTLA-4 with Bispecific Antibodies Promotes Human T cell Activation and Proliferation., Nov. 11, 2016, retrieved from the internet: http://files.shareholder.com/downloads/AMDA-2B2V8N/0x0x916284/D8084990-61EC-4DFE-8B76-60CF58B8C06F/CPI_bispecifics.pdf.
Hennecke et al., "Non-repetitive single-chain Fv linkers selected by selectively infective phage (SIP) technology.", Protein Eng. May 1998;11(5):405-10.
Hernandez-Caselles, et al., A study of CD33 (SIGLEC-3) antigen expression and function on activated human T and NK cells: two isoforms of CD33 are generated by alternative splicing, J. Leukoc. Biol., 2006, vol. 79, pp. 46-58.
Hexham, et al., Influence of relative binding affinity on efficacy in a panel of anti-CD3 scFv immunotoxins, Molecular Immunology, 2001, vol. 38, pp. 397-408.
Hinman et al., Preparation and characterization of monoclonal antibody conjugates of the calicheamicins: a novel and potent family of antitumor antibodies, 1993 Cancer Res. 53:3336-3342.
Hoffmann, et al., Serial killing of tumor cells by cytotoxic T cells redirected with a CD19-/CD3-bispecific single-chain antibody construct, Int. J. Cancer, 2005, vol. 115, pp. 98-104.

(56) References Cited

OTHER PUBLICATIONS

Holliger et al., "Diabodies": Small Bivalent and bispecific antibody fragments, 1993, Proc. Natl. Acad. Sci. U.S.A. 90:6444-6448.
Holliger et al., Engineering bispecific antibodies, 1993, Current Opinion Biotechnol. 4:446-449.
Houtenbos, et al., The novel bispecific diabody αCD40/αCD28 strengthens leukaemic dendritic cell-induced T-cell reactivity, British Journal of Haematology, 2008, vol. 142, pp. 273-283.
Hu et al., Minibody: A novel engineered anti-carcinoembryonic antigen antibody fragment (single-chain Fv-$C_H3$) which exhibits rapid, high-level targeting of xenografts, 1996, Cancer Res. 56:3055-3061.
Huston et al., Protein engineering antibody binding sites: recovery of specific activity in an anti-digoxin single-chain Fv analogue produced in *Escherichia coli*, 1988, Proc. Natl. Acad. Sci. U.S.A. 85:5879-5883.
Igawa et al., Reduced elimination of IgG antibodies by engineering the variable region, 2010, PEDS. 23(5): 385-392.
Igawa, $V_H/V_L$ interface engineering to promote selective expression and inhibit conformational isomerization of thrombopoietin receptor agonist single-chain diabody, Protein Engineering, Design & Selection, 2010, vol. 23, No. 8, pp. 667-677.
Ishigaki et al., Impact of Plasma Oxidized Low-Density Lipoprotein Removal on Atherosclerosis., Circulation 118: 75-83, 2008.
Jackson et al., In vitro antibody maturation, 1995, J. Immunol. 154(7):3310-9.
Jäger, et al., The Trifunctional Antibody Ertumaxomab Destroys Tumor Cells That Express Low Levels of Human Epidermal Growth Factor Receptor 2, Cancer Res, 2009, vol. 69(10), pp. 4270-4276.
Jefferis et al., Interaction sites on human IgG-Fc for FcγR: current models, 2002, Immunol Lett 82:57-65.
Jespers, et al., Crystal Structure of HEL4, a Soluble, Refoldable Human $V_H$ Single Domain with a Germ-line Scaffold, J. Mol. Biol., 2004, vol. 337, pp. 893-903.
Jimenez, et al., A recombinant, fully human, bispecific antibody neutralizes the biological activities mediated by both vascular endothelial growth factor receptors 2 and 3, Mol Cancer Ther, 2005, vol. 4(3), pp. 427-434.
Jin et al. The Design and Engineering of IgG-Like Bispecific Antibodies., Chapter 9, Bispecific Antibodies, pp. 151-169.
Jin, et al., MetMAb, the One-Armed 5D5 Anti-c-Met Antibody, Inhibits Orthotopic Pancreatic Tumor Growth and Improves Survival, Cancer Res 2008, vol. 68, pp. 4360-4368.
Johnson et al., Anti-tumor activity of CC49-doxorubicin immunoconjugates, 1995, Anticancer Res. 15:1387-93.
Johnson, et al., Effector Cell Recruitment with Novel Fv-based Dual-affinity Re-targeting Protein Leads to Potent Tumor Cytolysis and in Vivo B-cell Depletion, J. Mol. Biol., 2010, vol. 399, pp. 436-449.
Jones et al., Replacing the complementarity-determining regions in a human antibody with those from a mouse, 1986, Nature 321:522-525.
Jordan et al. Structural understanding of stabilization patterns in engineered bispecific Ig-like antibody molecules, Proteins 2009; 77:832-841, Jun. 19, 2009.
Jung, et al., Design of interchain disulfide bonds in the framework region of the Fv fragment of the monoclonal antibody B3, Proteins, 1994, vol. 19(1), pp. 35-47.
Jung, et al., Target Cell-restricted Triggering of the CD95 (APO-1/Fas) Death Receptor with Bispecific Antibody Fragments, Cancer Research, 2001, vol. 61, pp. 1846-1848.
Jungbluth et al., A monoclonal antibody recognizing human cancers with amplification/overexpression of the human epidermal growth factor receptor, 2003, Proc Natl Acad Sci U S A. 100(2):639-44.
Kabat et al., 1991, Sequences of proteins of immunological interest, Department of Health and Human Services, Bethesda, vol. 1, $5^{th}$ Ed.
Kakutani et al., Accumulation of LOX-1 ligand in plasma and atherosclerotic lesions of Watanabe heritable hyperlipidemic rabbits: identification by a novel enzyme immunoassay.,Biochem Biophys Res Commun. Mar. 23, 2001;282(1):180-5.

Kanakaraj, et al., Simultaneous targeting of TNF and Ang2 with a novel bispecific antibody enhances efficacy in an in vivo model of arthritis, mAbs, 2012, vol. 4, Issue 5, pp. 600-613, http://dx.doi.org/10.4161/mabs.21227 & Supplemental Data.
Kettleborough et al., Humanization of a mouse monoclonal antibody by CDR-grafting: the importance of framework residues on loop conformation, 1991, Protein Eng. 4(7):773-83.
Keyna, et al., Surrogate Light Chain-Dependent Selection of Ig Heavy Chain V Regions, J. Immunol., 1995, vol. 155, pp. 5536-5542.
Kharmate et al., Inhibition of tumor promoting signals by activation of SSTR2 and opioid receptors in human breast cancer cells., Cancer Cell Int. Sep. 23, 2013;13(1):93. doi: 10.1186/1475-2867-13-93.
Kiewe, et al., Phase I Trial of the Trifunctional Anti-HER2 x Anti-CD3 Antibody Ertumaxomab in Metastatic Breast Cancer, Clin Cancer Res., 2006, vol. 12(10), pp. 3085-3091.
Kim et al., "Localization of the site of murine IgG1 molecule that is involved in binding the murine intestinal Fc receptor," Eur. J. Immunol., 24:2429-2434, 1994.
Kim et al., Mutational approaches to improve the biophysical properties of human single-domain antibodies., Biochim Biophys Acta. Nov. 2014;1844(11):1983-2001. doi: 10.1016/j.bbapap.2014.07.008. Epub Jul. 24, 2014.
Kipriyanov, et al., Bispecific CD3 x CD19 Diabody for T Cell-Mediated Lysis of Malignant Human B Cells, Int. J. Cancer, 1998. vol. 77, pp. 763-772.
Kipriyanov, et al., Bispecific Tandem Diabody for Tumor Therapy with Improved Antigen Binding and Pharmacokinetics, J. Mol. Biol., 1999, vol. 293, pp. 41-56.
Kipriyanov, et al., Effect of Domain Order on the Activity of Bacterially Produced Bispecific Single-chain Fv Antibodies, J. Mol. Biol., 2003, vol. 330, pp. 99-111.
Kipriyanov, et al., Two amino acid mutations in an anti-human CD3 single chain Fv antibody fragment that affect the yield on bacterial secretion but not the affinity, Protein Engineering, 1997, vol. 10, No. 4, pp. 445-453.
Klein et al., Progression of metastatic human prostate cancer to androgen independence in immunodeficient SDIC mice, 1997, Nature Medicine 3: 402-408.
Klein, et al., Progress in overcoming the chain association issue in bispecific heterodimeric IgG antibodies, mAbs, Nov.-Dec. 2012, vol. 4, issue 6, pp. 653-663, doi: 10.4161/mabs.21379, Epub Aug. 27, 2012.
Klinger, et al., Immunopharmacologic response of patients with B-lineage acute lymphoblastic leukemia to continuous infusion of T cell-engaging CD19/CD3-bispecific BiTE antibody blinatumomab, Blood, 2012, vol. 119, No. 26, pp. 6226-6233.
Koristka, et al., Retargeting of Human Regulatory T Cells by Single-Chain Bispecific Antibodies, The Journal of Immunology, 2012, vol. 188, pp. 1551-1558, www.jimmunol.org/cgi/doi/10.4049/jimmunol.1101760.
Kostelny, et al., Formation of a Bispecific Antibody by the Use of Leucine Zippers, The Journal of Immunology 1992, vol. 148, pp. 1547-1553.
Krah et al., "Single-domain antibodies for biomedical applications.", Immunopharmacol Immunotoxicol. 2016;38(1):21-8. doi: 10.3109/08923973.2015.1102934. Epub Nov. 9, 2015.
Krauss et al., Specificity grafting of human antibody frameworks selected from a phage display library: generation of a highly stable humanized anti-CD22 single-chain Fv fragment, 2003, Protein Engineering 16(10):753-759.
Krupka, et al., CD33 target validation and sustained depletion of AML blasts in long-term cultures by the bispecific T-cell-engaging antibody AMG 330, Blood, 2014, vol. 123, No. 3, pp. 356-365, Prepublished online Dec. 3, 2013; doi:10.1182/blood-2013-08-523548 & Data Supplement.
Kung, et al., Monoclonal Antibodies Defining Distinctive Human T Cell Surface Antigens, Science, 1979, vol. 206, pp. 347-349.
Kuppen, peter et al., The development and purification of a bispecific antibody for lymphokine-activated killer cell targeting against the rat colon carcinoma CC531., Cancer Immunol Immunother. Jun. 1993;36(6):403-8.

(56) References Cited

OTHER PUBLICATIONS

Labrijn, et al., Efficient generation of stable bispecific IgG1 by controlled Fab-arm exchange, www.pnas.org/cgi/doi/10.1073/pnas.1220145110 & Supporting Information.

Laszlo et al., Cellular determinants for preclinical activity of a novel CD33/CD3 bispecific T-cell engager (BiTE) antibody, AMG 330, against human AML, blood 2014 123: 554-561, Dec. 5, 2013.

Lau et al., Conjugation of Doxorubicin to monoclonal anti-carcinoembryonic antigen antibody via novel thiol-directed cross-linking regents, 1995, Bioorg-Med-Chem. 3(10):1299-1304.

Lau et al., Novel doxorubicin-monoclonal anti-carcinoembryonic antigen antibody immunoconjugate activity in vitro, 1995, Bioorg-Med-Chem. 3(10):1305-12.

Lazar Declaration, Dec. 27, 2010, pp. 1-4.

Lewis, et al., Generation of bispecific IgG antibodies by structure-based design of an orthogonal Fab interface, Nature Biotechnology, 2014, doi:10.1038/nbt.2797 & Supplemental Information.

Li, et al., Construction and characterization of a humanized anti-human CD3 monoclonal antibody 12F6 with effective immunoregulation functions, Immunology, 2005, vol. 116, pp. 487-498.

Lindhofer, et al., Preferential Species-Restricted Heavy/Light Chain Pairing in Rat/Mouse Quadromas: Implications for a Single-Step Purification of Bispecific Antibodies, The Journal of Immunology, 1995, vol. 155, pp. 219-225.

Ling, et al., Interspecies Scaling of Therapeutic Monoclonal Antibodies: Initial Look, J Clin Pharmacol, 2009, vol. 49, pp. 1382-1402, doi: 10.1177/0091270009337134.

Link, et al., Production and Characterization of a Bispecific IgG Capable of Inducing T-Cell-Mediated Lysis of Malignant B Cells, Blood, 1993, vol. 81, No. 12, pp. 3343-3349.

Linke, et al., Catumaxomab, Clinical development and future directions, mAbs, 2010, vol. 2, Issue 2, pp. 129-136.

Little, et al., Letter to the Editor, "Flawed TandAb production," Molecular Immunology, 2007, vol. 44, p. 3083.

Liu et al, Asymmetrical Fc Engineering Greatly Enhances Antibody-dependent Cellular Cytotoxicity (ADCC) Effector Function and Stability of the Modified Antibodies, J. Biol. Chem. 2014, 289: 3571-3590, Dec. 5, 2013.

Liu et al., Eradication of large colon tumor xenografts by targeted delivery of maytansinoids, 1996 Proc. Natl. Acad. Sci. USA 93:8618-8623.

Liu, et al., Crystallization of a Deglycosylated T Cell Receptor (TCR) Complexed with an Anti-TCR Fab Fragment, The Journal of Biological Chemistry, 1996, vol. 271, No. 52, pp. 33639-33646.

Lode et al., Targeted therapy with a novel enediyene antibiotic calicheamicins $O_1^I$ effectively suppress growth and dissemination of liver metastases in a syngeneic model of murine neuroblastoma, 1998, Cancer Res. 58:2928.

Löffler, et al., A recombinant bispecific single-chain antibody, CD19 x CD3, induces rapid, and high lymphoma-directed cytotoxicity by unstimulated T lymphocytes, Blood, 2000, vol. 95, No. 6, pp. 2098-2103.

Lu, et al., A Fully Human Recombinant IgG-like Bispecific Antibody to Both the Epidermal Growth Factor Receptor and the Insulin-like Growth Factor Receptor for Enhanced Antitumor Activity, The Journal of Biological Chemistry, 2005, vol. 280, No. 20, pp. 19665-19672.

Lu, et al., Di-diabody: a novel tetravalent bispecific antibody molecule by design, Journal of Immunological Methods, 2003, vol. 279, pp. 219-232.

Lu, et al., Fab-scFv fusion protein: an efficient approach to production of bispecific antibody fragments, Journal of Immunological Methods, 2002, vol. 267, pp. 213-226.

Lu, et al., The effect of variable domain orientation and arrangement on the antigen-binding activity of a recombinant human bispecific diabody, Biochemical and Biophysical Research Communications, 2004, vol. 318, pp. 507-513.

Lum, et al., The new face of bispecific antibodies: targeting cancer and much more, Experimental Hematology, 2006, vol. 34, pp. 1-6.

Lutterbuese, et al., AACR Poster, "Conversion of Cetuximab, Panitumumab, Trastuzumab and Omalizumab into T Cell-engaging BiTE Antibodies Creates Novel Drug Candidates of High Potency," 2008.

Lutterbuese, et al., T cell-engaging BiTE antibodies specific for EGFR potently eliminate KRAS- and BRAF-mutated colorectal cancer cells, PNAS Early Edition, 2010, www.pnas.org/cgi/doi/10.1073/pnas.1000976107 & Supporting Information.

Ma, et al., Expression and Characterization of a Divalent Chimeric Anti-Human CD3 Single Chain Antibody, Scand.J.Immunol, 1996, vol. 43, pp. 134-139.

Mabry, et al., A dual-targeting PDGFRβ/VEGF-A molecule assembled from stable antibody fragments demonstrates anti-angiogenic activity in vitro and in vivo, mAbs, 2010, vol. 2, Issue 1, pp. 20-34; www.landesbioscience.com/journals/mabs/article/10498 & Supplemental Information.

Mabry, et al., Engineering of stable bispecific antibodies targeting IL-17A and IL-23, Protein Engineering, Design & Selection, 2009, vol. 23, No. 3, pp. 115-127, doi:10.1093/protein/gzp073 & Supplementary Figures 1-8.

Mack, et al., A small bispecific antibody construct expressed as a functional single-chain molecule with high tumor cell cytotoxicity, Proc. Natl. Acad. Sci. USA, 1995, vol. 92, pp. 7021-7025.

Mack, et al., Biologic Properties of a Bispecific Single-Chain Antibody Directed Against 17-1A (EpCAM) and CD3—Tumor Cell-Dependent T Cell Stimulation and Cytotoxic Activity, The Journal of Immunology, 1997, vol. 158, pp. 3965-3970.

MacroGenics Factsheet, Dual Affinity Re-Targeting ("DART") Platform, 2010.

Mandler et al., Immunoconjugates of geldanamycin and anti-HER2 Monoclonal antibodies: antiproliferative activity on human breast carcinoma cell lines, 2000, J. Nat. Cancer Inst. 92(19):1573-1581.

Mandler et al., Modifications in synthesis strategy improve the yield and efficacy of geldanamycin-herceptin immunoconjugates, 2002, Bioconjugate Chem. 13:786-791).

Mandler et al., Synthesis and evaluation of antiproliferative activity of a geldanaymcin-herceptin™ immunoconjugates, 2000, Bioorganic & Med. Chem. Letters 10:1025-1028.

Mandy, et al., Effect of Reduction of Several Disulfide Bonds on the Properties and Recombination of Univalent Fragments of Rabbit Antibody, The Journal of Biological Chemistry, 1963, vol. 238, No. 1, pp. 206-213.

Mandy, et al., Recombination of Univalent Subunits Derived from Rabbit Antibody, The Journal of Biological Chemistry, 1961, vol. 236, No. 12, pp. 3221-3226.

Marks et al., By-passing immunization: building high affinity human antibodies by chain shuffling, 1992, Biotechnology 10:779-783.

Martin, et al., Generation of the Germline Peripheral B Cell Repertoire: VH81X-λ B Cells Are Unable to Complete All Developmental Programs, J. Immunol., 1998, vol. 160, pp. 3748-3758.

Martinez, et al., Characterization of a novel modification on IgG2 light chain: Evidence for the presence of O-linked mannosylation, J. Chromatogr. A, 2007, vol. 1156 pp. 183-187.

Marvin, Bispecific antibodies for dual-modality cancer therapy: killing two signaling cascades with one stone, Curr Opin Drug Discov Devel, 2006, vol. 9(2), pp. 184-193.

Marvin, et al., Recombinant approaches to IgG-like bispecific antibodies, Acta Pharmacologica Sinica, 2005, vol. 26 (6), pp. 649-658.

Mateo et al, Humanization of a mouse nonoclonal antibody that blocks the epidermal growth factor receptor: recovery of antagonistic activity, 1997, Immunotechnology, 3(1):71-81.

McPhee, Engineering human immunodeficiency virus 1 protease heterodimers as macromolecular inhibitors of viral maturation, Proc. Natl. Acad. Sci. USA, 1996, vol. 93, pp. 11477-11481.

Meijer, et al., Isolation of Human Antibody Repertoires with Preservation of the Natural Heavy and Light Chain Pairing, J. Mol. Biol., 2006, vol. 358, pp. 764-772.

Merchant, et al., An efficient route to human bispecific IgG, Nature Biotechnology, 1998, vol. 16, pp. 677-681.

Mertens, Nico, "Tribodies: Fab-scFv fusion proteins as a platform to create multi-functional pharmaceuticals.", SpringerLink 2011,135-149.

(56) References Cited

OTHER PUBLICATIONS

Metz, et al., Bispecifc antibody derivatives with restricted binding functionalities that are activated by proteolytic processing, Protein Engineering, Design & Selection, 2012, vol. 25, No. 10, pp. 571-580.
Metz, et al., Bispecific digoxigenin-binding antibodies for targeted payload delivery, PNAS, 2011, vol. 108, No. 20, pp. 8194-8199.
Michaelson et al., Anti-tumor activity of stability-engineered IgG-like bispecific antibodies targeting TRAIL-R2 and LTbetaR, [mAbs 1:2, 128-141; Mar./Apr. 2009]; Mar. 11, 2009.
Michalk et al., Characterization of a novel single-chain bispecific antibody for retargeting of T cells to tumor cells via the TCR co-receptor CD8., PLoS One. Apr. 21, 2014;9(4):e95517. doi: 10.1371/journal.pone.0095517.
Miller et al., Stability engineering of scFvs for the development of bispecific and multivalent antibodies, PEDS, 2010, vol. 23, No. 7, pp. 549-557 & Supplementary Data.
Miller, biogen idec Stability Engineering and Production of IgG-like Bispecifc Antibodies, AAPS National Biotechnology Conference, Jun. 24 to Jun. 27, 2007.
Milutinovic, et al., Sanford Burnham Medical Research Institute / AACR Poster, #4318, "Development of a novel dual agonist Surrobody™ that simultaneously activates both death receptors DR4 and DR5 and induces cancer cell death with high potency".
Mimoto et al., Engineered antibody Fc variant with selectively enhanced FcγRIIb binding over both FcγRIIa(R131) and FcγRIIa(H131)., Protein Eng Des Sel. Oct. 2013;26(10):589-98. doi: 10.1093/protein/gzt022. Epub Jun. 5, 2013.
Mimoto, et al., Novel asymmetrically engineered antibody Fc variant with superior FcγR binding affinity and specificity compared with afucosylated Fc variant, mAbs, 2013, vol. 5, Issue 2, pp. 229-236.
Modjtahedi et al, Phase I trial and tumour localization of the anti-EGFR monoclonal antibody ICR62 in head and neck or lung cancer, 1996, Br J Cancer, 73(2):228-35.
Modjtahedi et al, Targeting of cells expressing wild-type EGFR and type-III mutant EGFR (EGFRVIII) by anti-EGFR MaB ICR62: a two-pronged attack for tumor therapy, 2003, Int J Cancer, 105(2):273-80.
Modjtahedi et al., Antitumor activity of combinations of antibodies directed against different epitopes on the extracellular domain of the human EGF receptor, 1993, J. Cell Biophys. 1993, 22(1-3):129-46.
Modjtahedi et al., The human EGF receptor as a target for cancer therapy: six new rat mAbs against the receptor on the breast carcinoma MDA-MB 468, 1993, Br J Cancer. 1993, 67(2):247-53.
Mølhøj, et al., CD19-/CD3-bispecific antibody of the BiTE class is far superior to tandem diabody with respect to redirected tumor cell lysis, Molecular Immunology 2007, vol. 44, pp. 1935-1943.
Moore et al., Tuning T Cell Affinity Improves Efficacy and Safety of Anti-CD38 x Anti-CD3 Bispecific Antibodies in Monkeys—a Potential Therapy for Multiple Myeloma., 57th ASH Annual Meeting and Exposition (Dec. 5-8, 2015), American Society of Hematology, Orlando, Florida.
Moore, et al., A novel bispecific antibody format enables simultaneous bivalent and monovalent co-engagement of distinct target antigens., MAbs. Nov.-Dec. 2011; 3(6): 546-557; Published online Nov. 1, 2011. doi: 10.4161/mabs.3.6.18123.
Moore, et al., Application of dual affinity retargeting molecules to achieve optimal redirected T-cell killing of B-cell lymphoma, Blood, 2011, vol. 117, No. 17, pp. 4542-4551.
Moretti et al., BEAT® the bispecific challenge: a novel and efficient platform for the expression of bispecific IgGs. BMC Proceedings 2013 7(Suppl 6):O9.
Morrison, et al., News and Views: Two heads are better than one, Nature Biotechnology, 2007, vol. 25, No. 11, pp. 1233-1234.
Mosmann, 1983, Rapid colorimetric assay for cellular growth and survival: application to proliferation and cytotoxicity assays, J. Immunol. Methods 65:55-63.
Muda, et al., Therapeutic assessment of SEED: a new engineered antibody platform designed to generate mono and bispecific antibodies, Protein Engineering, Design & Selection, 2011, vol. 24, No. 5, pp. 447-454.
Muramatsu et al., Production and characterization of an active single-chain variable fragment antibody recognizing CD25., Cancer Lett. Jul. 28, 2005;225(2):225-36. Epub Jan. 23, 2005.
Murthy et al., Binding of an antagonistic monoclonal antibody to an intact and fragmented EGF-receptor polypeptide, 1987, Arch Biochem Biophys. 252(2):549-60.
Nagorsen, et al., Blinatumomab: A historical perspective, Pharmacology & Therapeutics, 2012, vol. 136, pp. 334-342, http://dx.doi.org/10.1016/j.pharmthera.2012.07.013.
Nelson, et al., Point of View: Antibody fragments—Hope and hype, mAbs, 2010, vol. 2, Issue 1, pp. 77-83.
Neville et al., Enhancement of immunotoxin efficacy by acid-cleavable cross-ling agents utilizing diphtheria toxin and toxin mutants, 1989, Biol. Chem. 264:14653-14661.
Nielsen, et al., Human T cells resistant to complement lysis by bivalent antibody can be efficiently lysed by dimers of monovalent antibody, Blood, 2002, vol. 100, No. 12, pp. 4067-4073.
Nisonoff, et al., Letters to the Editors: Recombination of a Mixture of Univalent Antibody Fragments of Different Specificity, Arch. Biochem. Biophys., 1961, pp. 460-462.
Nisonoff, et al., Quantitative Estimation of the Hybridization of Rabbit Antibodies, Nature, 1962, vol. 194, No. 4826, pp. 355-359.
North, et al., A New Clustering of Antibody CDR Loop Conformations, J. Mol. Biol., 2011, vol. 406, pp. 228-256, doi:10.1016/j.jmb.2010.10.030.
O'Connor et al., Humanization of an antibody against human protein C and calcium-dependence involving framework residues, 1998, Protein Eng 11:321-8.
Olafsen, et al., Covalent disulfide-linked anti-CEA diabody allows site-specific conjugation and radiolabeling for tumor targeting applications, Protein Engineering, Design & Selection, 2004, vol. 17, No. 1, pp. 21-27.
Ott et al., CTLA-4 and PD-1/PD-L1 blockade: new immunotherapeutic modalities with durable clinical benefit in melanoma patients., Clin Cancer Res. Oct. 1, 2013;19(19):5300-9. doi: 10.1158/1078-0432.CCR-13-0143.
Page et al., 1993, Intermantional. Journal of Oncology 3:473-476.
Panke, et al., Quantification of cell surface proteins with bispecific antibodies, Protein Engineering, Design & Selection, 2013, vol. 26, No. 10, pp. 645-654.
Pessano, et al., the T3/T cell receptor complex: antigenic distinction between the two 20-kd T3 (T3-δ and T3-ε) subunits, The EMBO Journal, 1985, vol. 4, No. 2, pp. 337-344.
Pettit et al., Antineoplastic agents 365. Dolastatin 10 SAR probes, 1998, Anti-Cancer Drug Design 13:243-277.
Pettit et al., Dolastatins 24. Synthesis of (-)-dolastatin 10.I X-ray molecular structure of N,N-dimethylvalyl-valyl-dolaisoleuine tert-butyl ester, 1996, J. Chem. Soc. Perkin Trans. 1 5:859-863.
Pettit et al., Specific activities of dolastatin 10 and peptide derivatives against Cryptococcus neoformans, 1998, Antimicrob. Agents Chemother. 42(11):2961-2965.
Pettit et al., Structure-activity studies with chiral isomers and with segments of the antimitotic marine peptide dolastation 10, 1989, J. Am. Chem. Soc. 111:5463-5465.
Pettit, et al., The dolastatins; 18: Sterospecific synthesis of dolaproine1, 1996, Synthesis 719-725.
Pichler et al., Differences of T-Cell Activation by the Anti-CD3 Antibodies Leu4 and BMA030, Mar. 30, 1987.
Potapov et al., Protein—Protein Recognition: Juxtaposition of Domain and Interface Cores in Immunoglobulins and Other Sandwich-like Proteins, J. Mol. Biol., 2004, vol. 342, pp. 665-679.
Presta et al., Humanization of an anti-vascular endothelial growth factor monoclonal antibody for the therapy of solid tumors and other disorders, 1997, Cancer Res.57(20):4593-9.
Queen et al., A humanized antibody that binds to the interleukin 2 receptor, 1989, Proc Natl Acad Sci, USA 86:10029-33.
Rader et al., A phage display approach for rapid antibody humanization: designed combinatorial V gene libraries, 1998, Proc. Natl. Acad. Sci. USA 95: 8910-8915.

(56) References Cited

OTHER PUBLICATIONS

Raghavan et al., Fc receptors and their interactios with immunoglobulins, 1996, Annu Rev Cell Dev Biol 12:181-220.
Rattel, et al., AACR Poster, "Validation of Cynomolgus Monkeys as Relevant Species for Safety Assessment of a Novel Human BiTE Antibody Platform for Cancer Therapy," 2010.
Reddy et al., Elimination of Fc receptor-dependent effector functions of a modified IgG4 monoclonal antibody to human CD4., J Immunol. Feb. 15, 2000;164(4):1925-33.
Reiter et al., Disulfide stabilization of antibody Fv: computer predictions and experimental evaluation, Protein Eng., 1995, vol. 8(12), pp. 1323-31.
Reiter et al., Engineering interchain disulfide bonds into conserved framework regions of Fv fragments: improved biochemical characteristics of recombinant immunotoxins containing disulfide-stabilized Fv, Protein Eng., 1994, vol. 7(5), pp. 697-704.
Remington's Pharmaceutical Sciences 16th edition, Osol, A. Ed. (1980) (Book Abstract).
Repp, et al., Combined Fc-protein- and Fc-glyco-engineering of scFv-Fc fusion proteins synergistically enhances CD16a binding but does not further enhance NK-cell mediated ADCC, Journal of Immunological Methods, 2011, vol. 373, Issues 1-2, pp. 67-78.
Ridgway, et al., 'Knobs-into-holes' engineering of antibody CH3 domains for heavy chain heterodimerization, Protein Engineering,1996, vol. 9, No. 7, pp. 617-621.
Riechmann et al., Reshaping human antibodies for therapy, 1988, Nature 332:323-329.
Riethmüller, Symmetry breaking: bispecific antibodies, the beginnings, and 50 years on, Cancer Immunity, 2012, vol. 12, p. 12, pp. 1-7.
Rodeck et al., Interactions between growth factor receptors and corresponding monoclonal antibodies in human tumors, 1987, J Cell Biochem. 35(4):315-20.
Roguska et al., Humanization of murine monoclonal antibodies through variable domain resurfacing, 1994, Proc. Natl. Acad. Sci. USA 91:969-973.
Roosnek, et al., Triggering T Cells by Otherwise Inert Hybrid Anti-CD3/Antitumor Antibodies Requires Encounter with the Specific Target Cell, J. Exp. Med., 1989, vol. 170, pp. 297-302.
Roque et al., Antibodies and genetically engineered related molecules: production and purification, 2004, Biotechnol. Prog. 20:639-654.
Rose, et al., Mutation of Y407 in the CH3 domain dramatically alters glycosylation and structure of human IgG, mAbs, 2013, vol. 5, Issue 2, pp. 219-228.
Rose, et al., Quantitative Analysis of the Interaction Strength and Dynamics of Human IgG4 Half Molecules by Native Mass Spectrometry, Structure, 2011, vol. 19, pp. 1274-1282.
Rosok et al., A combinatorial library strategy for the rapid humanization of anticarcinoma BR 96 Fab, 1996, J. Biol. Chem. 271(37): 22611-22618.
Rossi, et al., A new class of bispecific antibodies to redirect T cells for cancer immunotherapy, mAbs 2014, vol. 6, Issue 2, pp. 381-391.
Roux, et al., Structural analysis of the nurse shark (new) antigen receptor (NAR): Molecular convergence of NAR and unusual mammalian immunoglobulins, Proc. Natl. Acad. Sci. USA, 1998, vol. 95, pp. 11804-11809.
Rudnick, et al., Affinity and Avidity in Antibody-Based Tumor Targeting, Cancer Biotherapy and Radiopharmaceuticals, 2009, vol. 24, No. 2, pp. 155-161, doi: 10.1089/cbr.2009.0627.
Röthlisberger, et al., Domain Interactions in the Fab Fragment: A Comparative Evaluation of the Single-chain Fv and Fab Format Engineered with Variable Domains of Different Stability, J. Mol. Biol. , 2005, vol. 347, pp. 773-789.
Salmeron et al., A conformational epitope expressed upon association of CD3-epsilon with either CD3-delta or CD3-gamma is the main target for recognition by anti-CD3 monoclonal antibodies, Nov. 1, 1991.

Sancho et al., CD3- Surface Expression Is Required for CD4-p56ick-mediated Up-regulation of T Cell Antigen Receptor-CD3 Signaling in T Cells, Apr. 16, 1992.
Schaefer, et al., A Two-in-One Antibody against HER3 and EGFR Has Superior Inhibitory Activity Compared with Monospecific Antibodies, Cancer Cell, 2011, vol. 20, pp. 472-486 & Supplemental Information, pp. 1-21.
Schaefer, et al., Immunoglobulin domain crossover as a generic approach for the production of bispecific IgG antibodies, PNAS, 2011, vol. 108, No. 27, pp. 11187-11192.
Schlapschy, et al., Functional humanization of an anti-CD16 Fab fragment: obstacles of switching from murine λ to human λ or κ light chains, Protein Engineering, Design & Selection, 2009, vol. 22, No. 3, pp. 175-188, doi:10.1093/protein/gzn066.
Schlereth, et al., Eradication of Tumors from a Human Colon Cancer Cell Line and from Ovarian Cancer Metastases in Immunodeficient Mice by a Single-Chain Ep-CAM-/CD3-Bispecific Antibody Construct, Cancer Res 2005, vol. 65(7), pp. 2882-2889.
Schlereth, et al., T-cell activation and B-cell depletion in chimpanzees treated with a bispecific anti-CD19/anti-CD3 single-chain antibody construct, Cancer Immunol Immunother, 2006, vol. 55, pp. 503-514, doi:10.1007/s00262-005-0001-1.
Schoonjans, et al., Fab Chains As an Efficient Heterodimerization Scaffold for the Production of Recombinant Bispecific and Trispecific Antibody Derivatives, The Journal of Immunology, 2000, vol. 165, pp. 7050-7057.
Schroder et al., The Peptides, vol. pp. 76-136, 1965, Academic Press.
Senter et al, Proceedings of the American Association for Cancer Research, 2004, vol. 45, Abstract No. 623.
Senter, Potent antibody drug conjugates for cancer therapy, 2009, Current Opin. Chem. Biol. 13:235.
Sforzini et al., Targeting of saporin to Hodgkin's lymphoma cells by anti-CD30 and anti-CD25 bispecific antibodies., Br J Haematol. Sep. 1998;102(4):1061-8.
Shalaby, et al., Development of Humanized Bispecific Antibodies Reactive with Cytotoxic Lymphocytes and Tumor Cells Overexpressing the HER2 Protooncogene, J.Exp.Med., 1992, vol. 175, pp. 217-225.
Shan, et al., Characterization of scFv-Ig Constructs Generated from the Anti-CD20 mAb 1F5 Using Linker Peptides of Varying Lengths, J Immunol, 1999, vol. 162, pp. 6589-6595.
Shearman, et al., Construction, Expression and Characterization of Humanized Antibodies Directed Against the Human α/β T Cell Receptor, The Journal of Immunology, 1991, vol. 147, No. 12, pp. 4366-4373.
Shen, et al., Catumaxomab, a rat/murine hybrid trifunctional bispecific monoclonal antibody for the treatment of cancer, Curr Opin Mol Ther, 2008, vol. 10(3), pp. 273-84.
Shen, et al., Single Variable Domain-IgG Fusion: A Novel Recombinant Approach to Fc Domain-Containing Bispecific Antibodies, The Journal of Biological Chemistry, 2006, vol. 281, No. 16, pp. 10706-10714.
Shields et al., Lack of fucose on human IgG1 N-linked oligosaccharide improves binding to human FcγRlll and antibody-dependent cellular toxicity, 2002, J Biol Chem 277:26733-26740.
Shier et al., Identification of functional and structural amino-acid residues by parsimonious mutagenesis, 1995, Gene 169:147-155.
Shinkawa et al., The absence of fucose but not the presence of galactose or bisecting N-acetylglucosamine of human IgG1 complex-type oligosaccharides shows the critical role of enhancing antibody-dependent cellular cytotoxicity, 2003, J Biol Chem 278:3466-3473.
Skehan et al., Identification of functional and structural amino-acid residues by parsimonious mutagenesis, 1990, J. Natl. Cancer Inst. 82(13):1107-12.
Smith et al., Mouse model recapitulating human Fcγ receptor structural and functional diversity., Proc Natl Acad Sci U S A. Apr. 17, 2012;109(16):6181-6. doi: 10.1073/pnas.1203954109. Epub Apr. 2, 2012.
Soumyarani et al, Oxidatively modified high density lipoprotein promotes inflammatory response in human monocytes-macrophages by enhanced production of ROS, TNF-α, MMP-9, and

(56) References Cited

OTHER PUBLICATIONS

MMP-2., Mol Cell Biochem. Jul. 2012;366(1-2):277-85. doi: 10.1007/s11010-012-1306-y. Epub Apr. 17, 2012.
Spies et al., Alternative molecular formats and therapeutic applications for bispecific antibodies., Mol Immunol. Jan. 27, 2015. pii: S0161-5890(15)00005-X. doi: 10.1016/j.molimm.2015.01.003.
Spiess, et al., Bispecific antibodies with natural architecture produced by co-culture of bacteria expressing two distinct half-antibodies, Nature Biotechnology, 2013, doi:10.1038/nbt.2621 & Supplemental Information.
Spranger et al., Mechanism of tumor rejection with doublets of CTLA-4, PD-1/PD-L1, or IDO blockade involves restored IL-2 production and proliferation of CD8(+) T cells directly within the tumor microenvironment., J Immunother Cancer. Feb. 18, 2014;2:3. doi: 10.1186/2051-1426-2-3. eCollection 2014.
Stamova, Unexpected recombinations in single chain bispecific anti-CD3-anti-CD33 antibodies can be avoided by a novel linker module, Oct. 29, 2011.
Stanfield, et al., Maturation of Shark Single-domain (IgNAR) Antibodies: Evidence for Induced-fit Binding, J. Mol. Biol., 2007, vol. 367, pp. 358-372.
Stewart, et al., Recombinant CD36 inhibits oxLDL-induced ICAM-1-dependent monocyte adhesion., Mol Immunol. Feb. 2006;43(3):255-67.
Strop, P. et al., Generating Bispecific Human IgG1 and IgG2 Antibodies from Any Antibody Pair, J. Mol. Biol., 2012, doi:10.1016/j.jmb.2012.04.020.
Szymkowski et al., Creating the next generation of protein therapeutics through rational drug design, Current opinion in drug discovery & development, Sep. 1, 2005, p. 590, XP055354917, England.
Tabrizi et al., Biodistribution mechanisms of therapeutic monoclonal antibodies in health and disease., AAPS J. Mar. 2010;12(1):33-43. doi: 10.1208/s12248-009-9157-5. Epub Nov. 19, 2009.
Tan et al., "Superhumanized" antibodies: reduction of immunogenic potential by complementarity-determining region grafting with human germline sequences: application to an anti-CD28, 2002, J. Immunol. 169:1119-1125.
Tan, Philip, Presentation at PepTalk, Jan. 25, 2013, "Bi-specific ADAPTIR Molecule Targeting CD86 and Delivering Monomeric IL10 to Inhibit Antigen Presenting Cells".
Tang et al., Selection of linkers for a catalytic single-chain antibody using phage display technology., Journal of Biological Chemistry, American Society for Biochemistry and Molecular Biology, US, vol. 271, No. 26, Jan. 1, 1996, pp. 15682-9258.
Tarcsa et al, Chapter 10 Dual-Variable Domain Immunoglobulin (DVD-Ig™) Technology: A Versatile, Novel Format for the Next Generation of Dual-Targeting Biologics, Bispecific Antibodies 2011, pp. 171-185, 2011.
Teachey, et al., Cytokine release syndrome after blinatumomab treatment related to abnormal macrophage activation and ameliorated with cytokine-directed therapy, Blood, 2013, vol. 121, No. 26, pp. 5154-5157.
Tedgui, et al., Cytokines in atherosclerosis: pathogenic and regulatory pathways., Physiol Rev. Apr. 2006;86(2):515-81.
Terry M., "FDA Places Clinical Hold on AML Drug Co-Developed by Johnson & Johnson (JNJ) and Genmab A/S (Gen Co.)", Biospace 2016, Retrieved from the internet: https://www.biospace.com/article/fda-places-clinical-hold-on-aml-drug-co-developed-by-johnson-and-johnson-and-genmab-a-s-/.
Thompson, et al., An Anti-CD3 Single-chain Immunotoxin with a Truncated Diphtheria Toxin Avoids Inhibition by Pre-existing Antibodies in Human Blood, J.Biol.Chem., 1995, vol. 270, No. 47, pp. 28037-28041.
Thompson, et al., Improved binding of a bivalent single-chain immunotoxin results in increased efficacy for in vivo T-cell depletion, Protein Engineering, 2001, vol. 14, No. 12, pp. 1035-1041.
Thorne, et al., CD36 is a receptor for oxidized high density lipoprotein: implications for the development of atherosclerosis., FEBS Lett. Mar. 20, 2007;581(6):1227-32. Epub Feb. 28, 2007.
Thorpe et al., New coupling agents for the synthesis of immunotoxins containing a hindered disulfide bond with improved stability in Vivo, 1987, Cancer Res. 47:5924-5931.
Thotakura et al., Enzymatic deglycosylating of glycoproteins, 1987, Meth. Enzymol. 138:350.
Thurman et al., Detection of complement activation using monoclonal antibodies against C3d., J Clin Invest. May 2013;123(5):2218-30. doi: 10.1172/JCI65861. Epub Apr. 24, 2013.
Tomlinson et. al., Methods for generating multivalent and bispecific antibody fragments, 2000, Methods Enzymol. 326:461-479.
Topp, et al., Targeted Therapy With the T-Cell—Engaging Antibody Blinatumomab of Chemotherapy-Refractory Minimal Residual Disease in B-Lineage Acute Lymphoblastic Leukemia Patients Results in High Response Rate and Prolonged Leukemia-Free Survival, J Clin Oncol vol. 29, No. 18, pp. 2493-2498.
Traunecker, et al., Bispecific single chain molecules (Janusins) target cytotoxic lymphocytes on HIV infected cells, The EMBO Journal, 1991, vol. 1, No. 12, pp. 3655-3659.
Tsurushita et al., Humanization of monoclonal antibodies, 2004, Molecular Biology of B Cells 533-545.
Umaña et al., Engineered glycoforms of an antineuro-blastoma IgG1 with optimized antibody-dependent cellular cytotoxic activity, 1999, Nat Biotechnol 17:176-180.
Valliere-Douglass, et al., O-Fucosylation of an antibody light chain: Characterization of a modification occurring on an IgG1 molecule, Glycobiology, 2009, vol. 19, No. 2, pp. 144-152, doi:10.1093/glycob/cwn116.
Van Boxel, et al., Some lessons from the systematic production and structural analysis of soluble $\alpha\beta$ T-cell receptors, Journal of Immunological Methods, 2009, vol. 350, pp. 14-21.
Van Wauwe, et al., OKT3: A Monoclonal Anti-Human T Lymphoctye Antibody with Potent Mitogenic Properties, The Journal of Immunology, 1980, vol. 124, No. 6, pp. 2708-2713.
Verdier, et al., Determination of lymphocyte subsets and cytokine levels in Cynomolgus monkeys, Toxicology, 1995, vol. 105, pp. 81-90.
Verhoeyen et al., Reshaping human antibodies: grafting an antilysozyme activity, 1988, Science, 239:1534-1536.
Veri, et al., Therapeutic Control of B Cell Activation via Recruitment of Fc$\gamma$ Receptor llb (CD32B) Inhibitory Function With a Novel Bispecific Antibody Scaffold, Arthritis & Rheumatism, 2010, vol. 62, No. 7, pp. 1933-1943.
Vettermann, et al., Powered by pairing: The surrogate light chain amplifies immunoglobulin heavy chain signaling and pre-selects the antibody repertoire, Seminars in Immunology 18, 2006, pp. 44-55.
Von Kreudenstein, et al., Improving biophysical properties of a bispecific antibody scaffold to aid developability: Quality by molecular design, mAbs, 2013, vol. 5, Issue 5, pp. 1-9, http://dx.doi.org/10.4161/mabs.25632 & Supplemental Material.
Wang et al., Conserved amino acid networks involved in antibody variable domain interactions, Proteins, 2009, vol. 76, pp. 99-114.
Wang et al., Expression and characterization of recombinant soluble monkey CD3 molecules: mapping the FN18 polymorphic epitope, Molecular Immunology, 2004, vol. 40, pp. 1179-1188.
Wang, et al., A block in both early T lymphocyte and natural killer cell development in transgenic mice with high-copy numbers of the human CD3E gene, Proc. Natl. Acad. Sci. USA, 1994, vol. 91, pp. 9402-9406.
Ward, et al., Protein Engineering of Homodimeric Tyrosyl-tRNA Synthetase to Produce Active Heterodimers, The Journal of Biological Chemistry, 1986, vol. 261, No. 21, pp. 9576-9578.
Wawrzynczak et al., Methods for preparing immunotoxins: Effect of the linkage on activity and stability. In Immunoconjugates. Antibody Conjugates in Radio imaging and Therapy of Cancer. (C.-W. Vogel, editor). New York, Oxford University Press, pp. 28-55.
Weatherill, et al., Towards a universal disulphide stabilised single chain Fv format: importance of interchain disulphide bond location and vL-vH orientation, Protein Engineering, Design & Selection, 2012, vol. 25, No. 7, pp. 321-329.
Weiner, et al., The Role of T Cell Activation Bispecific Antibody Therapy in Anti-CD3 X Antitumor, Journal of Immunology, 1994, vol. 152, pp. 2385-2392.

(56) References Cited

OTHER PUBLICATIONS

Wesolowski, et al., Single domain antibodies: promising experimental and therapeutic tools in infection and immunity, Med Microbiol Immunol, 2009, vol. 198, pp. 157-174.

Whitlow, et al., An improved linker for single-chain Fv with reduced aggregation and enhanced proteolytic stability, Protein Engineering, 1993, vol. 6 , No. 8, pp. 989-995.

Wigginton et al., An immunoglobulin E-reactive chimeric human immunoglobulin G1 anti-idiotype inhibits basophil degranulation through cross-linking of FcεRl with FcγRllb., Clinical & Experimental Allergy, 38: 313-319.

Wong, et al., The Mechanism of Anti-CD3 Monoclonal Antibodies, Transplantation, 1990, vol. 50, No. 4, pp. 683-689.

Woods, et al., LC-MS characterization and purity assessment of a prototype bispecific antibody, mAbs, 2013, vol. 5, Issue 5, pp. 711-722, http://dx.doi.org/10.4161/mabs.25488.

Woyke et al., In vitro activities and postantifungal effects of the potent dolastation 10 derivative auristatin PHE, 2001, Antimicrob. Agents and Chemother. 45(12):3580-3584.

Wu et al, Molectular construction and optimization of anti-human IL-11α/β dual variable domain immunoglobulin (DVD-Ig™) molecules, [mAbs 1:4, 339-347; Jul./Aug. 2009]; Landes Bioscience, Apr. 10, 2009.

Wu et al, Simultaneous targeting of multiple disease mediators by a dual-variable-domain immunoglobulin, (DVD-Ig™) molecules, Jul.-Aug. 2009; 339-347, Oct. 14, 2007.

Wu et al., Humanization of a murine monoclonal antibody by simultaneous optimization of framework and CDR residues, 1999, J. Mol. Biol. 294:151-162.

Wu, et al., Multimerization of a chimeric anti-CD20 single-chain Fv-Fc fusion protein is mediated through variable domain exchange, Protein Engineering, 2001, vol. 14, No. 12, pp. 1025-1033.

Wucherpfennig, et al., Structural Biology of the T-cell Receptor: Insights into Receptor Assembly, Ligand Recognition, and Initiation of Signaling, Cold Spring Harb Perspect Biol 2010;2:a005140.

Xie, et al., A new format of bispecific antibody: highly efficient heterodimerization, expression and tumor cell lysis, Journal of Immunological Methods, 2005, vol. 296 , pp. 95-101, doi:10.1016/j.jim.2004.11.005.

Xu, et al., Combinatorial surrobody libraries, PNAS, 2008, vol. 105, No. 31, pp. 10756-10761.

Xu, et al., Rapid optimization and prototyping for therapeutic antibody-like molecules, mAbs, 2013, vol. 5, Issue 2, pp. 237-254.

Xu, et al., Surrobodies with Functional Tails, J. Mol. Biol., 2010, vol. 397, pp. 352-360.

Yang et al., Differential in vitro activation of CD8-CD4+ and CD4-CD8+ T lymphocytes by combinations of anti-CD2 and anti-CD3 antibodies, Apr. 1, 1988.

Yelton et al., Affinity maturation of the BR96 anti-carcinoma antibody by codon-based mutagenesis, 1995, J. Immunol. 155:1994-2004.

Yeung, et al., Engineering human IgG1 affinity to human neonatal Fc receptor: impact of affinity improvement on pharmacokinetics in primates, J Immunol. Jun. 15, 2009;182(12):7663-71. doi: 10.4049/jimmunol.0804182.

Yoshino et al., Upgrading of flow cytometric analysis for absolute counts, cytokines and other antigenic molecules of cynomolgus monkeys (*Macaca fascicularis*) by using anti-human cross-reactive antibodies, Exp. Anim., 2000, vol. 49(2), pp. 97-100.

Yu et al., The biosynthetic gene cluster of the maytansinoids antitumor agent ansamitocin from actinosynnema pretiosum, 2002, PNAS 99:7968-7973.

Zalevsky et al. "Enhanced antibody half-life improves in vivo activity." Nature Biotechnology, vol. 28, No. 2, Feb. 1, 2010, pp. 157-159.

Zamyatnin AA., Amino acid, peptide, and protein volume in solution., *Annu. Rev Biophys Bioeng*. 1984;13:145-65.

Zeidler, et al., The Fc-region of a new class of intact bispecific antibody mediates activation of accessory cells and NK cells and induces direct phagocytosis of tumour cells, Br J Cancer, 2000, vol. 83(2), pp. 261-266.

Zhu, et al., Identification of Heavy Chain Residues in a Humanized Anti-CD3 Antibody Important for Efficient Antigen Binding and T Cell Activation, The Journal of Immunology, 1995, vol. 155, pp. 1903-1910.

Zhu, et al., Remodeling domain interfaces to enhance heterodimer formation, Protein Science, 1997, vol. 6, pp. 781-788.

Zeibig et al., Effect of the oxLDL Binding Protein Fc-CD68 on Plaque Extension and Vulnerability in Atherosclerosis., Circulation Research 108: 695-703, 2011.

Zuo, et al., An efficient route to the production of an IgG-like bispecific antibody, Protein Engineering, 2000, vol. 13, No. 5, pp. 361-367.

Sun et al., Anti-CD20/CD3 T cell-dependent bispecific antibody for the treatment of B cell malignancies., Science Translational Medicine May 13, 2015: vol. 7, Issue 287, pp. 287ra70 DOI: 10.1126/scitranslmed.aaa480.

Capizzi et al., Curative chemotherapy for acute myeloid leukemia: the development of high-dose ara-C from the laboratory to bedside., Invest New Drugs. 1996;14(3):249-56.

Giles et al., Intravenous corticosteroids to reduce gemtuzumab ozogamicin infusion reactions. Ann Pharmacother. Sep. 2003;37(9):1182-5.

Duong et al., Targeted treatment of acute myeloid leukemia in older adults: role of gemtuzumab ozogamicin., Clin Interv Aging. 2009;4:197-205. Epub May 14, 2009.

Sun et al. , Preclinical Characterization of Combinability and Potential Synergy of Anti-CD20/CD3 T-Cell Dependent Bispecific Antibody with Chemotherapy and PD-1/PD-L1 Blockade., Blood 2016 128:4168.

Gantke et al., Trispecific antibodies for CD16A-directed NK cell engagement and dual-targeting of tumor cells., Protein Eng Des Sel. Sep. 1, 2017;30(9):673-684. doi: 10.1093/protein/gzx043.

Zhang et al., The development of bispecific antibodies and their applications in tumor immune escape., Experimental Hematology & Oncology20176:12.

Krupka et al.,Blockade of the PD-1/PD-L1 axis augments lysis of AML cells by the CD33/CD3 BiTE antibody construct AMG 330: reversing a T-cell-induced immune escape mechanism., Leukemia. Feb. 2016;30(2):484-91. doi: 10.1038/leu.2015.214. Epub Aug. 4, 2015.

Osada et al., CEA/CD3-bispecific T cell-engaging (BiTE) antibody-mediated T lymphocyte cytotoxicity maximized by inhibition of both PD1 and PD-L1., Cancer Immunol Immunother. Jun. 2015;64(6):677-88. doi: 10.1007/s00262-015-1671-y. Epub Mar. 6, 2015.

Masarova et al., Immune Checkpoint Approaches in AML and MDS: A Next Frontier?, The Journal of Targeted Therapies in Cancer, Mar. 6, 2017 (Mar. 6, 2017), XP002784099.

Scott et al., Antibody therapy of cancer., Nat Rev Cancer. Mar. 22, 2012;12(4):278-87. doi: 10.1038/nrc3236.

Clynes et al., Redirected T Cell Cytotoxicity in Cancer Therapy., Annu Rev Med. Jan. 27, 2019;70:437-450. doi: 10.1146/annurev-med-062617-035821. Epub Oct. 31, 2018.

Merchant et al., Monovalent antibody design and mechanism of action of onartuzumab, a MET antagonist with anti-tumor activity as a therapeutic agent., Proc Natl Acad Sci U S A. Aug. 6, 2013;110(32):E2987-96. doi: 10.1073/pnas.1302725110. Epub Jul. 23, 2013.

Fos et al., ICOS ligation recruits the p50alpha PI3K regulatory subunit to the immunological synapse., J Immunol. Aug. 1, 2008;181(3):1969-77.

Sanmamed et al., Agonists of Co-stimulation in Cancer Immunotherapy Directed Against CD137, OX40, GITR, CD27, CD28, and ICOS., Semin Oncol. Aug. 2015;42(4):640-55. doi: 10.1053/j.seminoncol.2015.05.014. Epub Jun. 11, 2015.

Vieira et al., ICOS-mediated signaling regulates cytokine production by human T cells and provides a unique signal to selectively control the clonal expansion of Th2 helper cells., Eur J Immunol. May 2004;34(5):1282-90.

(56) References Cited

OTHER PUBLICATIONS

Madrenas et al., Conversion of CTLA-4 from inhibitor to activator of T cells with a bispecific tandem single-chain Fv ligand., J Immunol. May 15, 2004;172(10):5948-56.

Yokosuka et al., Spatiotemporal basis of CTLA-4 costimulatory molecule-mediated negative regulation of T cell activation., Immunity. Sep. 24, 2010;33(3):326-39. doi: 10.1016/j.immuni.2010.09.006.

Carpenter et al., Activation of human B cells by the agonist CD40 antibody CP-870,893 and augmentation with simultaneous toll-like receptor 9 stimulation., J Transl Med. Nov. 11, 2009;7:93. doi: 10.1186/1479-5876-7-93.

Fan et al., Engagement of the ICOS pathway markedly enhances efficacy of CTLA-4 blockade in cancer immunotherapy., J Exp Med. Apr. 7, 2014;211(4):715-25. doi: 10.1084/jem.20130590. Epub Mar. 31, 2014.

Gilboa et al., Use of oligonucleotide aptamer ligands to modulate the function of immune receptors., Clin Cancer Res. Mar. 1, 2013;19(5):1054-62. doi: 10.1158/1078-0432.CCR-12-2067.

Uy et al., Preliminary Results of a Phase 1 Study of Flotetuzumab, a CD123 x CD3 Bispecific Dart® Protein, in Patients with Relapsed/Refractory Acute Myeloid Leukemia and Myelodysplastic Syndrome., Blood 2017 130:637.

Vey et al., Interim Results from a Phase 1 First-in-Human study of flotetuzumab, a CD123 x CD3 bispecific DART molecule, in AML/MDS., Annals of Oncology (2017) 28 (suppl_5): v355-v371. 10.1093/annonc/mdx373.

Ravandi et al., Complete Responses in Relapsed/Refractory Acute Myeloid Leukemia (AML) Patients on a Weekly Dosing Schedule of XmAb14045, a CD123 x CD3 T Cell-Engaging Bispecific Antibody: Initial Results of a Phase 1 Study., Blood 2018 132:763; doi: https://doi.org/10.1182/blood-2018-99-119786.

U.S. Appl. No. 12/875,015, 2011-0054151, U.S. Pat. No. 9,493,578, Granted, filed Sep. 2, 2010, Mar. 3, 2011, Nov. 15, 2016.

U.S. Appl. No. 15/279,266, 2017-0058053, Abandoned, filed Sep. 28, 2016, Mar. 2, 2017.

U.S. Appl. No. 16/539,986, Pending, filed Aug. 13, 2019.

U.S. Appl. No. 13/648,951, 2013-0171095, Published, filed Oct. 10, 2012, Jul. 4, 2013.

U.S. Appl. No. 13/194,904, 2012-0028304, U.S. Pat. No. 8,637,641, Granted, filed Jul. 29, 2011, Feb. 2, 2012, Jan. 28, 2014.

U.S. Appl. No. 14/165,487, 2014-0249297, U.S. Pat. No. 9,605,061, Granted, filed Jan. 27, 2014, Sep. 4, 2014, Mar. 28, 2017.

U.S. Appl. No. 15/444,087, 2017-0174757, To Be Aband, filed Feb. 27, 2017, Jun. 22, 2017.

U.S. Appl. No. 13/568,028, Abandoned, filed Aug. 6, 2012.

U.S. Appl. No. 14/853,622, 2016-0068588, Published, filed Sep. 14, 2015, Mar. 10, 2016.

U.S. Appl. No. 13/887,234, Abandoned, filed May 3, 2013.

U.S. Appl. No. 14/156,431, 2014-0212435, Abandoned, filed Jan. 15, 2014, Jul. 31, 2014.

U.S. Appl. No. 14/156,432, 2014-0212436, U.S. Pat. No. 9,738,722, Granted, filed Jan. 15, 2014, Jul. 31, 2014, Aug. 22, 2017.

U.S. Appl. No. 14/808,826, 2016-0060360, Abandoned, filed Jul. 24, 2015, Mar. 3, 2016.

U.S. Appl. No. 15/682,380, 2018-0201686, Abandoned, filed Aug. 21, 2017, Jul. 19, 2018.

U.S. Appl. No. 14/155,248, 2014-0322217, Allowed, filed Jan. 4, 2014, Oct. 30, 2014.

U.S. Appl. No. 14/155,334, 2014-0370013, Published, filed Jan. 14, 2014, Dec. 18, 2014.

U.S. Appl. No. 14/155,344, 2014-0294833, U.S. Pat. No. 9,701,759, Granted, filed Jan. 14, 2014, Oct. 2, 2014, Jul. 11, 2017.

U.S. Appl. No. 14/205,227, 2014-0294835, Abandoned, filed Mar. 11, 2014, Oct. 2, 2014.

U.S. Appl. No. 14/205,248, 2014-0288275, U.S. Pat. No. 9,650,446, Granted, filed Mar. 11, 2014, Sep. 25, 2014, May 16, 2017.

U.S. Appl. No. 15/589,908, 2018-0142040, Published, filed May 8, 2017, May 24, 2018.

U.S. Appl. No. 15/633,629, 2018-0215834, Allowed, filed Jun. 26, 2017, Aug. 2, 2018.

U.S. Appl. No. 14/214,418, 2014-0356381, U.S. Pat. No. 10,106,624, Granted, filed Mar. 14, 2014, Dec. 4, 2014, Oct. 23, 2018.

U.S. Appl. No. 16/137,389, Abandoned, filed Sep. 20, 2018.

U.S. Appl. No. 14/214,475, 2014-0294836, Allowed, filed Mar. 14, 2014, Oct 2, 2014.

U.S. Appl. No. 14/217,166, 2014-0294759, Allowed, filed Mar. 17, 2014, Oct. 2, 2014.

U.S. Appl. No. 14/200,652, 2014-0302064, Published, filed Mar. 7, 2014, Oct. 9, 2014.

U.S. Appl. No. 14/207,489, 2014-0377270, U.S. Pat. No. 10,131,710, Granted, filed Mar. 12, 2014, Dec. 25, 2014, Nov. 20, 2018.

U.S. Appl. No. 16/162,172, 2019-0270810, Published, filed Oct. 16, 2018, Sep. 5, 2019.

U.S. Appl. No. 14/200,821, 2014-0294823, U.S. Pat. No. 9,605,084, Granted, filed Mar. 7, 2014, Oct. 2, 2014, Mar. 28, 2017.

U.S. Appl. No. 14/216,705, 2014-0363426, Published, filed Mar. 17, 2014, Dec. 11, 2014.

U.S. Appl. No. 15/444,026, 2018-0037668, U.S. Pat. No. 10,287,364, Granted, Feb. 27, 2017, Feb. 8, 2018, May 14, 2019.

U.S. Appl. No. 16/364,093, Pending, filed Mar. 25, 2019.

U.S. Appl. No. 14/673,695, 2015-0307629, Transferred, filed Mar. 30, 2015, Oct. 29, 2015.

U.S. Appl. No. 15/786,252, 2018-0094079, Published, filed Oct. 17, 2017, Apr. 5, 2018.

U.S. Appl. No. 14/952,705, 2016-0176969, Abandoned, filed Nov. 25, 2015, Jun. 23, 2016.

U.S. Appl. No. 14/952,714, 2016-0229924, Published, filed Nov. 25, 2015, Aug. 11, 2016.

U.S. Appl. No. 15/141,350, 2016-0355608, U.S. Pat. No. 10,259,887, Granted, Apr. 28, 2016, Dec. 8, 2016, Apr. 16, 2019.

U.S. Appl. No. 15/945,679, 2018-0282432, Published, filed Apr. 4, 2018, Oct. 4, 2018.

U.S. Appl. No. 15/945,681, 2018-0223000, Published, filed Apr. 4, 2018, Aug. 9, 2018.

U.S. Appl. No. 16/354,058, 2019-0202938, Published, filed Mar. 14, 2019, Jul. 4, 2019.

U.S. Appl. No. 14/952,786, 2016-0215063, Transferred, filed Nov. 25, 2015, Jul. 28, 2016.

U.S. Appl. No. 15/779,325, Pending, filed May 25, 2018.

U.S. Appl. No. 14/757,809, 2016-0355600, U.S. Pat. No. 10,428,155, Allowed, filed Dec. 22, 2015, Dec. 8, 2016, Oct. 1, 2019.

U.S. Appl. No. 16/530,946, Pending, filed Aug. 2, 2019.

U.S. Appl. No. 15/063,441, 2017-0037131, U.S. Pat. No. 10,227,411, Granted, Mar. 7, 2016, Feb. 9, 2017, Mar. 12, 2019.

U.S. Appl. No. 16/297,255, 2019-0194325, Published, filed Mar. 8, 2019, Jun. 27, 2019.

U.S. Appl. No. 15/372,360, 2017-0320947, U.S. Pat. No. 10,227,410, Granted, filed Dec. 7, 2016, Nov. 9, 2017, Mar. 12, 2019.

U.S. Appl. No. 16/489,539, Pending, filed Aug. 28, 2019.

U.S. Appl. No. 15/623,314, 2018-0118836, Published, filed Jun. 14, 2017, May 3, 2018.

U.S. Appl. No. 16/435,373, Pending, filed Jun. 7, 2019.

U.S. Appl. No. 16/435,375, Pending, filed Jun. 7, 2019.

U.S. Appl. No. 15/611,361, 2017-0349660, Published, filed Jun. 1, 2017, Dec. 7, 2017.

U.S. Appl. No. 15/611,683, 2017-0349657, Published, filed Jun. 1, 2017, Dec. 7, 2017.

U.S. Appl. No. 15/636,590, 2018-0118827, U.S. Pat. No. 10,316,088, Granted, filed Jun. 28, 2017, May 3, 2018, Jun. 11, 2019.

U.S. Appl. No. 16/393,900, 2019-0248898, Published, filed Apr. 24, 2019, Aug. 15, 2019.

U.S. Appl. No. 15/185,958, 2017-0081420, U.S. Pat. No. 9,850,320, Granted, filed Jun. 17, 2016, Mar. 23, 2017, Dec. 26, 2017.

U.S. Appl. No. 15/186,167, 2017-0081424, U.S. Pat. No. 9,856,327, Granted, filed Jun. 17, 2016, Mar. 23, 2017, Jan. 2, 2018.

U.S. Appl. No. 15/691,665, 2018-0127501, Published, filed Aug. 30, 2017, May 10, 2018.

U.S. Appl. No. 16/184,895, 2019-0263909, Published, filed Nov. 8, 2018, Aug. 29, 2019.

(56) References Cited

OTHER PUBLICATIONS

U.S. Appl. No. 16/184,929, 2019-0270816, Published, filed Nov. 8, 2018, Sep. 5, 2019.
U.S. Appl. No. 16/375,777, Pending, filed Apr. 4, 2019.

* cited by examiner

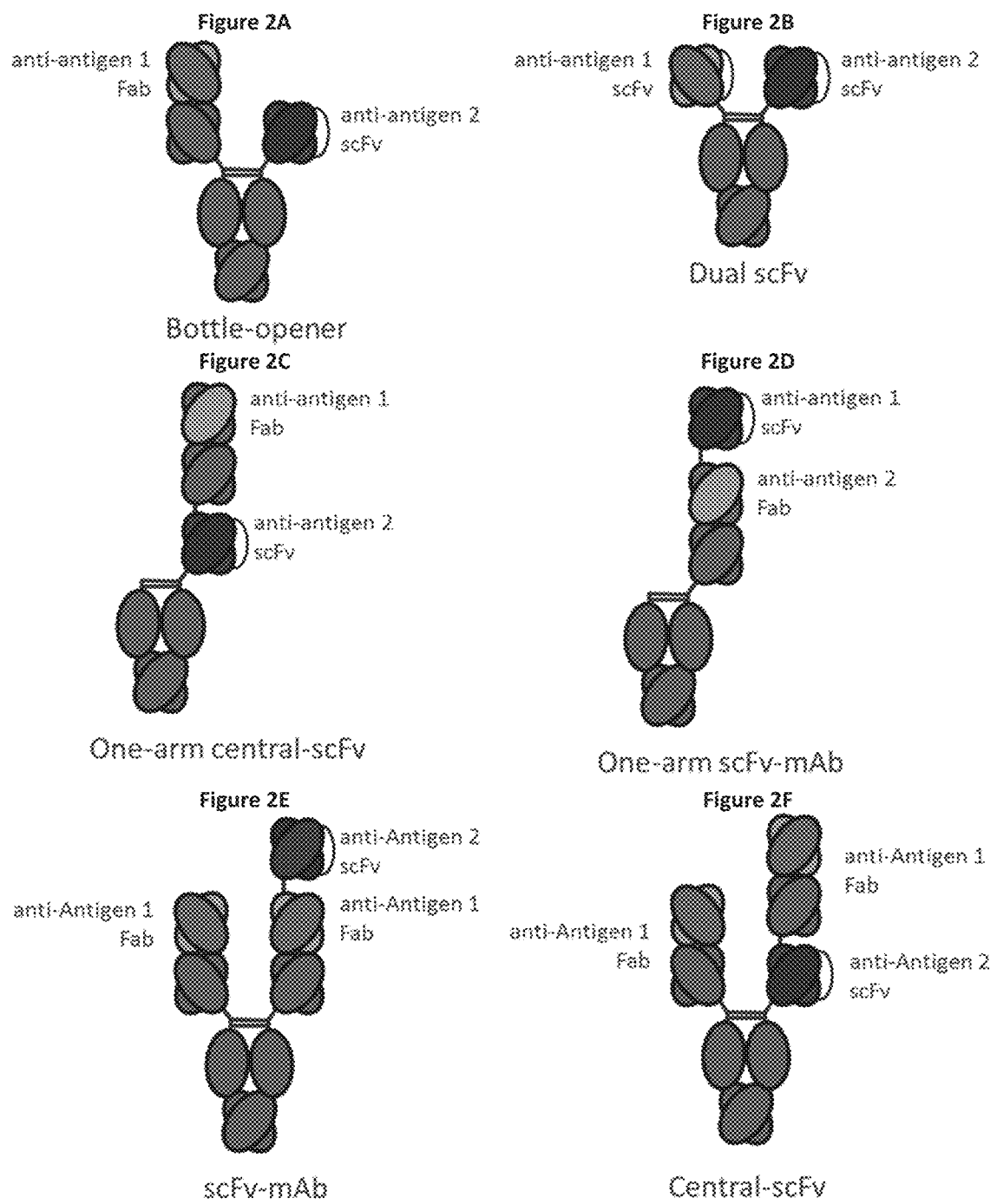

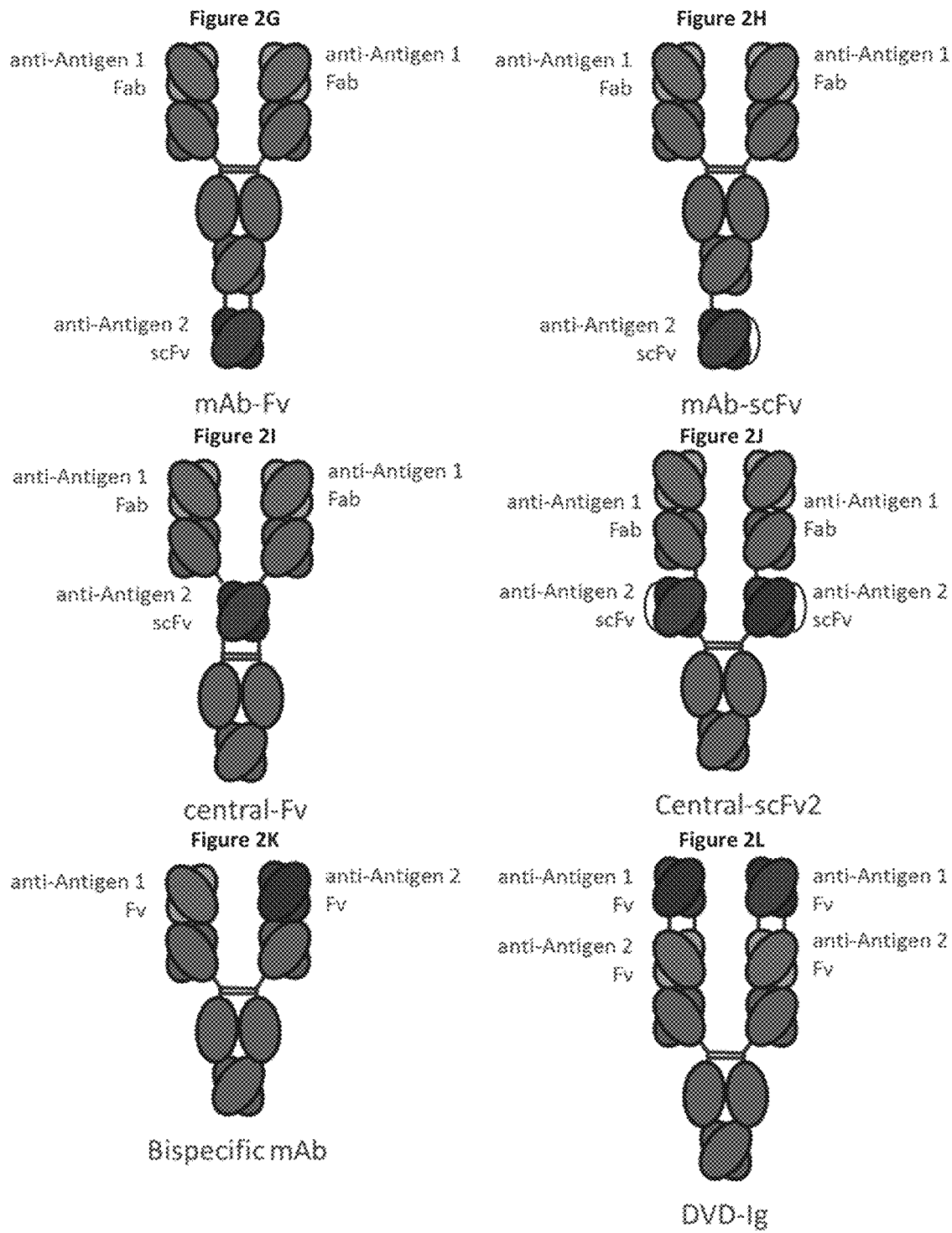

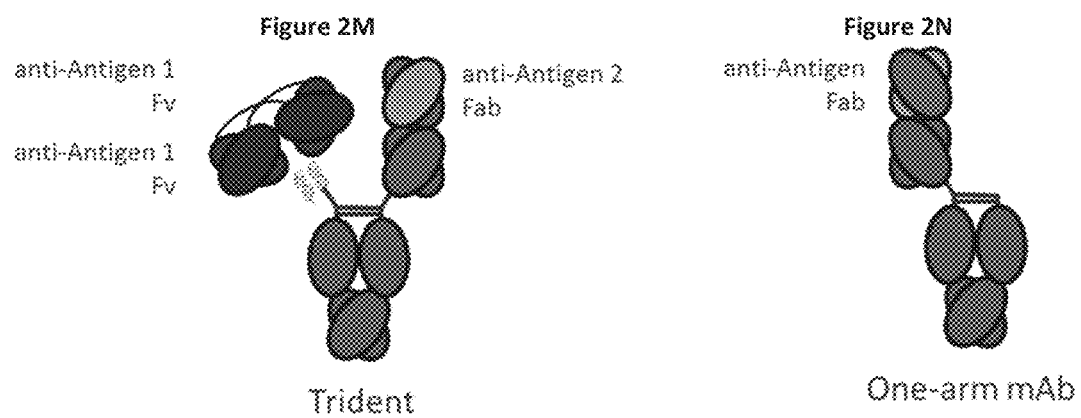

Figure 3A

>XENP023104 [ICOS]_H0.66_L0_Fab-IGG_L1.194_H1.279

| What | sequence | SEQ ID NO: |
|---|---|---|
| VH domain (Fab side) | QVQLVQSGAEVKKPGASVKVSCKASGYTFTGYYMHWVRQAPGQGLEWMGWINPHSGETIYAQKFQGRVTMTR DTSISTAYMELSSLRSEDTAVYYCARTYYDTSGYYHDAFDVWGQGTMVTVSS | 26643 |
| vhCDR1 (Fab side) | GYYMH | 26644 |
| vhCDR2 (Fab side) | WINPHSGETIYAQKFQG | 26645 |
| vhCDR3 (Fab side) | TYYDTSGYYHDAFDV | 26646 |
| VL domain (Fab side) | DIQMTQSPSSVSASVGDRVTITCRASQGISRLLAWYQQKPGKAPKLLIYVASSLQSGVPSRFSGSGSGTDFTLTISSLQ PEDFATYYCQQANSFPWTFGQGTKVEIK | 26658 |
| vlCDR1 (Fab side) | RASQGISRLLA | 26659 |
| vlCDR2 (fab side) | VASSLQS | 26660 |
| vlCDR3 (Fab side) | QQANSFPWT | 26661 |
| Full length Fab HC | QVQLVQSGAEVKKPGASVKVSCKASGYTFTGYYMHWVRQAPGQGLEWMGWINPHSGETIYAQKFQGRVTMTR DTSISTAYMELSSLRSEDTAVYYCARTYYDTSGYYHDAFDVWGQGTMVTVSSASTKGPSVFPLAPSSKSTSGGTAA LGCLVKDYFPEPVTVSWNSGALTSGVHTFPAVLQSSGLYSLSSVVTVPSSSLGTQTYICNVNHKPSDTKVDKKVEPKS CDKTHTCPPCPAPPVAGPSVFLFPPKPKDTLMISRTPEVTCVVVDVSHEDPEVKFNWYVDGVEVHNAKTKPREEEY NSTYRVVSVLTVLHQDWLNGKEYKCKVSNKALPAPIEKTISKAKGQPREPQVYTLPPSREEMTKNQVSLTCDVSGFYP SDIAVEWESDGQPENNYKTTPPVLDSDGSFFLYSKLTVDKSRWEQQGDVFSCSVLHEALHSHYTQKSLSLSPGK | 26642 |
| Full length Fab LC | DIQMTQSPSSVSASVGDRVTITCRASQGISRLLAWYQQKPGKAPKLLIYVASSLQSGVPSRFSGSGSGTDFTLTISSLQ PEDFATYYCQQANSFPWTFGQGTKVEIK/RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSFNRGEC | 26657 |

Figure 3B

| What | sequence | SEQ ID NO: |
|---|---|---|
| VH domain (scFv side) | EIVLTQSPATLSASPGERVTLTCRASQSVGNDVAWYQQKPGQAPRLLINYASHRYTGVPDRFTGSGYGTEFTLTISSV QSEDFGVYYCQQDFSSPRTFGGGTKVEIK | 26648 |
| vhCDR1 (scFv) | RASQSVGNDVA | 26651 |
| vhCDR2 (scFv) | YASHRYT | 26652 |
| vhCDR3 (scFv) | QQDFSSPRT | 26653 |
| VL domain (scFv side) | EVQLVESGGGLVKPGGSLRLSCVASGFTFSNYWMNWVRQAPGKGLEWVAEIRLYSNNYATHYAESVKGRFTISRD DSKSTLYLQMNNLKTEDTGVYYCTRYYGNYGGYFDVWGRGTLVTVSS | 26649 |
| vlCDR1 (scFv) | NYWMN | 26654 |
| vlCDR2 (scFv) | EIRLYSNNYATHYAESVKG | 26655 |
| vlCDR3 (scFv) | YYGNYGGYFDV | 26656 |
| scFv chain | EIVLTQSPATLSASPGERVTLTCRASQSVGNDVAWYQQKPGQAPRLLINYASHRYTGVPDRFTGSGYGTEFTLTISSV QSEDFGVYYCQQDFSSPRTFGGGTKVEIK/GKPGSGKPGSGKPGSGKPGS/EVQLVESGGGLVKPGGSLRLSCVASG FTFSNYWMNWVRQAPGKGLEWVAEIRLYSNNYATHYAESVKGRFTISRDDSKSTLYLQMNNLKTEDTGVYYCTRYY GNYGGYFDVWGRGTLVTVSS | |
| Full length scFv HC | EIVLTQSPATLSASPGERVTLTCRASQSVGNDVAWYQQKPGQAPRLLINYASHRYTGVPDRFTGSGYGTEFTLTISSV QSEDFGVYYCQQDFSSPRTFGGGTKVEIK/GKPGSGKPGSGKPGSGKPGS/EVQLVESGGGLVKPGGSLRLSCVASG FTFSNYWMNWVRQAPGKGLEWVAEIRLYSNNYATHYAESVKGRFTISRDDSKSTLYLQMNNLKTEDTGVYYCTRYY GNYGGYFDVWGRGTLVTVSS/EPKSSDKTHTCPPCPAPPVAGPSVFLFPPKPKDTLMISRTPEVTCVVVDVSHEDPE VKFNWYVDGVEVHNAKTKPREEQYNSTYRVVSVLTVLHQDWLNGKEYKCKVSNKALPAPIEKTISKAKGQPREPQV YTLPPSREQMTKNQVKLTCLVKGFYPSDIAVEWESNGQPENNYKTTPPVLDSDGSFFLYSKLTVDKSRWQQGNVFS CSVLHEALHSHYTQKSLSLSPGK | 26647 |

Figure 4A

| Monomer 1 | Monomer 2 |
|---|---|
| F405A | T394F |
| S364D | Y349K |
| S364E | L368K |
| S364E | Y349K |
| S364F | K370G |
| S364H | Y349K |
| S364H | Y349T |
| S364Y | K370G |
| T411K | K370E |
| V397S/F405A | T394F |
| K370R/T411K | K370E/T411E |
| L351E/S364D | Y349K/L351K |
| L351E/S364E | Y349K/L351K |
| L351E/T366D | L351K/T366K |
| P395T/V397S/F405A | T394F |
| S364D/K370G | S364Y/K370R |
| S364D/T394F | Y349K/F405A |
| S364E/F405A | Y349K/T394F |
| S364E/F405S | Y349K/T394Y |
| S364E/T411E | Y349K/D401K |
| S364H/D401K | Y349T/T411E |
| S364H/F405A | Y349T/T394F |
| S364H/T394F | Y349T/F405A |
| Y349C/S364E | Y349K/S354C |
| L351E/S364D/F405A | Y349K/L351K/T394F |
| L351K/S364H/D401K | Y349T/L351E/T411E |
| S364E/T411E/F405A | Y349K/T394F/D401K |
| S364H/D401K/F405A | Y349T/T394F/T411E |
| S364H/F405A/T411E | Y349T/T394F/D401K |

Figure 4B

| Monomer 1 | Monomer 2 |
|---|---|
| K370E/T411D | T411K |
| L368E/K409E | L368K |
| Y349T/T394F/S354C | S364H/F405A/Y349C |
| T411E | D401K |
| T411E | D401R/T411R |
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |
| L368E | S364K/K409V |
| L368D | S364K |
| L368D/K370S | S364K |
| L368D/K370S | S364K/E357L |
| L368D/K370S | S364K/E357Q |
| T411E/K360E/Q362E | D401K |
| K370S | S364K |
| L368E/K370S | S364K/E357Q |
| K370S | S364K/E357Q |
| T411E/K360D | D401K |
| T411E/K360E | D401K |
| T411E/Q362E | D401K |
| T411E/N390D | D401K |
| T411E | D401K/Q347K |
| T411E | D401K/Q347R |
| T411E/K360D/Q362E | D401K |

Figure 4C

| Monomer 1 | Monomer 2 |
|---|---|
| K392D/K409D | E356K/D399K |
| K370D/K392D/K409D | E356K/E357K/D399K |
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| I199T/N203D/K247Q/R355Q/Q419E/K447_ | Q196K/I199T/P217R/P228R/N276K |
| I199T/N203D/K247Q/R355Q/Q419E/K447_ | Q196K/I199T/N276K |
| I199T N203D K274Q R355Q N384S K392N V397M Q419E DEL447 | |
| N208D Q295E N384D Q418E N421D | |
| N208D Q295E Q418E N421D | |
| Q196K I199T P217R P228R N276K | |
| Q196K I199T N276K | |
| E269Q E272Q E283Q E357Q | |
| E269Q E272Q E283Q | |
| E269Q E272Q | |
| E269Q E283Q | |
| E272Q E283Q | |
| E269Q | |

Figure 4D

| Monomer 1 | Monomer 2 |
|---|---|
| T411E/K360E/N390D | D401K |
| T411E/Q362E/N390D | D401K |
| T411E/Q347R | D401K/K360D |
| T411E/Q347R | D401K/K360E |
| T411E/K360 | D401K/Q347K |
| T411E/K360D | D401K/Q347R |
| T411E/K360E | D401K/Q347K |
| T411E/K360E | D401K/Q347R |
| T411E/S364K | D401K/K370S |
| T411E/K370S | D401K/S364K |
| Q347E | E357Q |
| Q347E | E357Q/Q362K |
| K360D/Q362E | Q347R |
| K360D/Q362E | D401K |
| K360D/Q362E | Q347R/D401K |
| K360E/Q362E | Q347R |
| K360E/Q362E | D401K |
| K360E/Q362E | Q347R/D401K |
| Q362E/N390D | D401K |
| Q347E/K360D | D401N |
| K360D | Q347R/N390K |
| K360D | N390K/D401N |
| K360E | Y349H |
| K370S/Q347E | S364K |
| K370S/E357L | S364K |
| K370S/E357Q | S364K |
| K370S/Q347E/E357L | S364K |
| K370S/Q347E/E357Q | S364K |

Figure 4E

| Monomer 1 | Monomer 2 |
|---|---|
| L368D/K370S/Q347E | S364K |
| L368D/K370S/E357L | S364K |
| L368D/K370S/E357Q | S364K |
| L368D/K370S/Q347E/E357L | S364K |
| L368D/K370S/Q347E/E357Q | S364K |
| L368E/K370S/Q347E | S364K |
| L368E/K370S/E357L | S364K |
| L368E/K370S/E357Q | S364K |
| L368E/K370S/Q347E/E357L | S364K |
| L368E/K370S/Q347E/E357Q | S364K |
| L368D/K370T/Q347E | S364K |
| L368D/K370T/E357L | S364K |
| L368D/K370T/E357Q | S364K |
| L368D/K370T/Q347E/E357L | S364K |
| L368D/K370T/Q347E/E357Q | S364K |
| L368E/K370T/Q347E | S364K |
| L368E/K370T/E357L | S364K |
| L368E/K370T/E357Q | S364K |
| L368E/K370T/Q347E/E357L | S364K |
| L368E/K370T/Q347E/E357Q | S364K |
| T411E/Q362E | D401K/T411K |
| T411E/N390D | D401K/T411K |
| T411E/Q362E | D401R/T411R |
| T411E/N390D | D401R/T411R |
| Y407T | T366Y |
| F405A | T394W |
| T366Y/F405A | T394W/Y407T |
| Y407A | T366W |
| T366S/L368A/Y407V | T366W |

Figure 4F

| Monomer 1 | Monomer 2 |
|---|---|
| T366S/L368A/Y407V/Y349C | T366W/S354C |
| K392D/K409D | E356K/D399K |
| K370D/K392D/K409D | E356K/E357K/D399K |
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| I199T/N203D/K247Q/R355Q/Q419E/K447_ | Q196K/I199T/P217R/P228R/N276K |
| I199T/N203D/K247Q/R355Q/Q419E/K447_ | Q196K/I199T/N276K |
| I199T N203D K274Q R355Q N384S K392N V397M Q419E DEL447 | |
| N208D Q295E N384D Q418E N421D | |
| Q295E N384D Q418E N421D | |
| N208D Q295E Q418E N421D | |
| Q295E Q418E N421D | |
| Q196K I199T P217R P228R N276K | |
| Q196K I199T N276K | |
| E269Q E272Q E283Q E357Q | |
| E269Q E272Q E283Q | |
| E269Q E272Q | |
| E269Q E283Q | |
| E272Q E283Q | |
| E269Q | |

Figure 5

| Variant constant region | Substitutions |
|---|---|
| pI_ISO(-) | I199T N203D K274Q R355Q N384S K392N V397M Q419E DEL447 |
| pI_(-)_isosteric_A | N208D Q295E N384D Q418E N421D |
| pI_(-)_isosteric_A-Fc only | Q295E N384D Q418E N421D |
| pI_(-)_isosteric_B | N208D Q295E Q418E N421D |
| pI_(-)_isosteric_B-Fc only | Q295E Q418E N421D |
| pI_ISO(+RR) | Q196K I199T P217R P228R N276K |
| pI_ISO(+) | Q196K I199T N276K |
| pI_(+)_isosteric_A | E269Q E272Q E283Q E357Q |
| pI_(+)_isosteric_B | E269Q E272Q E283Q |
| pI_(+)_isosteric_E269Q/E272Q | E269Q E272Q |
| pI_(+)_isosteric_E269Q/E283Q | E269Q E283Q |
| pI_(+)_isosteric_E272Q/E283Q | E272Q E283Q |
| pI_(+)_isosteric_E269Q | E269Q |

Figure 6
Ablation variants

| Variant | Variant(s), cont. |
|---|---|
| G236R | P329K |
| S239G | A330L |
| S239K | A330S/P331S |
| S239Q | I332K |
| S239R | I332R |
| V266D | V266D/A327Q |
| S267K | V266D/P329K |
| S267R | S267R/A327Q |
| H268K | S267R/P329K |
| E269R | G236R/L328R |
| 299R | E233P/L234V/L235A/G236del/S239K |
| 299K | E233P/L234V/L235A/G236del/S267K |
| K322A | E233P/L234V/L235A/G236del/S239K/A327G |
| A327G | E233P/L234V/L235A/G236del/S267K/A327G |
| A327L | E233P/L234V/L235A/G236del |
| A327N | S239K/S267K |
| A327Q | 267K/P329K |
| L328E | |
| L328R | |
| P329A | |
| P329H | |

Figure 7A useful combinations

| scFv monomer (+) | Fab monomer (-) |
|---|---|
| Heterodimer pI variants S364K/E357Q | Heterodimerization pI variants L368D/K370S |
| Optional scFv charged linker including but not limited to (GKPGS)$_4$ (SEQ ID NO: 26209) | Isosteric pI substitutions N208D/Q295E/N384D/Q418E/N421D |
| FcKO E233P/L234V/L235A/G236del/S267K | FcKO E233P/L234V/L235A/G236del/S267K |
| ± 428L/434S for FcRn | ± 428L/434S for FcRn |
| scFv of ABD of either ICOS or a checkpoint inhibitor | Fv/Fab of the other of ABD of either ICOS or a checkpoint inhibitor |

Figure 7B

| scFv monomer | Fab monomer |
|---|---|
| Heterodimer pI variants S364K/E357Q | Heterodimerization pI variants L368D/K370S |
| Optional scFv charged linker including, but not limited to (GKPGS)$_4$ (SEQ ID NO: 26209) | pI substitutions I199T N203D K274Q R355Q Q419E K447del |
| FcKO E233P/L234V/L235A/G236del/S267K | FcKO E233P/L234V/L235A/G236del/S267K |
| ± 428L/434S for FcRn (optional) | ± 428L/434S for FcRn (optional) |
| scFv of either ICOS or a checkpoint inhibitor | Fv/Fab of the other of ABD of either ICOS or a checkpoint inhibitor |

Figure 8A

Positive charged scFv linkers

| Name | Sequence | Length | Charge | SEQ ID NO: |
|---|---|---|---|---|
| Gly-Ser 15 | GGGGSGGGGSGGGGS | 15 | 0 | 26200 |
| Whitlow linker | GSTSGSGKPGSGEGSTKG | 18 | +1 | 26201 |
| 6paxA_1 (+A) | IRPRAIGGSKPRVA | 14 | +4 | 26202 |
| +B | GKGGSGKGGSGKGGS | 15 | +3 | 26203 |
| +C | GGKGSGGKGSGGKGS | 15 | +3 | 26204 |
| +D | GGGKSGGGKSGGGKS | 15 | +3 | 26205 |
| +E | GKGKSGKGKSGKGKS | 15 | +6 | 26206 |
| +F | GGGKSGGKGSGKGGS | 15 | +3 | 26207 |
| +G | GKPGSGKPGSGKPGS | 15 | +3 | 26208 |
| +H | GKPGSGKPGSGKPGSGKPGS | 20 | +4 | 26209 |
| +I | GKGKSGKGKSGKGKSGKGKS | 20 | +8 | 26210 |

Negative charged scFv linkers

| Name | Sequence | Length | Charge | SEQ ID NO: |
|---|---|---|---|---|
| Gly-Ser 15 | GGGGSGGGGSGGGGSGGGGS | 20 | 0 | 26211 |
| 3hsc_2 (-A) | STAGDTHLGGEDFD | 14 | -4 | 26212 |
| -B | GEGGSGEGGSGEGGS | 15 | -3 | 26213 |
| -C | GGEGSGGEGSGGEGS | 15 | -3 | 26214 |
| -D | GGGESGGGESGGGES | 15 | -3 | 26215 |
| -E | GEGESGEGESGEGES | 15 | -6 | 26216 |
| -F | GGGESGGEGSGEGGS | 15 | -3 | 26217 |
| -G | GEGESGEGESGEGESGEGES | 20 | -8 | 26218 |

Figure 8B scFv Linkers

| Sequence | SEQ ID |
|---|---|
| GGGGSGGGGSGGGGS | (SEQ ID NO:26219) |
| GGGGSGGGGSGGGGSGGGGS | (SEQ ID NO:26220) |
| GSTSGSGKPGSGEGSTKG | (SEQ ID NO:26221) |
| PRGASKSGSASQTGSAPGS | (SEQ ID NO:26222) |
| GTAAAGAGAAGGAAAGAAG | (SEQ ID NO:26223) |
| GTSGSSGSGSGGSGSGGGG | (SEQ ID NO:26224) |
| GKPGSGKPGSGKPGSGKPGS | (SEQ ID NO:26225) |

Figure 9A

Bottle opener backbone 1

Fab side heavy chain (SEQ ID NO: 28669)

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK scFv heavy chain (SEQ ID NO: 28670)

EPKSSDKTHTCPPCPAPPVAGPSVFLFPPKPKDTLMISRTPEVTCVVVDVKHEDPEVKFNWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK constant light chain (SEQ ID NO: 28671)

RTVAAPSVFIFPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Bottle opener backbone 2

Fab side heavy chain (SEQ ID NO: 28672)

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK scFv heavy chain (SEQ ID NO: 28673)

EPKSSDKTHTCPPCPAPPVAGPSVFLFPPKPKDTLMISRTPEVTCVVVDVKHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQVKLTCLVK
GFYPSDIAVEWESNGQPENNYKTTPPVLDSDGSFFLYSKLTVDKSRWQQGNVFSCSVMHEALHNHYTQKSLSLSPGK

Figure 9B

Bottle opener backbone 3

```
Fab side heavy chain (SEQ ID NO: 28674)
```

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCEVSGFYPSDIAVEWESDGQPENNYKTTPPVLDSDGSFFLYSKLTVDKSRWEQGDVFSCS
VMHEALHNHYTQKSLSLSPGK

```
scFv heavy chain (SEQ ID NO: 28675)
```

EPKSSDKTHTCPPCPAPPVAGPSVFLFPPKPKDTLMISRTPEVTCVVVDVKHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQVKLTCLVK
GFYPSDIAVEWESNGQPENNYKTTPPVLDSDGSFFLYSKLTVDKSRWQQGNVFSCSVMHEALHNHYTQKSLSLSPGK

Bottle opener backbone 4

```
Fab side heavy chain (SEQ ID NO: 28676)
```

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTENEVSLTCLVKSGFYPSDIAVEWESDGQPENNYKTTPPVLDSDGSFFLYSKLEVDKSRWEQGDVFSC
SVMHEALHNHYTQKSLSLSPGK

```
scFv heavy chain (SEQ ID NO: 28677)
```

EPKSSDKTHTCPPCPAPPVAGPSVFLFPPKPKDTLMISRTPEVTCVVVDVKHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQVSLTCLVK
GFYPSDIAVEWESNGQPENNYKTTPPVLDSKGSFFLYSKLTVDKSRWQQGNVFSCSVMHEALHNHYTQKSLSLSPGK

Bottle opener backbone 5 (356D/358L allotype)

```
Fab side heavy chain (SEQ ID NO: 28678)
```

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSRDELTKNQVSLTCDVSGFYPSDIAVEWESDGQPENNYKTTPPVLDSDGSFFLYSKLTVDKSRWEQGDVFSCS
VMHEALHNHYTQKSLSLSPGK

```
scFv heavy chain (SEQ ID NO: 28679)
```

EPKSSDKTHTCPPCPAPPVAGPSVFLFPPKPKDTLMISRTPEVTCVVVDVKHEDPEVKFNWYVDGVEVHNAKTKPRE
EQYASTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

Figure 9C

Bottle opener backbone 6

```
Fab side heavy chain (SEQ ID NO: 28680)
```

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYASTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

```
scFv heavy chain (SEQ ID NO: 28681)
```

EPKSSDKTHTCPPCPAPPVAGPSVFLFPPKPKDTLMISRTPEVTCVVVDVKHEDPEVKFNWYVDGVEVHNAKTKPRE
EQYASTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

Bottle opener backbone 7

```
Fab side heavy chain (SEQ ID NO: 28682)
```

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYSSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

```
scFv heavy chain (SEQ ID NO: 28683)
```

EPKSSDKTHTCPPCPAPPVAGPSVFLFPPKPKDTLMISRTPEVTCVVVDVKHEDPEVKFNWYVDGVEVHNAKTKPRE
EQYSSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

Bottle opener backbone 8

```
Fab side heavy chain (SEQ ID NO: 28684)
```

ASTKGPSVFPLAPCSRSTSESTAALGCLVKDYFPEPVTVSWNSGALTSGVHTFPAVLQSSGLYSLSSVVTVPSSSLG
TKTYTCNVDHKPSDTKVDKRVESKYGPPCPPCPAPEFLGGPSVFLFPPKPKDTLMISRTPEVTCVVVDVKQEDPEVQ
FNWYVDGVEVHNAKTKPREEEFNSTYRVVSVLTVLHQDWLNGKEYKCKVSNKGLPSSIEKTISKAKGQPREPQVYTL
PPSQEEMTKNQVSLTCDVSGFYPSDIAVEWESDGQPENNYKTTPPVLDSDGSFFLYSKLTVDKSRWEEGDVFSCSVM
HEALHNHYTQKSLSLSLGK

```
scFv heavy chain (SEQ ID NO: 28685)
```

ESKYGPPCPPCPAPEFLGGPSVFLFPPKPKDTLMISRTPEVTCVVVDVKQEDPEVQFNWYVDGVEVHNAKTKPREEQ
FNSTYRVVSVLTVLHQDWLNGKEYKCKVSNKGLPSSIEKTISKAKGQPREPQVYTLPPSQEQMTKNQVKLTCLVKGF
YPSDIAVEWESNGQPENNYKTTPPVLDSDGSFFLYSKLTVDKSRWQEGNVFSCSVMHEALHNHYTQKSLSLSLGK

Figure 9D

Bottle opener backbone 9

Fab side heavy chain (SEQ ID NO: 28686)

ASTKGPSVFPLAPCSRSTSESTAALGCLVKDYFPEPVTVSWNSGALTSGVHTFPAVLQSSGLYSLSSVVTVPSSNFG
TQTYTCNVDHKPSDTKVDKTVERKCCVECPPCPAPPVAGPSVFLFPPKPKDTLMISRTPEVTCVVVDVSHEDPEVQF
NWYVDGVEVHNAKTKPREEEFNSTFRVVSVLTVVHQDWLNGKEYKCKVSNKGLPAPIEKTISKTKGQPREPQVYTLP
PSREEMTKNQVSLTCDVSGFYPSDIAVEWESDGQPENNYKTTPPMLDSDGSFFLYSKLTVDKSRWEQGDVFSCSVMH
EALHNHYTQKSLSLSPGK scFv heavy chain (SEQ ID NO: 28687)

ERKCSVECPPCPAPPVAGPSVFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPPSREQMTKNQVKLTCLVKGFY
PSDIAVEWESNGQPENNYKTTPPMLDSDGSFFLYSKLTVDKSRWQQGNVFSCSVMHEALHNHYTQKSLSLSPGK

Bottle opener backbone 10

Fab side heavy chain (SEQ ID NO: 28688)

ASTKGPSVFPLAPCSRSTSESTAALGCLVKDYFPEPVTVSWNSGALTSGVHTFPAVLQSSGLYSLSSVVTVPSSNFG
TQTYTCNVDHKPSDTKVDKTVERKCCVECPPCPAPPVAGPSVFLFPPKPKDTLMISRTPEVTCVVVDVKHEDPEVQF
NWYVDGVEVHNAKTKPREEEFNSTFRVVSVLTVVHQDWLNGKEYKCKVSNKGLPAPIEKTISKTKGQPREPQVYTLP
PSREEMTKNQVSLTCDVSGFYPSDIAVEWESDGQPENNYKTTPPMLDSDGSFFLYSKLTVDKSRWEQGDVFSCSVMH
EALHNHYTQKSLSLSPGK scFv heavy chain (SEQ ID NO: 28689)

ERKCSVECPPCPAPPVAGPSVFLFPPKPKDTLMISRTPEVTCVVVDVKHEDPEVQFNWYVDGVEVHNAKTKPREEQF
NSTFRVVSVLTVVHQDWLNGKEYKCKVSNKGLPAPIEKTISKTKGQPREPQVYTLPPSREQMTKNQVKLTCLVKGFY
PSDIAVEWESNGQPENNYKTTPPMLDSDGSFFLYSKLTVDKSRWQQGNVFSCSVMHEALHNHYTQKSLSLSPGK

Figure 10A

XENP016432 Nivolumab_H0L0_IgG1_PVA_/S267K

| What | sequence | SEQ ID NO: |
|---|---|---|
| Variable heavy (vh) domain | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS | 28690 |
| vhCDR1 | NSGMH | 28691 |
| vhCDR2 | VIWYDGSKRYYADSVKG | 28692 |
| vhCDR3 | NDDY | 28693 |
| Full length HC | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 28694 |
| Variable light (vl) domain | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK | 28695 |
| vlCDR1 | RASQSVSSYLA | 28696 |
| vlCDR2 | DASNRAT | 28697 |
| vlCDR3 | QQSSNWPRT | 28698 |
| Full length light chain | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 28699 |

Figure 10B

XENP024120 LOPD180[PD-1]_H1L1_IgG1_PVA_/S267K

| What | Sequence | SEQ ID NO: |
|---|---|---|
| Variable heavy (vh) domain | QVQLQESGPGLVKPSQTLSLTCTVSGGSISSGAYYWSWIRQHPGKGLEWIGYIYYNGNTYYNPSLRSRVTISVDTSKNQFSLKLSSVTAADTAVYYCVRASDYVWGGYHYFDAFDIWGRGTLVTVSS | 28700 |
| vhCDR1 | SGAYYWS | 28701 |
| vhCDR2 | YIYYNGNTYYNPSLRS | 28702 |
| vhCDR3 | ASDYVWGGYHYFDAFDI | 28703 |
| Full length HC | QVQLQESGPGLVKPSQTLSLTCTVSGGSISSGAYYWSWIRQHPGKGLEWIGYIYYNGNTYYNPSLRSRVTISVDTSKNQFSLKLSSVTAADTAVYYCVRASDYVWGGYHYFDAFDIWGRGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 28704 |
| Variable light (vl) domain | QSVLTQPPSASGTPGQRVTISCSGSNSNIGSNSVNWYQQLPGTAPKLLIYGNNQRPSGVPDRFSGSKSGTSASLAISGLQSEDEADYYCAAWDDSLNGPVFGGGTKVTVL | 28705 |
| vlCDR1 | SGSNSNIGSNSVN | 28706 |
| vlCDR2 | GNNQRPS | 28707 |
| vlCDR3 | AAWDDSLNGPV | 28708 |
| Full length light chain | QSVLTQPPSASGTPGQRVTISCSGSNSNIGSNSVNWYQQLPGTAPKLLIYGNNQRPSGVPDRFSGSKSGTSASLAISGLQSEDEADYYCAAWDDSLNGPVFGGGTKVTVL/GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 28709 |

Figure 10C

XENP024121 mAb7(1.2)[PD-1]_H1L1_IgG1_PVA_/S267K

| What | sequence | SEQ ID NO: |
|---|---|---|
| Variable heavy (vh) domain | QVQLQQPGTELMKPGASVKLSCKASGYTFTTYWMHWVKQRPGQGLEWIGEIDPSDSYVNYNQNFKGKATLTVDKSSSTAYIQLSSLT SEDSAVYFCARSPDYYGTSLAWFDYWGQGTLVTVST | 28710 |
| vhCDR1 | TYWMH | 28711 |
| vhCDR2 | EIDPSDSYVNYNQNFKG | 28712 |
| vhCDR3 | SPDYYGTSLAWFDY | 28713 |
| Full length HC | QVQLQQPGTELMKPGASVKLSCKASGYTFTTYWMHWVKQRPGQGLEWIGEIDPSDSYVNYNQNFKGKATLTVDKSSSTAYIQLSSLT SEDSAVYFCARSPDYYGTSLAWFDYWGQGTLVTVST/ASTKGPSVFPLAPSSKSTSGGTAALGCLVKDYFPEPVTVSWNSGALTSGVHT FPAVLQSSGLYSLSSVVTVPSSSLGTQTYICNVNHKPSDTKVDKKVEPKSCDKTHTCPPCPAPPVAGPSVFLFPPKPKDTLMISRTPEVTC VVVDVKHEDPEVKFNWYVDGVEVHNAKTKPREEEYNSTYRVVSVLTVLHQDWLNGKEYKCKVSNKALPAPIEKTISKAKGQPREPQVY TLPPSREEMTKNQVSLTCDVSGFYPSDIAVEWESDGQPENNYKTTPPVLDSDGSFFLYSKLTVDKSRWEQGDVFSCSVMHEALHNHYT QKSLSLSPGK | 28714 |
| Variable light (vl) domain | EIVLTQSPATLSLSPGERATLSCRASESVDNYGMSFMNWFQQKPGQPPKLLIHAASNQGSGVPSRFSGSGSGTDFTLTISSLEPEDFAVY FCQQSKEVPYTFGGGTKVEIK | 28715 |
| vlCDR1 | RASESVDNYGMSFMN | 28716 |
| vlCDR2 | AASNQGS | 28717 |
| vlCDR3 | QQSKEVPYT | 28718 |
| Full length light chain | EIVLTQSPATLSLSPGERATLSCRASESVDNYGMSFMNWFQQKPGQPPKLLIHAASNQGSGVPSRFSGSGSGTDFTLTISSLEPEDFAVY FCQQSKEVPYTFGGGTKVEIK/RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 28719 |

Figure 10D

XENP019686 1G6_H1.279_L1.194_IgG1_PVA_/S267K

| What | sequence | SEQ ID NO: |
|---|---|---|
| Variable heavy (vh) domain | EVQLVESGGGLVKPGGSLRLSCVASGFTFSNYWMNWVRQAPGKGLEWVAEIRLYSNNYATHYAESVKGRFTISRDDSKSTLYLQMNN LKTEDTGVYYCTRYYGNYGGYFDVWGRGTLVTVSS | 28720 |
| vhCDR1 | NYWMN | 28721 |
| vhCDR2 | EIRLYSNNYATHYAESVKG | 28722 |
| vhCDR3 | YYGNYGGYFDV | 28723 |
| Full length HC | EVQLVESGGGLVKPGGSLRLSCVASGFTFSNYWMNWVRQAPGKGLEWVAEIRLYSNNYATHYAESVKGRFTISRDDSKSTLYLQMNN LKTEDTGVYYCTRYYGNYGGYFDVWGRGTLVTVSS/ASTKGPSVFPLAPSSKSTSGGTAALGCLVKDYFPEPVTVSWNSGALTSGVHTF PAVLQSSGLYSLSSVVTVPSSSLGTQTYICNVNHKPSNTKVDKRVEPKSCDKTHTCPPCPAPPVAGPSVFLFPPKPKDTLMISRTPEVTCV VVDVKHEDPEVKFNWYVDGVEVHNAKTKPREEQYNSTYRVVSVLTVLHQDWLNGKEYKCKVSNKALPAPIEKTISKAKGQPREPQVY TLPPSREEMTKNQVSLTCLVKGFYPSDIAVEWESNGQPENNYKTTPPVLDSDGSFFLYSKLTVDKSRWQQGNVFSCSVMHEALHNHY TQKSLSLSPGK | 28724 |
| Variable light (vl) domain | EIVLTQSPATLSASPGERVTLTCRASQSVGNDVAWYQQKPGQAPRLLINYASHRYTGVPDRFTGSGYGTEFTLTISSVQSEDFGVYYCQ QDFSSPRTFGGGTKVEIK | 28725 |
| vlCDR1 | RASQSVGNDVA | 28726 |
| vlCDR2 | YASHRYT | 28727 |
| vlCDR3 | QQDFSSPRT | 28728 |
| Full length light chain | EIVLTQSPATLSASPGERVTLTCRASQSVGNDVAWYQQKPGQAPRLLINYASHRYTGVPDRFTGSGYGTEFTLTISSVQSEDFGVYYCQ QDFSSPRTFGGGTKVEIK/RTVAAPSVFIFPPSDEQLKSGTASVVCLLNNFYPREAKVQWKVDNALQSGNSQESVTEQDSKDSTYSLSST LTLSKADYEKHKVYACEVTHQGLSSPVTKSFNRGEC | 28729 |

Figure 10E

XENP020156 2E9_H1L1_IgG1_PVA_/S267K

| What | sequence | SEQ ID NO: |
|---|---|---|
| Variable heavy (vh) domain | QVQLVQSGAEVKKPGASVKVSCKASGYAFTNYWLGWVRQAPGQGLEWMGNFYPGSSNTYYNEKFQGRVTMTADKSISTAYMELSRLRSDDTAVYFCARHYGTNYRYFDVWGAGTLVTVSS | 28730 |
| vhCDR1 | NYWLG | 28731 |
| vhCDR2 | NFYPGSSNTYYNEKFQG | 28732 |
| vhCDR3 | HYGTNYRYFDV | 28733 |
| Full length HC | QVQLVQSGAEVKKPGASVKVSCKASGYAFTNYWLGWVRQAPGQGLEWMGNFYPGSSNTYYNEKFQGRVTMTADKSISTAYMELSRLRSDDTAVYFCARHYGTNYRYFDVWGAGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 28734 |
| Variable light (vl) domain | DIVLTQSPGTLSLSPGERATLSCRASQSVSNDVAWYQQKPGQSPRLLIYYASNRYTGVPDRFTGSGYGTDFTLTISRLEPEDFAVYFCQQDYSSPYTFGGGTKVEIK | 28735 |
| vlCDR1 | RASQSVSNDVA | 28736 |
| vlCDR2 | YASNRYT | 28737 |
| vlCDR3 | QQDYSSPYT | 28738 |
| Full length light chain | DIVLTQSPGTLSLSPGERATLSCRASQSVSNDVAWYQQKPGQSPRLLIYYASNRYTGVPDRFTGSGYGTDFTLTISRLEPEDFAVYFCQQDYSSPYTFGGGTKVEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 28739 |

Figure 11A XENP19690 1G6_H1.279_L1.194 anti-PD-1 Fv sequences

| What | sequence | SEQ ID NO: |
|---|---|---|
| Vh domain | EVQLVESGGGLVKPGGSLRLSCVASGFTFSNYWMNWVRQAPGKGLEWVAEIRLYSNNYATHYAESVKGRFTISRDDSKSTLYLQMN NLKTEDTGVYYCTRYIGNYGGYFDVWGRGTLVTVSS | 28740 |
| vhCDR1 | NYWMN | 28741 |
| vhCDR2 | EIRLYSNNYATHYAESVKG | 28742 |
| vhCDR3 | YIGNYGGYFDV | 28743 |
| scFv linker | GKPGSGKPGSGKPGSGKPGS | 28744 |
| Vl domain | EIVLTQSPATLSASPGERVTLTCRASQSVGNDVAWYQQKPGQAPRLLINYASHRYTGVPDRFTGSGYGTEFTLTISSVQSEDFGVY YCQDFSSPRTFGGGTKVEIK | 28745 |
| vlCDR1 | RASQSVGNDVA | 28746 |
| vlCDR2 | YASHRYT | 28747 |
| vlCDR3 | QDFSSPRT | 28748 |
| scFv | EVQLVESGGGLVKPGGSLRLSCVASGFTFSNYWMNWVRQAPGKGLEWVAEIRLYSNNYATHYAESVKGRFTISRDDSKSTLYLQMN NLKTEDTGVYYCTRYIGNYGGYFDVWGRGTLVTVSS/GKPGSGKPGSGKPGSGKPGS/EIVLTQSPATLSASPGERVTLTCRASQS VGNDVAWYQQKPGQAPRLLINYASHRYTGVPDRFTGSGYGTEFTLTISSVQSEDFGVYYCQDFSSPRTFGGGTKVEIK/ | 28749 |

Figure 11B 1G6_H1.280_L1.224 anti-PD-1 Fv sequences

| What | sequence | SEQ ID NO: |
|---|---|---|
| Variable heavy (vh) domain | EVQLVESGGGLVKPGGSLRLTCVASGFTFSNYWMNWVRQAPGKGLEWVAEIRLYSNNYATHYAESVKGRFTISRDDSKSTLYLQMN NLKTEDTGVYYCTRYIGNYGGYFDVWGRGTLVTVSS | 28750 |
| vhCDR1 | NYWMN | 28751 |
| vhCDR2 | EIRLYSNNYATHYAESVKG | 28752 |
| vhCDR3 | YIGNYGGYFDV | 28753 |
| scFv linker | GKPGSGKPGSGKPGSGKPGS | 28754 |
| Variable light (vl) domain | EIVLTQSPATLSVSPGERVTLTCRASQSVGNDVAWYQQKPGQAPRLLINYASHRYTSVPDRFTGSGYGTEFTLTISSVQSEDFAVY YCQDWSSPRTFGGGTKVEIK | 28755 |
| vlCDR1 | RASQSVGNDVA | 28756 |
| vlCDR2 | YASHRYT | 28757 |
| vlCDR3 | QDWSSPRT | 28758 |
| scFv | EVQLVESGGGLVKPGGSLRLTCVASGFTFSNYWMNWVRQAPGKGLEWVAEIRLYSNNYATHYAESVKGRFTISRDDSKSTLYLQMN NLKTEDTGVYYCTRYIGNYGGYFDVWGRGTLVTVSS/GKPGSGKPGSGKPGSGKPGS/EIVLTQSPATLSVSPGERVTLTCRASQS VGNDVAWYQQKPGQAPRLLINYASHRYTSVPDRFTGSGYGTEFTLTISSVQSEDFAVYYCQDWSSPRTFGGGTKVEIK | 28759 |

Figure 11C XENP19692 1G6_L1.194_H1.279 anti-PD-1 Fv sequences

| What | sequence | SEQ ID NO: |
|---|---|---|
| Variable heavy (vh) domain | EIVLTQSPATLSASPGERVTLTCRASQSVGNDVAWYQQKPGQAPRLLINYASRRYTGVPDRFTGSGYGTEFTLTISSVQSEDFGVY YCQQDFSSPRTFGGGTKVEIK | 28760 |
| vhCDR1 | RASQSVGNDVA | 28761 |
| vhCDR2 | YASRRYT | 28762 |
| vhCDR3 | QQDFSSPRT | 28763 |
| scFv linker | GKPGSGKPGSGKPGSGKPGS | 28764 |
| Variable light (vl) domain | EVQLVESGGGIVKPGGSLRLSCVASGFTFSNYWMNWVRQAPGKGLEWVAEIRLYSNRYATHYAESVKGRFTISRDDSKSTLYLQMN NLKTEDTGVYYCTRYYGNYGGYFDVWGRGTLVTVSS | 28765 |
| vlCDR1 | NYWMN | 28766 |
| vlCDR2 | EIRLYSNRYATHYAESVKG | 28767 |
| vlCDR3 | YYGNYGGYFDV | 28768 |
| scFv | EIVLTQSPATLSASPGERVTLTCRASQSVGNDVAWYQQKPGQAPRLLINYASRRYTGVPDRFTGSGYGTEFTLTISSVQSEDFGVY YCQQDFSSPRTFGGGTKVEIK/GKPGSGKPGSGKPGSGKPGS/EVQLVESGGGIVKPGGSLRLSCVASGFTFSNYWMNWVRQAPGK GLEWVAEIRLYSNRYATHYAESVKGRFTISRDDSKSTLYLQMNNLKTEDTGVYYCTRYYGNYGGYFDVWGRGTLVTVSS | 28769 |

Figure 11D XENP19669 1G6_L1.210_H1.288 anti-PD-1 Fv sequences

| What | sequence | SEQ ID NO: |
|---|---|---|
| Variable heavy (vh) domain | EIVLTQSPATLSASPGERVTLTCRASQSVGNRYAWYQQKPGQAPRLLINYASRRYTGVPDRFGCGTNVEIK | 28770 |
| vhCDR1 | RASQSVGNDVA | 28771 |
| vhCDR2 | YASRRYT | 28772 |
| vhCDR3 | QQDFSGPRT | 28773 |
| scFv linker | GKPGSGKFGSGKPGSGKFGS | 28774 |
| Variable light (vl) domain | EVQLVESGGGIVKPGGSLRLSCVASGFTFSNYWMNWVRQAPGKCLEWVAEIRLYSNRYATHYAESVKGRFTISRDDSKSTLYLQMN NLKTEDTGVYYCTRYYGNYGGYFDV | 28775 |
| vlCDR1 | NYWMN | 28776 |
| vlCDR2 | EIRLYSNRYATHYAESVKG | 28777 |
| vlCDR3 | YYGNYGGYFDV | 28778 |
| scFv | EIVLTQSPATLSASPGERVTLTCRASQSVGNRYAWYQQKPGQAPRLLINYASRRYTGVPDRFTGSGYGTEFTLTISSVQSEDFGVY YCQQDFSGPRTFGCGTNVEIK/GKPGSGKFGSGKPGSGKFGS/EVQLVESGGGIVKPGGSLRLSCVASGFTFSNYWMNWVRQAPGK CLEWVAEIRLYSNRYATHYAESVKGRFTISRDDSKSTLYLQMNNLKTEDTGVYYCTRYYGNYGGYFDVWGRGTLVTVSS | 28779 |

Figure 11E XENP20162 2E9_H1L1 anti-PD-1 Fv sequences

| What | sequence | SEQ ID NO: |
|---|---|---|
| Variable heavy (vh) domain | QVQLVQSGAEVKKPGASVKVSCKASGYAFTNYWLGWVRQAPGQGLEWMGNFYPGSSNTYYNEKFQGRVTMTADKSISTAYMELSRLRSDDTAVYFCARHYGTNYRYFDVWGAGTLVTVSS | 28780 |
| vhCDR1 | NYWLG | 28781 |
| vhCDR2 | NFYPGSSNTYYNEKFQG | 28782 |
| vhCDR3 | HYGTNYRYFDV | 28783 |
| scFv linker | GKPGSGKPGSGKPGSGKPGS | 28784 |
| Variable light (vl) domain | DIVLTQSPGTLSLSPGERATLSCRASQSVSNDVAWYQQKPGQSPRLLIYYASNRYTGVPDRFTGSGYGTDFTLTISRLEPEDFAVYFCQQDYSSPYTFGGGTKVEIK | 28785 |
| vlCDR1 | RASQSVSNDVA | 28786 |
| vlCDR2 | YASNRYT | 28787 |
| vlCDR3 | QQDYSSPYT | 28788 |
| scFv | QVQLVQSGAEVKKPGASVKVSCKASGYAFTNYWLGWVRQAPGQGLEWMGNFYPGSSNTYYNEKFQGRVTMTADKSISTAYMELSRLRSDDTAVYFCARHYGTNYRYFDVWGAGTLVTVSS/GKPGSGKPGSGKPGSGKPGS/DIVLTQSPGTLSLSPGERATLSCRASQSVSNDVAWYQQKPGQSPRLLIYYASNRYTGVPDRFTGSGYGTDFTLTISRLEPEDFAVYFCQQDYSSPYTFGGGTKVEIK | 28789 |

Figure 12A [CTLA-4]_H0.25_L0 Anti-CTLA-4 Fv sequences (XENP19235 Fab, XENP19769 scFv)

| What | sequence | SEQ ID NO: |
|---|---|---|
| Variable heavy (vh) domain | QVQLVESGGGVVQPGRSLRLSCAASGFTFSSYAMHWVRQAPGNGLEWVTFISYDGNNKYYADSVKGRFTISRDNSKNTLYLQMNSLRAEDTAIYYCARTGWLGPFDYWGQGTLVTVSS | 28790 |
| vhCDR1 | SYAMH | 28791 |
| vhCDR2 | FISYDGNNKYYADSVKG | 28792 |
| vhCDR3 | TGWLGPFDY | 28793 |
| scFv linker | GKPGSGKEGSGKPGSGKPGS | 28794 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28795 |
| vlCDR1 | RASQSVGSSYLA | 28796 |
| vlCDR2 | GAFSRAT | 28797 |
| vlCDR3 | QQYGSSPWT | 28798 |
| scFv | QVQLVESGGGVVQPGRSLRLSCAASGFTFSSYAMHWVRQAPGNGLEWVTFISYDGNNKYYADSVKGRFTISRDNSKNTLYLQMNSLRAEDTAIYYCARTGWLGPFDYWGQGTLVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK/ | 28799 |

Figure 12B [CTLA-4]_H0.26_L0 Anti-CTLA-4 Fv sequences (XENP19236 Fab, XENP19770 scFv)

| What | sequence | SEQ ID NO: |
|---|---|---|
| Variable heavy (vh) domain | QVQLVESGGGVVQPGRSLRLSCAASGFTFSSYGMHWVRQAPGKGLEWVTFISYDGNNKYYADSVKGRFTISRDNSKNTLYLQMNSLRAEDTAIYYCARTGWLGPFDYWGQGTLVTVSS | 28800 |
| vhCDR1 | SYGMH | 28801 |
| vhCDR2 | FISYDGNNKYYADSVKG | 28802 |
| vhCDR3 | TGWLGPFDY | 28803 |
| scFv linker | GKPGSGKPGSGKPGSGKPGS | 28804 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28805 |
| vlCDR1 | RASQSVGSSYLA | 28806 |
| vlCDR2 | GAFSRAT | 28807 |
| vlCDR3 | QQYGSSPWT | 28808 |
| scFv | QVQLVESGGGVVQPGRSLRLSCAASGFTFSSYGMHWVRQAPGKGLEWVTFISYDGNNKYYADSVKGRFTISRDNSKNTLYLQMNSLRAEDTAIYYCARTGWLGPFDYWGQGTLVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28809 |

Figure 12C [CTLA-4]_H0.27_L0 Anti-CTLA-4 Fv sequences (XENP19237 Fab, XENP19771 scFv)

| What | sequence | SEQ ID NO: |
|---|---|---|
| Variable heavy (vh) domain | QVQLVESGGGVVQPGRSLRLSCAASGFTFSSYSMRWVRQAPGKGLEWVTFISYDGNNKYYADSVKGRFTISRDNSKNTLYLQMNSLRAEDTAIYYCARTGWLGPFDYWGQGTLVTVSS | 28810 |
| vhCDR1 | SYSMR | 28811 |
| vhCDR2 | FISYDGNNKYYADSVKG | 28812 |
| vhCDR3 | TGWLGPFDY | 28813 |
| scFv linker | GKPGSGKPGSGKPGS | 28814 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28815 |
| vlCDR1 | RASQSVGSSYLA | 28816 |
| vlCDR2 | GAFSRAT | 28817 |
| vlCDR3 | QQYGSSPWT | 28818 |
| scFv | QVQLVESGGGVVQPGRSLRLSCAASGFTFSSYSMRWVRQAPGKGLEWVTFISYDGNNKYYADSVKGRFTISRDNSKNTLYLQMNSLRAEDTAIYYCARTGWLGPFDYWGQGTLVTVSS/GKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28819 |

Figure 12D [CTLA-4]_H0.29_L0 Fab XENP19773, scFv XENP19239

| What | sequence | SEQ ID NO: |
|---|---|---|
| Variable heavy (vh) domain | | |
| vhCDR1 | | |
| vhCDR2 | | |
| vhCDR3 | | |
| scFv linker | GKPGSGKPGSGKPGS | 28820 |
| Variable light (vl) domain | | |
| vlCDR1 | | |
| vlCDR2 | | |
| vlCDR3 | | |
| scFv | QVQLVESGGGVVQPGRSLRLSCAASGFTFSSYSMRWVRQAPGKGLEWVTFISYDGNNKYYADSVKGRFTISRDNSKNTLYLQMNSLRAEDTAIYYCARTGWLGPFDYWGQGTLVTVSS/GKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28821 |

Figure 12E [CTLA-4]_H0.38_L0 (Fab XENP19248, scFv XENP19782)

| What | sequence | SEQ ID NO: |
|---|---|---|
| Variable heavy (vh) domain | QVQLVESGGGVVQPGRSLRLSCAASGFTFSSYTMHWVRQAPGKGLEWVAFISYDGNNKYYADSVKGRFTISRDNSKNTL YLQMNSLRAEDTAIYYCARTGWLGPFDYWGQGTLVTVSS | 28822 |
| vhCDR1 | SYTMH | 28823 |
| vhCDR2 | FISYDGNNKYYADSVKG | 28824 |
| vhCDR3 | TGWLGPFDY | 28825 |
| scFv linker | GKPGSGKPGSGKPGSGKPGS | 28826 |
| Variable light (vl) domain | EIVLTQSPGTLSLSPGERATLSCRASQSVGSSYLAWYQQKPGQAPRLLIYGAFSRAHGIPDRFSGSGSGTDFTLTISRL EPEDFAVYYCQQYGSSPWTFGQGTKVEIK | 28827 |
| vlCDR1 | RASQSVGSSYLA | 28828 |
| vlCDR2 | GAFSRAT | 28829 |
| vlCDR3 | QQYGSSPWT | 28830 |
| scFv | QVQLVESGGGVVQPGRSLRLSCAASGFTFSSYTMHWVRQAPGKGLEWVAFISYDGNNKYYADSVKGRFTISRDNSKNTL YLQMNSLRAEDTAIYYCARTGWLGPFDYWGQGTLVTVSS/GKPGSGKPGSGKPGSGKPGS/EIVLTQSPGTLSLSPGER ATLSCRASQSVGSSYLAWYQQKPGQAPRLLIYGAFSRAHGIPDRFSGSGSGTDFTLTISRLEPEDFAVYYCQQYGSSPW TFGQGTKVEIK/ | 28831 |

Figure 12F [CTLA-4]_H0.39_L0 (Fab XENP19249, scFv XENP19783)

| What | sequence | SEQ ID NO: |
|---|---|---|
| Variable heavy (vh) domain | QVQLVESGGGVVQPGRSLRLSCAASGFTFSSYTMHWVRQAPGKGLEWVGFISYDGNNKYYADSVKGRFTISRDNSKNTL YLQMNSLRAEDTAIYYCARTGWLGPFDYWGQGTLVTVSS | 28832 |
| vhCDR1 | SYTMH | 28833 |
| vhCDR2 | FISYDGNNKYYADSVKG | 28834 |
| vhCDR3 | TGWLGPFDY | 28835 |
| scFv linker | GKPGSGKPGSGKPGSGKPGS | 28836 |
| Variable light (vl) domain | EIVLTQSPGTLSLSPGERATLSCRASQSVGSSYLAWYQQKPGQAPRLLIYGAFSRATGIPDRFSGSGSGTDFTLTISRL EPEDFAVYYCQQYGSSFWTFGQGTKVEIK | 28837 |
| vlCDR1 | RASQSVGSSYLA | 28838 |
| vlCDR2 | GAFSRAT | 28839 |
| vlCDR3 | QQYGSSFWT | 28840 |
| scFv | QVQLVESGGGVVQPGRSLRLSCAASGFTFSSYTMHWVRQAPGKGLEWVGFISYDGNNKYYADSVKGRFTISRDNSKNTL YLQMNSLRAEDTAIYYCARTGWLGPFDYWGQGTLVTVSS/GKPGSGKPGSGKPGSGKPGS/EIVLTQSPGTLSLSPGER ATLSCRASQSVGSSYLAWYQQKPGQAPRLLIYGAFSRATGIPDRFSGSGSGTDFTLTISRLEPEDFAVYYCQQYGSSPW TFGQGTKVEIK | 28841 |

Figure 12G [CTLA-4]_H0.4Q_L0 (Fab XENP19250, scFv XENP19784)

| What | sequence | SEQ ID NO: |
|---|---|---|
| Variable heavy (vh) domain | QVQLVESGGGVVQPGRSLRLSCAASGFTFSSYTMHWVRQAPGKGLEWVSFISYDGNNKYADSVKGRFTISRDNSKNTLYLQMNSLRAEDTAIYYCARTGWLGPFDYWGQGTLVTVSS | 28842 |
| vhCDR1 | SYTMH | 28843 |
| vhCDR2 | FISYDGNNKYADSVKG | 28844 |
| vhCDR3 | TGWLGPFDY | 28845 |
| scFv linker | GKPGSGKPGSGKPGSGKPGS | 28846 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28847 |
| vlCDR1 | RASQSVGSSYLA | 28848 |
| vlCDR2 | GAFSRAT | 28849 |
| vlCDR3 | QQYGSSPWT | 28850 |
| scFv | QVQLVESGGGVVQPGRSLRLSCAASGFTFSSYTMHWVRQAPGKGLEWVSFISYDGNNKYADSVKGRFTISRDNSKNTLYLQMNSLRAEDTAIYYCARTGWLGPFDYWGQGTLVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28851 |

Figure 12H [CTLA-4]_H0.7Q_L0 (Fab XENP19280, scFv XENP19818)

| What | sequence | SEQ ID NO: |
|---|---|---|
| Variable heavy (vh) domain | QVQLVESGGGVVQPGRSLRLSCAASGFTFSSYTMHWVRQAPGKGLEWVTFISYDGSNKYADSVKGRFTISRDNSKNTLYLQMNSLRAEDTAIYYCARTGWLGPFDYWGQGTLVTVSS | 28852 |
| vhCDR1 | SYTMH | 28853 |
| vhCDR2 | FISYDGSNKYADSVKG | 28854 |
| vhCDR3 | TGWLGPFDY | 28855 |
| scFv linker | GKPGSGKPGSGKPGSGKPGS | 28856 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28857 |
| vlCDR1 | RASQSVGSSYLA | 28858 |
| vlCDR2 | GAFSRAT | 28859 |
| vlCDR3 | QQYGSSPWT | 28860 |
| scFv | QVQLVESGGGVVQPGRSLRLSCAASGFTFSSYTMHWVRQAPGKGLEWVTFISYDGSNKYADSVKGRFTISRDNSKNTLYLQMNSLRAEDTAIYYCARTGWLGPFDYWGQGTLVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28861 |

Figure 12I [CTLA-4]_H0_L0.22 (Fab XENP19437, scFv XENP19910)

| What | sequence | SEQ ID NO: |
|---|---|---|
| Variable heavy (vh) domain | QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSS | 28862 |
| vhCDR1 | SYTMH | 28863 |
| vhCDR2 | FISYDGNNKYYADSVKG | 28864 |
| vhCDR3 | TGWLGPFDY | 28865 |
| scFv linker | GKPGSGKPGSGKPGSGKPGS | 28866 |
| Variable light (vl) domain | EIVLTQSPGTLSLSPGERATLSCRASQSVSSSYLAWYQQKPGQAPRLLIYGAFSRATGIPDRFSGSGSGTDFTLTISRLEPEDFAVYYCQQYGSSPWTFGQGTKVEIK | 28867 |
| vlCDR1 | RASQSVSSYLA | 28868 |
| vlCDR2 | GAFSRAT | 28869 |
| vlCDR3 | QQYGSSPWT | 28870 |
| scFv | QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSS/GKPGSGKPGSGKPGSGKPGS/EIVLTQSPGTLSLSPGERATLSCRASQSVSSSYLAWYQQKPGQAPRLLIYGAFSRATGIPDRFSGSGSGTDFTLTISRLEPEDFAVYYCQQYGSSPWTFGQGTKVEIK | 28871 |

Figure 12J [CTLA-4]_H2_L0 (Fab XENP19545 scFv XENP19552)

| What | sequence | SEQ ID NO: |
|---|---|---|
| Variable heavy (vh) domain | EVQLVESGGGLVQPGGSLRLSCAASGFTFSSYTMHWVRQAPGKGLEWVTFISYDGNNKYYPGSVKGRFTISRENAKNSLYLQMNSLRAGDTAVYYCARTGWLGPFDYWGQGTLVTVSS | 28872 |
| vhCDR1 | SYTMH | 28873 |
| vhCDR2 | FISYDGNNKYYPGSVKG | 28874 |
| vhCDR3 | TGWLGPFDY | 28875 |
| scFv linker | GKPGSGKPGSGKPGSGKPGS | 28876 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28877 |
| vlCDR1 | RASQSVGSSYLA | 28878 |
| vlCDR2 | GAFSRAT | 28879 |
| vlCDR3 | QQYGSSPWT | 28880 |
| scFv | EVQLVESGGGLVQPGGSLRLSCAASGFTFSSYTMHWVRQAPGKGLEWVTFISYDGNNKYYPGSVKGRFTISRENAKNSLYLQMNSLRAGDTAVYYCARTGWLGPFDYWGQGTLVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28881 |

Figure 12K [CTLA-4]_H3.21_L0.124 (Fab XENP20422, scFv XENP20431)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARGGLLGFFDLWGQGTMVTVSS | 28882 |
| vhCDR1 | SYTMH | 28883 |
| vhCDR2 | FISYDGNTKYYADSVKG | 28884 |
| vhCDR3 | GGLLGFFDL | 28885 |
| scFv linker | GKPGSGKPGSGKPGSGKPGS | 28886 |
| Variable light (vl) domain | EIVLTQSPATLSVSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 28887 |
| vlCDR1 | RASQSVGSSYLA | 28888 |
| vlCDR2 | GASSRAT | 28889 |
| vlCDR3 | QQYGSSPWT | 28890 |
| scFv | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARGGLLGFFDLWGQGTMVTVSS/GKPGSGKPGSGKPGSGKPGS/EIVLTQSPATLSVSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 28891 |

Figure 12L [CTLA-4]_H3.21_L0.129 (Fab XENP20423, scFv XENP20432)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARGGLLGFFDLWGQGTMVTVSS | 28892 |
| vhCDR1 | SYTMH | 28893 |
| vhCDR2 | FISYDGNTKYYADSVKG | 28894 |
| vhCDR3 | GGLLGFFDL | 28895 |
| scFv linker | GKPGSGKPGSGKPGSGKPGS | 28896 |
| Variable light (vl) domain | EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 28897 |
| vlCDR1 | RASQSVGSSYLA | 28898 |
| vlCDR2 | GASSRAT | 28899 |
| vlCDR3 | QQYGSSPWT | 28900 |
| scFv | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARGGLLGFFDLWGQGTMVTVSS/GKPGSGKPGSGKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 28901 |

Figure 12M [CTLA-4]_H3.21_L0.132 (Fab XENP20424, scFv XENP20433)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARGGLLGFFDLWGQGTMVTVSS | 28902 |
| vhCDR1 | SYTMH | 28903 |
| vhCDR2 | FISYDGNTKYYADSVKG | 28904 |
| vhCDR3 | GGLLGFFDL | 28905 |
| scFv linker | GKPGSGKPGSGKPGSGKPGS | 28906 |
| Variable light (vl) domain | EIVLTQSPATLSLSPGERATLSCRASQSVGSSYLAWYQQKPGQAPRLLIYGASSPATGIPDRFSGSGSGTDFTLTISRLEPEDFAVYYCQQYGSSPWTFGQGTKVEIK | 28907 |
| vlCDR1 | RASQSVGSSYLA | 28908 |
| vlCDR2 | GASSRAT | 28909 |
| vlCDR3 | QQYGSSPWT | 28910 |
| scFv | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARGGLLGFFDLWGQGTMVTVSS/GKPGSGKPGSGKPGSGKPGS/EIVLTQSPATLSLSPGERATLSCRASQSVGSSYLAWYQQKPGQAPRLLIYGASSPATGIPDRFSGSGSGTDFTLTISRLEPEDFAVYYCQQYGSSPWTFGQGTKVEIK | 28911 |

Figure 12N [CTLA-4]_H3.23_L0.124 (Fab XENP20425, scFv XENP20434)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGLLGFFDLWGQGTMVTVSS | 28912 |
| vhCDR1 | SYTMH | 28913 |
| vhCDR2 | FISYDGNYKYYADSVKG | 28914 |
| vhCDR3 | GGLLGFFDL | 28915 |
| scFv linker | GKPGSGKPGSGKPGSGKPGS | 28916 |
| Variable light (vl) domain | EIVLTQSPATLSVSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 28917 |
| vlCDR1 | RASQSVGSSYLA | 28918 |
| vlCDR2 | GASSRAT | 28919 |
| vlCDR3 | QQYGSSPWT | 28920 |
| scFv | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGLLGFFDLWGQGTMVTVSS/GKPGSGKPGSGKPGSGKPGS/EIVLTQSPATLSVSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 28921 |

Figure 12O [CTLA-4]_H3.23_L0.129 (Fab XENP20426, scFv XENP20435)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGPFDLWGQGTMVTVSS | 28922 |
| vhCDR1 | SYTMH | 28923 |
| vhCDR2 | FISYDGNYKYYADSVKG | 28924 |
| vhCDR3 | GGHLGPFDL | 28925 |
| scFv linker | GKPGSGKPGSGKPGSGKPGS | 28926 |
| Variable light (vl) domain | EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 28927 |
| vlCDR1 | RASQSVGSSYLA | 28928 |
| vlCDR2 | GASSRAT | 28929 |
| vlCDR3 | QQYGSSPWT | 28930 |
| scFv | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGPFDLWGQGTMVTVSS/GKPGSGKPGSGKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 28931 |

Figure 12P [CTLA-4]_H3.23_L0.132 (Fab XENP20427, scFv XENP20436)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGPFDLWGQGTMVTVSS | 28932 |
| vhCDR1 | SYTMH | 28933 |
| vhCDR2 | FISYDGNYKYYADSVKG | 28934 |
| vhCDR3 | GGHLGPFDL | 28935 |
| scFv linker | GKPGSGKPGSGKPGSGKPGS | 28936 |
| Variable light (vl) domain | EIVLTQSPATLSLSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 28937 |
| vlCDR1 | RASQSVSSSYLA | 28938 |
| vlCDR2 | GASSRAT | 28939 |
| vlCDR3 | QQYGSSPWT | 28940 |
| scFv | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGHLGPFDLWGQGTMVTVSS/GKPGSGKPGSGKPGSGKPGS/EIVLTQSPATLSLSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 28941 |

Figure 12Q [CTLA-4]_H3.25_L0.124 (Fab XENP20428, scFv XENP20437)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGLLGFFDLWGQGTMVTVSS | 28942 |
| vhCDR1 | SYTMH | 28943 |
| vhCDR2 | FISYDGNYKYYADSVKG | 28944 |
| vhCDR3 | GGLLGFFDL | 28945 |
| scFv linker | GKPGSGKPGSGKPGSGKPGS | 28946 |
| Variable light (vl) domain | EIVLTQSPATLSVSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 28947 |
| vlCDR1 | RASQSVGSSYLA | 28948 |
| vlCDR2 | GASSRAT | 28949 |
| vlCDR3 | QQYGSSPWT | 28950 |
| scFv | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGLLGFFDLWGQGTMVTVSS/GKPGSGKPGSGKPGSGKPGS/EIVLTQSPATLSVSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 28951 |

Figure 12R [CTLA-4]_H3.25_L0.129 (Fab XENP20429, scFv XENP20438)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGLLGFFDLWGQGTMVTVSS | 28952 |
| vhCDR1 | SYTMH | 28953 |
| vhCDR2 | FISYDGNYKYYADSVKG | 28954 |
| vhCDR3 | GGLLGFFDL | 28955 |
| scFv linker | GKPGSGKPGSGKPGSGKPGS | 28956 |
| Variable light (vl) domain | EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 28957 |
| vlCDR1 | RASQSVGSSYLA | 28958 |
| vlCDR2 | GASSRAT | 28959 |
| vlCDR3 | QQYGSSPWT | 28960 |
| scFv | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGLLGFFDLWGQGTMVTVSS/GKPGSGKPGSGKPGSGKPGS/EIVLTQSPATLSLSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 28961 |

Figure 12S [CTLA-4]_H3.25_L0.132 (Fab XENP20430, scFv XENP20439)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGLLGFFDLWGQGTMVTVSS | 28962 |
| vhCDR1 | SYTMH | 28963 |
| vhCDR2 | FISYDGNYKYYADSVKG | 28964 |
| vhCDR3 | GGLLGFFDL | 28965 |
| scFv linker | GKPGSGKPGSGKPGS | 28966 |
| Variable light (vl) domain | EIVLTQSPATLSLSPGERATLSCRASQSVSSSYLAWYQQKPGQAPRLLIYGASSRAHGIPDRFSGSGSGTDFTLTISRLEPEDFAVYYCQQYGSSPWTFGQGTKVEIK | 28967 |
| vlCDR1 | RASQSVSSSYLA | 28968 |
| vlCDR2 | GASSRAH | 28969 |
| vlCDR3 | QQYGSSPWT | 28970 |
| scFv | EVQLVESGGGLVKPGGSLRLSCAASGFTFSSYTMHWVRQAPGKGLEWVSFISYDGNYKYYADSVKGRFTISRDNAKNSLYLQMNSLRAEDTAVYYCARGGLLGFFDLWGQGTMVTVSS/GKPGSGKPGSGKPGS/EIVLTQSPATLSLSPGERATLSCRASQSVSSSYLAWYQQKPGQAPRLLIYGASSRAHGIPDRFSGSGSGTDFTLTISRLEPEDFAVYYCQQYGSSPWTFGQGTKVEIK | 28971 |

Figure 12T [CTLA-4]_H3.4_L0.118 (Fab XENP20341, scFv XENP20378)

| What | sequence | SEQ ID NO: |
|---|---|---|
| Variable heavy (vh) domain | EVQLVESGGGLVKPGGSLRLSCAASGFTFSSYIMHWVRQAPGKGLEWVSFISYDGNEKYYADSVKGRFTISRDNAKNSLYLQMNSLRAEDTAVYYCARTGHLGFFDLWGQGTMVTVSS | 28972 |
| vhCDR1 | SSYIMH | 28973 |
| vhCDR2 | FISYDGNEKYYADSVKG | 28974 |
| vhCDR3 | TGHLGFFDL | 28975 |
| scFv linker | GKPGSGKPGSGKPGS | 28976 |
| Variable light (vl) domain | EIVLTQSPATLSVSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28977 |
| vlCDR1 | RASQSVGSSYLA | 28978 |
| vlCDR2 | GAFSRAT | 28979 |
| vlCDR3 | QQYGSSPWT | 28980 |
| scFv | EVQLVESGGGLVKPGGSLRLSCAASGFTFSSYIMHWVRQAPGKGLEWVSFISYDGNEKYYADSVKGRFTISRDNAKNSLYLQMNSLRAEDTAVYYCARTGHLGFFDLWGQGTMVTVSS/GKPGSGKPGSGKPGS/EIVLTQSPATLSVSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28981 |

Figure 12U [CTLA-4]_H3.4_L0.119 (Fab XENP20342, scFv XENP20379)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGFFDLWGQGTMVTVSS | 28982 |
| vhCDR1 | SYTMH | 28983 |
| vhCDR2 | FISYDGNHKYYADSVKG | 28984 |
| vhCDR3 | TGHLGFFDL | 28985 |
| scFv linker | GKPGSGKPGSGKPGSGKPGS | 28986 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28987 |
| vlCDR1 | RASQSVGSSYLA | 28988 |
| vlCDR2 | GAFSRAT | 28989 |
| vlCDR3 | QQYGSSPWT | 28990 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGFFDLWGQGTMVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28991 |

Figure 12V [CTLA-4]_H3.4_L0.12 (Fab XENP20071, scFv XENP20078)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGFFDLWGQGTMVTVSS | 28992 |
| vhCDR1 | SYTMH | 28993 |
| vhCDR2 | FISYDGNHKYYADSVKG | 28994 |
| vhCDR3 | TGHLGFFDL | 28995 |
| scFv linker | GKPGSGKPGSGKPGSGKPGS | 28996 |
| Variable light (vl) domain | EIVLTQSPGTLSVSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 28997 |
| vlCDR1 | RASQSVGSSYLA | 28998 |
| vlCDR2 | GAFSRAT | 28999 |
| vlCDR3 | QQYGSSPWT | 29000 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGFFDLWGQGTMVTVSS/GKPGSGKPGSGKPGSGKPGS/EIVLTQSPGTLSVSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 29001 |

Figure 12W [CTLA-4]_H3.4_L0.121 (Fab XENP20344, scFv XENP20381)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 29002 |
| vhCDR1 | SYTMH | 29003 |
| vhCDR2 | FISYDGNHKYYADSVKG | 29004 |
| vhCDR3 | TGHLGPFDL | 29005 |
| scFv linker | GKPGSGKPGSGKPGSGKPGS | 29006 |
| Variable light (vl) domain | EIVLTQSPGTLSVSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 29007 |
| vlCDR1 | RASQSVGSSYLA | 29008 |
| vlCDR2 | GASSRAT | 29009 |
| vlCDR3 | QQYGSSPWT | 29010 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPGTLSVSPGERATLSCRASQSVGSSYLAWYQQKPGQAPRLLIYGASSRATGIPDRFSGSGSGTDFTLTISRLEPEDFAVYYCQQYGSSPWTFGQGTKVEIK | 29011 |

Figure 12X [CTLA-4]_H3.4_L0.122 (Fab XENP20345, scFv XENP20382)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 29012 |
| vhCDR1 | SYTMH | 29013 |
| vhCDR2 | FISYDGNHKYYADSVKG | 29014 |
| vhCDR3 | TGHLGPFDL | 29015 |
| scFv linker | GKPGSGKPGSGKPGSGKPGS | 29016 |
| Variable light (vl) domain | EIVLTQSPATLSLSPGERATLSCRASQSVGSSYLAWYQQKPGQAPRLLIYGAFSRAHGIPDRFSGSGSGTDFTLTISRLEPEDFAVYYCQQYGSSPWTFGQGTKVEIK | 29017 |
| vlCDR1 | RASQSVGSSYLA | 29018 |
| vlCDR2 | GAFSRAH | 29019 |
| vlCDR3 | QQYGSSPWT | 29020 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPATLSLSPGERATLSCRASQSVGSSYLAWYQQKPGQAPRLLIYGAFSRAHGIPDRFSGSGSGTDFTLTISRLEPEDFAVYYCQQYGSSPWTFGQGTKVEIK | 29021 |

Figure 12Y [CTLA-4]_H3.4_L0.123 (Fab XENP20346, scFv XENP20383)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 29022 |
| vhCDR1 | SYTMH | 29023 |
| vhCDR2 | FISYDGNHKYYADSVKG | 29024 |
| vhCDR3 | TGHLGPFDL | 29025 |
| scFv linker | GKPGSGKPGSGKPGSGKPGS | 29026 |
| Variable light (vl) domain | EIVLTQSPATLSVSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 29027 |
| vlCDR1 | RASQSVGSSYLA | 29028 |
| vlCDR2 | GAFSRAT | 29029 |
| vlCDR3 | QQYGSSPWT | 29030 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPATLSVSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 29031 |

Figure 12Z [CTLA-4]_H3.4_L0.124 (Fab XENP20347, scFv XENP20384)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 29032 |
| vhCDR1 | SYTMH | 29033 |
| vhCDR2 | FISYDGNHKYYADSVKG | 29034 |
| vhCDR3 | TGHLGPFDL | 29035 |
| scFv linker | GKPGSGKPGSGKPGSGKPGS | 29036 |
| Variable light (vl) domain | EIVLTQSPATLSVSPGERATLSCRASQSVGSSYLAWYQQKPGQAPRLLIYGASSRAHGIPDRFSGSGSGTDFTLTISRLEPEDFAVYYCQQYGSSPWTFGQGTKVEIK | 29037 |
| vlCDR1 | RASQSVGSSYLA | 29038 |
| vlCDR2 | GASSRAH | 29039 |
| vlCDR3 | QQYGSSPWT | 29040 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPATLSVSPGERATLSCRASQSVGSSYLAWYQQKPGQAPRLLIYGASSRAHGIPDRFSGSGSGTDFTLTISRLEPEDFAVYYCQQYGSSPWTFGQGTKVEIK | 29041 |

Figure 12AA [CTLA-4]_H3.4_L0.125 (Fab XENP20348, scFv XENP20385)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMN SLRAEDTAVYYCARTGHLGPFDLWGQGTMVTVSS | 29042 |
| vhCDR1 | SYTMH | 29043 |
| vhCDR2 | FISYDGNHKYYADSVKG | 29044 |
| vhCDR3 | TGHLGPFDL | 29045 |
| scFv linker | GKPGSGKPGSGKPGSGKPGS | 29046 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDF AVYYCQQYGSSPWTFGQGTKVEIK | 29047 |
| vlCDR1 | RASQSVGSSYLA | 29048 |
| vlCDR2 | GAFSRAT | 29049 |
| vlCDR3 | QQYGSSPWT | 29050 |
| scFv | EVQLVESGGGLVKPGGSLRLSCAASGFTFSSYTMHWVRQAPGKGLEWVSFISYDGNHKYYADSVKGRFTISRDNAKNSLYLQMN SLRAEDTAVYYCARTGHLGPFDLWGQGTMVTVSS/GKPGSGKPGSGKPGSGKPGS/EIVLTQSPGTLSLSPGERATLSCRASQS VGSSYLAWYQQKPGQAPRLLIYGAFSRATGIPDRFSGSGSGTDFTLTISRLEPEDFAVYYCQQYGSSPWTFGQGTKVEIK | 29051 |

Figure 12BB [CTLA-4]_H3.4_L0.126 (Fab XENP20349, scFv XENP20386)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMN SLRAEDTAVYYCARTGHLGPFDLWGQGTMVTVSS | 29052 |
| vhCDR1 | SYTMH | 29053 |
| vhCDR2 | FISYDGNHKYYADSVKG | 29054 |
| vhCDR3 | TGHLGPFDL | 29055 |
| scFv linker | GKPGSGKPGSGKPGSGKPGS | 29056 |
| Variable light (vl) domain | EIVLTQSPGTLSLSPGERATLSCRASQSVGSSYLAWYQQKPGQAPRLLIYGASSRAHGIPDRFSGSGSGTDFTLTISRLEPEDF AVYYCQQYGSSPWTFGQGTKVEIK | 29057 |
| vlCDR1 | RASQSVGSSYLA | 29058 |
| vlCDR2 | GASSRAH | 29059 |
| vlCDR3 | QQYGSSPWT | 29060 |
| scFv | EVQLVESGGGLVKPGGSLRLSCAASGFTFSSYTMHWVRQAPGKGLEWVSFISYDGNHKYYADSVKGRFTISRDNAKNSLYLQMN SLRAEDTAVYYCARTGHLGPFDLWGQGTMVTVSS/GKPGSGKPGSGKPGSGKPGS/EIVLTQSPGTLSLSPGERATLSCRASQS VGSSYLAWYQQKPGQAPRLLIYGASSRAHGIPDRFSGSGSGTDFTLTISRLEPEDFAVYYCQQYGSSPWTFGQGTKVEIK | 29061 |

Figure 12CC [CTLA-4]_H3.4_L0.127 (Fab XENP20350, scFv XENP20387)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 29062 |
| vhCDR1 | SYTMH | 29063 |
| vhCDR2 | FISYDGNHKYYADSVKG | 29064 |
| vhCDR3 | TGHLGPFDL | 29065 |
| scFv linker | GKPGSGKPGSGKPGSGKPGS | 29066 |
| Variable light (vl) domain | EIVLTQSPGTLSVSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 29067 |
| vlCDR1 | RASQSVSSSYLA | 29068 |
| vlCDR2 | GASSRAT | 29069 |
| vlCDR3 | QQYGSSPWT | 29070 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPGTLSVSPGERATLSCRASQSVSSSYLAWYQQKPGQAPRLLIYGASSRATGIPDRFSGSGSGTDFTLTISRLEPEDFAVYYCQQYGSSPWTFGQGTKVEIK | 29071 |

Figure 12DD [CTLA-4]_H3.4_L0.128 (Fab XENP20351, scFv XENP20388)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS | 29072 |
| vhCDR1 | SYTMH | 29073 |
| vhCDR2 | FISYDGNHKYYADSVKG | 29074 |
| vhCDR3 | TGHLGPFDL | 29075 |
| scFv linker | GKPGSGKPGSGKPGSGKPGS | 29076 |
| Variable light (vl) domain | EIVLTQSPATLSLSPGERATLSCRASQSVSSSYLAWYQQKPGQAPRLLIYGAFSRATGIPDRFSGSGSGTDFTLTISRLEPEDFAVYYCQQYGSSPWTFGQGTKVEIK | 29077 |
| vlCDR1 | RASQSVSSSYLA | 29078 |
| vlCDR2 | GAFSRAT | 29079 |
| vlCDR3 | QQYGSSPWT | 29080 |
| scFv | EVQLVESGGGLVKPGGSLRLSCAASGFTFSSYTMHWVRQAPGKGLEWVSFISYDGNHKYYADSVKGRFTISRDNAKNSLYLQMNSLRAEDTAVYYCARTGHLGPFDLWGQGTMVTVSS/GKPGSGKPGSGKPGSGKPGS/EIVLTQSPATLSLSPGERATLSCRASQSVSSSYLAWYQQKPGQAPRLLIYGAFSRATGIPDRFSGSGSGTDFTLTISRLEPEDFAVYYCQQYGSSPWTFGQGTKVEIK | 29081 |

Figure 12EE [CTLA-4]_H3.4_L0.129 (Fab XENP20352, scFv XENP20389)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQM NSLRAEDTAVYYCARTGHLGPFDLWGQGTMVTVSS | |
| vhCDR1 | SYTMH | |
| vhCDR2 | FISYDGNHKYYADSVKG | |
| vhCDR3 | TGHLGPFDL | |
| scFv linker | GKPGSGKPGSGKPGS | 29082 |
| Variable light (vl) domain | EIVLTQSPATLSLSPGERATLSCRASQSVGSSYLAWYQQKPGQAPRLLIYGASSRATGIPDRFSGSGSGTDFTLTISRLEPED FAVYYCQQYGSSPWTFGQGTKVEIK | 29083 |
| vlCDR1 | RASQSVGSSYLA | 29084 |
| vlCDR2 | GASSRAT | 29085 |
| vlCDR3 | QQYGSSPWT | 29086 |
| scFv | EVQLVESGGGLVKPGGSLRLSCAASGFTFSSYTMHWVRQAPGKGLEWVSFISYDGNHKYYADSVKGRFTISRDNAKNSLYLQM NSLRAEDTAVYYCARTGHLGPFDLWGQGTMVTVSS/GKPGSGKPGSGKPGS/EIVLTQSPATLSLSPGERATLSCRAS QSVGSSYLAWYQQKPGQAPRLLIYGASSRATGIPDRFSGSGSGTDFTLTISRLEPEDFAVYYCQQYGSSPWTFGQGTKVEIK | 29087 |

Figure 12FF [CTLA-4]_H3.4_L0.130 (Fab XENP20353, scFv XENP20390)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQM NSLRAEDTAVYYCARTGHLGPFDLWGQGTMVTVSS | 29088 |
| vhCDR1 | SYTMH | 29089 |
| vhCDR2 | FISYDGNHKYYADSVKG | 29090 |
| vhCDR3 | TGHLGPFDL | 29091 |
| scFv linker | GKPGSGKPGSGKPGS | 29092 |
| Variable light (vl) domain | EIVLTQSPATLSVSPGERATLSCRASQSVSSSYLAWYQQKPGQAPRLLIYGASSRATGIPDRFSGSGSGTDFTLTISRLEPED FAVYYCQQYGSSPWTFGQGTKVEIK | 29093 |
| vlCDR1 | RASQSVSSSYLA | 29094 |
| vlCDR2 | GASSRAT | 29095 |
| vlCDR3 | QQYGSSPWT | 29096 |
| scFv | EVQLVESGGGLVKPGGSLRLSCAASGFTFSSYTMHWVRQAPGKGLEWVSFISYDGNHKYYADSVKGRFTISRDNAKNSLYLQM NSLRAEDTAVYYCARTGHLGPFDLWGQGTMVTVSS/GKPGSGKPGSGKPGS/EIVLTQSPATLSVSPGERATLSCRAS QSVSSSYLAWYQQKPGQAPRLLIYGASSRATGIPDRFSGSGSGTDFTLTISRLEPEDFAVYYCQQYGSSPWTFGQGTKVEIK | 29097 |

Figure 12GG [CTLA-4]_H3.4_L0.131 (Fab XENP20354, scFv XENP20391)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQM NSLRAEDTAVYYCARTGHLGPFDLWGQGTMVTVSS | 29098 |
| vhCDR1 | SYTMH | 29099 |
| vhCDR2 | FISYDGNHKYYADSVKG | 29100 |
| vhCDR3 | TGHLGPFDL | 29101 |
| scFv linker | GKPGSGKPGSGKPGSGKPGS | 29102 |
| Variable light (vl) domain | EIVLTQSPGTLSLSPGERATLSCRASQSVSSSYLAWYQQKPGQAPRLLIYGASSRATGIPDRFSGSGSGTDFTLTISRLEPED FAVYYCQQYGSSPWTFGQGTKVEIK | 29103 |
| vlCDR1 | RASQSVSSSYLA | 29104 |
| vlCDR2 | GASSRAT | 29105 |
| vlCDR3 | QQYGSSPWT | 29106 |
| scFv | EVQLVESGGGLVKPGGSLRLSCAASGFTFSSYTMHWVRQAPGKGLEWVSFISYDGNHKYYADSVKGRFTISRDNAKNSLYLQM NSLRAEDTAVYYCARTGHLGPFDLWGQGTMVTVSS/GKPGSGKPGSGKPGSGKPGS/EIVLTQSPGTLSLSPGERATLSCRAS QSVSSSYLAWYQQKPGQAPRLLIYGASSRATGIPDRFSGSGSGTDFTLTISRLEPEDFAVYYCQQYGSSPWTFGQGTKVEIK | 29107 |

Figure 12HH [CTLA-4]_H3.4_L0.132 (Fab XENP20355, scFv XENP20392)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNHKYYADSVKGRFTISRDNAKNSLYLQM NSLRAEDTAVYYCARTGHLGPFDLWGQGTMVTVSS | 29108 |
| vhCDR1 | SYTMH | 29109 |
| vhCDR2 | FISYDGNHKYYADSVKG | 29110 |
| vhCDR3 | TGHLGPFDL | 29111 |
| scFv linker | GKPGSGKPGSGKPGSGKPGS | 29112 |
| Variable light (vl) domain | EIVLTQSPATLSLSPGERATLSCRASQSVSSSYLAWYQQKPGQAPRLLIYGASSRAHGIPDRFSGSGSGTDFTLTISRLEPED FAVYYCQQYGSSPWTFGQGTKVEIK | 29113 |
| vlCDR1 | RASQSVSSSYLA | 29114 |
| vlCDR2 | GASSRAH | 29115 |
| vlCDR3 | QQYGSSPWT | 29116 |
| scFv | EVQLVESGGGLVKPGGSLRLSCAASGFTFSSYTMHWVRQAPGKGLEWVSFISYDGNHKYYADSVKGRFTISRDNAKNSLYLQM NSLRAEDTAVYYCARTGHLGPFDLWGQGTMVTVSS/GKPGSGKPGSGKPGSGKPGS/EIVLTQSPATLSLSPGERATLSCRAS QSVSSSYLAWYQQKPGQAPRLLIYGASSRAHGIPDRFSGSGSGTDFTLTISRLEPEDFAVYYCQQYGSSPWTFGQGTKVEIK | 29117 |

Figure 12II [CTLA-4]_H3.5_L2.1 (Fab XENP20357, scFv XENP20394)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARTGHLGPFDLWGQGTMVTVSS | 29118 |
| vhCDR1 | SYTMH | 29119 |
| vhCDR2 | FISYDGNTKYYADSVKG | 29120 |
| vhCDR3 | TGHLGPFDL | 29121 |
| scFv linker | GKPGSGKPGSGKPGSGKPGS | 29122 |
| Variable light (vl) domain | EIVMTQSPATLSVSPGERATLSCRASQSVGSSYLAWYQQKPGQAPRLLIYGAFSRATGIPARFSGSGSGTEFTLTISSLQSEDFAVYYCQQYGSSPWTFGQGTKVEIK | 29123 |
| vlCDR1 | RASQSVGSSYLA | 29124 |
| vlCDR2 | GAFSRAT | 29125 |
| vlCDR3 | QQYGSSPWT | 29126 |
| scFv | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARTGHLGPFDLWGQGTMVTVSS/GKPGSGKPGSGKPGSGKPGS/EIVMTQSPATLSVSPGERATLSCRASQSVGSSYLAWYQQKPGQAPRLLIYGAFSRATGIPARFSGSGSGTEFTLTISSLQSEDFAVYYCQQYGSSPWTFGQGTKVEIK | 29127 |

Figure 12JJ [CTLA-4]_H3.5_L2.2 (Fab XENP20358, scFv XENP20395)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARTGHLGPFDLWGQGTMVTVSS | 29128 |
| vhCDR1 | SYTMH | 29129 |
| vhCDR2 | FISYDGNTKYYADSVKG | 29130 |
| vhCDR3 | TGHLGPFDL | 29131 |
| scFv linker | GKPGSGKPGSGKPGSGKPGS | 29132 |
| Variable light (vl) domain | EIVMTQSPATLSVSPGERATLSCRASQSVGSSYLAWYQQKPGQAPRLLIYGASSRAKGIPARFSGSGSGTEFTLTISSLQSEDFAVYYCQQYGSSPWTFGQGTKVEIK | 29133 |
| vlCDR1 | RASQSVGSSYLA | 29134 |
| vlCDR2 | GASSRAT | 29135 |
| vlCDR3 | QQYGSSPWT | 29136 |
| scFv | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARTGHLGPFDLWGQGTMVTVSS/GKPGSGKPGSGKPGSGKPGS/EIVMTQSPATLSVSPGERATLSCRASQSVGSSYLAWYQQKPGQAPRLLIYGASSRAKGIPARFSGSGSGTEFTLTISSLQSEDFAVYYCQQYGSSPWTFGQGTKVEIK | 29137 |

Figure 12KK [CTLA-4]_H3.5_L2.3 (Fab XENP20359, scFv XENP20396)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARTGHLGPFDLWGQGTMVTVSS | 29138 |
| vhCDR1 | SYTMH | 29139 |
| vhCDR2 | FISYDGNTKYYADSVKG | 29140 |
| vhCDR3 | TGHLGPFDL | 29141 |
| scFv linker | GKPGSGKPGSGKPGSGKPGS | 29142 |
| Variable light (vl) domain | EIVMTQSPATLSVSPGERATLSCRASQSVGSSYLAWYQQKPGQAPRLLIYGASSRATGIPARFSGSGSGTEFTLTISSLQSEDFAVYYCQQYGSSPWTFGQGTKVEIK | 29143 |
| vlCDR1 | RASQSVGSSYLA | 29144 |
| vlCDR2 | GASSRAT | 29145 |
| vlCDR3 | QQYGSSPWT | 29146 |
| scFv | EVQLVESGGGLVKPGGSLRLSCAASGFTFSSYTMHWVRQAPGKGLEWVSFISYDGNTKYYADSVKGRFTISRDNAKNSLYLQMNSLRAEDTAVYYCARTGHLGPFDLWGQGTMVTVSS/GKPGSGKPGSGKPGSGKPGS/EIVMTQSPATLSVSPGERATLSCRASQSVGSSYLAWYQQKPGQAPRLLIYGASSRATGIPARFSGSGSGTEFTLTISSLQSEDFAVYYCQQYGSSPWTFGQGTKVEIK | 29147 |

Figure 12LL [CTLA-4]_H3_L0 (Fab XENP19546, scFv XENP19553)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGMLGPFDYWGQGTLVTVSS | 29148 |
| vhCDR1 | SYTMH | 29149 |
| vhCDR2 | FISYDGNNKYYADSVKG | 29150 |
| vhCDR3 | TGMLGPFDY | 29151 |
| scFv linker | GKPGSGKPGSGKPGSGKPGS | 29152 |
| Variable light (vl) domain | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 29153 |
| vlCDR1 | RASQSVGSSYLA | 29154 |
| vlCDR2 | GAFSRAT | 29155 |
| vlCDR3 | QQYGSSPWT | 29156 |
| scFv | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGMLGPFDYWGQGTLVTVSS/GKPGSGKPGSGKPGSGKPGS/EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 29157 |

Figure 12MM [CTLA-4]_H3_L0.22 (Fab XENP20011)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS | 29158 |
| vhCDR1 | SYTMH | 29159 |
| vhCDR2 | FISYDGNNKYYADSVKG | 29160 |
| vhCDR3 | TGWLGPFDY | 29161 |
| scFv linker | GKPGSGKPGSGKPGS | 29162 |
| Variable light (vl) domain | EIVLTQSPGTLSLSPGERATLSCRASQSVSSSYLAWYQQKPGQAPRLLIYGAFSRATGIPDRFSGSGSGTDFTLTISRLEPEDFAVYYCQQYGSSPWTFGQGTKVEIK | 29163 |
| vlCDR1 | RASQSVSSSYLA | 29164 |
| vlCDR2 | GAFSRAT | 29165 |
| vlCDR3 | QQYGSSPWT | 29166 |
| scFv | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS/GKPGSGKPGSGKPGS/EIVLTQSPGTLSLSPGERATLSCRASQSVSSSYLAWYQQKPGQAPRLLIYGAFSRATGIPDRFSGSGSGTDFTLTISRLEPEDFAVYYCQQYGSSPWTFGQGTKVEIK | 29167 |

Figure 12NN [CTLA-4]_H3_L0.44 (Fab XENP20052)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS | 29168 |
| vhCDR1 | SYTMH | 29169 |
| vhCDR2 | FISYDGNNKYYADSVKG | 29170 |
| vhCDR3 | TGWLGPFDY | 29171 |
| scFv linker | GKPGSGKPGSGKPGS | 29172 |
| Variable light (vl) domain | EIVLTQSPGTLSLSPGERATLSCRASQSVSSSYLSWYQQKPGQAPRLLIYGAFSRATGIPDRFSGSGSGTDFTLTISRLEPEDFAV YYCQQYGSSPWTFGQGTKVEIK | 29173 |
| vlCDR1 | RASQSVSSSYLS | 29174 |
| vlCDR2 | GAFSRAT | 29175 |
| vlCDR3 | QQYGSSPWT | 29176 |
| scFv | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS/GKPGSGKPGSGKPGS/EIVLTQSPGTLSLSPGERATLSCRASQSVSSSYLSWYQQKPGQAPRLLIYGAFSRATGIPDRFSGSGSGTDFTLTISRLEPEDFAVYYCQQYGSSPWTFGQGTKVEIK | 29177 |

Figure 12OO [CTLA-4] H3_L0.67 (Fab XENP20018)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS | 29178 |
| vhCDR1 | SYTMH | 29179 |
| vhCDR2 | FISYDGNNKYYADSVKG | 29180 |
| vhCDR3 | TGWLGPFDY | 29181 |
| scFv linker | GKPGSGKPGSGKPGSGKPGS | 29182 |
| Variable light (vl) domain | EIVLTQSPGTLSLSPGERATLSCKASQSVGSSYLAWYQQKPGQAPRLLIYDAFSRATGIPDRFSGSGSGTDFTLTISRLEPEDFAVYYCQQYGSSPWTFGQGTKVEIK | 29183 |
| vlCDR1 | RASQSVGSSYLA | 29184 |
| vlCDR2 | DAFSRAT | 29185 |
| vlCDR3 | QQYGSSPWT | 29186 |
| scFv | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS/GKPGSGKPGSGKPGSGKPGS/EIVLTQSPGTLSLSPGERATLSCKASQSVGSSYLAWYQQKPGQAPRLLIYDAFSRATGIPDRFSGSGSGTDFTLTISRLEPEDFAVYYCQQYGSSPWTFGQGTKVEIK | 29187 |

Figure 12PP [CTLA-4] H3_L0.74 (Fab XENP20020)

| What | sequence | SEQ ID NO: |
|---|---|---|
| Variable heavy (vh) domain | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS | 29188 |
| vhCDR1 | SYTMH | 29189 |
| vhCDR2 | FISYDGNNKYYADSVKG | 29190 |
| vhCDR3 | TGWLGPFDY | 29191 |
| scFv linker | GKPGSGKPGSGKPGSGKPGS | 29192 |
| Variable light (vl) domain | EIVLTQSPGTLSLSPGERATLSCRASQSVGSSYLAWYQQKPGQAPRLLIYGAYSRATGIPDRFSGSGSGTDFTLTISRLEPEDFAVYYCQQYGSSPWTFGQGTKVEIK | 29193 |
| vlCDR1 | RASQSVGSSYLA | 29194 |
| vlCDR2 | GAYSRAT | 29195 |
| vlCDR3 | QQYGSSPWT | 29196 |
| scFv | EVQLVESGGGLVKPGGSLRLSCAASGFTFSSYTMHWVRQAPGKGLEWVSFISYDGNNKYYADSVKGRFTISRDNAKNSLYLQMNSLRAEDTAVYYCARTGWLGPFDYWGQGTLVTVSS/GKPGSGKPGSGKPGSGKPGS/EIVLTQSPGTLSLSPGERATLSCRASQSVGSSYLAWYQQKPGQAPRLLIYGAYSRATGIPDRFSGSGSGTDFTLTISRLEPEDFAVYYCQQYGSSPWTFGQGTKVEIK | 29197 |

Figure 13A
7G8_H3.30_L1.34 (Fab XENP22594)

| What | sequence | SEQ ID NO: |
|---|---|---|
| Variable heavy (vh) domain | EVQLVESGGGLVQPGGSLRLSCAASGFTFDDAWMSWVRQAPGKGLEWVAEISTKANNHATYYAESVKGRFTISRDDSKSSVYLQMNSLRAEDTAVYYCTRLATWDWYFDVWGQGTTVTVSS | 29198 |
| vhCDR1 | DAWMS | 29199 |
| vhCDR2 | EISTKANNHATYYAESVKG | 29200 |
| vhCDR3 | LATWDWYFDV | 29201 |
| Variable light (vl) domain | DIVLTQSPSSLSASVGDRVTITCRASQSVDYDGDSYMNWYQQKPGKPPKLLIYAASELESGIPARFSGSGSGTDFTLTISSLQPEDFATYYCQQSNEDPFTFGSGTKLEIK | 29202 |
| vlCDR1 | RASQSVDYDGDSYMN | 29203 |
| vlCDR2 | AASELES | 29204 |
| vlCDR3 | QQSNEDPFT | 29205 |

Figure 13B
2A11_H1.144_L2.142 (Fab XENP22656)

| What | sequence | SEQ ID NO: |
|---|---|---|
| Variable heavy (vh) domain | EVQLVQSGAEVKKPGATVKISCKASGFNIKDYEMHWVQQAPGKGLEWMGWIDPELGDTEYAPKFQGRVTITADTSTNTAYMELSSLRSEDTAVYYCYARGVYQALDYWGQGTLVTVSS | 29206 |
| vhCDR1 | DYFMH | 29207 |
| vhCDR2 | WIDPELGDTEYAPKFQG | 29208 |
| vhCDR3 | RGVYQALDY | 29209 |
| Variable light (vl) domain | DIQMTQSPAFLSVTPGEKVTITCQASQDIGNYLNWFQQKPGQTVKLLIYFTSYLHSGVPSRFSGSGSGTDYTFTISSLEAEDRAATYFCQQGNTLFYTFGGGTKVEIK | 29210 |
| vlCDR1 | QASQDIGNYLN | 29211 |
| vlCDR2 | FTSYLHS | 29212 |
| vlCDR3 | QQGNTLFYT | 29213 |

Figure 13C
7G8_H3.18_L1.11 (Fab XENP21670)

| What | sequence | SEQ ID NO: |
|---|---|---|
| Variable heavy (vh) domain | EVQLVESGGGLVQPGGSLRLSCAASGFTFDDAWMDWVRQAPGKGLEWVAEISTKANNHATYYAESVK GRFTISRDDSKSSVYLQMNSLRAEDTAVYYCTRLANWDYFDVWGQGTTVTVSS | 29214 |
| vhCDR1 | DAWMD | 29215 |
| vhCDR2 | EISTKANNHATYYAESVKG | 29216 |
| vhCDR3 | LANWDYFDV | 29217 |
| Variable light (vl) domain | DIVLTQSPSSLSASVGDRVTITCRASQSVDYDGDSYMNWYQQKPGKPPKLLIYAASELESGIPARLS GSGSGTDFTLTISSLQPEDFATYYCQQSNEDPFTFGSGTKLEIK | 29218 |
| vlCDR1 | RASQSVDYDGDSYMN | 29219 |
| vlCDR2 | AASELES | 29220 |
| vlCDR3 | QQSNEDPFT | 29221 |

Figure 13D
2A11_H0L0 (Fab XENP20930)

| What | sequence | SEQ ID NO: |
|---|---|---|
| Variable heavy (vh) domain | EVKLEESGGGLVQPGGSMKLSCAASGFTFSDAWMDWVRQSPEKGLEWVAEIRTKANNHATYYAESVK GRFTISRDDSKSSVYLQMNSLRAEDTGIYYCTRLANWDYFDVWGAGTTVTVSS | 29222 |
| vhCDR1 | DAWMD | 29223 |
| vhCDR2 | EIRTKANNHATYYAESVKG | 29224 |
| vhCDR3 | LANWDYFDV | 29225 |
| Variable light (vl) domain | DIVLTQSPASLAVSLGQRATISCKASQSVDYDGDSYMNWYQQKPGQPPKLLIYAASNLESGIPARLS GSGSGTDFTLNIHPVEEEDAATYYCQQSNEDPFTFGSGTKLEVK | 29226 |
| vlCDR1 | KASQSVDYDGDSYMN | 29227 |
| vlCDR2 | AASNLES | 29228 |
| vlCDR3 | QQSNEDPFT | 29229 |

Figure 13E
2A11_H1.125_L2.113 (Fab XENP21921)

| What | sequence | SEQ ID NO: |
|---|---|---|
| Variable heavy (vh) domain | EVQLVQSGAEVKKPGATVKISCKASGFNIKHYFMHWVQQAPGKGLEWMGWIDPYLGDTEYAPKFQGR VTITADTSTNTAYMELSSLRSEDTAVYYCYARGVYQALDYWGQGTLVTVSS | 29230 |
| vhCDR1 | HYFMH | 29231 |
| vhCDR2 | WIDPYLGDTEYAPKFQG | 29232 |
| vhCDR3 | RGVYQALDY | 29233 |
| Variable light (vl) domain | DIQMTQSPAFLSVTPGEKVTITCQASQDIGNYLNWFQQKPDQTVKLLIYFTSYLHSGVPSRFSGSGS GTDYTFTISSLEAEDAATYFCQQGNTLPYTFGGGTKVEIK | 29234 |
| vlCDR1 | QASQDIGNYLN | 29235 |
| vlCDR2 | FTSYLHS | 29236 |
| vlCDR3 | QQGNTLPYT | 29237 |

Figure 13F
2A11_H1L2 (Fab XENP20847)

| What | sequence | SEQ ID NO: |
|---|---|---|
| Variable heavy (vh) domain | EVQLVQSGAEVKKPGATVKISCKASGFNIKDYYMHWVQQAPGKGLEWMGWIDPENGDTEYAPKFQGR VTITADTSTNTAYMELSSLRSEDTAVYYCYARGVRQALDYWGQGTLVTVSS | 29238 |
| vhCDR1 | DYYMH | 29239 |
| vhCDR2 | WIDPENGDTEYAPKFQG | 29240 |
| vhCDR3 | RGVRQALDY | 29241 |
| Variable light (vl) domain | DIQMTQSPAFLSVTPGEKVTITCQASQDIGNYLNWFQQKPDQTVKLLIYYTSRLHSGVPSRFSGSGS GTDYTFTISSLEAEDAATYFCQQGNTLPYTFGGGTKVEIK | 29242 |
| vlCDR1 | QASQDIGNYLN | 29243 |
| vlCDR2 | YTSRLHS | 29244 |
| vlCDR3 | QQGNTLPYT | 29245 |

Figure 13G
2A11_H1_L2.25 (Fab XENP21372)

| What | sequence | SEQ ID NO: |
|---|---|---|
| Variable heavy (vh) domain | EVQLVQSGAEVKKPGATVKISCKASGFNIKDYYMHWVQQAPGKGLEWMGWIDPENGDTEYAPKFQGR VTITADTSTNTAYMELSSLRSEDTAVYYCYAPGVRQALDYWGQGTLVTVSS | 29246 |
| vhCDR1 | DYYMH | 29247 |
| vhCDR2 | WIDPENGDTEYAPKFQG | 29248 |
| vhCDR3 | RGVRQALDY | 29249 |
| Variable light (vl) domain | DIQMTQSPAFLSVTPGEKVTITCQASQDIGNALNWFQQKPDQTVKLLIYYTSRLASGVPSRFSGSGS GTDYTFTISSLEAEDAATYFCQQGNTLPYTFGGGTKVEIK | 29250 |
| vlCDR1 | QASQDIGNALN | 29251 |
| vlCDR2 | YTSRLAS | 29252 |
| vlCDR3 | QQGNTLPYT | 29253 |

Figure 13H
2A11_H1_L2.47 (Fab XENP21394)

| What | sequence | SEQ ID NO: |
|---|---|---|
| Variable heavy (vh) domain | EVQLVQSGAEVKKPGATVKISCKASGFNIKDYYMHWVQQAPGKGLEWMGWIDPENGDTEYAPKFQGR VTITADTSTNTAYMELSSLRSEDTAVYYCYAPGVRQALDYWGQGTLVTVSS | 29254 |
| vhCDR1 | DYYMH | 29255 |
| vhCDR2 | WIDPENGDTEYAPKFQG | 29256 |
| vhCDR3 | RGVRQALDY | 29257 |
| Variable light (vl) domain | DIQMTQSPAFLSVTPGEKVTITCQASQDIGNYLNWFQQKPDQTVKLLIYYTSHLASGVPSRFSGSGS GTDYTFTISSLEAEDAATYFCQQGNTLPYTFGGGTKVEIK | 29258 |
| vlCDR1 | QASQDIGNYLN | 29259 |
| vlCDR2 | YTSHLAS | 29260 |
| vlCDR3 | QQGNTLPYT | 29261 |

Figure 13I
2A11_H1_L2.50 (Fab XENP21401)

| What | sequence | SEQ ID NO: |
|---|---|---|
| Variable heavy (vh) domain | EVQLVQSGAEVKKPGATVKISCKASGFNIKDYYMHWVQQAPGKGLEWMGWIDPENGDTEYAPKFQGR VTITADTSTNTAYMELSSLRSEDTAVYYCYARGVRQALDYWGQGTLVTVSS | 29262 |
| vhCDR1 | DYYMH | 29263 |
| vhCDR2 | WIDPENGDTEYAPKFQG | 29264 |
| vhCDR3 | RGVRQALDY | 29265 |
| Variable light (vl) domain | DIQMTQSPAFLSVTPGEKVTITCQASQDIGNYLNWFQQKPDQTVKLLIYYTSYLHSGVPSRFSGSGS GTDYTFTISSLEAEDAATYFCQQGNTLPYTFGGGTKVEIK | 29266 |
| vlCDR1 | QASQDIGNYLN | 29267 |
| vlCDR2 | YTSYLHS | 29268 |
| vlCDR3 | QQGNTLPYT | 29269 |

Figure 13J
2A11_H1L2 (Fab XENP20847)

| What | sequence | SEQ ID NO: |
|---|---|---|
| Variable heavy (vh) domain | EVQLVQSGAEVKKPGATVKISCKASGFNIKDYYMHWVQQAPGKGLEWMGWIDPENGDTEYAPKFQGR VTITADTSTNTAYMELSSLRSEDTAVYYCYARGVRQALDYWGQGTLVTVSS | 29270 |
| vhCDR1 | DYYMH | 29271 |
| vhCDR2 | WIDPENGDTEYAPKFQG | 29272 |
| vhCDR3 | RGVRQALDY | 29273 |
| Variable light (vl) domain | DIQMTQSPAFLSVTPGEKVTITCQASQDIGNYLNWFQQKPDQTVKLLIYYTSRLASGVPSRFSGSGS GTDYTFTISSLEAEDAATYFCQQGNTLPYTFGGGTKVEIK | 29274 |
| vlCDR1 | QASQDIGNYLN | 29275 |
| vlCDR2 | YTSRLAS | 29276 |
| vlCDR3 | QQGNTLPYT | 29277 |

Figure 13K
7G8_H3.23_L1.11 (Fab XENP21670)

| What | sequence | SEQ ID NO: |
|---|---|---|
| Variable heavy (vh) domain | EVQLVESGGGLVQPGGSLRLSCAASGFTFDDAWMDWVRQAPGKGLEWVAEISTKANNHATYYAESVKGRFTISRDDSKSSVYLQMNSLRAEDTAVYYCTRLATWDWYFDVWGQGTTVTVSS | 29278 |
| vhCDR1 | DAWMD | 29279 |
| vhCDR2 | EISTKANNHATYYAESVKG | 29280 |
| vhCDR3 | LATWDWYFDV | 29281 |
| Variable light (vl) domain | DTVLTQSPSSLSASVGDRVTITCRASQSVDYDGDSYMNWYQQKPGKPPKLLIYAASELESGIPARLSGSGSGTDFTLTISSLQPEDFATYYCQQSNEDPFTFGSGTKLEIK | 29282 |
| vlCDR1 | RASQSVDYDGDSYMN | 29283 |
| vlCDR2 | AASELES | 29284 |
| vlCDR3 | QQSNEDPFT | 29285 |

Figure 13L
7G8_H3.28_L1 (Fab XENP21892)

| What | sequence | SEQ ID NO: |
|---|---|---|
| Variable heavy (vh) domain | EVQLVESGGGLVQPGGSLRLSCAASGFTFDDAWMDWVRQAPGKGLEWVAEISTKAYNHATYYAESVKGRFTISRDDSKSSVYLQMNSLRAEDTAVYYCTRLATWDWYFDVWGQGTTVTVSS | 29286 |
| vhCDR1 | DAWMD | 29287 |
| vhCDR2 | EISTKAYNHATYYAESVKG | 29288 |
| vhCDR3 | LATWDWYFDV | 29289 |
| Variable light (vl) domain | DTVLTQSPSSLSASVGDRVTITCRASQSVDYDGDSYMNWYQQKPGKPPKLLIYAASNLESGIPARLSGSGSGTDFTLTISSLQPEDFATYYCQQSNEDPFTFGSGTKLEIK | 29290 |
| vlCDR1 | RASQSVDYDGDSYMN | 29291 |
| vlCDR2 | AASNLES | 29292 |
| vlCDR3 | QQSNEDPFT | 29293 |

Figure 13M
7G8_H3.28_L1.11 (Fab XENP21893)

| What | sequence | SEQ ID NO: |
|---|---|---|
| Variable heavy (vh) domain | EVQLVESGGGLVQPGGSLRLSCAASGFTFDDAWMDWVRQAPGKGLEWVARISTKAYNHATYYAESVK GRFTISRDDSKSSVYLQMNSLRAEDTAVYYCTRLATWDWYFDVWGQGTTVTVSS | 29294 |
| vhCDR1 | DAWMD | 29295 |
| vhCDR2 | EISTKAYNHATYYAESVKG | 29296 |
| vhCDR3 | LATWDWYFDV | 29297 |
| Variable light (vl) domain | DTVLTQSPSSLSASVGDRVTITCRASQSVDYDGDSYMNWYQQKPGKPPKLLIYAASELESGIPARLS GSGSGTDFTLTISSLQPEDFATYYCQQSNEDPFTFGSGTKLEIK | 29298 |
| vlCDR1 | RASQSVDYDGDSYMN | 29299 |
| vlCDR2 | AASELES | 29300 |
| vlCDR3 | QQSNEDPFT | 29301 |

Figure 13N
7G8_H3.28_L1.13 (Fab XENP21894)

| What | sequence | SEQ ID NO: |
|---|---|---|
| Variable heavy (vh) domain | EVQLVESGGGLVQPGGSLRLSCAASGFTFDDAWMDWVRQAPGKGLEWVARISTKAYNHATYYAESVK GRFTISRDDSKSSVYLQMNSLRAEDTAVYYCTRLATWDWYFDVWGQGTTVTVSS | 29302 |
| vhCDR1 | DAWMD | 29303 |
| vhCDR2 | EISTKAYNHATYYAESVKG | 29304 |
| vhCDR3 | LATWDWYFDV | 29305 |
| Variable light (vl) domain | DTVLTQSPSSLSASVGDRVTITCRASQSVDHDGDSYMNWYQQKPGKPPKLLIYAASELESGIPARLS GSGSGTDFTLTISSLQPEDFATYYCQQSNEDPFTFGSGTKLEIK | 29306 |
| vlCDR1 | RASQSVDHDGDSYMN | 29307 |
| vlCDR2 | AASELES | 29308 |
| vlCDR3 | QQSNEDPFT | 29309 |

Figure 14A (anti-TIM3 variable heavy and light chains + CDRs)

| What: anti-TIM3 XENP21503 1D10_H0L0 | sequence | SEQ ID NO: |
|---|---|---|
| Variable heavy (vh) domain | EVQLVESGGGLVKPGGSLKFSCAASGFAFSSFDMSWVRQTPEKRLEWVAYISSDGASTFYPDTMKGRFTI SRDNAKNTLYLQMSSLKSEDTAMYYCTRLGAYWGQGTLVTVSA | 29310 |
| vhCDR1 | SFDM | 29311 |
| vhCDR2 | YISSDGASTFYPDTMKG | 29312 |
| vhCDR3 | LGAY | 29313 |
| Variable light (vl) domain | DVVMTQTPLTLSVTIGQPASISCKSSQSLLDSDGKTYLNWLLQRPGQSPKRLIYLVSKLDSGVPDRFTGS GSGTDFTIKISRVEAEDLGVYYCWQGTHFPYTFGGGTKLEIK | 29314 |
| vlCDR1 | KSSQSLLDSDGKTYLN | 29315 |
| vlCDR2 | VSKLDS | 29316 |
| vlCDR3 | WQGTHFPYT | 29317 |

Figure 14B

| What: anti-TIM3 XENP21492 1D12_H0L0 | sequence | SEQ ID NO: |
|---|---|---|
| Variable heavy (vh) domain | EVQLVESGGGLVKPGGSLKFSCAASGFAFSSFDMSWVRQTPEKRLEWVAYISSDGASTFYPDTMKGRFTI SRDNAKNTLYLQMSSLKSEDTAMYYCTRLGAYWGQGTLVTVSA | 29318 |
| vhCDR1 | SFDMS | 29319 |
| vhCDR2 | YISSDGASTFYPDTMKG | 29320 |
| vhCDR3 | LGAY | 29321 |
| Variable light (vl) domain | DIVLTQSPASLAVSLGQRATISCRASESVEYYGTSLMQWYQQKPGQPPKLLIYAASNVESGVPARFSGSG SGTDFSLNIHPVEEDDIAMYFCQQSRKVPWTFGGGTKLEIK | 29322 |
| vlCDR1 | RASESVEYYGTSLQ | 29323 |
| vlCDR2 | AASNVES | 29324 |
| vlCDR3 | QQSRKVPWT | 29325 |

Figure 14C (anti-TIM3 variable heavy and light chains + CDRs)

| What: anti-TIM3 XENP21189 3H3_H1L2.1 | sequence | SEQ ID NO: |
|---|---|---|
| Variable heavy (vh) domain | QVTLKESGPVLVKPTETLTLTCTVSGFSLNGYGVNWVRQPPGKGLEWLAMIWGDGSTDYNSALKSRLTIS KDNSKSQVVLTMTNMDPVDTATYYCARSYYTSDEDYWGQGTLVTVSS | 29326 |
| vhCDR1 | GYGVN | 29327 |
| vhCDR2 | MIWGDGSTDYNSALKS | 29328 |
| vhCDR3 | SYYTSDEDY | 29329 |
| Variable light (vl) domain | DIVMTQSPDSLAVSLGERATINCKSSQSLLNSRTRKNYLAWYQQKPGQSPKLLIYWASTRESGVPDRFTG SGSGTDFTLTISSLQAEDVAVYYCKQSYSLRTFGGGTKVEIK | 29330 |
| vlCDR1 | KSSQSLLNSRTRKNYLA | 29331 |
| vlCDR2 | WASTRES | 29332 |
| vlCDR3 | KQSYSLRT | 29333 |

Figure 14D

| What: anti-TIM3 XENP21493 6C8_H0L0 | sequence | SEQ ID NO: |
|---|---|---|
| Variable heavy (vh) domain | QVQLKESGPGLVAPSQSLSITCTVSGFSLNGYGVNWVRQPPGKGLEWLGMIWGDGSTDYNSALKSRLSIS KDNSKSQVFLKMNSLQTDDTARYYCARSYYTSDEDYWGQGTLVTVSA | 29334 |
| vhCDR1 | GYGVN | 29335 |
| vhCDR2 | MIWGDGSTDYNSALKS | 29336 |
| vhCDR3 | SYYTSDEDY | 29337 |
| Variable light (vl) domain | DIVMTQSQKFMSTSVGDRVSVTCKASQNVGSNVAWCQQKPGQSPKALIYSASFRYSGVPDRFTGSGSGTD FTLTISNVQSEDLAEYFCQQYNSYPYTFGGGTKLEIK | 29338 |
| vlCDR1 | KASQNVGSNVA | 29339 |
| vlCDR2 | SASFRYS | 29340 |
| vlCDR3 | QQYNSYPYT | 29341 |

Figure 14E (anti-TIM3 variable heavy and light chains + CDRs)

| What: anti-TIM3 XENP21494 6D9H0_1D12_0 | sequence | SEQ ID NO: |
|---|---|---|
| Variable heavy (vh) domain | QVQLKQSGPGLVQPSQSLSITCTVSGFSLTSYGVHWVRQSPGKGLEWLGVIWSGGSTEYNAAFISRLSIS KDNSKSQVFFKMNSLQADDTAIYYCARGGLLSPFDYWGQGTTLTVSS | 29342 |
| vhCDR1 | SYGVH | 29343 |
| vhCDR2 | VIWSGGSTEYNAAFIS | 29344 |
| vhCDR3 | GGLLSPFDY | 29345 |
| Variable light (vl) domain | DIVLTQSPASLAVSLGQRATISCPASESVEYYGTSLMQWYQQKPGQPPKLLIYAASNVESGVPARFSGSG SGTDFSLNIHPVEEDIAMYFCQQSRKVPWTFGGGTKLEIK | 29346 |
| vlCDR1 | RASESVEYYGTSLMQ | 29347 |
| vlCDR2 | AASNVES | 29348 |
| vlCDR3 | QQSRKVPWT | 29349 |

Figure 14F

| What: anti-TIM3 XENP21495 7A9_H0L0 | sequence | SEQ ID NO: |
|---|---|---|
| Variable heavy (vh) domain | EVKLLESGGGLVQPGGSLKLSCAASGFDFSRYWMSWVRQAPGKGLEWIGEINPDSSTINYTPSLKDKFLI SRDNAKNTLYLQMSKVRSEDTALYYCARFNGYYVGTIFPFAYWGQGTLVTVSA | 29350 |
| vhCDR1 | RYWMS | 29351 |
| vhCDR2 | EINPDSSTINYTPSLKD | 29352 |
| vhCDR3 | FNGYYVGTIFPFAY | 29353 |
| Variable light (vl) domain | QAVVTQESALTTSPGETVTLTCRSSTGAVTTSNYANWVQEKPDHLFTGLIGGTNNRAPGVPARFSGSLIG DKAALTITGAQTEDEAIYFCALWYSNHWVFGGGTKLTVLG | 29354 |
| vlCDR1 | RSSTGAVTTSNYAN | 29355 |
| vlCDR2 | GTNNRAP | 29356 |
| vlCDR3 | ALWYSNHWV | 29357 |

Figure 14G (anti-TIM3 variable heavy and light chains + CDRs)

| What: anti-TIM3 XENP21496 7B11_HOLO | sequence | SEQ ID NO: |
|---|---|---|
| Variable heavy (vh) domain | QVQLKQSGPGLVQPSQSLSITCTVSGFSLTSYAVNWVRQSPGKGLEWLGVIWSGGSTDYNAAFISRLSIS KDNSKSQVFFKMNSLQANDTAIYYCVSLYYRYDGFDYWGQGTLVTVSA | 29358 |
| vhCDR1 | SYAVN | 29359 |
| vhCDR2 | VIWSGGSTDYNAAFIS | 29360 |
| vhCDR3 | LYYRYDGFDY | 29361 |
| Variable light (vl) domain | DIVLTQSQKFLSTSVGDRVSVTCKASQNVGTHVARYQQKPGQSPKALVYSASYRYSGVPDRFTGSGSGTD FTLTISNVQSEDLAEYFCQQYNSYPLTFGGGTKLEIK | 29362 |
| vlCDR1 | KASQNVGTHVA | 29363 |
| vlCDR2 | SASYRYS | 29364 |
| vlCDR3 | QQYNSYPLT | 29365 |

Figure 14H

| What: anti-TIM3 XENP21501 B11var_HOLO | sequence | SEQ ID NO: |
|---|---|---|
| Variable heavy (vh) domain | QVQLKQSGPGLVQPSQSLSITCTVSGFSLTSYAVNWVRQSPGKGLEWLGVIWSGGSTDYNAAFISRLSIS KDNSKSQVFFKMNSLQADDTAIYYCVSLYYRYDGFDYWGQGTLVTVSA | 29366 |
| vhCDR1 | SYAVN | 29367 |
| vhCDR2 | VIWSGGSTDYNAAFIS | 29368 |
| vhCDR3 | LYYRYDGFDY | 29369 |
| Variable light (vl) domain | DIVLTQSQKFLSTSVGDRVSVTCKASQNVGTHVARYQQKPGQSPKALVYSASYRYSGVPDRFTGSGSGTD FTLTISNVQSEDLAEYFCQQYNSYPLTFGGGTKLEIK | 29370 |
| vlCDR1 | KASQNVGTHVA | 29371 |
| vlCDR2 | SASYRYS | 29372 |
| vlCDR3 | QQYNSYPLT | 29373 |

Figure 14I (anti-TIM3 variable heavy and light chains + CDRs)

| What: anti-TIM3 XENP21502 7C2_H0L0 | sequence | SEQ ID NO: |
|---|---|---|
| Variable heavy (vh) domain | EVKVVESGGGLVKPGGSLKLSCAASGFTFSRYAMSWVRQTPEKRLEWVASISSGGSTYYPDSVQGRFTIS RDNARNILYLQMSSLRSEDTAMYYCARGDYEGYFDYWGQGTSLTVSS | 29374 |
| vhCDR1 | RYAMS | 29375 |
| vhCDR2 | SISSGGSTYYPDSVQG | 29376 |
| vhCDR3 | GDYEGYFDY | 29377 |
| Variable light (vl) domain | DIVMTQSPSSLAMSVGQKVTMSCKSSQSLLNSINQKNYLAWYQQKPGQSPKLLVYFASTRESGVPDRFIG SGSGTDFTLTISSVQAEDLADYFCQQHYSTPLTFGAGTKLELK | 29378 |
| vlCDR1 | KSSQSLLNSINQKNYLA | 29379 |
| vlCDR2 | FASTRES | 29380 |
| vlCDR3 | QQHYSTPLT | 29381 |

Figure 15A

XENP016434 YW243.55.S70[PD-L1]_H0L0_IgG1_PVA_/S267K

| What | sequence | SEQ ID NO: |
|---|---|---|
| Variable heavy (vh) domain | EVQLVESGGGLVQPGGSLRLSCAASGFTFSDSWIHWVRQAPGKGLEWVAWISPYGGSTYYADSVKGRFTISADTSKNTAYLQMNSLR AEDTAVYYCARRHWPGGFDYWGQGTLVTVSS | 29382 |
| vhCDR1 | DSWIH | 29383 |
| vhCDR2 | WISPYGGSTYYADSVKG | 29384 |
| vhCDR3 | RHWPGGFDY | 29385 |
| Full length HC | EVQLVESGGGLVQPGGSLRLSCAASGFTFSDSWIHWVRQAPGKGLEWVAWISPYGGSTYYADSVKGRFTISADTSKNTAYLQMNSLR AEDTAVYYCARRHWPGGFDYWGQGTLVTVSS/ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCDKTHTCPPCPAPPVAGPSVFLFPPKPKDTLMISRTPEVTCVVVD VKHEDPEVKFNWYVDGVEVHNAKTKPREEQYNSTYRVVSVLTVLHQDWLNGKEYKCKVSNKALPAPIEKTISKAKGQPREPQVYTLPP SREEMTKNQVSLTCLVKGFYPSDIAVEWESNGQPENNYKTTPPVLDSDGSFFLYSKLTVDKSRWQQGNVFSCSVMHEALHNHYTQKS LSLSPGK | 29386 |
| Variable light (vl) domain | DIQMTQSPSSLSASVGDRVTITCRASQDVSTAVAWYQQKPGKAPKLLIYSASFLYSGVPSRFSGSGSGTDFTLTISSLQPEDFATYYCQQY LYHPATFGQGTKVEIK | 29387 |
| vlCDR1 | RASQDVSTAVA | 29388 |
| vlCDR2 | SASFLYS | 29389 |
| vlCDR3 | QQYLYHPAT | 29390 |
| Full length light chain | DIQMTQSPSSLSASVGDRVTITCRASQDVSTAVAWYQQKPGKAPKLLIYSASFLYSGVPSRFSGSGSGTDFTLTISSLQPEDFATYYCQQY LYHPATFGQGTKVEIK/RTVAAPSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC | 29391 |

Figure 15B

XENP024118 avelumab[PD-L1]_H1L1_IgG1_PVA_/S267K

| What | sequence | SEQ ID NO: |
|---|---|---|
| Variable heavy (vh) domain | EVQLLESGGGLVQPGGSLRLSCAASGFTFSSYIMMWVRQAPGKGLEWVSSIYPSGGITFYADTVKGRFTISRDNSKNTLYLQMNSLRAEDTAVYYCARIKLGTVTTVDYWGQGTLVTVSS | 29392 |
| vhCDR1 | SYIMM | 29393 |
| vhCDR2 | SIYPSGGITFYADTVKG | 29394 |
| vhCDR3 | IKLGTVTTVDY | 29395 |
| Full length HC | EVQLLESGGGLVQPGGSLRLSCAASGFTFSSYIMMWVRQAPGKGLEWVSSIYPSGGITFYADTVKGRFTISRDNSKNTLYLQMNSLRAEDTAVYYCARIKLGTVTTVDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 29396 |
| Variable light (vl) domain | QSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTRVFGTGTKVTVL | 29397 |
| vlCDR1 | TGTSSDVGGYNYVS | 29398 |
| vlCDR2 | DVSNRPS | 29399 |
| vlCDR3 | SSYTSSSTRV | 29400 |
| Full length light chain | QSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTRVFGTGTKVTVL/GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 29401 |

Figure 15C

XENP024119 durvalumab[PD-L1]_H1L1_IgG1_PVA_/S267K

| What | sequence | SEQ ID NO: |
|---|---|---|
| Variable heavy (vh) domain | EVQLVESGGGLVQPGGSLRLSCAASGFTFSRYWMSWVRQAPGKGLEWVANIKQDGSEKYYVDSVKGRFTISRDNAKNSLYLQMNSL RAEDTAVYYCAREGGWFGELAFDYWGQGTLVTVSS | 29402 |
| vhCDR1 | RYWMS | 29403 |
| vhCDR2 | NIKQDGSEKYYVDSVKG | 29404 |
| vhCDR3 | EGGWFGELAFDY | 29405 |
| Full length HC | EVQLVESGGGLVQPGGSLRLSCAASGFTFSRYWMSWVRQAPGKGLEWVANIKQDGSEKYYVDSVKGRFTISRDNAKNSLYLQMNSL RAEDTAVYYCAREGGWFGELAFDYWGQGTLVTVSS/ASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTCPPCPAPPVAGPSVFLFPPKPKDTLMISRTPEVTC VVVDVKHEDPEVKFNWYVDGVEVHNAKTKPREEQYNSTYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVLDSDGSFFLYSKLTVDKSRWQQGNVFSCSVMHEALHNH YTQKSLSLSPGK | 29406 |
| Variable light (vl) domain | EIVLTQSPGTLSLSPGERATLSCRASQRVSSSYLAWYQQKPGQAPRLLIYDASSRATGIPDRFSGSGSGTDFTLTISRLEPEDFAVYYCQQY GSLPWTFGQGTKVEIK | 29407 |
| vlCDR1 | RASQRVSSSYLA | 29408 |
| vlCDR2 | DASSRAT | 29409 |
| vlCDR3 | QQYGSLPWT | 29410 |
| Full length light chain | EIVLTQSPGTLSLSPGERATLSCRASQRVSSSYLAWYQQKPGQAPRLLIYDASSRATGIPDRFSGSGSGTDFTLTISRLEPEDFAVYYCQQY GSLPWTFGQGTKVEIK/RTVAAPSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC | 29411 |

Figure 16

XENP014410 20H4.9[4-1BB]_H0L0_IgG1_PVA_/S267K

| What | sequence | SEQ ID NO: |
|---|---|---|
| Variable heavy (vh) domain | QVQLQQWGAGLLKPSETLSLTCAVYGGSFSGYYWSWIRQSPEKGLEWIGEINHGGYVTYNPSLESRVTISVDTSKNQFSLKLSSVTAAD TAVYYCARDYGPGNYDWYFDLWGRGTLVTVSS | 29412 |
| vhCDR1 | GYYWS | 29413 |
| vhCDR2 | EINHGGYVTYNPSLES | 29414 |
| vhCDR3 | DYGPGNYDWYFDL | 29415 |
| Full length HC | QVQLQQWGAGLLKPSETLSLTCAVYGGSFSGYYWSWIRQSPEKGLEWIGEINHGGYVTYNPSLESRVTISVDTSKNQFSLKLSSVTAAD TAVYYCARDYGPGNYDWYFDLWGRGTLVTVSSASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCPPCPAPPVAGPSVFLFPPKPKDTLMISRTPEVTCVVV DVKHEDPEVKFNWYVDGVEVHNAKTKPREEQYNSTYRVVSVLTVLHQDWLNGKEYKCKVSNKALPAPIEKTISKAKGQPREPQVYTLP PSREEMTKNQVSLTCLVKGFYPSDIAVEWESNGQPENNYKTTPPVLDSDGSFFLYSKLTVDKSRWQQGNVFSCSVMHEALHNHYTQK SLSLSPGK | 29416 |
| Variable light (vl) domain | EIVLTQSPATLSLSPGERATLSCRASQSVSSYLAWYQQKPGQAPRLLIYDASNRATGIPARFSGSGSGTDFTLTISSLEPEDFAVYYCQQRS NWPPALTFGGGTKVEIK | 29417 |
| vlCDR1 | RASQSVSSYLA | 29418 |
| vlCDR2 | DASNRAT | 29419 |
| vlCDR3 | QQRSNWPPALT | 29420 |
| Full length light chain | EIVLTQSPATLSLSPGERATLSCRASQSVSSYLAWYQQKPGQAPRLLIYDASNRATGIPARFSGSGSGTDFTLTISSLEPEDFAVYYCQQRS NWPPALTFGGGTKVEIKRTVAAPSVFIFPPSDEQLKSGTASVVCLLNNFYPREAKVQWKVDNALQSGNSQESVTEQDSKDSTYSLSST LTLSKADYEKHKVYACEVTHQGLSSPVTKSFNRGEC | 29421 |

Figure 17

XENP016437 11D4[OX40]_H0L0_IgG1_PVA_/5267K

| What | sequence | SEQ ID NO: |
|---|---|---|
| Variable heavy (vh) domain | EVQLVESGGGLVQPGGSLRLSCAASGFTFSSYSMNWVRQAPGKGLEWVSYISSSSSTIDYADSVKGRFTISRDNAKNSLYLQMNSLRDEDTAVYYCARESGWYLFDYWGQGTLVTVSS | 29422 |
| vhCDR1 | SYSMN | 29423 |
| vhCDR2 | YISSSSTIDYADSVKG | 29424 |
| vhCDR3 | ESGWYLFDY | 29425 |
| Full length HC | EVQLVESGGGLVQPGGSLRLSCAASGFTFSSYSMNWVRQAPGKGLEWVSYISSSSSTIDYADSVKGRFTISRDNAKNSLYLQMNSLRDEDTAVYYCARESGWYLFDYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 29426 |
| Variable light (vl) domain | DIQMTQSPSSLSASVGDRVTITCRASQGISSWLAWYQQKPEKAPKSLIYAASSLQSGVPSRFSGSGSGTDFTLTISSLQPEDFATYYCQQYNSYPPTFGGGTKVEIK | 29427 |
| vlCDR1 | RASQGISSWLA | 29428 |
| vlCDR2 | AASSLQS | 29429 |
| vlCDR3 | QQYNSYPPT | 29430 |
| Full length light chain | DIQMTQSPSSLSASVGDRVTITCRASQGISSWLAWYQQKPEKAPKSLIYAASSLQSGVPSRFSGSGSGTDFTLTISSLQPEDFATYYCQQYNSYPPTFGGGTKVEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 29431 |

Figure 18

XENP016438 1D8[GITR]_H0L0_IgG1_PVA_/S267K

| What | sequence | SEQ ID NO: |
|---|---|---|
| Variable heavy (vh) domain | QVTLKESGPGILKPSQTLSLTCSFSGFSLSTSGMGVGWIRQPSGKGLEWLAHIWWDDDKYYSPSLKSQLTISKDTSRNQVFLKITSLDTA DTATYYCVRSYYYGSSGAMDYWGQGTSVTVSS | 29432 |
| vhCDR1 | TSGMGVG | 29433 |
| vhCDR2 | HIWWDDDKYYSPSLKS | 29434 |
| vhCDR3 | SYYYGSSGAMDY | 29435 |
| Full length HC | QVTLKESGPGILKPSQTLSLTCSFSGFSLSTSGMGVGWIRQPSGKGLEWLAHIWWDDDKYYSPSLKSQLTISKDTSRNQVFLKITSLDTA DTATYYCVRSYYYGSSGAMDYWGQGTSVTVSS/ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCPPCPAPPVAGPSVFLFPPKPKDTLMISRTPEVTCVVV DVKHEDPEVKFNWYVDGVEVHNAKTKPREEQYNSTYRVVSVLTVLHQDWLNGKEYKCKVSNKALPAPIEKTISKAKGQPREPQVYTLP PSREEMTKNQVSLTCLVKGFYPSDIAVEWESNGQPENNYKTTPPVLDSDGSFFLYSKLTVDKSRWQQGNVFSCSVMHEALHNHYTQK SLSLSPGK | 29436 |
| Variable light (vl) domain | DIVMTQTPLSLPVSLGDQASISCRSSQSLVHSDGNTYLHWYLQKPGQSPKLLIYKVSKRFSGVPDRFSGSGSGTDFTLKISRVEAEDLGVY FCSQSTHVPPTFGGGTKLEIK | 29437 |
| vlCDR1 | RSSQSLVHSDGNTYLH | 29438 |
| vlCDR2 | KVSKRFS | 29439 |
| vlCDR3 | SQSTHVPPT | 29440 |
| Full length light chain | DIVMTQTPLSLPVSLGDQASISCRSSQSLVHSDGNTYLHWYLQKPGQSPKLLIYKVSKRFSGVPDRFSGSGSGTDFTLKISRVEAEDLGVY FCSQSTHVPPTFGGGTKLEIK/RTVAAPSVFIFPPSDEQLKSGTASVVCLLNNFYPREAKVQWKVDNALQSGNSQESVTEQDSKDSTYSL SSTLTLSKADYEKHKVYACEVTHQGLSSPVTKSFNRGEC | 29441 |

Figure 19A

XENP016435 [anti-ICOS]_H0L0_IgG1_PVA_/S267K

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYDSSGYYHDAFDIWGQGTMVTVSS | 29442 |
| vhCDR1 | GYYMH | 29443 |
| vhCDR2 | WINPHSGGTNYAQKFQG | 29444 |
| vhCDR3 | TYYDSSGYYHDAFDI | 29445 |
| Full length HC | QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYDSSGYYHDAFDIWGQGTMVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 29446 |
| Variable light (vl) domain | DIQMTQSPSSVSASVGDRVTITCRASQGISRLLAWYQQKPGKAPKLLIYVASSLQSGVPSRFSGSGSGTDFTLTISSLQPEDFATYYCQQANSFPWTFGQGTKVEIK | 29447 |
| vlCDR1 | RASQGISRLLA | 29448 |
| vlCDR2 | VASSLQS | 29449 |
| vlCDR3 | QQANSFPWT | 29450 |
| Full length light chain | DIQMTQSPSSVSASVGDRVTITCRASQGISRLLAWYQQKPGKAPKLLIYVASSLQSGVPSRFSGSGSGTDFTLTISSLQPEDFATYYCQQANSFPWTFGQGTKVEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 29451 |

Figure 19B

XENP021820 GSK_314.8[IC0S]_H0L0_IgG1_PVA_/S267K

| What | sequence | SEQ ID NO: |
|---|---|---|
| Variable heavy (vh) domain | QVQLQQPGTELMKPGASVKLSCKASGYTFTTYWMHWVKQRPGQGLEWIGEIDPSDSYVNYNQNFKGKATLTVDKSSSTAYIQLSSLT SEDSAVYFCARSPDYYGTSLAWFDYWGQGTLVTVST | 29452 |
| vhCDR1 | TYWMH | 29453 |
| vhCDR2 | EIDPSDSYVNYNQNFKG | 29454 |
| vhCDR3 | SPDYYGTSLAWFDY | 29455 |
| Full length HC | QVQLQQPGTELMKPGASVKLSCKASGYTFTTYWMHWVKQRPGQGLEWIGEIDPSDSYVNYNQNFKGKATLTVDKSSSTAYIQLSSLT SEDSAVYFCARSPDYYGTSLAWFDYWGQGTLVTVST/ASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTCPPCPAPPVAGPSVFLFPPKPKDTLMISRTPEVTC VVVDVKHEDPEVKFNWYVDGVEVHNAKTKPREEQYNSTYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVLDSDGSFFLYSKLTVDKSRWQQGNVFSCSVMHEALHNH YTQKSLSLSPGK | 29456 |
| Variable light (vl) domain | DIVMTQAAPSVPVTPGESVSISCRSSKSPLHSNGNIYLYWFLQRPGQSPQLLIYRMSNLASGVPDRFSGSGSGTTFTLKISRVEAEDVGV YYCMQHLEYPYTFGGGTKLEIK | 29457 |
| vlCDR1 | RSSKSPLHSNGNIYLY | 29458 |
| vlCDR2 | RMSNLAS | 29459 |
| vlCDR3 | MQHLEYPYT | 29460 |
| Full length light chain | DIVMTQAAPSVPVTPGESVSISCRSSKSPLHSNGNIYLYWFLQRPGQSPQLLIYRMSNLASGVPDRFSGSGSGTTFTLKISRVEAEDVGV YYCMQHLEYPYTFGGGTKLEIK/RTVAAPSVFIFPPSDEQLKSGTASVVCLLNNFYPREAKVQWKVDNALQSGNSQESVTEQDSKDSTY SLSSTLTLSKADYEKHKVYACEVTHQGLSSPVTKSFNRGEC | 29461 |

Figure 19C

XENP021821 GSK_88.2[ICOS]_H0L0_IgG1_PVA_/S267K

| What | sequence | SEQ ID NO: |
|---|---|---|
| Variable heavy (vh) domain | QVQLQQPGAELVRPGASVKLSCKASGYSFTSYWINWVKQRPGQGLEWIGNIYPSDSYTNYNQMFKDKATLTVDKSSNTAYMQLTSP TSEDSAVYYCTRWNLSYFDNNYYLDYWGQGTTLTVSS | 29462 |
| vhCDR1 | SYWIN | 29463 |
| vhCDR2 | NIYPSDSYTNYNQMFKD | 29464 |
| vhCDR3 | WNLSYYFDNNYYLDY | 29465 |
| Full length HC | QVQLQQPGAELVRPGASVKLSCKASGYSFTSYWINWVKQRPGQGLEWIGNIYPSDSYTNYNQMFKDKATLTVDKSSNTAYMQLTSP TSEDSAVYYCTRWNLSYFDNNYYLDYWGQGTTLTVSS/ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEPKSCDKTHTCPPCPAPPVAGPSVFLFPPKPKDTLMISRTPEV TCVVVDVKHEDPEVKFNWYVDGVEVHNAKTKPREEQYNSTYRVVSVLTVLHQDWLNGKEYKCKVSNKALPAPIEKTISKAKGQPREP QVYTLPPSREEMTKNQVSLTCLVKGFYPSDIAVEWESNGQPENNYKTTPPVLDSDGSFFLYSKLTVDKSRWQQGNVFSCSVMHEALH NHYTQKSLSLSPGK | 29466 |
| Variable light (vl) domain | DIVMTQAAPSVPVTPGESVSISCRSSKSLLHSNGNTYLYWFLQRPGQSPQLLIYRMSNLASGVPDRFSGSGSGTAFTLRISRVEAEDVGV YCMQHLEYPWTFGGGTKLEIK | 29467 |
| vlCDR1 | RSSKSLLHSNGNTYLY | 29468 |
| vlCDR2 | RMSNLAS | 29469 |
| vlCDR3 | MQHLEYPWT | 29470 |
| Full length light chain | DIVMTQAAPSVPVTPGESVSISCRSSKSLLHSNGNTYLYWFLQRPGQSPQLLIYRMSNLASGVPDRFSGSGSGTAFTLRISRVEAEDVGV YCMQHLEYPWTFGGGTKLEIK/RTVAAPSVFIFPPSDEQLKSGTASVVCLLNNFYPREAKVQWKVDNALQSGNSQESVTEQDSKDST YSLSSTLTLSKADYEKHKVYACEVTHQGLSSPVTKSFNRGEC | 29471 |

Figure 19D

XENP021822 jMab-138[ICOS]_H0L0_IgG1_PVA_/S267K

| What | sequence | SEQ ID NO: |
|---|---|---|
| Variable heavy (vh) domain | EVQLVESGGGLVQPGGSLRLSCAASGFTFSSYDMHWVRQATGKGLEWVSAIGTAGDTYYPGSVKGRFTISRENAKNSLYLQMNSLRAGDTAVYYCVRDNRKVTHEHYYYGMDVWGQGTTVTVSS | 29472 |
| vhCDR1 | SYDMH | 29473 |
| vhCDR2 | AIGTAGDTYYPGSVKG | 29474 |
| vhCDR3 | DNRKVTHEHYYYGMDV | 29475 |
| Full length HC | EVQLVESGGGLVQPGGSLRLSCAASGFTFSSYDMHWVRQATGKGLEWVSAIGTAGDTYYPGSVKGRFTISRENAKNSLYLQMNSLRAGDTAVYYCVRDNRKVTHEHYYYGMDVWGQGTTVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 29476 |
| Variable light (vl) domain | EIVLTQSPGTLSLSPGERATLSCRASQNIRSSYLAWYQQKPGQAPGLLIYGASSRATGIPDRFSGSGSGTDFTLTISRLEPEDFAVYYCQQFGSSPMCSFGQGTKLEIK | 29477 |
| vlCDR1 | RASQNIRSSYLA | 29478 |
| vlCDR2 | GASSRAT | 29479 |
| vlCDR3 | QQFGSSPMCS | 29480 |
| Full length light chain | EIVLTQSPGTLSLSPGERATLSCRASQNIRSSYLAWYQQKPGQAPGLLIYGASSRATGIPDRFSGSGSGTDFTLTISRLEPEDFAVYYCQQFGSSPMCSFGQGTKLEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 29481 |

Figure 19E

XENP021823 jMab-139[ICOS]_H0L0_IgG1_PVA_/S267K

| What | sequence | SEQ ID NO: |
|---|---|---|
| Variable heavy (vh) domain | EVQLVESGGGLVQPGGSLRLSCAASGFTFSSYDMHWVRQATGKGLEWVSAIGTAGDTYYPGSVKGRFTISRENAKNSLYLQMNSLRA GDTAVYYCVRDKRTVTHEHYYYYGMDVWGQGTTVTVSS | 29482 |
| vhCDR1 | SYDMH | 29483 |
| vhCDR2 | AIGTAGDTYYPGSVKG | 29484 |
| vhCDR3 | DKRTVTHEHYYYYGMDV | 29485 |
| Full length HC | EVQLVESGGGLVQPGGSLRLSCAASGFTFSSYDMHWVRQATGKGLEWVSAIGTAGDTYYPGSVKGRFTISRENAKNSLYLQMNSLRA GDTAVYYCVRDKRTVTHEHYYYYGMDVWGQGTTVTVSS/ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVEPKSCDKTHTCPPCPAPPVAGPSVFLFPPKPKDTLMISRTPE VTCVVVDVKHEDPEVKFNWYVDGVEVHNAKTKPREEQYNSTYRVVSVLTVLHQDWLNGKEYKCKVSNKALPAPIEKTISKAKGQPRE PQVYTLPPSREEMTKNQVSLTCLVKGFYPSDIAVEWESNGQPENNYKTTPPVLDSDGSFFLYSKLTVDKSRWQQGNVFSCSVMHEAL HNHYTQKSLSLSPGK | 29486 |
| Variable light (vl) domain | EIVLTQSPGTLSLSPGERATLSCRASQSISSSLAWYQQKPGQAPGLLIFGASSRATGIPDRFSGSGSGTDFTLTISRLEPEDFAVYYCQQF GSSPMCSFGQGTKLEIK | 29487 |
| vlCDR1 | RASQSISSSLA | 29488 |
| vlCDR2 | GASSRAT | 29489 |
| vlCDR3 | QQFGSSPMCS | 29490 |
| Full length light chain | EIVLTQSPGTLSLSPGERATLSCRASQSISSSLAWYQQKPGQAPGLLIFGASSRATGIPDRFSGSGSGTDFTLTISRLEPEDFAVYYCQQF GSSPMCSFGQGTKLEIK/RTVAAPSVFIFPPSDEQLKSGTASVVCLLNNFYPREAKVQWKVDNALQSGNSQESVTEQDSKDSTYSLSSTL TLSKADYEKHKVYACEVTHQGLSSPVTKSFNRGEC | 29491 |

Figure 19F

XENP022346 WO2016059602_GSK[ICOS]_H0L0_IgG1_PVA_/S267K

| What | sequence | SEQ ID NO: |
|---|---|---|
| Variable heavy (vh) domain | QVQLVQSGAEVKKPGSSVKVSCKASGYTFTDYAMHWVRQAPGQGLEWMGLISIYSDHTNYNQKFQGRVTITADKSTSTAYMELSSLR SEDTAVYYCGRNNYGNYGWYFDVWGQGTTVTVSS | 29492 |
| vhCDR1 | DYAMH | 29493 |
| vhCDR2 | LISIYSDHTNYNQKFQG | 29494 |
| vhCDR3 | NNYGNYGWYFDV | 29495 |
| Full length HC | QVQLVQSGAEVKKPGSSVKVSCKASGYTFTDYAMHWVRQAPGQGLEWMGLISIYSDHTNYNQKFQGRVTITADKSTSTAYMELSSLR SEDTAVYYCGRNNYGNYGWYFDVWGQGTTVTVSS/ASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTCPPCPAPPVAGPSVFLFPPKPKDTLMISRTPEVTC VVVDVSHEDPEVKFNWYVDGVEVHNAKTKPREEQYNSTYRVVSVLTVLHQDWLNGKEYKCKVSNKALPAPIEKTISKAKGQPREPQV YTLPPSREEMTKNQVSLTCLVKGFYPSDIAVEWESNGQPENNYKTTPPVLDSDGSFFLYSKLTVDKSRWQQGNVFSCSVMHEALHNH YTQKSLSLSPGK | 29496 |
| Variable light (vl) domain | EIVLTQSPATLSLSPGERATLSCCASSSVSYMHWYQQKPGQAPRLLIYDTSKLASGIPARFSGSGSGTDYTLTISSLEPEDFAVYYCFQGSG YPYTFGQGTKLEIK | 29497 |
| vlCDR1 | SASSSVSYMH | 29498 |
| vlCDR2 | DTSKLAS | 29499 |
| vlCDR3 | FQGSGYPYT | 29500 |
| Full length light chain | EIVLTQSPATLSLSPGERATLSCCASSSVSYMHWYQQKPGQAPRLLIYDTSKLASGIPARFSGSGSGTDYTLTISSLEPEDFAVYYCFQGSG YPYTFGQGTKLEIK/RTVAAPSVFIFPPSDEQLKSGTASVVCLLNNFYPREAKVQWKVDNALQSGNSQESVTEQDSKDSTYSLSSTLTLSK ADYEKHKVYACEVTHQGLSSPVTKSFNRGEC | 29501 |

Figure 19G

XENP023057 Jounce_37A10S713[COS]_H0L0_IgG1_PVA_/S267K

| What | sequence | SEQ ID NO: |
|---|---|---|
| Variable heavy (vh) domain | EVQLVESGGGLVQPGGSLRLSCAASGFTFSDYWMDWVRQAPGKGLVWVSNIDEDGSITEYSPFVKGRFTISRDNAKNTLYLQMNSLR AEDTAVYYCTRWGRFGFDSWGQGTLVTVSS | 29502 |
| vhCDR1 | DYWMD | 29503 |
| vhCDR2 | NIDEDGSITEYSPFVKG | 29504 |
| vhCDR3 | WGRFGFDS | 29505 |
| Full length HC | EVQLVESGGGLVQPGGSLRLSCAASGFTFSDYWMDWVRQAPGKGLVWVSNIDEDGSITEYSPFVKGRFTISRDNAKNTLYLQMNSLR AEDTAVYYCTRWGRFGFDSWGQGTLVTVSS/ASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKKVEPKSCDKTHTCPPCPAPPVAGPSVFLFPPKPKDTLMISRTPEVTCVVVDV KHEDPEVKFNWYVDGVEVHNAKTKPREEQYNSTYRVVSVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFFLYSKLTVDKSRWQQGNVFSCSVMHEALHNHYTQKSL SLSPGK | 29506 |
| Variable light (vl) domain | DIVMTQSPDSLAVSLGERATINCKSSQSLLSGSFNYLTWYQQKPGQPPKLLIFYASTRHTGVPDRFSGSGSGTDFTLTISSLQAEDVAVYY CHHHYNAPPTFGPGTKVDIK | 29507 |
| vlCDR1 | KSSQSLLSGSFNYLT | 29508 |
| vlCDR2 | YASTRHT | 29509 |
| vlCDR3 | HHHYNAPPT | 29510 |
| Full length light chain | DIVMTQSPDSLAVSLGERATINCKSSQSLLSGSFNYLTWYQQKPGQPPKLLIFYASTRHTGVPDRFSGSGSGTDFTLTISSLQAEDVAVYY CHHHYNAPPTFGPGTKVDIK/RTVAAPSVFIFPPSDEQLKSGTASVVCLLNNFYPREAKVQWKVDNALQSGNSQESVTEQDSKDSTYSL SSTLTLSKADYEKHKVYACEVTHQGLSSPVTKSFNRGEC | 29511 |

Figure 20A

XENP022091 [ICOS]_H0_L0.7_Fab

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGGTNYAQKFQGRVTMTRDTSISTAYMELS RLRSDDTAVYYCARTYYYDSSGYYHDAFDIWGQGTMVTVSS | 29512 |
| vhCDR1 | GYYMH | 29513 |
| vhCDR2 | WINPHSGGTNYAQKFQG | 29514 |
| vhCDR3 | TYYYDSSGYYHDAFDI | 29515 |
| Full length HC | QVQLVQSGAEVKKPGASVKVSCKASGYTFTGYYMHWVRQAPGQGLEWMGWINPHSGGTNYAQKFQGRVTMTRDTSISTAYMELS RLRSDDTAVYYCARTYYYDSSGYYHDAFDIWGQGTMVTVSS/ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSCGS | 29516 |
| Variable light (vl) domain | DIQMTQSPSSVSASVGDRVTITCRASQGISSYLAWYQQKPGKAPKLLIYVASSLQSGVPSRFSGSGSGTDFTLTISSLQPEDFATYYCQQA NSFPWTFGQGTKVEIK | 29517 |
| vlCDR1 | RASQGISSYLA | 29518 |
| vlCDR2 | VASSLQS | 29519 |
| vlCDR3 | QQANSFPWT | 29520 |
| Full length light chain | DIQMTQSPSSVSASVGDRVTITCRASQGISSYLAWYQQKPGKAPKLLIYVASSLQSGVPSRFSGSGSGTDFTLTISSLQPEDFATYYCQQA NSFPWTFGQGTKVEIK/RTVAAPSVFIFPPSDEQLKSGTASVVCLLNNFYPREAKVQWKVDNALQSGNSQESVTEQDSKDSTYSLSSTL TLSKADYEKHKVYACEVTHQGLSSPVTKSFNRGEC | 29521 |

Figure 20B

XENP022780 [ICOS]_H0_L0.34_Fab

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGGTNYAQKFQGRVTMTRDTSISTAYMELS RLRSDDTAVYYCARTYYYDSSGYYHDAFDIWGQGTMVTVSS | 29522 |
| vhCDR1 | GYYMH | 29523 |
| vhCDR2 | WINPHSGGTNYAQKFQG | 29524 |
| vhCDR3 | TYYYDSSGYYHDAFDI | 29525 |
| Full length HC | QVQLVQSGAEVKKPGASVKVSCKASGYTFTGYYMHWVRQAPGQGLEWMGWINPHSGGTNYAQKFQGRVTMTRDTSISTAYMELS RLRSDDTAVYYCARTYYYDSSGYYHDAFDIWGQGTMVTVSS/ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSCGS | 29526 |
| Variable light (vl) domain | DIQMTQSPSSVSASVGDRVTITCQASQDISRLLAWYQQKPGKAPKLLIYVASSLQSGVPSRFSGSGSGTDFTLTISSLQPEDFATYYCQQ AESFPWTFGQGTKVEIK | 29527 |
| vlCDR1 | QASQDISRLLA | 29528 |
| vlCDR2 | VASSLQS | 29529 |
| vlCDR3 | QQAESFPWT | 29530 |
| Full length light chain | DIQMTQSPSSVSASVGDRVTITCQASQDISRLLAWYQQKPGKAPKLLIYVASSLQSGVPSRFSGSGSGTDFTLTISSLQPEDFATYYCQQ AESFPWTFGQGTKVEIK/RTVAAPSVFIFPPSDEQLKSGTASVVCLLNNFYPREAKVQWKVDNALQSGNSQESVTEQDSKDSTYSLSSTL TLSKADYEKHKVYACEVTHQGLSSPVTKSFNRGEC | 29531 |

Figure 20C

XENP022782 [ICOS]_H0_L0.36_Fab

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGGTNYAQKFQGRVTMTRDTSISTAYMELS RLRSDDTAVYYCARTYYYDSSGYYHDAFDIWGQGTMVTVSS | 29532 |
| vhCDR1 | GYYMH | 29533 |
| vhCDR2 | WINPHSGGTNYAQKFQG | 29534 |
| vhCDR3 | TYYYDSSGYYHDAFDI | 29535 |
| Full length HC | QVQLVQSGAEVKKPGASVKVSCKASGYTFTGYYMHWVRQAPGQGLEWMGWINPHSGGTNYAQKFQGRVTMTRDTSISTAYMELS RLRSDDTAVYYCARTYYYDSSGYYHDAFDIWGQGTMVTVSS/ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSCGS | 29536 |
| Variable light (vl) domain | DIQMTQSPSSVSASVGDRVTITCQASQDISSLLAWYQQKPGKAPKLLIYVASSLQSGVPSRFSGSGSGTDFTLTISSLQPEDFATYYCQQA ESFPWTFGQGTKVEIK | 29537 |
| vlCDR1 | QASQDISSLLA | 29538 |
| vlCDR2 | VASSLQS | 29539 |
| vlCDR3 | QQAESFPWT | 29540 |
| Full length light chain | DIQMTQSPSSVSASVGDRVTITCQASQDISSLLAWYQQKPGKAPKLLIYVASSLQSGVPSRFSGSGSGTDFTLTISSLQPEDFATYYCQQA ESFPWTFGQGTKVEIK/RTVAAPSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC | 29541 |

Figure 20D

XENP022783 [ICOS]_H0_L0.37_Fab

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGGTNYAQKFQGRVTMTRDTSISTAYMELS RLRSDDTAVYYCARTYYYDSSGYYHDAFDIWGQGTMVTVSS | 29542 |
| vhCDR1 | GYYMH | 29543 |
| vhCDR2 | WINPHSGGTNYAQKFQG | 29544 |
| vhCDR3 | TYYYDSSGYYHDAFDI | 29545 |
| Full length HC | QVQLVQSGAEVKKPGASVKVSCKASGYTFTGYYMHWVRQAPGQGLEWMGWINPHSGGTNYAQKFQGRVTMTRDTSISTAYMELS RLRSDDTAVYYCARTYYYDSSGYYHDAFDIWGQGTMVTVSS/ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSCGS | 29546 |
| Variable light (vl) domain | DIQMTQSPSSVSASVGDRVTITCQASQDISRLLAWYQQKPGKAPKLLIYAASSLQSGVPSRFSGSGSGTDFTLTISSLQPEDFATYYCQQ AESFPWTFGQGTKVEIK | 29547 |
| vlCDR1 | QASQDISRLLA | 29548 |
| vlCDR2 | AASSLQS | 29549 |
| vlCDR3 | QQAESFPWT | 29550 |
| Full length light chain | DIQMTQSPSSVSASVGDRVTITCQASQDISRLLAWYQQKPGKAPKLLIYAASSLQSGVPSRFSGSGSGTDFTLTISSLQPEDFATYYCQQ AESFPWTFGQGTKVEIK/RTVAAPSVFIFPPSDEQLKSGTASVVCLLNNFYPREAKVQWKVDNALQSGNSQESVTEQDSKDSTYSLSSTL TLSKADYEKHKVYACEVTHQGLSSPVTKSFNRGEC | 29551 |

Figure 20E

XENP022784 [ICOS]_H0_L0.38_Fab

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGGTNYAQKFQGRVTMTRDTSISTAYMELS RLRSDDTAVYYCARTYYYDSSGYYHDAFDIWGQGTMVTVSS | 29552 |
| vhCDR1 | GYYMH | 29553 |
| vhCDR2 | WINPHSGGTNYAQKFQG | 29554 |
| vhCDR3 | TYYYDSSGYYHDAFDI | 29555 |
| Full length HC | QVQLVQSGAEVKKPGASVKVSCKASGYTFTGYYMHWVRQAPGQGLEWMGWINPHSGGTNYAQKFQGRVTMTRDTSISTAYMELS RLRSDDTAVYYCARTYYYDSSGYYHDAFDIWGQGTMVTVSS/ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSCGS | 29556 |
| Variable light (vl) domain | DIQMTQSPSSVSASVGDRVTITCQASQDISSLLAWYQQKPGKAPKLLIYAASSLQSGVPSRFSGSGSGTDFTLTISSLQPEDFATYCQQ AESFPWTFGQGTKVEIK | 29557 |
| vlCDR1 | QASQDISSLLA | 29558 |
| vlCDR2 | AASSLQS | 29559 |
| vlCDR3 | QQAESFPWT | 29560 |
| Full length light chain | DIQMTQSPSSVSASVGDRVTITCQASQDISSLLAWYQQKPGKAPKLLIYAASSLQSGVPSRFSGSGSGTDFTLTISSLQPEDFATYCQQ AESFPWTFGQGTKVEIK/RTVAAPSVFIFPPSDEQLKSGTASVVCLLNNFYPREAKVQWKVDNALQSGNSQESVTEQDSKDSTYSLSSTL TLSKADYEKHKVYACEVTHQGLSSPVTKSFNRGEC | 29561 |

Figure 20F

XENP023088 [ICOS]_H0.66_L0_Fab

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGETIYAQKFQGRVTMTRDTSISTAYMELSSLRSEDTAVYYCARTYYYDTSGYYHDAFDVWGQGTMVTVSS | 29562 |
| vhCDR1 | GYYMH | 29563 |
| vhCDR2 | WINPHSGETIYAQKFQG | 29564 |
| vhCDR3 | TYYYDTSGYYHDAFDV | 29565 |
| Full length HC | QVQLVQSGAEVKKPGASVKVSCKASGYTFTGYYMHWVRQAPGQGLEWMGWINPHSGETIYAQKFQGRVTMTRDTSISTAYMELSSLRSEDTAVYYCARTYYYDTSGYYHDAFDVWGQGTMVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGS | 29566 |
| Variable light (vl) domain | DIQMTQSPSSVSASVGDRVTITCRASQGISRLLAWYQQKPGKAPKLLIYVASSLQSGVPSRFSGSGSGTDFTLTISSLQPEDFATYYCQQANSFPWTFGQGTKVEIK | 29567 |
| vlCDR1 | RASQGISRLLA | 29568 |
| vlCDR2 | VASSLQS | 29569 |
| vlCDR3 | QQANSFPWT | 29570 |
| Full length light chain | DIQMTQSPSSVSASVGDRVTITCRASQGISRLLAWYQQKPGKAPKLLIYVASSLQSGVPSRFSGSGSGTDFTLTISSLQPEDFATYYCQQANSFPWTFGQGTKVEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 29571 |

Figure 206

XENP023409 [ICOS]_H0.66_L0.34_Fab

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGETIYAQKFQGRVTMTRDTSISTAYMELSSLRSEDTAVYYCARTYYYDTSGYYHDAFDVWGQGTMVTVSS | 29572 |
| vhCDR1 | GYYMH | 29573 |
| vhCDR2 | WINPHSGETIYAQKFQG | 29574 |
| vhCDR3 | TYYYDTSGYYHDAFDV | 29575 |
| Full length HC | QVQLVQSGAEVKKPGASVKVSCKASGYTFTGYYMHWVRQAPGQGLEWMGWINPHSGETIYAQKFQGRVTMTRDTSISTAYMELSSLRSEDTAVYYCARTYYYDTSGYYHDAFDVWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGS | 29576 |
| Variable light (vl) domain | DIQMTQSPSSVSASVGDRVTITCQASQDISRLLAWYQQKPGKAPKLLIYVASSLQSGVPSRFSGSGSGTDFTLTISSLQPEDFATYYCQQAESFPWTFGQGTKVEIK | 29577 |
| vlCDR1 | QASQDISRLLA | 29578 |
| vlCDR2 | VASSLQS | 29579 |
| vlCDR3 | QQAESFPWT | 29580 |
| Full length light chain | DIQMTQSPSSVSASVGDRVTITCQASQDISRLLAWYQQKPGKAPKLLIYVASSLQSGVPSRFSGSGSGTDFTLTISSLQPEDFATYYCQQAESFPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 29581 |

Figure 21A

| XENP | $T_m$ (°C) | $\Delta T_m$ (°C) |
|---|---|---|
| 22050 | 72 | 0 |
| 22051 | 72.5 | 0.5 |
| 22052 | 72 | 0 |
| 22053 | 70.5 | -1.5 |
| 22054 | 72 | 0 |
| 22055 | 72 | 0 |
| 22056 | 70.5 | -1.5 |
| 22057 | 72.5 | 0.5 |
| 22058 | 71.5 | -0.5 |
| 22059 | 71.5 | -0.5 |
| 22060 | 71.5 | -0.5 |
| 22061 | 70.5 | -1.5 |
| 22062 | 72.5 | 0.5 |
| 22063 | 68 | -4 |
| 22064 | 71.5 | -0.5 |
| 22065 | 70.5 | -1.5 |
| 22066 | 71 | -1 |
| 22067 | 71.5 | -0.5 |
| 22068 | 71 | -1 |
| 22069 | 72.5 | 0.5 |
| 22070 | 73 | 1 |
| 22071 | 73 | 1 |
| 22072 | 73 | 1 |
| 22073 | 72.5 | 0.5 |
| 22074 | 71 | -1 |
| 22075 | 66.5 | -5.5 |
| 22076 | 71.5 | -0.5 |
| 22077 | 70.5 | -1.5 |
| 22078 | 70 | -2 |
| 22079 | 74.5 | 2.5 |
| 22080 | 73.5 | 1.5 |
| 22081 | 73 | 1 |
| 22082 | 75.5 | 3.5 |
| 22083 | 76 | 4 |
| 22084 | 72 | 0 |
| 22085 | 71 | -1 |
| 22086 | 70 | -2 |
| 22087 | 74 | 2 |
| 22088 | 73 | 1 |
| 22089 | 70.5 | -1.5 |
| 22090 | 70 | -2 |
| 22091 | 72.5 | 0.5 |

Figure 21B

| | | |
|---|---|---|
| 22092 | 71 | -1 |
| 22093 | 73 | 1 |
| 22094 | 74.5 | 2.5 |
| 22095 | 74 | 2 |
| 22096 | 72 | 0 |
| 22101 | 70 | -2 |
| 22102 | 72 | 0 |
| 22103 | 71.5 | -0.5 |
| 22104 | 73 | 1 |
| 22106 | 71 | -1 |
| 22107 | 68.5 | -3.5 |
| 22108 | 71.5 | -0.5 |
| 22767 | 74 | 2 |
| 22768 | 76.5 | 4.5 |
| 22769 | 74.5 | 2.5 |
| 22771 | 71 | -1 |
| 22772 | 75 | 3 |
| 22773 | 75.5 | 3.5 |
| 22774 | 73 | 1 |
| 22775 | 76 | 4 |
| 22776 | 73.5 | 1.5 |
| 22777 | 75 | 3 |
| 22778 | 73 | 1 |
| 22779 | 76 | 4 |
| 22780 | 73 | 1 |
| 22781 | 75 | 3 |
| 22782 | 72.5 | 0.5 |
| 22783 | 75.5 | 3.5 |
| 22784 | 74.5 | 2.5 |
| 22861 | 76 | 4 |
| 22862 | 76 | 4 |
| 22863 | 75.5 | 3.5 |
| 22938 | 75.5 | 3.5 |
| 22939 | 76.5 | 4.5 |
| 22940 | 78.5 | 6.5 |
| 22941 | 76.5 | 4.5 |
| 22944 | 74 | 2 |
| 22945 | 76 | 4 |
| 22946 | 76.5 | 4.5 |
| 23086 | 72.5 | 0.5 |
| 23087 | 68 | -4 |
| 23088 | 73.5 | 1.5 |
| 23089 | 69 | -3 |
| 23409 | 74.5 | 2.5 |

Figure 22A

| XENP | Antigen | $K_D$ (nM) | $k_a$ (1/Ms) | $k_d$ (1/s) |
|---|---|---|---|---|
| 22050 | huICOS | 3.538 | 5.04E+04 | 1.79E-04 |
| 22051 | huICOS | 798.8 | 7.99E+02 | 6.38E-04 |
| 22052 | huICOS | <0.001 | 3.32E+04 | <1.0E-07 |
| 22053 | huICOS | 13.85 | 1.09E+05 | 1.52E-03 |
| 22054 | huICOS | <0.001 | 4.65E+04 | <1.0E-07 |
| 22055 | huICOS | 1.725 | 9.15E+04 | 1.58E-04 |
| 22056 | huICOS | 3.765 | 4.54E+04 | 1.71E-04 |
| 22057 | huICOS | 13.19 | 3.10E+04 | 4.09E-04 |
| 22058 | huICOS | 2.69 | 3.17E+04 | 8.52E-05 |
| 22059 | huICOS | 2.289 | 1.04E+05 | 2.38E-04 |
| 22060 | huICOS | 3.361 | 6.48E+04 | 2.18E-04 |
| 22061 | huICOS | 2.373 | 8.81E+04 | 2.09E-04 |
| 22062 | huICOS | 2.442 | 4.94E+04 | 1.21E-04 |
| 22063 | huICOS | 4.835 | 6.80E+04 | 3.29E-04 |
| 22064 | huICOS | 5.521 | 4.03E+04 | 2.23E-04 |
| 22065 | huICOS | 3.605 | 9.15E+04 | 3.30E-04 |
| 22066 | huICOS | 1.073 | 1.76E+04 | 1.89E-05 |
| 22067 | huICOS | 2.187 | 7.67E+04 | 1.68E-04 |
| 22068 | huICOS | 3.329 | 3.45E+04 | 1.15E-04 |
| 22069 | huICOS | <0.001 | 2.00E+04 | <1.0E-07 |
| 22070 | huICOS | very weak | very weak | very weak |
| 22071 | huICOS | <0.001 | 2.19E+04 | <1.0E-07 |
| 22072 | huICOS | <0.001 | 2.17E+04 | <1.0E-07 |
| 22073 | huICOS | 171.8 | 2.43E+03 | 4.17E-04 |
| 22074 | huICOS | <0.001 | 2.04E+04 | <1.0E-07 |
| 22075 | huICOS | very weak | very weak | very weak |
| 22076 | huICOS | very weak | very weak | very weak |
| 22077 | huICOS | 9.747 | 4.71E+04 | 4.59E-04 |
| 22078 | huICOS | 117 | 1.81E+03 | 2.12E-04 |
| 22079 | huICOS | very weak | very weak | very weak |
| 22080 | huICOS | very weak | very weak | very weak |
| 22081 | huICOS | very weak | very weak | very weak |
| 22082 | huICOS | very weak | very weak | very weak |
| 22083 | huICOS | very weak | very weak | very weak |
| 22084 | huICOS | 2.411 | 9.50E+04 | 2.29E-04 |
| 22085 | huICOS | 1.785 | 9.63E+04 | 1.72E-04 |
| 22086 | huICOS | <0.001 | 4.84E+04 | <1.0E-07 |
| 22087 | huICOS | 0.9926 | 8.66E+04 | 8.59E-05 |
| 22088 | huICOS | 0.606 | 9.51E+04 | 5.77E-05 |
| 22089 | huICOS | 5.14 | 8.77E+04 | 4.51E-04 |
| 22090 | huICOS | very weak | very weak | very weak |

Figure 22B

| XENP | Antigen | $K_D$ (nM) | $k_a$ (1/Ms) | $k_d$ (1/s) |
|---|---|---|---|---|
| 22091 | huICOS | 51.33 | 3.29E+04 | 1.69E-03 |
| 22092 | huICOS | 70.14 | 7.93E+04 | 5.56E-03 |
| 22093 | huICOS | 19.27 | 3.47E+04 | 6.68E-04 |
| 22094 | huICOS | 32.62 | 2.80E+04 | 9.13E-04 |
| 22095 | huICOS | 3.472 | 1.24E+05 | 4.31E-04 |
| 22096 | huICOS | 3.023 | 8.14E+04 | 2.46E-04 |
| 22101 | huICOS | 2.61 | 6.08E+04 | 1.59E-04 |
| 22102 | huICOS | 4.746 | 1.00E+05 | 4.77E-04 |
| 22103 | huICOS | 5.838 | 4.94E+04 | 2.89E-04 |
| 22104 | huICOS | 3.862 | 7.78E+04 | 3.01E-04 |
| 22105 | huICOS | 2.49 | 9.40E+04 | 2.34E-04 |
| 22106 | huICOS | 3.446 | 6.62E+04 | 2.28E-04 |
| 22107 | huICOS | 530.3 | 1.06E+03 | 5.60E-04 |
| 22108 | huICOS | 192 | 5.94E+03 | 1.14E-03 |

Figure 22C

| XENP | Antigen | $K_D$ (nM) | $k_a$ (1/Ms) | $k_d$ (1/s) |
|---|---|---|---|---|
| 22050 | huICOS | <0.001 | 3.34E+04 | <1.0E-07 |
| 22052 | huICOS | <0.001 | 4.37E+04 | <1.0E-07 |
| 22053 | huICOS | 13 | 6.83E+04 | 8.86E-04 |
| 22054 | huICOS | very weak | very weak | very weak |
| 22057 | huICOS | 0.00722 | 1.06E+05 | 7.65E-07 |
| 22064 | huICOS | <0.001 | 4.79E+04 | <1.0E-07 |
| 22065 | huICOS | <0.001 | 3.41E+04 | <1.0E-07 |
| 22069 | huICOS | <0.001 | 4.57E+03 | <1.0E-07 |
| 22073 | huICOS | very weak | very weak | very weak |
| 22074 | huICOS | 1.31 | 7.57E+04 | 9.88E-05 |
| 22077 | huICOS | very weak | very weak | very weak |
| 22084 | huICOS | <0.001 | 1.19E+04 | <1.0E-07 |
| 22089 | huICOS | 3.12 | 5.78E+04 | 1.80E-04 |
| 22091 | huICOS | 142 | 1.50E+04 | 2.13E-03 |
| 22093 | huICOS | 399 | 7.82E+02 | 3.12E-04 |
| 22094 | huICOS | 14.2 | 7.46E+04 | 1.06E-03 |
| 22095 | huICOS | 11 | 6.60E+04 | 7.25E-04 |
| 22102 | huICOS | 0.886 | 9.10E+04 | 8.07E-05 |
| 22103 | huICOS | 1.5 | 7.23E+04 | 1.09E-04 |
| 22104 | huICOS | 1.33 | 3.66E+04 | 4.86E-05 |
| 22106 | huICOS | 2060 | 4.81E+02 | 9.93E-04 |
| 22108 | huICOS | 17.5 | 7.61E+04 | 1.33E-03 |

Figure 23

| XENP | Antigen | $K_D$ (nM) | $k_a$ (1/Ms) | $k_d$ (1/s) |
|---|---|---|---|---|
| 22050 | huICOS | 1.936 | 7.65E+04 | 1.48E-04 |
| 22091 | huICOS | 54.56 | 3.00E+04 | 1.64E-03 |
| 22780 | huICOS | 3.131 | 6.41E+04 | 2.01E-04 |
| 22781 | huICOS | 14.64 | 1.03E+05 | 1.50E-03 |
| 22782 | huICOS | 7.457 | 5.62E+04 | 4.19E-04 |
| 22783 | huICOS | 39.55 | 3.49E+04 | 1.38E-03 |
| 22784 | huICOS | 27.81 | 9.13E+04 | 2.54E-03 |
| 22861 | huICOS | 5206 | 1.36E+03 | 7.07E-03 |
| 22862 | huICOS | 239.4 | 2.51E+04 | 6.00E-03 |
| 22863 | huICOS | 102.3 | 3.49E+04 | 3.57E-03 |
| 22929 | huICOS | 12.39 | 4.56E+04 | 5.65E-04 |
| 22938 | huICOS | 43.94 | 3.89E+04 | 1.71E-03 |
| 22939 | huICOS | 24.49 | 5.84E+04 | 1.43E-03 |
| 22940 | huICOS | 18.9 | 7.10E+04 | 1.34E-03 |
| 22941 | huICOS | 81.29 | 3.80E+04 | 3.09E-03 |
| 22944 | huICOS | 4.415 | 6.29E+04 | 2.78E-04 |
| 22945 | huICOS | 40.62 | 5.31E+04 | 2.16E-03 |
| 22946 | huICOS | 19.38 | 6.71E+04 | 1.30E-03 |

Figure 24A

XENP024352 [anti-ICOS]_H0L0_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGGTNYAQKFQGRVTMTRDTSISTAYMELS RLRSDDTAVYYCARTYYYDSSGYYHDAFDIWGQGTMVTVSS | 29582 |
| vhCDR1 | GYYMH | 29583 |
| vhCDR2 | WINPHSGGTNYAQKFQG | 29584 |
| vhCDR3 | TYYYDSSGYYHDAFDI | 29585 |
| scFv linker | GKPGSGKPGSGKPGSGKPGS | 29586 |
| Variable light (vl) domain | DIQMTQSPSSVSASVGDRVTITCRASQGISRLLAWYQQKPGKAPKLLIYVASSLQSGVPSRFSGSGSGTDFTLTISSLQPEDFATYYCQQA NSFPWTFGQGTKVEIK | 29587 |
| vlCDR1 | RASQGISRLLA | 29588 |
| vlCDR2 | VASSLQS | 29589 |
| vlCDR3 | QQANSFPWT | 29590 |
| scFv | QVQLVQSGAEVKKPGASVKVSCKASGYTFTGYYMHWVRQAPGQGLEWMGWINPHSGGTNYAQKFQGRVTMTRDTSISTAYMELS RLRSDDTAVYYCARTYYYDSSGYYHDAFDIWGQGTMVTVSS/GKPGSGKPGSGKPGSGKPGS/DIQMTQSPSSVSASVGDRVTITCRA SQGISRLLAWYQQKPGKAPKLLIYVASSLQSGVPSRFSGSGSGTDFTLTISSLQPEDFATYYCQQANSFPWTFGQGTKVEIK/GS | 29591 |

Figure 24B

XENP024353 [anti-ICOS]_L0H0_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYYDSSGYYHDAFDIWGQGTMVTVSS | 29592 |
| vhCDR1 | GYYMH | 29593 |
| vhCDR2 | WINPHSGGTNYAQKFQG | 29594 |
| vhCDR3 | TYYYDSSGYYHDAFDI | 29595 |
| scFv linker | GKPGSGKPGSGKPGSGKPGS | 29596 |
| Variable light (vl) domain | DIQMTQSPSSVSASVGDRVTITCRASQGISRLLAWYQQKPGKAPKLLIYVASSLQSGVPSRFSGSGSGTDFTLTISSLQPEDFATYYCQQANSFPWTFGQGTKVEIK | 29597 |
| vlCDR1 | RASQGISRLLA | 29598 |
| vlCDR2 | VASSLQS | 29599 |
| vlCDR3 | QQANSFPWT | 29600 |
| scFv | DIQMTQSPSSVSASVGDRVTITCRASQGISRLLAWYQQKPGKAPKLLIYVASSLQSGVPSRFSGSGSGTDFTLTISSLQPEDFATYYCQQANSFPWTFGQGTKVEIK/GKPGSGKPGSGKPGSGKPGS/QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYYDSSGYYHDAFDIWGQGTMVTVSS/GS | 29601 |

Figure 24C

XENP024354 [anti-ICOS]_H0.40_L0.22_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGETNYAQKFQGRVTMTRDTSISTAYMELS SLRSEDTAVYYCARTYYYDTSGYYHDAFDVWGQGTMVTVSS | 29602 |
| vhCDR1 | GYYMH | 29603 |
| vhCDR2 | WINPHSGETNYAQKFQG | 29604 |
| vhCDR3 | TYYYDTSGYYHDAFDV | 29605 |
| scFv linker | GKPGSGKPGSGKPGSGKPGS | 29606 |
| Variable light (vl) domain | DIQMTQSPSSVSASVGDRVTITCRASQDISRLLAWYQQKPGKAPKLLIYAASSLQSGVPSRFSGSGSGTDFTLTISSLQPEDFATYCQQA NSFPWTFGQGTKVEIK | 29607 |
| vlCDR1 | RASQDISRLLA | 29608 |
| vlCDR2 | AASSLQS | 29609 |
| vlCDR3 | QQANSFPWT | 29610 |
| scFv | QVQLVQSGAEVKKPGASVKVSCKASGYTFTGYYMHWVRQAPGQGLEWMGWINPHSGETNYAQKFQGRVTMTRDTSISTAYMELS SLRSEDTAVYYCARTYYYDTSGYYHDAFDVWGQGTMVTVSS/GKPGSGKPGSGKPGSGKPGS/DIQMTQSPSSVSASVGDRVTITCRA SQDISRLLAWYQQKPGKAPKLLIYAASSLQSGVPSRFSGSGSGTDFTLTISSLQPEDFATYCQQANSFPWTFGQGTKVEIK/GS | 29611 |

Figure 24D

XENP024355 [anti-ICOS]_H0.40_L0.45_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGETNYAQKFQGRVTMTRDTSISTAYMELS SLRSEDTAVYYCARTYYYDTSGYYHDAFDVWGQGTMVTVSS | 29612 |
| vhCDR1 | GYYMH | 29613 |
| vhCDR2 | WINPHSGETNYAQKFQG | 29614 |
| vhCDR3 | TYYYDTSGYYHDAFDV | 29615 |
| scFv linker | GKPGSGKPGSGKPGSGKPGS | 29616 |
| Variable light (vl) domain | DIQMTQSPSSVSASVGDRVTITCRASQDISRLLAWYQQKPGKAPKLLIYAASSLQSGVPSRFSGSGSGTDFTLTISSLQPEDFATYYCQQA QSFPWTFGQGTKVEIK | 29617 |
| vlCDR1 | RASQDISRLLA | 29618 |
| vlCDR2 | AASSLQS | 29619 |
| vlCDR3 | QQAQSFPWT | 29620 |
| scFv | QVQLVQSGAEVKKPGASVKVSCKASGYTFTGYYMHWVRQAPGQGLEWMGWINPHSGETNYAQKFQGRVTMTRDTSISTAYMELS SLRSEDTAVYYCARTYYYDTSGYYHDAFDVWGQGTMVTVSS/GKPGSGKPGSGKPGSGKPGS/DIQMTQSPSSVSASVGDRVTITCRA SQDISRLLAWYQQKPGKAPKLLIYAASSLQSGVPSRFSGSGSGTDFTLTISSLQPEDFATYYCQQAQSFPWTFGQGTKVEIK/GS | 29621 |

Figure 24E

XENP024356 [anti-ICOS]_H0.66_L0.22_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGETIYAQKFQGRVTMTRDTSISTAYMELSSLRSEDTAVYYCARTYYYDTSGYYHDAFDVWGQGTMVTVSS | 29622 |
| vhCDR1 | GYYMH | 29623 |
| vhCDR2 | WINPHSGETIYAQKFQG | 29624 |
| vhCDR3 | TYYYDTSGYYHDAFDV | 29625 |
| scFv linker | GKPGSGKPGSGKPGSGKPGS | 29626 |
| Variable light (vl) domain | DIQMTQSPSSVSASVGDRVTITCRASQDISRLLAWYQQKPGKAPKLLIYAASSLQSGVPSRFSGSGSGTDFTLTISSLQPEDFATYYCQQANSFPWTFGQGTKVEIK | 29627 |
| vlCDR1 | RASQDISRLLA | 29628 |
| vlCDR2 | AASSLQS | 29629 |
| vlCDR3 | QQANSFPWT | 29630 |
| scFv | QVQLVQSGAEVKKPGASVKVSCKASGYTFTGYYMHWVRQAPGQGLEWMGWINPHSGETIYAQKFQGRVTMTRDTSISTAYMELSSLRSEDTAVYYCARTYYYDTSGYYHDAFDVWGQGTMVTVSS/GKPGSGKPGSGKPGSGKPGS/DIQMTQSPSSVSASVGDRVTITCRASQDISRLLAWYQQKPGKAPKLLIYAASSLQSGVPSRFSGSGSGTDFTLTISSLQPEDFATYYCQQANSFPWTFGQGTKVEIK/GS | 29631 |

Figure 24F

XENP024357 [anti-ICOS]_H0.66_L0.45_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGETIYAQKFQGRVTMTRDTSISTAYMELSSLRSEDTAVYYCARTYYYDTSGYYHDAFDVWGQGTMVTVSS | 29632 |
| vhCDR1 | GYYMH | 29633 |
| vhCDR2 | WINPHSGETIYAQKFQG | 29634 |
| vhCDR3 | TYYYDTSGYYHDAFDV | 29635 |
| scFv linker | GKPGSGKPGSGKPGSGKPGS | 29636 |
| Variable light (vl) domain | DIQMTQSPSSVSASVGDRVTITCRASQDISRLLAWYQQKPGKAPKLLIYAASSLQSGVPSRFSGSGSGTDFTLTISSLQPEDFATYYCQQAQSFPWTFGQGTKVEIK | 29637 |
| vlCDR1 | RASQDISRLLA | 29638 |
| vlCDR2 | AASSLQS | 29639 |
| vlCDR3 | QQAQSFPWT | 29640 |
| scFv | QVQLVQSGAEVKKPGASVKVSCKASGYTFTGYYMHWVRQAPGQGLEWMGWINPHSGETIYAQKFQGRVTMTRDTSISTAYMELSSLRSEDTAVYYCARTYYYDTSGYYHDAFDVWGQGTMVTVSS/GKPGSGKPGSGKPGSGKPGS/DIQMTQSPSSVSASVGDRVTITCRASQDISRLLAWYQQKPGKAPKLLIYAASSLQSGVPSRFSGSGSGTDFTLTISSLQPEDFATYYCQQAQSFPWTFGQGTKVEIK/GS | 29641 |

Figure 24G

XENP024609 [anti-ICOS]_L0.45_H0.40_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGETNYAQKFQGRVTMTRDTSISTAYMELS SLRSEDTAVYYCARTYYYDTSGYYHDAFDVWGQGTMVTVSS | 29642 |
| vhCDR1 | GYYMH | 29643 |
| vhCDR2 | WINPHSGETNYAQKFQG | 29644 |
| vhCDR3 | TYYYDTSGYYHDAFDV | 29645 |
| scFv linker | GKPGSGKPGSGKPGSGKPGS | 29646 |
| Variable light (vl) domain | DIQMTQSPSSVSASVGDRVTITCRASQDISRLLAWYQQKPGKAPKLLIYAASSLQSGVPSRFSGSGSGTDFTLTISSLQPEDFATYYCQQA QSFPWTFGQGTKVEIK | 29647 |
| vlCDR1 | RASQDISRLLA | 29648 |
| vlCDR2 | AASSLQS | 29649 |
| vlCDR3 | QQAQSFPWT | 29650 |
| scFv | DIQMTQSPSSVSASVGDRVTITCRASQDISRLLAWYQQKPGKAPKLLIYAASSLQSGVPSRFSGSGSGTDFTLTISSLQPEDFATYYCQQA QSFPWTFGQGTKVEIK/GKPGSGKPGSGKPGSGKPGS/QVQLVQSGAEVKKPGASVKVSCKASGYTFTGYYMHWVRQAPGQGLEW MGWINPHSGETNYAQKFQGRVTMTRDTSISTAYMELSSLRSEDTAVYYCARTYYYDTSGYYHDAFDVWGQGTMVTVSS/GS | 29651 |

Figure 24H

XENP024689 [anti-ICOS]_L0.45_H0.37_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGGTNYAQKFQGRVTMTRDTSISTAYMELSSLRSEDTAVYYCARTYYYDTSGYYHDAFDVWGQGTMVTVSS | 29652 |
| vhCDR1 | GYYMH | 29653 |
| vhCDR2 | WINPHSGGTNYAQKFQG | 29654 |
| vhCDR3 | TYYYDTSGYYHDAFDV | 29655 |
| scFv linker | GKPGSGKPGSGKPGSGKPGS | 29656 |
| Variable light (vl) domain | DIQMTQSPSSVSASVGDRVTITCRASQDISRLLAWYQQKPGKAPKLLIYAASSLQSGVPSRFSGSGSGTDFTLTISSLQPEDFATYYCQQAQSFPWTFGQGTKVEIK | 29657 |
| vlCDR1 | RASQDISRLLA | 29658 |
| vlCDR2 | AASSLQS | 29659 |
| vlCDR3 | QQAQSFPWT | 29660 |
| scFv | DIQMTQSPSSVSASVGDRVTITCRASQDISRLLAWYQQKPGKAPKLLIYAASSLQSGVPSRFSGSGSGTDFTLTISSLQPEDFATYYCQQAQSFPWTFGQGTKVEIK/GKPGSGKPGSGKPGSGKPGS/QVQLVQSGAEVKKPGASVKVSCKASGYTFTGYYMHWVRQAPGQGLEWMGWINPHSGGTNYAQKFQGRVTMTRDTSISTAYMELSSLRSEDTAVYYCARTYYYDTSGYYHDAFDVWGQGTMVTVSS/GS | 29661 |

Figure 241

XENP024690 [anti-ICOS]_L0.45_H0.68_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGETNYAQKFQGRVTMTRDTSISTAYMELSRLRSDDTAVYYCARTYYYDTSGYYHDAFDVWGQGTMVTVSS | 29662 |
| vhCDR1 | GYYMH | 29663 |
| vhCDR2 | WINPHSGETNYAQKFQG | 29664 |
| vhCDR3 | TYYYDTSGYYHDAFDV | 29665 |
| scFv linker | GKPGSGKPGSGKPGSGKPGS | 29666 |
| Variable light (vl) domain | DIQMTQSPSSVSASVGDRVTITCRASQDISRLLAWYQQKPGKAPKLLIYAASSLQSGVPSRFSGSGSGTDFTLTISSLQPEDFATYYCQQAQSFPWTFGQGTKVEIK | 29667 |
| vlCDR1 | RASQDISRLLA | 29668 |
| vlCDR2 | AASSLQS | 29669 |
| vlCDR3 | QQAQSFPWT | 29670 |
| scFv | DIQMTQSPSSVSASVGDRVTITCRASQDISRLLAWYQQKPGKAPKLLIYAASSLQSGVPSRFSGSGSGTDFTLTISSLQPEDFATYYCQQAQSFPWTFGQGTKVEIK/GKPGSGKPGSGKPGSGKPGS/QVQLVQSGAEVKKPGASVKVSCKASGYTFTGYYMHWVRQAPGQGLEWMGWINPHSGETNYAQKFQGRVTMTRDTSISTAYMELSRLRSDDTAVYYCARTYYYDTSGYYHDAFDVWGQGTMVTVSS/GS | 29671 |

Figure 24J

XENP024691 [anti-ICOS]_L0.45_H0.35_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYYDTSGYYHDAFDVWGQGTMVTVSS | 29672 |
| vhCDR1 | GYYMH | 29673 |
| vhCDR2 | WINPHSGGTNYAQKFQG | 29674 |
| vhCDR3 | TYYYDTSGYYHDAFDV | 29675 |
| scFv linker | GKPGSGKPGSGKPGSGKPGS | 29676 |
| Variable light (vl) domain | DIQMTQSPSSVSASVGDRVTITCRASQDISRLLAWYQQKPGKAPKLLIYAASSLQSGVPSRFSGSGSGTDFTLTISSLQPEDFATYYCQQAQSFPWTFGQGTKVEIK | 29677 |
| vlCDR1 | RASQDISRLLA | 29678 |
| vlCDR2 | AASSLQS | 29679 |
| vlCDR3 | QQAQSFPWT | 29680 |
| scFv | DIQMTQSPSSVSASVGDRVTITCRASQDISRLLAWYQQKPGKAPKLLIYAASSLQSGVPSRFSGSGSGTDFTLTISSLQPEDFATYYCQQAQSFPWTFGQGTKVEIK/GKPGSGKPGSGKPGSGKPGS/QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYYDTSGYYHDAFDVWGQGTMVTVSS/GS | 29681 |

Figure 24K

XENP024692 [anti-ICOS]_L0.45_H0.34_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYYDSSGYYHDAFDVWGQGTMVTVSS | 29682 |
| vhCDR1 | GYYMH | 29683 |
| vhCDR2 | WINPHSGGTNYAQKFQG | 29684 |
| vhCDR3 | TYYYDSSGYYHDAFDV | 29685 |
| scFv linker | GKPGSGKPGSGKPGSGKPGS | 29686 |
| Variable light (vl) domain | DIQMTQSPSSVSASVGDRVTITCRASQDISRLLAWYQQKPGKAPKLLIYAASSLQSGVPSRFSGSGSGTDFTLTISSLQPEDFATYYCQQAQSFPWTFGQGTKVEIK | 29687 |
| vlCDR1 | RASQDISRLLA | 29688 |
| vlCDR2 | AASSLQS | 29689 |
| vlCDR3 | QQAQSFPWT | 29690 |
| scFv | DIQMTQSPSSVSASVGDRVTITCRASQDISRLLAWYQQKPGKAPKLLIYAASSLQSGVPSRFSGSGSGTDFTLTISSLQPEDFATYYCQQAQSFPWTFGQGTKVEIK/GKPGSGKPGSGKPGSGKPGS/QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYYDSSGYYHDAFDVWGQGTMVTVSS/GS | 29691 |

Figure 24L

XENP024693 [anti-ICOS]_L0.46_H0.40_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGETNYAQKFQGRVTMTRDTSISTAYMELSSLRSEDTAVYYCARTYYYDTSGYYHDAFDVWGQGTMVTVSS | 29692 |
| vhCDR1 | GYYMH | 29693 |
| vhCDR2 | WINPHSGETNYAQKFQG | 29694 |
| vhCDR3 | TYYYDTSGYYHDAFDV | 29695 |
| scFv linker | GKPGSGKPGSGKPGSGKPGS | 29696 |
| Variable light (vl) domain | DIQMTQSPSSVSASVGDRVTITCRASQSISRLLAWYQQKPGKAPKLLIYAASSLQSGVPSRFSGSGSGTDFTLTISSLQPEDFATYYCQQAQSFPWTFGQGTKVEIK | 29697 |
| vlCDR1 | RASQSISRLLA | 29698 |
| vlCDR2 | AASSLQS | 29699 |
| vlCDR3 | QQAQSFPWT | 29700 |
| scFv | DIQMTQSPSSVSASVGDRVTITCRASQSISRLLAWYQQKPGKAPKLLIYAASSLQSGVPSRFSGSGSGTDFTLTISSLQPEDFATYYCQQAQSFPWTFGQGTKVEIK/GKPGSGKPGSGKPGSGKPGS/QVQLVQSGAEVKKPGASVKVSCKASGYTFTGYYMHWVRQAPGQGLEWMGWINPHSGETNYAQKFQGRVTMTRDTSISTAYMELSSLRSEDTAVYYCARTYYYDTSGYYHDAFDVWGQGTMVTVSS/GS | 29701 |

Figure 24M

XENP024694 [anti-ICOS]_L0.47_H0.40_scFv

| What | sequence | SEQ ID NO: |
|---|---|---|
| Variable heavy (vh) domain | QVQLVQSGAEVKKPGASVKVSCKASGYTFTGYYMHWVRQAPGQGLEWMGWINPHSGETNYAQKFQGRVTMTRDTSISTAYMELSSLRSEDTAVYYCARTYYYDTSGYYHDAFDVWGQGTMVTVSS | 29702 |
| vhCDR1 | GYYMH | 29703 |
| vhCDR2 | WINPHSGETNYAQKFQG | 29704 |
| vhCDR3 | TYYYDTSGYYHDAFDV | 29705 |
| scFv linker | GKPGSGKPGSGKPGSGKPGS | 29706 |
| Variable light (vl) domain | DIQMTQSPSSVSASVGDRVTITCRASQDISRLLAWYQQKPGKAPKLLIYSASSLQSGVPSRFSGSGSGTDFTLTISSLQPEDFATYYCQQAQSFPWTFGQGTKVEIK | 29707 |
| vlCDR1 | RASQDISRLLA | 29708 |
| vlCDR2 | SASSLQS | 29709 |
| vlCDR3 | QQAQSFPWT | 29710 |
| scFv | DIQMTQSPSSVSASVGDRVTITCRASQDISRLLAWYQQKPGKAPKLLIYSASSLQSGVPSRFSGSGSGTDFTLTISSLQPEDFATYYCQQAQSFPWTFGQGTKVEIK/GKPGSGKPGSGKPGSGKPGS/QVQLVQSGAEVKKPGASVKVSCKASGYTFTGYYMHWVRQAPGQGLEWMGWINPHSGETNYAQKFQGRVTMTRDTSISTAYMELSSLRSEDTAVYYCARTYYYDTSGYYHDAFDVWGQGTMVTVSS/GS | 29711 |

Figure 25

| XENP | $T_m$ (°C) | $\Delta T_m$ (°C) |
|---|---|---|
| 24352 | 56 | 0 |
| 24354 | 65.5 | 9.5 |
| 24353 | 59 | 3 |
| 24355 | 67 | 11 |
| 24356 | 64.5 | 8.5 |
| 24357 | 66 | 10 |
| 24609 | 69 | 13 |
| 24689 | 66.5 | 10.5 |
| 24690 | 69 | 13 |
| 24691 | 66.5 | 10.5 |
| 24692 | 67 | 11 |
| 24693 | 67.5 | 11.5 |
| 24694 | 68.5 | 12.5 |

Figure 26A

XENP22730

>XENP022730 [ICOS]_H0L0_Fab-1G6_L1.194_H1.279 Fab-Fc Heavy Chain (SEQ ID NO: 29712)
QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYDSSG
YHDAFDIWGQGTMVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSDT
KVDKKVEPKSCDKTHTCPPCPAPPVAGPSVFLFPPKPKDTLMISRTPEVTCVVVDVSHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWQEGDVFSCSVLHEAL
HSHYTQKSLSLSPGK >XENP022730 [ICOS]_H0L0_Fab-1G6_L1.194_H1.279 scFv-Fc Heavy Chain (SEQ ID NO: 29713)
EIVLTQSPATLSASPGERVTLTCRASQSVGNDVAWYQQKPGQAPRLLINYASHRYTGVPDRFTGSGYGTEFTLTISSVQSEDFGVYYCQQDFSSPRTFGGGTKVEIK/GKPG
SGKPGSGKPGSGKPGS/EVQLVESGGGLVKPGGSLRLSCVASGFTFSNYWMNWVRQAPGKGLEWVAEIRLYSNNYATHYAESVKGRFTISRDDSKSTLYLQMNNLKTED
TGVYYCTRYYGNYGGYFDVWGRGTLVTVSS/EPKSSDKTHTCPPCPAPPVAGPSVFLFPPKPKDTLMISRTPEVTCVVVDVKHEDPEVKFNWYVDGVEHNAKTKPREEQ
YNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFL
YSKLTVDKSRWQQGNVFSCSVLHEALHSHYTQKSLSLSPGK >XENP022730 [ICOS]_H0L0_Fab-1G6_L1.194_H1.279 Light Chain (SEQ ID NO: 29714)
DIQMTQSPSSVSASVGDRVTITCRASQGISRLLAWYQQKPGKAPKLLIYVASSLQSGVPSRFSGSGSGTDFTLTISSLQPEDFATYYCQQANSFPWTFGQGTKVEIK/RTVAA
PSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 26B

XENP23377

>XENP023377_11D4[OX40]_H0L0_Fab-1G6_L1.194_H1.279_scFv Fab-Fc Heavy Chain (SEQ ID NO: 29715)
EVQLVESGGGLVQPGGSLRLSCAASGFTFSSYSMNWVRQAPGKGLEWVSYISSSSTIDYADSVKGRFTISRDNAKNSLYLQMNSLRDEDTAVYYCARESGWVLFDYWGQ
GTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESDGQPENNYKTTPPVLDSDGSFFLYSKLTVDKSRWQEGDVFSCSVMHEALHNHYTQKSLSLSP
GK >XENP023377_11D4[OX40]_H0L0_Fab-1G6_L1.194_H1.279_scFv scFv-Fc Heavy Chain (SEQ ID NO: 29716)
EIVLTQSPATLSASPGERVTLTCRASQSVGNDVAWYQQKPGQAPRLLINYASHRYTGVPDRFTGSGYGTEFTLTISSVQSEDFGVYYCQQDFSSPRTFGGGTKVEIK/GKPG
SGKPGSGKPGSGKPGS/EVQLVESGGGLVKPGGSLRLSCVASGFTFSNYWMNWVRQAPGKGLEWVAEIRLYSNINYATHYAESVKGRFTISRDDSKSTLYLQMNNLKTED
TGVYYCTRYYGNYGGYFDVWGRGTLVTVSS/EPKSSDKTHTCPPCPAPPVAGPSVFLFPPKPKDTLMISRTPEVTCVVVDVKHEDPEVKFNWYVDGVEVHNAKTPREEQ
YNSTYRVVSVLTVLHQDWLNGKEYKCKVSNKALPAPIEKTISKAKGQPREQMTKNQVKLTCLVKGFYPSDIAVEWESNGQPENNYKTTPPVLDSDGSFFL
YSKLTVDKSRWQQGNVFSCSVMHEALHNHYTQKSLSLSPGK >XENP023377_11D4[OX40]_H0L0_Fab-1G6_L1.194_H1.279_scFv Light Chain (SEQ ID NO: 29717)
DIQMTQSPSSLSASVGDRVTITCRASQGISSWLAWYQQKPEKAPKSLIYAASSLQSGVPSRFSGSGSGTDFTLTISSLQPEDFATYYCQQYNSYPPTFGGGTKVEIK/RTVAA
PSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 26C

XENP23378

>XENP023378 1D8[GITR]_H0L0_Fab-1G6_L1.194_H1.279_scFv Fab-Fc Heavy Chain (SEQ ID NO: 29718)
QVTLKESGPGILKPSQTLSLTCSFSGFSLSTSGMGVGWIRQPSGKGLEWLAHIWWDDDKYYSPSLKSQLTISKDTSRNQVFLKITSLDTADTATYYCVRSYYYGSSGAMDYW
GQGTSVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKS
CDKTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPA
PIEKTISKAKGQPREPQVYTLPPSREEMTKNQVSLTCLVKGFYPSDIAVEWESDGQPENNYKTTPPVLDSDGSFFLYSKLTVDKSRWQEGNVFSCSVMHEALHNHYTQKSL
SLSPGK >XENP023378 1D8[GITR]_H0L0_Fab-1G6_L1.194_H1.279_scFv scFv-Fc Heavy Chain (SEQ ID NO: 29719)
EIVLTQSPATLSASPGERVTLTCRASQSVGNDVAWYQQKPGQAPRLLINVASHRYTGVPDRFTGSGYGTEFTLTISSVQSEDFGVYYCQQDFSSPRTFGGGTKVEIK/GKPG
SGKPGSGKPGSGKPGS/EVQLVESGGGLVKPGGSLRLSCVASGFTFSNYWMNWVRQAPGKGLEWVAEIRLYSNNYATHYAESVKGRFTISRDDSKSTLYLQMNNLKTED
TGVYYCTRYYGNYGGYFDVWGRGTLVTVSS/EPKSSDKTHTCPPCPAPPVAGPSVFLFPPKPKDTLMISRTPEVTCVVVDVKHEDPEVKFNWYVDGVEVHNAKTKPREEQ
YNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFL
YSKLTVDKSRWQQGNVFSCSVMHEALHNHYTQKSLSLSPGK >XENP023378 1D8[GITR]_H0L0_Fab-1G6_L1.194_H1.279_scFv Light Chain (SEQ ID NO: 29720)
DIVMTQTPLSLPVSLGDQASISCRSSQSLVHSDGNTYLHWYLQKPGQSPKLLIYKVSKRFSGVPDRFSGSGSGTDFTLKISRVEAEDLGVYFCSQTHVPPTFGGGTKLEIK/R
TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 26D

XENP23379

>XENP023379_20H4.9[4-1BB]_H0L0_Fab-1G6_L1.194_H1.279_scFv Fab-Fc Heavy Chain (SEQ ID NO: 29721)
QVQLQQWGAGLLKPSETLSLTCAVYGGSFSGYYWSWIRQSPEKGLEWIGEINHGGYVTYNPSLESRVTISVDTSKNQFSLKLSSVTAADTAVYYCARDYGPGNYDWYFDL
WGRGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPK
SCDKTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALP
APIEKTISKAKGQPREPQVYTLPPSREEMTKNQVSLTCDVSGFYPSDIAVEWESNGQPENNYKTTPPVLDSDGSFFLYSKLTVDKSRWQEGDVFSCSVMHEALHNHYTQKS
LSLSPGK >XENP023379_20H4.9[4-1BB]_H0L0_Fab-1G6_L1.194_H1.279_scFv scFv-Fc Heavy Chain (SEQ ID NO: 29722)
EIVLTQSPATLSASPGERVTLTCRASQSVGNDVAWYQQKPGQAPRLLINYASHRYTGVPDRFTGSGYGTEFTLTISSVQSEDFGVYYCQQDFSSPRTFGGGTKVEIK/GKPG
SGKPGSGKPGSGKPGS/EVQLVESGGGLVKPGGSLRLSCVASGFTFSNYWMNWVRQAPGKGLEWVAEIRLYSNNYATHYAESVKGRFTISRDDSKSTLYLQMNNLKTED
TGVYYCTRYYGNYGGYFDVWGRGTLVTVSS/EPKSSDKTHTCPPCPAPPVAGPSVFLFPPKPKDTLMISRTPEVTCVVVDVKHEDPEVKFNWYVDGVEVHNAKTKPREEQ
YNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFL
YSKLTVDKSRWQQGNVFSCSVMHEALHNHYTQKSLSLSPGK >XENP023379_20H4.9[4-1BB]_H0L0_Fab-1G6_L1.194_H1.279_scFv Light Chain (SEQ ID NO: 29723)
EIVLTQSPATLSLSPGERATLSCRASQSVSSYLAWYQQKPGQAPRLLIYDASNRATGIPARFSGSGSGTDFTLTISSLEPEDFAVYYCQQRSNWPPALTFGGGTKVEIK/RTVA
APSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 32A

XENP20896

>XENP020896 [ICOS]_H0L0_Fab-1G6_L1.194_H1.279 Fab-Fc Heavy Chain (SEQ ID NO: 29724)

QVQLVQSGAEVKKPGASVKVSCKASGYTFTGYYMHWVRQAPGQGLEWMGWINPHSGGTNYAQKFQGRVTMTRDTSISTAYME
LSRLRSDDTAVYYCARTYYDSSGYYHDAFDIWGQGTMVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVMHEALHNHYTQKSLSLSPGK

>XENP020896 [ICOS]_H0L0_Fab-1G6_L1.194_H1.279 scFv-Fc Heavy Chain (SEQ ID NO: 29725)

EIVLTQSPATLSASPGERVTLTCRASQSVGNDVAWYQQKPGQAPRLLINYASHRYTGVPDRFTGSGYGTEFTLTISSVQSED
FGVYYCQQDFSSPRTFGGGTKVEIK/GKPGSGKPGSGKPGSGKPGS/EVQLVESGGGLVKPGGSLRLSCVASGFTFSNYWMN
WVRQAPGKGLEWVAEIRLYSNNYATHYAESVKGRFTISRDDSKSTLYLQMNNLKTEDTGVYYCTRYYGNYGGYFDVWGRGTL
VTVSS/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

>XENP020896 [ICOS]_H0L0_Fab-1G6_L1.194_H1.279 Light Chain (SEQ ID NO: 29726)

DIQMTQSPSSVSASVGDRVTITCRASQGISRLLAWYQQKPGKAPKLLIYVASSLQSGVPSRFSGSGSGTDFTLTISSLQPED
FATYYCQQANSFPWTFGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

XENP22433

>XENP022433 [ICOS]_H0_L0.7_Fab-1G6_L1.194_H1.279 Fab-Fc Heavy Chain (SEQ ID NO: 29727)

QVQLVQSGAEVKKPGASVKVSCKASGYTFTGYYMHWVRQAPGQGLEWMGWINPHSGGTNYAQKFQGRVTMTRDTSISTAYME
LSRLRSDDTAVYYCARTYYDSSGYYHDAFDIWGQGTMVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVMHEALHNHYTQKSLSLSPGK

>XENP022433 [ICOS]_H0_L0.7_Fab-1G6_L1.194_H1.279 scFv-Fc Heavy Chain (SEQ ID NO: 29728)

EIVLTQSPATLSASPGERVTLTCRASQSVGNDVAWYQQKPGQAPRLLINYASHRYTGVPDRFTGSGYGTEFTLTISSVQSED
FGVYYCQQDFSSPRTFGGGTKVEIK/GKPGSGKPGSGKPGSGKPGS/EVQLVESGGGLVKPGGSLRLSCVASGFTFSNYWMN
WVRQAPGKGLEWVAEIRLYSNNYATHYAESVKGRFTISRDDSKSTLYLQMNNLKTEDTGVYYCTRYYGNYGGYFDVWGRGTL
VTVSS/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

>XENP022433 [ICOS]_H0_L0.7_Fab-1G6_L1.194_H1.279 Light Chain (SEQ ID NO: 29729)

DIQMTQSPSSVSASVGDRVTITCRASQGISSYLAWYQQKPGKAPKLLIYVASSLQSGVPSRFSGSGSGTDFTLTISSLQPED
FATYYCQQANSFPWTFGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

Figure 32B

XENP22744

>XENP022744 [ICOS]_H0_L0.34_Fab-1G6_L1.194_H1.279 Fab-Fc Heavy Chain (SEQ ID NO: 29730)

QVQLVQSGAEVKKPGASVKVSCKASGYTFTGYYMHWVRQAPGQGLEWMGWINPHSGGTNYAQKFQGRVTMTRDTSISTAYME
LSRLRSDDTAVYYCARTYYYDSSGYYHDAFDIWGQGTMVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVMHEALHNHYTQKSLSLSPGK

>XENP022744 [ICOS]_H0_L0.34_Fab-1G6_L1.194_H1.279 scFv-Fc Heavy Chain (SEQ ID NO: 29731)

EIVLTQSPATLSASPGERVTLTCRASQSVGNDVAWYQQKPGQAPRLLINYASHRYTGVPDRFTGSGYGTEFTLTISSVQSED
FGVYYCQQDFSSPRTFGGGTKVEIK/GKPGSGKPGSGKPGSGKPGS/EVQLVESGGGLVKPGGSLRLSCVASGFTFSNYWMN
WVRQAPGKGLEWVAEIRLYSNNYATHYAESVKGRFTISRDDSKSTLYLQMNNLKTEDTGVYYCTRYYGNYGGYFDVWGRGTL
VTVSS/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

>XENP022744 [ICOS]_H0_L0.34_Fab-1G6_L1.194_H1.279 Light Chain (SEQ ID NO: 29732)

DIQMTQSPSSVSASVGDRVTITCQASQDISRLLAWYQQKPGKAPKLLIYVASSLQSGVPSRFSGSGSGTDFTLTISSLQPED
FATYYCQQAESFPWTFGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

XENP22746

>XENP022746 [ICOS]_H0_L0.36_Fab-1G6_L1.194_H1.279 Fab-Fc Heavy Chain (SEQ ID NO: 29733)

QVQLVQSGAEVKKPGASVKVSCKASGYTFTGYYMHWVRQAPGQGLEWMGWINPHSGGTNYAQKFQGRVTMTRDTSISTAYME
LSRLRSDDTAVYYCARTYYYDSSGYYHDAFDIWGQGTMVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVMHEALHNHYTQKSLSLSPGK

>XENP022746 [ICOS]_H0_L0.36_Fab-1G6_L1.194_H1.279 scFv-Fc Heavy Chain (SEQ ID NO: 29734)

EIVLTQSPATLSASPGERVTLTCKASQSVGNDVAWYQQKPGQAPRLLINYASHRYTGVPDRFTGSGYGTEFTLTISSVQSED
FGVYYCQQDFSSPRTFGGGTKVEIK/GKPGSGKPGSGKPGSGKPGS/EVQLVESGGGLVKPGGSLRLSCVASGFTFSNYWMN
WVRQAPGKGLEWVAEIRLYSNNYATHYAESVKGRFTISRDDSKSTLYLQMNNLKTEDTGVYYCTRYYGNYGGYFDVWGRGTL
VTVSS/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

>XENP022746 [ICOS]_H0_L0.36_Fab-1G6_L1.194_H1.279 Light Chain (SEQ ID NO: 29735)

DIQMTQSPSSVSASVGDRVTITCQASQDISSLLAWYQQKPGKAPKLLIYVASSLQSGVPSRFSGSGSGTDFTLTISSLQPED
FATYYCQQAESFPWTFGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

Figure 32C

XENP22747

>XENP022747 [ICOS]_H0_L0.37_Fab-1G6_L1.194_H1.279 Fab-Fc Heavy Chain (SEQ ID NO: 29736)

QVQLVQSGAEVKKPGASVKVSCKASGYTFTGYYMHWVRQAPGQGLEWMGWINPHSGGTNYAQKFQGRVTMTRDTSISTAYME
LSRLRSDDTAVYYCARTYYYDSSGYYHDAFDIWGQGTMVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVMHEALHNHYTQKSLSLSPGK

>XENP022747 [ICOS]_H0_L0.37_Fab-1G6_L1.194_H1.279 scFv-Fc Heavy Chain (SEQ ID NO: 29737)

EIVLTQSPATLSASPGERVTLTCRASQSVGNDVAWYQQKPGQAPRLLINYASHRYTGVPDRFTGSGYGTEFTLTISSVQSED
FGVYYCQQDFSSPRTFGGGTKVEIK/GKPGSGKPGSGKPGSGKPGS/EVQLVESGGGLVKPGGSLRLSCVASGFTFSNYWMN
WVRQAPGKGLEWVAEIRLYSNNYATHYAESVKGRFTISRDDSKSTLYLQMNNLKTEDTGVYYCTRYYGNYGGYFDVWGRGTL
VTVSS/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

>XENP022747 [ICOS]_H0_L0.37_Fab-1G6_L1.194_H1.279 Light Chain (SEQ ID NO: 29738)

DIQMTQSPSSVSASVGDRVTITCQASQDISRLLAWYQQKPGKAPKLLIYAASSLQSGVPSRFSGSGSGTDFTLTISSLQPED
FATYYCQQAESFPWTFGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

XENP22748

>XENP022748 [ICOS]_H0_L0.38_Fab-1G6_L1.194_H1.279 Fab-Fc Heavy Chain (SEQ ID NO: 29739)

QVQLVQSGAEVKKPGASVKVSCKASGYTFTGYYMHWVRQAPGQGLEWMGWINPHSGGTNYAQKFQGRVTMTRDTSISTAYME
LSRLRSDDTAVYYCARTYYYDSSGYYHDAFDIWGQGTMVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVMHEALHNHYTQKSLSLSPGK

>XENP022748 [ICOS]_H0_L0.38_Fab-1G6_L1.194_H1.279 scFv-Fc Heavy Chain (SEQ ID NO: 29740)

EIVLTQSPATLSASPGERVTLTCKASQSVGNDVAWYQQKPGQAPRLLINYASHRYTGVPDRFTGSGYGTEFTLTISSVQSED
FGVYYCQQDFSSPRTFGGGTKVEIK/GKPGSGKPGSGKPGSGKPGS/EVQLVESGGGLVKPGGSLRLSCVASGFTFSNYWMN
WVRQAPGKGLEWVAEIRLYSNNYATHYAESVKGRFTISRDDSKSTLYLQMNNLKTEDTGVYYCTRYYGNYGGYFDVWGRGTL
VTVSS/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

>XENP022748 [ICOS]_H0_L0.38_Fab-1G6_L1.194_H1.279 Light Chain (SEQ ID NO: 29741)

DIQMTQSPSSVSASVGDRVTITCQASQDISSLLAWYQQKPGKAPKLLIYAASSLQSGVPSRFSGSGSGTDFTLTISSLQPED
FATYYCQQAESFPWTFGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

Figure 32D

XENP23092

>XENP023092 [ICOS]_H0.66_L0_Fab-1G6_L1.194_H1.279 Fab-Fc Heavy Chain (SEQ ID NO: 29742)

QVQLVQSGAEVKKPGASVKVSCKASGYTFTGYYMHWVRQAPGQGLEWMGWINPHSGETIYAQKFQGRVTMTRDTSISTAYME
LSSLRSEDTAVYYCARTYYYDTSGYYHDAFDVWGQGTMVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVMHEALHNHYTQKSLSLSPGK

>XENP023092 [ICOS]_H0.66_L0_Fab-1G6_L1.194_H1.279 scFv-Fc Heavy Chain (SEQ ID NO: 29743)

EIVLTQSPATLSASPGERVTLTCRASQSVGNDVAWYQQKPGQAPRLLINYASHRYTGVPDRFTGSGYGTEFTLTISSVQSED
FGVYYCQQDFSSPRTFGGGTKVEIK/GKPGSGKPGSGKPGSGKPGS/EVQLVESGGGLVKPGGSLRLSCVASGFTFSNYWMN
WVRQAPGKGLEWVAEIRLYSNNYATHYAESVKGRFTISRDDSKSTLYLQMNNLKTEDTGVYYCTRYYGNYGGYFDVWGRGTL
VTVSS/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

>XENP023092 [ICOS]_H0.66_L0_Fab-1G6_L1.194_H1.279 Light Chain (SEQ ID NO: 29744)

DIQMTQSPSSVSASVGDRVTITCRASQGISRLLAWYQQKPGKAPKLLIYVASSLQSGVPSRFSGSGSGTDFTLTISSLQPED
FATYYCQQANSFPWTFGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

XENP23410

>XENP023410 [ICOS]_H0.66_L0.34_Fab-1G6_L1.194_H1.279 Fab-Fc Heavy Chain (SEQ ID NO: 29745)

QVQLVQSGAEVKKPGASVKVSCKASGYTFTGYYMHWVRQAPGQGLEWMGWINPHSGETIYAQKFQGRVTMTRDTSISTAYME
LSSLRSEDTAVYYCARTYYYDTSGYYHDAFDVWGQGTMVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVMHEALHNHYTQKSLSLSPGK

>XENP023410 [ICOS]_H0.66_L0.34_Fab-1G6_L1.194_H1.279 scFv-Fc Heavy Chain (SEQ ID NO: 29746)

EIVLTQSPATLSASPGERVTLTCRASQSVGNDVAWYQQKPGQAPRLLINYASHRYTGVPDRFTGSGYGTEFTLTISSVQSED
FGVYYCQQDFSSPRTFGGGTKVEIK/GKPGSGKPGSGKPGSGKPGS/EVQLVESGGGLVKPGGSLRLSCVASGFTFSNYWMN
WVRQAPGKGLEWVAEIRLYSNNYATHYAESVKGRFTISRDDSKSTLYLQMNNLKTEDTGVYYCTRYYGNYGGYFDVWGRGTL
VTVSS/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

>XENP023410 [ICOS]_H0.66_L0.34_Fab-1G6_L1.194_H1.279 Light Chain (SEQ ID NO: 29747)

DIQMTQSPSSVSASVGDRVTITCQASQDISRLLAWYQQKPGKAPKLLIYVASSLQSGVPSRFSGSGSGTDFTLTISSLQPED
FATYYCQQAESFPWTFGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

Figure 33A

XENP22730

>XENP022730 [ICOS]_H0L0_Fab-1G6_L1.194_H1.279 Fab-Fc Heavy Chain (SEQ ID NO: 29748)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYRDAFDIWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVLHEALHSHYTQKSLSLSPGK

>XENP022730 [ICOS]_H0L0_Fab-1G6_L1.194_H1.279 scFv-Fc Heavy Chain (SEQ ID NO: 29749)

EIVLTQSPATLSASPGERVTLTCRASQSVGNDVAWYQQKPGQAPRLLINYASHRYTGVPDRFTGSGYGTEFTLTISS
VQSEDFGVYYCQQDFSSPRTFGGGTKVEIK/GKPGSGKPGSGKPGSGKPGS/EVQLVESGGGLVKPGGSLRLSCVAS
GFTFSNYWMNWVRQAPGKGLEWVAEIRLYSNNYATHYAESVKGRFTISRDDSKSTLYLQMNNLKTEDTGVYYCTRYY
GNYGGYFDVWGRGTLVTVSS/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

>XENP022730 [ICOS]_H0L0_Fab-1G6_L1.194_H1.279 Light Chain (SEQ ID NO: 29750)

DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XENP22974

>XENP022974 [ICOS]_H0_L0.34_Fab-1G6_L1.194_H1.279 Fab-Fc Heavy Chain (SEQ ID NO: 29751)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYRDAFDIWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVLHEALHSHYTQKSLSLSPGK

>XENP022974 [ICOS]_H0_L0.34_Fab-1G6_L1.194_H1.279 scFv-Fc Heavy Chain (SEQ ID NO: 29752)

EIVLTQSPATLSASPGERVTLTCRASQSVGNDVAWYQQKPGQAPRLLINYASHRYTGVPDRFTGSGYGTEFTLTISS
VQSEDFGVYYCQQDFSSPRTFGGGTKVEIK/GKPGSGKPGSGKPGSGKPGS/EVQLVESGGGLVKPGGSLRLSCVAS
GFTFSNYWMNWVRQAPGKGLEWVAEIRLYSNNYATHYAESVKGRFTISRDDSKSTLYLQMNNLKTEDTGVYYCTRYY
GNYGGYFDVWGRGTLVTVSS/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Figure 33B

>XENP022974 [ICOS]_H0_L0.34_Fab-1G6_L1.194_H1.279 Light Chain (SEQ ID NO: 29753)

DIQMTQSPSSVSASVGDRVTITCQASQDISRLLAWYQQKPGKAPKLLIYVASSLQSGVPSRFSGSGSGTDFTLTISS
LQPEDFATYYCQQAESFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XENP23104

>XENP023104 [ICOS]_H0.66_L0_Fab-1G6_L1.194_H1.279 Fab-Fc Heavy Chain (SEQ ID NO: 29754)

QVQLVQSGAEVKKPGASVKVSCKASGYTFTGYYMHWVRQAPGQGLEWMGWINPHSGETIYAQKFQGRVTMTRDTSIS
TAYMELSSLRSEDTAVYYCARTYYYDTSGYYHDAFDVWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVLHEALHSHYTQKSLSLSPGK

>XENP023104 [ICOS]_H0.66_L0_Fab-1G6_L1.194_H1.279 scFv-Fc Heavy Chain (SEQ ID NO: 29755)

EIVLTQSPATLSASPGERVTLTCRASQSVGNDVAWYQQKPGQAPRLLINYASHRYTGVPDRFTGSGYGTEFTLTISS
VQSEDFGVYYCQQDFSSPRTFGGGTKVEIK/GKPGSGKPGSGKPGSGKPGS/EVQLVESGGGLVKPGGSLRLSCVAS
GFTFSNYWMNWVRQAPGKGLEWVAEIRLYSNNYATHYAESVKGRFTISRDDSKSTLYLQMNNLKTEDTGVYYCTRYY
GNYGGYFDVWGRGTLVTVSS/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

>XENP023104 [ICOS]_H0.66_L0_Fab-1G6_L1.194_H1.279 Light Chain (SEQ ID NO: 29756)

DIQMTQSPSSVSASVGDRVTITCRASQGISPLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XENP23411

>XENP023411 [ICOS]_H0.66_L0.34_Fab-1G6_L1.194_H1.279 Fab-Fc Heavy Chain (SEQ ID NO: 29757)

QVQLVQSGAEVKKPGASVKVSCKASGYTFTGYYMHWVRQAPGQGLEWMGWINPHSGETIYAQKFQGRVTMTRDTSIS
TAYMELSSLRSEDTAVYYCARTYYYDTSGYYHDAFDVWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVLHEALHSHYTQKSLSLSPGK

Figure 33C

>XENP023411 [ICOS]_H0.66_L0.34_Fab-1G6_L1.194_H1.279 scFv-Fc Heavy Chain (SEQ ID NO: 29758)

EIVLTQSPATLSASPGERVTLTCRASQSVGNDVAWYQQKPGQAPRLLINYASHRYTGVPDRFTGSGYGTEFTLTISS
VQSEDFGVYYCQQDFSSPRTFGGGTKVEIK/GKPGSGKPGSGKPGSGKPGS/EVQLVESGGGLVKPGGSLRLSCVAS
GFTFSNYWMNWVRQAPGKGLEWVAEIRLYSNNYATHYAESVKGRFTISRDDSKSTLYLQMNNLKTEDTGVYYCTRYY
GNYGGYFDVWGRGTLVTVSS/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

>XENP023411 [ICOS]_H0.66_L0.34_Fab-1G6_L1.194_H1.279 Light Chain (SEQ ID NO: 29759)

DIQMTQSPSSVSASVGDRVTITCQASQDISRLLAWYQQKPGKAPKLLIYVASSLQSGVPSRFSGSGSGTDFTLTISS
LQPEDFATYYCQQAESFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 34A

| XENP | Antigen | $K_D$ (nM) | $k_a$ (1/Ms) | $k_d$ (1/s) |
|---|---|---|---|---|
| 22438 | huICOS | 2.28 | 2.49E+05 | 5.69E-04 |
| 22437 | huICOS | 0.5613 | 2.05E+05 | 1.15E-04 |
| 22436 | huICOS | 1.813 | 2.49E+05 | 4.52E-04 |
| 22435 | huICOS | 1.411 | 2.27E+05 | 3.20E-04 |
| 22434 | huICOS | 2.766 | 2.33E+05 | 6.44E-04 |
| 22433 | huICOS | 3.8 | 1.88E+05 | 7.15E-04 |
| 22432 | huICOS | 0.6282 | 2.02E+05 | 1.27E-04 |
| 20896 | huICOS | 0.4358 | 2.20E+05 | 9.57E-05 |

Figure 34B

| XENP | Antigen | $K_D$ (nM) | $k_a$ (1/Ms) | $k_d$ (1/s) |
|---|---|---|---|---|
| 20896 | huICOS | <0.001 | 8.58E+04 | <1.0E-07 |
| 22432 | huICOS | 1.78 | 8.46E+04 | 1.50E-04 |
| 22433 | huICOS | 9.68 | 5.78E+04 | 5.59E-04 |
| 22434 | huICOS | 3.99 | 7.48E+04 | 2.99E-04 |
| 22435 | huICOS | 3.44 | 1.28E+05 | 4.40E-04 |
| 22436 | huICOS | 1.43 | 1.03E+05 | 1.47E-04 |
| 22437 | huICOS | 0.34 | 7.82E+04 | 2.66E-05 |
| 22438 | huICOS | 6.2 | 9.80E+04 | 6.07E-04 |

Figure 34C

| XENP | Antigen | $K_D$ (nM) | $k_a$ (1/Ms) | $k_d$ (1/s) |
|---|---|---|---|---|
| 20896 | huICOS | 1.58 | 6.55E+04 | 1.04E-04 |
| 22433 | huICOS | 11.6 | 6.19E+04 | 7.21E-04 |
| 22740 | huICOS | 11.5 | 7.56E+04 | 8.68E-04 |
| 22741 | huICOS | 13 | 8.00E+04 | 1.04E-03 |
| 22742 | huICOS | 2.08 | 8.49E+04 | 1.76E-04 |
| 22743 | huICOS | 4.41 | 9.21E+04 | 4.06E-04 |
| 22744 | huICOS | 2.15 | 6.07E+04 | 1.30E-04 |
| 22745 | huICOS | 9.12 | 7.87E+04 | 7.18E-04 |
| 22746 | huICOS | 4.52 | 5.97E+04 | 2.70E-04 |
| 22747 | huICOS | 10.1 | 5.56E+04 | 5.63E-04 |
| 22748 | huICOS | 11.9 | 6.64E+04 | 7.88E-04 |

Figure 35

| XENP | huICOS $K_D$ (nM) | huICOS $k_a$ (1/Ms) | huICOS $k_d$ (1/s) | cynoICOS $K_D$ (nM) | cynoICOS $k_a$ (1/Ms) | cynoICOS $k_d$ (1/s) |
|---|---|---|---|---|---|---|
| 20896 | 2.09 | 5.45E+04 | 1.14E-04 | 2.41 | 5.70E+04 | 1.38E-04 |
| 22433 | 41.30 | 2.64E+04 | 1.09E-03 | 35.30 | 3.10E+04 | 1.10E-03 |
| 22744 | 3.91 | 3.50E+04 | 1.37E-04 | 5.82 | 3.27E+04 | 1.90E-04 |
| 22745 | 17.60 | 6.01E+04 | 1.06E-03 | 14.50 | 7.84E+04 | 1.14E-03 |
| 22746 | 10.10 | 3.76E+04 | 3.81E-04 | 11.90 | 3.14E+04 | 3.73E-04 |
| 22747 | 18.40 | 5.05E+04 | 9.27E-04 | 21.50 | 4.53E+04 | 9.73E-04 |
| 22748 | 42.30 | 4.26E+04 | 1.80E-03 | 39.40 | 4.93E+04 | 1.94E-03 |
| 23090 | 2.73 | 5.60E+04 | 1.53E-04 | ND | ND | ND |
| 23091 | 5.62 | 4.75E+04 | 2.67E-04 | ND | ND | ND |
| 23092 | 4.30 | 5.80E+04 | 2.50E-04 | ND | ND | ND |
| 23093 | 5.43 | 5.70E+04 | 3.09E-04 | ND | ND | ND |
| 23410 | 9.04 | 3.56E+04 | 3.22E-04 | ND | ND | ND |

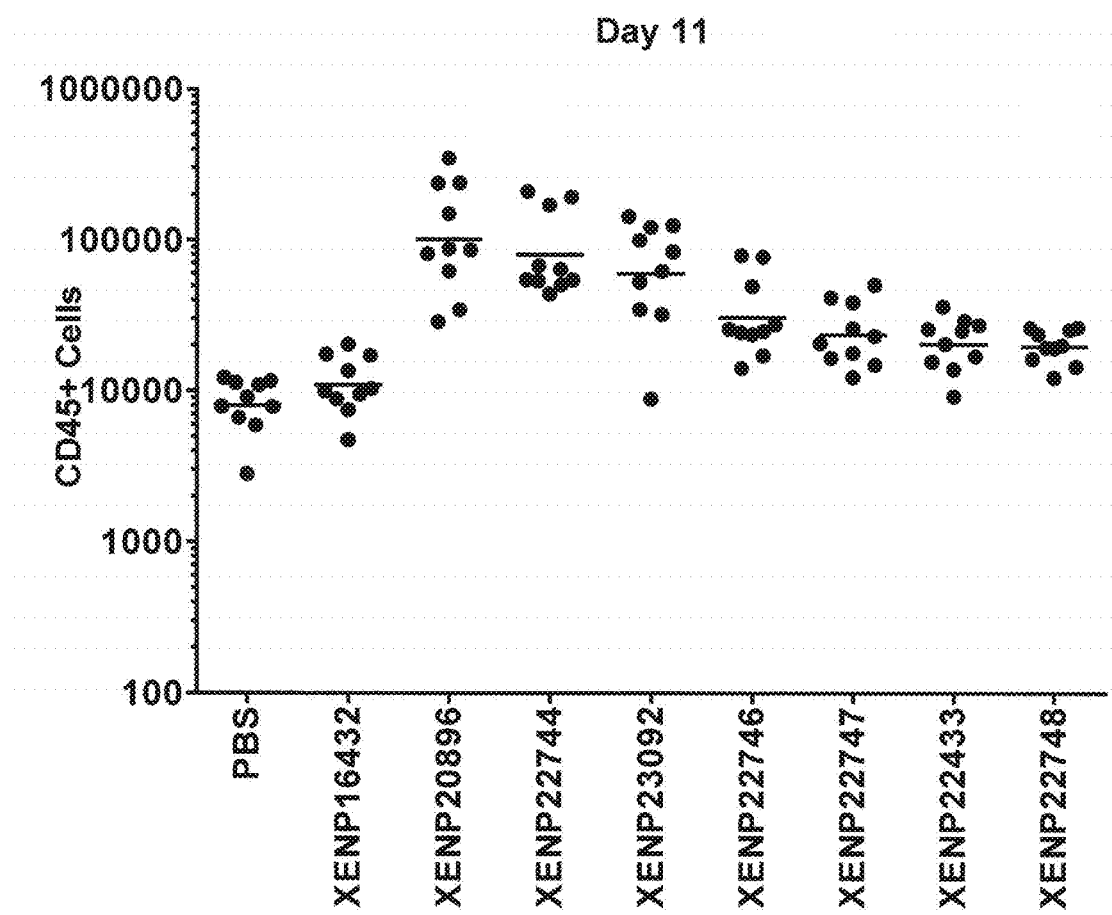

Figure 48A

XENP21828

>XENP021828 GSK_314.8[ICOS]_H0L0_Fab-1G6_L1.194_H1.279_scFv Fab-Fc Heavy Chain (SEQ ID NO: 29760)

QVQLQQPGTELMKPGASVKLSCKASGYTFTTYWMHWVKQRPGQGLEWIGEIDPSDSYVNYNQMFKGKATLTVDKSSSTAYIQ
LSSLTSEDSAVYFCARSDYYGTSLAWFDYWGQGTLVTVST/ASTKGPSVFPLAPSSKSTSGGTAALGCLVKDYFPEPVTVS
WNSGALTSGVHTFPAVLQSSGLYSLSSVVTVPSSSLGTQTYICNVNHKPSDTKVDKKVEPKSCDKTHTCPPCPAPPVAGPSV
FLFPPKPKDTLMISRTPEVTCVVVDVKHEDPEVKFNWYVDGVEVHNAKTKPREEEYNSTYRVVSVLTVLHQDWLNGKEYKCK
VSNKALPAPIEKTISKAKGQPREPQVYTLPPSREEMTKNQVSLTCDVSGFYPSDIAVEWESDGQPENNYKTTPPVLDSDGSF
FLYSKLTVDKSRWEQGDVFSCSVMHEALHNHYTQKSLSLSPGK

>XENP021828 GSK_314.8[ICOS]_H0L0_Fab-1G6_L1.194_H1.279_scFv scFv-Fc Heavy Chain (SEQ ID NO: 29761)

EIVLTQSPATLSASPGERVTLTCRASQSVGNDVAWYQQKPGQAPRLLINYASHRYTGVPDRFTGSGYGTEFTLTISSVQSED
FGVYYCQQDFSSPRTFGGGTKVEIK/GKPGSGKPGSGKPGSGKPGS/EVQLVESGGGLVKPGGSLRLSCVASGFTFSNYWMN
WVRQAPGKGLEWVAEIRLYSNNYATHYAESVKGRFTISRDDSKSTLYLQMNNLKTEDTGVYYCTRYYGNYGGYFDVWGRGTL
VTVSS/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

>XENP021828 GSK_314.8[ICOS]_H0L0_Fab-1G6_L1.194_H1.279_scFv Light Chain (SEQ ID NO: 29762)

DIVMTQAAPSVPVTPGESVSISCRSSKSPLRSNGNIYLYWFLQRPGQSPQLLIYRMSNLASGVPDRFSGSGSGTTFTLKISR
VEAEDVGVYYCMQHLEYPYTFGGGTKLEIK/RTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC

XENP21829

>XENP021829 GSK_88.2[ICOS]_H0L0_Fab-1G6_L1.194_H1.279_scFv Fab-Fc Heavy Chain (SEQ ID NO: 29763)

QVQLQQPGAELVRPGASVKLSCKASGYSFTEYWINWVKQRPGQGLEWIGNIYPSDSYTNYNQMFKDKATLTVDKSSNTAYMQ
LTSPTSEDSAVYYCTRWNLSYYFDNNYYLDYWGQGTTLTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSDTKVDKKVEPKSCDKTHTCPPCPAPPVAGPS
VFLFPPKPKDTLMISRTPEVTCVVVDVKHEDPEVKFNWYVDGVEVHNAKTKPREEEYNSTYRVVSVLTVLHQDWLNGKEYKC
KVSNKALPAPIEKTISKAKGQPREPQVYTLPPSREEMTKNQVSLTCDVSGFYPSDIAVEWESDGQPENNYKTTPPVLDSDGS
FFLYSKLTVDKSRWEQGDVFSCSVMHEALHNHYTQKSLSLSPGK

>XENP021829 GSK_88.2[ICOS]_H0L0_Fab-1G6_L1.194_H1.279_scFv scFv-Fc Heavy Chain (SEQ ID NO: 29764)

EIVLTQSPATLSASPGERVTLTCRASQSVGNDVAWYQQKPGQAPRLLINYASHRYTGVPDRFTGSGYGTEFTLTISSVQSED
FGVYYCQQDFSSPRTFGGGTKVEIK/GKPGSGKPGSGKPGSGKPGS/EVQLVESGGGLVKPGGSLRLSCVASGFTFSNYWMN
WVRQAPGKGLEWVAEIRLYSNNYATHYAESVKGRFTISRDDSKSTLYLQMNNLKTEDTGVYYCTRYYGNYGGYFDVWGRGTL
VTVSS/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK

Figure 48B

>XENP021829 GSK_88.2[ICOS]_H0L0_Fab-1G6_L1.194_H1.279_scFv Light Chain (SEQ ID NO: 29765)

DIVMTQAAPSVPVTPGESVSISCRSSKSLLHSNGNTYLYWFLQRPGQSPQLLIYRMSNLASGVPDRFSGSGSGTAFT
LRISRVEAEDVGVYYCMQHLEYPWTFGGGTKLEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

XENP21830

>XENP021830 jMab-138[ICOS]_H0L0_Fab-1G6_L1.194_H1.279_scFv Fab-Fc Heavy Chain (SEQ ID NO: 29766)

EVQLVESGGGLVQPGGSLRLSCAASGFTFSSYDMHWVRQATGKGLEWVSAIGTAGDTYYPGSVKGRFTISRENAKNS
LYLQMNSLRAGDTAVYYCVRDNRKVTHEHYYYGMDVWGQGTTVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

>XENP021830 jMab-138[ICOS]_H0L0_Fab-1G6_L1.194_H1.279_scFv scFv-Fc Heavy Chain (SEQ ID NO: 29767)

EIVLTQSPATLSASPGERVTLTCRASQSVGNDVAWYQQKPGQAPRLLINYASHRYTGVPDRFTGSGYGTEFTLTISS
VQSEDFGVYYCQQDFSSPRTFGGGTKVEIK/GKPGSGKPGSGKPGSGKPGS/EVQLVESGGGLVKPGGSLRLSCVAS
GFTFSNYWMNWVRQAPGKGLEWVAEIRLYSNNYATHYAESVKGRFTISRDDSKSTLYLQMNNLKTEDTGVYYCTRYY
GNYGGYFDVWGRGTLVTVSS/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

>XENP021830 jMab-138[ICOS]_H0L0_Fab-1G6_L1.194_H1.279_scFv Light Chain (SEQ ID NO: 29768)

EIVLTQSPGTLSLSPGERATLSCRASQNIRSSYLAWYQQKPGQAPGLLIYGASSRATGIPDRFSGSGSGTDFTLTIS
RLEPEDFAVYYCQQFGSSPMCSFGQGTKLEIK/RTVAAPSVFIFPPSDEQLKSGTASVVCLLNNFYPREAKVQWKVD
NALQSGNSQESVTEQDSKDSTYSLSSTLTLSKADYEKHKVYACEVTHQGLSSPVTKSFNRGEC

XENP21831

>XENP021831 jMab-139[ICOS]_H0L0_Fab-1G6_L1.194_H1.279_scFv Fab-Fc Heavy Chain (SEQ ID NO: 29769)

EVQLVESGGGLVQPGGSLRLSCAASGFTFSSYDMHWVRQATGKGLEWVSAIGTAGDTYYPGSVKGRFTISRENAKNS
LYLQMNSLRAGDTAVYYCVRDKRTVTHEHYYYGMDVWGQGTTVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

Figure 48C

>XENP021831 jMab-139[ICOS]_H0L0_Fab-1G6_L1.194_H1.279_scFv scFv-Fc Heavy Chain (SEQ ID NO: 29770)

EIVLTQSPATLSASPGERVTLTCRASQSVGNDVAWYQQKPGQAPRLLINYASHRYTGVPDRFTGSGYGTEFTLTISS
VQSEDFGVYYCQQDFSSPRTFGGGTKVEIK/GKPGSGKPGSGKPGSGKPGS/EVQLVESGGGLVKPGGSLRLSCVAS
GFTFSNYWMNWVRQAPGKGLEWVAEIRLYSNNYATHYAESVKGRFTISRDDSKSTLYLQMNNLKTEDTGVYYCTRYY
GNYGGYFDVWGRGTLVTVSS/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

>XENP021831 jMab-139[ICOS]_H0L0_Fab-1G6_L1.194_H1.279_scFv Light Chain (SEQ ID NO: 29771)

EIVLTQSPGTLSLSPGERATLSCRASQSISSSSLAWYQQKPGQAPGLLIFGASSRATGIPDRFSGSGSGTDFTLTIS
RLEPEDFAVYYCQQFGSSPMCSFGQGTKLEIK/RTVAAPSVFIFPPSDEQLKSGTASVVCLLNNFYPREAKVQWKVD
NALQSGNSQESVTEQDSKDSTYSLSSTLTLSKADYEKHKVYACEVTHQGLSSPVTKSFNRGEC

XENP22348

>XENP022348 WO2016059602_GSK_H0L0_Fab-1G6_L1.194_H1.279_scFv Fab-Fc Heavy Chain (SEQ ID NO: 29772)

QVQLVQSGAEVKKPGSSVKVSCKASGYTFTDYAMHWVRQAPGQGLEWMGLISIYSDHTNYNQKFQGRVTITADKSTS
TAYMELSSLRSEDTAVYYCGRMNYGNYGWYFDVWGQGTTVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK

>XENP022348 WO2016059602_GSK_H0L0_Fab-1G6_L1.194_H1.279_scFv scFv-Fc Heavy Chain (SEQ ID NO: 29773)

EIVLTQSPATLSASPGERVTLTCRASQSVGNDVAWYQQKPGQAPRLLINYASHRYTGVPDRFTGSGYGTEFTLTISS
VQSEDFGVYYCQQDFSSPRTFGGGTKVEIK/GKPGSGKPGSGKPGSGKPGS/EVQLVESGGGLVKPGGSLRLSCVAS
GFTFSNYWMNWVRQAPGKGLEWVAEIRLYSNNYATHYAESVKGRFTISRDDSKSTLYLQMNNLKTEDTGVYYCTRYY
GNYGGYFDVWGRGTLVTVSS/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

>XENP022348 WO2016059602_GSK_H0L0_Fab-1G6_L1.194_H1.279_scFv Light Chain (SEQ ID NO: 29774)

EIVLTQSPATLSLSPGERATLSCSASSSVSYMHWYQQKPGQAPRLLIYDTSKLASGIPARFSGSGSGTDYTLTISSL
EPEDFAVYYCFQGSGYPYTFGQGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

Figure 48D

XENP23059

>XENP023059 Jounce_37A10S713[ICOS]_H0L0_Fab-1G6_[PD-1]_L1.194_H1.279_scFv Fab-Fc Heavy Chain (SEQ ID NO: 29775)

EVQLVESGGGLVQPGGSLRLSCAASGFTFSDYWMDWVRQAPGKGLVWVSNIDEDGSITEYSPFVKGRFTISRDNAKN
TLYLQMNSLRAEDTAVYYCTRWGRFGFDSWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSDTKVDKKVEPKSCDKTHTCPPCP
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK

>XENP023059 Jounce_37A10S713[ICOS]_H0L0_Fab-1G6_[PD-1]_L1.194_H1.279_scFv scFv-Fc Heavy Chain (SEQ ID NO: 29776)

EIVLTQSPATLSASPGERVTLTCRASQSVGNDVAWYQQKPGQAPRLLINYASHRYTGVPDRFTGSGYGTEFTLTISS
VQSEDFGVYYCQQDFSSPRTFGGGTKVEIK/GKPGSGKPGSGKPGSGKPGS/EVQLVESGGGLVKPGGSLRLSCVAS
GFTFSNYWMNWVRQAPGKGLEWVAEIRLYSNNYATHYAESVKGRFTISRDDSKSTLYLQMNNLKTEDTGVYYCTRYY
GNYGGYFDVWGRGTLVTVSS/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

>XENP023059 Jounce_37A10S713[ICOS]_H0L0_Fab-1G6_[PD-1]_L1.194_H1.279_scFv Light Chain (SEQ ID NO: 29777)

DIVMTQSPDSLAVSLGERATINCKSSQSLLSGSFNYLTWYQQKPGQPPKLLIFYASTRHTGVPDRFSGSGSGTDFTL
TISSLQAEDVAVYYCHHHYNAPPTFGPGTKVDIK/RTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC

Figure 52

| | | XENP23104 | XENP16435 | XENP19686 | XENP16435 + XENP19686 |
|---|---|---|---|---|---|
| Th17 | IL17A | 14.6 | 7.8 | 2.0 | 5.9 |
| | IL17F | 5.4 | 3.3 | 1.8 | 3.9 |
| | IL22 | 3.6 | 2.5 | 1.3 | 2.7 |
| | IL21 | 2.0 | 1.4 | 1.0 | 1.5 |
| | CCL20 | 2.5 | 1.7 | 1.4 | 1.7 |
| | IL1R1 | 1.1 | 1.2 | 1.1 | 1.4 |
| | IL23R | 1.2 | 1.2 | 1.1 | 1.1 |
| | STAT3 | 1.0 | 0.9 | 1.1 | 0.9 |
| | RORC | 1.3 | 1.4 | 1.2 | 1.2 |
| | CCR6 | 0.8 | 1.0 | 1.0 | 1.0 |
| Th1 | IFNG | 13.1 | 3.5 | 1.8 | 5.7 |
| | TNF | 1.8 | 1.6 | 1.0 | 1.6 |
| | IL12A | 0.8 | 0.8 | 1.1 | 0.9 |
| | IL12B | 2.3 | 1.4 | 1.3 | 1.4 |
| | TBX21 | 1.6 | 1.3 | 1.1 | 1.4 |
| | STAT1 | 0.9 | 1.0 | 1.1 | 1.0 |
| | STAT4 | 0.9 | 0.9 | 1.0 | 0.8 |
| | IRF1 | 1.0 | 0.9 | 1.0 | 1.0 |
| | CXCR3 | 0.9 | 1.0 | 1.0 | 0.9 |
| | CCR5 | 0.8 | 0.8 | 1.0 | 0.7 |
| Th2 | IL4 | 1.2 | 1.1 | 1.2 | 1.2 |
| | IL5 | 4.3 | 3.6 | 1.8 | 3.2 |
| | IL9 | 10.3 | 3.1 | 2.5 | 5.1 |
| | IL13 | 2.4 | 1.9 | 1.4 | 1.8 |
| | IL24 | 1.7 | 1.3 | 1.3 | 2.0 |
| | TNFSF4 | 1.0 | 1.1 | 0.8 | 0.9 |
| | GATA3 | 1.3 | 1.1 | 1.2 | 1.1 |
| | STAT6 | 0.9 | 1.0 | 1.0 | 0.9 |
| | CCR2 | 0.8 | 0.9 | 1.0 | 0.9 |
| | CCR3 | 1.0 | 0.8 | 0.8 | 0.9 |
| Treg | TGFB1 | 1.1 | 1.1 | 1.0 | 1.0 |
| | SMAD3 | 0.7 | 0.8 | 0.9 | 0.8 |
| | ITGAE | 0.9 | 0.8 | 1.0 | 0.8 |
| | FOXP3 | 1.1 | 1.0 | 1.4 | 1.3 |

Figure 55A

Central scFv

Fab-Fc Heavy Chain (SEQ ID NO: 29778)

VH1/ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVD
KKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLT
VDKSRWQQGDVFSCSVMHEALHNHYTQKSLSLSPGK

Fab-scFv-Fc Heavy Chain (SEQ ID NOS 29779-29780)

VH1/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVD
KKVEPKSCCKPGSGKPGS/VH2-scFv linker-
VL2/GGGGSGGGGSGGGGSKTHTCPPCPAPPVAGPSVFLFPPKPKDTLMISRTPEVTCVVVDVKHEDPEVKFNWYVDGVEVHNAKTKPREEQYNSTYRVVSVLT
VLHQDWLNGKEYKCKVSNKALPAPIEKTISKAKGQPENNYKTTPPVLDSDGSFFL
YSKLTVDKSRWQQGNVFSCSVMHEALHNHYTQKSLSLSPGK

Light Chain (SEQ ID NO: 29781)

VL1/RTVAAPSVFIFPPSDEQLKSGTASVVCLLNNFYPREAKVQWKVDNALQSGNSQESVTEQDSKDSTYSLSSTLTLSKADYEKHKVYACEVTHQGLS
SPVTKSFNRGEC

Central scFv2

Heavy Chain (SEQ ID NOS 29782-29783)

VH1/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVD
KKVEPKSCGGGSGGGGSGGGGS/VH2-scFv linker-
VL2/GGGGSGGGGSGGGGSKTHTCPPCPAPPVAGPSVFLFPPKPKDTLMISRTPEVTCVVVDVKHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFL
YSKLTVDKSRWQQGNVFSCSVMHEALHNHYTQKSLSLSPGK

Figure 55B

Light Chain (SEQ ID NO: 29784)

VL1 / RTVAAPSVFIFPPSDEQLKSGTASVVCLLNNFYPREAKVQWKVDNALQSGNSQESVTEQDSKDSTYSLSSTLTLSKADYEKHKVYACEVTHQGLS
SPVTKSFNRGEC

Bispecific mAb

Heavy Chain 1 (SEQ ID NO: 29785)

VH1 / ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVD
KKVEPKSCDKTHTCPPCPAPPVAGPSVFLFPPKPKDTLMISRTPEVTCVVVDVKHEDPEVKFNWYVDGVEVHNAKTKPREEYNSTYRVVSVLTVLHQD
WLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLT
VDKSRWEQGDVFSCSVMHEALHNHYTQKSLSLSPGK

Heavy Chain 2 (SEQ ID NO: 29786)

VH2 / ASTKGPSVFPLAPSSKSTSGGTAALGCLVKDYFPEPVTVSWNSGALTSGVHTFPAVLQSSGLYSLSSVVTVPSSSLGTKTYTCNVNHKPSNTKVD
KKVERKSCDKTHTCPRCPAPPVAGPSVFLFPPKPKDTLMISRTPEVTCVVVDVKHEDPEVKFKWYVDGVEVHNAKTKPREEQYNSTYRVVSVLTVLHQD
WLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK

Light Chain 1 (SEQ ID NO: 29787)

VL1 / RTVAAPSVFIFPPSDEQLKSGTASVVCLLNNFYPREAKVQWKVDNALQSGNSQESVTEQDSKDSTYSLSSTLTLSKADYEKHKVYACEVTHQGLS
SPVTKSFNRGEC

Light Chain 2 (SEQ ID NO: 29788)

VL2 / RTVAAPSVFIFPPSDEQLKSGTASVVCLLNNFYPREAKVQWKVDNALQSGNSQESVTEQDSKDSTYSLSSTLTLSKADYEKHKVYACEVTHQGLS
SPVTKSFNRGEC

Figure 55C

DVD-Ig

Heavy Chain (SEQ ID NO: 29789)

VH1/ASTKGPSVFPLAP/VH2/ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPPVAGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK

Light Chain (SEQ ID NO: 29790)

VL1/RTVAAPSVFIFPP/VL2/RTVAAPSVFIFPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Trident

Heavy Chain 1 (SEQ ID NO: 29791)

VL1/GGGSGGGG/VH1/GGCGGGGEVAACEKEVAALEKEVAALEKEPKSSDKTHTCPPCPAPPVAGPSVFLFPPKPKDTLMISRTPEVTCVVV
DVSHEDPEVKFNWYVDGVEVHNAKTKPREEEYNSTYRVVSVLTVLHQDWLNGKEYKCKVSNKALPAPIEKTISKAKGQFREPQVYTLPPSREMTKNQV
SLTCDVSGFYPSDIAVEWESNGQPENNYKTTPPVLDSDGSFFLYSKLTVDKSRWQQGDVFSCSVMHEALHNHYTQKSLSLSPGK

Heavy Chain 2 (SEQ ID NO: 29792)

VH2/ASTKGPSVFPLAPSSKSTSGGTAALGCLVKDYFPEPVTVSWNSGALTSGVHTFPAVLQSSGLYSLSSVVTVPSSSLGTKTYTCNVNHKPSNTKVD
KKVERKSCDKTHTCPPCPAPPVAGPSVFLFPPKPKDTLMISRTPEVTCVVVDVSHEDPEVKFKWYVDGVEVHNAKTKPREEQYNSTYRVVSVLTVLHQD
WLNGKEYKCKVSNKALPAPIEKTISKAKGQPREPQVKLTCLVKGFYPSDIAVEWESNGQPENNYKTTPPVLDSDGSFFLYSKLT
VDKSRWQQGNVFSCSVMHEALHNHYTQKSLSLSPGK

Light Chain 1 (SEQ ID NO: 29793)

VL1/GGGSGGGG/VH1/GGCGGGGKVAACKEKVAALKEKVAALKE

Figure 55D

Light Chain 2 (SEQ ID NO: 29794)

VL2/RTVAAPSVFIFPPSDEQLKSGTASVVCLLNNFYPREAKVQWKVDNALQSGNSQESVTEQDSKDSTYSLSSTLTLSKADYEKHKVYACEVTHQGLS
SPVTKSFNRGEC

Figure 56A

XENP18920

>XENP18920 nivolumab[PD-1]_H0L0_Fab-[anti-ICOS]_H0L0_scFv Fab-Fc Heavy Chain (SEQ ID NO: 29795)

QVQLVESGGGVVQPGRSLRLDCKASGITFSNSGMHWVRQAPGKGLEWVAVIWYDGSKRYYADSKPYYADSVKGRFTISRDNSKNTLFLQMNSLRAEDTAVYYCATNDDYWGQGTLV
TVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEWESDGQPENNYKTTPPVLDSDGSFFLYSKLTVDKSRWQEGDVFSCSVMHEALHNHYTQKS
LSLSPGK

>XENP18920 nivolumab[PD-1]_H0L0_Fab-[anti-ICOS]_H0L0_scFv scFv-Fc Heavy Chain (SEQ ID NO: 29796)

QVQLVESGGGVVQPGRSLRLSCKASGITFSNSGMHWVRQAPGKGLEWVAVIWYDGSKRYYADSVKGRFTISRDNSKNTLFLQMNSLRAEDTAVYYCATNDDYWGQGTLV
TVSS/GKPGSGKPGSGKPGSGKPGS/EIVLTQSPATLSLSPGERATLSCRASQSVSSYLAWYQQKPGQAPRLLIYDASNRATGIPARFSGSGSGTDFTLTISSLEPEDF
AVYYCQQSSNWPRTFGQGTKVEIK/EPKSSDKTHTCPPCPAPPVAGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREQMTKNQVKLFCLVKGFYPSDIAVEWESNGQPENNYKTTPPVLDSDGSFFLYSK
LTVDKSRWQQGNVFSCSVMHEALHNHYTQKSLSLSPGK

>XENP18920 nivolumab[PD-1]_H0L0_scFv Light Chain (SEQ ID NO: 29797)

EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK/R
TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 56B

XENP24130

>XENP024130_LOPD180[PD-1]_H1L1_Fab-[anti-ICOS]_H0L0_scFv Fab-Fc Heavy Chain (SEQ ID NO: 29798)
QVQLQESGPGLVKPSQTLSLTCTVSGGSISSGAYYWSWIRQHPGKGLEWIGYIYYNGNTYYNPSLPSRVTISVDTSKNQFSLKLSSVTAADTAVYYCVRASDYVWGGYH
YFDAFDLWGRGTLVTVSS/ASTKGPSVFPLAPSSKSTSGGTAALGCLVKDYFPEPVTVSWNSGALTSGVHTFPAVLQSSGLYSLSSVVTVPSSSLGTQTFICNVNHKPS
DTKVDKKVEPKSCDKTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCS
VMHEALHNHYTQKSLSLSPGK >XENP024130_LOPD180[PD-1]_H1L1_Fab-[anti-ICOS]_H0L0_scFv scFv-Fc Heavy Chain (SEQ ID NO: 29799)
QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYYDSSGYYH
DAFDIWGQGTMVTVSS/GKPGSGKPGSGKPGS/DIQMTQSPSSVSASVGDRVTITCRASQGISRLLAWYQQKPGKAPKLLIYVASSLQSGVPSRFSGSGSGTDF
TLTISSLQPEDFATYYCQQANSFPWTFGQGTKVEIK/EPKSSDKTHTCPPCPAPPVAGPSVFLFPPKPKDTLMISRTPEVTCVVVDVKHEDPEVKFNWYVDGVEVHNAK
TKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPV
LDSDGSFFLYSRLTVDKSRWQQGNVFSCSVMHEALHNHYTQKSLSLSPGK >XENP024130_LOPD180[PD-1]_H1L1_Fab-[anti-ICOS]_H0L0_scFv Light Chain (SEQ ID NO: 29800)
QSVLTQPPSASGTPGQRVTISCSGSNSNIGSNSVNWYQQLPGTAPKLLIYGNNQRPSGVPDRFSGSKSGTSASLAISGLQSEDEADYYCAAWDDSLNGPVFGGGTKVTV
L/GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

Figure 57A

XENP23406

>XENP023406_[anti-ICOS]_H0L0_Fab-[anti-ICOS]_H0L0_Fab-Fc Heavy Chain (SEQ ID NO: 29801)

QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYDSSGYYHDAFDIW
GQGTMVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK

>XENP023406_[anti-ICOS]_H0L0_Fab-scFv-Fc Heavy Chain (SEQ ID NO: 29802)

QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYDSSGYYHDAFDIW
GQGTMVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCG
KPGSGKPGS/EIVLTQSPATLSASPGERVTLTCRASQSVGNDVAWYQQKPGQAPRLLINYASHRYTGSGYGTEFTLTISSVQSEDFGVYYCQQDFSSPRTFGGGTKVE
IK/GKPGSGKPGSGKPGS/EVQLVESGGGLVKPGGSLRLSCVASGFTFSNYWMNWVRQAPGKGLEWVAEIRLKSNNYATHYAESVKGRFTISRDDSKSTLYLQMNNLKTE
DTGVYYCTRNYGNYGGYFDVWGRGTLVTVSS/GGGGSGGGGSKTHTCPPCPAPPVAGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKL
TVDKSRWQQGNVFSCSVMHEALHNHYTQKSLSLSPGK

>XENP023406_[anti-ICOS]_H0L0_Fab_1G6_L1.194_H1.279_scFv Light Chain (SEQ ID NO: 29803)

DIQMTQSPSSVSASVGDRVTITCRASQGISRLLAWYQQKPGKAPKLLIYVASSLQSGVPSRFSGSGSGTDFTLTISSLQPEDFATYYCQQANSFPWTFGQGTKVEIK/RTVAAPS
VFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

XENP23407

>XENP023407_[anti-ICOS]_H0L0_Fab-Fc Heavy Chain (SEQ ID NO: 29804)

QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYDSSGYYHDAFDIW
GQGTMVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCD
KTHTCPPCPAPELLGGPSVFLFPPKPKDTLMISRTPEVTCVVVDVSHEDPEVKFNWYVDGVEVHNAKTKPREEYNSTYRVVSVLTVLHQDWLNGKEYKCKVSNKAFPAPIEKTI
SKAKGQPREPQVYTLPPSREEMTKNQVSLTCLVKGFYPSDIAVEWESDGQPENNYKTTPPVLDSDGSFFLYSKLTVDKSRWQQGNVFSCSVMHEALHNHYTQKSLSLSPGK

Figure 57B

>XENP023407 [anti-ICOS]_H0L0_Fab-[anti-ICOS]_H0L0_Fab-1G6_L1.194_H1.279_scFv_Fab-scFv-Fc Heavy Chain (SEQ ID NO: 29805)

QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARHYYDSSGYYHDAFDIW
GQGTMVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCG
KPGSGKPGS/EIVLTQSPATLSASPGERVTITCRASQSVGNDVAWYQQKPGQAPRLLINYASRYTGVPDRFTGSGYGTEFTLTISSVQSEDFGVYYCQQDESSPRTFGGGTKVE
IK/GKPGSGKPGSGKPGS/EVQLVESGGGLVKPGGSLRLSCVASG/GGGSGGGGSGGGGS/DIQMTQSPSSVSASVGDRVTITCRASQGISRLLAWYQQKPGKAPKLLIYAASSLQSGVPSRFSGSGSGTDFTLTIS
DTGVYYCTRYYGNYGGYFDVWGRGTLVTVSS/GGGSGGGGSGGGGS/DIQMTQSPSSVSASVGDRVTITCRASQGISRLLAWYQQKPGKAPKLLIYAASSLQSGVPSRFSGSGSGTDFTLTIS
QYNSTYRVVSVLFVLHQDWLNGKEYKCKVSNKAFPAPIEKTISKAKGQPREPQVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

>XENP023407 [anti-ICOS]_H0L0_Fab-[anti-ICOS]_H0L0_Fab-1G6_L1.194_H1.279_scFv Light Chain (SEQ ID NO: 29806)

DIQMTQSPSSVSASVGDRVTITCRASQGISRLLAWYQQKPGKAPKLLIYAASSLQSGVPSRFSGSGSGTDFTLTISSLQPEDFATYYCQQANSFWTFGQGTKVEIK/RTVAAPS
VFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

XENP24128

>XENP024128 1G6_L1.194_H1.279_Fab-1G6_L1.194_H1.279_Fab-scFv Fab-Fc Heavy Chain (SEQ ID NO: 29807)

EVQLVESGGGLVKPGGSLRLSCVASGFTFSNYWMNWVRQAPGKGLEWVAEIRLYSNNYATHYAESVKGRFTISRDDSKSTLYLQMNNLKTEDTGVYYCTRYYGNYGGYFDVWGRG
TLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESDGQPENNYKTTPPVLDSDGSFFLYSKLTVDKSRWQEGGVFSCSVMHEALHNHYTQKSLSLSPGK

>XENP024128 1G6_L1.194_H1.279_Fab-1G6_L1.194_H1.279_Fab-scFv Fab-scFv-Fc Heavy Chain (SEQ ID NO: 29808)

EVQLVESGGGLVKPGGSLRLSCVASGFTFSNYWMNWVRQAPGKGLEWVAEIRLYSNNYATHYAESVKGRFTISRDDSKSTLYLQMNNLKTEDTGVYYCTRYYGNYGGYFDVWGRG
TLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCGKPG
SGKPGS/QVQLVQSGTMVTVSS/GKPGSGKPGSGAEVKKPGASVKVSCKASGYTFTGYYMEWVRQAPGQGLEWMGWINPHSGGTNYAQKFQGRVTMTRDTSISTAYMELSRLSLQSSGVPSRFSGSGSGTDFTLTIS
SGKPGS/QVQLVQSGTMVTVSS/GKPGSGKPGSGAEVKKPGASVKVSCKASGYTFTGYYMEWVRQAPGQGLEWMGWINPHSGGTNYAQKFQGRVTMTRDTSISTAYMELSRLSDDTAVYYCARTYYDSSGYY
HDAFDIWGQGTMVTVSS/GKPGSGKPGSGGGGSGGGGS/DIQMTQSPSSVSASVGDRVTITCRASQGISRLLAWYQQKPGKAPKLLIYAASSLQSGVPSRFSGSGSGTDFTLTIS
SLQPEDFATYYCQQANSFWTFGQGTKVEIK/GGGSGGGGSGGGGS/GKPGSGKPGSGKPGS/
YNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSK
TVDKSRWQQGNVFSCSVMHEALHNHYTQKSLSLSPGK

Figure 57C

>XENP024128_1G6_L1.194_H1.279_Fab-1G6_L1.194_H1.279_Fab_[anti-ICOS]_H0L0_scFv Light Chain (SEQ ID NO: 29809)

EIVLTQSPATLSASPGERVTLTCRASQSVGNDVAWYQQKPGQAPRLLINYASHRYEGVPDRFTGSGYGTEFTLTISSVQSEDFGVYYCQQDESSPRTFGGGTKVEIK/R
TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 58

XENP24123

>XENP24123_1G6_H1.279_L1.194_Fab_(G4S)2_[anti-ICOS1_H0L0_scFv20_Fc_IgG1 Heavy Chain (SEQ ID NO: 29810)

EVQLVESGGGLVKPGGSLRLSCVASGFTFSNYWMNWVRQAPGKGLEWVAEIRLKSNNYATHYAESVKGRFTISRDDSKSTLYLQMNNLKTEDTGVYYCTRYYGNYGYE
DVWGRGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVD
KKVEPKSCGGGGSGGGGS/QVQLVQSGAEVKKPGASVKVSCKASGYTFTGYYMHWVRQAPGQGLEWMGWINPHSGGTNYAQKFQGRVTMTRDTSISTAYMELSRLRSDD
TAVYYCARTYYYDSSGYYHDAFDIWGQGTMVTVSS/GGGGSGGGGSGGGGS/DIQMTQSPSSVSASVGDRVTITCRASQGISRLLAWYQQKPGKAPKLLIYYAS
SLQSGVPSRFSGSGSGTDFTLTISSLQPEDFATYYCQQANSFPWTFGQGTKVEIK/GGGGSGGGGSGGGGSFPWTFGQGTKVEIK/GGGGSGGGGSGGGGSKTHTCPPCPAPPVAGPSVFLFPPKPKDTLMISRTPEVT
CVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCSVMHEALHNHYTQKSLSLSPGK

>XENP24123_1G6_H1.279_L1.194_Fab_(G4S)2_[anti-ICOS1_H0L0_scFv20_Fc_IgG1 Light Chain (SEQ ID NO: 29811)

EIVLTQSPATLSASPGERVTLTCRASQSVGNDVAWYQQKPGQAPRLLINYASHRYTGVPDRFTGSGYGTEFTLTISSVQSEDFGVYYCQQDESSPRTFGGGTKVEIK/R
TVAAPSVFIFPPSDEQLKSGTASVVCLLNNFYPREAKVQNKVDNALQSGNSQESVTEQDSKDSTYSLSSTLTLSKADYEKHKVYACEVTHQGLSSPVTKSFNRGEC

XENP24125

>XENP24125_LOPD180[PD-1]_H1L1_Fab_(G4S)2_[anti-ICOS1_H0L0_scFv20_Fc_IgG1 Heavy Chain (SEQ ID NO: 29812)

QVQLQESGPGLVKPSQTLSLTCTVSGGSISSSGAYYWSWIRQHPGKGLEWIGYIYYNGNTYYNPSLRSRVTISVDTSKNQFSLKLSSVTAADTAVYYCVRASDYWGGYE
YEDAFDLWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPS
NTKVDKKVEPKSCGGGGSGGGGS/QVQLVQSGAEVKKPGASVKVSCKASGYTFTGYYMHWVRQAPGQGLEWMGWINPHSGGTNYAQKFQGRVTMTRDTSISTAYMELSR
LRSDDTAVYYCARTYYYDSSGYYHDAFDIWGQGTMVTVSS/GGGGSGGGGSGGGGS/DIQMTQSPSSVSASVGDRVTITCRASQGISRLLAWYQQKPGKAPKLL
IYYASSLQSGVPSRFSGSGSGTDFTLTISSLQPEDFATYYCQQANSFPWTFGQGTKVEIK/GGGGSGGGGSGGGGSNKALPAPIEKTISKAKGQPREPQVYTLPPSREEMTKNQVSLTCLV
CVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCSVMHEALHNHYTQKSLSLSPGK

>XENP24125_LOPD180[PD-1]_H1L1_Fab_(G4S)2_[anti-ICOS1_H0L0_scFv20_Fc_IgG1 Light Chain (SEQ ID NO: 29813)

QSVLTQPPSASGTPGQRVTISCSGSNSNIGSNSVNWYQQLPGTAPKLLIYGNNQRPSGVPDRFSGSKSGTSASLAISGLQSEDEADYYCAAWDDSLNGPVFGGGTKVTV
L/GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

Figure 59

>XENP024134_1G6_H1.279_L1.194_Fab-[anti-ICOS]_H0L0_Fab-IgG1 Heavy Chain 1 (SEQ ID NO: 29814)
EVQLVESGGGLVKPGGSLRLSCVASGFTFSNYWMNWVRQAPGKGLEWVAEIRLYSNNYATHYAESVKGRFTISRDDSKSTLYLQMNNLKTEDTGVYYCTRYYGNYGGYF
DVWGRGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVD
KKVEPKSCDKTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGDVFSCSVMHEA
LHNHYTQKSLSLSPGK >XENP024134_1G6_H1.279_L1.194_Fab-[anti-ICOS]_H0L0_Fab-IgG1 Heavy Chain 2 (SEQ ID NO: 29815)
QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYDSSGYYH
DAFDIWGQGTMVTVSS/ASTKGPSVFPLAPSSKSTSGGTAALGCLVKDYFPEPVTVSWNSGALTSGVHTFPAVLQSSGLYSLSSVVTVPSSSLGTKTYTCNVNHKPSNT
KVDKKVERKSCDKTHTCPRCPAPPVAGPSVFLFPPKPKDTLMISRTPEVTCVVVDVKHEDPEVKFKWYVDGVEVHNAKTKPREEQYNSTYRVVSVLTVLHQDWLNGKEY
KCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVM
HEALHNHYTQKSLSLSPGK >XENP024134_1G6_H1.279_L1.194_Fab-[anti-ICOS]_H0L0_Fab-IgG1 Light Chain 1 (SEQ ID NO: 29816)
EIVLTQSPATLSASPGERVTLTCRASQSVGNDVAWYQQKPGQAPRLLINYASHRYTGVPDRFTGSGYGTEFTLTISSVQSEDFGVYYCQQDESSPRTFGGGTKVEIK/R
TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC >XENP024134_1G6_H1.279_L1.194_Fab-[anti-ICOS]_H0L0_Fab-IgG1 Light Chain 2 (SEQ ID NO: 29817)
DIQMTQSPSSVSASVGDRVTITCRASQGISRLLAWYQQKPGKAPKLLIYVASSLQSGVPSRFSGSGSGTDFTLTISSLQPEDFATYYCQQANSFPWTFGQGTKVEIK/R
TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 60

>XENP024122_1G6_H1.279_L1.194_[anti-ICOS]_H0L0_IgG1 Heavy Chain (SEQ ID NO: 29818)
EVQLVESGGGLVKPGGSLRLSCVASGFTFSNYWMNWVRQAPGKGLEWVAEIRLKSNNYATHYAESVKGRFTISRDDSKSTLYLQMNNLKTEDTGVYYCTRYYGNIGGYF
DYWGRGTLVTVSS/ASTKGPSVFPLAP/QVQLVQSGAEVKKPGASVKVSCKASGYTFTGYYMHWVRQAPGQGLEWMGWINPHSGGTNYAQKFQGRVTMTRDTSISTAYM
ELSRLRSDDTAVYYCARTYYDSSGYHDAFDIWGQGTMVTVSS/ASTKGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK >XENP024122_1G6_H1.279_L1.194_[anti-ICOS]_H0L0_IgG1 Light Chain (SEQ ID NO: 29819)
EIVLTQSPATLSASPGERVTLFCRASQSVGNDVAWYQQKPGQAPRLLINYASHRYTGVPDRFTGSGYGTEFTLTISSVQSEDRGVYYCQQDESSFRTFGGGTKVEIK/R
TVAAPSVFIFPP/DIQMTQSPSSVSASVGDRVTITCRASQGISRLLAWYQQKPGKAFKLLIYVASSLQSGVPSRFSGSGSGTDFTLTISSLQPEDFATYYCQQANSFPW
TFGQGTKVEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSP
VTKSFNRGEC

Figure 61A

XENP24132

>XENP24132_1G6_L1.194_1G6_H1.279_DART-[anti-ICOS]_H0L0_Fab-Fc_IgG1_Heavy Chain 1 (SEQ ID NO: 29820)
EIVLTQSPATLSASPGERVTLTCRASQSVGNDVAWYQQKPGQAPRLLINYASHRYTGVPDRFTGSSGYGTEFTLTISSVQSEDFGVYYCQQDFSSPRTFGGGTKVEIK/G
GGSGGGG/EVQLVESGGGLVKPGGSLRLSCVASGFTFSNYWMNWVRQAPGKGLEWVAEIRLYSNNYATHYAESVKGRFTISRDDSKSTLYLQMNNLKTEDTGVYYCTRY
YGNYGGYFDVWGRGTLVTVSS/GGCGGGEVAACEKEVAALEKEVKCKVSNKALPAPIEKTISKAKGQPREPQVYTLPPSREEMTKNQVSLTCDVSGFYPSDIA
DPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWQQGNVFSCSVMHEALHNHYTQKSLSLSPGK >XENP24132_1G6_L1.194_1G6_H1.279_DART-[anti-ICOS]_H0L0_Fab-Fc_IgG1_Heavy Chain 2 (SEQ ID NO: 29821)
QVQLVQSGAEVKKPGASVKVSCKASGYTFTGYMHWVRQAPGQGLEWMGWINPHSGGTNYAQKFQGRVTMTRDTSISTAYMELSRLRSDDTAVYYCARTYYDSSGYYH
DAFDIWGQGTMVTVSS/ASTKGPSVFPLAPSSKSTSGGTAALGCLVKDYFPEPVTVSWNSGALTSGVHTFPAVLQSSGLYSLSSVVTVPSSSLGTKTYTCNVNHKPSNT
KVDKKVERKSCDKTHTCPRCPAPPVAGPSVFLFPPKPKDTLMISRTPEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVM
HEALHNHYTQKSLSLSPGK >XENP24132_1G6_L1.194_1G6_H1.279_DART-[anti-ICOS]_H0L0_Fab-Fc_IgG1_Light Chain 1 (SEQ ID NO: 29822)
EIVLTQSPATLSASPGERVTLTCRASQSVGNDVAWYQQKPGQAPRLLINYASHRYTGVPDRFTGSSGYGTEFTLTISSVQSEDFGVYYCQQDFSSPRTFGGGTKVEIK/G
GGSGGGG/EVQLVESGGGLVKPGGSLRLSCVASGFTFSNYWMNWVRQAPGKGLEWVAEIRLYSNNYATHYAESVKGRFTISRDDSKSTLYLQMNNLKTE
DTGVYYCTRYYGNYGGYFDVWGRGTLVTVSS/GGCGGGKVAACEKEVAALKEKVAALKE >XENP24132_1G6_L1.194_1G6_H1.279_DART-[anti-ICOS]_H0L0_Fab-Fc_IgG1_Light Chain 2 (SEQ ID NO: 29823)
DIQMTQSPSSVSASVGDRVTITCRASQGISRLLAWYQQKPGKAPKLLIYVASSLQSGVPSRFSGSGSGTDFTLTISSLQPEDFATYYCQQANSFPWTFGQGTKVEIK/R
TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

XENP24133

>XENP24133_mAb7(1.2)[PD-1]_L1_mAb7(1.2)[PD-1]_H1_DART-[anti-ICOS]_H0L0_Fab-Fc_IgG1_Heavy Chain 1 (SEQ ID NO: 29824)
EIVLTQSPATLSLSPGERATLSCRASESVDNYGMSFMNWFQQKPGQPPKLLIHAASNQGSGVPSRFSGSGSGTDFTLTISSLEPEDFAVYFCQQSKEVPYTFGGGTKVE
IK/GGGSGGGG/QVQLVQSGAEVKKPGASVKVSCKASGYSFTSYWMNWVRQAPGQGLEWIGVIHPSDSETWLDQKFKDRVTITVDKSTSTAYMELSSLRSEDTAVYYCA
RERYGTSPFAYWGQGTLVTVSS/GGCGGGEVAACEKEVAALEKEVKCKVSNKALPAPIEKTISKAKGQPREPQVYTLPPSREEMTKNQVSLTCDVSGFYPSDI
EDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

Figure 61B

>XENP024133_mAb7(1.2)_[PD-1]_L1_mAb7(1.2)_[PD-1]_H1_DART-[anti-ICOS]_H0L0_Fab-Fc_IgG1 Heavy Chain 2 (SEQ ID NO: 29825)
QVQLVQSGAEVKKPGASVKVSCKASGYTFTGYYMHWVRQAPGQGLEWMGWINPHSGGTNYAQKFQGRVTMTRDTSISTAYMELSRLRSDDTAVYYCARTYYYDSSGYYH
DAFDIWGQGTMVTVSS/ASTKGPSVFPLAPSSKSTSGGTAALGCLVKDYFPEPVTVSWNSGALTSGVHTFPAVLQSSGLYSLSSVVTVPSSSLGTKTYTCNVNHKPSNT
KVDKKVERKSCDKTHTCPRCPAPPVAGPSVFLFPPKPKDTLMISRTPEVTCVVVDVKHEDPEVKFKWYVDGVEVHNAKTKPREEQYNSTYRVVSVLTVLHQDWLNGKEY
KCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVM
HEALHNHYTQKSLSLSPGK >XENP024133_mAb7(1.2)_[PD-1]_L1_mAb7(1.2)_[PD-1]_H1_DART-[anti-ICOS]_H0L0_Fab-Fc_IgG1 Light Chain 1 (SEQ ID NO: 29826)
EIVLTQSPATLSLSPGERATLSCRASESVDNYGMSFMNWFQQKPGQPPKLLIHAASNQGSGVPSRFSGSGSGTDFTLTISSLEPEDFAVYFCQQSKEVPYTFGGGTKVE
IK/GGGSGGGG/QVQLVQSGAEVKKPGASVKVSCKAGASVFTSYWMNWVRQAPGQGLEWIGVIHPSDSETWLDQSFKDRVTITVDKSTSTAYMELSSLR
SEDTAVYYCAREHYGTSFFAYWGQGTLVTVSS/GGCGGGKVAACKEKVAALKEKVAALKE >XENP024133_mAb7(1.2)_[PD-1]_L1_mAb7(1.2)_[PD-1]_H1_DART-[anti-ICOS]_H0L0_Fab-Fc_IgG1 Light Chain 2 (SEQ ID NO: 29827)
DIQMTQSPSSVSASVGDRVTITCRASQGISRLLAWYQQKPGKAPKLLIYVASSLQSGVPSRFSGSGSGTDFTLTISSLQPEDFATYCQQANSFWLFGQGTKVEIK/R
TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 63

>XENP021749_[anti-ICOS]_H0L0_Fab-[anti-CTLA-4]_H3.23_L0.129_scFv Fab-Fc Heavy
Chain (SEQ ID NO: 29828)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYBDAFDIWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

>XENP021749_[anti-ICOS]_H0L0_Fab-[anti-CTLA-4]_H3.23_L0.129_scFv scFv-Fc
Heavy Chain (SEQ ID NO: 29829)

EVQLVESGGGLVKPGGSLRLSCAASGFTFSSYTMHWVRQAPGKGLEWVSFISYDGNYKYYADSVKGRFTISRDNAKN
SLYLQMNSLRAEDTAVYYCARGGHLGPFDLWGQGTMVTVSS/GKPGSGKPGSGKPGSGKPGS/EIVLTQSPATLSLS
PGERATLSCRASQSVGSSYLAWYQQKPGQAPRLLIYGASSRATGIPDRFSGSGSGTDFTLTISRLEPEDFAVYYCQQ
YGSSPWTFGQGTKVEIK/EPKSSDKTHTCPPCPAPPVAGPSVFLFPPKPKDTLMISRTPEVTCVVVDVKHEDPEVKF
NWYVDGVEVHNAKTKPREEQYNSTYRVVSVLTVLHQDWLNGKEYKCKVSNKALPAPIEKTISKAKGQPREPQVYTLP
PSREQMTKNQVLTCLVKGFYPSDIAVEWESNGQPENNYKTTPPVLDSDGSFFLYSKLTVDKSRWQQGNVFSCSVMH
EALHNHYTQKSLSLSPGK

>XENP021749_[anti-ICOS]_H0L0_Fab-[anti-CTLA-4]_H3.23_L0.129_scFv Light Chain
(SEQ ID NO: 29830)

DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 64A

XENP24359

>XENP024359 7G8_H3.30_L1.34_Fab-[anti-ICOS]_H0L0_Fab Heavy Chain 1 (SEQ ID NO: 29831)

EVQLVESGGGLVQPGGSLRLSCAASGFTFDDAWMSWVRQAPGKGLEWVAEISTKANNHATYYAESVKGRFTISRDDS
KSSVYLQMNSLRAEDTAVYYCTRLATWDWYFDVWGQGTTVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK

>XENP024359 7G8_H3.30_L1.34_Fab-[anti-ICOS]_H0L0_Fab Heavy Chain 2 (SEQ ID NO: 29832)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCL
VKDYFPEPVTVSWNSGALTSGVHTFPAVLQSSGLYSLSSVVTVPSSSLGTKTYTCNVNHKPSNTKVDKKVERKSCDK
THTCPRCPAPPVAGPSVFLFPPKPKDTLMISRTPEVTCVVVDVKHEDPEVKFKWYVDGVEVHNAKTKPREEQYNSTY
RVVSVLTVLHQDWLNGKEYKCKVSNKALPAPIEKTISKAKGQPREPQVYTLPPSREQMTKNQVKLTCLVKGFYPSDI
AVEWESNGQPENNYKTTPPVLDSDGSFFLYSKLTVDKSRWQQGNVFSCSVMHEALHNHYTQKSLSLSPGK

>XENP024359 7G8_H3.30_L1.34_Fab-[anti-ICOS]_H0L0_Fab Light Chain 1 (SEQ ID NO: 29833)

DIVLTQSPSSLSASVGDRVTITCRASQSVDYDGDSYMNWYQQKPGKPPKLLIYAASELESGIPARFSGSGSGTDFTL
TISSLQPEDFATYYCQQSNEDPFTFGSGTKLEIK/RTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC

>XENP024359 7G8_H3.30_L1.34_Fab-[anti-ICOS]_H0L0_Fab Light Chain 2 (SEQ ID NO: 29834)

DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XENP24360

>XENP024360 2A11_H1.144_L2.142_Fab-[anti-ICOS]_H0L0_Fab Heavy Chain 1 (SEQ ID NO: 29835)

EVQLVQSGAEVKKPGATVKISCKASGFNIKDYFMHWVQQAPGKGLEWMGWIDPELGDTEYAPKFQGRVTITADTSTN
TAYMELSSLRSEDTAVYYCYARGVYQALDIWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK

Figure 64B

>XENP024360_2A11_H1.144_L2.142_Fab-[anti-ICOS]_H0L0_Fab Heavy Chain 2 (SEQ ID NO: 29836)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCL
VKDYFPEPVTVSWNSGALTSGVHTFPAVLQSSGLYSLSSVVTVPSSSLGTKTYTCNVNHKPSNTKVDKKVERKSCDK
THTCPRCPAPPVAGPSVFLFPPKPKDTLMISRTPEVTCVVVDVKHEDPEVKFKWYVDGVEVHNAKTKPREEQYNSTY
RVVSVLTVLHQDWLNGKEYKCKVSNKALPAPIEKTISKAKGQPREPQVYTLPPSREQMTKNQVKLTCLVKGFYPSDI
AVEWESNGQPENNYKTTPPVLDSDGSFFLYSKLTVDKSRWQQGNVFSCSVMHEALHNHYTQKSLSLSPGK

>XENP024360_2A11_H1.144_L2.142_Fab-[anti-ICOS]_H0L0_Fab Light Chain 1 (SEQ ID NO: 29837)

DIQMTQSPAFLSVTPGEKVTITCQASQDIGNYLNWFQQKPGQTVKLLIYFTSYLHSGVPSRFSGSGSGTDYTFTISS
LEAEDAATYFCQQGNTLPYTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

>XENP024360_2A11_H1.144_L2.142_Fab-[anti-ICOS]_H0L0_Fab Light Chain 2 (SEQ ID NO: 29838)

DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 65

>XENP024361_3H3_H1_L2.1_Fab-[anti-ICOS]_H0L0_Fab Heavy Chain 1 (SEQ ID NO 29839)
QVTLKESGPVLVKPTETLTLTCTVSGFSLNGYGVNWVRQPPGKGLEWLAMIWGDGSTDYNSALKSRLTISKDNSKSQ
VVLTMTNMDPVDTATYYCARSYYTSDEDYWGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSDTKVDKKVEPKSCDKTHTCPPCP
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK >XENP024361_3H3_H1_L2.1_Fab-[anti-ICOS]_H0L0_Fab Heavy Chain 2 (SEQ ID NO 29840)
QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCL
VKDYFPEPVTVSWNSGALTSGVHTFPAVLQSSGLYSLSSVVTVPSSSLGTKTYTCNVNHKPSNTKVDKKVERKSCDK
THTCPRCPAPPVAGPSVFLFPPKPKDTLMISRTPEVTCVVVDVKHEDPEVKFKWYVDGVEVHNAKTKPREEQYNSTY
RVVSVLTVLHQDWLNGKEYKCKVSNKALPAPIEKTISKAKGQPREPQVYTLPPSREQMTKNQVKLTCLVKGFYPSDI
AVEWESNGQPENNYKTTPPVLDSDGSFFLYSKLTVDKSRWQQGNVFSCSVMHEALHNHYTQKSLSLSPGK >XENP024361_3H3_H1_L2.1_Fab-[anti-ICOS]_H0L0_Fab Light Chain 1 (SEQ ID NO 29841)
DIVMTQSPDSLAVSLGERATINCKSSQSLLNSRTRKNYLAWYQQKPGQSPKLLIYWASTRESGVPDRFTGSGSGTDF
TLTISSLQAEDVAVYYCKQSYSLRTFGGGTKVEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC >XENP024361_3H3_H1_L2.1_Fab-[anti-ICOS]_H0L0_Fab Light Chain 2 (SEQ ID NO 29842)
DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 66A

XENP21748

>XENP021748 YW243.55.S70[PD-L1]_H0L0_Fab-[anti-ICOS]_H0L0_scFv Fab-Fc Heavy
Chain (SEQ ID NO: 29843)

EVQLVESGGGLVQPGGSLRLSCAASGFTFSDSWIHWVRQAPGKGLEWVAWISPYGGSTYYADSVKGRFTISADTSKN
TAYLQMNSLRAEDTAVYYCARRHWPGGFDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK

>XENP021748 YW243.55.S70[PD-L1]_H0L0_Fab-[anti-ICOS]_H0L0_scFv scFv-Fc Heavy
Chain (SEQ ID NO: 29844)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/GKPGSGKPGSGKPGSGKPGS/DIQMTQS
PSSVSASVGDRVTITCRASQGISRLLAWYQQKPGKAPKLLIYVASSLQSGVPSRFSGSGSGTDFTLTISSLQPEDFA
TYYCQQANSFPWTFGQGTKVEIK/EPKSSDKTHTCPPCPAPPVAGPSVFLFPPKPKDTLMISRTPEVTCVVVDVKHE
DPEVKFNWYVDGVEVHNAKTKPREEQYNSTYRVVSVLTVLHQDWLNGKEYKCKVSNKALPAPIEKTISKAKGQPREP
QVYTLPPSREQMTKNQVKLTCLVKGFYPSDIAVEWESNGQPENNYKTTPPVLDSDGSFFLYSKLTVDKSRWQQGNVF
SCSVMHEALHNHYTQKSLSLSPGK

>XENP021748 YW243.55.S70[PD-L1]_H0L0_Fab-[anti-ICOS]_H0L0_scFv Light Chain
(SEQ ID NO: 29845)

DIQMTQSPSSLSASVGDRVTITCRASQDVSTAVAWYQQKPGKAPKLLIYSASFLYSGVPSRFSGSGSGTDFTLTISS
LQPEDFATYYCQQYLYHPATFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XENP24129

>XENP024129 durvalumab[PD-L1]_H1L1_Fab-[anti-ICOS]_H0L0_scFv Fab-Fc Heavy
Chain (SEQ ID NO: 29846)

EVQLVESGGGLVQPGGSLRLSCAASGFTFSRYWMSWVRQAPGKGLEWVANIKQDGSEKYYVDSVKGRFTISRDNAKN
SLYLQMNSLRAEDTAVYYCAREGGWFGELAFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK

Figure 66B

>XENP024129 durvalumab[PD-L1]_H1L1_Fab-[anti-ICOS]_H0L0_scFv scFv-Fc Heavy Chain (SEQ ID NO: 29847)

QVQLVQSGAEVKKPGASVKVSCKASGYTFT<u>GYYMH</u>WVRQAPGQGLEWMG<u>WINPHSGGTNYAQKFQG</u>RVTMTRDTSIS
TAYMELSRLRSDDTAVYYCAR<u>TYYYDSSGIYHDAFDI</u>WGQGTMVTVSS/<u>GKPGSGKPGSGKPGSGKPGS</u>/DIQMTQS
PSSVSASVGDRVTITC<u>RASQGISRLLA</u>WYQQKPGKAPKLLIY<u>VASSLQS</u>GVPSRFSGSGSGTDFTLTISSLQPEDFA
TYYC<u>QQANSFPWT</u>FGQGTKVEIK/EPKSSDKTHTCPPCPAPPVAGPSVFLFPPKPKDTLMISRTPEVTCVVVDVKHE
DPEVKFNWYVDGVEVHNAKTKPREEQYNSTYRVVSVLTVLHQDWLNGKEYKCKVSNKALPAPIEKTISKAKGQPREP
QVYTLPPSREQMTKNQVKLTCLVKGFYPSDIAVEWESNGQPENNYKTTPPVLDSDGSFFLYSKLTVDKSRWQQGNVF
SCSVMHEALHNHYTQKSLSLSPGK

>XENP024129 durvalumab[PD-L1]_H1L1_Fab-[anti-ICOS]_H0L0_scFv Light Chain (SEQ ID NO: 29848)

EIVLTQSPGTLSLSPGERATLSC<u>RASQRVSSSYLA</u>WYQQKPGQAPRLLIY<u>DASSRAT</u>GIPDRFSGSGSGTDFTLTIS
RLEPEDFAVYYC<u>QQYGSLFWT</u>FGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

XENP24131

>XENP024131 avelumab[PD-L1]_H1L1_Fab-[anti-ICOS]_H0L0_scFv Fab-Fc Heavy Chain (SEQ ID NO: 29849)

EVQLLESGGGLVQPGGSLRLSCAASGFTFS<u>SYIMM</u>WVRQAPGKGLEWVS<u>SIYPSGGITFYADTVKG</u>RFTISRDNSKN
TLYLQMNSLRAEDTAVYYCAR<u>IKLGTVTTVDY</u>WGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK

>XENP024131 avelumab[PD-L1]_H1L1_Fab-[anti-ICOS]_H0L0_scFv scFv-Fc Heavy Chain (SEQ ID NO: 29850)

QVQLVQSGAEVKKPGASVKVSCKASGYTFT<u>GYYMH</u>WVRQAPGQGLEWMG<u>WINPHSGGTNYAQKFQG</u>RVTMTRDTSIS
TAYMELSRLRSDDTAVYYCAR<u>TYYYDSSGYYHDAFDI</u>WGQGTMVTVSS/<u>GKPGSGKPGSGKPGSGKPGS</u>/DIQMTQS
PSSVSASVGDRVTITC<u>RASQGISRLLA</u>WYQQKPGKAPKLLIY<u>VASSLQS</u>GVPSRFSGSGSGTDFTLTISSLQPEDFA
TYYC<u>QQANSFPWT</u>FGQGTKVEIK/EPKSSDKTHTCPPCPAPPVAGPSVFLFPPKPKDTLMISRTPEVTCVVVDVKHE
DPEVKFNWYVDGVEVHNAKTKPREEQYNSTYRVVSVLTVLHQDWLNGKEYKCKVSNKALPAPIEKTISKAKGQPREP
QVYTLPPSREQMTKNQVKLTCLVKGFYPSDIAVEWESNGQPENNYKTTPPVLDSDGSFFLYSKLTVDKSRWQQGNVF
SCSVMHEALHNHYTQKSLSLSPGK

>XENP024131 avelumab[PD-L1]_H1L1_Fab-[anti-ICOS]_H0L0_scFv Light Chain (SEQ ID NO: 29851)

QSALTQPASVSGSPGQSITISC<u>TGTSSDVGGYNYVS</u>WYQQHPGKAPKLMIY<u>DVSNRPS</u>GVSNRFSGSKSGNTASLTI
SGLQAEDEADYYC<u>SSYTSSSTRV</u>FGTGTKVTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 66C

XENP24124

>XENP024124 durvalumab[PD-L1]_H1L1_Fab_(G4S)2_[anti-ICOS]_H0L0_scFv20_Fc_IgG1
Heavy Chain (SEQ ID NO: 29852)

EVQLVESGGGLVQPGGSLRLSCAASGFTFSRYWMSWVRQAPGKGLEWVANIKQDGSEKYYVDSVKGRFTISRDNAKN
SLYLQMNSLRAEDTAVYYCAREGGWFGELAFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCGGGGSG
GGGS/QVQLVQSGAEVKKPGASVKVSCKASGYTFTGYYMHWVRQAPGQGLEWMGWINPHSGGTNYAQKFQGRVTMTR
DTSISTAYMELSRLRSDDTAVYYCARTYYYDSSGYYHDAFDIWGQGTMVTVSS/GGGGSGGGGSGGGGSGGGGS/DI
QMTQSPSSVSASVGDRVTITCRASQGISRLLAWYQQKPGKAPKLLIYVASSLQSGVPSRFSGSGSGTDFTLTISSLQ
PEDFATYYCQQANSFPWTFGQGTKVEIK/GGGGSGGGGSKTHTCPPCPAPPVAGPSVFLFPPKPKDTLMISRTPEVT
CVVVDVKHEDPEVKFNWYVDGVEVHNAKTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPGK

>XENP024124 durvalumab[PD-L1]_H1L1_Fab_(G4S)2_[anti-ICOS]_H0L0_scFv20_Fc_IgG1
Light Chain (SEQ ID NO: 29853)

EIVLTQSPGTLSLSPGERATLSCRASQRVSSSYLAWYQQKPGQAPRLLIYDASSRATGIPDRFSGSGSGTDFTLTIS
RLEPEDFAVYYCQQYGSLPWTFGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

Figure 68A

XENP20266

>XENP020266 [ICOS]_H0L0 one-arm mAb Fab-Fc Heavy Chain (SEQ ID NO: 29854)

QVQLVQSGAEVKKPGASVKVSCKASGYTFT GYYMH WVRQAPGQGLEWMG WINPHSGGTNYAQKFQG RVTMTRDTSIS
TAYMELSRLRSDDTAVYYCAR TYYDSSGIYRDAFDI WGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

>XENP020266 [ICOS]_H0L0 one-arm mAb Fc-only Heavy Chain (SEQ ID NO: 29855)

ERKSSDKTHTCPRCPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

>XENP020266 [ICOS]_H0L0 one-arm mAb Light Chain (SEQ ID NO: 29856)

DIQMTQSPSSVSASVGDRVTITC RASQGISRLLA WYQQKPGKAPKLLIY VASSLQS GVPSRFSGSGSGTDFTLTISS
LQPEDFATYYC QQANSFPWT FGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XENP21861

>XENP021861 GSK_314.8[ICOS]_H0L0 one-arm mAb Fab-Fc Heavy Chain (SEQ ID NO: 29857)

QVQLQQPGTELMKPGASVKLSCKASGYTFT TYWMH WVKQRPGQGLEWIG EIDPSDSYVNYNQNFKG KATLTVDKSSS
TAYIQLSSLTSEDSAVYFCAR SPDYYGTSLAWFDY WGQGTLVTVST/ASTKGPSVFPLAPSSKSTSGGTAALGCLVK
DYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVKHEDPEVKFNWYVDGVEVHNAKTKPREEEYNSTYRV
VSVLTVLHQDWLNGKEYKCKVSNKALPAPIEKTISKAKGQPREPQVYTLPPSREEMTKNQVSLTCDVSGFYPSDIAV
EWESDGQPENNYKTTPPVLDSDGSFFLYSKLTVDKSRWEQGDVFSCSVMHEALHNHYTQKSLSLSPGK

>XENP021861 GSK_314.8[ICOS]_H0L0 one-arm mAb Fc-only Heavy Chain (SEQ ID NO: 29858)

ERKSSDKTHTCPRCPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

>XENP021861 GSK_314.8[ICOS]_H0L0 one-arm mAb Light Chain (SEQ ID NO: 29859)

DIVMTQAAPSVPVTPGESVSISC RSSKSPLHSNGNIYLY WFLQRPGQSPQLLIY RMSNLAS GVPDRFSGSGSGTTFT
LKISRVEAEDVGVYYC MQHLEYPYT FGGGTKLEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

Figure 688

XENP21863

>XENP021863 jMab-138[ICOS]_H0L0 one-arm mAb Fab-Fc Heavy Chain (SEQ ID NO: 29860)

EVQLVESGGGLVQPGGSLRLSCAASGFTFSSYDMHWVRQATGKGLEWVSAIGTAGDTYYPGSVKGRFTISRENAKNSLYLQM
NSLRAGDTAVYYCVRDNRKVTHEHYYYYGMDVWGQGTTVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVMHEALHNHYTQKSLSLSPGK

>XENP021863 jMab-138[ICOS]_H0L0 one-arm mAb Fc-only Heavy Chain (SEQ ID NO: 29861)

ERKSSDKTHTCPRCPAPPVAGPSVFLFPPKPKDTLMISRTPEVTCVVVDVKHEDPEVKFKWYVDGVEVHNAKTKPREEQYNS
TYRVVSVLTVLHQDWLNGKEYKCKVSNKALPAPIEKTISKAKGQPREPQVYTLPPSREQMTKNQVKLTCLVKGFYPSDIAVE
WESNGQPENNYKTTPPVLDSDGSFFLYSKLTVDKSRWQQGNVFSCSVMHEALHNHYTQKSLSLSPGK

>XENP021863 jMab-138[ICOS]_H0L0 one-arm mAb Light Chain (SEQ ID NO: 29862)

EIVLTQSPGTLSLSPGERATLSCRASQNIPSSYLAWYQQKPGQAPGLLIYGASSRATGIPDRFSGSGSGTDFTLTISRLEPE
DFAVYYCQQFGSSPMCSFGQGTKLEIK/RTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGEC

XENP22349

>XENP022349 WO2016059602[ICOS]_GSK_H0L0 one-arm mAb Fab-Fc Heavy Chain (SEQ ID NO: 29863)

QVQLVQSGAEVKKPGSSVKVSCKASGYTFTDYAMHWVRQAPGQGLEWMGLISIYSDHTNYNQKFQGRVTITADKSTSTAYME
LSSLRSEDTAVYYCGRNNYGNYGWYFDVWGQGTTVTVSS/ASTKGPSVFPLAPSSKSTSGGTAALGCLVKDYFPEPVTVSWN
SGALTSGVHTFPAVLQSSGLYSLSSVVTVPSSSLGTQTYICNVNHKPSDTKVDKKVEPKSCDKTHTCPPCPAPPVAGPSVFL
FPPKPKDTLMISRTPEVTCVVVDVKHEDPEVKFNWYVDGVEVHNAKTKPREEEYNSTYRVVSVLTVLHQDWLNGKEYKCKVS
NKALPAPIEKTISKAKGQPREPQVYTLPPSREEMTKNQVSLTCDVSGFYPSDIAVEWESDGQPENNYKTTPPVLDSDGSFFL
YSKLTVDKSRWEQGDVFSCSVMHEALHNHYTQKSLSLSPGK

>XENP022349 WO2016059602[ICOS]_GSK_H0L0 one-arm mAb Fc-only Heavy Chain (SEQ ID NO: 29864)

ERKSSDKTHTCPRCPAPPVAGPSVFLFPPKPKDTLMISRTPEVTCVVVDVKHEDPEVKFKWYVDGVEVHNAKTKPREEQYNS
TYRVVSVLTVLHQDWLNGKEYKCKVSNKALPAPIEKTISKAKGQPREPQVYTLPPSREQMTKNQVKLTCLVKGFYPSDIAVE
WESNGQPENNYKTTPPVLDSDGSFFLYSKLTVDKSRWQQGNVFSCSVMHEALHNHYTQKSLSLSPGK

>XENP022349 WO2016059602[ICOS]_GSK_H0L0 one-arm mAb Light Chain (SEQ ID NO: 29865)

EIVLTQSPATLSLSPGERATLSCSASSSVSYMHWYQQKPGQAPRLLIYDTSKLASGIPARFSGSGSGTDYTLTISSLEPEDF
AVYYCFQGSGYPYTFGQGTKLEIK/RTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

Figure 68C

XENP22439

>XENP022439 [ICOS]_H0_L0.5 one-arm mAb Fab-Fc Heavy Chain (SEQ ID NO: 29866)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

>XENP022439 [ICOS]_H0_L0.5 one-arm mAb Fc-only Heavy Chain (SEQ ID NO: 29867)

ERKSSDKTHTCPRCPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

>XENP022439 [ICOS]_H0_L0.5 one-arm mAb Light Chain (SEQ ID NO: 29868)

DIQMTQSPSSVSASVGDRVTITCRASQGISSLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XENP22440

>XENP022440 [ICOS]_H0_L0.7 one-arm mAb Fab-Fc Heavy Chain (SEQ ID NO: 29869)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

>XENP022440 [ICOS]_H0_L0.7 one-arm mAb Fc-only Heavy Chain (SEQ ID NO: 29870)

ERKSSDKTHTCPRCPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

>XENP022440 [ICOS]_H0_L0.7 one-arm mAb Light Chain (SEQ ID NO: 29871)

DIQMTQSPSSVSASVGDRVTITCRASQGISSYLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 68D

XENP22441

>XENP022441 [ICOS]_H0_L0.9 one-arm mAb Fab-Fc Heavy Chain (SEQ ID NO: 29872)

QVQLVQSGAEVKKPGASVKVSCKASGYTFT<u>GYYMH</u>WVRQAPGQGLEWMG<u>WINPHSGGTNYAQKFQG</u>RVTMTRDTSIS
TAYMELSRLRSDDTAVYYCAR<u>TYYYDSSGIYHDAFDI</u>WGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

>XENP022441 [ICOS]_H0_L0.9 one-arm mAb Fc-only Heavy Chain (SEQ ID NO: 29873)

ERKSSDKTHTCPRCPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

>XENP022441 [ICOS]_H0_L0.9 one-arm mAb Light Chain (SEQ ID NO: 29874)

DIQMTQSPSSVSASVGDRVTITC<u>RASQGISRYLA</u>WYQQKPGKAPKLLIY<u>AASSLQS</u>GVPSRFSGSGSGTDFTLTISS
LQPEDFATYYC<u>QQANSFPWT</u>FGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XENP22442

>XENP022442 [ICOS]_H0_L0.10 one-arm mAb Fab-Fc Heavy Chain (SEQ ID NO: 29875)

QVQLVQSGAEVKKPGASVKVSCKASGYTFT<u>GYYMH</u>WVRQAPGQGLEWMG<u>WINPHSGGTNYAQKFQG</u>RVTMTRDTSIS
TAYMELSRLRSDDTAVYYCAR<u>TYYYDSSGYYHDAFDI</u>WGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

>XENP022442 [ICOS]_H0_L0.10 one-arm mAb Fc-only Heavy Chain (SEQ ID NO: 29876)

ERKSSDKTHTCPRCPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

>XENP022442 [ICOS]_H0_L0.10 one-arm mAb Light Chain (SEQ ID NO: 29877)

DIQMTQSPSSVSASVGDRVTITC<u>RASQGISRLLA</u>WYQQKPGKAPKLLIY<u>AASSLQS</u>GVPSRFSGSGSGTDFTLTISS
LQPEDFATYYC<u>QQANSFPWT</u>FGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 68E

XENP22443

>XENP022443 [ICOS]_H0_L0.14 one-arm mAb Fab-Fc Heavy Chain (SEQ ID NO: 29878)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

>XENP022443 [ICOS]_H0_L0.14 one-arm mAb Fc-only Heavy Chain (SEQ ID NO: 29879)

ERKSSDKTHTCPRCPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

>XENP022443 [ICOS]_H0_L0.14 one-arm mAb Light Chain (SEQ ID NO: 29880)

DIQMTQSPSSVSASVGDRVTITCRASQGISRLLAWYQQKPGKAPKLLIYVASSLQSGVPSRFSGSGSGTDFTLTISS
LQPEDFATYYCQQSNSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XENP22444

>XENP022444 [ICOS]_H0_L0.15 one-arm mAb Fab-Fc Heavy Chain (SEQ ID NO: 29881)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

>XENP022444 [ICOS]_H0_L0.15 one-arm mAb Fc-only Heavy Chain (SEQ ID NO: 29882)

ERKSSDKTHTCPRCPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

>XENP022444 [ICOS]_H0_L0.15 one-arm mAb Light Chain (SEQ ID NO: 29883)

DIQMTQSPSSVSASVGDRVTITCRASQGISRLLAWYQQKPGKAPKLLIYVASSLQSGVPSRFSGSGSGTDFTLTISS
LQPEDFATYYCQQAESFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 68F

XENP22445

>XENP022445 [ICOS]_H0_L0.20 one-arm mAb Fab-Fc Heavy Chain (SEQ ID NO: 29884)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

>XENP022445 [ICOS]_H0_L0.20 one-arm mAb Fc-only Heavy Chain (SEQ ID NO: 29885)

ERKSSDKTHTCPRCPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

>XENP022445 [ICOS]_H0_L0.20 one-arm mAb Light Chain (SEQ ID NO: 29886)

DIQMTQSPSSVSASVGDRVTITCRASQGISRLLAWYQQKPGKAPKLLIYAASSLQSGVPSRFSGSGSGTDFTLTISS
LQPEDFATYYCQQANSYPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

XENP22766

>XENP022766 [ICOS]_H0_L0.38 one-arm mAb Fab-Fc Heavy Chain (SEQ ID NO: 29887)

QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

>XENP022766 [ICOS]_H0_L0.38 one-arm mAb Fc-only Heavy Chain (SEQ ID NO: 29888)

ERKSSDKTHTCPRCPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

>XENP022766 [ICOS]_H0_L0.38 one-arm mAb Light Chain (SEQ ID NO: 29889)

DIQMTQSPSSVSASVGDRVTITCQASQDISSLLAWYQQKPGKAPKLLIYAASSLQSGVPSRFSGSGSGTDFTLTISS
LQPEDFATYYCQQAESFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 68G

XENP23096

\>XENP023096 [ICOS]_H0.66_L0 one-arm mAb Fab-Fc Heavy Chain (SEQ ID NO: 29890)

QVQLVQSGAEVKKPGASVKVSCKASGYTFTGYYMHWVRQAPGQGLEWMGWINPHSGETIYAQKFQGRVTMTRDTSIS
TAYMELSSLRSEDTAVYYCARTYYYDTSGYYHDAFDVWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

\>XENP023096 [ICOS]_H0.66_L0 one-arm mAb Fc-only Heavy Chain (SEQ ID NO: 29891)

ERKSSDKTHTCPRCPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

\>XENP023096 [ICOS]_H0.66_L0 one-arm mAb Light Chain (SEQ ID NO: 29892)

DIQMTQSPSSVSASVGDRVTITCRASQGISRLLAWYQQKPGKAPKLLIYVASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 69

| XENP | Antigen | K$_D$ (nM) | k$_a$ (1/Ms) | k$_d$ (1/s) |
|---|---|---|---|---|
| 22445 | huICOS | 3.239 | 2.35E+05 | 7.60E-04 |
| 22444 | huICOS | 1.594 | 2.40E+05 | 3.83E-04 |
| 22443 | huICOS | 1.415 | 2.69E+05 | 3.80E-04 |
| 22442 | huICOS | 2.813 | 2.58E+05 | 7.26E-04 |
| 22441 | huICOS | 5.596 | 2.39E+05 | 1.34E-03 |
| 22440 | huICOS | 4.128 | 2.08E+05 | 8.57E-04 |
| 22439 | huICOS | 0.6324 | 1.80E+05 | 1.14E-04 |
| 20266 | huICOS | 1.502 | 2.34E+05 | 3.52E-04 |

Figure 72A

Prototype Costim x PD-1 Bispecific

>XENP023377 11D4[OX40]_H0L0_Fab-1G6_L1.194_H1.279_scFv Fab-Fc Heavy Chain (SEQ ID NO: 29893)
EVQLVESGGGLVQPGGSLRLSCAASGFTFSSYSMNWVRQAPGKGLEWVSYISSSSSTIDYADSVKGRFTISRDNAKNSL
YLQMNSLRDEDTAVYYCARESGWYLFDYWGQGTLVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSDTKVDKKVEPKSCDKTHTCPPCPAPPVAG
PSVFLFPPKPKDTLMISRTPEVTCVVVDVKHEDPEVKFNWYVDGVEVHNAKTKPREEEYNSTYRVVSVLTVLHQDWLN
GKEYKCKVSNKALPAPIEKTISKAKGQPREPQVYTLPPSREEMTKNQVSLTCDVSGFYPSDIAVEWESDGQPENNYKTTP
PVLDSDGSFFLYSKLTVDKSRWEQGDVFSCSVMHEALHNHYTQKSLSLSPGK >XENP023377 11D4[OX40]_H0L0_Fab-1G6_L1.194_H1.279_scFv scFv-Fc Heavy Chain (SEQ ID NO: 29894)
EIVLTQSPATLSASPGERVTLTCRASQSVGNDVAWYQQKPGQAPRLLINYASHRYTGVPDRFTGSGYGTEFTLTISSVQS
EDFGVYYCQQDFSSPRTFGGGTKVEIK/GKPGSGKPGSGKPGSGKPGS/EVQLVESGGGLVKPGGSLRLSCVASGFTFS
NYWMNWVRQAPGKGLEWVAEIRLYSNNYATHYAESVKGRFTISRDDSKSTLYLQMNNLKTEDTGVYYCTRYYGNYG
GYFDVWGRGTLVTVSS/EPKSSDKTHTCPPCPAPPVAGPSVFLFPPKPKDTLMISRTPEVTCVVVDVKHEDPEVKFNWY
VDGVEVHNAKTKPREEQYNSTYRVVSVLTVLHQDWLNGKEYKCKVSNKALPAPIEKTISKAKGQPREPQVYTLPPSREQ
MTKNQVKLTCLVKGFYPSDIAVEWESNGQPENNYKTTPPVLDSDGSFFLYSKLTVDKSRWQQGNVFSCSVMHEALHN
HYTQKSLSLSPGK >XENP023377 11D4[OX40]_H0L0_Fab-1G6_L1.194_H1.279_scFv Light Chain (SEQ ID NO: 29895)
DIQMTQSPSSLSASVGDRVTITCRASQGISSWLAWYQQKPEKAPKSLIYAASSLQSGVPSRFSGSGSGTDFTLTISSLQPE
DFATYYCQQYNSYPPTFGGGTKVEIK/RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC >XENP023378 1D8[GITR]_H0L0_Fab-1G6_L1.194_H1.279_scFv Fab-Fc Heavy Chain (SEQ ID NO: 29896)
QVTLKESGPGILKPSQTLSLTCSFSGFSLSTSGMGVGWIRQPSGKGLEWLAHIWWDDDKYYSPSLKSQLTISKDTSRNQ
VFLKITSLDTADTATYYCVRSYYYGSSGAMDYWGQGTSVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSDTKVDKKVEPKSCDKTHTCPPCPAPP
VAGPSVFLFPPKPKDTLMISRTPEVTCVVVDVKHEDPEVKFNWYVDGVEVHNAKTKPREEEYNSTYRVVSVLTVLHQD
WLNGKEYKCKVSNKALPAPIEKTISKAKGQPREPQVYTLPPSREEMTKNQVSLTCDVSGFYPSDIAVEWESDGQPENNY
KTTPPVLDSDGSFFLYSKLTVDKSRWEQGDVFSCSVMHEALHNHYTQKSLSLSPGK >XENP023378 1D8[GITR]_H0L0_Fab-1G6_L1.194_H1.279_scFv scFv-Fc Heavy Chain (SEQ ID NO: 29897)
EIVLTQSPATLSASPGERVTLTCRASQSVGNDVAWYQQKPGQAPRLLINYASHRYTGVPDRFTGSGYGTEFTLTISSVQS
EDFGVYYCQQDFSSPRTFGGGTKVEIK/GKPGSGKPGSGKPGSGKPGS/EVQLVESGGGLVKPGGSLRLSCVASGFTFS
NYWMNWVRQAPGKGLEWVAEIRLYSNNYATHYAESVKGRFTISRDDSKSTLYLQMNNLKTEDTGVYYCTRYYGNYG
GYFDVWGRGTLVTVSS/EPKSSDKTHTCPPCPAPPVAGPSVFLFPPKPKDTLMISRTPEVTCVVVDVKHEDPEVKFNWY
VDGVEVHNAKTKPREEQYNSTYRVVSVLTVLHQDWLNGKEYKCKVSNKALPAPIEKTISKAKGQPREPQVYTLPPSREQ
MTKNQVKLTCLVKGFYPSDIAVEWESNGQPENNYKTTPPVLDSDGSFFLYSKLTVDKSRWQQGNVFSCSVMHEALHN
HYTQKSLSLSPGK

Figure 72B

>XENP023378 1D8[GITR]_H0L0_Fab-1G6_L1.194_H1.279_scFv Light Chain (SEQ ID NO: 29898)
DIVMTQTPLSLPVSLGDQASISCRSSQSLVHSDGNTYLHWYLQKPGQSPKLLIYKVSKRFSGVPDRFSGSGSGTDFTLKIS
RVEAEDLGVYFCSQSTHVPPTFGGGTKLEIK/RTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC >XENP023379 20H4.9[4-1BB]_H0L0_Fab-1G6_L1.194_H1.279_scFv Fab-Fc Heavy Chain (SEQ ID NO: 29899)
QVQLQQWGAGLLKPSETLSLTCAVYGGSFSGYYWSWIRQSPEKGLEWIGEINHGGYVTYNPSLESRVTISVDTSKNQFS
LKLSSVTAADTAVYYCARDYGPGNYDWYFDLWGRGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSDTKVDKKVEPKSCDKTHTCPPCPAPP
VAGPSVFLFPPKPKDTLMISRTPEVTCVVVDVKHEDPEVKFNWYVDGVEVHNAKTKPREEEYNSTYRVVSVLTVLHQD
WLNGKEYKCKVSNKALPAPIEKTISKAKGQPREPQVYTLPPSREEMTKNQVSLTCDVSGFYPSDIAVEWESDGQPENNY
KTTPPVLDSDGSFFLYSKLTVDKSRWEQGDVFSCSVMHEALHNHYTQKSLSLSPGK >XENP023379 20H4.9[4-1BB]_H0L0_Fab-1G6_L1.194_H1.279_scFv scFv-Fc Heavy Chain (SEQ ID NO: 29900)
EIVLTQSPATLSASPGERVTLTCRASQSVGNDVAWYQQKPGQAPRLLINYASHRYTGVPDRFTGSGYGTEFTLTISSVQS
EDFGVYYCQQDFSSPRTFGGGTKVEIK/GKPGSGKPGSGKPGSGKPGS/EVQLVESGGGLVKPGGSLRLSCVASGFTFS
NYWMNWVRQAPGKGLEWVAEIRLYSNNYATHYAESVKGRFTISRDDSKSTLYLQMNNLKTEDTGVYYCTRYYGNYG
GYFDVWGRGTLVTVSS/EPKSSDKTHTCPPCPAPPVAGPSVFLFPPKPKDTLMISRTPEVTCVVVDVKHEDPEVKFNWY
VDGVEVHNAKTKPREEQYNSTYRVVSVLTVLHQDWLNGKEYKCKVSNKALPAPIEKTISKAKGQPREPQVYTLPPSREQ
MTKNQVKLTCLVKGFYPSDIAVEWESNGQPENNYKTTPPVLDSDGSFFLYSKLTVDKSRWQQGNVFSCSVMHEALHN
HYTQKSLSLSPGK >XENP023379 20H4.9[4-1BB]_H0L0_Fab-1G6_L1.194_H1.279_scFv Light Chain (SEQ ID NO: 29901)
EIVLTQSPATLSLSPGERATLSCRASQSVSSYLAWYQQKPGQAPRLLIYDASNRATGIPARFSGSGSGTDFTLTISSLEPED
FAVYYCQQRSNWPPALTFGGGTKVEIK/RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSFNRGEC

Additional CTLA-4 x ICOS Bispecific SEQ

>XENP019192 ipilimumab[CTLA-4]_H0L0_Fab-[anti-ICOS]-H0L0_scFv Fab-Fc Heavy Chain (SEQ ID NO: 29902)
QVQLVESGGGVVQPGRSLRLSCAASGFTFSSYTMHWVRQAPGKGLEWVTFISYDGNNKYYADSVKGRFTISRDNSKN
TLYLQMNSLRAEDTAIYYCARTGWLGPFDYWGQGTLVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVA
GPSVFLFPPKPKDTLMISRTPEVTCVVVDVKHEDPEVKFNWYVDGVEVHNAKTKPREEEYNSTYRVVSVLTVLHQDWL
NGKEYKCKVSNKALPAPIEKTISKAKGQPREPQVYTLPPSREEMTKNQVSLTCDVSGFYPSDIAVEWESDGQPENNYKT
TPPVLDSDGSFFLYSKLTVDKSRWEQGDVFSCSVMHEALHNHYTQKSLSLSPGK

Figure 72C

>XENP019192 ipilimumab[CTLA-4]_H0L0_Fab-[anti-ICOS]-H0L0_scFv scFv-Fc Heavy Chain (SEQ ID NO: 29903)
QVQLVQSGAEVKKPGASVKVSCKASGYTFT<u>GYYMH</u>WVRQAPGQGLEWMG<u>WINPHSGGTNYAQKFQG</u>RVTMTRD
TSISTAYMELSRLRSDDTAVYYCAR<u>TYYYDSSGYYHDAFDI</u>WGQGTMVTVSS/<u>GKPGSGKPGSGKPGSGKPGS</u>/DIQMT
QSPSSVSASVGDRVTITC<u>RASQGISRLLA</u>WYQQKPGKAPKLLIY<u>VASSLQS</u>GVPSRFSGSGSGTDFTLTISSLQPEDFATYY
CQQANSFPWTFGQGTKVEIK/EPKSSDKTHTCPPCPAPPVAGPSVFLFPPKPKDTLMISRTPEVTCVVVDVKHEDPEVK
FNWYVDGVEVHNAKTKPREEQYNSTYRVVSVLTVLHQDWLNGKEYKCKVSNKALPAPIEKTISKAKGQPREPQVYTLP
PSREQMTKNQVKLTCLVKGFYPSDIAVEWESNGQPENNYKTTPPVLDSDGSFFLYSKLTVDKSRWQQGNVFSCSVMH
EALHNHYTQKSLSLSPGK >XENP019192 ipilimumab[CTLA-4]_H0L0_Fab-[anti-ICOS]-H0L0_scFv Light Chain (SEQ ID NO: 29904)
EIVLTQSPGTLSLSPGERATLSC<u>RASQSVGSSYLA</u>WYQQKPGQAPRLLIY<u>GAFSRAT</u>GIPDRFSGSGSGTDFTLTISRLEPE
DFAVYYC<u>QQYGSSPWT</u>FGQGTKVEIK/RTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC

Figure 73A

Prototype anti-4-1BB mAb

\>XENP014410 20H4.9[4-1BB]_H0L0_IgG1_PVA_/S267K Heavy Chain (SEQ ID NO: 29905)
QVQLQQWGAGLLKPSETLSLTCAVYGGSFS<u>GYYWS</u>WIRQSPEKGLEWIG<u>EINHGGYVTYNPSLESR</u>VTISVDTSKNQFS
LKLSSVTAADTAVYYCAR<u>DYGPGNYDWYFDL</u>WGRGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCPAPP
VAGPSVFLFPPKPKDTLMISRTPEVTCVVVDVKHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK \>XENP014410 20H4.9[4-1BB]_H0L0_IgG1_PVA_/S267K Light Chain (SEQ ID NO: 29906)
EIVLTQSPATLSLSPGERATLSC<u>RASQSVSSYLA</u>WYQQKPGQAPRLLIY<u>DASNRAT</u>GIPARFSGSGSGTDFTLTISSLEPED
FAVYYC<u>QQRSNWPPALT</u>FGGGTKVEIK/RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSFNRGEC

Prototype anti-OX40 mAb

\>XENP016437 11D4[OX40]_H0L0_IgG1_PVA_/S267K Heavy Chain (SEQ ID NO: 29907)
EVQLVESGGGLVQPGGSLRLSCAASGFTFS<u>SYSMN</u>WVRQAPGKGLEWVS<u>YISSSSSTIDYADSVK</u>GRFTISRDNAKNSL
YLQMNSLRDEDTAVYYCAR<u>ESGWYLFDY</u>WGQGTLVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVEPKSCDKTHTCPPCPAPPVAG
PSVFLFPPKPKDTLMISRTPEVTCVVVDVKHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK \>XENP016437 11D4[OX40]_H0L0_IgG1_PVA_/S267K Light Chain (SEQ ID NO: 29908)
DIQMTQSPSSLSASVGDRVTITC<u>RASQGISSWLA</u>WYQQKPEKAPKSLIY<u>AASSLQS</u>GVPSRFSGSGSGTDFTLTISSLQPE
DFATYYC<u>QQYNSYPPT</u>FGGGTKVEIK/RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC

Prototype anti-GITR mAb

\>XENP016438 1D8[GITR]_H0L0_IgG1_PVA_/S267K Heavy Chain (SEQ ID NO: 29909)
QVTLKESGPGILKPSQTLSLTCSFSGFSLS<u>TSGMGVG</u>WIRQPSGKGLEWLA<u>HIWWDDDKYYSPSLK</u>SQLTISKDTSRNQ
VFLKITSLDTADTATYYCVR<u>SYYYGSSGAMDY</u>WGQGTSVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCPAPP
VAGPSVFLFPPKPKDTLMISRTPEVTCVVVDVKHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK

Figure 73B

>XENP016438 1D8[GITR]_H0L0_IgG1_PVA_/S267K Light Chain (SEQ ID NO: 29910)
DIVMTQTPLSLPVSLGDQASISCRSSQSLVHSDGNTYLHWYLQKPGQSPKLLIYKVSKRFSGVPDRFSGSGSGTDFTLKIS
RVEAEDLGVYFCSQSTHVPPTFGGGTKLEIK/RTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC

Prototype anti-ICOS mAbs

>XENP021820 GSK_314.8[ICOS]_H0L0_IgG1_PVA_/S267K Heavy Chain (SEQ ID NO: 29911)
QVQLQQPGTELMKPGASVKLSCKASGYTFTTYWMHWVKQRPGQGLEWIGEIDPSDSYVNYNQNFKGKATLTVDKSS
STAYIQLSSLTSEDSAVYFCARSPDYYGTSLAWFDYWGQGTLVTVST/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK >XENP021820 GSK_314.8[ICOS]_H0L0_IgG1_PVA_/S267K Light Chain (SEQ ID NO: 29912)
DIVMTQAAPSVPVTPGESVSISCRSSKSPLHSNGNIYLYWFLQRPGQSPQLLIYRMSNLASGVPDRFSGSGSGTTFTLKIS
RVEAEDVGVYYCMQHLEYPYTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC >XENP021821 GSK_88.2[ICOS]_H0L0_IgG1_PVA_/S267K Heavy Chain (SEQ ID NO: 29913)
QVQLQQPGAELVRPGASVKLSCKASGYSFTSYWINWVKQRPGQGLEWIGNIYPSDSYTNYNQMFKDKATLTVDKSSN
TAYMQLTSPTSEDSAVYYCTRWNLSYYFDNNYYLDYWGQGTTLVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHTCPP
CPAPPVAGPSVFLFPPKPKDTLMISRTPEVTCVVVDVKHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHYTQKSLSLSPGK >XENP021821 GSK_88.2[ICOS]_H0L0_IgG1_PVA_/S267K Light Chain (SEQ ID NO: 29914)
DIVMTQAAPSVPVTPGESVSISCRSSKSLLHSNGNTYLYWFLQRPGQSPQLLIYRMSNLASGVPDRFSGSGSGTAFTLRIS
RVEAEDVGVYYCMQHLEYPWTFGGGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC >XENP021822 jMab-138[ICOS]_H0L0_IgG1_PVA_/S267K Heavy Chain (SEQ ID NO: 29915)
EVQLVESGGGLVQPGGSLRLSCAASGFTFSSYDMHWVRQATGKGLEWVSAIGTAGDTYYPGSVKGRFTISRENAKNSL
YLQMNSLRAGDTAVYYCVRDNRKVTHEHYYYGMDVWGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSCDKTHTC
PPCPAPPVAGPSVFLFPPKPKDTLMISRTPEVTCVVVDVKHEDPEVKFNWYVDGVEVHNAKTKPREEQYNSTYRVVSV
LTVLHQDWLNGKEYKCKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPGK

Figure 73C

>XENP021822 jMab-138[ICOS]_H0L0_IgG1_PVA_/S267K Light Chain (SEQ ID NO: 29916)
EIVLTQSPGTLSLSPGERATLSCRASQNIRSSYLAWYQQKPGQAPGLLIYGASSRATGIPDRFSGSGSGTDFTLTISRLEPE
DFAVYYCQQFGSSPMCSFGQGTKLEIK/RTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC >XENP021823 jMab-139[ICOS]_H0L0_IgG1_PVA_/S267K Heavy Chain (SEQ ID NO: 29917)
EVQLVESGGGLVQPGGSLRLSCAASGFTFSSYDMHWVRQATGKGLEWVSAIGTAGDTYYPGSVKGRFTISRENAKNSL
YLQMNSLRAGDTAVYYCVRDKRTVTHEHYYYGMDVWGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDKTHTCP
PCPAPPVAGPSVFLFPPKPKDTLMISRTPEVTCVVVDVKHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHYTQKSLSLSPGK >XENP021823 jMab-139[ICOS]_H0L0_IgG1_PVA_/S267K Light Chain (SEQ ID NO: 29918)
EIVLTQSPGTLSLSPGERATLSCRASQSISSSSLAWYQQKPGQAPGLLIFGASSRATGIPDRFSGSGSGTDFTLTISRLEPED
FAVYYCQQFGSSPMCSFGQGTKLEIK/RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC >XENP022346 WO2016059602_GSK[ICOS]_H0L0_IgG1_PVA_/S267K Heavy Chain (SEQ ID NO: 29919)
QVQLVQSGAEVKKPGSSVKVSCKASGYTFTDYAMHWVRQAPGQGLEWMGLISIYSDHTNYNQKFQGRVTITADKST
STAYMELSSLRSEDTAVYYCGRNNYGNYGWYFDVWGQGTTVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKTHTCPPC
PAPPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK >XENP022346 WO2016059602_GSK[ICOS]_H0L0_IgG1_PVA_/S267K Light Chain (SEQ ID NO: 29920)
EIVLTQSPATLSLSPGERATLSCSASSSVSYMHWYQQKPGQAPRLLIYDTSKLASGIPARFSGSGSGTDYTLTISSLEPEDF
AVYYCFQGSGYPYTFGQGTKLEIK/RTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGEC >XENP023057 Jounce_37A10S713[ICOS]_H0L0_IgG1_PVA_/S267K Heavy Chain (SEQ ID NO: 29921)
EVQLVESGGGLVQPGGSLRLSCAASGFTFSDYWMDWVRQAPGKGLVWVSNIDEDGSITEYSPFVKGRFTISRDNAKN
TLYLQMNSLRAEDTAVYYCTRWGRFGFDSWGQGTTVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKKVEPKSCDKTHTCPPCPAPPVA
GPSVFLFPPKPKDTLMISRTPEVTCVVVDVKHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

Figure 73D

\>XENP023057 Jounce_37A10S713[ICOS]_H0L0_IgG1_PVA_/S267K Light Chain (SEQ ID NO: 29922)
DIVMTQSPDSLAVSLGERATINC<u>KSSQSLLSGSFNYLT</u>WYQQKPGQPPKLLIF<u>YASTRHT</u>GVPDRFSGSGSGTDFTLTISS
LQAEDVAVYYC<u>HHHYNAPPT</u>FGPGTKVDIK/RTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC

Prototype anti-PD-L1 mAbs

\>XENP016434 YW243.55.S70[PD-L1]_H0L0_IgG1_PVA_/S267K Heavy Chain (SEQ ID NO: 29923)
EVQLVESGGGLVQPGGSLRLSCAASGFTFS<u>DSWIH</u>WVRQAPGKGLEWVA<u>WISPYGGSTYYADSVKG</u>RFTISADTSKNT
AYLQMNSLRAEDTAVYYCARR<u>HWPGGFDY</u>WGQGTLVTVSS/ASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDKKVEPKSCDKTHTCPPCPAPPV
AGPSVFLFPPKPKDTLMISRTPEVTCVVVDVKHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK \>XENP016434 YW243.55.S70[PD-L1]_H0L0_IgG1_PVA_/S267K Light Chain (SEQ ID NO: 29924)
DIQMTQSPSSLSASVGDRVTITC<u>RASQDVSTAVA</u>WYQQKPGKAPKLLIY<u>SASFLYS</u>GVPSRFSGSGSGTDFTLTISSLQPE
DFATYYC<u>QQYLYHPAT</u>FGQGTKVEIK/RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC \>XENP024118 avelumab[PD-L1]_H1L1_IgG1_PVA_/S267K Heavy Chain (SEQ ID NO: 29925)
EVQLLESGGGLVQPGGSLRLSCAASGFTFS<u>SYIMM</u>WVRQAPGKGLEWVS<u>SIYPSGGITFYADTVKG</u>RFTISRDNSKNTL
YLQMNSLRAEDTAVYYCAR<u>IKLGTVTTVDY</u>WGQGTLVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKKVEPKSCDKTHTCPPCPAPPVA
GPSVFLFPPKPKDTLMISRTPEVTCVVVDVKHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK \>XENP024118 avelumab[PD-L1]_H1L1_IgG1_PVA_/S267K Light Chain (SEQ ID NO: 29926)
QSALTQPASVSGSPGQSITISC<u>TGTSSDVGGYNYVS</u>WYQQHPGKAPKLMIY<u>DVSNRPS</u>GVSNRFSGSKSGNTASLTISG
LQAEDEADYYC<u>SSYTSSSTRV</u>FGTGTKVTVL/GQPKAAPSVTLFPPSSEELQANKATLVCLISDFYPGAVTVAWKADSSPV
KAGVETTTPSKQSNNKYAASSYLSLTPEQWKSHRSYSCQVTHEGSTVEKTVAPTECS \>XENP024119 durvalumab[PD-L1]_H1L1_IgG1_PVA_/S267K Heavy Chain (SEQ ID NO: 29927)
EVQLVESGGGLVQPGGSLRLSCAASGFTFS<u>RYWMS</u>WVRQAPGKGLEWVA<u>NIKQDGSEKYYVDSVKG</u>RFTISRDNAK
NSLYLQMNSLRAEDTAVYYCAR<u>EGGWFGELAFDY</u>WGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCPPCP
APPVAGPSVFLFPPKPKDTLMISRTPEVTCVVVDVKHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK

Figure 73E

\>XENP024119 durvalumab[PD-L1]_H1L1_IgG1_PVA_/S267K Light Chain (SEQ ID NO: 29928)
EIVLTQSPGTLSLSPGERATLSC<u>RASQRVSSSYLA</u>WYQQKPGQAPRLLIY<u>DASSRAT</u>GIPDRFSGSGSGTDFTLTISRLEPE
DFAVYYC<u>QQYGSLPWT</u>FGQGTKVEIK/RTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC

Prototype anti-PD-1 mAbs

\>XENP024120 LOPD180[PD-1]_H1L1_IgG1_PVA_/S267K Heavy Chain (SEQ ID NO: 29929)
QVQLQESGPGLVKPSQTLSLTCTVSGGSIS<u>SGAYYWS</u>WIRQHPGKGLEWIG<u>YIYYNGNTYYNPSLRS</u>RVTISVDTSKNQF
SLKLSSVTAADTAVYYCVR<u>ASDYVWGGYHYFDAFDL</u>WGRGTLVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKKVEPKSCDKTHTCPP
CPAPPVAGPSVFLFPPKPKDTLMISRTPEVTCVVVDVKHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHYTQKSLSLSPGK \>XENP024120 LOPD180[PD-1]_H1L1_IgG1_PVA_/S267K Light Chain (SEQ ID NO: 29930)
QSVLTQPPSASGTPGQRVTISC<u>SGSNSNIGSNSVN</u>WYQQLPGTAPKLLIY<u>GNNQRPS</u>GVPDRFSGSKSGTSASLAISGL
QSEDEADYYC<u>AAWDDSLNGPV</u>FGGGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS \>XENP024121 mAb7(1.2)[PD-1]_H1L1_IgG1_PVA_/S267K Heavy Chain (SEQ ID NO: 29931)
QVQLVQSGAEVKKPGASVKVSCKASGYSFT<u>SYWMN</u>WVRQAPGQGLEWIG<u>VIHPSDSETWLDQKFKD</u>RVTITVDKST
STAYMELSSLRSEDTAVYYCAR<u>EHYGTSPFAY</u>WGQGTLVTVSS/ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCPAPP
VAGPSVFLFPPKPKDTLMISRTPEVTCVVVDVKHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPGK \>XENP024121 mAb7(1.2)[PD-1]_H1L1_IgG1_PVA_/S267K Light Chain (SEQ ID NO: 29932)
EIVLTQSPATLSLSPGERATLSC<u>RASESVDNYGMSFMN</u>WFQQKPGQPPKLLIH<u>AASNQGS</u>GVPSRFSGSGSGTDFTLTIS
SLEPEDFAVYFC<u>QQSKEVPYT</u>FGGGTKVEIK/RTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC

Figure 73F

Additional ICOS x PD-L1

>XENP021832 GSK_314.8[ICOS]_H0L0_Fab-YW243.55.S70[PD-L1]_H0L0_scFv Fab-Fc Heavy Chain (SEQ ID NO: 29933)
QVQLQQPGTELMKPGASVKLSCKASGYTFT<u>TYWMH</u>WVKQRPGQGLEWIG<u>EIDPSDSYVNYNQNFKG</u>KATLTVDKSSTAYIQLSS
LTSEDSAVYFCAR<u>SPDYYGTSLAWFDY</u>WGQGTLVTVST/ASTKGPSVFPLAPSSKSTSGGTAALGCLVKDYFPEPVTVSWNSGALTS
GVHTFPAVLQSSGLYSLSSVVTVPSSSLGTQTYICNVNHKPSDTKVDKKVEPKSCDKTHTCPPCPAPPVAGPSVFLFPPKPKDTLMISR
TPEVTCVVVDVKHEDPEVKFNWYVDGVEVHNAKTKPREEEYNSTYRVVSVLTVLHQDWLNGKEYKCKVSNKALPAPIEKTISKAKG
QPREPQVYTLPPSREEMTKNQVSLTCDVSGFYPSDIAVEWESDGQPENNYKTTPPVLDSDGSFFLYSKLTVDKSRWEQGDVFSCSV
MHEALHNHYTQKSLSLSPGK >XENP021832 GSK_314.8[ICOS]_H0L0_Fab-YW243.55.S70[PD-L1]_H0L0_scFv scFv-Fc Heavy Chain (SEQ ID NO: 29934)
EVQLVESGGGLVQPGGSLRLSCAASGFTFS<u>DSWIH</u>WVRQAPGKGLEWVA<u>WISPYGGSTYYADSVKG</u>RFTISADTSKNTAYLQMNS
LRAEDTAVYYCAR<u>RHWPGGFDY</u>WGQGTLVTVSS/<u>GGGGSGGGGSGGGGS</u>/DIQMTQSPSSLSASVGDRVTITC<u>RASQDVSTAVA</u>
<u>WYQQKPGKAPKLLIY</u><u>SASFLYS</u>GVPSRFSGSGSGTDFTLTISSLQPEDFATYYC<u>QQYLYHPAT</u>FGQGTKVEIK/EPKSSDKTHTCPPCPA
PPVAGPSVFLFPPKPKDTLMISRTPEVTCVVVDVKHEDPEVKFNWYVDGVEVHNAKTKPREEQYNSTYRVVSVLTVLHQDWLNGK
EYKCKVSNKALPAPIEKTISKAKGQPREPQVYTLPPSREQMTKNQVKLTCLVKGFYPSDIAVEWESNGQPENNYKTTPPVLDSDGSFF
LYSKLTVDKSRWQQGNVFSCSVMHEALHNHYTQKSLSLSPGK >XENP021832 GSK_314.8[ICOS]_H0L0_Fab-YW243.55.S70[PD-L1]_H0L0_scFv Light Chain (SEQ ID NO: 29935)
DIVMTQAAPSVPVTPGESVSISC<u>RSSKSPLHSNGNIYLY</u>WFLQRPGQSPQLLIY<u>RMSNLAS</u>GVPDRFSGSGSGTTFTLKISRVEAEDVG
VYYC<u>MQHLEYPYT</u>FGGGTKLEIK/RTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC >XENP021833 GSK_88.2[ICOS]_H0L0_Fab-YW243.55.S70[PD-L1]_H0L0_scFv Fab-Fc Heavy Chain (SEQ ID NO: 29936)
QVQLQQPGAELVRPGASVKLSCKASGYSFT<u>SYWIN</u>WVKQRPGQGLEWIG<u>NIYPSDSYTNYNQMFKD</u>KATLTVDKSSNTAYMQLTS
PTSEDSAVYYCTR<u>WNLSYYFDNNYYLDY</u>WGQGTTLVTVSS/ASTKGPSVFPLAPSSKSTSGGTAALGCLVKDYFPEPVTVSWNSGALT
SGVHTFPAVLQSSGLYSLSSVVTVPSSSLGTQTYICNVNHKPSDTKVDKKVEPKSCDKTHTCPPCPAPPVAGPSVFLFPPKPKDTLMIS
RTPEVTCVVVDVKHEDPEVKFNWYVDGVEVHNAKTKPREEEYNSTYRVVSVLTVLHQDWLNGKEYKCKVSNKALPAPIEKTISKAK
GQPREPQVYTLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK >XENP021833 GSK_88.2[ICOS]_H0L0_Fab-YW243.55.S70[PD-L1]_H0L0_scFv scFv-Fc Heavy Chain (SEQ ID NO: 29937)
EVQLVESGGGLVQPGGSLRLSCAASGFTFS<u>DSWIH</u>WVRQAPGKGLEWVA<u>WISPYGGSTYYADSVKG</u>RFTISADTSKNTAYLQMNS
LRAEDTAVYYCAR<u>RHWPGGFDY</u>WGQGTLVTVSS/<u>GGGGSGGGGSGGGGS</u>/DIQMTQSPSSLSASVGDRVTITC<u>RASQDVSTAVA</u>
<u>WYQQKPGKAPKLLIY</u><u>SASFLYS</u>GVPSRFSGSGSGTDFTLTISSLQPEDFATYYC<u>QQYLYHPAT</u>FGQGTKVEIK/EPKSSDKTHTCPPCPA
PPVAGPSVFLFPPKPKDTLMISRTPEVTCVVVDVKHEDPEVKFNWYVDGVEVHNAKTKPREEQYNSTYRVVSVLTVLHQDWLNGK
EYKCKVSNKALPAPIEKTISKAKGQPREPQVYTLPPSREQMTKNQVKLTCLVKGFYPSDIAVEWESNGQPENNYKTTPPVLDSDGSFF
LYSKLTVDKSRWQQGNVFSCSVMHEALHNHYTQKSLSLSPGK

Figure 73G

>XENP021833 GSK_88.2[ICOS]_H0L0_Fab-YW243.55.S70[PD-L1]_H0L0_scFv Light Chain (SEQ ID NO: 29938)
DIVMTQAAPSVPVTPGESVSISC<u>RSSKSLLHSNGNTYLY</u>WFLQRPGQSPQLLIY<u>RMSNLAS</u>GVPDRFSGSGSGTAFTLRIS
RVEAEDVGVYYC<u>MQHLEYPWT</u>FGGGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC >XENP021834 jMab-138[ICOS]_H0L0_Fab-YW243.55.S70[PD-L1]_H0L0_scFv Fab-Fc Heavy Chain (SEQ ID NO: 29939)
EVQLVESGGGLVQPGGSLRLSCAASGFTFS<u>SYDMH</u>WVRQATGKGLEWVS<u>AIGTAGDTYYPGSVKG</u>RFTISRENAKNSL
YLQMNSLRAGDTAVYYCVR<u>DNRKVTHEHYYYGMDV</u>WGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVSVL
TVLHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK >XENP021834 jMab-138[ICOS]_H0L0_Fab-YW243.55.S70[PD-L1]_H0L0_scFv scFv-Fc Heavy Chain (SEQ ID NO: 29940)
EVQLVESGGGLVQPGGSLRLSCAASGFTFS<u>DSWIH</u>WVRQAPGKGLEWVA<u>WISPYGGSTYYADSVKG</u>RFTISADTSKNT
AYLQMNSLRAEDTAVYYCARR<u>HWPGGFDY</u>WGQGTLVTVSS/<u>GGGGSGGGGSGGGGS</u>/DIQMTQSPSSLSASVGDR
VTITC<u>RASQDVSTAVA</u>WYQQKPGKAPKLLIY<u>SASFLYS</u>GVPSRFSGSGSGTDFTLTISSLQPEDFATYYC<u>QQYLYHPAT</u>FG
QGTKVEIK/EPKSSDKTHTCPPCPAPPVAGPSVFLFPPKPKDTLMISRTPEVTCVVVDVKHEDPEVKFNWYVDGVEVHN
AKTKPREEQYNSTYRVVSVLTVLHQDWLNGKEYKCKVSNKALPAPIEKTISKAKGQPREPQVYTLPPSREQMTKNQVKL
TCLVKGFYPSDIAVEWESNGQPENNYKTTPPVLDSDGSFFLYSKLTVDKSRWQQGNVFSCSVMHEALHNHYTQKSLSL
SPGK >XENP021834 jMab-138[ICOS]_H0L0_Fab-YW243.55.S70[PD-L1]_H0L0_scFv Light Chain (SEQ ID NO: 29941)
EIVLTQSPGTLSLSPGERATLSC<u>RASQNIRSSYLA</u>WYQQKPGQAPGLLIY<u>GASSRAT</u>GIPDRFSGSGSGTDFTLTISRLEPE
DFAVYYC<u>QQFGSSPMCS</u>FGQGTKLEIK/RTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC >XENP021835 jMab-139[ICOS]_H0L0_Fab-YW243.55.S70[PD-L1]_H0L0_scFv Fab-Fc Heavy Chain (SEQ ID NO: 29942)
EVQLVESGGGLVQPGGSLRLSCAASGFTFS<u>SYDMH</u>WVRQATGKGLEWVS<u>AIGTAGDTYYPGSVKG</u>RFTISRENAKNSL
YLQMNSLRAGDTAVYYCVR<u>DKRTVTHEHYYYGMDV</u>WGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK

Figure 73H

>XENP021835 jMab-139[ICOS]_H0L0_Fab-YW243.55.S70[PD-L1]_H0L0_scFv scFv-Fc Heavy Chain (SEQ ID NO: 29943)
EVQLVESGGGLVQPGGSLRLSCAASGFTFSDSWIHWVRQAPGKGLEWVAWISPYGGSTYYADSVKGRFTISADTSKNT
AYLQMNSLRAEDTAVYYCARRHWPGGFDYWGQGTLVTVSS/GGGGSGGGGSGGGGS/DIQMTQSPSSLSASVGDR
VTITCRASQDVSTAVAWYQQKPGKAPKLLIYSASFLYSGVPSRFSGSGSGTDFTLTISSLQPEDFATYYCQQYLYHPATFG
QGTKVEIK/EPKSSDKTHTCPPCPAPPVAGPSVFLFPPKPKDTLMISRTPEVTCVVVDVKHEDPEVKFNWYVDGVEVHN
AKTKPREEQYNSTYRVVSVLTVLHQDWLNGKEYKCKVSNKALPAPIEKTISKAKGQPREPQVYTLPPSREQMTKNQVKL
TCLVKGFYPSDIAVEWESNGQPENNYKTTPPVLDSDGSFFLYSKLTVDKSRWQQGNVFSCSVMHEALHNHYTQKSLSL
SPGK >XENP021835 jMab-139[ICOS]_H0L0_Fab-YW243.55.S70[PD-L1]_H0L0_scFv Light Chain (SEQ ID NO: 29944)
EIVLTQSPGTLSLSPGERATLSCRASQSISSSSLAWYQQKPGQAPGLLIFGASSRATGIPDRFSGSGSGTDFTLTISRLEPED
FAVYYCQQFGSSPMCSFGQGTKLEIK/RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC >XENP021836 jMab-136[ICOS]_H0L0_Fab-YW243.55.S70[PD-L1]_H0L0_scFv Fab-Fc Heavy Chain (SEQ ID NO: 29945)
QVQLVQSGAEVKKPGASVKVSCKASGYTFTGYYMHWVRQAPGQGLEWMGWINPHSGGTNYAQKFQGRVTMTRD
TSISTAYMELSRLRSDDTAVYYCARTYYYDSSGYYHDAFDIWGQGTMVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEWES
DGQPENNYKTTPPVLDSDGSFFLYSKLTVDKSRWEQGDVFSCSVMHEALHNHYTQKSLSLSPGK >XENP021836 jMab-136[ICOS]_H0L0_Fab-YW243.55.S70[PD-L1]_H0L0_scFv scFv-Fc Heavy Chain (SEQ ID NO: 29946)
EVQLVESGGGLVQPGGSLRLSCAASGFTFSDSWIHWVRQAPGKGLEWVAWISPYGGSTYYADSVKGRFTISADTSKNT
AYLQMNSLRAEDTAVYYCARRHWPGGFDYWGQGTLVTVSS/GGGGSGGGGSGGGGS/DIQMTQSPSSLSASVGDR
VTITCRASQDVSTAVAWYQQKPGKAPKLLIYSASFLYSGVPSRFSGSGSGTDFTLTISSLQPEDFATYYCQQYLYHPATFG
QGTKVEIK/EPKSSDKTHTCPPCPAPPVAGPSVFLFPPKPKDTLMISRTPEVTCVVVDVKHEDPEVKFNWYVDGVEVHN
AKTKPREEQYNSTYRVVSVLTVLHQDWLNGKEYKCKVSNKALPAPIEKTISKAKGQPREPQVYTLPPSREQMTKNQVKL
TCLVKGFYPSDIAVEWESNGQPENNYKTTPPVLDSDGSFFLYSKLTVDKSRWQQGNVFSCSVMHEALHNHYTQKSLSL
SPGK >XENP021836 jMab-136[ICOS]_H0L0_Fab-YW243.55.S70[PD-L1]_H0L0_scFv Light Chain (SEQ ID NO: 29947)
DIQMTQSPSSVSASVGDRVTITCRASQGISRLLAWYQQKPGKAPKLLIYVASSLQSGVPSRFSGSGSGTDFTLTISSLQPE
DFATYYCQQANSFPWTFGQGTKVEIK/RTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC

Figure 74A

Anti-PD-1-Fab x Anti-ICOS-scFv Bottle-openers

>XENP018920 nivolumab[PD-1]_H0L0_Fab-[anti-ICOS]_H0L0_scFv Fab-Fc Heavy Chain
(SEQ ID NO: 29948)
QVQLVESGGGVVQPGRSLRLDCKASGITFSNSGMHWVRQAPGKGLEWVAVIWYDGSKRYYADSVKGRFTISRDNSKN
TLFLQMNSLRAEDTAVYYCATNDDYWGQGTLVTVSS/ASTKGPSVFPLAPSSKSTSGGTAALGCLVKDYFPEPVTVS
WNSGALTSGVHTFPAVLQSSGLYSLSSVVTVPSSSLGTQTYICNVNHKPSDTKVDKKVEPKSCDKTHTCPPCPAPPV
AGPSVFLFPPKPKDTLMISRTPEVTCVVVDVKHEDPEVKFNWYVDGVEVHNAKTKPREEEYNSTYRVVSVLTVLHQD
WLNGKEYKCKVSNKALPAPIEKTISKAKGQPREPQVYTLPPSREEMTKNQVSLTCDVSGFYPSDIAVEWESDGQPEN
NYKTTPPVLDSDGSFFLYSKLTVDKSRWEQGDVFSCSVMHEALHNHYTQKSLSLSPGK >XENP018920 nivolumab[PD-1]_H0L0_Fab-[anti-ICOS]_H0L0_scFv scFv-Fc Heavy
Chain (SEQ ID NO: 29949)
QVQLVESGGGVVQPGRSLRLSCKASGITFSNSGMHWVRQAPGKGLEWVAVIWYDGSKRYYADSVKGRFTISRDNSKN
TLFLQMNSLRAEDTAVYYCATNDDYWGQGTLVTVSS/GKPGSGKPGSGKPGSGKPGS/EIVLTQSPATLSLSPGERA
TLSCRASQSVSSYLAWYQQKPGQAPRLLIYDASNRATGIPARFSGSGSGTDFTLTISSLEPEDFAVYYCQQSSNWPR
TFGQGTKVEIK/EPKSSDKTHTCPPCPAPPVAGPSVFLFPPKPKDTLMISRTPEVTCVVVDVKHEDPEVKFNWYVDG
VEVHNAKTKPREEQYNSTYRVVSVLTVLHQDWLNGKEYKCKVSNKALPAPIEKTISKAKGQPREPQVYTLPPSREQM
TKNQVKLTCLVKGFYPSDIAVEWESNGQPENNYKTTPPVLDSDGSFFLYSKLTVDKSRWQQGNVFSCSVMHEALHNH
YTQKSLSLSPGK >XENP018920 nivolumab[PD-1]_H0L0_Fab-[anti-ICOS]_H0L0_scFv Light Chain (SEQ
ID NO: 29950)
EIVLTQSPATLSLSPGERATLSCRASQSVSSYLAWYQQKPGQAPRLLIYDASNRATGIPARFSGSGSGTDFTLTISS
LEPEDFAVYYCQQSSNWPRTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC >XENP024130 LOPD180[PD-1]_H1L1_Fab-[anti-ICOS]_H0L0_scFv Fab-Fc Heavy Chain
(SEQ ID NO: 29951)
QVQLQESGPGLVKPSQTLSLTCTVSGGSISSGAYYWSWIRQHPGKGLEWIGYIYYNGNTYYNPSLRSRVTISVDTSK
NQFSLKLSSVTAADTAVYYCVRASDYVWGGYHYFDAFDLWGRGTLVTVSS/ASTKGPSVFPLAPSSKSTSGGTAALG
CLVKDYFPEPVTVSWNSGALTSGVHTFPAVLQSSGLYSLSSVVTVPSSSLGTQTYICNVNHKPSDTKVDKKVEPKSC
DKTHTCPPCPAPPVAGPSVFLFPPKPKDTLMISRTPEVTCVVVDVKHEDPEVKFNWYVDGVEVHNAKTKPREEEYNS
TYRVVSVLTVLHQDWLNGKEYKCKVSNKALPAPIEKTISKAKGQPREPQVYTLPPSREEMTKNQVSLTCDVSGFYPS
DIAVEWESDGQPENNYKTTPPVLDSDGSFFLYSKLTVDKSRWEQGDVFSCSVMHEALHNHYTQKSLSLSPGK >XENP024130 LOPD180[PD-1]_H1L1_Fab-[anti-ICOS]_H0L0_scFv scFv-Fc Heavy Chain
(SEQ ID NO: 29952)
QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGIYHDAFDIWGQGTMVTVSS/GKPGSGKPGSGKPGSGKPGS/DIQMTQS
PSSVSASVGDRVTITCRASQGISRLLAWYQQKPGKAPKLLIYAASSLQSGVPSRFSGSGSGTDFTLTISSLQPEDFA
TYYCQQANSFPWTFGQGTKVEIK/EPKSSDKTHTCPPCPAPPVAGPSVFLFPPKPKDTLMISRTPEVTCVVVDVKHE
DPEVKFNWYVDGVEVHNAKTKPREEQYNSTYRVVSVLTVLHQDWLNGKEYKCKVSNKALPAPIEKTISKAKGQPREP
QVYTLPPSREQMTKNQVKLTCLVKGFYPSDIAVEWESNGQPENNYKTTPPVLDSDGSFFLYSKLTVDKSRWQQGNVF
SCSVMHEALHNHYTQKSLSLSPGK >XENP024130 LOPD180[PD-1]_H1L1_Fab-[anti-ICOS]_H0L0_scFv Light Chain (SEQ ID
NO: 29953)
QSVLTQPPSASGTPGQRVTISCSGSNSNIGSNSVNWYQQLPGTAPKLLIYGNNQRPSGVPDRFSGSKSGTSASLAIS
GLQSEDEADYYCAAWDDSLNGPVFGGGTKVTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 74B

ICOS x PD-1 Bottle-openers with different ICOS ABDs

>XENP021828 GSK_314.8[ICOS]_H0L0_Fab-1G6_L1.194_H1.279_scFv Fab-Fc Heavy
Chain (SEQ ID NO: 29954)
QVQLQQPGTELMKPGASVKLSCKASGYTFTTYWMHWVKQRPGQGLEWIGEIDPSDSYVNYNQNFKGKATLTVDKSSS
TAYIQLSSLTSEDSAVYFCARSPDYYGTSLAWFDYWGQGTLVTVST/ASTKGPSVFPLAPSSKSTSGGTAALGCLVK
DYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVKHEDPEVKFNWYVDGVEVHNAKTKPREEEYNSTYRV
VSVLTVLHQDWLNGKEYKCKVSNKALPAPIEKTISKAKGQPREPQVYTLPPSREEMTKNQVSLTCDVSGFYPSDIAV
EWESDGQPENNYKTTPPVLDSDGSFFLYSKLTVDKSRWEQGDVFSCSVMHEALHNHYTQKSLSLSPGK >XENP021828 GSK_314.8[ICOS]_H0L0_Fab-1G6_L1.194_H1.279_scFv scFv-Fc Heavy
Chain (SEQ ID NO: 29955)
EIVLTQSPATLSASPGERVTLTCRASQSVGNDVAWYQQKPGQAPRLLINYASHRYTGVPDRFTGSGYGTEFTLTISS
VQSEDFGVYYCQQDFSSPRTFGGGTKVEIK/GKPGSGKPGSGKPGSGKPGS/EVQLVESGGGLVKPGGSLRLSCVAS
GFTFSNYWMNWVRQAPGKGLEWVAEIRLYSNNYATHYAESVKGRFTISRDDSKSTLYLQMNNLKTEDTGVYYCTRYY
GNYGGYFDVWGRGTLVTVSS/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK >XENP021828 GSK_314.8[ICOS]_H0L0_Fab-1G6_L1.194_H1.279_scFv Light Chain (SEQ
ID NO: 29956)
DIVMTQAAPSVPVTPGESVSISCRSSKSPLHSNGNIYLYWFLQRPGQSPQLLIYRMSNLASGVPDRFSGSGSGTTFT
LKISRVEAEDVGVYYCMQHLEYPYTFGGGTKLEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC >XENP021829 GSK_88.2[ICOS]_H0L0_Fab-1G6_L1.194_H1.279_scFv Fab-Fc Heavy Chain
(SEQ ID NO: 29957)
QVQLQQPGAELVRPGASVKLSCKASGYSFTSYWINWVKQRPGQGLEWIGNIYPSDSYTNYNQMFKDKATLTVDKSSN
TAYMQLTSPTSEDSAVYYCTRWNLSYYFDNNYYLDYWGQGTTLTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK >XENP021829 GSK_88.2[ICOS]_H0L0_Fab-1G6_L1.194_H1.279_scFv scFv-Fc Heavy
Chain (SEQ ID NO: 29958)
EIVLTQSPATLSASPGERVTLTCRASQSVGNDVAWYQQKPGQAPRLLINYASHRYTGVPDRFTGSGYGTEFTLTISS
VQSEDFGVYYCQQDFSSPRTFGGGTKVEIK/GKPGSGKPGSGKPGSGKPGS/EVQLVESGGGLVKPGGSLRLSCVAS
GFTFSNYWMNWVRQAPGKGLEWVAEIRLYSNNYATHYAESVKGRFTISRDDSKSTLYLQMNNLKTEDTGVYYCTRYY
GNYGGYFDVWGRGTLVTVSS/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK >XENP021829 GSK_88.2[ICOS]_H0L0_Fab-1G6_L1.194_H1.279_scFv Light Chain (SEQ
ID NO: 29959)
DIVMTQAAPSVPVTPGESVSISCRSSKSLLHSNGNTYLYWFLQRPGQSPQLLIYRMSNLASGVPDRFSGSGSGTAFT
LRISRVEAEDVGVYYCMQHLEYPWTFGGGTKLEIK/RTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

Figure 74C

>XENP021830 jMab-138[ICOS]_H0L0_Fab-1G6_L1.194_H1.279_scFv Fab-Fc Heavy Chain (SEQ ID NO: 29960)
EVQLVESGGGLVQPGGSLRLSCAASGFTFSSYIMHWVRQATGKGLEWVSAIGTAGDTYYPGSVKGRFTISRENAKNSLYLQMNSLR
AGDTAVYYCVRDNRKVTHEHYYYGMDVWGQGTTVTVSS/ASTKGPSVFPLAPSSKSTSGGTAALGCLVKDYFPEPVTVSWNSGAL
TSGVHTFPAVLQSSGLYSLSSVVTVPSSSLGTQTYICNVNHKPSDTKVDKKVEPKSCDKTHTCPPCPAPPVAGPSVFLFPPKPKDT
LMISRTPEVTCVVVDVKHEDPEVKFNWYVDGVEVHNAKTKPREEEYNSTYRVVSVLTVLHQDWLNGKEYKCKVSNKALPAPIEKTI
SKAKGQPREPQVYTLPPSREEMTKNQVSLTCDVSGFYPSDIAVEWESDGQPENNYKTTPPVLDSDGSFFLYSKLTVDKSRWEQGDV
FSCSVMHEALHNHYTQKSLSLSPGK >XENP021830 jMab-138[ICOS]_H0L0_Fab-1G6_L1.194_H1.279_scFv scFv-Fc Heavy Chain (SEQ ID NO: 29961)
EIVLTQSPATLSASPGERVTLTCRASQSVGNDVAWYQQKPGQAPRLLINYASHRYTGVPDRFTGSGYGTEFTLTISSVQSEDFGVY
YCQQDFSSPRTFGGGTKVEIK/GKPGSGKPGSGKPGSGKPGS/EVQLVESGGGLVKPGGSLRLSCVASGFTFSNYWMNWVRQAPGK
GLEWVAEIRLYSNNYATHYAESVKGRFTISRDDSKSTLYLQMNNLRTEDTGVYYCTRYYGNYGGYFDVWGRGTLVTVSS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREQMTKNQVKLTCLVKGFYPSDIAVEWESNGQPENNYKTT
PPVLDSDGSFFLYSKLTVDKSRWQQGNVFSCSVMHEALHNHYTQKSLSLSPGK >XENP021830 jMab-138[ICOS]_H0L0_Fab-1G6_L1.194_H1.279_scFv Light Chain (SEQ ID NO: 29962)
EIVLTQSPGTLSLSPGERATLSCRASQNIFSSYLAWYQQKPGQAPGLLIYGASSRATGIPDRFSGSGSGTDFTLTISRLEPEDFAV
YYCQQFGSSPMCSFGQGTKLEIK/RTVAAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC >XENP021831 jMab-139[ICOS]_H0L0_Fab-1G6_L1.194_H1.279_scFv Fab-Fc Heavy Chain (SEQ ID NO: 29963)
EVQLVESGGGLVQPGGSLRLSCAASGFTFSSYDMHWVRQATGKGLEWVSAIGTAGDTYYPGSVKGRFTISRENAKNSLYLQMNSLR
AGDTAVYYCVRDKPTVTHEHYYYGMDVWGQGTTVTVSS/ASTKGPSVFPLAPSSKSTSGGTAALGCLVKDYFPEPVTVSWNSGAL
TSGVHTFPAVLQSSGLYSLSSVVTVPSSSLGTQTYICNVNHKPSDTKVDKKVEPKSCDKTHTCPPCPAPPVAGPSVFLFPPKPKDT
LMISRTPEVTCVVVDVKHEDPEVKFNWYVDGVEVHNAKTKPREEEYNSTYRVVSVLTVLHQDWLNGKEYKCKVSNKALPAPIEKTI
SKAKGQPREPQVYTLPPSREEMTKNQVSLTCDVSGFYPSDIAVEWESDGQPENNYKTTPPVLDSDGSFFLYSKLTVDKSRWEQGDV
FSCSVMHEALHNHYTQKSLSLSPGK >XENP021831 jMab-139[ICOS]_H0L0_Fab-1G6_L1.194_H1.279_scFv scFv-Fc Heavy Chain (SEQ ID NO: 29964)
EIVLTQSPATLSASPGERVTLTCRASQSVGNDVAWYQQKPGQAPRLLINYASHRYTGVPDRFTGSGYGTEFTLTISSVQSEDFGVY
YCQQDFSSPRTFGGGTKVEIK/GKPGSGKPGSGKPGSGKPGS/EVQLVESGGGLVKPGGSLRLSCVASGFTFSNYWMNWVRQAPGK
GLEWVAEIRLYSNNYATHYAESVKGRFTISRDDSKSTLYLQMNNLRTEDTGVYYCTRYYGNYGGYFDVWGRGTLVTVSS/EPKSSD
KTHTCPPCPAPPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREQMTKNQVKLTCLVKGFYPSDIAVEWESNGQPENNYKTT
PPVLDSDGSFFLYSKLTVDKSRWQQGNVFSCSVMHEALHNHYTQKSLSLSPGK >XENP021831 jMab-139[ICOS]_H0L0_Fab-1G6_L1.194_H1.279_scFv Light Chain (SEQ ID NO: 29965)
EIVLTQSPGTLSLSPGERATLSCRASQSISSSSLAWYQQKPGQAPGLLIFGASSRATGIPDRFSGSGSGTDFTLTISRLEPEDFAV
YYCQQFGSSPMCSFGQGTKLEIK/RTVAAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC >XENP022348 WO2016059602_GSK_H0L0_Fab-1G6_L1.194_H1.279_scFv Fab-Fc Heavy Chain (SEQ ID NO: 29966)
QVQLVQSGAEVKKPGSSVKVSCKASGYTFTDYAMHWVRQAPGQGLEWMGLISIYSDHTRYNQKFQGRVTITADKSTSTAYMELSSL
RSEDTAVYYCGRNNYGNYGWYFDVWGQGTTVTVSS/ASTKGPSVFPLAPSSKSTSGGTAALGCLVKDYFPEPVTVSWNSGALTSGV
HTFPAVLQSSGLYSLSSVVTVPSSSLGTQTYICNVNHKPSDTKVDKKVEPKSCDKTHTCPPCPAPPVAGPSVFLFPPKPKDTLMIS
RTPEVTCVVVDVKHEDPEVKFNWYVDGVEVHNAKTKPREEEYNSTYRVVSVLTVLHQDWLNGKEYKCKVSNKALPAPIEKTISKAK
GQPREPQVYTLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

Figure 74D

>XENP022348 WO2016059602_GSK_H0L0_Fab-1G6_L1.194_H1.279_scFv scFv-Fc Heavy
Chain (SEQ ID NO: 29967)
EIVLTQSPATLSASPGERVTLTCRASQSVGNDVAWYQQKPGQAPRLLINYASHRYTGVPDRFTGSGYGTEFTLTISS
VQSEDFGVYYCQQDFSSPRTFGGGTKVEIK/GKPGSGKPGSGKPGSGKPGS/EVQLVESGGGLVKPGGSLRLSCVAS
GFTFSNYWMNWVRQAPGKGLEWVAEIRLYSNNYATHYAESVKGRFTISRDDSKSTLYLQMNNLKTEDTGVYYCTRYY
GNYGGYFDVWGRGTLVTVSS/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK >XENP022348 WO2016059602_GSK_H0L0_Fab-1G6_L1.194_H1.279_scFv Light Chain (SEQ
ID NO: 29968)
EIVLTQSPATLSLSPGERATLSCSASSSVSYMHWYQQKPGQAPRLLIYDTSKLASGIPARFSGSGSGTDYTLTISSL
EPEDFAVYYCFQGSGYPYTFGQGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

Anti-PD-L1 x anti-ICOS Antibodies

>XENP021748 YW243.55.S70[PD-L1]_H0L0_Fab-[anti-ICOS]_H0L0_scFv Fab-Fc Heavy
Chain (SEQ ID NO: 29969)
EVQLVESGGGLVQPGGSLRLSCAASGFTFSDSWIHWVRQAPGKGLEWVAWISPYGGSTYYADSVKGRFTISADTSKN
TAYLQMNSLRAEDTAVYYCARRHWPGGFDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK >XENP021748 YW243.55.S70[PD-L1]_H0L0_Fab-[anti-ICOS]_H0L0_scFv scFv-Fc Heavy
Chain (SEQ ID NO: 29970)
QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/GKPGSGKPGSGKPGSGKPGS/DIQMTQS
PSSVSASVGDRVTITCRASQGISRLLAWYQQKPGKAPKLLIYAASSLQSGVPSRFSGSGSGTDFTLTISSLQPEDFA
TYYCQQANSFPWTFGQGTKVEIK/EPKSSDKTHTCPPCPAPPVAGPSVFLFPPKPKDTLMISRTPEVTCVVVDVKHE
DPEVKFNWYVDGVEVHNAKTKPREEQYNSTYRVVSVLTVLHQDWLNGKEYKCKVSNKALPAPIEKTISKAKGQPREP
QVYTLPPSREQMTKNQVKLTCLVKGFYPSDIAVEWESNGQPENNYKTTPPVLDSDGSFFLYSKLTVDKSRWQQGNVF
SCSVMHEALHNHYTQKSLSLSPGK >XENP021748 YW243.55.S70[PD-L1]_H0L0_Fab-[anti-ICOS]_H0L0_scFv Light Chain
(SEQ ID NO: 29971)
DIQMTQSPSSLSASVGDRVTITCRASQDVSTAVAWYQQKPGKAPKLLIYSASFLYSGVPSRFSGSGSGTDFTLTISS
LQPEDFATYYCQQYLYHPATFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Anti-ICOS x anti-CTLA-4 Bottle Opener

>XENP021749 [anti-ICOS]_H0L0_Fab-[anti-CTLA-4]_H3.23_L0.129_scFv Fab-Fc Heavy
Chain (SEQ ID NO: 29972)
QVQLVQSGAEVKKPGASVKVSCKASGYTFTGYYMHWVRQAPGQGLEWMGWINPHSGGTNYAQKFQGRVTMTRDTSIS
TAYMELSRLRSDDTAVYYCARTYYYDSSGYYHDAFDIWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK

Figure 74E

>XENP021749 [anti-ICOS]_H0L0_Fab-[anti-CTLA-4]_H3.23_L0.129_scFv scFv-Fc Heavy Chain (SEQ ID NO: 29973)
EVQLVESGGGLVKPGGSLRLSCAASGFTFSSYTMHWVRQAPGKGLEWVSFISYDGNYKYYADSVKGRFTISRDNAKNSLYLQ
MNSLRAEDTAVYYCARGGHLGPFDLWGQGTMVTVSS/GKPGSGKPGSGKPGSGKPGS/EIVLTQSPATLSLSPGERATLSCR
ASQSVGSSYLAWYQQKPGQAPRLLIYGASSRATGIPDRFSGSGSGTDFTLTISRLEPEDFAVYYCQQYGSSPWTFGQGTKVE
IK/EPKSSDKTHTCPPCPAPPVAGPSVFLFPPKPKDTLMISRTPEVTCVVVDVKHEDPEVKFNWYVDGVEVHNAKTKPREEQ
YNSTYRVVSVLTVLHQDWLNGKEYKCKVSNKALPAPIEKTISKAKGQPREPQVYTLPPSREQMTKNQVKLTCLVKGFYPSDI
AVEWESNGQPENNYKTTPPVLDSDGSFFLYSKLTVDKSRWQQGNVFSCSVMHEALHNHYTQKSLSLSPGK >XENP021749 [anti-ICOS]_H0L0_Fab-[anti-CTLA-4]_H3.23_L0.129_scFv Light Chain (SEQ ID NO: 29974)
DIQMTQSPSSVSASVGDRVTITCRASQGISRLLAWYQQKPGKAPKLLIYYASSLQSGVPSRFSGSGSGTDFTLTISSLQPED
FATYYCQQANSFPWTFGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

ICOS one-arm from alternative ICOS ABDs

>XENP021861 GSK_314.8[ICOS]_H0L0 one-arm mAb Fab-Fc Heavy Chain (SEQ ID NO: 29975)
QVQLQQPGTELMKPGASVKLSCKASGYTFTTYWMHWVKQRPGQGLEWIGEIDPSDSYVNYNQNFKGKATLTVDKSSSTAYIQ
LSSLTSEDSAVYFCARSPDYYGTSLAWFDYWGQGTLVTVST/ASTKGPSVFPLAPSSKSTSGGTAALGCLVKDYFPEPVTVS
WNSGALTSGVHTFPAVLQSSGLYSLSSVVTVPSSSLGTQTYICNVNHKPSDTKVDKKVEPKSCDKTHTCPPCPAPPVAGPSV
FLFPPKPKDTLMISRTPEVTCVVVDVKHEDPEVKFNWYVDGVEVHNAKTKPREEEYNSTYRVVSVLTVLHQDWLNGKEYKCK
VSNKALPAPIEKTISKAKGQPREPQVYTLPPSREEMTKNQVSLTCDVSGFYPSDIAVEWESDGQPENNYKTTPPVLDSDGSF
FLYSKLTVDKSRWEQGDVFSCSVMHEALHNHYTQKSLSLSPGK >XENP021861 GSK_314.8[ICOS]_H0L0 one-arm mAb Fc-only Heavy Chain (SEQ ID NO: 29976)
ERKSSDKTHTCPRCPAPPVAGPSVFLFPPKPKDTLMISRTPEVTCVVVDVKHEDPEVKFKWYVDGVEVHNAKTKPREEQYNS
TYRVVSVLTVLHQDWLNGKEYKCKVSNKALPAPIEKTISKAKGQPREPQVYTLPPSREQMTKNQVKLTCLVKGFYPSDIAVE
WESNGQPENNYKTTPPVLDSDGSFFLYSKLTVDKSRWQQGNVFSCSVMHEALHNHYTQKSLSLSPGK >XENP021861 GSK_314.8[ICOS]_H0L0 one-arm mAb Light Chain (SEQ ID NO: 29977)
DIVMTQAAPSVPVTPGESVSISCRSSKSFLHSNGNIYLYWFLQRPGQSPQLLIYRMSNLASGVPDRFSGSGSGTTFTLKISR
VEAEDVGVYYCMQHLEYPYTFGGGTKLEIK/RTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC >XENP021863 jMab-138[ICOS]_H0L0 one-arm mAb Fab-Fc Heavy Chain (SEQ ID NO: 29978)
EVQLVESGGGLVQPGGSLRLSCAASGFTFSSYDMHWVRQATGKGLEWVSAIGTAGDTYYPGSVKGRFTISRENAKNSLYLQM
NSLRAGDTAVYYCVRDNRKVTHEHYYYGMDVWGQGTTVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVMHEALHNHYTQKSLSLSPGK >XENP021863 jMab-138[ICOS]_H0L0 one-arm mAb Fc-only Heavy Chain (SEQ ID NO: 29979)
ERKSSDKTHTCPRCPAPPVAGPSVFLFPPKPKDTLMISRTPEVTCVVVDVKHEDPEVKFKWYVDGVEVHNAKTKPREEQYNS
TYRVVSVLTVLHQDWLNGKEYKCKVSNKALPAPIEKTISKAKGQPREPQVYTLPPSREQMTKNQVKLTCLVKGFYPSDIAVE
WESNGQPENNYKTTPPVLDSDGSFFLYSKLTVDKSRWQQGNVFSCSVMHEALHNHYTQKSLSLSPGK >XENP021863 jMab-138[ICOS]_H0L0 one-arm mAb Light Chain (SEQ ID NO: 29980)
EIVLTQSPGTLSLSPGERATLSCRASQNIRSSYLAWYQQKPGQAPGLLIYGASSRATGIPDRFSGSGSGTDFTLTISRLEPE
DFAVYYCQQFGSSPMCSFGQGTKLEIK/RTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGEC

Figure 74F

>XENP022349 WO2016059602[ICOS]_GSK_H0L0 one-arm mAb Fab-Fc Heavy Chain (SEQ ID NO: 29981)
QVQLVQSGAEVKKPGSSVKVSCKASGYTFTDYAMHWVRQAPGQGLEWMGLISIYSDHTNYNQKFQGRVTITADKSTS
TAYMELSSLRSEDTAVYYCGRNNYGNYGNYFDVWGQGTTVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK >XENP022349 WO2016059602[ICOS]_GSK_H0L0 one-arm mAb Fc-only Heavy Chain (SEQ ID NO: 29982)
ERKSSDKTHTCPRCPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK >XENP022349 WO2016059602[ICOS]_GSK_H0L0 one-arm mAb Light Chain (SEQ ID NO: 29983)
EIVLTQSPATLSLSPGERATLSCSASSSVSYMHWYQQKPGQAPRLLIYDTSKLASGIPARFSGSGSGTDYTLTISSL
EPEDFAVYYCFQGSGYPYTFGQGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

Figure 75A mAb-scFv backbone 1 (356E/358M allotype)

monomer 1 (Fab-scFv side) (SEQ ID NO: 29984)

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK monomer 2 (Fab side) (SEQ ID NO: 29985)

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK constant light chain (SEQ ID NO: 29986)

RTVAAPSVFIFPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Figure 75B mAb-scFv backbone 2

Fab-scFv-Hc - 356D/358L allotype (SEQ ID NO: 29987)

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

>mAb-scFv Fab-Hc - 356D/358L allotype (SEQ ID NO: 29988)

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSRDQLTKNQVKLTCLVKGFYPSDIAVEWESNGQPENNYKTTPPVLDSDGSFFLYSKLTVDKSRWQQGNVFSCS
VMHEALHNHYTQKSLSLSPGK mAb-scFv backbone 3

>mAb-scFv Fab-scFv-Hc - N297A (SEQ ID NO: 29989)

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYASTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

>mAb-scFv Fab-Hc - N297A (SEQ ID NO: 29990)

ASTKGPSVFPLAPSSKSTSGGTAALGCLVKDYFPEPVTVSWNSGALTSGVHTFPAVLQSSGLYSLSSVVTVPSSSLG
TQTYICNVNHRKPSDTKVDKKVEPKSSDKTHTCPPCPAPPVAGPSVFLFPPKPKDTLMISRTPEVTCVVVDVKHEDPE
VKFNWYVDGVEVHNAKTKPREEQYASTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK

Figure 75C mAb-scFv backbone 4

>mAb-scFv Fab-scFv-Hc - N297S (SEQ ID NO: 29991)

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYSSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

>mAb-scFv Fab-Hc - N297S (SEQ ID NO: 29992)

ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSSDKTHTCPPCPAPPVAGPSVFLFPPKPKDTLMISRTPEVTCVVVDVKHEDPE
VKFNWYVDGVEVHNAKTKPREEQYSSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VMHEALHNHYTQKSLSLSPGK mAb-scFv backbone 5 mAb-scFv Fab-scFv-IgG4-Hc (SEQ ID NO: 29993)

ASTKGPSVFPLAPCSRSTSESTAALGCLVKDYFPEPVTVSWNSGALTSGVHTFPAVLQSSGLYSLSSVVTVPSSSLG
TKTYTCNVDHKPSDTKVDKRVESKYGPPCPPCPAPEFLGGPSVFLFPPKPKDTLMISRTPEVTCVVVDVKQEDPEVQ
FNWYVDGVEVHNAKTKPREEEFNSTYRVVSVLTVLHQDWLNGKEYKCKVSNKGLPSSIEKTISKAKGQPREPQVYTL
PPSQEEMTKNQVSLTCDVSGFYPSDIAVEWESDGQPENNYKTTPPVLDSDGSFFLYSKLTVDKSRWEEGDVFSCSVM
HEALHNHYTQKSLSLSLGK

>mAb-scFv Fab-IgG4-Hc (SEQ ID NO: 29994)

ASTKGPSVFPLAPCSRSTSESTAALGCLVKDYFPEPVTVSWNSGALTSGVHTFPAVLQSSGLYSLSSVVTVPSSSLG
TKTYTCNVDHKPSDTKVDKRVESKYGPPCPPCPAPEFLGGPSVFLFPPKPKDTLMISRTPEVTCVVVDVKQEDPEVQ
FNWYVDGVEVHNAKTKPREEQFNSTYRVVSVLTVLHQDWLNGKEYKCKVSNKGLPSSIEKTISKAKGQPREPQVYTL
PPSQEQMTKNQVKLTCLVKGFYPSDIAVEWESNGQPENNYKTTPPVLDSDGSFFLYSKLTVDKSRWQEGNVFSCSVM
HEALHNHYTQKSLSLSLGK

Figure 75D mAb-scFv backbone 6

>mAb-scFv Fab-scFv-IgG2-Hc - without S267K (SEQ ID NO: 29995)

ASTKGPSVFPLAPCSRSTSESTAALGCLVKDYFPEPVTVSWNSGALTSGVHTFPAVLQSSGLYSLSSVVTVPSSNFG
TQTYTCNVDHKPSDTKVDKTVERKCCVECPPCPAPPVAGPSVFLFPPKPKDTLMISRTPEVTCVVVDVSHEDPEVQF
NWYVDGVEVHNAKTKPREEEFNSTFRVVSVLTVVHQDWLNGKEYKCKVSNKGLPAPIEKTISKTKGQPREPQVYTLP
PSREEMTKNQVSLTCDVSGFYPSDIAVEWESDGQPENNYKTTPPMLDSDGSFFLYSKLTVDKSRWEQGDVFSCSVMH
EALHNHYTQKSLSLSPGK

>mAb-scFv Fab-IgG2-Hc - without S267K (SEQ ID NO: 29996)

ASTKGPSVFPLAPCSRSTSESTAALGCLVKDYFPEPVTVSWNSGALTSGVHTFPAVLQSSGLYSLSSVVTVPSSNFG
TQTYTCNVDHKPSDTKVDKTVERKCSVECPPCPAPPVAGPSVFLFPPKPKDTLMISRTPEVTCVVVDVSHEDPEVQF
NWYVDGVEVHNAKTKPREEQFNSTFRVVSVLTVVHQDWLNGKEYKCKVSNKGLPAPIEKTISKTKGQPREPQVYTLP
PSREQMTKNQVKLTCLVKGFYPSDIAVEWESNGQPENNYKTTPPMLDSDGSFFLYSKLTVDKSRWQQGNVFSCSVMH
EALHNHYTQKSLSLSPGK mAb-scFv backbone 7

>mAb-scFv Fab-scFv-IgG2-Hc - with S267K (SEQ ID NO: 29997)

ASTKGPSVFPLAPCSRSTSESTAALGCLVKDYFPEPVTVSWNSGALTSGVHTFPAVLQSSGLYSLSSVVTVPSSNFG
TQTYTCNVDHKPSDTKVDKTVERKCCVECPPCPAPPVAGPSVFLFPPKPKDTLMISRTPEVTCVVVDVKHEDPEVQF
NWYVDGVEVHNAKTKPREEEFNSTFRVVSVLTVVHQDWLNGKEYKCKVSNKGLPAPIEKTISKTKGQPREPQVYTLP
PSREEMTKNQVSLTCDVSGFYPSDIAVEWESDGQPENNYKTTPPMLDSDGSFFLYSKLTVDKSRWEQGDVFSCSVMH
EALHNHYTQKSLSLSPGK

>mAb-scFv Fab-IgG2-Hc - with S267K (SEQ ID NO: 29998)

ASTKGPSVFPLAPCSRSTSESTAALGCLVKDYFPEPVTVSWNSGALTSGVHTFPAVLQSSGLYSLSSVVTVPSSNFG
TQTYTCNVDHKPSDTKVDKTVERKCSVECPPCPAPPVAGPSVFLFPPKPKDTLMISRTPEVTCVVVDVKHEDPEVQF
NWYVDGVEVHNAKTKPREEQFNSTFRVVSVLTVVHQDWLNGKEYKCKVSNKGLPAPIEKTISKTKGQPREPQVYTLP
PSREQMTKNQVKLTCLVKGFYPSDIAVEWESNGQPENNYKTTPPMLDSDGSFFLYSKLTVDKSRWQQGNVFSCSVMH
EALHNHYTQKSLSLSPGK

Figure 76A additional anti-PD-1 sequences

Merck Pembrolizumab VH (SEQ ID NO: 29999)

QVQLVQSGVEVKKPGASVKVSCKASGYTFTNYYMYWVRQAPGQGLEWMGGINPSNGGTNFNEKFKNRVTLTTDSST
TTAYMELKSLQFDDTAVYYCARRDYRFDMGFDYWGQGTTVTVSS

Merck Pembrolizumab VL (SEQ ID NO: 30000)

EIVLTQSPATLSLSPGERATLSCRASKGVSTSGYSYLHWYQQKPGQAPRLLIYLASYLESGVPARFSGSGSGTDFTLTISS
LEPEDFAVYYCQHSRDLPLTFGGGTKVEIK

BMS nivolumab VH (SEQ ID NO: 30001)

QVQLVESGGGVVQPGRSLRLDCKASGITFSNSGMHWVRQAPGKGLEWVAVIWYDGSKRYYADSVKGRFTISRDNSKN
TLFLQMNSLRAEDTAVYYCATNDDYWGQGTLVTVSS

BMS nivolumab VL (SEQ ID NO: 30002)

EIVLTQSPATLSLSPGERATLSCRASQSVSSYLAWYQQKPGQAPRLLIYDASNRATGIPARFSGSGSGTDFTLTISSLEPED
FAVYYCQQSSNWPRTFGQGTKVEIK

Teva pidilizumab VH (SEQ ID NO: 30003)

QVQLVQSGSELKKPGASVKISCKASGYTFTNYGMNWVRQAPGQGLQWMGWINTDSGESTYAEEFKGRFVFSLDTSVN
TAYLQITSLTAEDTGMYFCVRVGYDALDYWGQGTLVTVSS

Teva pidilizumab VL (SEQ ID NO: 30004)

EIVLTQSPSSLSASVGDRVTITCSARSSVSYMHWFQQKPGKAPKLWIYRTSNLASGVPSRFSGSGSGTSYCLTINSLQPED
FATYYCQQRSSFPLTFGGGTKLEIK

Pfizer MK-3475 VH (SEQ ID NO: 30005)

QVQLVQSGVEVKKPGASVKVSCKASGYTFTNYYMYWVRQAPGQGLEWMGGINPSNGGTNFNEKFKNRVTLTTDSST
TTAYMELKSLQFDDTAVYYCARRDYRFDMGFDYWGQGTTVTVSS

Pfizer MK-3475 VL (SEQ ID NO: 30006)

EIVLTQSPATLSLSPGERATLSCRASKGVSTSGYSYLHWYQQKPGQAPRLLIYLASYLESGVPARFSGSGSGTDFTLTISS
LEPEDFAVYYCQHSRDLPLTFGGGTKVEIK

Novartis/Dana Farber BAP049 clone E VH (SEQ ID NO: 30007)

EVQLVQSGAEVKKPGESLRISCKGSGYTFTTYWMHWVRQATGQGLEWMGNIYPGTGGSNFDEKFKNRVTITADKSTS
TAYMELSSLRSEDTAVYYCTRWTTGTGAYWGQGTTVTVSS

Novartis/Dana Farber BAP049 clone E VL (SEQ ID NO: 30008)

EIVLTQSPATLSLSPGERATLSCKSSQSLLDSGNQKNFLTWYQQKPGQAPRLLIYWASTRESGVPSRFSGSGSGTDFTFTI
SSLEAEDAATYYCQNDYSYPYTFGQGTKVEIK

Novartis/Dana Farber BAP049 clone B VH (SEQ ID NO: 30009)

EVQLVQSGAEVKKPGESLRISCKGSGYTFTTYWMHWVRQATGQGLEWMGNIYPGTGGSNFDEKFKNRVTITADKSTS
TAYMELSSLRSEDTAVYYCTRWTTGTGAYWGQGTTVTVSS

Novartis/Dana Farber BAP049 clone B VL (SEQ ID NO: 30010)

EIVLTQSPATLSLSPGERATLSCKSSQSLLDSGNQKNFLTWYQQKPGKAPKLLIYWASTRESGVPSRFSGSGSGTDFTFTI
SSLQPEDIATYYCQNDYSYPYTFGQGTKVEIK

Figure 76B

Regeneron H7798N VH (SEQ ID NO: 30011)

EVQLLESGGVLVQPGGSLRLSCAASGFTFSNFGMTWVRQAPGKGLEWVSGISGGGRDTYFADSVKGRFTISRDNSKNT
LYLQMNSLKGEDTAVYYCVKWGNIYFDYWGQGTLVTVSS

Regeneron H7798N VH (SEQ ID NO: 30012)

DIQMTQSPSSLSASVGDSITITCRASLSINTFLNWYQQKPGKAPNLLIYAASSLHGGVPSRFSGSGSGTDFTLTIRTLQPED
FATYYCQQSSNTPFTFGPGTVVDFR

Medimmune h1H3 Var 6 VH (SEQ ID NO: 30013)

EVQLVESGGGLVQPGGSLRLSCAASGFTFSDYGMHWVRQAPGKGLEWVAYISSGSYTIYYADSVKGRFTISRDNAKNT
LYLQMSSLRAEDTAVYYCARRGYGSFYEYYFDYWGQGTTVTVSS

Medimmune h1H3 Var 6 VL (SEQ ID NO: 30014)

QIVLTQSPATLSLSPGERATLSCSASSSVSYMYWYQQKPGQAPRLLIYLTSNRATGIPARFSGSGSGTDYTLTISSLEPEDF
AVYYCQQWSSNPFTFGQGTKLEIK

Tesarao TSR-042/APE2058 VH (SEQ ID NO: 30015)

EVQLLESGGGLVQPGGSLRLSCAASGFTFSSYDMSWVRQAPGKGLEWVSTISGGGSYTYYQDSVKGRFTISRDNSKNTL
YLQMNSLRAEDTAVYYCASPYYAMDYWGQGTTVTVSS

Tesarao TSR-042/APE2058 VL (SEQ ID NO: 30016)

DIQLTQSPSFLSAYVGDRVTITCKASQDVGTAVAWYQQKPGKAPKLLIYWASTLHTGVPSRFSGSGSGTEFTLTISSLQP
EDFATYYCQHYSSYPWTFGQGTKLEIK

Incyte Camrelizumab VH (SEQ ID NO: 30017)

EVQLVESGGGLVQPGGSLRLSCAASGFTFSSYMMSWVRQAPGKGLEWVATISGGGANTYYPDSVKGRFTISRDNAKNS
LYLQMNSLRAEDTAVYYCARQLYYFDYWGQGTTVTVSS

Incyte Camrelizumab VL (SEQ ID NO: 30018)

DIQMTQSPSSLSASVGDRVTITCLASQTIGTWLTWYQQKPGKAPKLLIYTATSLADGVPSRFSGSGSGTDFTLTISSLQPE
DFATYYCQQVYSIPWTFGGGTKVEIK

Beigene 317-4B6 VH (SEQ ID NO: 30019)

QVQLQESGPGLVKPSETLSLTCTVSGFSLTSYGVHWIRQPPGKGLEWIGVIYADGSTNYNPSLKSRVTISKDTSKNQVSL
KLSSVTAADTAVYYCARAYGNYWYIDVWGQGTTVTVSS

Beigene 317-4B6 VL (SEQ ID NO: 30020)

DIVMTQSPDSLAVSLGERATINCKSSESVSNDVAWYQQKPGQPPKLLINYAFHRFTGVPDRFSGSGYGTDFTLTISSLQA
EDVAVYYCHQAYSSPYTFGQGTKLEIK

Beigene 326-4A3 VH (SEQ ID NO: 30021)

QVQLVQSGSELKKPGASVKVSCKASGYTFTNYGMNWVRQAPGQGLKWMGWINNNNAEPTYAQDFRGRFVFSLDTSA
STAYLQISSLKTEDTAVYYCARDVMDYWGQGTLVTVSS

Beigene 326-4A3 VL (SEQ ID NO: 30022)

DIVLTQSPASLAVSPGQRATITCRASESVDNYGYSFMHWYQQKPGQPPKLLIYRASNLESGVPARFSGSGSGTDFTLTIN
PVEAEDTANYYCQQSKEYPTFGGGTKVEIK

Figure 76C

Macrogenics mAb 7 (1.2) VH (SEQ ID NO: 30023)

QVQLVQSGAEVKKPGASVKVSCKASGYSFTSYWMNWVRQAPGQGLEWIGVIHPSDSETWLDQKFKDRVTITVDKSTS
TAYMELSSLRSEDTAVYYCAREHYGTSPFAYWGQGTLVTVSS

Macrogenics mAb 7 (1.2) VL (SEQ ID NO: 30024)

EIVLTQSPATLSLSPGERATLSCRASESVDNYGMSFMNWFQQKPGQPPKLLIHAASNQGSGVPSRFSGSGSGTDFTLTISS
LEPEDFAVYFCQQSKEVPYTFGGGTKVEIK

Junmeng Clone 38 VH (SEQ ID NO: 30025)

QGQLVQSGAEVKKPGASVKVSCKASGYTFTDYEMHWVRQAPIHGLEWIGVIESETGGTAYNQKFKGRVTITADKSTST
AYMELSSLRSEDTAVYYCAREGITTVATTYYWYFDVWGQGTTVTVSS

Junmeng Clone 38 VL (SEQ ID NO: 30026)

DVVMTQSPLSLPVTLGQPASISCRSSQSIVHSNGNTYLEWYLQKPGQSPQLLIYKVSNRFSGVPDRFSGSGSGTDFTLKIS
RVEAEDVGVYYCFQGSHVPLTFGQGTKLEIK

Junmeng Clone 39 VH (SEQ ID NO: 30027)

QGQLVQSGAEVKKPGASVKVSCKASGYTFTDYEMHWVRQAPGQGLEWMGVIESETGGTAYNQKFKGRAKITADKST
STAYMELSSLRSEDTAVYYCTREGITTVATTYYWYFDVWGQGTTVTVSS

Junmeng Clone 39 VL (SEQ ID NO: 30028)

DVVMTQSPLSLPVTLGQPASISCRSSQSIVHSNGNTYLEWYLQKPGQSPQLLIYKVSNRFSGVPDRFSGSGSGTDFTLKIS
RVEAEDVGVYYCFQGSHVPLTFGQGTKLEIK

Junmeng Clone 41 VH (SEQ ID NO: 30029)

QGQLVQSGAEVKKPGASVKVSCKASGYTFTDYEMHWVRQAPGQGLEWMGVIESETGGTAYNQKFQGRVTLTADKSS
STAYMELSSLRSEDTAVYYCTREGITTVATTYYWYFDVWGQGTLVTVSS

Junmeng Clone 41 VL (SEQ ID NO: 30030)

DVVMTQSPLSLPVTLGQPASISCRSSQSIVHSNGNTYLEWYLQKPGQSPQLLIYKVSNRFSGVPDRFSGSGSGTDFTLKIS
RVEAEDVGVYYCFQGSHVPLTFGQGTKLEIK

Junmeng Clone 48 VH (SEQ ID NO: 30031)

QGQLVQSGAEVKKPGASVKVSCKASGYTFTDYEMHWVRQAPGQGLEWMGVIESETGGTAYNQKFKGRAKITADKST
STAYMELSSLRSEDTAVYYCTREGITTVATTYYWYFDVWGQGTTVTVSS

Junmeng Clone 48 VL (SEQ ID NO: 30032)

DVVMTQSPLSLPVTLGQPASISCRSSQSIVHSNGNTYLEWYLQKPGQSPRLLIYKVSNRFSGVPDRFSGSGSGTDFTLKIS
RVEAEDVGVYYCFQGSHVPLTFGQGTKLEIK

Wyeth PD1-17 VH (SEQ ID NO: 30033)

QVQLQESGPGVVKPSGTLSLTCAISGGSIGSGGSIRSTRWWSWVRQSPGKGLEWIGEIYHSGSTNYNPSLKSRVTISLDKS
RNHFSLRLNSVTAADTAVYYCARQDYGDSGDWYFDLWGKGTMVTVSS

Wyeth PD1-17 VL (SEQ ID NO: 30034)

NFMLTQPHSVSESPGKTVTISCTRSSGSIASNSVQWYQQRPGSSPTTVIYEDNQRPSGVPDRFSGSIDSSSNSASLTVSGLK
TEDEADYYCQSSDSSAVVFGSGTKLTVL

Figure 76D

Wyeth PD1-28 VH (SEQ ID NO: 30035)

EVQLVQSGAEVKKPGASVKVSCKASGYRFTSYGISWVRQAPGQGLEWMGWISAYNGNTNYAQKLQGRVTMTTDTST
NTAYMELRSLRSDDTAVYYCARDADYSSGSGYWGQGTLVTVSS

Wyeth PD1-28 VL (SEQ ID NO: 30036)

SYELTQPPSVSVSPGQTARITCSGDALPKQYAYWYQQKPGQAPVMVIYKDTERPSGIPERFSGSSSGTKVTLTISGVQAE
DEADYYCQSADNSITYRVFGGGTKVTVL

Wyeth PD1-33 VH (SEQ ID NO: 30037)

QVQLVQSGAEVKKPGASVRVSCKASGYTLTSYYIHWVRQAPGQGLEWMGIINPRGATISYAQKFQGRVTMTRDTSTST
VYMELRNLKSEDTALYYCATAGIYGFDFDYWGRGTLVTVSS

Wyeth PD1-33 VL (SEQ ID NO: 30038)

QSALTQPASVSGSPGQSITISCTGTSNDVGGYNYVSWYQHHPGKAPKLIIYDVTNRPSGVSDRFSGSKSGNTASLTISGLL
AEDEGDYYCSSYTIVTNPEVLFGGGTKLTV

Wyeth PD1-35 VH (SEQ ID NO: 30039)

QVQLQESGPGLVKPSQTLSLTCTVSGGSISSGAYYWSWIRQHPGKGLEWIGYIYYNGNTYYNPSLRSLVTISVDASKNQF
SLKLSSVTAADTAVYYCARASDYVWGGYRYMDAFDIWGRGTLJTVSS

Wyeth PD1-35 VL (SEQ ID NO: 30040)

QSVLTQPPSASGTPGQRVTISCSGSNSNIGSNSVNWYQQLPGTAPKLLIYGNNQRPSGVPDRFSGSKSGTSASLAISGLQS
ENEADYYCAAWDDSLNGPVFGRGTKVTVL

Wyeth LOPD180 VH (SEQ ID NO: 30041)

QVQLQESGPGLVKPSQTLSLTCTVSGGSISSGAYYWSWIRQHPGKGLEWIGYIYYNGNTYYNPSLRSRVTISVDTSKNQF
SLKLSSVTAADTAVYYCVRASDYVWGGYHYFDAFDLWGRGTLVTVSS

Wyeth LOPD180 VL (SEQ ID NO: 30042)

QSVLTQPPSASGTPGQRVTISCSGSNSNIGSNSVNWYQQLPGTAPKLLIYGNNQRPSGVPDRFSGSKSGTSASLAISGLQS
EDEADYYCAAWDDSLNGPVFGGGTKVTVL

UCB Ab948 VH (SEQ ID NO: 30043)

EVQLQESGPGLVKPSQTLSLTCTVTGYSITSDYAWNWIRQPPGKKLEWMGYINYSGSTSYNPSLKSRVTISRDTSKNQFS
LKLSSVTAADTAVYYCARWIGSSAWYFDVWGQGTLVTVSS

UCB Ab948 VL (SEQ ID NO: 30044)

DVLMTQTPLSLSVTPGQPASISCRSGQNIVHSNGNTYLEWYLQKPGQSPKLLIYKVSNRFFGVPDRISGSGSGTDFTLKIS
RVEAEDVGVYFCFQGSHVPFTFGQGTKLEIK

Dana-Farber EH-12.2h7 VH (SEQ ID NO: 30045)

QVQLVQSGHEVKQPGASVKMSCKASGYSFTSSWIHWVRQAPGQGLEWIGYIYPSTGFTEYNQKFKDRATLTADKSTST
AYMELSSLRSEDTAVYYCARWRDSSGYHAMDYWGQGTLVTVSS

Dana-Farber EH-12.2h7 VH (SEQ ID NO: 30046)

EIVLTQSPATLSLSPGQRLTISCRASQSVSTSGYSYMHWYQQKPDQSPKLLIKFGSNLESGIPARFSGSGSGTDFTLTISSLE
PEDFATYYCQHSWEIPYTFGQGTKLEIK

Figure 76E

Sorrento RG1H10 VH (SEQ ID NO: 30047)

QVQLVQSGSELKKPGASVKISCKASGYIFSDNGVNWVRQAPGQGLEWMGWINTKIGNPTYAQGFTGRFVFSLDTSISTT
YLQISSLQAGDTAVYYCAREHDYYYGMDVWGQGTTVTVSS

Sorrento RG1H10 VL (SEQ ID NO: 30048)

QSALTQPPSASGSPGQSVTISCTGTSSDVGGYNYVSWYQHHPGKAPKLMIYEVSKRPSGVPDRFSGSKSAITASLTISGLL
TEDEADYYCSAWDDSLNADVFGGGTKVTVL

Sorrento RG1H10-H2A-22-1S VH (SEQ ID NO: 30049)

QVQLVQSGSELKKPGASVKISCKASGYIFSDNGVNWVRQAPGQGLEWMGWINTKDGNPTYAQGFTGRFVFSLDTSIST
TYLQISSLQAGDTAVYYCAREHDYYYGMDVWGQGTTVTVSS

Sorrento RG1H10-H2A-22-1S VL (SEQ ID NO: 30050)

QSALTQPPSASGSPGQSVTISCTGTSSDVGGYNYVSWYQHHPGKAPKLMIYEVSKRPSGVPDRFSGSKSAITASLTISGLL
TEDEADYYCSAWDDSLNADVFGGGTKVTVL

Sorrento RG1H10-H2A-27-2S VH (SEQ ID NO: 30051)

QVQLVQSGSELKKPGASVKISCKASGYIFSDNGVNWVRQAPGQGLEWMGWINTKTGNPTYAQGFTGRFVFSLDTSIST
TYLQISSLQAGDTAVYYCAREHDYYYGMDVWGQGTTVTVSS

Sorrento RG1H10-H2A-27-2S VL (SEQ ID NO: 30052)

QSALTQPPSASGSPGQSVTISCTGTSSDVGGYNYVSWYQHHPGKAPKLMIYEVSKRPSGVPDRFSGSKSAITASLTISGLL
TEDEADYYCSAWDDSLNADVFGGGTKVTVL

Sorrento RG1H10-3C VH (SEQ ID NO: 30053)

QVQLVQSGSELKKPGASVKISCKASGYTFSDNGVNWVRQAPGQGLEWMGWINTKDGNPTYAQGFTGRFVFSLDTSIST
TYLQISSLQAGDTAVYYCAREHDYYYGMDVWGQGTTVTVSS

Sorrento RG1H10-3C VL (SEQ ID NO: 30054)

QSALTQPPSASGSPGQSVTISCTGTSSDVGGYNYVSWYQHHPGKAPKLMIYEVSKRPSGVPDRFSGSKSAITASLTISGLL
TEDEADYYCSAWDDSLNADVFGGGTKVTVL

Sorrento RG1H10-16C VH (SEQ ID NO: 30055)

QVQLVQSGSELKKPGASVKISCKASGYTFSDNGVNWVRQAPGQGLEWMGWINTKTGNPTYAQGFTGRFVFSLDTSIST
TYLQISSLQAGDTAVYYCAREHDYYYGMDVWGQGTTVTVS

Sorrento RG1H10-16C VL (SEQ ID NO: 30056)

QSALTQPPSASGSPGQSVTISCTGTSSDVGGYNYVSWYQHHPGKAPKLMIYEVSKRPSGVPDRFSGSKSAITASLTISGLL
TEDEADYYCSAWDDSLNADVFGGGTKVTVL

Sorrento RG1H10-17C VH (SEQ ID NO: 30057)

QVQLVQSGSELKKPGASVKISCKASGYKFSDNGVNWVRQAPGQGLEWMGWINTKSGNPTYAQGFTGRFVFSLDTSIST
TYLQISSLQAGDTAVYYCAREHDYYYGMDVWGQGTTVTVSS

Sorrento RG1H10-17C VL (SEQ ID NO: 30058)

QSALTQPPSASGSPGQSVTISCTGTSSDVGGYNYVSWYQHHPGKAPKLMIYEVSKRPSGVPDRFSGSKSAITASLTISGLL
TEDEADYYCSAWDDSLNADVFGGGTKVTVL

Figure 76F

Sorrento RG1H10-19C VH (SEQ ID NO: 30059)

QVQLVQSGSELKKPGASVKISCKASGYKFSDNGVNWVRQAPGQGLEWMGWINTKTGNPTYAQGFTGRFVFSLDTSIST
TYLQISSLQAGDTAVYYCAREHDYYYGMDVWGQGTTVTVSS

Sorrento RG1H10-19C VL (SEQ ID NO: 30060)

QSALTQPPSASGSPGQSVTISCTGTSSDVGGYNYVSWYQHHPGKAPKLMIYEVSKRPSGVPDRFSGSKSAITASLTISGLL
TEDEADYYCSAWDDSLNADVFGGGTKVTVL

Sorrento RG1H10-21C VH (SEQ ID NO: 30061)

QVQLVQSGSELKKPGASVKISCKASGYTFSDNGVNWVRQAPGQGLEWMGWINTKSGNPTYAQGFTGRFVFSLDTSIST
TYLQISSLQAGDTAVYYCAREHDYYYGMDVWGQGTTVTVSS

Sorrento RG1H10-21C VL (SEQ ID NO: 30062)

QSALTQPPSASGSPGQSVTISCTGTSSDVGGYNYVSWYQHHPGKAPKLMIYEVSKRPSGVPDRFSGSKSAITASLTISGLL
TEDEADYYCSAWDDSLNADVFGGGTKVTVL

Sorrento RG1H10-23C2 VH (SEQ ID NO: 30063)

QVQLVQSGSELKKPGASVKISCKASGYKFSDNGVNWVRQAPGQGLEWMGWINTKDGNPTYAQGFTGRFVFSLDTSIST
TYLQISSLQAGDTAVYYCAREHDYYYGMDVWGQGTTVTVSS

Sorrento RG1H10-23C2 VL (SEQ ID NO: 30064)

QSALTQPPSASGSPGQSVTISCTGTSSDVGGYNYVSWYQHHPGKAPKLMIYEVSKRPSGVPDRFSGSKSAITASLTISGLL
TEDEADYYCSAWDDSLNADVFGGGTKVTVL

Rinat mAb 7 VH (SEQ ID NO: 30065)

QVQLVQSGAEVKKPGASVKVSCKASGYTFTSYWINWVRQAPGQGLEWMGNIYPGSSLTNYNEKFKNRVTMTRDTSTS
TVYMELSSLRSEDTAVYYCARLSTGTFAYWGQGTLVTVSS

Rinat mAb 7 VL (SEQ ID NO: 30066)

DIVMTQSPDSLAVSLGERATINCKSSQSLWDSGNQKNFLTWYQQKPGQPPKLLIYWTSYRESGVPDRFSGSGSGTDFTL
TISSLQAEDVAVYYCQNDYFYPHTFGGGTKVEIK

Celgene PD1AB-6 VH (SEQ ID NO: 30067)

EVQLVQSGAEVKKPGATVKISCKASGFNIKDTYMHWVQQAPGKGLEWMGRIDPANGDRKYDPKFQGRVTITADTSTD
TAYMELSSLRSEDTAVYYCARSGPVYYYGSSYVMDYWGQGTTVTVSS

Celgene PD1AB-6 VL (SEQ ID NO: 30068)

DIVMTQSPDSLAVSLGERATINCKSGQSVLYSSNQKNFLAWYQQKPGQPPKLLIYWASTRESGVPDRFSGSGSGTDFTL
TISSLQAEDVAVYYCHQYLYSWTFGQGTKLEIK

Figure 77A additional ICOS sequences

GSK 88.2 VH (SEQ ID NO: 30069)

QVQLQQPGAELVRPGASVKLSCKASGYSFTSYWINWVKQRPGQGLEWIGNIYPSDSYTNYNQMFKDKATLTVDKSSN
TAYMQLTSPTSEDSAVYYCTRWNLSYYFDNNYYLDYWGQGTTLTVSS

GSK 88.2 VL (SEQ ID NO: 30070)

DIVMTQAAPSVPVTPGESVSISCRSSKSLLHSNGNTYLYWFLQRPGQSPQLLIYRMSNLASGVPDRFSGSGSGTAFTLRIS
RVEAEDVGVYYCMQHLEYPWTFGGGTKLEIK

GSK 314.8 VH (SEQ ID NO: 30071)

QVQLQQPGTELMKPGASVKLSCKASGYTFTTYWMHWVKQRPGQGLEWIGEIDPSDSYVNYNQNFKGKATLTVDKSSS
TAYIQLSSLTSEDSAVYFCARSPDYYGTSLAWFDYWGQGTLVTVST

GSK 314.8 VL (SEQ ID NO: 30072)

DIVMTQAAPSVPVTPGESVSISCRSSKSPLHSNGNIYLYWFLQRPGQSPQLLIYRMSNLASGVPDRFSGSGSGTTFTLKISR
VEAEDVGVYYCMQHLEYPYTFGGGTKLEIK

GSK H2L5 VH (SEQ ID NO: 30073)

QVQLVQSGAEVKKPGSSVKVSCKASGYTFTDYAMHWVRQAPGQGLEWMGLISIYSDHTNYNQKFQGRVTITADKSTS
TAYMELSSLRSEDTAVYYCGRNNYGNYGWYFDVWGQGTTVTVSS

GSK H2L5 VL (SEQ ID NO: 30074)

EIVLTQSPATLSLSPGERATLSCSASSSVSYMHWYQQKPGQAPRLLIYDTSKLASGIPARFSGSGSGTDYTLTISSLEPEDF
AVYYCFQGSGYPYTFGQGTKLEIK

Jounce 37A10S713 VH (SEQ ID NO: 30075)

EVQLVESGGGLVQPGGSLRLSCAASGFTFSDYWMDWVRQAPGKGLVWVSNIDEDGSITEYSPFVKGRFTISRDNAKNT
LYLQMNSLRAEDTAVYYCTRWGRFGFDSWGQGTLVTVSS

Jounce 37A10S713 VL (SEQ ID NO: 30076)

DIVMTQSPDSLAVSLGERATINCKSSQSLLSGSFNYLTWYQQKPGQPPKLLIFYASTRHTGVPDRFSGSGSGTDFTLTISS
LQAEDVAVYYCHHHYNAPPTFGPGTKVDIK

Japan Tobacco Jmab-136 VH (SEQ ID NO: 30077)

QVQLVQSGAEVKKPGASVKVSCKASGYTFTGYYMHWVRQAPGQGLEWMGWINPHSGGTNYAQKFQGRVTMTRDTS
ISTAYMELSRLRSDDTAVYYCARTYYYDSSGYYHDAFDIWGQGTMVTVSS

Japan Tobacco Jmab-136 VL (SEQ ID NO: 30078)

DIQMTQSPSSVSASVGDRVTITCRASQGISRLLAWYQQKPGKAPKLLIYVASSLQSGVPSRFSGSGSGTDFTLTISSLQPE
DFATYYCQQANSFPWTFGQGTKVEIK

Japan Tobacco Jmab-138 VH (SEQ ID NO: 30079)

EVQLVESGGGLVQPGGSLRLSCAASGFTFSSYDMHWVRQATGKGLEWVSAIGTAGDTYYPGSVKGRFTISRENAKNSL
YLQMNSLRAGDTAVYYCVRDNRKVTHEHYYYYGMDVWGQGTTVTVSS

Japan Tobacco Jmab-138 VL (SEQ ID NO: 30080)

EIVLTQSPGTLSLSPGERATLSCRASQNIRSSYLAWYQQKPGQAPGLLIYGASSRATGIPDRFSGSGSGTDFTLTISRLEPE
DFAVYYCQQFGSSPMCSFGQGTKLEIK

Figure 77B

Japan Tobacco Jmab-139 VH (SEQ ID NO: 30081)

EVQLVESGGGLVQPGGSLRLSCAASGFTFSSYDMHWVRQATGKGLEWVSAIGTAGDTYYPGSVKGRFTISRENAKNSL
YLQMNSLRAGDTAVYYCVRDKRTVTHEHYYYYGMDVWGQGTTVTVSS

Japan Tobacco Jmab-139 VL (SEQ ID NO: 30082)

EIVLTQSPGTLSLSPGERATLSCRASQSISSSSLAWYQQKPGQAPGLLIFGASSRATGIPDRFSGSGSGTDFTLTISRLEPED
FAVYYCQQFGSSPMCSFGQGTKLEIK

Figure 78A additional PD-L1 sequences

AstraZeneca/Celgene/MedImmune 2.14H9 OPT VH (SEQ ID NO: 30083)

EVQLVESGGGLVQPGGSLRLSCAASGFTFSRYWMSWVRQAPGKGLEWVANIKQDGSEKYYVDSVKGRFTISRDNAKN
SLYLQMNSLRAEDTAVYYCAREGGWFGELAFDYWGQGTLVTVSS

AstraZeneca/Celgene/MedImmune 2.14H9 OPT VL (SEQ ID NO: 30084)

EIVLTQSPGTLSLSPGERATLSCRASQRVSSSYLAWYQQKPGQAPRLLIYDASSRATGIPDRFSGSGSGTDFTLTISRLEPE
DFAVYYCQQYGSLPWTFGQGTKVEIK

Genentech atezolizumab VH (SEQ ID NO: 30085)

EVQLVESGGGLVQPGGSLRLSCAASGFTFSDSWIHWVRQAPGKGLEWVAWISPYGGSTYYADSVKGRFTISADTSKNT
AYLQMNSLRAEDTAVYYCARRHWPGGFDYWGQGTLVTVSA

Genentech atezolizumab VL (SEQ ID NO: 30086)

DIQMTQSPSSLSASVGDRVTITCRASQDVSTAVAWYQQKPGKAPKLLIYSASFLYSGVPSRFSGSGSGTDFTLTISSLQPE
DFATYYCQQYLYHPATFGQGTKVEIKR

Merck/Pfizer avelumab VH (SEQ ID NO: 30087)

EVQLLESGGGLVQPGGSLRLSCAASGFTFSSYIMMWVRQAPGKGLEWVSSIYPSGGITFYADTVKGRFTISRDNSKNTL
YLQMNSLRAEDTAVYYCARIKLGTVTTVDYWGQGTLVTVSS

Merck/Pfizer avelumab VL (SEQ ID NO: 30088)

QSALTQPASVSGSPGQSITISCTGTSSDVGGYNYVSWYQQHPGKAPKLMIYDVSNRPSGVSNRFSGSKSGNTASLTISGL
QAEDEADYYCSSYTSSSTRVFGTGTKVTVL

Medarex 12A4 VH (SEQ ID NO: 30089)

QVQLVQSGAEVKKPGSSVKVSCKTSGDTFSTYAISWVRQAPGQGLEWMGGIIPIFGKAHYAQKFQGRVTITADESTSTA
YMELSSLRSEDTAVYFCARKFHFVSGSPFGMDVWGQGTTVTVSS

Medarex 12A4 VL (SEQ ID NO: 30090)

EIVLTQSPATLSLSPGERATLSCRASQSVSSYLAWYQQKPGQAPRLLIYDASNRATGIPARFSGSGSGTDFTLTISSLEPED
FAVYYCQQRSNWPTFGQGTKVEIK

Medarex 3G10 VH (SEQ ID NO: 30091)

QVQLVQSGAEVKKPGASVKVSCKASGYTFTDYGFSWVRQAPGQGLEWMGWITAYNGNTNYAQKLQGRVTMTTDTS
TSTVYMELRSLRSDDTAVYYCARDYFGMDVWGQGTTVTVSS

Medarex 3G10 VL (SEQ ID NO: 30092)

EIVLTQSPATLSLSPGERATLSCRASQSVSSYLVWYQQKPGQAPRLLIYDASNRATGIPARFSGSGSGTDFTLTISSLEPED
FAVYYCQQRSNWPRTFGQGTKVEIK

Medarex 10A5 VH (SEQ ID NO: 30093)

QVQLVQSGAEVKKPGASVKVSCKASGYTFTSYDVHWVRQAPGQRLEWMGWLHADTGITKFSQKFQGRVTITRDTSAS
TAYMELSSLRSEDTAVYYCARERIQLWFDYWGQGTLVTVSS

Medarex 10A5 VL (SEQ ID NO: 30094)

DIQMTQSPSSLSASVGDRVTITCRASQGISSWLAWYQQKPEKAPKSLIYAASSLQSGVPSRFSGSGSGTDFTLTISSLQPED
FATYYCQQYNSYPYTFGQGTKLEIK

Figure 78B

Amplimmune/GSK/MedImmune h3D10 Var1 VH (SEQ ID NO: 30095)

QVQLVQSGAEVKKPGASVKVSCKASGYTFPDYYMNWVRQAPGQGLEWMGDIDPNYGGTNYAQKFQGRVTMTRDTS
ISTAYMELSRLRSDDTAVYYCARGALTDWGQGTMVTVSS

Amplimmune/GSK/MedImmune h3D10 Var1 VL (SEQ ID NO: 30096)

EIVLTQSPATLSLSPGERATLSCRASSSVSYIYWFQQKPGQAPRLLIYAAFNRATGIPARFSGSGSGTDYTLTISSLEPEDFA
VYYCQQWSNNPLTFGQGTKVEIK

Amplimmune/GSK/MedImmune h3D10 Var2 VH (SEQ ID NO: 30097)

QVQLVQSGAEVKKPGASVKVSCKASGYTFPDYYMNWVRQAPGQSLEWMGDIDPNYGGTNYNQKFQGRVTMTRDTSI
STAYMELSRLRSDDTAVYYCARGALTDWGQGTMVTVSS

Amplimmune/GSK/MedImmune h3D10 Var2 VL (SEQ ID NO: 30098)

EIVLTQSPATLSLSPGERATLSCRASSSVSYIYWFQQKPGQSPRPLIYAAFNRATGIPARFSGSGSGTDYTLTISSLEPEDFA
VYYCQQWSNNPLTFGQGTKVEIK

Amplimmune/GSK/MedImmune h3D10 Var3 VH (SEQ ID NO: 30099)

QVQLVQSGAEVKKPGASVKVSCKASGYTFPDYYMNWVRQAPGQSLEWMGDIDPNYGGTNYNQKFQGRVTMTRDTSI
STAYMELSRLRSDDTAVYYCARGALTDWGQGTMVTVSS

Amplimmune/GSK/MedImmune h3D10 Var3 VL (SEQ ID NO: 30100)

QIVLTQSPATLSLSPGERATLSCRASSSVSYIYWFQQKPGQSPRPLIYATFNLASGIPARFSGSGSGTSYTLTISRLEPEDFA
VYYCQQWSNNPLTFGQGTKVEIK

Amplimmune/GSK/MedImmune h3D10 Var4 VH (SEQ ID NO: 30101)

EVQLVQSGAEVKKPGASVKVSCKASGYTFPDYYMNWVRQAPGQSLEWMGDIDPNYGGTNYNQKFQGRVTMTVDRS
SSTAYMELSRLRSDDTAVYYCARGALTDWGQGTMVTVSS

Amplimmune/GSK/MedImmune h3D10 Var4 VL (SEQ ID NO: 30102)

EIVLTQSPATLSLSPGERATLSCRASSSVSYIYWFQQKPGQSPRPLIYAAFNRATGIPARFSGSGSGTDYTLTISSLEPEDFA
VYYCQQWSNNPLTFGQGTKVEIK

Amplimmune/GSK/MedImmune h3D10 Var5 VH (SEQ ID NO: 30103)

EVQLVESGGGLVQPGRSLRLSCTASGYTFPDYYMNWVRQAPGKGLEWVGDIDPNYGGTTYNQSVKGRFTISVDRSKSI
AYLQMSSLKTEDTAVYYCARGALTDWGQGTMVTVSS

Amplimmune/GSK/MedImmune h3D10 Var5 VL (SEQ ID NO: 30104)

DIQLTQSPSILSASVGDRVTITCRASSSVSYIYWFQQKPGKAPKPLIYATFNLASGVPSRFSGSGSGTSYTLTISSLQPEDFA
TYYCQQWSNNPLTFGQGTKVEIK

Amplimmune/GSK/MedImmune h3D10 Var6 VH (SEQ ID NO: 30105)

EVQLVESGGGLVQPGRSLRLSCTASGYTFPDYYMNWVRQAPGKGLEWVGDIDPNYGGTTYAASVKGRFTISVDRSKSI
AYLQMSSLKTEDTAVYYCTRGALTDWGQGTMVTVSS

Amplimmune/GSK/MedImmune h3D10 Var6 VL (SEQ ID NO: 30106)

EIVLTQSPATLSLSPGERATLSCRASSSVSYIYWFQQKPGQAPRLLIYAAFNRATGIPARFSGSGSGTDYTLTISSLEPEDFA
VYYCQQWSNNPLTFGQGTKVEIK

Figure 78C

Amplimmune/GSK/MedImmune h3D10 Var7 VH (SEQ ID NO: 30107)

QVQLVQSGAEVKKPGASVKVSCKASGYTFPDYYMNWVRQAPGQGLEWMGDIDPNYGGTNYAQKFQGRVTMTRDTS
ISTAYMELSRLRSDDTAVYYCARGALTDWGQGTMVTVSS

Amplimmune/GSK/MedImmune h3D10 Var7 VL (SEQ ID NO: 30108)

DIQLTQSPSSLSASVGDRVTITCRASSGVSYIYWFQQKPGKAPKLLIYAAFNLASGVPSRFSGSGSGTEYTLTISSLQPEDF
ATYYCQQWSNNPLTFGQGTKVEIK

Amplimmune/GSK/MedImmune h3D10 Var8 VH (SEQ ID NO: 30109)

EVQLVESGGGLVQPGRSLRLSCTASGYTFPDYYMNWVRQAPGKGLEWVGDIDPNYGGTTYNQSVKGRFTISVDRSKSI
AYLQMSSLKTEDTAVYYCARGALTDWGQGTMVTVSS

Amplimmune/GSK/MedImmune h3D10 Var8 VL (SEQ ID NO: 30110)

QIVLTQSPATLSLSPGERATLSCRASSSVSYIYWFQQKPGQSPRPLJYATFNLASGIPARFSGSGSGTSYTLTISRLEPEDFA
VYYCQQWSNNPLTFGQGTKVEIK

Amplimmune/GSK/MedImmune h3D10 Var9 VH (SEQ ID NO: 30111)

EVQLVESGGGLVQPGRSLRLSCTASGYTFPDYYMNWVRQAPGKGLEWVGDIDPNYGGTTYNQSVKGRFTISVDRSKSI
AYLQMSSLKTEDTAVYYCARGALTDWGQGTMVTVSS

Amplimmune/GSK/MedImmune h3D10 Var9 VL (SEQ ID NO: 30112)

DIQLTQSPSSLSASVGDRVTITCRASSGVSYIYWFQQKPGKAPKPLIYAAFNLASGVPSRFSGSGSGTEYTLTISSLQPEDF
ATYYCQQWSNNPLTFGQGTKVEIK

Amplimmune/GSK/MedImmune h3D10 Var10 VH (SEQ ID NO: 30113)

EVQLVESGGGLVQPGRSLRLSCTASGYTFPDYYMNWVRQAPGKGLEWVGDIDPNYGGTTYNQSVKGRFTISVDRSKSI
AYLQMSSLKTEDTAVYYCARGALTDWGQGTMVTVSS

Amplimmune/GSK/MedImmune h3D10 Var10 VL (SEQ ID NO: 30114)

DIQLTQSPSILSASVGDRVTITCRASSSVSYIYWFQQKPGKAPKPLIYATFNLASGVPSRFSGSGSGTSYTLTISSLQPEDFA
TYYCQQWSNNPLTFGQGTKVEIK

Amplimmune/GSK/MedImmune h3D10 Var11 VH (SEQ ID NO: 30115)

EVQLVESGGGLVQPGRSLRLSCTASGYTFPDYYMNWVRQAPGKGLEWVGDIDPNYGGTTYAASVKGRFTISVDRSKSI
AYLQMSSLKTEDTAVYYCTRGALTDWGQGTMVTVSS

Amplimmune/GSK/MedImmune h3D10 Var11 VL (SEQ ID NO: 30116)

EIVLTQSPATLSLSPGERATLSCRASSSVSYIYWFQQKPGQAPRLLIYAAFNRATGIPARFSGSGSGTDYTLTISSLEPEDFA
VYYCQQWSNNPLTFGQGTKVEIK

Amplimmune/GSK/MedImmune h3D10 Var12 VH (SEQ ID NO: 30117)

QVQLVQSGAEVKKPGASVKVSCKASGYTFPDYYMNWVRQAPGQGLEWMGDIDPNYGGTNYAQKFQGRVTMTRDTS
ISTAYMELSRLRSDDTAVYYCARGALTDWGQGTMVTVSS

Amplimmune/GSK/MedImmune h3D10 Var12 VL (SEQ ID NO: 30118)

DIQLTQSPSSLSASVGDRVTITCRASSGVSYIYWFQQKPGKAPKLLIYAAFNLASGVPSRFSGSGSGTEYTLTISSLQPEDF
ATYYCQQWSNNPLTFGQGTKVEIK

Figure 78D

Amplimmune/GSK/MedImmune h3D10 Var13 VH (SEQ ID NO: 30119)

EVQLVESGGGLVQPGRSLRLSCTASGYTFPDYYMNWVRQAPGKGLEWVGDIDPNYGGTTYNQSVKGRFTISVDRSKSI
AYLQMSSLKTEDTAVYYCARGALTDWGQGTMVTVSS

Amplimmune/GSK/MedImmune h3D10 Var13 VL (SEQ ID NO: 30120)

QIVLTQSPATLSLSPGERATLSCRASSSVSYIYWFQQKPGQSPRPLIYATFNLASGIPARFSGSGSGTSYTLTISRLEPEDFA
VYYCQQWSNNPLTFGQGTKVEIK

Amplimmune/GSK/MedImmune h3D10 Var14 VH (SEQ ID NO: 30121)

EVQLVQSGAEVKKPGASVKVSCKASGYTFPDYYMNWVRQAPGQSLEWMGDIDPNYGGTNYNQKFQGRVTMTVDRS
SSTAYMELSRLRSDDTAVYYCARGALTDWGQGTMVTVSS

Amplimmune/GSK/MedImmune h3D10 Var14 VL (SEQ ID NO: 30122)

DIQLTQSPSILSASVGDRVTITCRASSSVSYIYWFQQKPGKAPKPLIYATFNLASGVPSRFSGSGSGTSYTLTISSLQPEDFA
TYYCQQWSNNPLTFGQGTKVEIK

Eli Lily Antibody A VH (SEQ ID NO: 30123)

QVQLVQSGAEVKKPGSSVKVSCKASGGTFSSYAISWVRQAPGQGLEWMGGIIPIFGTANYAQKFQGRVTITADKSTSTA
YMELSSLRSEDTAVYYCARSPDYSPYYYYGMDVWGQGTTVTVSS

Eli Lily Antibody A VL (SEQ ID NO: 30124)

QSVLTQPPSASGTPGQRVTISCSGSSSNIGSNTVNWYQQLPGTAPKLLIYGNSNRPSGVPDRFSGSKSGTSASLAISGLQSE
DEADYYCQSYDSSLSGSVFGGGIKLTVLG

Cytomyx C5H9v2 VH (SEQ ID NO: 30125)

EVQLLESGGGLVQPGGSLRLSCAASGFTFSSYAMSWVRQAPGKGLEWVSSIWRNGIVTVYADSVKGRFTISRDNSKNT
LYLQMNSLRAEDTAVYYCAKWSAAFDYWGQGTLVTVSS

Cytomyx C5H9v2 VL (SEQ ID NO: 30126)

DIQMTQSPSSLSASVGDRVTITCRASQSISSYLNWYQQKPGKAPKLLIYAASSLQSGVPSRFSGSGSGTDFTLTISSLQPED
FATYYCQQDNGYPSTFGGGTKVEIKR

Dana-Farber/Novartis Humanized 29E.2A3 VH (SEQ ID NO: 30127)

CKASGYTFTSYVMHWVKQAPGQRLEWIGYVNPFNDGTKYNEMFKGRATLTSDKSTSTAYMELSSLRSEDTAVYYCAR
QAWGYPWGQGTLVTVSS

Dana-Farber/Novartis Humanized 29E.2A3 VL (SEQ ID NO: 30128)

DIVLTQSPATLSLSPGERATLSCRATESVEYYGTSLVQWYQQKPGQPPKLLIYAASSVDSGVPSRFSGSGSGTDFTLTINS
LEAEDAATYFCQQSRRVPYTFGQGTKLEIK

Dana-Farber/Novartis 1B9 VH (SEQ ID NO: 30129)

DVQLQESGPGLVKPSQSLSLTCTVTGYSITSDHAWNWIRQVPGNKLEWMGYITYRGSTTYSPSLKSRISITRDTSKNQFF
LQLNSVTTEDTATYYCARSMITGYYVMDYWGQGTSVTVSS

Dana-Farber/Novartis 1B9 VL (SEQ ID NO: 30130)

DIVMTQSHKFMSTSLGDRVTITCKASQDVGISVVWYQQKPGQSPKLLIYWASTRHTGVPDRFTGSGSGTDFTLTINNVQ
SEDLADYFCQQYSSYPLTVGAGTKLELK

Figure 78E

Dana-Farber/Novartis 4H1 VH (SEQ ID NO: 30131)

DVQLQESGPGLVKPSQSLSLTCTVTDYSITSDYAWTWIRQFPGNKLEWMGYITYRGTTRYNPSLTSRISFTRDTSKNQLF
LQLNSVTTEDTGTYCCARSMITTGYYAMDYWGQGTSVTSS

Dana-Farber/Novartis 4H1 VL (SEQ ID NO: 30132)

DIVMTQSHKFMSTSVGDRVSISCKASQDVGISVAWYQQKPGQSPKLLIYWASTRHTGVPVRFTGSGSGTDFTLTISNVQ
SEDLADYFCQQYSSYPPTFGAGTKLELK

Dana-Farber/Novartis mAb-42 VH (SEQ ID NO: 30133)

QVQLVQSGAEVKKPGSSVKVSCKASGGTFSSYAISWVRQAPGQGLEWMGGIIPIFGTANYAQKFQGRVTITADKSTSTA
YMELSSLRSEDTAVYYCARGRQMFGAGIDFWGPGTLVTVSS

Dana-Farber/Novartis mAb-42 VL (SEQ ID NO: 30134)

NFMLTQPHSVSESPGKTVTISCTRSSGSIDSNYVQWYQQRPGSAPTTVIYEDNQRPSGVPDRFSGSIDSSSNSASLTISGLK
TEDEADYYCQSYDSNNRHVIFGGGTKLTVL

Dana-Farber/Novartis BAP058-03 VH (SEQ ID NO: 30135)

EVQLVQSGAEVKKPGATVKISCKVSGYTFTSYWMYWVRQATGQGLEWMGRIDPNSGSTKYNEKFKNRVTITADKSTS
TAYMELSSLRSEDTAVYYCARDYRKGLYAMDYWGQGTTVTVSS

Dana-Farber/Novartis BAP058-03 VL (SEQ ID NO: 30136)

EIVLTQSPDFQSVTPKEKVTITCKASQDVGTAVAWYLQKPGQSPQLLIYWASTRHTGVPDRFSGSGSGTDFTLKISRVEA
EDVGVYYCQQYNSYPLTFGQGTKVEIK

Dana-Farber/Novartis BAP058-04 VH (SEQ ID NO: 30137)

EVQLVQSGAEVKKPGESLRISCKGSGYTFTSYWMYWVRQAPGQGLEWMGRIDPNSGSTKYNEKFKNRVTISVDTSKN
QFSLKLSSVTAADTAVYYCARDYRKGLYAMDYWGQGTTVTVSS

Dana-Farber/Novartis BAP058-04 VL (SEQ ID NO: 30138)

EIVLTQSPDFQSVTPKEKVTITCKASQDVGTAVAWYLQKPGQSPQLLIYWASTRHTGVPSRFSGSGSGTDFTFTISSLQPE
DIATYYCQQYNSYPLTFGQGTKVEIK

Dana-Farber/Novartis BAP058-06 VH (SEQ ID NO: 30139)

EVQLVQSGAEVKKPGESLRISCKGSGYTFTSYWMYWIRQPPGKGLEWIGRIDPNSGSTKYNEKFKNRVTITADKSTSTA
YMELSSLRSEDTAVYYCARDYRKGLYAMDYWGQGTTVTVSS

Dana-Farber/Novartis BAP058-06 VL (SEQ ID NO: 30140)

EIVLTQSPDFQSVTPKEKVTITCKASQDVGTAVAWYLQKPGQSPQLLIYWASTRHTGVPSRFSGSGSGTDFTFTISSLQPE
DIATYYCQQYNSYPLTFGQGTKVEIK

Dana-Farber/Novartis BAP058-07 VH (SEQ ID NO: 30141)

QVQLVQSGAEVKKPGASVKVSCKASGYTFTSYWMYWIRQSPSRGLEWLGRIDPNSGSTKYNEKFKNRFTISRDDSKNT
AYLQMNSLKTEDTAVYYCARDYRKGLYAMDYWGQGTTVTVSS

Dana-Farber/Novartis BAP058-07 VL (SEQ ID NO: 30142)

EIVLTQSPATLSLSPGERATLSCKASQDVGTAVAWYLQKPGQSPQLLIYWASTRHTGIPPRFSGSGYGTDFTLTINNIESE
DAAYYFCQQYNSYPLTFGQGTKVEIK

Figure 78F

Dana-Farber/Novartis BAP058-11 VH (SEQ ID NO: 30143)

EVQLVQSGAEVKKPGATVKISCKVSGYTFTSYWMYWVRQATGQGLEWMGRIDPNSGSTKYNEKFKNRVTITADKSTS
TAYMELSSLRSEDTAVYYCARDYRKGLYAMDYWGQGTTVTVSS

Dana-Farber/Novartis BAP058-11 VL (SEQ ID NO: 30144)

DVVMTQSPLSLPVTLGQPASISCKASQDVGTAVAWYQQKPGQAPRLLIYWASTRHTGVPSRFSGSGSGTEFTLTISSLQP
DDFATYYCQQYNSYPLTFGQGTKVEIK

Dana-Farber/Novartis BAP058-13 VH (SEQ ID NO: 30145)

EVQLVQSGAEVKKPGATVKISCKVSGYTFTSYWMYWVRQARGQRLEWIGRIDPNSGSTKYNEKFKNRFTISRDNSKNT
LYLQMNSLRAEDTAVYYCARDYRKGLYAMDYWGQGTTVTVSS

Dana-Farber/Novartis BAP058-13 VL (SEQ ID NO: 30146)

AIQLTQSPSSLSASVGDRVTITCKASQDVGTAVAWYLQKPGQSPQLLIYWASTRHTGVPSRFSGSGSGTDFTFTISSLEAE
DAATYYCQQYNSYPLTFGQGTKVEIK

Sorrento H6 VH (SEQ ID NO: 30147)

QMQLVQSGAEVKKPGSSVKVSCKASGGTFSSYAISWVRQAPGQGLEWMGGIIPIFGTANYAQKFQGRVTITADESTSTA
YMELSSLRSEDTAVYYCARGNIVATITPLDYWGQGTLVTVSS

Sorrento H6 VL (SEQ ID NO: 30148)

SYELMQPPSVSVAPGKTATIACGGENIGRKTVHWYQQKPGQAPVLVIYYDSDRPSGIPERFSGSNSGNTATLTISRVEAG
DEADYYCQVWDSSSDHRIFGGGTKLTVL

Sorrento RC5 VH (SEQ ID NO: 30149)

EVQLLESGGGVVQPGGSLRLSCAASGFTFSSYWMSWVRQAPGKGLEWVANIKQDGSEKYYVDSVKGRFTISRDNSKN
TVSLQMNSLRAEDTAVYYCAKDRYYNFPLGMDVWGQGTTVTVSS

Sorrento RC5 VL (SEQ ID NO: 30150)

AIRMTQSPSSLSASVGDRVTITCRASQSISSYLNWYQQKPGKAPKLLIYTTSSLKSGVPSRFSGSGSGTDFTLTISRLQPED
FATYYCQQSYSSTWTFGRGTKVEIK

Sorrento SH1A1Q VH (SEQ ID NO: 30151)

EVQLVQSGAEVKKPGSSVKVSCKASGGTFSSYAISWVRQAPGQGLEWMGGIIPIFGTANYAQKFQGRVTITADKSTSTA
YMELSSLRSEDTAVYYCAREGTIYDSSGYSFDYWGQGTLVTVSS

Sorrento SH1A1Q VL (SEQ ID NO: 30152)

QSVLTQPPSVSAAPGQKVTISCSGNNSNIANNYVSWYQQLPGTAPKLLIYDNNYRPSGIPDRFSGSKSGTSATLDITGLQT
GDEADYYCGVWDGSLTTGVFGGGTKLTVL

Sorrento SH1B3 VH (SEQ ID NO: 30153)

QVQLVESGGGVVQPGRSLRLSCAASGFTFSSYAMHWVRQAPGKGLEWVAVISFDGSNKYYADSVRGRFTISRDNSKNT
LYLQMNSLRTEDTAVYYCARGWLDRDIDYWGQGTLVTVSS

Sorrento SH1B3 VL (SEQ ID NO: 30154)

LPVLTQPASVSGSPGQSITISCTGTTSDIGGYDYVSWYQQHPGKAPKLMIYDVSKRPSGVSNRFSGSKSGNTASLTISGLQ
AEDEADYYCSSYTSSSTHVFGTGTKLTVL

Figure 78G

Sorrento SH1D1 VH (SEQ ID NO: 30155)

EVQLVESGGGVVQPGRSLRLSCAASGFTFSSYAMHWVRQAPGKGLEWVAVISFDGSNKYYADSVRGRFTISRDNSKNT
LYLQMNSLRTEDTAVYYCARGWLDRDIDYWGQGTLVTVSS

Sorrento SH1D1 VL (SEQ ID NO: 30156)

QSALTQPASVSGSPGQSITISCTGTSSDVGGYNYVSWYQQHPGKAPKLMIYDVSNRPSGVSNRFSGSKSGNTASLTISGL
QAEDEADYYCSSYRSSTLGPVFGGGTKLTVL

Sorrento SH1D2 VH (SEQ ID NO: 30157)

QVQLVESGGGVVQPGRSLRLSCAASGFTFSSYAMHWVRQAPGKGLEWVAVISFDGSNKYYADSVRGRFTISRDNSKNT
LYLQMNSLRTEDTAVYYCARGWLDRDIDYWGQGTLVTVSS

Sorrento SH1D2 VL (SEQ ID NO: 30158)

QAGLTQPPSVSEAPRQRVTISCSGSSSNIGNNAVNWYQQLPGKAPKLLIYYDDLLPSGVSDRFSGSKSGTSASLAISGLQS
EDEADYYCAAWDDSLNGYVFGTGTKLTVL

Sorrento SH1D12 VH (SEQ ID NO: 30159)

EVQLVESGGGVVQPGRSLRLSCAASGFTFSSYAMHWVRQAPGKGLEWVAVISFDGSNKYYADSVRGRFTISRDNSKNT
LYLQMNSLRTEDTAVYYCARGWLDRDIDYWGQGTLVTVSS

Sorrento SH1D12 VL (SEQ ID NO: 30160)

QSALTQPRSVSGSPGQSVTISCTGTSSDVGGYNYVSWYQQHPGKAPKLMIYDVSKRPSGVPDRFSGSKSGNTASLTISGL
QAEDEADYYCSSYTSSTTHVFGTGTKVTVL

Sorrento SH1E1 VH (SEQ ID NO: 30161)

EVQLVESGGGVVQPGRSLRLSCAASGFTFSSYAMHWVRQAPGKGLEWVAVISFDGSNKYYADSVRGRFTISRDNSKNT
LYLQMNSLRTEDTAVYYCARGWLDRDIDYWGQGTLVTVSS

Sorrento SH1E1 VL (SEQ ID NO: 30162)

QSVVTQPPSVSAAPGQKVTISCSGSSSNIGNNYVSWYQQLPGTAPKLLIYDNNKRPSGIPDRFSGSKSGTSATLGITGLQT
GDEADYYCGTWDSSLSVWVFGGGTQLTVL

Sorrento SH1G9 VH (SEQ ID NO: 30163)

QVQLVESGGGVVQPGRSLRLSCAASGFTFSSYAMHWVRQAPGKGLEWVAVISFDGSNKYYADSVRGRFTISRDNSKNT
LYLQMNSLRTEDTAVYYCARGWLDRDIDYWGQGTLVTVSS

Sorrento SH1G9 VL (SEQ ID NO: 30164)

QSVLTQPASVSGSPGQSITISCTGTSSDVGGYNYVSWYQQHPGRAPRLMIYDVSNRPSGVSNRFSGSKSGNTASLTISGL
QAEDEGDYYCSSYTSGGTLGPVFGGGTKLTVL

Sorrento SH1E6 VH (SEQ ID NO: 30165)

QVQLVQSGAEVKKPGSSVKVSCKASGGTFSRYGVHWVRQAPGQGLEWMGRLIPIVSMTNYAQKFQDRVSITTDKSTG
TAYMELRSLTSEDTALYYCASVGQQLPWVFFAWGQGTLVTVSS

Sorrento SH1E6 VL (SEQ ID NO: 30166)

QSVVTQPPSVSAAPGQKVTISCSGSSSNIGNNYVSWYQQLPGTAPKLLIYDNNKRPSGIPDRFSGSKSGTSATLGITGLQT
GDEADYYCGTWDSSLSAVVFGGGTKLTVL

Figure 78H

Sorrento SH1A2 VH (SEQ ID NO: 30167)

QMQLVQSGGGVVQPGRSLRLSCAASGFTFSSYAMHWVRQAPGKGLEWVAVISFDGSNKYYADSVRGRFTISRDNSKN
TLYLQMNSLRTEDTAVYYCARGWLDRDIDYWGQGTLVTVSS

Sorrento SH1A2 VL (SEQ ID NO: 30168)

QSVVTQPPSVSAAPGQKVTISCSGSSSNIGNNYVSWYQQVPGTAPKLLIYDNNKRPSGIPDRFSGSNSDTSATLGITGLQT
GDEADYYCGTWDSSLSAWVFGGGTKLTVL

Sorrento SH1B1 VH (SEQ ID NO: 30169)

QVQLVQSGGGVVQPGRSLRLSCAASGFTFSSYAMHWVRQAPGKGLEWVAVISFDGSNKYYADSVRGRFTISRDNSKN
TLYLQMNSLRTEDTAVYYCARGWLDRDIDYWGQGTLVTVSS

Sorrento SH1B1 VL (SEQ ID NO: 30170)

QSVVTQPPSVSAAPGQKVTISCSGSSSNIGNNYVSWYQQLPGTAPKLLIYDNNKRPSGIPDRFSGSKSGTSATLGITGLQT
GDEADYYCGTWDSSLSAGSVVFGGGTKLTVL

Sorrento H6B1L VH (SEQ ID NO: 30171)

QMQLVQSGAEVKKPGSSVKVSCKASGGTFSSYAYSWVRQAPGQGLEWMGGIIPSFGTANYAQKFQGRVTITADESTST
AYMELSSLRSEDTAVYYCARGPIVATITPLDYWGQGTLVTVSS

Sorrento H6B1L VL (SEQ ID NO: 30172)

SYELMQPPSVSVAPGKTATIACGGENIGRKTVHWYQQKPGQAPVLVIYYDSDRPSGIPERFSGSNSGNTATLTISRVEAG
DEADYYCLVWDSSSDHRIFGGGTKLTVL

Sorrento H6A1 VH (SEQ ID NO: 30173)

QMQLVQSGAEVKKPGSSVKVSCKASGGTFSSYAYSWVRQAPGQGLEWMGGIIPIFGTANYAQKFQGRVTITADESTST
AYMELSSLRSEDTAVYYCARGPIVATITPLDYWGQGTLVTVSS

Sorrento H6A1 VL (SEQ ID NO: 30174)

SYELMQPPSVSVAPGKTATIACGGENIGRKTVHWYQQKPGQAPVLVIYYDSDRPSGIPERFSGSNSGNTATLTISRVEAG
DEADYYCQVWDSSSDHRIFGGGTKLTVL

Sorrento H6B1 VH (SEQ ID NO: 30175)

QMQLVQSGAEVKKPGSSVKVSCKASGGTFSSYAYSWVRQAPGQGLEWMGGIIPSFGTANYAQKFQGRVTITADESTST
AYMELSSLRSEDTAVYYCARGPIVATITPLDYWGQGTLVTVSS

Sorrento H6B1 VL (SEQ ID NO: 30176)

SYELMQPPSVSVAPGKTATIACGGENIGRKTVHWYQQKPGQAPVLVIYYDSDRPSGIPERFSGSNSGNTATLTISRVEAG
DEADYYCQVWDSSSDHRIFGGGTKLTVL

Sorrento H6B2 VH (SEQ ID NO: 30177)

QMQLVQSGAEVKKPGSSVKVSCKASGGTFSSYAISWVRQAPGQGLEWMGGIIPAFGTANYAQKFQGRVTITADESTST
AYMELSSLRSEDTAVYYCARGPIVATITPLDYWGQGTLVTVSS

Sorrento H6B2 VL (SEQ ID NO: 30178)

SYELMQPPSVSVAPGKTATIACGGENIGRKTVHWYQQKPGQAPVLVIYYDSDRPSGIPERFSGSNSGNTATLTISRVEAG
DEADYYCQVWDSSSDHRIFGGGTKLTVL

Figure 78I

Sorrento G12 VH (SEQ ID NO: 30179)

EVQLVQSGAEVKKPGASVKVSCKASGYTFTGYYMHWVRQAPGQGLEWMGWINPNSDNTGSAQKFQGRVFMTKTTS
LNTAYMELSGLRSEDTAIYYCARERSSGYFDFWGQGTLVTVSS

Sorrento G12 VL (SEQ ID NO: 30180)

DIVMTQSPSSLSASVGDRVTITCRASQSISSYLNWYQQKPGKAPKLLIYAASSLQSGVPSRFSGSGSGTDFTLTISSLQPED
FATYYCQQSYSTPITFGQGTRLEIK

Sorrento RSA1 VH (SEQ ID NO: 30181)

EVQLVQSGGGLVQPGGSLRLSCAASGFTFSSYSMNWVRQAPGKGLEWVSYISSSSSTIYYADSVKGRFTISRDNAKNSL
YLQMNSLRDEDTAVYYCARGDYYYGMDVWGQGTTVTVSS

Sorrento RSA1 VL (SEQ ID NO: 30182)

NIQMTQSPSSVSASVGDRVTITCRASQDISRWLAWYQQKPGKAPKLLIYAASSLQSGVPSRFSGSGSGTDFALTISSLQPE
DFATYYCQQADSFFSITFGQGTRLEIK

Sorrento RA3 VH (SEQ ID NO: 30183)

QMQLVQSGAEVKKPGSSVKVSCKASGGTFSRYGVHWVRQAPGQGLEWMGRLIPIVSMTNYAQKFQDRVSITTDKSTG
TAYMELRSLTSEDTALYYCASVGQQLPWVFFAWGQGTLVTVSS

Sorrento RA3 VL (SEQ ID NO: 30184)

DIQMTQSPSSLSASVGDRVTITCQASQDISNYLNWYQQKPGKAPKLLIYDASTLQSGVPSRFSGSGSGTDFTLTISSLQPE
DFATYYCQQSYSSHWTFGQGTKVEIK

Sorrento SH1E2 VH (SEQ ID NO: 30185)

EVQLVESGAEVKKPGSSVKVSCKASGGTFSSYAISWVRQAPGQGLEWMGGIIPIFGTANYAQKFQGRVTITADESTSTA
YMELSSLRSEDTAVYYCARAPYYYYYMDVWGQGTTVTVSS

Sorrento SH1E2 VL (SEQ ID NO: 30186)

QSALTQPASVSGSLGQSVTISCTGSSSDVGSYNLVSWYQQHPGKAPNLMIYDVSKRSGVSNRFSGSKSGNTASLTISGLQ
AEDEADYYCSSYTGISTVVFGGGTKLTVL

Sorrento SH1E4 VH (SEQ ID NO: 30187)

QVQLVQSGAEVKKPGSSVKVSCKASGGTFSRYGVHWVRQAPGQGLEWMGRLIPIVSMTNYAQKFQDRVSITTDKSTG
TAYMELRSLTSEDTALYYCASVGQQLPWVFFAWGQGTLVTVSS

Sorrento SH1E4 VL (SEQ ID NO: 30188)

QSVLTQPPSASGSPGQSVTISCTGTSSDIGGYDSVSWYQQHPGKAPKLMIYDVSKRPSGVSNRFSGSKSGNTASLTISGLQ
AEDEADYYCSSYTSSSIFFYVFGTGTKVTVL

Sorrento SH1B11 VH (SEQ ID NO: 30189)

QVQLVQSGSELKKPGSSVKVSCKASGYSFSGYYIHWVRQAPGQGLEWMGWIDPNSGVTNYVRRFQGRVTMTRDTSLS
TAYMELSGLTADDTAVYYCARDENLWQFGYLDYWGQGTLVTVSS

Sorrento SH1B11 VL (SEQ ID NO: 30190)

DIVMTQSPSSLSASIGDRVTITCRASQRISAYVNWYQQKPGKAPKVLIYAASSLRSGVPSRFSGSGSGTDFTLTISSLQPED
FATYYCQQTYSSPWTFGQGTKVEIK

Figure 78J

Sorrento SH1C8 VH (SEQ ID NO: 30191)

EVQLVESGGGVVQPGRSLRLSCAASGFTFSSYAMHWVRQAPGKGLEWVAVISYDGSNKYYADSVKGRFTISRDNSKN
TLYLQMNSLRAEDTAVYYCARGQWLVTELDYWGQGTLVTVSS

Sorrento SH1C8 VL (SEQ ID NO: 30192)

QSVVTQPPSVSAAPGQKVTISCSGSSSDIGNHYVSWYQQLPGTAPKLLIYDNNQRPSGIPDRFSGSKSGTSATLAITGLQT
GDEADYYCGTWDNSLSPHLLFGGGTKLTVL

Regeneron H1H9364P2 VH (SEQ ID NO: 30193)

EVQLVESGGGLVQPGRSLRLSCAASGFTFDDYALHWVRQAPGKGLEWVSGISWTGGTIDYADSVKGRFTISRDNAKNS
LYLQMSSLRTEDTAIYYCTRDIRGNWKYGGWFDPWGQGTLVTVSS

Regeneron H1H9364P2 VL (SEQ ID NO: 30194)

DIQMTQSPSSLSASVGDRVTITCRASQSISSYLNWYQQKPGKAPKLLIYAASSLQSGVPSRFSGSGSGTDFTLTISSLQPED
FATYYCQQSYSTPPITFGQGTRLEIK

Regeneron H1H9373P2 VH (SEQ ID NO: 30195)

QVQLVQSGTEVKKPGASVKVSCKASGYTFTAYYMHWVRQAPGQGLDWMGWISPNSGFTNYAQKFQGRVTMTRDTSI
NTFYMELSGLRSDDTAVYYCAREGSTHHNSFDPWGQGTLVTVSS

Regeneron H1H9373P2 VL (SEQ ID NO: 30196)

DIQMTQSPSSLSASVGDRVTITCRASQSISSYLNWYQQKPGKAPKLLIYAASSLQSGVPSRFSGSGSGTDFTLTISSLQPED
FATYYCQQSYSTPPITFGQGTRLEIK

Regeneron H1H8314N VH (SEQ ID NO: 30197)

EVQLVESGGGVVRPGGSLRLSCAASGFTFDDYGMTWVRQAPGRGLEWVSGIHWHGKRTGYADSVKGRFTISRDNAK
KSLYLQMNSLKGEDTALYHCVRGGMSTGDWFDPWGQGTLVIVSS

Regeneron H1H8314N VL (SEQ ID NO: 30198)

DIQMTQSPSSLSASLGDRVTITCRASQSINSYLNWYQQKPGKAPKLLIYVASSLQSGVPSRFSGSGSGTEFTLTISNLQPED
FATYYCQQSYSTPPITFGQGTRLEIK

Inserm PDL1.3.1 VH (SEQ ID NO: 30199)

EVQLQQSGTELVKPGASVKLSCTTSGFNIQDTYMHWVKQRPEQGLEWIGWIDPANGNTKYDPKFQGKATHADTSSNT
AYLQLRGLTSEDTAVYYCARSGVSTAHFDYWGQGTTLTVSS

Inserm PDL1.3.1 VL (SEQ ID NO: 30200)

QIVLSQSPAILSASPGEKVTMTCRASSSVSFMHWYQQKPGSSPKPWIYATSNLASGVPTRFSGSGSGTSYSLTLSRVEAE
DAATYYCQQWSSYPRTFGGGTKLEIK

Figure 79A additional CTLA-4 sequences

Medarex Ipilimumab VH (SEQ ID NO: 30201)

QVQLVESGGGVVQPGRSLRLSCAASGFTFSSYTMHWVRQAPGKGLEWVTFISYDGNNKYYADSVKGRFTISRDNSKNT
LYLQMNSLRAEDTAIYYCARTGWLGPFDYWGQGTLVTVSS

Medarex Ipilimumab VL (SEQ ID NO: 30202)

EIVLTQSPGTLSLSPGERATLSCRASQSVGSSYLAWYQQKPGQAPRLLIYGAFSRATGIPDRFSGSGSGTDFTLTISRLEPE
DFAVYYCQQYGSSPWTFGQGTKVEIK

Amgen/MedImmune/Pfizer Tremelimumab VH (SEQ ID NO: 30203)

QVQLVESGGGVVQPGRSLRLSCAASGFTFSSYGMHWVRQAPGKGLEWVAVIWYDGSNKYYADSVKGRFTISRDNSKN
TLYLQMNSLRAEDTAVYYCARDPRGATLYYYYYGMDVWGQGTTVTVSS

Amgen/MedImmune/Pfizer Tremelimumab VL (SEQ ID NO: 30204)

DIQMTQSPSSLSASVGDRVTITCRASQSINSYLDWYQQKPGKAPKLLIYAASSLQSGVPSRFSGSGSGTDFTLTISSLQPED
FATYYCQQYYSTPFTFGPGTKVEIK

Agenus AGEN1884 VH (SEQ ID NO: 30205)

EVQLVESGGGLVKPGGSLRLSCAASGFTFSSYSMNWVRQAPGKGLEWVSSISSSSSYIYYADSVKGRFTISRDNAKNSL
YLQMNSLRAEDTAVYYCARVGLMGPFDIWGQGTMVTVSS

Agenus AGEN1884 VL (SEQ ID NO: 30206)

EIVLTQSPGTLSLSPGERATLSCRASQSVSRYLGWYQQKPGQAPRLLIYGASTRATGIPDRFSGSGSGTDFTLTITRLEPED
FAVYYCQQYGSSPWTFGQGTKVEIK

Tegenero 4.3F6B5 VH (SEQ ID NO: 30207)

EVQLQPSGPVLVKPGASVKISCKASGYTFTDYKIHWVKQSHGKSLEWIGYIYPYSGSSDYNQKFKSKATLTVDNSSTTA
YMELRSLTSEDSAVYYCARGGDAMDYWGQGTAVTVSS

Tegenero 4.3F6B5 VL (SEQ ID NO: 30208)

DILMTQSPASLSASVGETVTITCGASENIYGALNWYQRKQGKSPQLLIYGATNLADGMSSRFSGSGLGRQYYLKISSLHP
DDVATYFCQNILGTWTFGGGTKLEIKR

Tegenero 4.8H10H5 VH (SEQ ID NO: 30209)

DVKLVESGGGLVKLGGSLKLSCAASGFTFNIYYMSWVRQTPEKRLELVAAINPDGGNTYYPDTVKGRFTISRDNAKNT
LYLQMSSLKSEDSALYYCARYGGPGFDSWGQGTTLTVSS

Tegenero 4.8H10H5 VL (SEQ ID NO: 30210)

ENVLTQSPAIMSASPGERVTMTCSASSSVSYMHWYQQKSNTSPKLWIYDTSKLASGVPGRFSGSGSRNSYSLTISSMEAE
DVATYYCFPGSGFPFMYTFGGGTKLEIKR

Tegenero TGN2122.C VH (SEQ ID NO: 30211)

QVQLVQSGAEVKKPGASVKVSCKASGYTFTDYKIHWVRQAPGQGLEWIGYIYPYSGSSDYNQKFKSRATLTVDNSIST
AYMELSRLRSDDTAVYYCARGGDAMDYWGQGTLVTVSS

Tegenero TGN2122.C VL (SEQ ID NO: 30212)

DIQMTQSPSSLSASVGDRVTITCGASENIYGALNWYQRKPGKAPKLLIYGATNLADGVPSRFSGSGSGRDYTLTISSLQP
EDFATYFCQNILGTWTFGGGTKVEIK

Figure 79B

Tegenero TGN2122.H VH (SEQ ID NO: 30213)

EVQLVESGGGLVQPGGSLRLSCAASGFTFNIYYMSWVRQAPGKGLELVAAINPDGGNTYYPDTVKGRFTISRDNAKNS
LYLQMNSLRAEDTAVYYCARYGGPGFDSWGQGTLVTVSS

Tegenero TGN2122.H VL (SEQ ID NO: 30214)

ENVLTQSPATLSLSPGERATLSCSASSSVSYMHWYQQKPGQAPRLWIYDTSKLASGIPARFSGSGSRNDYTLTISSLEPED
FAVYYCFPGSGFPFMYTFGGGTKVEIK

Sorrento F7 VH (SEQ ID NO: 30215)

QVQLVQSGAEVKKPGASVKVSCKASGYAFDGHYMHWVRQAPGQRLEWMGWVDPHSGATNYAQNFQGGVTMTRDT
SINTVYMELSSLKSDDTAVYYCARDFYDTSAKSGAFDIWGQGTMVTVSS

Sorrento F7 VL (SEQ ID NO: 30216)

AIQLTQSPSSVSASVGDRVTITCRASQGISSWLAWYQQKPGKAPKLLIYAASSLQSGVPSRFSGSGSGTDFTLTISSLQPED
FATYYCQQVNSFPWAFGQGTKVEIK

Sorrento E8 VH (SEQ ID NO: 30217)

QVQLVQSGAEVKKPGASVKVSCEASGYTFTNYYIHWLRQAPGQGLEWMGIINPSGGSTTYAQKFQGRITMTRDTSTNT
LYMELSSLRSEDTAIYYCARRDCRGPSCYFAYWGQGTTVTVSS

Sorrento E8 VL (SEQ ID NO: 30218)

DIVMTQSPSSLSASVGDRVTITCRASQSISSYLNWYQQKPGKAPKLLIYAASSLQSGVPPRFSGSGSGTEFTLTISSLQPED
FATYYCQQANSFPPTFGQGTKVDIK

Sorrento CT1E1 VH (SEQ ID NO: 30219)

EVQLVESGGGLVQPGRSLRLSCRGSNFNFDDLAISWVRQAPGKGLEWLGFVRSKAYGETTDYVASVKGRFTISRDDSK
FIAWLQMDSLKTDDTAVYYCTTFNYWGQGTLVTVSS

Sorrento CT1E1 VL (SEQ ID NO: 30220)

QPVLTQPPSVSVAPGKTARISCGGNNIASEAVHWYQKKPGQAPVLVIYYDSDRPSGIPERFSGSNSGNTATLRISRVDAG
DEADYYCQVWDRTTDQPVFGGGTKLTVL

Figure 80A additional LAG-3 sequences

Medarex BMS-986016 VH (SEQ ID NO: 30221)

QVQLQQWGAGLLKPSETLSLTCAVYGGSFSDYYWNWIRQPPGKGLEWIGEINHRGSTNSNPSLKSRVTLSLDTSKNQFS
LKLRSVTAADTAVYYCAFGYSDYEYNWFDPWGQGTLVTVSS

Medarex BMS-986016 VL (SEQ ID NO: 30222)

EIVLTQSPATLSLSPGERATLSCRASQSISSYLAWYQQKPGQAPRLLIYDASNRATGIPARFSGSGSGTDFTLTISSLEPEDF
AVYYCQQRSNWPLTFGQGTNLEIK

Immutep/INSERM/Novartis IMP731 VH (SEQ ID NO: 30223)

QVQLKESGPGLVAPSQSLSITCTVSGFSLTAYGVNWVRQPPGKGLEWLGMIWDDGSTDYNSALKSRLSISKDNSKSQVF
LKMNSLQTDDTARYYCAREGDVAFDYWGQGTTLTVSS

Immutep/INSERM/Novartis IMP731 VH (SEQ ID NO: 30224)

DIVMTQSPSSLAVSVGQKVTMSCKSSQSLLNGSNQKNYLAWYQQKPGQSPKLLVYFASTRDSGVPDRFIGSGSGTDFTL
TISSVQAEDLADYFCLQHFGTPPTFGGGTKLEIK

Immutep/INSERM/Novartis 13E2 VH (SEQ ID NO: 30225)

QVTLKESGPGILQPSQTLSLTCSFSGFSLSTSGMGLGWIRQPSGKGLEWLTHIWWDDIKRYNPDLRSRLTISKDTSSSQIFL
KIASVDTADTATYYCARIVEGSYSSSYFDVWGAGTTVTVSS

Immutep/INSERM/Novartis 13E2 VH (SEQ ID NO: 30226)

DIVMTQPHKFMSTSVEDRVTITCKASQDVIFDVAWYQQKPGQSPKLLIYSASSRVSGVPDRFTGSGSGTDFTFTISSVQA
EDLAVYYCQQHYSTPYTFGGGTTLEIK

Immutep/INSERM/Novartis 34F4 VH (SEQ ID NO: 30227)

QVTLKESGPGILQPSQTLSLTCSFSGFSLNTSGMGVGWIRQPSGKGLEWLTHIWWDDVKRYNPALKSRLTISKDTSSSQV
FLKIASVDTADTATYYCARIEGDTYYDYYFDYWGQGVTLTVSS

Immutep/INSERM/Novartis 34F4 VH (SEQ ID NO: 30228)

DIVMTQSHKLMSTSVGDGLSITCKASQDVSIAVVWYQQKPGQSPKLLIYSASFRYTGVPDRFTGSGSGTDFTFTISSVQA
EDLAVYYCQQHYSIPWTFGGGTKLEIK

Immutep/INSERM/Novartis IMP761 VH (SEQ ID NO: 30229)

QITLKESGPTLVKPTQTLTLTCTFSGFSLSTSGMGLGWIRQPPGKTLEWLTHIWWDDIKRYNPDLRSRLSITKDTSKNQV
VLTMTNMDPLDTGTYYCARIVEGSYSSSYFDVWGQGTLVTVSS

Immutep/INSERM/Novartis IMP761 VH (SEQ ID NO: 30230)

DIVMTQTPSSLSASVGDRVTITCKASQDVIFDVAWYQQRPGQAPKLLIYSASSRVSGVPSRFSGSGSGTDFTLTISSLQPE
DFATYYCQQHYSTPYTFGQGTRLDIK

GSK H5L7 VH (SEQ ID NO: 30231)

QVQLQESGPGLVKPSETLSLTCTVSGFSLTAYGVNWIRQPPGKGLEWIGMIWDDGSTDYDSALKSRVTISVDTSKNQFS
LKLSSVTAADTAVYYCAREGDVAFDYWGQGTLVTVSS

GSK H5L7 VL (SEQ ID NO: 30232)

DIQMTQSPSSLSASVGDRVTITCKSSQSLLNPSNQKNYLAWYQQKPGKAPKLLVYFASTRDSGVPSRFSGSGSGTDFTLT
ISSLQPEDFATYYCLQHFGTPPTFGQGTKLEIKR

Figure 80B

Merck hu22D2 VH (SEQ ID NO: 30233)

QMQLVQSGPEVKKPGTSVKVSCKASGYTFTDYNVDWVRQARGQRLEWIGDINPNNGGTIYAQKFQERVTITVDKSTST
AYMELSSLRSEDTAVYYCARNYRWFGAMDHWGQGTTVTVSS

Merck hu22D2 VL (SEQ ID NO: 30234)

DIVMTQTPLSLSVTPGQPASISCKASQSLDYEGDSDMNWYLQKPGQPPQLLIYGASNLESGVPDRFSGSGSGTDFTLKIS
RVEAEDVGVYYCQQSTEDPRTFGGGTKVEIK

Regeneron H4sH15482P VH (SEQ ID NO: 30235)

QVQLVESGGGVVQPGRSLRLSCVASGFTFSSYGMHWVRQAPGKGLEWVAIIWYDGSNKYYADSVKGRFTISRDNSKN
TQYLQMNSLRAEDTAVYYCASVATSGDFDYYGMDVWGQGTTVTVSS

Regeneron H4sH15482P VH (SEQ ID NO: 30236)

EIVLTQSPATLSLSPGERTTLSCRASQRISTYLAWYQQKPGQAPRLLIYDASKRATGIPARFSGSGSGTGFTLTISSLEPEDF
AVYYCQQRSNWPLTFGGGTKVEIK

Sorrento L35D4 VH (SEQ ID NO: 30237)

QVQLVQSGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

Sorrento L35D4 VL (SEQ ID NO: 30238)

QSVLTQPPSASGSPGQSVTISCTGTSSDVGGYNYVSWYQQYPGKAPRLMIFEVTERASGVPDRFSGSKSGNTASLTVSGL
QTEDEAVYFCSSYSGSNNPGAMFGGGTKLTVL

Sorrento L35G6 VH (SEQ ID NO: 30239)

QVQLVQSGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

Sorrento L35G6 VL (SEQ ID NO: 30240)

QAGLTQPASVSGSPGQSITISCTGSSSDVGGYSYVSWYQKHPGKAPKLMIYDVTNRPSGVSNRFSGSKSGNTASLTISGL
QAEDEADYYCSTYTRSNTLVFGPGTKVTVL

Sorrento L33H11 VH (SEQ ID NO: 30241)

QVQLVQSGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

Sorrento L33H11 VL (SEQ ID NO: 30242)

LPVLTQPASVSGSPGQSITISCTGTSSDVGGYNYVSWYQQHPGKAPKLMIYDVTNRPSGVSNRFSGSKSGNTASLTISGL
QAEDEADYYCSSYTSSNTLLFGGGTQLTVL

Sorrento L32A9 VH (SEQ ID NO: 30243)

QVQLVQSGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

Sorrento L32A9 VL (SEQ ID NO: 30244)

QSVVTQPPSVSAAPGQKVTISCSGSSSNIGNNYVSWYQQLPGTAPKLLIYDNNKRHSGIPDRFSGSTSDTSATLGITRLQT
GDEADYYCGTWDSSLSAYVFGTGTKVTVL

Figure 89C

Sorrento L32D10 VH (SEQ ID NO: 30245)

QVQLVQSGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

Sorrento L32D10 VL (SEQ ID NO: 30246)

QSVLTQPPSASGSPGQSVTISCTGTSSDVGGYDYVSWYQQHQGKAPKLMIYDVSNRPSGVSNRFSGSKSGNTASLTISGL
QAEDEADYYCSSYTSSTTLVFGGGTKLTVL

Sorrento L32A4 VH (SEQ ID NO: 30247)

QVQLVQSGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

Sorrento L32A4 VL (SEQ ID NO: 30248)

QSVLTQPASVSGSPGQSITISCTGTSSDIGAYNFVSWYQQHPGKAPKLMIYGVSNRPSGVSSRFSGSKSGSTASLTISGLQ
AEDEADYYCSSYTTSGSAVFGTGTKLTVL

Sorrento L3A1 VH (SEQ ID NO: 30249)

EVQLLESGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

Sorrento L3A1 VL (SEQ ID NO: 30250)

QSVLTQPASVSGSPGQSITISCTGTSSDIGAYNFVSWYQQHPGKAPKLMIYGVSNRPSGVSSRFSGSKSGSTASLTITGLQ
AEDEADYYCSSYTTSGSAVFGTGTKLTVL

Sorrento L3A10 VH (SEQ ID NO: 30251)

EVQLLESGGGVVQPGRSLRVSCAASGFTFSNHAMHWVRQAPGKGLEWVAVISYDGSKKFYSDSVRGRFTISRDNSKNT
LYLQMNSLRPEDTAVYYCAKGAHGYTSGWHDYWGQGTLVTVSS

Sorrento L3A10 VL (SEQ ID NO: 30252)

DVVMTQSPSSLSASVGDRVSITCRASQNIGRYLNWYQQKPGKAPKLLVSAASSLQGGVPSRFSGSGSGTDFTLTISRLQP
EDFATYFCQQTYSSPQCTFGQGTKVDIK

Sorrento L3C5 VH (SEQ ID NO: 30253)

QVQLVQSGSELKKPGASVKVSCKASGYTFTNYYMHWVRQAPGQGLEWMGIINPSGGATNYAQKFQGRVTMTRDTST
STVYMELSSLRSEDTAVYYCARDSGYDLGYGMDVWGQGTLVTVSS

Sorrento L3C5 VL (SEQ ID NO: 30254)

QSVLTQPASVSGSPGQSITISCTGTSSDVGGYNYVSWYQQHPGKAPKLMIYDVSNRPSGASNRFSGSKSGNTASLTISGL
QAEDEADYYCSSYTNRNTLLFGGGTKLTVL

Sorrento L3E3 VH (SEQ ID NO: 30255)

EVQLLESGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

Sorrento L3E3 VL (SEQ ID NO: 30256)

QSVLTQPASASGSPGQSITISCTGTSSDVGGYNYVSWYQQHPGKAPKLMIYDVSNRPSGVSNRFSGSKSGNTASLTISGL
QAEDEANYYCSSYTSSSTNVFGTGTKVTVL

Figure 81A additional TIM-3 sequences

AnaptysBio/Tesaro APE5137 VH (SEQ ID NO: 30257)

EVQLLESGGGLVQPGGSLRLSCAAASGFTFSSYDMSWVRQAPGKGLDWVSTISGGGTYTYYQDSVKGRFTISRDNSKN
TLYLQMNSLRAEDTAVYYCASMDYWGQGTTVTVSSA

AnaptysBio/Tesaro APE5137 VL (SEQ ID NO: 30258)

DIQMTQSPSSLSASVGDRVTITCRASQSIRRYLNWYHQKPGKAPKLLIYGASTLQSGVPSRFSGSGSGTDFTLTISSLQPE
DFAVYYCQQSHSAPLTFGGGTKVEIKR

AnaptysBio/Tesaro APE5121 VH (SEQ ID NO: 30259)

EVQVLESGGGLVQPGGSLRLYCVASGFTFSGSYAMSWVRQAPGKGLEWVSAISGSGGSTYYADSVKGRFTISRDNSKN
TLYLQMNSLRAEDTAVYYCAKKYYVGPADYWGQGTLVTVSSG

AnaptysBio/Tesaro APE5121 VL (SEQ ID NO: 30260)

DIVMTQSPDSLAVSLGERATINCKSSQSVLYSSNNKNYLAWYQHKPGQPPKLLIYWASTRESGVPDRFSGSGSGTDFTL
TISSLQAEDVAVYYCQQYYSSPLTFGGGTKIEVK

Dana-Farber/Novartis ABTIM3-hum03 VH (SEQ ID NO: 30261)

QVQLVQSGAEVKKPGASVKVSCKASGYTFTSYNMHWVRQAPGQGLEWIGDIYPGQGDTSYNQKFKGRATMTADKST
STVYMELSSLRSEDTAVYYCARVGGAFPMDYWGQGTLVTVSS

Dana-Farber/Novartis ABTIM3-hum03 VL (SEQ ID NO: 30262)

DIVLTQSPDSLAVSLGERATINCRASESVEYYGTSLMQWYQQKPGQPPKLLIYAASNVESGVPDRFSGSGSGTDFTLTISS
LQAEDVAVYYCQQSRKDPSTFGGGTKVEIK

Dana-Farber/Novartis ABTIM3-hum11 VH (SEQ ID NO: 30263)

QVQLVQSGAEVKKPGSSVKVSCKASGYTFTSYNMHWVRQAPGQGLEWMGDIYPGNGDTSYNQKFKGRVTITADKST
STVYMELSSLRSEDTAVYYCARVGGAFPMDYWGQGTTVTVSS

Dana-Farber/Novartis ABTIM3-hum11 VL (SEQ ID NO: 30264)

AIQLTQSPSSLSASVGDRVTITCRASESVEYYGTSLMQWYQQKPGKAPKLLIYAASNVESGVPSRFSGSGSGTDFTLTISS
LQPEDFATYFCQQSRKDPSTFGGGTKVEIK

Dana-Farber/Novartis ABTIM3-hum21 VH (SEQ ID NO: 30265)

QVQLVQSGAEVKKPGASVKVSCKASGYTFTSYNMHWVRQAPGQGLEWIGDIYPGQGDTSYNQKFKGRATMTADKST
STVYMELSSLRSEDTAVYYCARVGGAFPMDYWGQGTLVTVSS

Dana-Farber/Novartis ABTIM3-hum21 VL (SEQ ID NO: 30266)

DIVLTQSPDSLAVSLGERATINCRASESVEYYGTSLMQWYQQKPGQPPKLLIYAASNVESGVPDRFSGSGSGTDFTLTISS
LQAEDVAVYYCQQSRKDPSTFGGGTKVEIK

KHK 4177 VH (SEQ ID NO: 30267)

QVQLQESGPGLVKPSETLSLTCTVSGGSISSYYWSWIRQPPGKGLEWIGYIFHSGSTNYNPSLKSRVTISVDTSKNQFSLK
LSSVTAADTAVYYCARDGEYFDMLTGFDYWGQGTLVTVSS

KHK 4177 VL (SEQ ID NO: 30268)

RCDIQMTQSPSSLSASVGDRVTITCRASQGISSWLAWYQQKPEKAPKSLIYAASSLQSGVPSRFSGSGSGTDFTLTISSLQP
EDFATYYCQQYNSYPRTFGQGTKVEIK

Figure 81B

KHK 4545 VH (SEQ ID NO: 30269)

QVQLQESGPGLVKPSETLSLTCTVSGGSFSRGGYYWNWIRQPPGKGLEWIGYIYYSGSTNYNPSLKSRVTISLDTSKNQF
SLKLSSVTAADTAVYYCARDHYSSSWTFDYWGQGTLVTVSS

KHK 4545 VL (SEQ ID NO: 30270)

EIVLTQSPATLSLSPGERATLSCRASQSVSSYLAWYQQKPGQAPRLLIYDASNRATGIPARFSGSGSGTDFTLTISSLEPED
FAVYYCQQRSNWPPTFGQGTKLEIK

KHK 8123 VH (SEQ ID NO: 30271)

QVQLVQSGAEVKKPGASVKVSCKASGYTFTSYWMHWVRQAPGQGLEWMGEINPSNGRTNYNEKFKTRVTITADTSTS
TAYMELSSLRSEDTAVYYCARGYYLYFDYWGQGTLVTVSS

KHK 8123 VL (SEQ ID NO: 30272)

DIQMTQSPSSLSASVGDRVTITCHASQGIRINIGWYQQKPGKAPKLLIYHGTNLEDGVPSRFSGSGSGTDFTLTISSLQPED
FATYYCVQYGQFPWTFGQGTKLEIK

Jounce mAb15 VH (SEQ ID NO: 30273)

QVQLKESGPGLVAPSQSLSITCTVSGFSLTGYGVTWVRQPPGKGLEWLGMIWGDGNTDYNSGLKSRLNISKDNSKSQV
FLKMNSLQTDDTARYYCARSYYYGPPDYWGQGTTLTVSS

Jounce mAb15 VL (SEQ ID NO: 30274)

DIVMTQSPSSLAMSVGQKVTMSCKSSQSLLNSRSQKNYLAWYQRKPGQSPKLLLYFASTRESGVPDRFIGSGSGTDFTL
TISSVQAEDLADYFCHQHYNTPYTFGGGTKLEIK

Jounce mAb58 VH (SEQ ID NO: 30275)

QIQLVQSGPELKKPGETVKISCKASGYTFTTYGMSWVKQAPGKGLKLMGWINTYSGAPTYADDFKGRFAFSLETSASA
AYLQINNLKNEDTATYFCARKPPHYYVNSFDYWGQGTTLTVSS

Jounce mAb58 VL (SEQ ID NO: 30276)

DIVMTQSPATLSVTPGDRVSLSCRASQSISDYLHWYQQKSHESPRLLIKYASQSISGIPSRFSGSGSGSDFTLSINSVEPEDV
GVYYCQNGHSFPYTFGGGTKLEIK

Roche TIM3-0433 VH (SEQ ID NO: 30277)

QITLKESGPTLVKPTQTLTLTCTFSGFSLSTSGMSVGWIRQPPGKGLEWLAHIWLNDDVFFNPALKSRLTITKDTSKNQV
VLTMTNMDPVDTATYYCVRANGYLYALDYWGQGTLVTVSS

Roche TIM3-0433 VH (SEQ ID NO: 30278)

ETTLTQSPAFMSATPGDKVNIACSASSSVSYTQWYQQKPGEAPKLWIYDAFKLAPGIPPRFSGSGYGTDFTLTINNIESED
AAYYFCHQWSSYPWTFGQGTKLEIK

Roche TIM3-0434 VH (SEQ ID NO: 30279)

QITLKESGPTLVKPTQTLTLTCTFSGFSLSTSGMSVGWIRQPPGKGLEWLAHIWLNDDVFFNPALKSRLTITKDTSKNQV
VLTMTNMDPVDTATYYCVRANGYLYALDYWGQGTLVTVSS

Roche TIM3-0434 VH (SEQ ID NO: 30280)

DIQLTQSPSFLSASVGDRVTITCSASSSVSYTQWYQQKPGKAPKLWIYDAFKLAPGVPSRFSGSGSGTEFTLTISSLQPEDF
ATYFCHQWSSYPWTFGQGTKLEIK

Figure 81C

Roche TIM3-0438 VH (SEQ ID NO: 30281)

EVQLVESGGGLVQPGGSLRLSCAASGFNIKTTYMHWVRQAPGKGLEWVGRIDPADDNTKYAPKFQGKATISADTSKN
TAYLQMNSLRAEDTAVYYCVRDFGYVAWFAYWGQGTLVTVSS

Roche TIM3-0438 VH (SEQ ID NO: 30282)

DIVMTQSPLSLPVTPGEPASISCRASQSVDNYVAWYLQKPGQSPQLLIYYASNRYIGVPDRFSGSGSGTDFTLKISRVEAE
DVGVYYCQQHYSSPYTFGQGTKVEIK

Roche TIM3-0443 VH (SEQ ID NO: 30283)

EVQLVESGGGLVQPGGSLRLSCAASGFNIKTTYMHWVRQAPGKGLEWVGRIDPADDNTKYAPKFQGKATISADTSKN
TAYLQMNSLRAEDTAVYYCVRDFGYVAWFAYWGQGTLVTFSS

Roche TIM3-0443 VH (SEQ ID NO: 30284)

DIVMTQSPLSLPVTPGEPASISCRASQSVDNYVAWYLQKPGQSPQLLIYYASNRYIGVPDRFSGSGSGTDFTLKISRVEAE
DVGVYYCQQHYSSPYTFGQGTKVEIK

Figure 82 additional BTLA sequences

Medarex 3C2 VH (SEQ ID NO: 30285)

QVQLQESGPGLVKPSETLSLTCTISGGSISNYYWNWIRQPPGKGLEWIGYIYYSTSTKYNPSLKSRVTMSVETSKNQFSL
KLSSVTAADTAVYYCARVKVYSTGWFFDYWGQGTLVTVSS

Medarex 3C2 VL (SEQ ID NO: 30286)

AIQLTQSPSSLSASVGDRVTITCRASQGISSALAWYQQKPGKAPKLLIYDASSLESGVPSRFSGSGSGTDFTLTISSLQPED
FATYYCQQFNSYPLTFGGGTKVEIK

Medarex 11E2 VH (SEQ ID NO: 30287)

EVQLVESGGGVIRPGGSLRLSCAASGFTFDDYGMSWVRQAPGKGLEWVSGINWNGGSTGYAASVKGRFTISRDNAKN
SLYLQMNSLRAEDSALYYCARDYYYGPGSPNYFYYAMDVWGQGTTVTVSS

Medarex 11E2 VL (SEQ ID NO: 30288)

DIQMTQSPSSLSASVGDRVTITCRASQGISSWLAWYQQKPEKAPKSLIYAASSLQSGVPSRFSGSGSGTDFTLTISSLQPED
FATYYCQQYNSYPRTFGQGTKVEIK

Medarex 4C7 VH (SEQ ID NO: 30289)

QVQLQESGPGLVKPSETLSLTCTVHGGSINHYYWSWIRQPPGKGLEWIGYIYYSGSTKYNPSLKSRVSISVDTSKNQFSL
KLTSVTAADTAVYYCAREWPYYYYEMDVWGQGTTVTVSS

Medarex 4C7 VL (SEQ ID NO: 30290)

EIVLTQSPGTLSLSPGERATLSCRASQSVSSSYLAWYQQKPGQAPRLLIYGASSRATGIPDRFSGSGSGTDFTLTISRLEPE
DFAVYYCQQYGSSFRTFGQGTKVEIK

Medarex 8D5 VH (SEQ ID NO: 30291)

EVQLVESGGGLVQPGGSLRLSCAASGFTISSYDMHWVRQATGKGLEWVSVIGPAGDTYYPGSVKGRFTISRENAKNSL
YLQMNSLRAGDTAVYYCAREGMAAHNYYGMDVWGQGTTVTVSS

Medarex 8D5 VL (SEQ ID NO: 30292)

EIVLTQSPATLSLSPGERATLSCRASQSVSSYLAWYQQKPGQAPRLLIYDASNRATGIPARFSGSGSGTDFTLTISSLEPED
FAVYYCQQRSNWPPITFGQGTRLEIK

Figure 83A additional TIGIT sequences

Genentech 10A7 VH (SEQ ID NO: 30293)

EVQLVESGGGLTQPGKSLKLSCEASGFTFSSFTMHWVRQSPGKGLEWVAFIRSGSGIVFYADAVRGRFTISRDNAKNLL
FLQMNDLKSEDTAMYYCARRPLGHNTFDSWGQGTLVTVSS

Genentech 10A7 VL (SEQ ID NO: 30294)

DIVMTQSPSSLAVSPGEKVTMTCKSSQSLYYSGVKENLLAWYQQKPGQSPKLLIYYASIRFTGVPDRFTGSGSGTDYTLT
ITSVQAEDMGQYFCQQGINNPLTFGDGTKLEIK

Genentech 1F4 VH (SEQ ID NO: 30295)

EVQLQQSGPELVKPGTSMKISCKASGYSFTGHLMNWVKQSHGKNLEWIGLIIPYNGGTSYNQKFKGKATLTVDKSSST
AYMELLSLTSDDSAVYFCSRGLRGFYAMDYWGQGTSVTVSS

Genentech 1F4 VL (SEQ ID NO: 30296)

DVVLTQTPLSLSVSFGDQVSISCRSSQSLVNSYGNTFLSWYLHKPGQSPQLLIFGISNRFSGVPDRFSGSGSGTDFTLKISTI
KPEDLGMYYCLQGTHQPPTFGPGTKLEVK

Genentech 4.1D3 VH (SEQ ID NO: 30297)

QVQLQQSGPGLVKPSQTLSLTCAISGDSVSSNSAAWNWIRQSPSRGLEWLGKTYYRFKWYSDYAVSVKGRITINPDTSK
NQFSLQLNSVTPEDTAVFYCTRESTTYDLLAGPFDYWGQGTLVTVSS

Genentech 4.1D3 VL (SEQ ID NO: 30298)

DIVMTQSPDSLAVSLGERATINCKSSQTVLYSSNNKKYLAWYQQKPGQPPNLLIYWASTRESGVPDRFSGSGSGTDFTL
TISSLQAEDVAVYYCQQYYSTPFTFGPGTKVEIK

Genentech 4.1D3.Q1E VH (SEQ ID NO: 30299)

EVQLQQSGPGLVKPSQTLSLTCAISGDSVSSNSAAWNWIRQSPSRGLEWLGKTYYRFKWYSDYAVSVKGRITINPDTSK
NQFSLQLNSVTPEDTAVFYCTRESTTYDLLAGPFDYWGQGTLVTVSS

Genentech 4.1D3.Q1E VL (SEQ ID NO: 30300)

DIVMTQSPDSLAVSLGERATINCKSSQTVLYSSNNKKYLAWYQQKPGQPPNLLIYWASTRESGVPDRFSGSGSGTDFTL
TISSLQAEDVAVYYCQQYYSTPFTFGPGTKVEIK

Merck MEB125.31C6.A1.205 VH4/VL1 VH (SEQ ID NO: 30301)

EVQLVQSGAEVKKPGASVKVSCKASGYTFSSYVMHWVRQAPGQGLEWIGYIDPYNDGAKYAQKFQGRVTLTSDKSTS
TVYMELSSLRSEDTAVYYCARGGPYGWYFDVWGQGTTVTVSS

Merck MEB125.31C6.A1.205 VH4/VL1 VL (SEQ ID NO: 30302)

DIQMTQSPSSLSASVGDRVTITCRASEHIYSYLSWYQQKPGKAPKLLIYNAKTLAEGVPSRFSGSGSGTDFTLTISSLQPE
DFATYYCQHHFGSPLTFGQGTRLEIK

Merck MEB125.31C6.A1.205 VH5/VL4 VH (SEQ ID NO: 30303)

EVQLVQSGAEVKKPGSSVKVSCKASGYTFSSYVMHWVRQAPGQGLEWIGYIDPYNDGAKYAQKFQGRVTLTSDKSTS
TAYMELSSLRSEDTAVYYCARGGPYGWYFDVWGQGTTVTVSS

Merck MEB125.31C6.A1.205 VH5/VL4 VL (SEQ ID NO: 30304)

DIQMTQSPSSLSASVGDRVTITCRASEHIYSYLSWYQQKPGKVPKLLIYNAKTLAEGVPSRFSGSGSGTQFTLTISSLQPE
DVATYYCQHHFGSPLTFGQGTRLEIK

Figure 83B

Merck MEB125.31C6.A1.205 VH5/VL3 VH (SEQ ID NO: 30305)

EVQLVQSGAEVKKPGSSVKVSCKASGYTFSSYVMHWVRQAPGQGLEWIGYIDPYNDGAKYAQKFQGRVTLTSDKSTS
TAYMELSSLRSEDTAVYYCARGGPYGWYFDVWGQGTTVTVSS

Merck MEB125.31C6.A1.205 VH5/VL3 VL (SEQ ID NO: 30306)

DIQMTQSPSSLSASVGDRVTITCRASEHIYSYLSWYQQKPGKVPKLLIYNAKTLAEGVPSRFSGSGSGTDFTLTISSLQPE
DVATYYCQHHFGSPLTFGQGTRLEIK

Merck Hu14D7 VH1 (SEQ ID NO: 30307)

EVQLVESGGGLVQPGGSLKLSCAASGFTFSGAWMDWVRQAPGKGLEWVAEIRTKVNNHATNYGESVKGRFTISRDDS
KSTVYLQMNSLRAEDTAVYYCRGALYDGFYFDYWGQGTLVTVSS

Merck Hu14D7 VH2 (SEQ ID NO: 30308)

EVQLVESGGGLVQPGGSLKLSCAASGFTFSGAWMDWVRQAPGKGLEWVAEIRTKVNNHATNYGESVKGRFTISRDDS
KSSVYLQMNSLRAEDTAVYYCRGALYDGFYFDYWGQGTLVTVSS

Merck Hu14D7 VH3 (SEQ ID NO: 30309)

EVQLVESGGGLVQPGGSLKLSCAASGFTFSGAWMDWVRQAPGKGLEWVAEIRTKVNNHATNYGESVKGRFTISRDDS
KNTVYLQMNSLRAEDTAVYYCRGALYDGFYFDYWGQGTLVTVSS

Merck Hu14D7 VL1 (SEQ ID NO: 30310)

EIVLTQSPATLSLSPGERATLSCSASSSVSSGYLYWYQQKPGQAPKLWIYGTSTLASGVPARFSGSGSGTDYTLTISSLEP
EDFAVYYCHQWSSFPYTFGQGTKLEIK

Merck Hu14D7 VL2 (SEQ ID NO: 30311)

EIVLTQSPATLSLSPGERATLSCSASSSVSSGYLYWYQQKPGQAPRLWIYGTSTLASGVPARFSGSGSGTDYTLTISSLEPE
DFAVYYCHQWSSFPYTFGQGTKLEIK

Merck Hu14D7 VL3 (SEQ ID NO: 30312)

EIVLTQSPATLSLSPGERATLSCSASSSVSSGYLYWYQQKPGQAPRLWIYGTSTLASGIPARFSGSGSGTDYTLTISSLEPE
DFAVYYCHQWSSFPYTFGQGTKLEIK

Merck Hu26B10 VH1 (SEQ ID NO: 30313)

EVQLVQSGAEVKKPGASVKISCKTSGYTFTEFTMHWVKQAPGKGLEWIGGLKPDNGGISYNQKFKGRATLTVDKSTNT
AYMELSSLRSEDTAVYYCARGAYYRYDADYWGQGTLVTVSS

Merck Hu26B10 VH2 (SEQ ID NO: 30314)

EVQLVQSGAEVKKPGASVKISCKTSGYTFTEFTMHWVRQAPGKGLEWIGGLKPDNGGISYNQKFKGRATLTVDKSTST
AYMELSSLRSEDTAVYYCARGAYYRYDADYWGQGTLVTVSS

Merck Hu26B10 VH3 (SEQ ID NO: 30315)

EVQLVQSGAEVKKPGASVKISCKVSGYTFTEFTMHWVRQAPGKGLEWIGGLKPDNGGISYNQKFKGRATLTVDTSTST
AYMELSSLRSEDTAVYYCARGAYYRYDADYWGQGTLVTVSS

Merck Hu26B10 VL1 (SEQ ID NO: 30316)

DIQLTQSPSSLSASVGDRVTITCKASQDVKTAVAWYQQKPGKAPKLLIYSASYRNTGVPDRFSGSGSGTDFTFTISSLQPE
DFATYYCQQHYSTPFTFGQGTKLEIK

Figure 83C

Merck Hu26B10 VL2 (SEQ ID NO: 30317)

DIQLTQSPSSLSASVGDRVTITCKASQDVKTAVAWYQQKPGKAPKLLIYSASYRNTGVPSRFSGSGSGTDFTFTISSLQPE
DFATYYCQQHYSTPFTFGQGTKLEIK

Merck Hu26B10 VL3 (SEQ ID NO: 30318)

DIQLTQSPSSLSASVGDRVTITCKASQDVKTAVAWYQQKPGKAPKLLIYSASYRNTGVPSRFSGSGSGTDFTLTISSLQPE
DFATYYCQQHYSTPFTFGQGTKLEIK

BMS 15A6 VH (SEQ ID NO: 30319)

QLQLQESGPGLVKPSETLSLTCTVSGGSISSSRYFWGWIRQPPGKGLEWIGYIYYRGSTYYNPSLKSRVTIAVDTSKNQFS
LKLSSVTAADTAVYYCASSSAWYFDYWGQGNLVTVSS

BMS 15A6 VL (SEQ ID NO: 30320)

EIVLTQSPGTLSLSPGERATLSCRASQSVSSSYLAWYQQKPGQAPRLLIYGASSRATGIPDRFSGSGSGTDFTLTISRLEPE
DFAVYYCQQYGSLYTFGQGTKLEIK

BMS 22G2 VH (SEQ ID NO: 30321)

QVHLQESGPGLVKPSETLSLTCTVSGGSVSSGIYYWSWIRQPPGKGLEWIGYIYYSGSTNYNPSLKSRVTISVDTSKNQFS
LKLSSVTAADTAVYYCARDYYVSGNYYNVDYYFFGVDVWGQGTTVTVSS

BMS 22G2 VL (SEQ ID NO: 30322)

EIVLTQSPATLSLSPGERATLSCRASQSVSSYLAWYQQKPGQAPRLLIYDASNRATGIPARFSGSGSGTDFTLTISSLEPED
FAVYYCQQRSNWPPLFTFGPGTKVDIK

BMS 11G11 VH (SEQ ID NO: 30323)

QLQLQESGPGLVKPSETLSLTCTVSGGSISSSSHYWGWIRQPPGKGLEWIGNIFYSGHTYYNPSLKSRVTISVDTSKNQFS
LKLSSVTAADTAVYYCARQGLLWFGGLSPYYFDYWGQGTLVTVSS

BMS 11G11 VL (SEQ ID NO: 30324)

EIVLTQSPATLSLSPGERATLSCRASQSVSSYLAWYQQKPGQAPRLLIYDASNRATGIPARFSGSGSGTDFTLTISSLEPED
FAVYYCQQRSNWPTFGQGTKLEIK

BMS 10D7 VH (SEQ ID NO: 30325)

QGQLVQSGAEVKKPGSSVKVSCKASGGIFRNYAISWVRQAPGQGLEWMGGIIPFFGTANYAQKFQGRVTITADESTSTA
YMELSSLRSEDTAVYYCARGGAAAGTTRYGYYYYGMDVWGQGTTVTVSS

BMS 10D7 VL (SEQ ID NO: 30326)

DIQMTQSPSSLSASVGDRVTITCRASQGISSWLAWYQQKPEKAPKSLIYAASSLQSGVPSRFSGSGSGTDFTLTISSLQPED
FATYYCQQYNSYPITFGQGTRLEIK

Oncomed 313R19 VH (SEQ ID NO: 30327)

QVQLQESGPGLVKPSETLSLTCTVSGFSLSSSYMSWIRQPPGKGLEWIGHGSNGNTYYANWAKGRVTISKSSNQVSLKL
SSVTAADTAVYYCARGGYRTSGMDPWGQGTLVTVSS

Oncomed 313R19 VL (SEQ ID NO: 30328)

DIQMTQSPSSLSASVGDRVTITCQASQNIYSDLAWYQQKPGKAPKLLIYRASTLASGVPSRFSGSGSGTDFTLTISSLQPE
DFATYYCQQEHLVAWIYNVFGQGTKVEIKR

Figure 83D

Oncomed 313M32 VH (SEQ ID NO: 30329)

QVQLQESGPGLVKPSETLSLTCAVSGYSITSDYAWNWIRQPPGKGLEWIGYISYSGSTSYNPSLRSRVTISRDTSKNQFFL
KLSSVTAADTAVYYCARRQVGLGFAYWGQGTLVTVSS

Oncomed 313M32 VL (SEQ ID NO: 30330)

DIQMTQSPSSLSASVGDRVTITCKASQDVSTAVAWYQQKPGKAPKLLIYSASYRYTGVPSRFSGSGSGTDFTFTISSLQPE
DIATYYCQQHYSTPWTFG

Figure 84A (anti BTLA4 variable heavy and light chains + CDRs)

| What: anti-BTLA XENP20269 9C6_H0L0 | sequence | SEQ ID NO: |
|---|---|---|
| Variable heavy (vh) domain | QVQLKESGPGLVAPSQSLSITCTVSGFSLIGYGVNWVRQPPGKGLEWLGMIWIDGSTDYNSALKSRLSIN KDNSKSQVFLKMNSLQTDDTARYYCARDRPDGRAMDYWGQGTSVTVSS | 30331 |
| vhCDR1 | GYGVN | 30332 |
| vhCDR2 | MIWIDGSTDYNSALKS | 30333 |
| vhCDR3 | DRPDGRAMDY | 30334 |
| Variable light (vl) domain | SIVMTQTPKFLLVSAGDRVTITCKASQSVSNDVAWYQQKPGQSPKLLIYYASNRYTGVPDRFTGSGYGTD FTFTISTVQAEDLAVYFCQQDYSSPTFGGGTKLEIK | 30335 |
| vlCDR1 | KASQSVSNDVA | 30336 |
| vlCDR2 | YASNRYT | 30337 |
| vlCDR3 | QQDYSSPT | 30338 |

Figure 84B

| What: anti-BTLA XENP20872 9C6_H1.1L1 | sequence | SEQ ID NO: |
|---|---|---|
| Variable heavy (vh) domain | QVQLKESGAEVKKPGASVKVSCKVSGFSLTGYGVNWVRQAPGQGLEWMGMIWIDGSTDYNSKFQGRVTMT KDNSKSTVYMELSSLRSEDTAVYYCARDRPDGRAMDYWGQGTMVTVSS | 30339 |
| vhCDR1 | GYGVN | 30340 |
| vhCDR2 | MIWIDGSTDYNSKFQG | 30341 |
| vhCDR3 | DRPDGRAMDY | 30342 |
| Variable light (vl) domain | SIVMTQSPDSLAVSLGERATINCKASQSVSNDVAWYQQKPGQSPKLLIYYASNRYTGVPDRFTGSGYGTD FTLTISSLQAEDVAVYFCQQDYSSPTFGGGTKLEIK | 30343 |
| vlCDR1 | KASQSVSNDVA | 30344 |
| vlCDR2 | YASNRYT | 30345 |
| vlCDR3 | QQDYSSPT | 30346 |

Figure 84C (anti BTLA variable heavy and light chains + CDRs)

| What: anti-BTLA XENP020882 9C6_H1.1L1 | sequence | SEQ ID NO: |
|---|---|---|
| Variable heavy (vh) domain | QVQLVQSGAEVKKPGASVKVSCKVSGFSLTGYGVNWVRQAPGQGLEWMGMIWIDGSTDYNSKFQGRLSIN KDNSKSTVYMELSSLRSEDTAVYYCARDRPDGRAMDYWGQGTMVTVSS | 30347 |
| vhCDR1 | GYGVN | 30348 |
| vhCDR2 | MIWIDGSTDYNSKFQG | 30349 |
| vhCDR3 | DRPDGRAMDY | 30350 |
| Variable light (vl) domain | SIVMTQSPDSLAVSLGERATINCKASQSVSNDVAWYQQKPGQSPKLLIYYASNRYTGVPDRFTGSGYGTD FTLTISSLQAEDVAVYFCQQDYSSPTFGGGTKLEIK | 30351 |
| vlCDR1 | KASQSVSNDVA | 30352 |
| vlCDR2 | YASNRYT | 30353 |
| vlCDR3 | QQDYSSPT | 30354 |

Figure 85

| 1st/2nd antigens | PD-1 | PD-L1 | CTLA-4 | LAG-3 | TIM-3 | BTLA | TIGIT |
|---|---|---|---|---|---|---|---|
| ICOS | A, B, C, H, I | B, H, I | B, D, E, H, I | B, F, H, I | B, H, I | B, G, H, I | B, H, I |
| GITR | A, C, H, I | H, I | D, E, H, I | F, H, I | H, I | G, H, I | H, I |
| OX40 | A, C, H, I | H, I | D, E, H, I | F, H, I | H, I | G, H, I | H, I |
| 4-1BB | A, C, H, I | H, I | D, E, H, I | F, H, I | H, I | G, H, I | H, I |

Figure 86

XENP22917

\>XENP022917 [ICOS]_H0_L0.38_Fab-1G6_L1.194_H1.279 Fab-Fc Heavy Chain (SEQ ID NO: 30355)
QVQLVQSGAEVKKPGASVKVSCKASGYTFTGYYMHWVRQAPGQGLEWMGWINPHSGGTNYAQKFQGRVTMTRDTSISTAYME
LSRLRSDDTAVYYCARTYYYDSSGYYHDAFDIWGQGTMVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVLHEALHSHYTQKSLSLSPGK \>XENP022917 [ICOS]_H0_L0.38_Fab-1G6_L1.194_H1.279 scFv-Fc Heavy Chain (SEQ ID NO: 30356)
EIVLTQSPATLSASPGERVTLTCRASQSVGNDVAWYQQKPGQAPRLLINYASHRYTGVPDRFTGSGYGTEFTLTISSVQSED
FGVYYCQQDFSSPRTFGGGTKVEIK/GKPGSGKPGSGKPGSGKPGS/EVQLVESGGGLVKPGGSLRLSCVASGFTFSNYWMN
WVRQAPGKGLEWVAEIRLYSNNYATHYAESVKGRFTISRDDSKSTLYLQMNNLKTEDTGVYYCTRYYGNYGGYFDVWGRGTL
VTVSS/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVLHEALHSHYTQKSLSLSPGK \>XENP022917 [ICOS]_H0_L0.38_Fab-1G6_L1.194_H1.279 Light Chain (SEQ ID NO: 30357)
DIQMTQSPSSVSASVGDRVTITCQASQDISSLLAWYQQKPGKAPKLLIYAASSLQSGVPSRFSGSGSGTDFTLTISSLQPED
FATYYCQQAESFPWTFGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

XENP22977

\>XENP022977 [ICOS]_H0_L0.37_Fab-1G6_L1.194_H1.279 Fab-Fc Heavy Chain (SEQ ID NO: 30358)
QVQLVQSGAEVKKPGASVKVSCKASGYTFTGYYMHWVRQAPGQGLEWMGWINPHSGGTNYAQKFQGRVTMTRDTSISTAYME
LSRLRSDDTAVYYCARTYYYDSSGYYHDAFDIWGQGTMVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAPPVAGP
SVFLFPPKPKDTLMISRTPEVTCVVVDVKHEDPEVKFNWYVDGVEVHNAKTKPREEEYNSTYRVVSVLTVLHQDWLNGKEYK
CKVSNKALPAPIEKTISKAKGQPREPQVYTLPPSREEMTKNQVSLTCDVSGFYPSDIAVEWESDGQPENNYKTTPPVLDSDG
SFFLYSKLTVDKSRWEQGDVFSCSVLHEALHSHYTQKSLSLSPGK \>XENP022977 [ICOS]_H0_L0.37_Fab-1G6_L1.194_H1.279 scFv-Fc Heavy Chain (SEQ ID NO: 30359)
EIVLTQSPATLSASPGERVTLTCRASQSVGNDVAWYQQKPGQAPRLLINYASHRYTGVPDRFTGSGYGTEFTLTISSVQSED
FGVYYCQQDFSSPRTFGGGTKVEIK/GKPGSGKPGSGKPGSGKPGS/EVQLVESGGGLVKPGGSLRLSCVASGFTFSNYWMN
WVRQAPGKGLEWVAEIRLYSNNYATHYAESVKGRFTISRDDSKSTLYLQMNNLKTEDTGVYYCTRYYGNYGGYFDVWGRGTL
VTVSS/EPKSSDKTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVLHEALHSHYTQKSLSLSPGK \>XENP022977 [ICOS]_H0_L0.37_Fab-1G6_L1.194_H1.279 Light Chain (SEQ ID NO: 30360)
DIQMTQSPSSVSASVGDRVTITCQASQDISRLLAWYQQKPGKAPKLLIYAASSLQSGVPSRFSGSGSGTDFTLTISSLQPED
FATYYCQQAESFPWTFGQGTKVEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

Figure 96

**>XENP024901[ICOS] H0.66 L0 Fab-empty Fc(216) IgG1 PVA /S267K pI(-
) Isosteric A L368D/K370S/M428L/N434S-IgG1 C220S/S364K/E357Q/M428L/N434SXXX**

*XENP024901[ICOS]_H0.66_L0_Fab_IgG1_PVA_/S267K_pI(-
)_Isosteric_A_L368D/K370S/M428L/N434S Fab-Fc Heavy Chain* (SEQ ID NO: 30361)
QVQLVQSGAEVKKPGASVKVSCKASGYTFTGYYMHWVRQAPGQGLEWMGWINPRSGETIYAQKFQGRVTMTRDTSIS
TAYMELSSLRSEDTAVYYCARTYYYDTSGYYRDAFDVWGQGTMVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVLHEALHSHYTQKSLSLSPGK

*XENP024901 empty_Fc(216)_IgG1_C220S/S364K/E357Q/M428L/N434S empty-Fc Heavy
Chain* (SEQ ID NO: 30362)
EPKSSDKTHTCPPCPAPPVAGPSVFLFPPKPKDTLMISRTPEVTCVVVDVKHEDPEVKFNWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVLHEALHSHYTQKSLSLSPGK

*XENP024901[ICOS]_ L0 Light Chain* (SEQ ID NO: 30363)
DIQMTQSPSSVSASVGDRVTITCRASQGISRLLAWYQQKPGKAPKLLIYAASSLQSGVPSRFSGSGSGTDFTLTISS
LQPEDFATYYCQQANSFPWTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 97

A) XENP016470 huPD-L1 Fc(216) huIgG1-mIgG2aa Hinge(KasI) mIgG2aa CH2 CH3 (SEQ
ID NO: 30364)
FTVTVPKDLYVVEYGSNMTIECKFPVEKQLDLAALIVYWEMEDKNIIQFVHGEEDLKVQHSSYRQRARLLKDQLSLG
NAALQITDVKLQDAGVYRCMISYGGADYKRITVKVNAPYNKINQRILVVDPVTSEHELTCQAEGYPKAEVIWTSSDH
QVLSGKTTTTNSKREEKLFNVTSTLRINTTTNEIFYCTFRRLDPEENHTAELVIPELPLAHPPNER/EPKSSDKTHT
CPPCPAPNLLGGPSVFIFPPKIKDVLMISLSPMVTCVVVDVSEDDPDVQISWFVNNVEVLTAQTQTHREDYNSTLRV
VSALPIQHQDWMSGKEFKCKVNNKALPAPIERTISKPKGSVRAPQVYVLPPPEEEMTKKQVTLTCMVTDFMPEDIYV
EWTNNGKTELNYKNTEPVLDSDGSYFMYSKLRVEKKNWVERNSYSCSVVHEGLHNHHTTKSFSRTPGK

B) XENP017869 huPD-L2 Fc(216) huIgG1-mIgG2aa Hinge(KasI) mIgG2aa CH2 CH3 (SEQ
ID NO: 30365)
LFTVTVPKELYIIEHGSNVTLECNFDTGSHVNLGAITASLQKVENDTSPHRERATLLEEQLPLGKASFHIPQVQVRD
EGQYQCIIIYGVAWDYKYLTLKVKASYRKINTHILKVPETDEVELTCQATGYPLAEVSWPNVSVPANTSHSRTPEGL
YQVTSVLRLKPPPGRNFSCVFWNTHVRELTLASIDLQSQMEPRTHPT/EPKSSDKTHTCPPCPAPNLLGGPSVFIFP
PKIKDVLMISLSPMVTCVVVDVSEDDPDVQISWFVNNVEVLTAQTQTHREDYNSTLRVVSALPIQHQDWMSGKEFKC
KVNNKALPAPIERTISKPKGSVRAPQVYVLPPPEEEMTKKQVTLTCMVTDFMPEDIYVEWTNNGKTELNYKNTEPVL
DSDGSYFMYSKLRVEKKNWVERNSYSCSVVHEGLHNHHTTKSFSRTPGK — XmAb23104 (EC$_{80}$: 0.9 μg/mL; EC$_{50}$: 0.1 μg/mL; EC$_{20}$: 0.1 μg/mL)
▲ XENP20111 (EC$_{80}$: 0.9 μg/mL; EC$_{50}$: 1.9 μg/mL; EC$_{20}$: 3.9 μg/mL)
● XENP16432 (EC$_{80}$: 0.2 μg/mL; EC$_{50}$: 0.1 μg/mL; EC$_{20}$: 0.05 μg/mL)
■ XENP24901

— XmAb23104 (EC$_{80}$: 0.3 μg/mL; EC$_{50}$: 0.1 μg/mL; EC$_{20}$: 0.01 μg/mL)
▲ XENP20111 (EC$_{80}$: 0.6 μg/mL; EC$_{50}$: 1.5 μg/mL; EC$_{20}$: 3.4 μg/mL)
● XENP16432 (EC$_{80}$: 0.2 μg/mL; EC$_{50}$: 0.1 μg/mL; EC$_{20}$: 0.06 μg/mL)
■ XENP24901

Figure 99

>XENP023642 huICOSL Fc(216) IgG1 C220S/PVA /S267K (SEQ ID NO: 30366)
DTQEKEVRAMVGSDVELSCACPEGSRFDLNDVYVYWQTSESKTVVTYHIPQNSSLENVDSRYRNRALMSPAGMLRGD
FSLRLFNVTPQDEQKFHCLVLSQSLGFQEVLSVEVTLHVAANFSVPVVSAPHSPSQDELTFTCTSINGYPRPNVYWI
NKTDNSLLDQALQNDTVFLNMRGLYDVVSVLRIARTPSVNIGCCIENVLLQQNLTVGSQTGNDIGERDKITENPVST
GEKNAAT/EPKSSDKTHTCPPCPAPPVAGPSVFLFPPKPKDTLMISRTPEVTCVVVDVKHEDPEVKFNWYVDGVEVH
NAKTKPREEQYNSTYRVVSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNVFSCSVMHEALHNHYTQK
SLSLSPGK

Figure 100

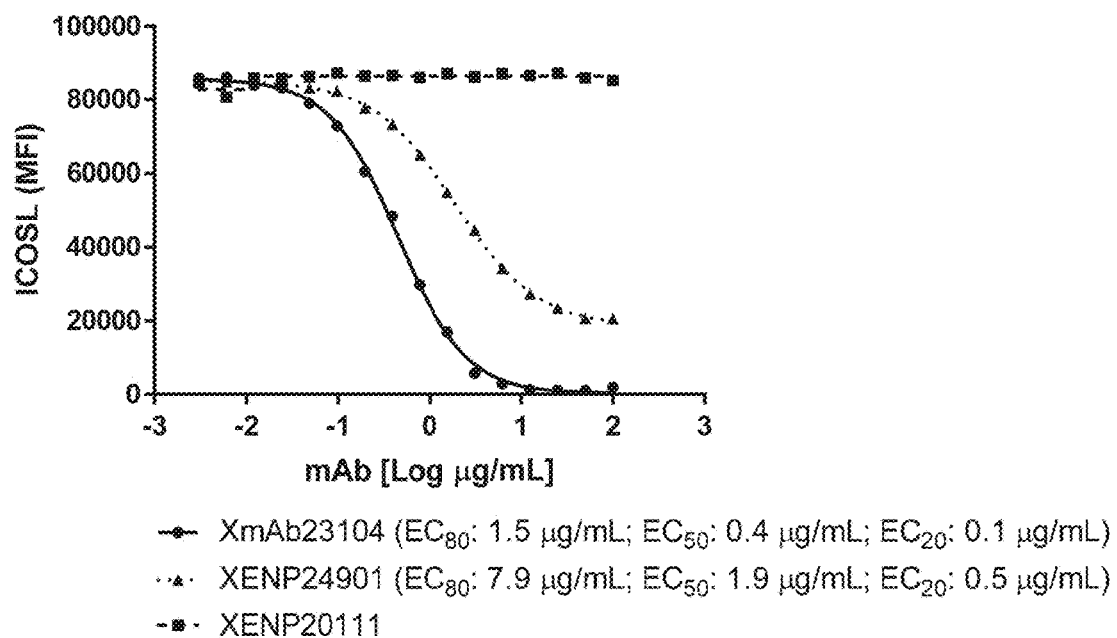

→ XmAb23104 (EC$_{80}$: 1.5 µg/mL; EC$_{50}$: 0.4 µg/mL; EC$_{20}$: 0.1 µg/mL)
⋯▲⋯ XENP24901 (EC$_{80}$: 7.9 µg/mL; EC$_{50}$: 1.9 µg/mL; EC$_{20}$: 0.5 µg/mL)
-■- XENP20111

Figure 104

>XENP021622 empty-Fc(216) 1G6_L1.194_H1.279_scFv(GKPGS)4-IgG1_pI(-
)_Isosteric_A_C220S/PVA_/S267K/L368D/K370S/M428L/N434S-
Fc(216)_IgG1_C220S/PVA_/S267K/S364K/E357Q/M428L/N434S XENP021622 empty-Fc(216)_pI(-
)_Isosteric_A_C220S/PVA_/S267K/L368D/K370S/M428L/N434S empty-Fc Heavy Chain
(SEQ ID NO: 30367)
EPKSSDKTHTCPPCPAPPVAGPSVFLFPPKPKDTLMISRTPEVTCVVVDVKHEDPEVKFNWYVDGVEVHNAKTKPRE
EEYNSTYRVVSVLTVLHQDWLNGKEYKCKVSNKALPAPIEKTISKAKGQPREPQVYTLPPSREEMTKNQVSLTCDVS
GFYPSDIAVEWESDGQPENNYKTTPPVLDSDGSFFLYSKLTVDKSRWEQGDVFSCSVLHEALHSHYTQKSLSLSPGK XENP021622
1G6_L1.194_H1.279_scFv(GKPGS)4_IgG1_C220S/PVA_/S267K/S364K/E357Q/M428L/N434S
scFv-Fc Heavy Chain (SEQ ID NO: 30368)
EIVLTQSPATLSASPGERVTLTCRASQSVGNDVAWYQQKPGQAPRLLINYASHRYTGVPDRFTGSGYGTEFTLTISS
VQSEDFGVYYCQQDFSSPRTFGGGTKVEIK/GKPGSGKPGSGKPGSGKPGS/EVQLVESGGGLVKPGGSLRLSCVAS
GFTFSNYWMNWVRQAPGKGLEWVAEIRLYSNNYATHYAESVKGRFTISRDDSKSTLYLQMNNLKTEDTGVYYCTRYY
GNYGGYFDVWGRGTLVTVSS/EPKSSDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREQMTKNQVKLTCLVKGFYPSDIAVEWESNGQPENNYKTTPPVLDSDGSFFLYSKLTVDKSRWQQGNVFSCS
VLHEALHSHYTQKSLSLSPGK

Figure 105

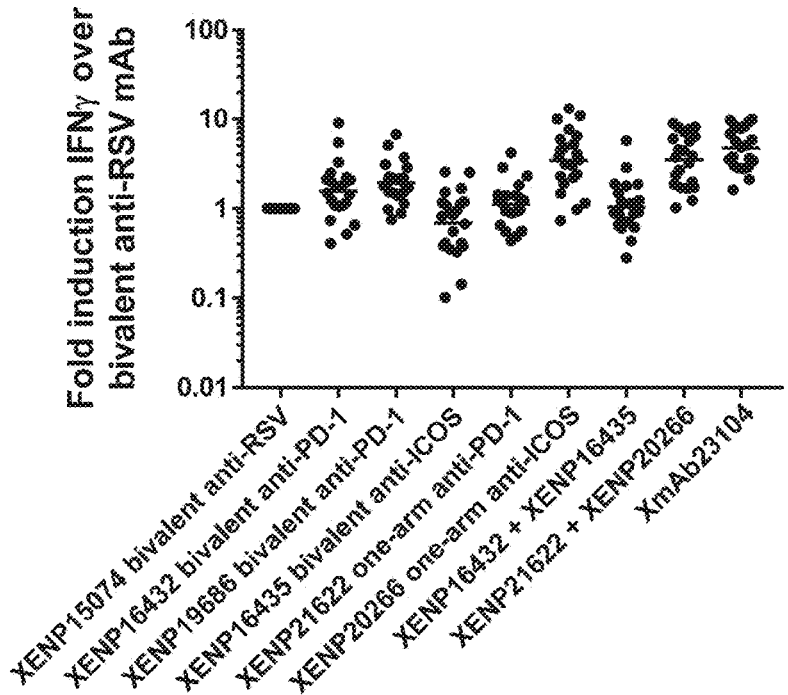

Figure 108

>XENP016433 Ipilimumab H0L0 IgG1 PVA /S267K

*XENP016433 Ipilimumab_H0L0_IgG1_PVA_/S267K Heavy Chain* (SEQ ID NO: 30369)
QVQLVESGGGVVQPGRSLRLSCAASGFTFSSYTMHWVRQAPGKGLEWVTFISYDGNNKYYADSVKGRFTISRDNSKN
TLYLQMNSLRAEDTAIYYCARTGWLGPFDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVDKKVEPKSCDKTHTCPPC
PAPPVAGPSVFLFPPKPKDTLMISRTPEVTCVVVDVKHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPGK

*XENP016433 Ipilimumab_H0L0_IgG1_PVA_/S267K Light Chain* (SEQ ID NO: 30370)
EIVLTQSPGTLSLSPGERATLSCRASQSVGSSYLAWYQQKPGQAPRLLIYGAFSRATGIPDRFSGSGSGTDFTLTIS
RLEPEDFAVYYCQQYGSSPWTFGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

Figure 117

>XENP020053 [αCTLA-4]_H3L0.22-1G6_L1.194_H1.279 Fab-Fc Heavy Chain (SEQ ID NO: 30371)
EVQLVESGGGLVKPGGSLRLSCAASGFTFSSYTMHWVRQAPGKGLEWVSFISYDGNNK
YYADSVKGRFTISRDNAKNSLYLQMNSLRAEDTAVYYCARTGWLGPFDYWGQGTLVT
VSS/ASTKGPSVFPLAPSSKSTSGGTAALGCLVKDYFPEPVTVSWNSGALTSGVHTFPAV
LQSSGLYSLSSVVTVPSSSLGTQTYICNVNHKPSDTKVDKKVEPKSCDKTHTCPPCPAPP
VAGPSVFLFPPKPKDTLMISRTPEVTCVVVDVKHEDPEVKFNWYVDGVEVHNAKTKPR
EEEYNSTYRVVSVLTVLHQDWLNGKEYKCKVSNKALPAPIEKTISKAKGQPREPQVYTL
PPSREEMTKNQVSLTCDVSGFYPSDIAVEWESDGQPENNYKTTPPVLDSDGSFFLYSKLT
VDKSRWEQGDVFSCSVMHEALHNHYTQKSLSLSPGK >XENP020053 [αCTLA-4]_H3L0.22-1G6_L1.194_H1.279 scFv-Fc Heavy Chain (SEQ ID NO: 30372)
EIVLTQSPATLSASPGERVTLTCRASQSVGNDVAWYQQKPGQAPRLLINYASHRYTGVP
DRFTGSGYGTEFTLTISSVQSEDFGVYYCQQDFSSPRTFGGGTKVEIK/GKPGSGKPGSGK
PGSGKPGS/EVQLVESGGGLVKPGGSLRLSCVASGFTFSNYWMNWVRQAPGKGLEWVA
EIRLYSNNYATHYAESVKGRFTISRDDSKSTLYLQMNNLKTEDTGVYYCTRYYGNYGG
YFDVWGRGTLVTVSS/EPKSSDKTHTCPPCPAPPVAGPSVFLFPPKPKDTLMISRTPEVTC
VVVDVKHEDPEVKFNWYVDGVEVHNAKTKPREEQYNSTYRVVSVLTVLHQDWLNGK
EYKCKVSNKALPAPIEKTISKAKGQPREPQVYTLPPSREQMTKNQVKLTCLVKGFYPSDI
AVEWESNGQPENNYKTTPPVLDSDGSFFLYSKLTVDKSRWQQGNVFSCSVMHEALHN
HYTQKSLSLSPGK >XENP020053 [αCTLA-4]_H3L0.22-1G6_L1.194_H1.279 Light Chain (SEQ ID NO: 30373)
EIVLTQSPGTLSLSPGERATLSCRASQSVSSSYLAWYQQKPGQAPRLLIYGAFSRATGIPD
RFSGSGSGTDFTLTISRLEPEDFAVYYCQQYGSSPWTFGQGTKVEIK/RTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC

Figure 120

>XENP29154_TGN1412_hu5.11A1[CD28]_H1L1_IgG4_K447del

XENP29154_TGN1412_hu5.11A1[CD28]_H1_IgG4_K447del Heavy Chain (SEQ ID NO: 30374)

EVQLVESGGGLVQPGGSLRLSCAASGFTFSDSWIHWVRQAPGKGLEWVAWISPYGGSTYYA
DSVKGRFTISADTSKNTAYLQMNSLRAEDTAVYYCARRHWPGGFDYWGQGTLVTVSS/ASTK
GPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPPVAGPSVFLFPPKPK
DTLMISRTPEVTCVVVDVKHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYP
SDIAVEWESNGQPENNYKTTPPVLDSDGSFFLYSKLTVDKSRWQQGNVFSCSVMHEALHNHY
TQKSLSLSPGK

XENP29154 TGN1412_hu5.11A1[CD28]_ L1 Light Chain (SEQ ID NO: 30375)

DIQMTQSPSSLSASVGDRVTITCRASQDVSTAVAWYQQKPGKAPKLLIYSASFLYSGVPSRFS
GSGSGTDFTLTISSLQPEDFATYYCQQYLYHPATFGQGTKVEIK/RTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC

Figure 124

| XmAb23104 Binding Partner | Human | | | Cynomolgus Monkey | | |
|---|---|---|---|---|---|---|
| | $K_D$ (M) | $k_a$ (1/Ms) | $k_d$ (1/s) | $K_D$ (M) | $k_a$ (1/Ms) | $k_d$ (1/s) |
| PD-1 | $2.8 \times 10^{-9}$ | $2.4 \times 10^{5}$ | $6.8 \times 10^{-4}$ | $5.8 \times 10^{-9}$ | $2.1 \times 10^{5}$ | $1.2 \times 10^{-3}$ |
| ICOS | $2.9 \times 10^{-9}$ | $6.6 \times 10^{4}$ | $1.9 \times 10^{-4}$ | $2.6 \times 10^{-9}$ | $6.6 \times 10^{4}$ | $1.7 \times 10^{-4}$ |

| Receptor | $K_D$ (M) | |
|---|---|---|
| | XmAb23104 | XENP20896 |
| Human FcRn | $1.5 \times 10^{-7}$ | $2.6 \times 10^{-6}$ |
| Cynomolgus Monkey FcRn | $9.1 \times 10^{-8}$ | $1.6 \times 10^{-6}$ to $5.5 \times 10^{-7a}$ |
| Mouse FcRn | $5.6 \times 10^{-8}$ | $1.6 \times 10^{-7}$ |

Figure 138

> XENP23058_Jounce_37A10S713_[ICOS]_H0L0_IgG1_WT Heavy Chain (SEQ ID NO: 30376)

EVQLVESGGGLVQPGGSLRLSCAASGFTFSDYWMDWVRQAPGKGLVWVSNIDEDG
SITEYSPFVKGRFTISRDNAKNTLYLQMNSLRAEDTAVYYCTRWGRFGFDSWGQGTL
VTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK

> XENP23058_Jounce_37A10S713_[ICOS]_H0L0_IgG1_WT Light Chain (SEQ ID NO: 30377)

DIVMTQSPDSLAVSLGERATINCKSSQSLLSGSFNYLTWYQQKPGQPPKLLIFYASTRH
TGVPDRFSGSGSGTDFTLTISSLQAEDVAVYYCHHHYNAPPTFGPGTKVDIKRTVAAP
SVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

Figure 139

> XENP23057_Jounce_37A10S713_[ICOS]_H0L0_IgG1_PVA_/S267K Heavy Chain
(SEQ ID NO: 30378)

EVQLVESGGGLVQPGGSLRLSCAASGFTFSDYWMDWVRQAPGKGLVWVSNIDEDG
SITEYSPFVKGRFTISRDNAKNTLYLQMNSLRAEDTAVYYCTRWGRFGFDSWGQGTL
VTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPP
CPAPPVAGPSVFLFPPKPKDTLMISRTPEVTCVVVDVKHEDPEVKFNWYVDGVEVHN
AKTKPREEQYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK

> XENP23057_Jounce_37A10S713_[ICOS]_H0L0_IgG1_PVA_/S267K Light Chain
(SEQ ID NO: 30379)

DIVMTQSPDSLAVSLGERATINCKSSQSLLSGSFNYLTWYQQKPGQPPKLLIFYASTRH
TGVPDRFSGSGSGTDFTLTISSLQAEDVAVYYCHHHYNAPPTFGPGTKVDIKRTVAAP
SVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

US 10,981,992 B2

BISPECIFIC IMMUNOMODULATORY ANTIBODIES THAT BIND COSTIMULATORY AND CHECKPOINT RECEPTORS

PRIORITY CLAIM

This application claims priority to U.S. Patent Application Nos. 62/583,431, filed Nov. 8, 2017; 62/614,271, filed Jan. 5, 2018; 62/640,468, filed Mar. 8, 2018; 62/683,554, filed Jun. 11, 2018 and 62/724,502; filed Aug. 29, 2018, all of which are expressly incorporated herein by reference in their entirety, with particular reference to the figures, legends, and claims therein.

SEQUENCE LISTING

The instant application contains a Sequence Listing which has been submitted electronically in ASCII format and is hereby incorporated by reference in its entirety. Said ASCII copy, created on Nov. 8, 2017 and amended on May 22, 2019, is named 067461-5216-US_SL.txt and is 28,257,248 kilobytes in size.

BACKGROUND OF THE INVENTION

Tumor-reactive T cells lose their cytotoxic ability over time due to up-regulation of inhibitory immune checkpoints such as PD-1 and CTLA-4. Two parallel therapeutic strategies are being pursued for de-repressing tumor-reactive T cells so that they can continue to kill tumor cells.

The first approach is immune immunomodulatory blockade by treating with antagonistic monoclonal antibodies that bind to either the immunomodulatory itself (PD-1, CTLA-4, etc.) or its ligand (PD-L1, PD-L2, CD80, CD86, etc.), thus removing the inhibitory signals holding back tumor-reactive T cells from tumor cell killing. Immunomodulatory receptors such as CTLA-1, PD-1 (programmed cell death 1), TIM-3 (T cell immunoglobulin and mucin domain 3), LAG-3 (lymphocyte-activation gene 3), TIGIT (T cell immunoreceptor with Ig and ITIM domains), and others, inhibit the activation, proliferation, and/or effector activities of T cells and other cell types. Guided by the hypothesis that immunomodulatory receptors suppress the endogenous T cell response against tumor cells, preclinical and clinical studies of anti-CTLA4 and anti-PD1 antibodies, including nivolumab, pembrolizumab, ipilimumab, and tremelimumab, have indeed demonstrated that immunomodulatory blockade results in impressive anti-tumor responses, stimulating endogenous T cells to attack tumor cells, leading to long-term cancer remissions in a fraction of patients with a variety of malignancies. Unfortunately, only a subset of patients responds these therapies, with response rates generally ranging from 10 to 30% and sometimes higher for each monotherapy, depending on the indication and other factors.

The second approach for de-repressing tumor-reactive T cells is T cell costimulation by treating with agonistic antibodies that bind to costimulatory proteins such as ICOS, thus adding a positive signal to overcome the negative signaling of the immune checkpoints.

Accordingly, the invention is directed to bispecific antibodies that bind to costimulatory receptors (e.g. ICOS, GITR, OX40, 4-1BB) as well as checkpoint receptors (e.g. PD-1, PD-L1, CTLA-4, LAG-3, TIM-3, BTLA and TIGIT.

SUMMARY OF THE INVENTION

Accordingly, in one aspect, the invention provides bispecific antibodies that monovalently binds a human costimulatory receptor and monovalently binds a human checkpoint receptor for use in activating T cells for the treatment of cancer.

In some aspects, the costimulatory receptor is selected from the group consisting of ICOS, GITR, OX40 and 4-1BB.

In additional aspects, the checkpoint receptor is selected from the group consisting of PD-1, PD-L1, CTLA-4, LAG-3, TIGIT and TIM-3.

In further aspects, the antibody binds an antigen pair selected from: ICOS and PD-1, ICOS and CTLA-4, ICOS and LAG-3, ICOS and TIM-3, ICOS and PD-L1, ICOS and BTLA, ICOS and TIGIT, GITR and TIGIT, GITR and PD-1, GITR and CTLA-4, GITR and LAG-3, GITR and TIM-3, GITR and PD-L1, GITR and BTLA, OX40 and PD-1, OX40 and TIGIT, OX40 and CTLA-4, IC OX40 OS and LAG-3, OX40 and TIM-3, OX40 and PD-L1, OX40 and BTLA, 4-1BB and PD-1, 4-1BB and CTLA-4, 4-1BB and LAG-3, 4-1BB and TIM-3, 4-1BB and PD-L1, TIGIT and 4-1BB and 4-1BB and BTLA.

In additional aspects, the bispecific antibody has a format selected from those outlined in FIG. 2.

In further aspects, the invention provides heterodimeric antibodies comprising: a) a first heavy chain comprising a first Fc domain, an optional domain linker and a first antigen binding domain comprising an scFv that binds a first antigen; b) a second heavy chain comprising a heavy chain comprising a heavy chain constant domain comprising a second Fc domain, a hinge domain, a CH1 domain and a variable heavy domain; and c) a light chain comprising a variable light domain and a light chain constant domain; wherein said variable heavy domain and said variable light domain form a second antigen binding domain that binds a second antigen, wherein one of said first and second antigen binding domains binds human ICOS and the other binds human PD-1.

In an additional aspect, the invention provides heterodimeric bispecific antibodies comprising: a) a first heavy chain comprising: i) a first variant Fc domain; and ii) a single chain Fv region (scFv) that binds a first antigen, wherein said scFv region comprises a first variable heavy chain, a variable light chain and a charged scFv linker, wherein said charged scFv linker covalently attaches said first variable heavy chain and said variable light chain; and b) a second heavy chain comprising a VH-CH1-hinge-CH2-CH3 monomer, wherein VH is a second variable heavy chain and CH2-CH3 is a second variant Fc domain; and c) a light chain; wherein said second variant Fc domain comprises amino acid substitutions N208D/Q295E/N384D/Q418E/N241D, wherein said first and second variant Fc domains each comprise amino acid substitutions E233P/L234V/L235A/G236del/S267K; and wherein said first variant Fc domain comprises amino acid substitutions S364K/E357Q and second variant Fc domain comprises amino acid substitutions L368D/K370S, wherein one of said first and second antigen binding domains binds human ICOS and the other binds human PD-1, and wherein numbering is according to the EU index as in Kabat.

In some aspects the heterodimeric antibodies have first and second variant Fc domains that each comprise M428L/N434S.

In an additional aspect, the invention provides heterodimeric antibodies comprising: a) a first heavy chain comprising: i) a first variant Fc domain; and ii) a single chain Fv region (scFv) that binds a first antigen, wherein said scFv region comprises a first variable heavy chain, a variable light chain and a charged scFv linker, wherein said charged scFv linker covalently attaches said first variable heavy chain and said variable light chain; and b) a second heavy chain comprising a VH-CH1-hinge-CH2-CH3 monomer, wherein VH is a second variable heavy chain and CH2-CH3 is a second variant Fc domain; and c) a light chain; wherein said first and second variant Fc domains comprises a set of heterodimerization variants selected from the group consisting of L368D/K370S: S364K/E357Q; L368D/K370S: S364K; L368E/K370S: S364K; T411E/K360E/Q362E: D401K; and T366S/L368A/Y407V: T366W, and wherein one of said first and second antigen binding domains binds human ICOS and the other binds human PD-1, and wherein numbering is according to the EU index as in Kabat.

In a further aspect, the invention provides nucleic acid compositions comprising nucleic acids that encode the heterodimeric antibodies of the invention, expression vector compositions comprising the nucleic acids, and host cells comprising the expression vector compositions.

In an additional aspect, the invention provides heterodimeric antibodies for use in the activation of T cells for the treatment of cancer.

BRIEF DESCRIPTION OF THE DRAWINGS

FIG. 2A to 2N depict several formats for the bispecific antibodies of the present invention. The first is the "bottle opener" format, with a first and a second anti-antigen binding domain. Additionally, mAb-Fv, mAb-scFv, Central-scFv, Central-Fv, one armed central-scFv, one scFv-mAb, scFv-mAb dual scFv format are all shown. FIG. 2J depicts the "central-scFv2" format, with two Fab-scFv arms, wherein the Fabs bind a first antigen and the scFvs bind a second antigen. FIG. 2K depicts the bispecific mAb format, with a first Fab arm binding a first antigen and a second Fab arm binding a second antigen. FIG. 2L depicts the DVD-IgG format (see, e.g., U.S. Pat. No. 7,612,181, hereby expressly incorporated by reference and as discussed below). FIG. 2M depicts the Trident format (see, e.g., WO 2015/184203, hereby expressly incorporated by reference and as discussed below). For all of the scFv domains depicted, they can be either N- to C-terminus variable heavy-(optional linker)-variable light, or the opposite. In addition, for the one armed scFv-mAb, the scFv can be attached either to the N-terminus of a heavy chain monomer or to the N-terminus of the light chain.

FIGS. 3A and 3B depicts the sequences of XENP23104, a bottle opener format with the ICOS as the Fab side ([ICOS]_H0.66_L0) and the PD-1 as the scFv (1G6_L1.94_H1.279), and includes the M428L/4345 variant to extend serum half life. The CDRs are underlined, the scFv linker is double underlined (in the sequences, the scFv linker is a positively charged scFv (GKPGS)4 linker (SEQ ID NO: 26209), although as will be appreciated by those in the art, this linker can be replaced by other linkers, including uncharged or negatively charged linkers, some of which are depicted in FIG. 8), and the slashes indicate the border(s) of the variable domains. In addition, the naming convention illustrates the orientation of the scFv from N- to C-terminus; some of the sequences herein are oriented as VH-scFv linker-VL (from N- to C-terminus), while some are oriented as VL-scFv linker-VH (from N- to C-terminus), although as will be appreciated by those in the art, these sequences may also be used in the opposition orientation from their depiction herein. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems.

FIG. 4A to 4F depict useful pairs of heterodimerization variant sets (including skew and pI variants). On FIGS. 4C and F, there are variants for which there are no corresponding "monomer 2" variants; these are pI variants which can be used alone on either monomer, or included on the Fab side of a bottle opener, for example, and an appropriate charged scFv linker can be used on the second monomer that utilizes a scFv as the second antigen binding domain. Suitable charged linkers are shown in FIG. 8.

FIG. 5 depict a list of isosteric variant antibody constant regions and their respective substitutions. pI_(−) indicates lower pI variants, while pI_(+) indicates higher pI variants. These can be optionally and independently combined with other heterodimerization variants of the invention (and other variant types as well, as outlined herein).

FIG. 6 depict useful ablation variants that ablate FcγR binding (sometimes referred to as "knock outs" or "KO" variants). Generally, ablation variants are found on both monomers, although in some cases they may be on only one monomer.

FIGS. 7A and 7B show two particularly useful embodiments of the invention. The "non-Fv" components of this embodiment is shown in FIG. 9A, although the other formats of FIG. 9 can be used as well.

FIGS. 8A and 8B depict a number of charged scFv linkers that find use in increasing or decreasing the pI of heterodimeric antibodies that utilize one or more scFv as a component. The (+H) positive linker finds particular use herein. A single prior art scFv linker with single charge is references as "Whitlow", from Whitlow et al., Protein Engineering 6(8):989-995 (1993). It should be noted that this linker was used for reducing aggregation and enhancing proteolytic stability in scFvs.

FIG. 9A to 9D shows the sequences of several useful bottle opener format backbones based on human IgG1, without the Fv sequences (e.g. the scFv and the vh and vl for the Fab side). Bottle opener backbone 1 is based on human IgG1 (356E/358M allotype), and includes the S364K/E357Q: L368D/K370S skew variants, the N208D/Q295E/N384D/Q418E/N421D pI variants on the Fab side and the E233P/L234V/L235A/G236del/S267K ablation variants on both chains. Bottle opener backbone 2 is based on human IgG1 (356E/358M allotype), and includes different skew variants, the N208D/Q295E/N384D/Q418E/N421D pI variants on the Fab side and the E233P/L234V/L235A/G236del/S267K ablation variants on both chains. Bottle opener backbone 3 is based on human IgG1 (356E/358M allotype), and includes different skew variants, the N208D/Q295E/N384D/Q418E/N421D pI variants on the Fab side and the E233P/L234V/L235A/G236del/S267K ablation variants on both chains. Bottle opener backbone 4 is based on human IgG1 (356E/358M allotype), and includes different skew variants, the N208D/Q295E/N384D/Q418E/N421D pI variants on the Fab side and the E233P/L234V/L235A/G236del/S267K ablation variants on both chains. Bottle opener backbone 5 is based on human IgG1 (356D/358L allotype), and includes the S364K/E357Q: L368D/K370S skew variants, the N208D/Q295E/N384D/Q418E/N421D pI variants on the Fab side and the E233P/L234V/L235A/G236del/S267K ablation variants on both chains. Bottle opener backbone 6 is based on human IgG1 (356E/358M allotype), and includes the S364K/E357Q:L368D/K370S skew variants, N208D/Q295E/N384D/Q418E/N421D pI variants on the Fab side and the E233P/L234V/L235A/G236del/S267K ablation variants on both chains, as well as an N297A variant on both chains. Bottle opener backbone 7 is identical to 6 except the mutation is N297S. Alternative formats for bottle opener backbones 6 and 7 can exclude the ablation variants E233P/L234V/L235A/G236del/S267K in both chains. Backbone 8 is based on human IgG4, and includes the S364K/E357Q: L368D/K370S skew variants, the N208D/Q295E/N384D/Q418E/N421D pI variants on the Fab side and the E233P/L234V/L235A/G236del/S267K ablation variants on both chains, as well as a S228P (EU numbering, this is S241P in Kabat) variant on both chains that ablates Fab arm exchange as is known in the art. Alternative formats for bottle opener backbone 8 can exclude the ablation variants E233P/L234V/L235A/G236del/S267K in both chains Backbone 9 is based on human IgG2, and includes the S364K/E357Q:L368D/K370S skew variants, the N208D/Q295E/N384D/Q418E/N421D pI variants on the Fab side. Backbone 10 is based on human IgG2, and includes the S364K/E357Q: L368D/K370S skew variants, the N208D/Q295E/N384D/Q418E/N421D pI variants on the Fab side as well as a S267K variant on both chains.

Figure 1:
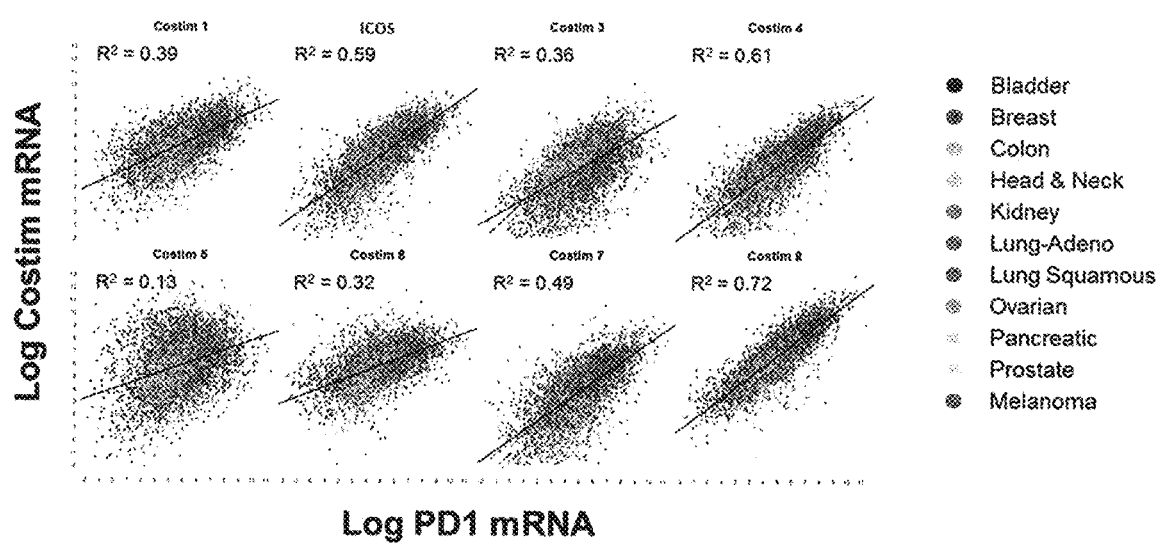
FIG. 1 presents expression data (RNAseq V2 RSEM) of PD-1 and T cell costimulatory receptors for bladder, breast, colon, head & neck, kidney, lung-adeno, lung squamous, ovarian, pancreatic, prostate, and melanoma cancer compiled from The Cancer Genome Atlas (TCGA). The square of the Pearson correlation coefficient was calculated for PD-1 against T cell costimulatory receptors.

As will be appreciated by those in the art and outlined below, these sequences can be used with any vh and vl pairs outlined herein, with one monomer including a scFv (optionally including a charged scFv linker) and the other monomer including the Fab sequences (e.g. a vh attached to the "Fab side heavy chain" and a vl attached to the "constant light chain"). That is, any Fv sequences outlined herein for anti-CTLA-4, anti-PD-1, anti-LAG-3, anti-TIM-3, anti-TIGIT and anti-BTLA, whether as scFv (again, optionally with charged scFv linkers) or as Fabs, can be incorporated into these FIG. 37 backbones in any combination. The constant light chain depicted in FIG. 9A can be used for all of the constructs in the figure, although the kappa constant light chain can also be substituted.

It should be noted that these bottle opener backbones find use in the Central-scFv format of FIG. 1F, where an additional, second Fab (vh-CH1 and vl-constant light) with the same antigen binding as the first Fab is added to the N-terminus of the scFv on the "bottle opener side".

Included within each of these backbones are sequences that are 90, 95, 98 and 99% identical (as defined herein) to the recited sequences, and/or contain from 1, 2, 3, 4, 5, 6, 7, 8, 9 or 10 additional amino acid substitutions (as compared to the "parent" of the Figure, which, as will be appreciated by those in the art, already contain a number of amino acid modifications as compared to the parental human IgG1 (or IgG2 or IgG4, depending on the backbone). That is, the recited backbones may contain additional amino acid modifications (generally amino acid substitutions) in addition to the skew, pI and ablation variants contained within the backbones of this figure.

FIG. 10A to 10E depicts the sequences for a select number of anti-PD-1 antibodies. It is important to note that these sequences were generated based on human IgG1, with an ablation variant (E233P/L234V/L235A/G236del/S267K, "IgG1_PVA_/S267K") which is depicted in FIG. 6A. The CDRs are underlined. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems.

FIG. 11A to 11E depict a select number of PD-1 ABDs, with additional anti-PD-1 ABDs being listed as SEQ 1-2392, 3125-3144, 4697-7594 and 4697-21810. The CDRs are underlined, the scFv linker is double underlines (in the sequences, the scFv linker is a positively charged scFv (GKPGS)4 linker (SEQ ID NO: 26209), although as will be appreciated by those in the art, this linker can be replaced by other linkers, including uncharged or negatively charged linkers, some of which are depicted in FIG. 8), and the slashes indicate the border(s) of the variable domains. In addition, the naming convention illustrates the orientation of the scFv from N- to C-terminus; some of the sequences in this Figure are oriented as VH-scFv linker-VL (from N- to C-terminus), while some are oriented as VL-scFv linker-VH (from N- to C-terminus), although as will be appreciated by those in the art, these sequences may also be used in the opposition orientation from their depiction herein. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

FIG. 12A to 12PP depict a select number of CTLA-4 ABDs, with additional anti-CTLA-4 ABDs being listed as SEQ ID NO:2393-2414 and 3737-3816. The CDRs are underlined, the scFv linker is double underlines (in the sequences, the scFv linker is a positively charged scFv (GKPGS)4 linker (SEQ ID NO: 26209), although as will be appreciated by those in the art, this linker can be replaced by other linkers, including uncharged or negatively charged linkers, some of which are depicted in FIG. 8), and the slashes indicate the border(s) of the variable domains. In addition, the naming convention illustrates the orientation of the scFv from N- to C-terminus; some of the sequences in this Figure are oriented as VH-scFv linker-VL (from N- to C-terminus), while some are oriented as VL-scFv linker-VH (from N- to C-terminus), although as will be appreciated by those in the art, these sequences may also be used in the opposition orientation from their depiction herein. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

FIG. 13A to 13N depict a select number of LAG-3 ABDs, with additional anti-LAG-3 ABDs being listed as SEQ ID NO:2415-2604 and 3817-3960. The CDRs are underlined, the scFv linker is double underlines (in the sequences, the scFv linker is a positively charged scFv (GKPGS)4 linker (SEQ ID NO: 26209), although as will be appreciated by those in the art, this linker can be replaced by other linkers, including uncharged or negatively charged linkers, some of which are depicted in FIG. 8), and the slashes indicate the border(s) of the variable domains> In addition, the naming convention illustrates the orientation of the scFv from N- to C-terminus; some of the sequences in this Figure are oriented as VH-scFv linker-VL (from N- to C-terminus), while some are oriented as VL-scFv linker-VH (from N- to C-terminus), although as will be appreciated by those in the art, these sequences may also be used in the opposition orientation from their depiction herein. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

FIG. 14A to 14I depicts the sequences for a select number of anti-TIM-3 antibodies. It is important to note that these sequences were generated based on human IgG1 backbone, with an ablation variant (E233P/L234V/L235A/G236del/S267K, "IgG1_PVA_/S267K") although other formats can be used as well. The CDRs are underlined. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems.

FIG. 15A to 15C depicts the sequences for a select number of anti-PD-L1 antibodies. It is important to note that these sequences were generated based on human IgG1 backbone, with an ablation variant (E233P/L234V/L235A/G236del/S267K, "IgG1_PVA_/S267K") as outlined herein, although other formats can be used as well. The CDRs are underlined. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems.

FIG. 16 depicts the sequences for a prototype anti-4-1BB antibody. It is important to note that these sequences were generated based on human IgG1 backbone, with an ablation variant (E233P/L234V/L235A/G236del/S267K, "IgG1_PVA_/S267K"), although the other formats can be used as well. The CDRs are underlined. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems.

FIG. 17 depicts the sequences for a prototype anti-OX40 antibody. It is important to note that these sequences were generated based on human IgG1 backbone, with an ablation variant (E233P/L234V/L235A/G236del/S267K, "IgG1_PVA_/S267K"), although other formats can be used as well. The CDRs are underlined. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems.

FIG. 18 depicts the sequences for a prototype anti-GITR antibody. It is important to note that these sequences were generated based on human IgG1 backbone, with an ablation variant (E233P/L234V/L235A/G236del/S267K, "IgG1_PVA_/S267K"), although other formats can be used as well. The CDRs are underlined. As noted herein and is true for every sequence herein containing CDRs, the exact identification of the CDR locations may be slightly different depending on the numbering used as is shown in Table 1, and thus included herein are not only the CDRs that are underlined but also CDRs included within the VH and VL domains using other numbering systems.

FIG. 19A to 19G depicts the sequences for prototype anti-ICOS antibodies. It is important to note that these sequences were generated based on human IgG1 backbone, with an ablation variant (E233P/L234V/L235A/G236del/S267K, "IgG1_PVA_/S267K"), although other formats can be used as well. The CDRs are underlined. As noted herein and is true for every sequence herein containing CDRs, the exact identification of the CDR locations may be slightly different depending on the numbering used as is shown in Table X, and thus included herein are not only the CDRs that are underlined but also CDRs included within the VH and VL domains using other numbering systems.

FIG. 20A to 20G depicts sequences for exemplary anti-ICOS Fabs. The CDRs are underlined and slashes (/) indicate the border(s) of the variable regions. As noted herein and is true for every sequence herein containing CDRs, the exact identification of the CDR locations may be slightly different depending on the numbering used as is shown in Table X, and thus included herein are not only the CDRs that are underlined but also CDRs included within the VH and VL domains using other numbering systems. Furthermore, as for all the sequences in the Figures, these VH and VL sequences can be used either in a scFv format or in a Fab format. It is important to note that these sequences were generated using six-histidine (His6 or HHHHHH) (SEQ ID NO: 28666) C-terminal tags at the C-terminus of the heavy chains, which have been removed.

FIG. 21A to 21B depicts melting temperatures (Tm) and changes in melting temperature from the parental Fab (XENP22050) as determined by DSF of variant anti-ICOS Fabs engineered for stability.

FIG. 22A to 22C depicts equilibrium dissociation constants (KD), association rates (ka), and dissociation rates (kd) of variant anti-ICOS Fabs for murine Fc fusions of human ICOS captured on AMC biosensors as determined by Octet.

FIG. 23 depicts equilibrium dissociation constants (KD), association rates (ka), and dissociation rates (kd) of variant anti-ICOS Fabs for biotinylated IgG1 Fc fusions of human ICOS captured on SA biosensors as determined by Octet.

FIG. 24A to 24M depicts sequences for exemplary anti-ICOS scFvs. The CDRs are underlined, the scFv linker is double underline (in the sequences, the scFv linker is a positively charged scFv (GKPGS)4 linker (SEQ ID NO: 26209), although as will be appreciated by those in the art, this linker can be replaced by other linkers, including uncharged or negatively charged linkers, some of which are depicted in Figure X), and slashes (/) indicate the border(s) of the variable regions. The naming convention illustrates the orientation of the scFv from N- to C-terminus; some of the sequences in this Figure are oriented as VH-scFv linker-VL (from N- to C-terminus, see FIG. 24), while some are oriented as VL-scFv linker-VH (from N- to C-terminus, see FIG. 24B), although as will be appreciated by those in the art, these sequences may also be used in the opposition orientation from their depiction herein. As noted herein and is true for every sequence herein containing CDRs, the exact identification of the CDR locations may be slightly different depending on the numbering used as is shown in Table X, and thus included herein are not only the CDRs that are underlined but also CDRs included within the VH and VL domains using other numbering systems. Furthermore, as for all the sequences in the Figures, these VH and VL sequences can be used either in a scFv format or in a Fab format. It is important to note that these sequences were generated using polyhistidine (His6 or HHHHHH) (SEQ ID NO: 28666) C-terminal tags at the C-terminus of the heavy chains, which have been removed.

FIG. 25 depicts melting temperatures (Tm) and changes in melting temperature from the parental scFv (XENP24352; oriented as VH-scFv linker-VL from N- to C-terminus) as determined by DSF of variant anti-ICOS scFvs engineered for stability.

FIG. 26A to 26D depicts the amino acid sequences of prototype anti-costim x anti-checkpoint antibodies in the bottle-opener format (Fab-scFv-Fc). The antibodies are named using the Fab variable region first and the scFv variable region second, separated by a dash, followed by the chain designation (Fab-Fc heavy chain, scFv-Fc heavy chain or light chain). CDRs are underlined and slashes indicate the border(s) of the variable regions. The scFv domain has different orientations (N- to C-terminus) of either VH-scFv linker-VL or VL-scFv linker-VH as indicated, although this can be reversed. In addition, each sequence outlined herein can include or exclude the M428L/N434S variants in one or preferably both Fc domains, which results in longer half-life in serum.

Figure 27:
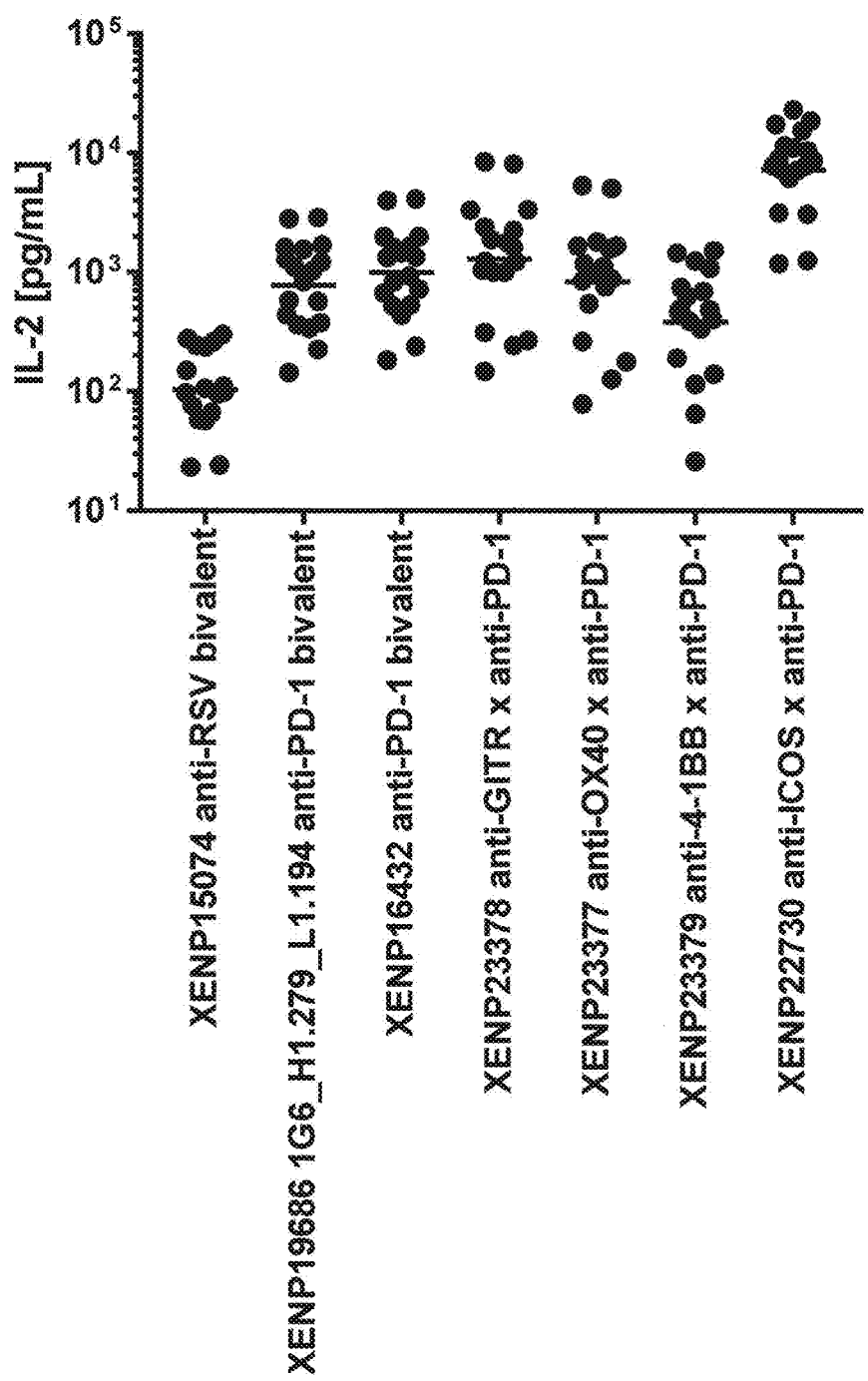

FIG. 27 depicts induction of cytokine secretion by prototype costim/checkpoint bottle-openers in an SEB-stimulated PBMC assay.

Figure 28:
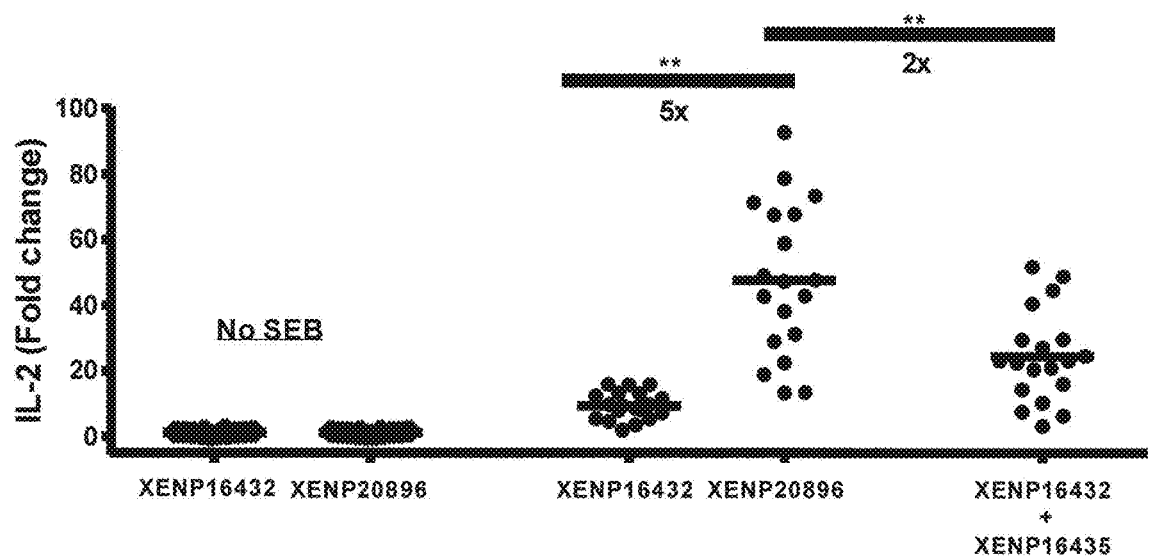

FIG. 28 depicts induction of IL-2 secretion in naive (non-SEB stimulated) and SEB-stimulated PBMCs following treatment with the indicated test articles.

Figure 29:
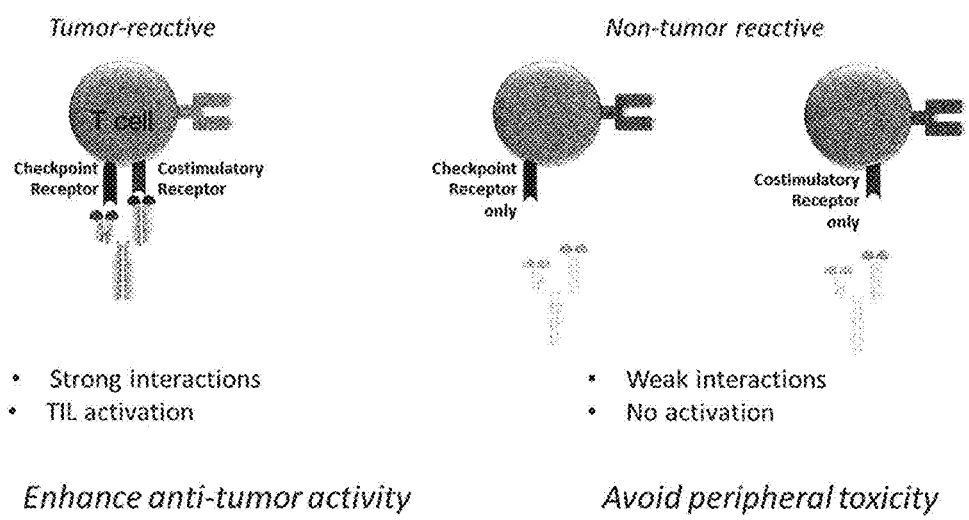

FIG. 29 depicts a schematic associated with the benefit of a costim x checkpoint blockade bispecific antibody, showing that because tumor TILs co-express immune checkpoint receptors and costimulatory receptors, a bispecific antibody increases specificity, enhancing anti-tumor activity and avoiding peripheral toxicity.

Figure 30:
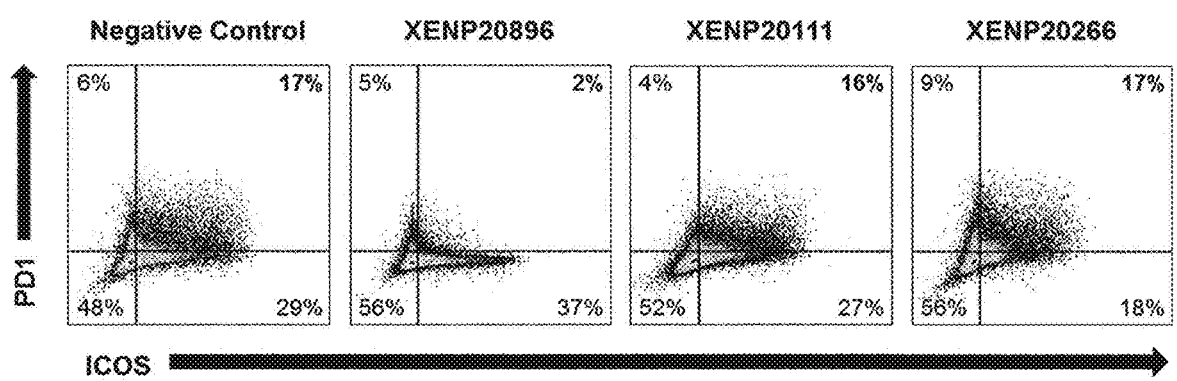

FIG. 30 depicts that double-positive cells are selectively occupied by exemplary anti-ICOS x anti-PD-1 antibody (XENP20896) as compared to one-arm anti-PD-1 antibody (XENP20111) and one-arm anti-ICOS antibody (XENP20266).

Figure 31A:
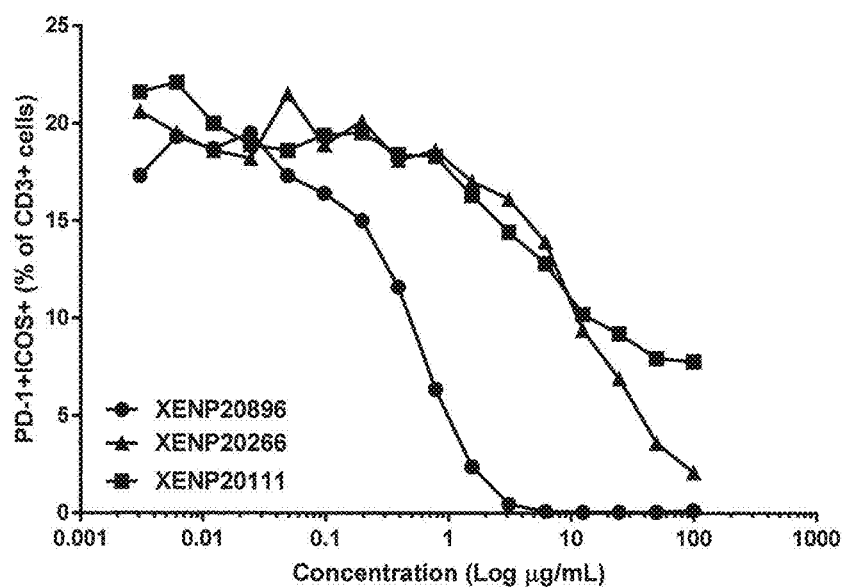
Figure 31B:
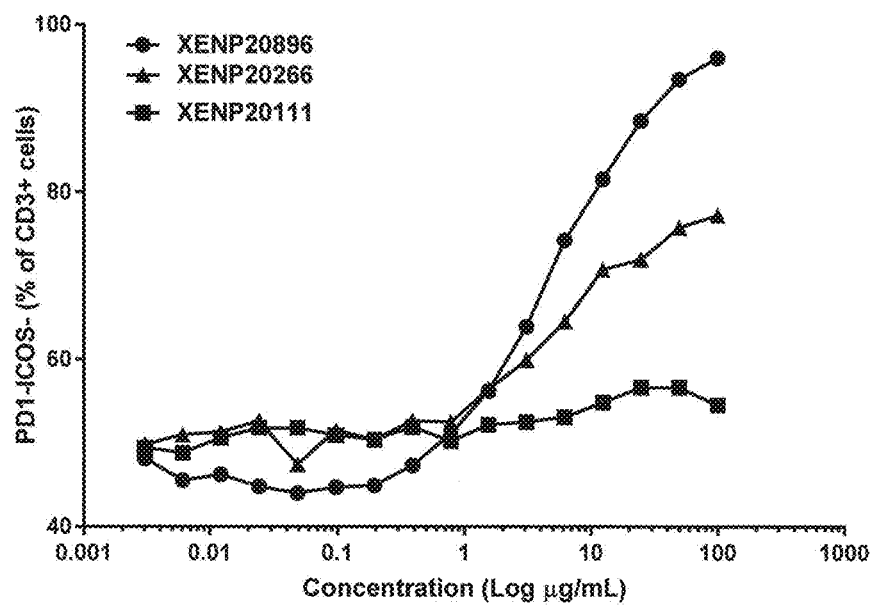

FIG. 31A to 31B shows the receptor occupancy of anti-ICOS x anti-PD-1 bispecific antibody (XENP20896), one-arm anti-ICOS antibody (XENP20266) and one-arm anti-PD-1 antibody (XENP20111) on A) PD-1 and ICOS double-positive T cells and B) PD-1 and ICOS double-negative T cells after SEB stimulation of human PBMCs.

FIG. 32A to 32D depicts the amino acid sequences of exemplary anti-ICOS x anti-PD-1 antibodies in the bottle-opener format (Fab-scFv-Fc). The antibodies are named using the Fab variable region first and the scFv variable region second, separated by a dash, followed by the chain designation (Fab-Fc heavy chain, scFv-Fc heavy chain or light chain). CDRs are underlined and slashes indicate the border(s) of the variable regions. The scFv domain has different orientations (N- to C-terminus) of either VH-scFv linker-VL or VL-scFv linker-VH as indicated, although this can be reversed. In addition, each sequence outlined herein can include or exclude the M428L/N434S variants in one or preferably both Fc domains, which results in longer half-life in serum.

FIG. 33A to 33C depicts the amino acid sequences of exemplary anti-ICOS x anti-PD-1 antibodies in the bottle-opener format (Fab-scFv-Fc) which include the M428L/N434S variants in one or preferably both Fc domains, which results in longer half-life in serum. The antibodies are named using the Fab variable region first and the scFv variable region second, separated by a dash, followed by the chain designation (Fab-Fc heavy chain, scFv-Fc heavy chain or light chain). CDRs are underlined and slashes indicate the border(s) of the variable regions. The scFv domain has different orientations (N- to C-terminus) of either VH-scFv linker-VL or VL-scFv linker-VH as indicated, although this can be reversed.

FIG. 34A to 34C depicts equilibrium dissociation constants (KD), association rates (ka), and dissociation rates (kd) of variant anti-ICOS x anti-PD-1 bispecific antibodies for murine Fc fusion of human ICOS captured on AMC biosensors as determined by Octet.

FIG. 35 depicts equilibrium dissociation constants (KD), association rates (ka), and dissociation rates (kd) of variant anti-ICOS x anti-PD-1 bispecific antibodies for biotinylated IgG1 Fc fusions of human and ICOS captured on SA/SAX biosensors as determined by Octet.

Figure 36A:
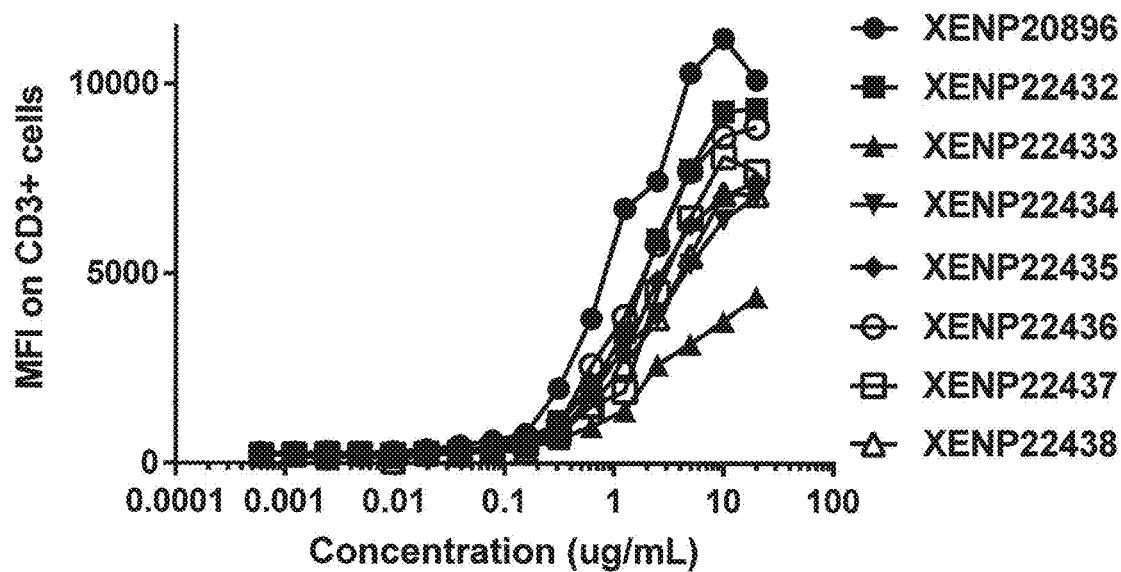
Figure 36B:
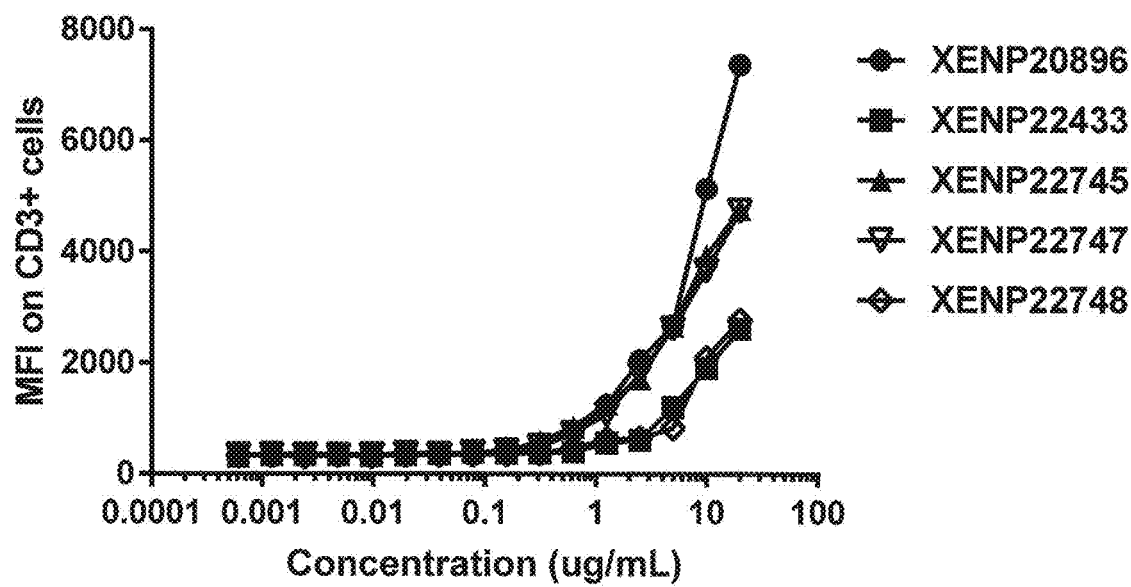

FIGS. 36A and 36B depicts cell surface binding of variant anti-ICOS x anti-PD-1 bispecific to human T cells in SEB-stimulated PBMC assays in two separate experiments depicted in A) and B).

Figure 37:
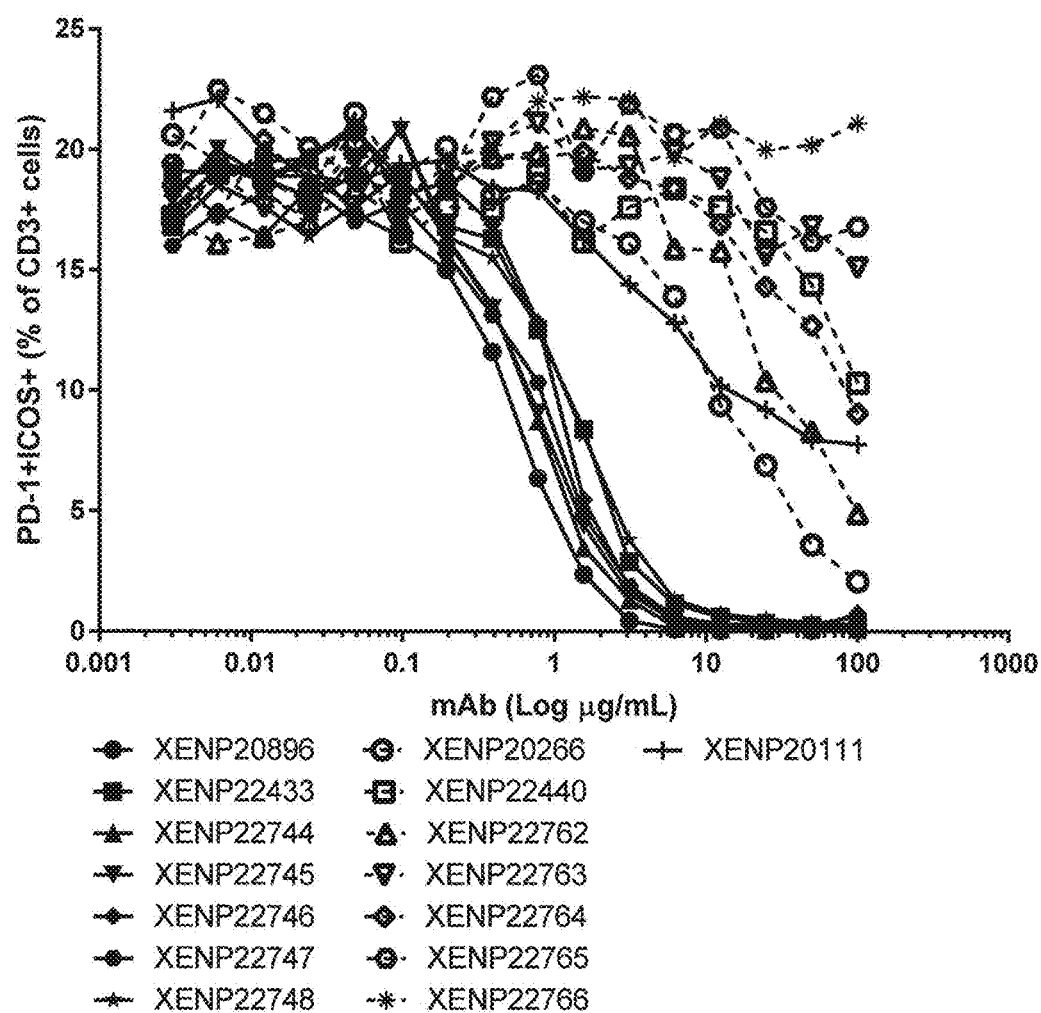

FIG. 37 shows the receptor occupancy of variant anti-ICOS x anti-PD-1 bispecific antibodies, one-arm anti-ICOS antibodies and one-arm anti-PD-1 antibody (XENP20111) on PD-1 and ICOS double-positive T cells after SEB stimulation of human PBMCs.

Figure 38A:
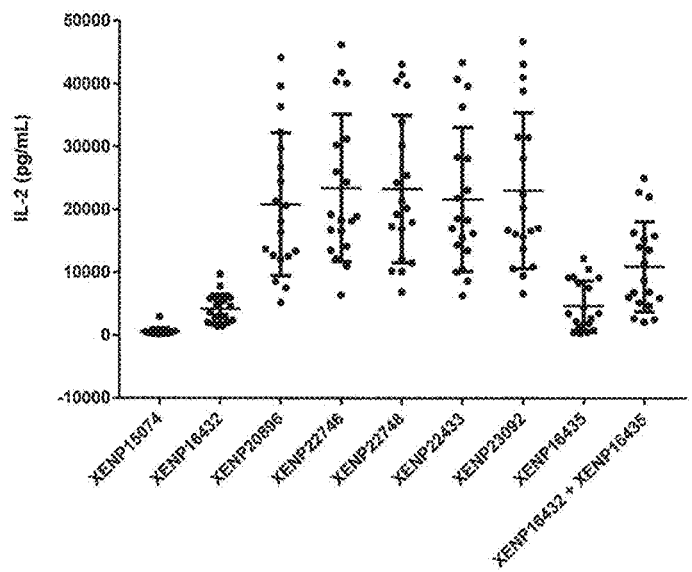
Figure 38B:
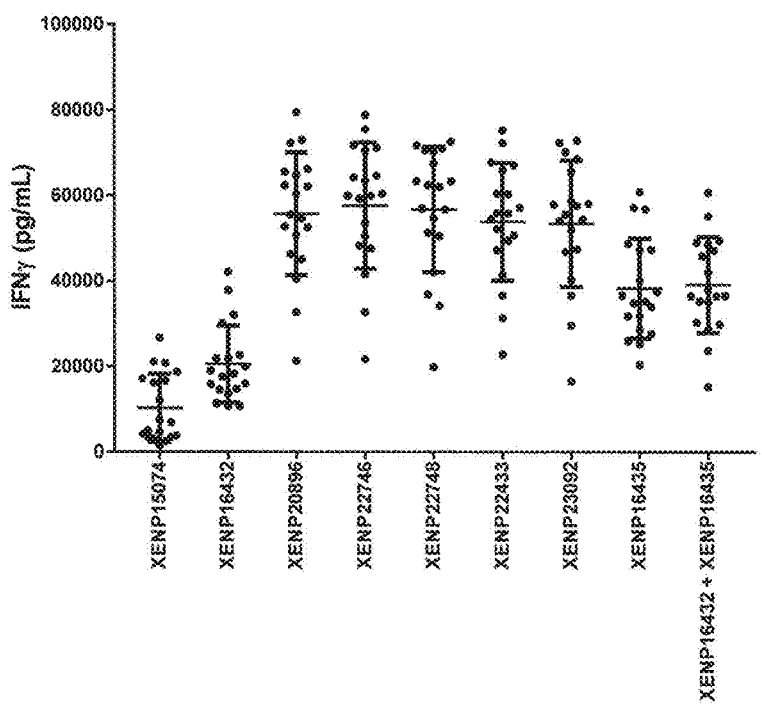

FIGS. 38A and 38B show that variant anti-ICOS x anti-PD-1 bispecific antibodies promote A) IL-2 and B) IFNγ secretion from SEB stimulated PBMCs.

Figure 39A:
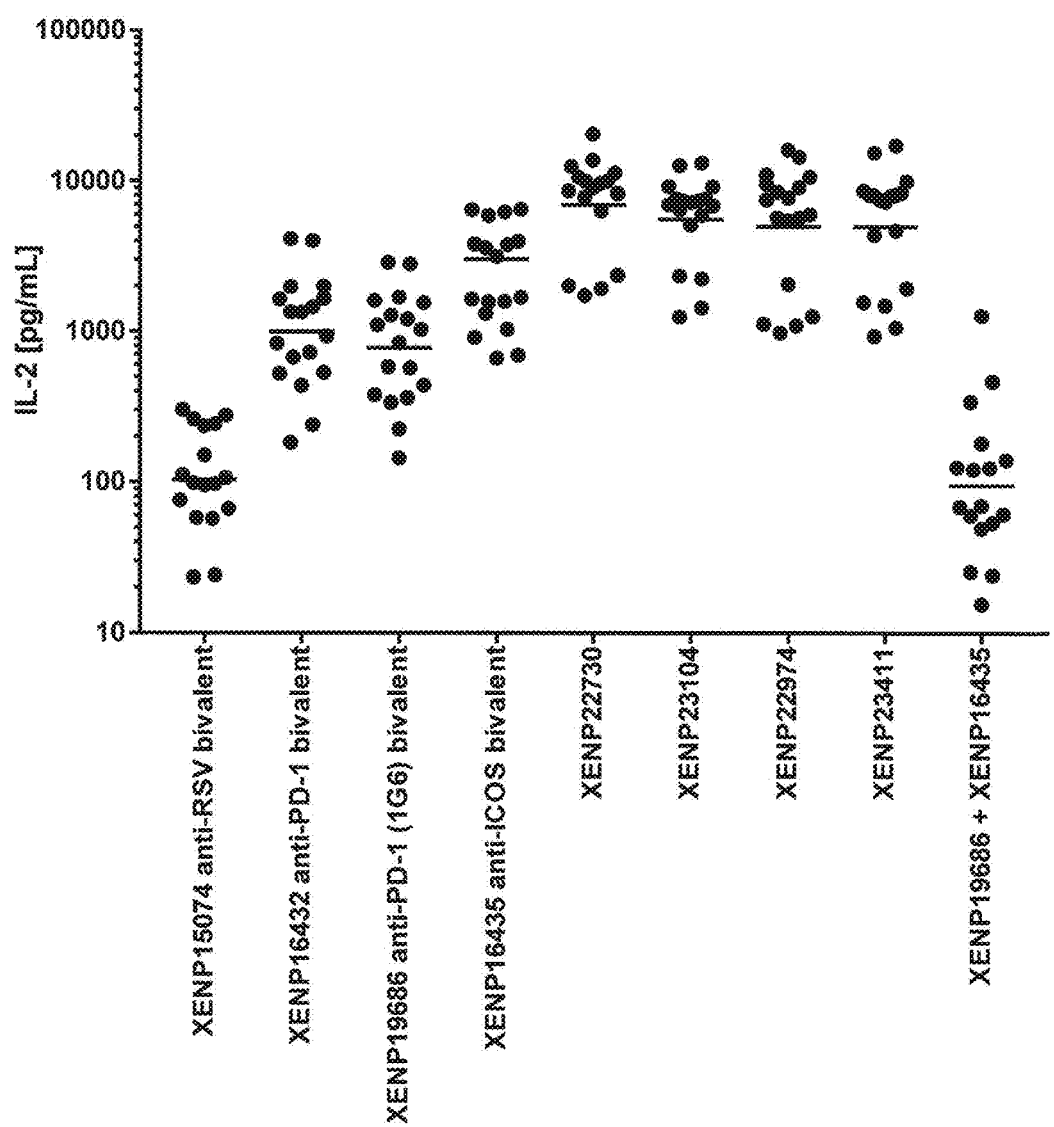
Figure 39B:
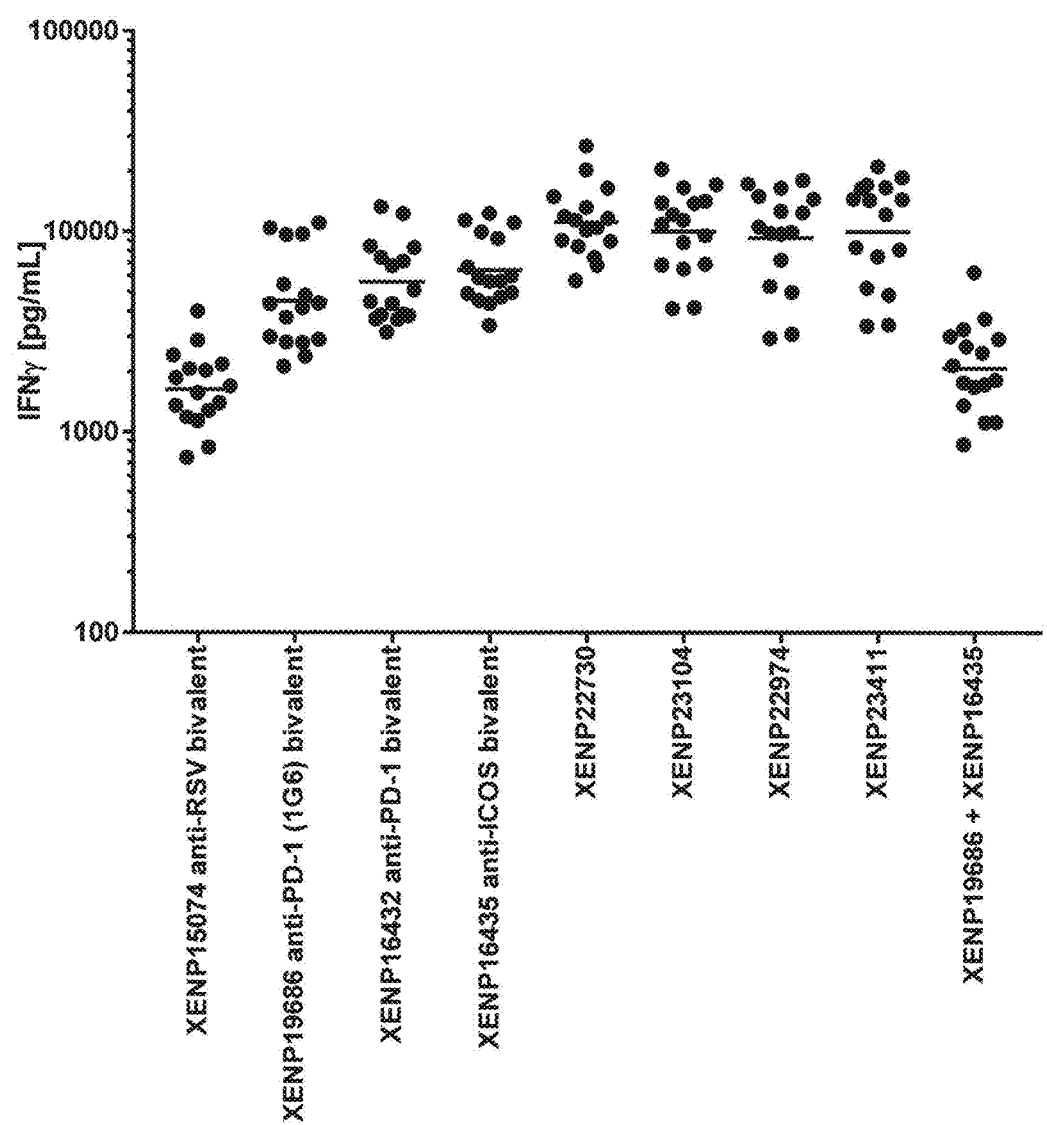

FIGS. 39A and 39B show that variant anti-ICOS x anti-PD-1 bispecific antibodies promote A) IL-2 and B) IFNγ secretion from SEB-stimulated PBMCs.

Figure 40A:
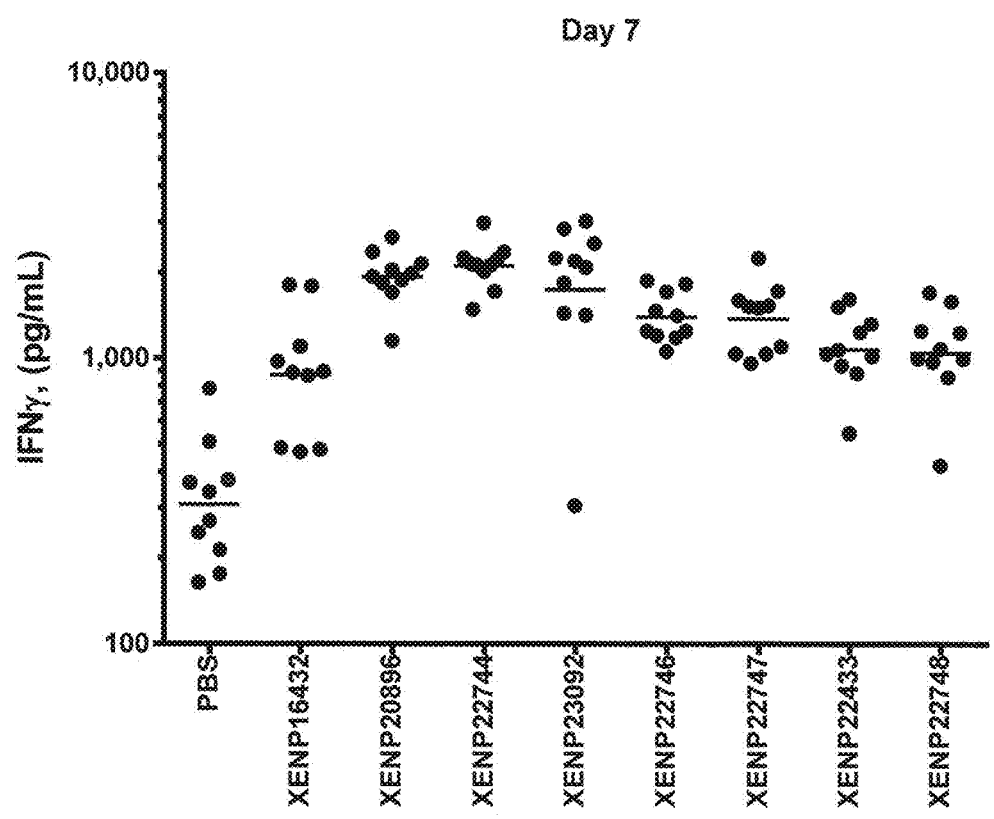
Figure 40B:
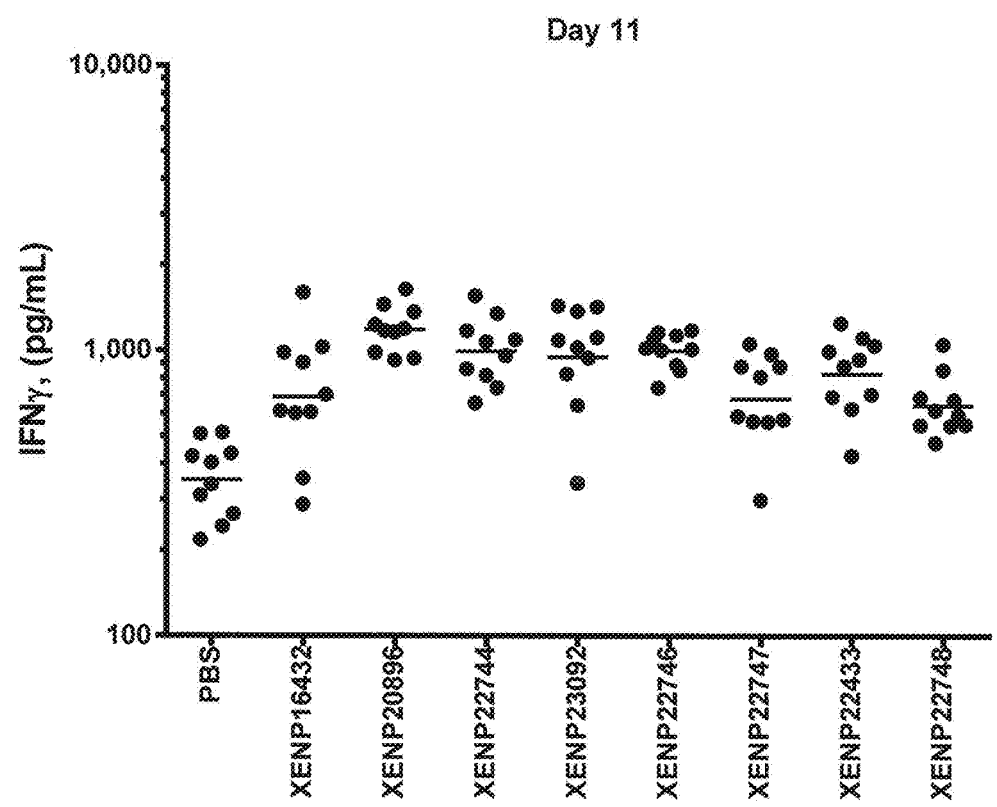

FIGS. 40A and 40B depicts the concentration of IFNγ in mice on Day A) 7 and B) 11 after engraftment with human PBMCs and treatment with the indicated test articles.

Figure 41B:
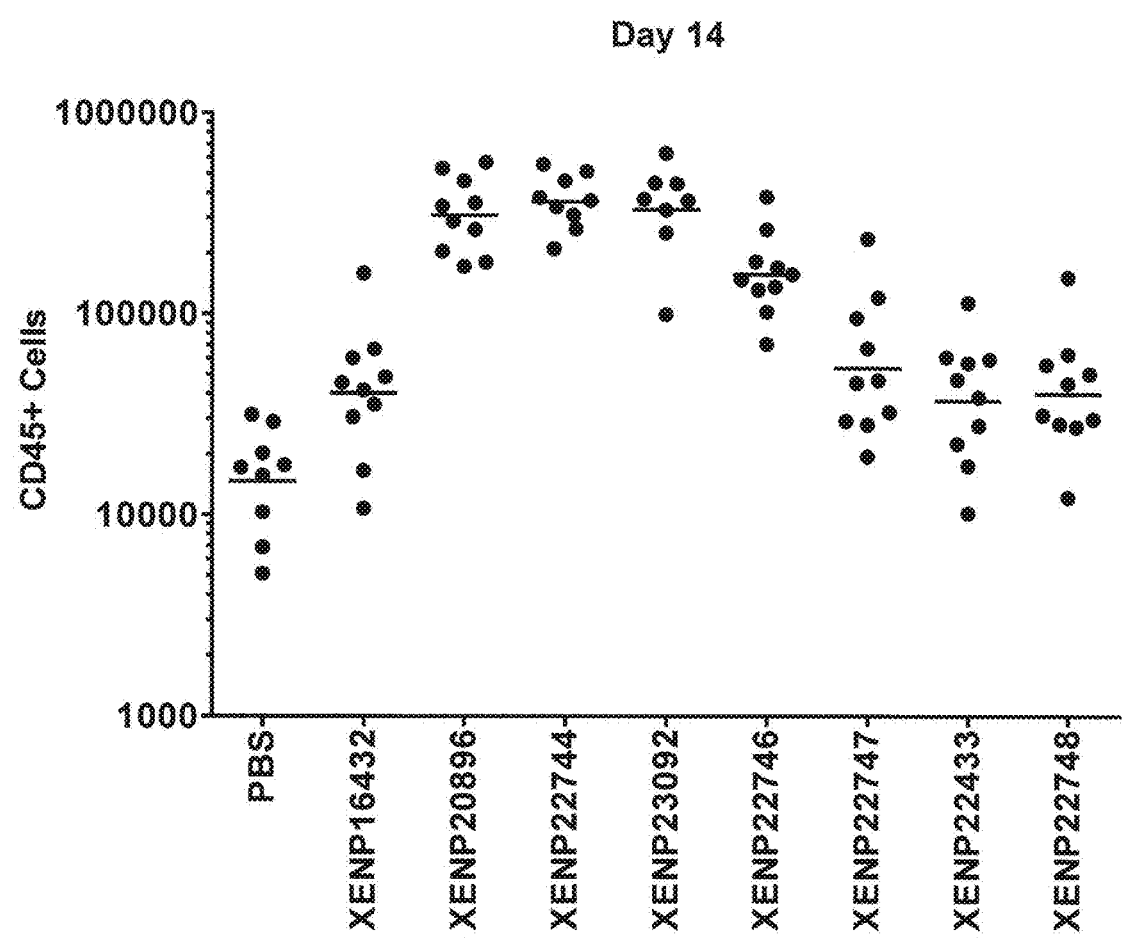

FIGS. 41A and 41B depicts CD45+ cell counts in mice as determined by flow cytometry on Day A) 11 and B) 14 after engraftment with human PBMCs and treatment with the indicated test articles.

Figure 42A:
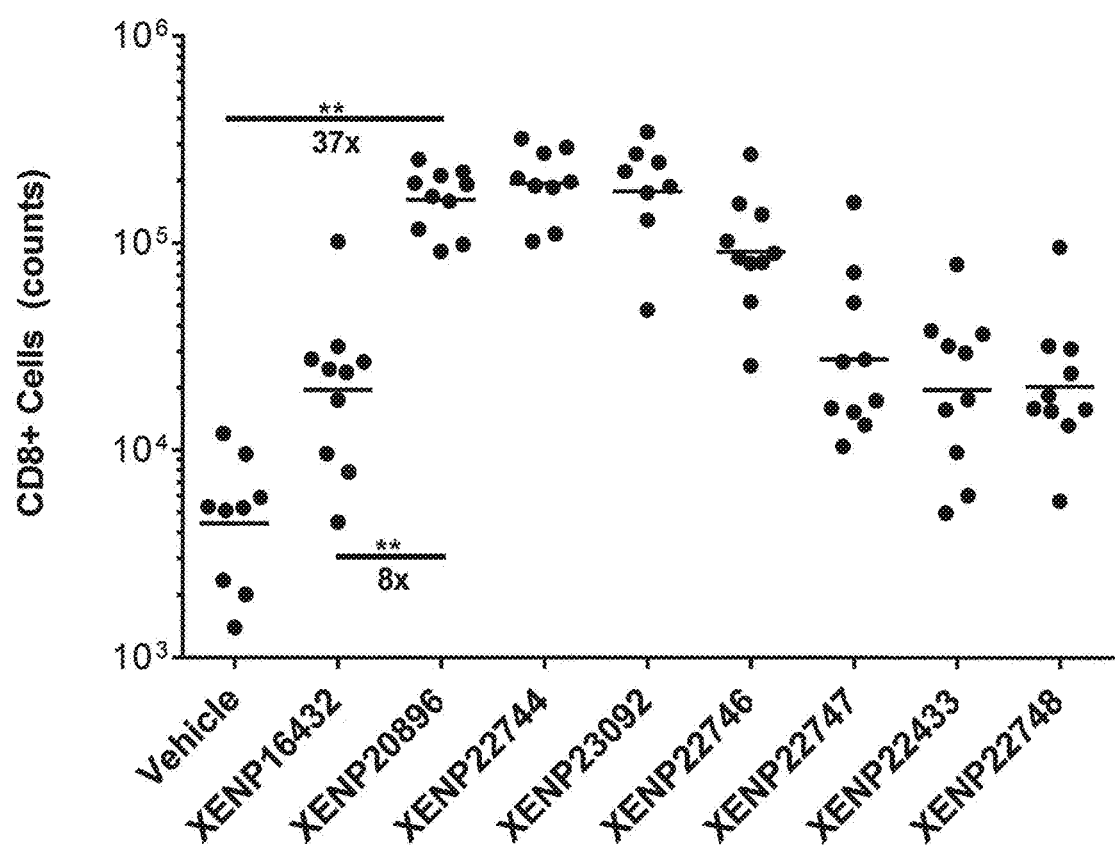
Figure 42B:
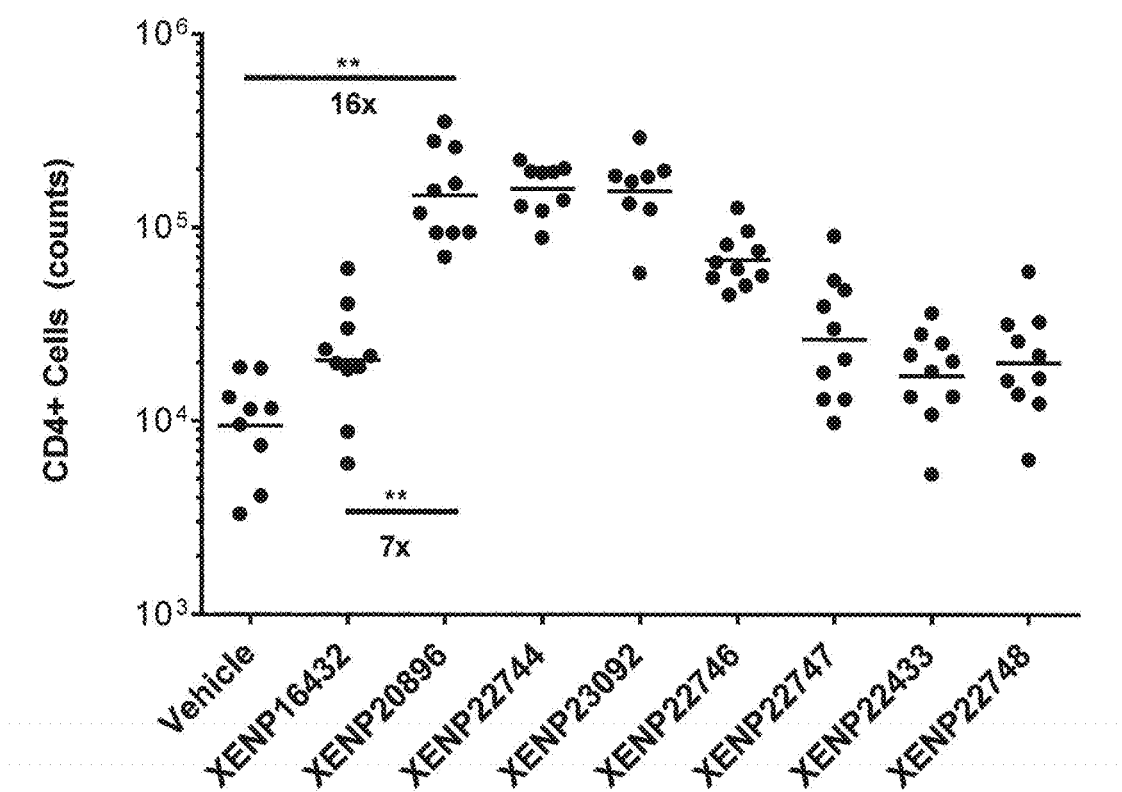

FIGS. 42A and 42B depicts A) CD8+ T cell and B) CD4+ T cell counts in mice as determined by flow cytometry on Day 14 after engraftment with human PBMCs and treatment with the indicated test articles (**p≤0.01).

Figure 43:
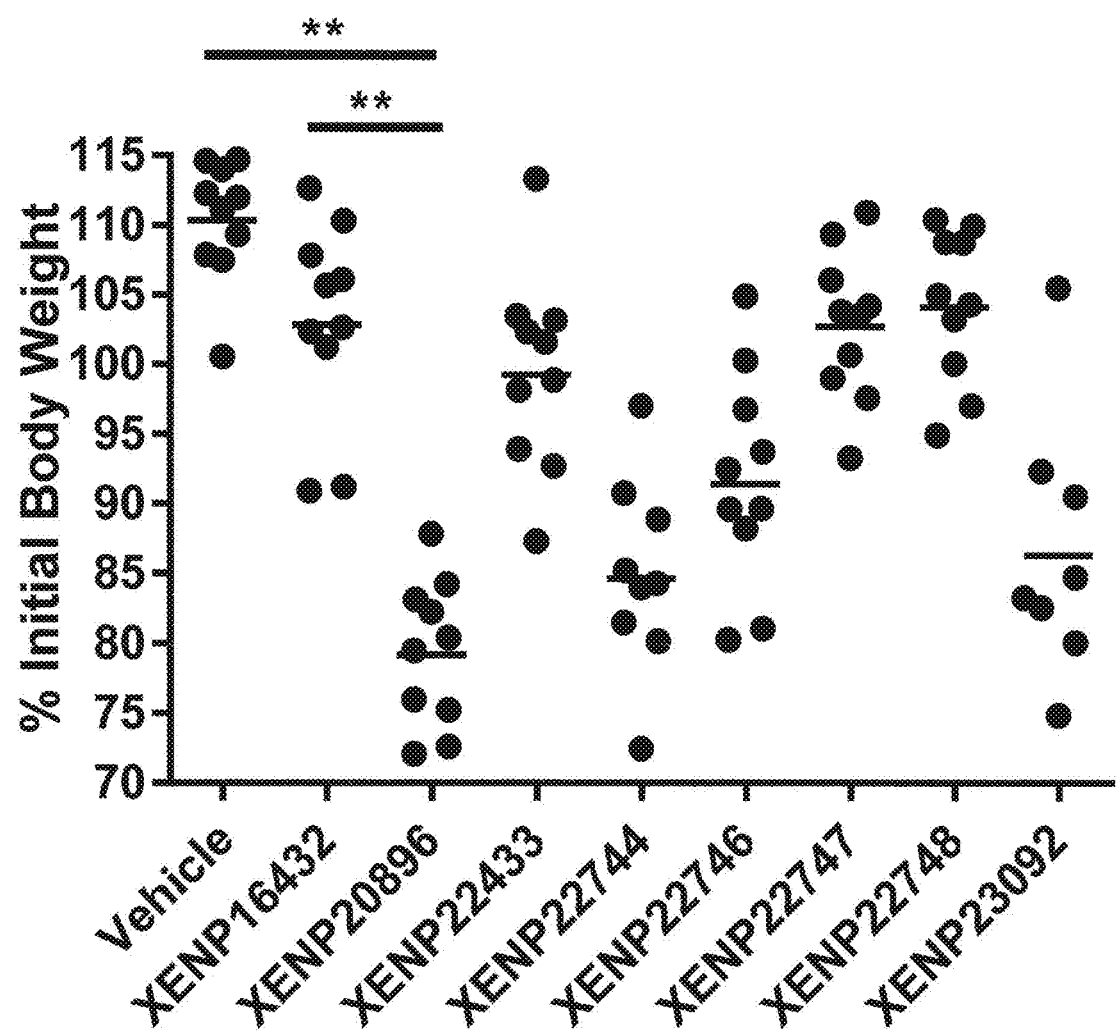

FIG. 43 depicts the change in body weight in mice by Day 14 after engraftment with human PBMCs and treatment with the indicated test articles (**p≤0.01).

Figure 44A:
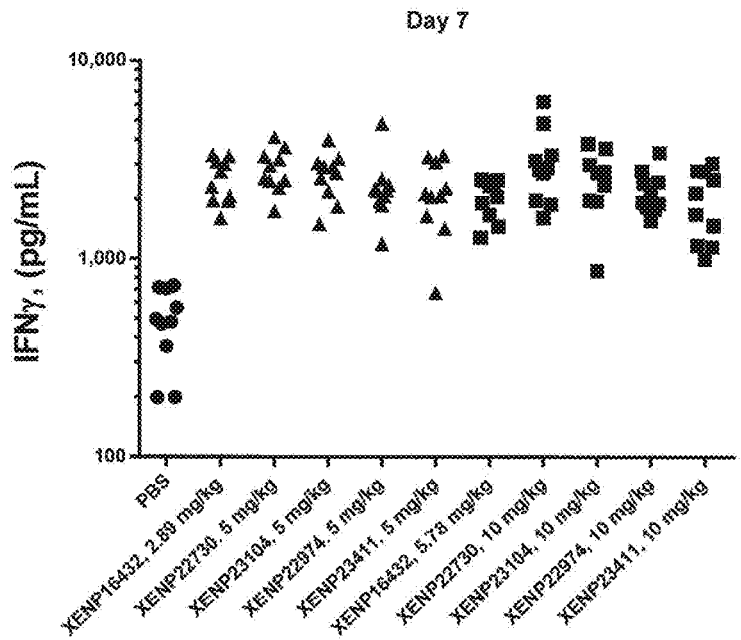
Figure 44B:
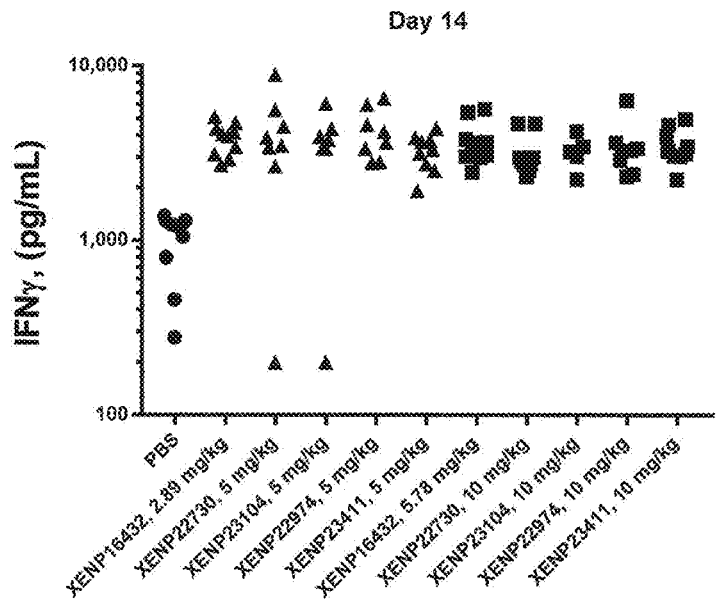

FIGS. 44A and 44B depicts the concentration of IFNγ in mice on Day A) 7 and B) 14 after engraftment with human PBMCs and treatment with the indicated test articles.

Figure 45:
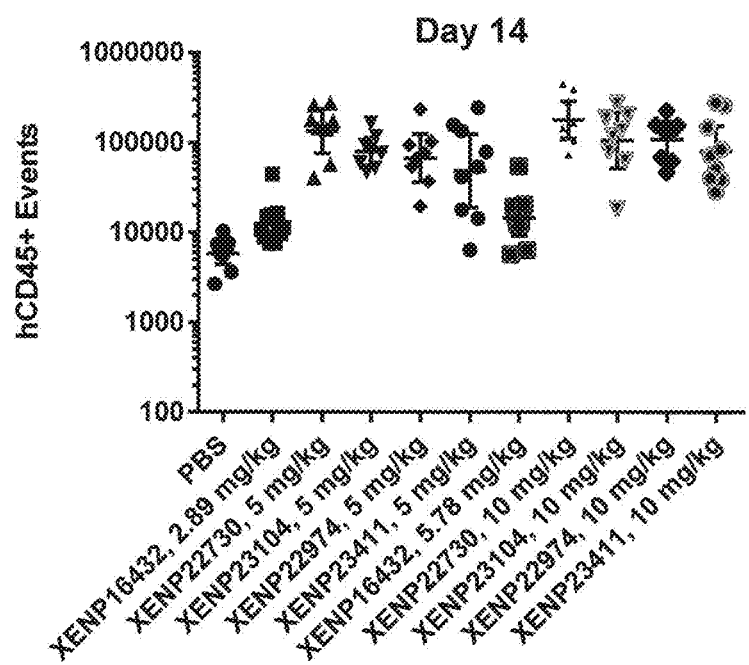

FIG. 45 depicts CD45+ cell counts in mice as determined by flow cytometry on Day 14 after engraftment with human PBMCs and treatment with the indicated test articles.

Figure 46A:
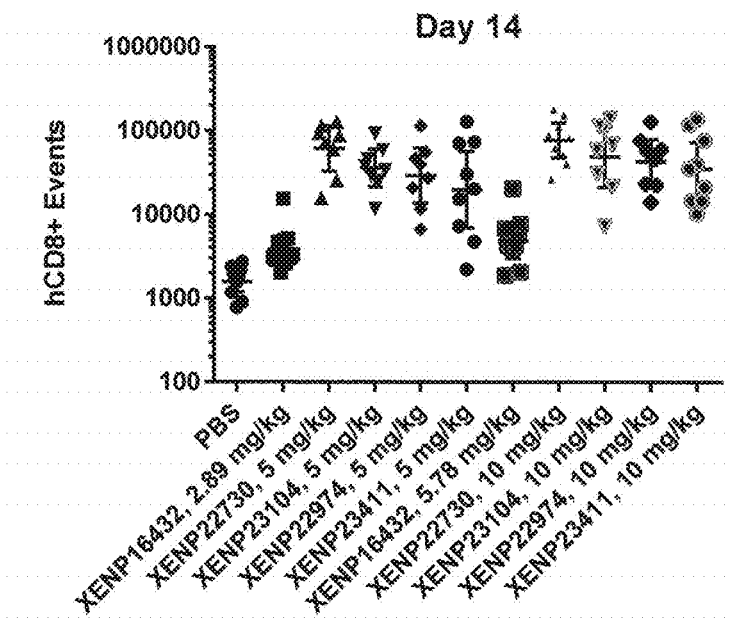
Figure 46B:
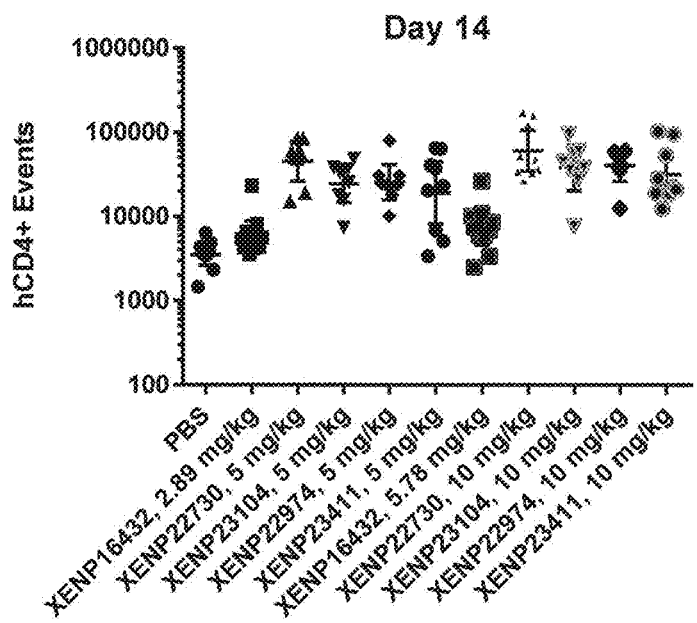
Figure 46C:
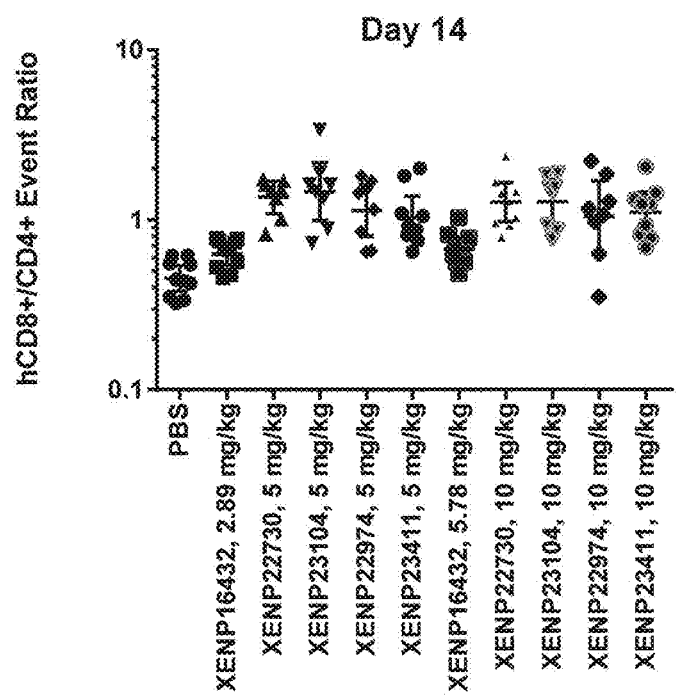

FIG. 46A to 46C depicts A) CD8+ T cell and B) CD4+ T cell counts in mice as determined by flow cytometry on Day 14 after engraftment with human PBMCs and treatment with the indicated test articles."

Figure 47A:
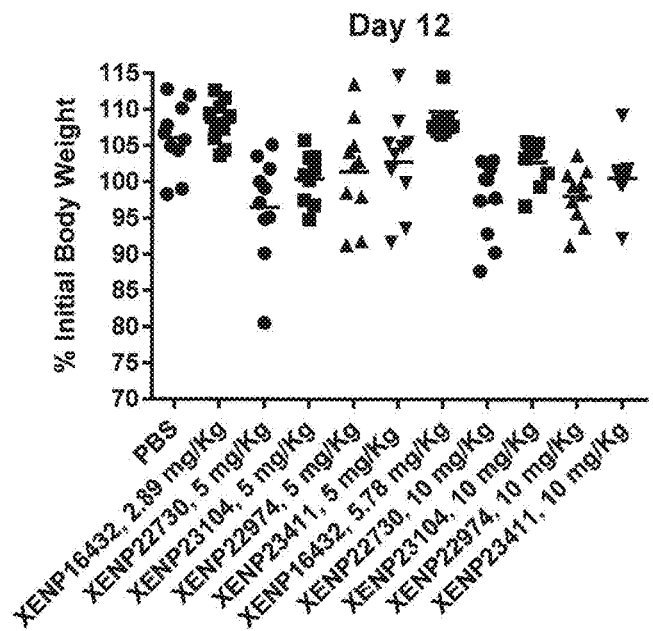
Figure 47B:
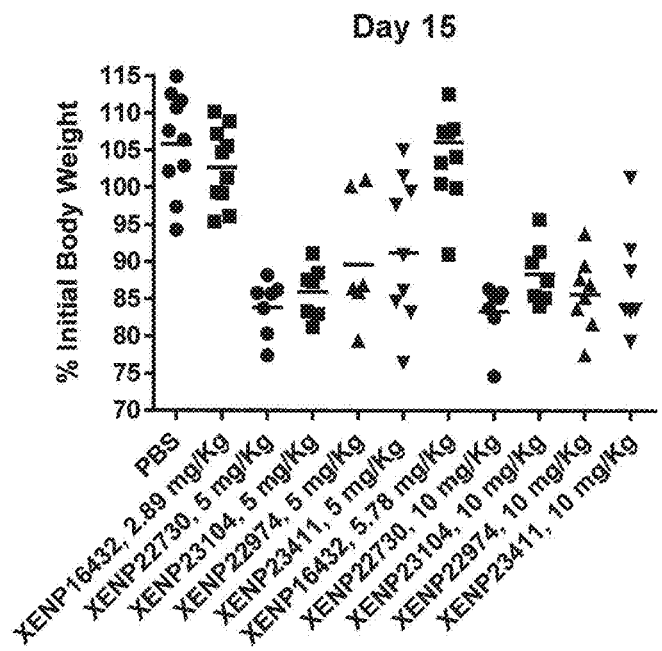

FIGS. 47A and 47B depicts the change in body weight in mice by Day 12 and 15 after engraftment with human PBMCs and treatment with the indicated test articles.

FIG. 48A to 48 depicts the amino acid sequences of exemplary anti-ICOS x anti-PD-1 antibodies in the bottle-opener format (Fab-scFv-Fc) with alternative ICOS ABDs. The antibodies are named using the Fab variable region first and the scFv variable region second, separated by a dash, followed by the chain designation (Fab-Fc heavy chain, scFv-Fc heavy chain or light chain). CDRs are underlined and slashes indicate the border(s) of the variable regions. The scFv domain has different orientations (N- to C-terminus) of either VH-scFv linker-VL or VL-scFv linker-VH as indicated, although this can be reversed. In addition, each sequence outlined herein can include or exclude the M428L/N434S variants in one or preferably both Fc domains, which results in longer half-life in serum.

Figure 49:
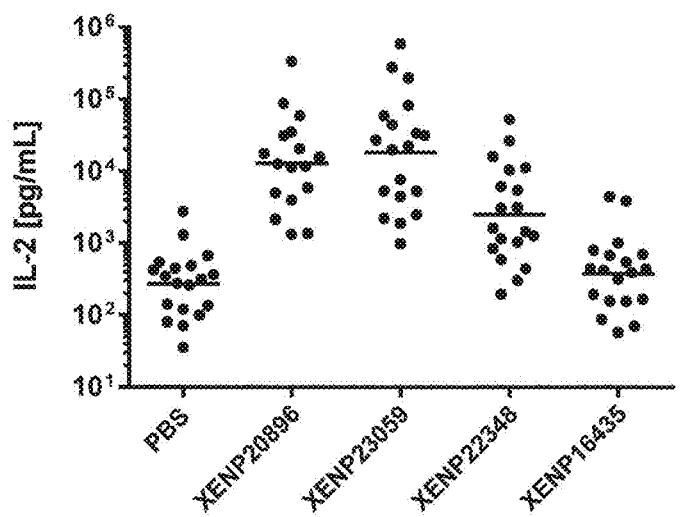

FIG. 49 depict cytokine release assay for IL-2 after SEB-stimulation of human PBMCs and treatment with alternative anti-ICOS x anti-PD-1 bispecific antibodies.

Figure 50:
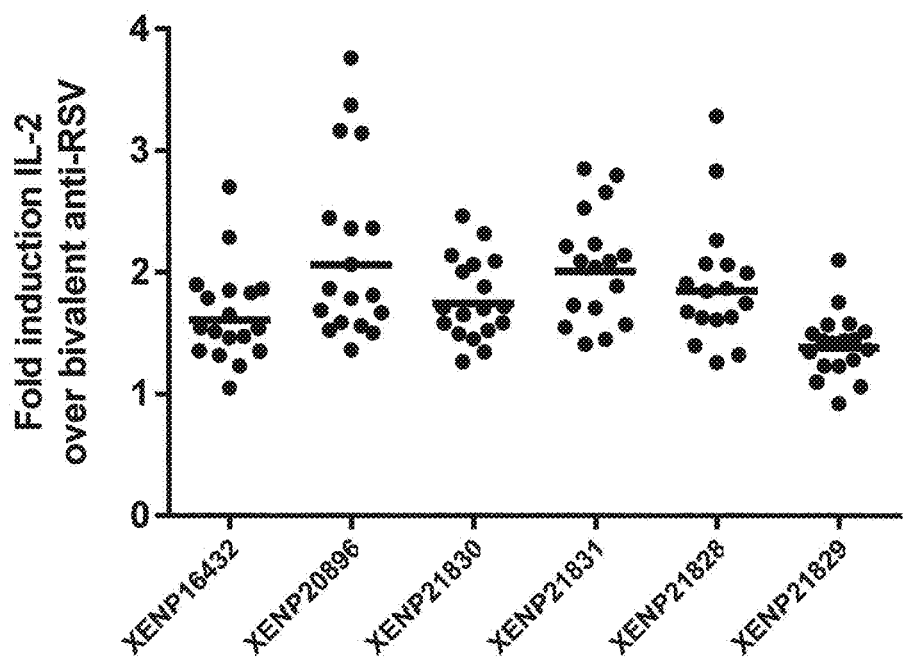

FIG. 50 depict cytokine release assay for IL-2 (as fold induction over bivalent anti-RSV mAb) after SEB-stimulation of human PBMCs and treatment with alternative anti-ICOS x anti-PD-1 bispecific antibodies.

Figure 51:
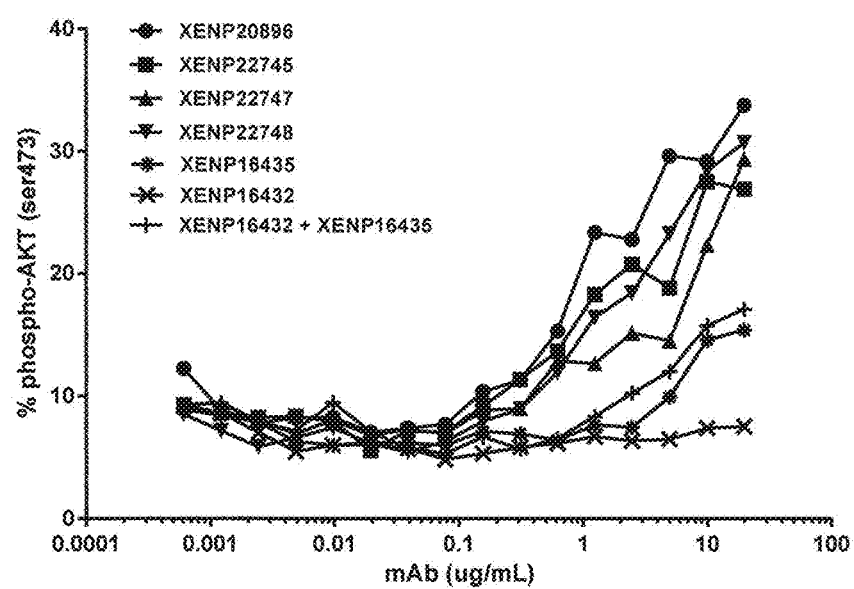
Figure 53A:
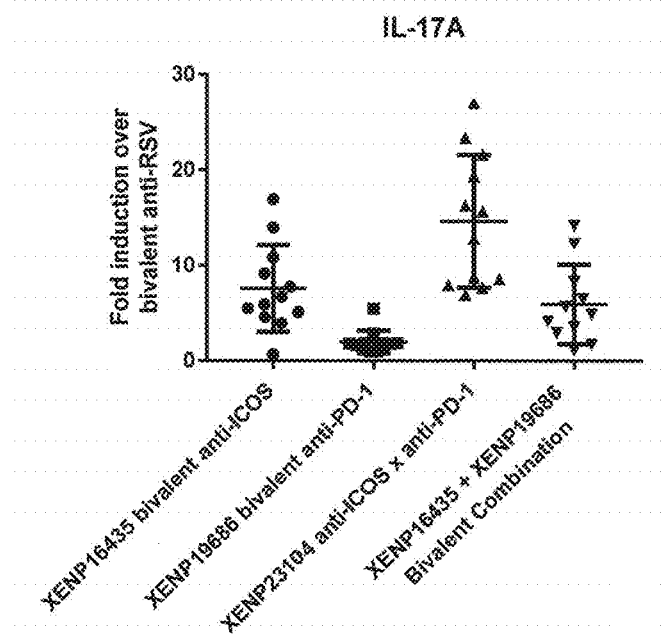
Figure 53B:
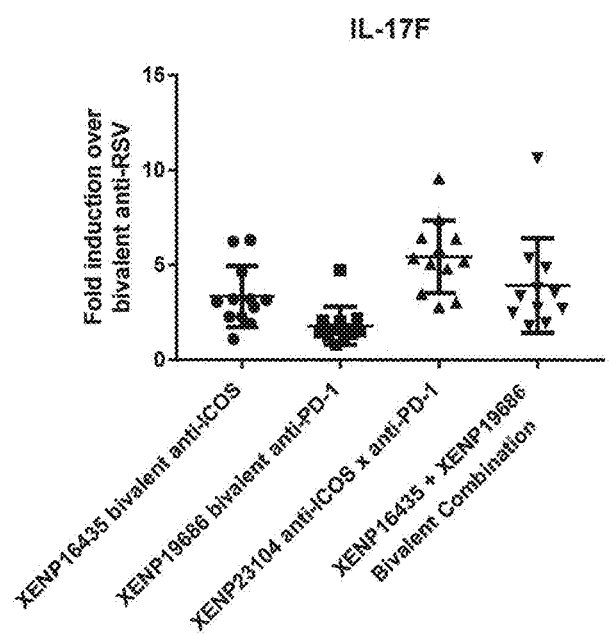
Figure 53C:
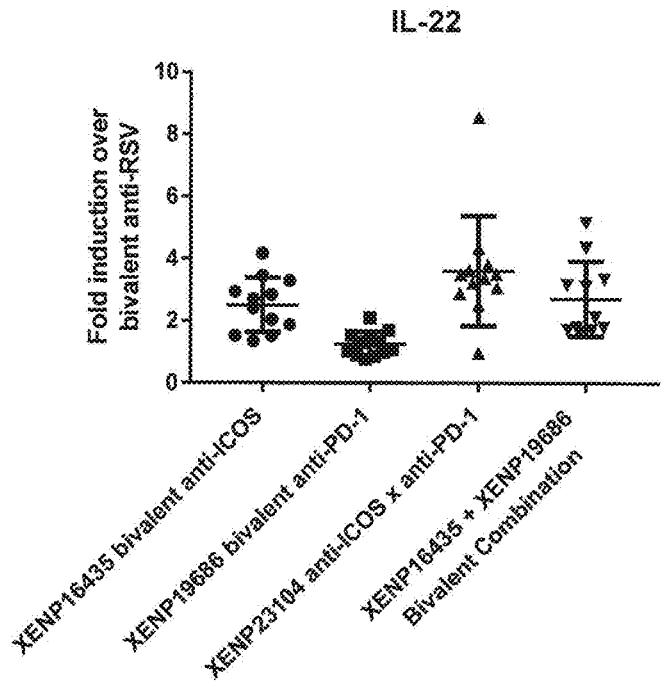
Figure 53D:
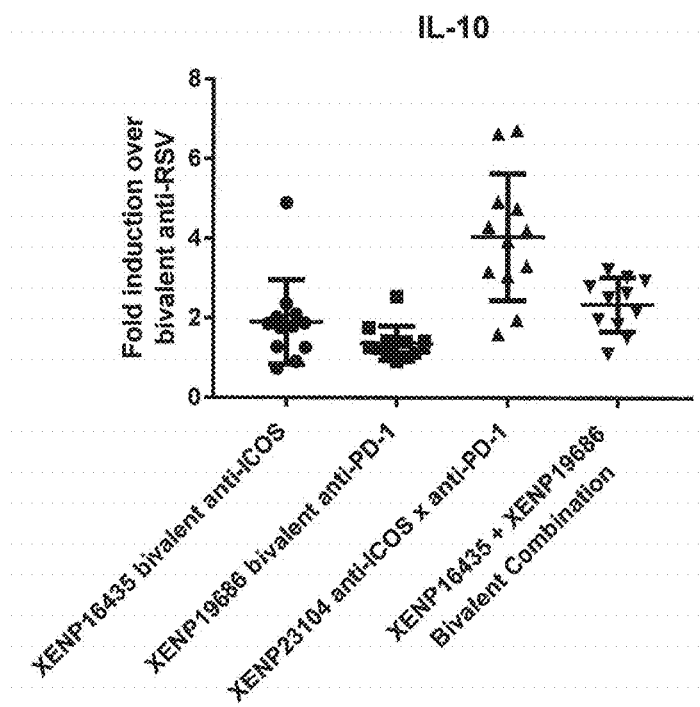
Figure 53E:
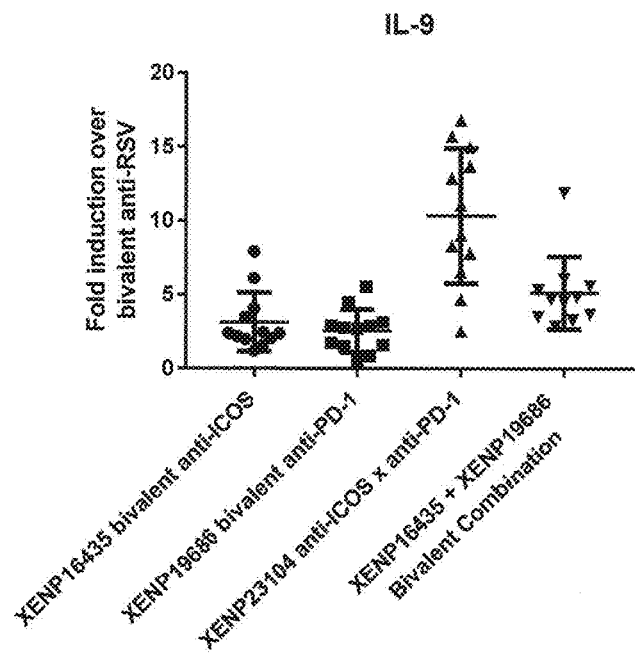
Figure 53F:
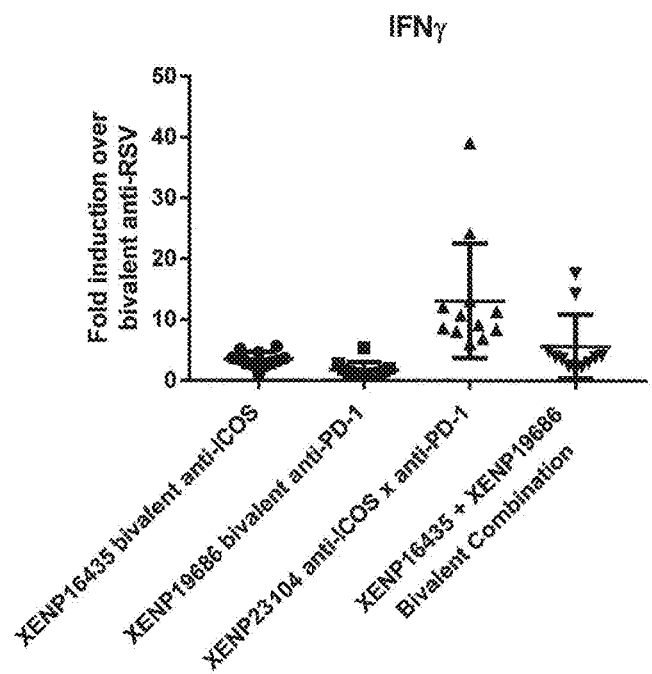

FIG. 51 depicts AKT phosphorylation in SEB-stimulated purified CD3+ T cells after treatment with anti-ICOS x anti-PD-1 bispecific antibodies.

FIG. 52 depicts fold induction of A) IL-17A, B) IL17F, C) IL-22, D) IL-10, E) IL-9, and F) IFNγ gene expression by the indicated test articles over induction by bivalent anti-RSV as determined by NanoString.

FIG. 53A to 53F depict mean fold induction in expression of selected immune response genes by indicated test articles over treatment with bivalent anti-RSV mAb as determined by NanoString. The shading intensity corresponds to the magnitude of the fold change.

Figure 54:
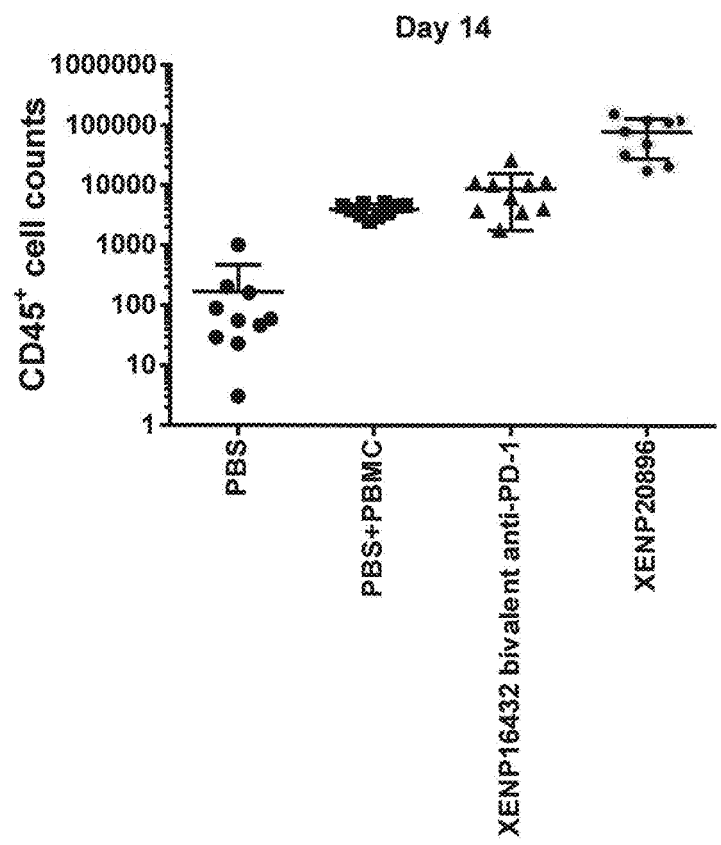

FIG. 54 depicts CD45+ cell counts in mice as determined by flow cytometry on Day 14 after engraftment with human PBMCs and treatment with the indicated test articles.

FIGS. 55A to 55D, similar to FIG. 9 and FIG. 75, depicts the sequences of the "backbone" portion (e.g. without the Fvs) of a number of additional formats, including the Central scFv of FIG. 2F, the Central-scFv2 format of FIG. 2J, the bispecific mAb of FIG. 2K, the DVD-Ig of FIG. 2L and the Trident format of FIG. 2M. In FIG. 2L, the DVD-Ig® linkers are shown with double underlining, with other linkers found in WO2007/024715, hereby incorporated by reference in its entirety and in particular for those sequences. In the Trident format, other Trident linkers and coil-coil sequences are shown in WO 2015/184203, hereby incorporated by reference in its entirety and in particular for those sequences. As will be appreciated by those in the art, bolded domains (e.g. "VH1", VH2-scFv linker-VL2", etc.) are separated with slashes "/", and may include optional domain linkers as needed. All of these backbones utilize the kappa constant region for the light chain, although the lambda chain can also be used. As for FIG. 9 and FIG. 75, these backbones can be combined with any vh and vl domains as outlined herein.

FIGS. 56A and 56B depicts the amino acid sequence of illustrative anti-PD-1 x anti-ICOS antibodies in the bottle-opener format (Fab-scFv-Fc). The antibodies are named using the Fab variable region first and the scFv variable region second, separated by a dash, followed by the chain designation (Fab-Fc heavy chain, scFv-Fc heavy chain or light chain). CDRs are underlined and slashes indicate the border(s) of the variable regions. The scFv domain has different orientations (N- to C-terminus) of either VH-scFv linker-VL or VL-scFv linker-VH as indicated, although this can be reversed. In addition, each sequence outlined herein can include or exclude the M428L/N434S variants in one or preferably both Fc domains, which results in longer half-life in serum.

FIG. 57A to 57C depicts the amino acid sequence of illustrative anti-PD-1 x anti-ICOS antibodies in the central-scFv format. The antibodies are named using the first Fab-Fc variable region first and the Fab-scFv-Fc variable region second, separated by a dash, followed by the chain designation (Fab-Fc heavy chain, Fab-scFv-Fc heavy chain or light chain). CDRs are underlined and slashes indicate the border(s) of the variable regions. The scFv domain has different orientations (N- to C-terminus) of either VH-scFv linker-VL or VL-scFv linker-VH as indicated, although this can be reversed. In addition, each sequence outlined herein can include or exclude the M428L/N434S variants in one or preferably both Fc domains, which results in longer half-life in serum.

FIG. 58 depicts the amino acid sequence of illustrative anti-PD-1 x anti-ICOS antibodies in the central-scFv2 format. The antibodies are named using the Fab variable region first and the scFv variable region second, followed by the chain designation (heavy chain or light chain). CDRs are underlined and slashes indicate the border(s) of the variable regions. The scFv domain has different orientations (N- to C-terminus) of either VH-scFv linker-VL or VL-scFv linker-VH as indicated, although this can be reversed. In addition, each sequence outlined herein can include or exclude the M428L/N434S variants in one or preferably both Fc domains, which results in longer half-life in serum.

FIG. 59 depicts the amino acid sequence of an illustrative anti-PD-1 x anti-ICOS antibody in the bispecific mAb format. The antibodies are named using the first Fab variable region for a first antigen and the second Fab variable region for a second antigen, separated by a dash, followed by the chain designation (Heavy Chain 1 or Light Chain 1 for the first antigen and Heavy Chain 2 or Light Chain 2 for the second antigen). CDRs are underlined and slashes indicate the border(s) of the variable regions. Each sequence outlined herein can include or exclude the M428L/N434S variants in one or preferably both Fc domains, which results in longer half-life in serum.

FIG. 60 depicts the amino acid sequence of an illustrative anti-PD-1 x anti-ICOS antibody in the DVD-IgG format. The antibodies are named using the first variable region for a first antigen and the second Fab variable region for a second antigen, followed by the chain designation (Heavy Chain or Light Chain). CDRs are underlined and slashes indicate the border(s) of the variable regions. Each sequence outlined herein can include or exclude the M428L/N434S variants in one or preferably both Fc domains, which results in longer half-life in serum.

FIGS. 61A and 61B depicts the amino acid sequence of an illustrative anti-PD-1 x anti-ICOS antibody in the Trident format. The antibodies are named using the VL and VH of a first antigen which comprises a DART and the Fab variable region for a second antigen, separated by a dash, followed by the chain designation (Heavy Chain or Light Chain). CDRs are underlined and slashes indicate the border(s) of the variable regions. Each sequence outlined herein can include or exclude the M428L/N434S variants in one or preferably both Fc domains, which results in longer half-life in serum.

Figure 62:
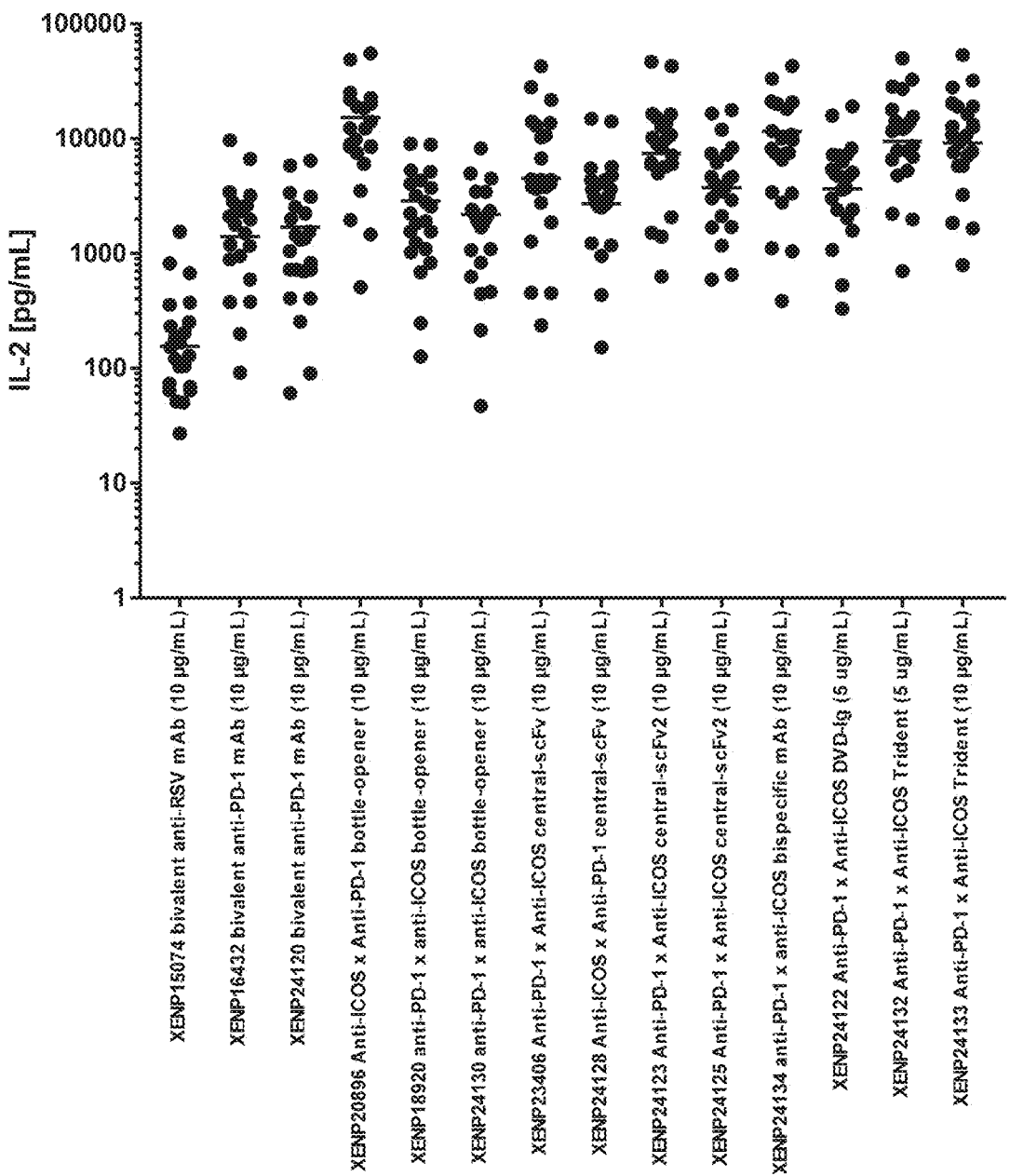

FIG. 62 depicts induction of cytokine secretion (IL-2) by alternative format costim x checkpoint blockade bispecific antibodies in an SEB-stimulated PBMC assay.

FIG. 63 depicts the amino acid sequences of an illustrative anti-ICOS x anti-CTLA-4 antibody in the bottle-opener format (Fab-scFv-Fc). The antibodies are named using the Fab variable region first and the scFv variable region second, separated by a dash, followed by the chain designation (Fab-Fc heavy chain, scFv-Fc heavy chain or light chain). CDRs are underlined and slashes indicate the border(s) of the variable regions. The scFv domain has different orientations (N- to C-terminus) of either VH-scFv linker-VL or VL-scFv linker-VH as indicated, although this can be reversed. In addition, each sequence outlined herein can include or exclude the M428L/N434S variants in one or preferably both Fc domains, which results in longer half-life in serum.

FIGS. 64A and 64B depicts the amino acid sequence of illustrative anti-LAG-3 x anti-ICOS antibodies in the bispecific mAb format. The antibodies are named using the first Fab variable region for a first antigen and the second Fab variable region for a second antigen, separated by a dash, followed by the chain designation (Heavy Chain 1 or Light Chain 1 for the first antigen and Heavy Chain 2 or Light Chain 2 for the second antigen). CDRs are underlined and slashes indicate the border(s) of the variable regions. Each sequence outlined herein can include or exclude the M428L/N434S variants in one or preferably both Fc domains, which results in longer half-life in serum.

FIG. 65 depicts the amino acid sequence of an illustrative anti-TIM-3 x anti-ICOS antibody in the bispecific mAb format. The antibodies are named using the first Fab variable region for a first antigen and the second Fab variable region for a second antigen, separated by a dash, followed by the chain designation (Heavy Chain 1 or Light Chain 1 for the first antigen and Heavy Chain 2 or Light Chain 2 for the second antigen). CDRs are underlined and slashes indicate the border(s) of the variable regions. Each sequence outlined herein can include or exclude the M428L/N434S variants in one or preferably both Fc domains, which results in longer half-life in serum.

FIG. 66A to 66C depicts the amino acid sequences of anti-ICOS x anti-PD-L1 antibodies in the bottle-opener format (Fab-scFv-Fc) and central-scFv2 format. The bottle-openers are named using the Fab variable region first and the scFv variable region second, separated by a dash, followed by the chain designation (Fab-Fc heavy chain, scFv-Fc heavy chain or light chain). Central-scFv2s are named using the Fab variable region first and the scFv variable region second, followed by the chain designation (heavy chain or light chain). CDRs are underlined and slashes indicate the border(s) of the variable regions. CDRs are underlined and slashes indicate the border(s) of the variable regions. The scFv domain has different orientations (N- to C-terminus) of either VH-scFv linker-VL or VL-scFv linker-VH as indicated, although this can be reversed. In addition, each sequence outlined herein can include or exclude the M428L/N434S variants in one or preferably both Fc domains, which results in longer half-life in serum.

Figure 67:
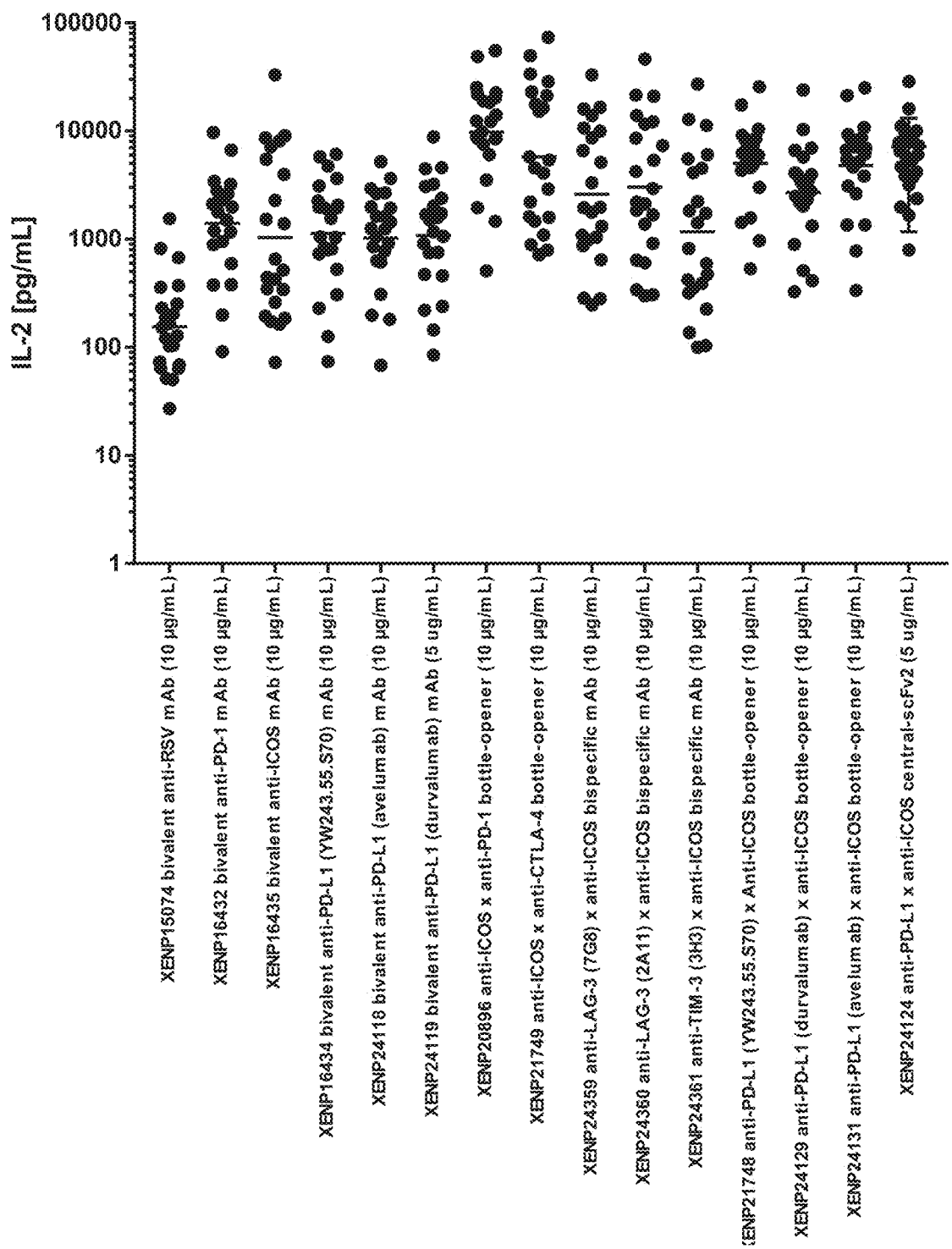

FIG. 67 depicts induction of cytokine secretion (IL-2) by additional costim x checkpoint blockade bispecific antibodies in an SEB-stimulated PBMC assay.

FIG. 68A to 68G depict amino acid sequences for exemplary one-arm anti-ICOS Fab-Fc antibodies. CDRs are underlined and slashes indicate the border(s) of variable regions. These are referred to as "one-arm" or "one armed" formats as one amino acid chain is only an Fc domain, with the other side being an anti-ICOS Fab side. The Fc domain contains the S364K/E357Q skew variants, as well as the pI(−)_Isosteric_A variants depicted in Figure X. The Fab Fc domain contains the L368D/K370S skew variants as well as the pI ISO(+RR) variants depicted in Figure X. Both Fc domains include the ablation variants (E233P/L234V/L235A/G236del/S267K).

FIG. 69 depicts equilibrium dissociation constants (KD), association rates (ka), and dissociation rates (kd) of variant one-arm anti-ICOS Fab-Fc antibodies for murine Fc fusions of human ICOS captured on AMC biosensors as determined by Octet.

Figure 70:
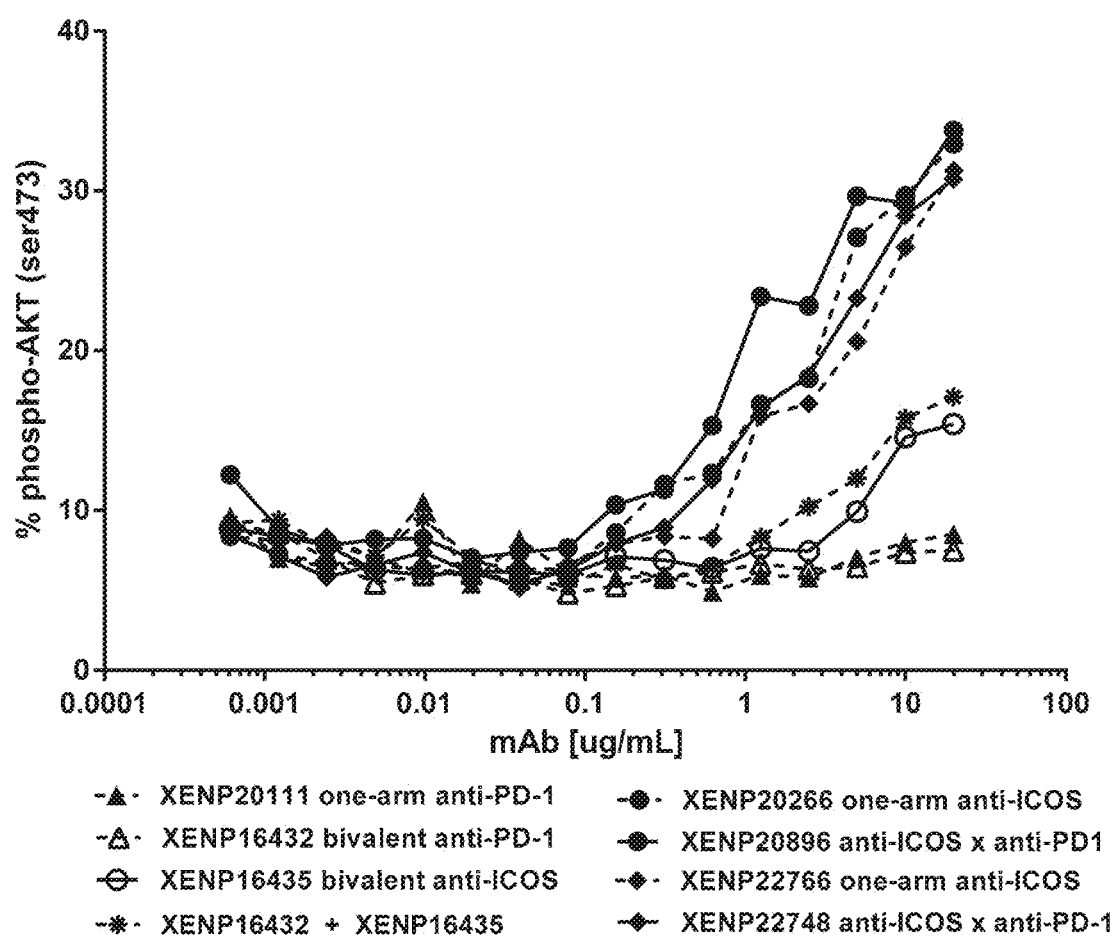

FIG. 70 depicts AKT phosphorylation in SEB-stimulated purified CD3+ T cells after treatment with bivalent and monovalent anti-PD-1 antibodies and anti-ICOS x anti-PD-1 bispecific antibodies.

Figure 71:
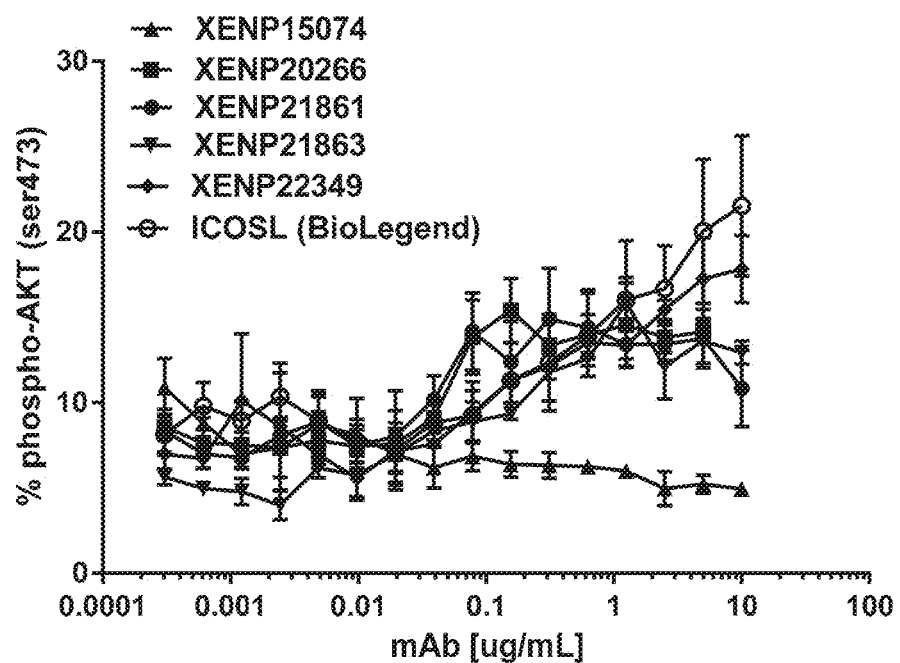

FIG. 71 depicts AKT phosphorylation in purified CD3+ T cells after treatment with monovalent anti-ICOS Fab-Fc antibodies with alternative anti-ICOS ABDs.

FIG. 72A to 72C depict some prototype bispecific antibodies (OX40 X PD-1, GITR X PD-1, 4-1BB X PD-1, CTLA-4 X ICOS).

FIG. 73A to 73H depict some prototype mAbs (4-1BB, OX40, GITR, ICOS, PD-L1 and PD-1), the Fvs of which can be used in combination with the other Fvs of the invention and in any format (bottle opener, mAb-Fv, mAb-scFv, central-scFv, bispecific mAb, central-Fv, one armed central-scFv, one armed scFv-mAb, dual scFv, DVD-Ig or Trident). Some additional ICOS X PD-L1 bottle opener sequences are shown as well.

FIG. 74A to 74F depict additional PD-1 X ICOS bottle openers, in some cases with the PD-1 Fv being in the Fab format and the ICOS Fv in a scFv format and in other cases reversed.

FIG. 75A to 75D shows the sequences of a mAb-scFv backbone of use in the invention, to which the Fv sequences of the invention are added. mAb-scFv backbone 1 is based on human IgG1 (356E/358M allotype), and includes the S364K/E357Q: L368D/K370S skew variants, the N208D/Q295E/N384D/Q418E/N421D pI variants on the Fab side and the E233P/L234V/L235A/G236del/S267K ablation variants on both chains. Backbone 2 is based on human IgG1 (356D/358L allotype), and includes the S364K/E357Q: L368D/K370S skew variants, the N208D/Q295E/N384D/Q418E/N421D pI variants on the Fab side and the E233P/L234V/L235A/G236del/S267K ablation variants on both chains. Backbone 3 is based on human IgG1 (356E/358M allotype), and includes the S364K/E357Q: L368D/K370S skew variants, N208D/Q295E/N384D/Q418E/N421D pI variants on the Fab side and the E233P/L234V/L235A/G236del/S267K ablation variants on both chains, as well as an N297A variant on both chains. Backbone 4 is identical to 3 except the mutation is N297S. Alternative formats for mAb-scFv backbones 3 and 4 can exclude the ablation variants E233P/L234V/L235A/G236del/S267K in both chains. Backbone 5 is based on human IgG4, and includes the S364K/E357Q:L368D/K370S skew variants, the N208D/Q295E/N384D/Q418E/N421D pI variants on the Fab side and the E233P/L234V/L235A/G236del/S267K ablation variants on both chains, as well as a S228P (EU numbering, this is S241P in Kabat) variant on both chains that ablates Fab arm exchange as is known in the art Backbone 6 is based on human IgG2, and includes the S364K/E357Q: L368D/K370S skew variants, the N208D/Q295E/N384D/Q418E/N421D pI variants on the Fab side. Backbone 7 is based on human IgG2, and includes the S364K/E357Q: L368D/K370S skew variants, the N208D/Q295E/N384D/Q418E/N421D pI variants on the Fab side as well as a S267K variant on both chains.

As will be appreciated by those in the art and outlined below, these sequences can be used with any vh and vl pairs outlined herein, with one monomer including both a Fab and an scFv (optionally including a charged scFv linker) and the other monomer including the Fab sequence (e.g. a vh attached to the "Fab side heavy chain" and a vl attached to the "constant light chain"). That is, any Fv sequences outlined herein for anti-CTLA-4, anti-PD-1, anti-LAG-3, anti-TIM-3, anti-TIGIT, anti-BTLA, anti-ICOS, anti-GITR, anti-OX40 and anti-4-1BB, whether as scFv (again, optionally with charged scFv linkers) or as Fabs, can be incorporated into this FIG. 75 backbone in any combination. The monomer 1 side is the Fab-scFv pI negative side, and includes the heterodimerization variants L368D/K370S, the isosteric pI variants N208D/Q295E/N384D/Q418E/N421D, the ablation variants E233P/L234V/L235A/G236del/S267K, (all relative to IgG1). The monomer 2 side is the scFv pI positive side, and includes the heterodimerization variants 364K/E357Q. However, other skew variant pairs can be substituted, particularly [S364K/E357Q: L368D/K370S]; [L368D/K370S: S364K]; [L368E/K370S: S364K]; [T411T/E360E/Q362E: D401K]; [L368D/K370S: S364K/E357L], [K370S: S364K/E357Q], [T366S/L368A/Y407V: T366W] and [T366S/L368A/Y407V/Y394C: T366W/S354C].

The constant light chain depicted in FIG. 75A can be used for all of the constructs in the figure, although the kappa constant light chain can also be substituted.

It should be noted that these mAb-scFv backbones find use in the both the mAb-Fv format of FIG. 1H (where one monomer comprises a vl at the C-terminus and the other a vh at the C-terminus) as well as the scFv-mAb format (with a scFv domain added to the C-terminus of one of the monomers).

Included within each of these backbones are sequences that are 90, 95, 98 and 99% identical (as defined herein) to the recited sequences, and/or contain from 1, 2, 3, 4, 5, 6, 7, 8, 9 or 10 additional amino acid substitutions (as compared to the "parent" of the Figure, which, as will be appreciated by those in the art, already contain a number of amino acid modifications as compared to the parental human IgG1 (or IgG2 or IgG4, depending on the backbone). That is, the recited backbones may contain additional amino acid modifications (generally amino acid substitutions) in addition to the skew, pI and ablation variants contained within the backbones of this figure.

FIG. 76A to 76F depict a number of prior art sequences for Fvs that bind human PD-1 as vh and vl sequences. As will be appreciated by those in the art, any of these Fvs can be combined with an Fv that binds a costimulatory receptor (e.g. ICOS, GITR, OX40 or 4-1BB, including the Fv sequences contained herein) and in any format (bottle opener, mAb-Fv, mAb-scFv, central-scFv, bispecific mAb, central-Fv, one armed central-scFv, one armed scFv-mAb, dual scFv, DVD-Ig or Trident). In particular they can be combined with ICOS]_H0L0 and [ICOS]H0.66_L0 ABDs.

FIGS. 77A and 77B depict a number of prior art sequences for Fvs that bind human ICOS as vh and vl sequences. As will be appreciated by those in the art, any of these Fvs can be combined with an Fv that binds a checkpoint receptor (e.g. PD-1, PD-L1, CTLA-4, TIM-3, LAG-3, TIGIT and BTLA, including the Fv sequences contained herein) and in any format (bottle opener, mAb-Fv, mAb-scFv, central-scFv, bispecific mAb, central-Fv, one armed central-scFv, one armed scFv-mAb, dual scFv, DVD-Ig or Trident). In particular they can be combined with PD-1 ABDs having the identifiers 1G6_H1.279_L1.194; 1G6_H1.280_L1.224; 1G6_L1.194_H1.279; 1G6_L1.210_H1.288; and 2E9_H1L1.

FIG. 78A to 78J depict a number of prior art sequences for Fvs that bind human PD-L1 as vh and vl sequences. As will be appreciated by those in the art, any of these Fvs can be combined with an Fv that binds a costimulatory receptor (e.g. ICOS, GITR, OX40 or 4-1BB, including the Fv sequences contained herein) and in any format (bottle opener, mAb-Fv, mAb-scFv, central-scFv, bispecific mAb, central-Fv, one armed central-scFv, one armed scFv-mAb, dual scFv, DVD-Ig or Trident). In particular they can be combined with ICOS]_H0L0 and [ICOS]_H0.66 L0 ABDs.

FIGS. 79A and 79B depict a number of prior art sequences for Fvs that bind human CTLA-4 as vh and vl sequences. As will be appreciated by those in the art, any of these Fvs can be combined with an Fv that binds a costimulatory receptor (e.g. ICOS, GITR, OX40 or 4-1BB, including the Fv sequences contained herein) and in any format (bottle opener, mAb-Fv, mAb-scFv, central-scFv, bispecific mAb, central-Fv, one armed central-scFv, one armed scFv-mAb, dual scFv, DVD-Ig or Trident). In particular they can be combined with ICOS]_H0L0 and [ICOS]_H0.66 L0 ABDs.

FIG. 80A to 80C depict a number of prior art sequences for Fvs that bind human LAG-3 as vh and vl sequences. As will be appreciated by those in the art, any of these Fvs can be combined with an Fv that binds a costimulatory receptor (e.g. ICOS, GITR, OX40 or 4-1BB, including the Fv sequences contained herein) and in any format (bottle opener, mAb-Fv, mAb-scFv, central-scFv, bispecific mAb, central-Fv, one armed central-scFv, one armed scFv-mAb, dual scFv, DVD-Ig or Trident). In particular they can be combined with ICOS]_H0L0 and [ICOS]H0.66_L0 ABDs.

FIG. 81A to 81C depict a number of prior art sequences for Fvs that bind human TIM-3 as vh and vl sequences. As will be appreciated by those in the art, any of these Fvs can be combined with an Fv that binds a costimulatory receptor (e.g. ICOS, GITR, OX40 or 4-1BB, including the Fv sequences contained herein) and in any format (bottle opener, mAb-Fv, mAb-scFv, central-scFv, bispecific mAb, central-Fv, one armed central-scFv, one armed scFv-mAb, dual scFv, DVD-Ig or Trident). In particular they can be combined with ICOS]_H0L0 and [ICOS]_H0.66_L0 ABDs.

FIG. 82 depict a number of prior art sequences for Fvs that bind human BTLA as vh and vl sequences. As will be appreciated by those in the art, any of these Fvs can be combined with an Fv that binds a costimulatory receptor (e.g. ICOS, GITR, OX40 or 4-1BB, including the Fv sequences contained herein) and in any format (bottle opener, mAb-Fv, mAb-scFv, central-scFv, bispecific mAb, central-Fv, one armed central-scFv, one armed scFv-mAb, dual scFv, DVD-Ig or Trident). In particular they can be combined with ICOS]_H0L0 and [ICOS]H0.66_L0 ABDs.

FIG. 83A to 83D depict a number of prior art sequences for Fvs that bind human TIGIT as vh and vl sequences. As will be appreciated by those in the art, any of these Fvs can be combined with an Fv that binds a costimulatory receptor (e.g. ICOS, GITR, OX40 or 4-1BB, including the Fv sequences contained herein) and in any format (bottle opener, mAb-Fv, mAb-scFv, central-scFv, bispecific mAb, central-Fv, one armed central-scFv, one armed scFv-mAb, dual scFv, DVD-Ig or Trident). In particular they can be combined with ICOS]_H0L0 and [ICOS]H0.66_L0 ABDs.

FIG. 84A to 84C depict a number of BTLA ABDs, with additional anti-BTLA ABDs being listed as SEQ ID NO: 3705-3736. The CDRs are underlined, the scFv linker is double underlined (in the sequences, the scFv linker is a positively charged scFv (GKPGS)4 linker (SEQ ID NO: 26209), although as will be appreciated by those in the art, this linker can be replaced by other linkers, including uncharged or negatively charged linkers, some of which are depicted in FIG. 8), and the slashes indicate the border(s) of the variable domains. As above, the naming convention illustrates the orientation of the scFv from N- to C-terminus;

in the sequences listed in this figure, they are all oriented as vh-scFv linker-vl (from N- to C-terminus), although these sequences may also be used in the opposite orientation, (from N- to C-terminus) vl-linker-vh. As noted herein and is true for every sequence herein containing CDRs, the exact identification of the CDR locations may be slightly different depending on the numbering used as is shown in Table 1, and thus included herein are not only the CDRs that are underlined but also CDRs included within the vh and vl domains using other numbering systems. Furthermore, as for all the sequences in the Figures, these vh and vl sequences can be used either in a scFv format or in a Fab format.

FIG. 85 is a matrix of possible combinations of the costim and checkpoint ABDs, with all possible combinations possible. An "A" in the box means that the PD-1 ABD is 1G6_L1.194_H1.279. A "B" in the box means that the ICOS ABD is [ICOS]H.066_L0. A "C" in the box means that the PD-1 is the scFv in the pair. A "D" in the box means the CTLA-4 ABD is a Fab and is [CTLA-4]_H3_L0.22. An "E" in the box means that the CTLA-4 ABD is a scFv and is [CTLA-4]_H3.23_L0.22. An "F" in the box means that the LAG-3 ABD is 7G8_H3.30_L1.34. A "G" in the box means that the BTLA ABD is 9C6_H1.1_L1. An "H" in the box means that combination is a bottle opener. An "I" in the box means the combination is Central-scFv format.

FIG. 86 depicts two more ICOS X PD-1 bottle openers.

Figure 87A:
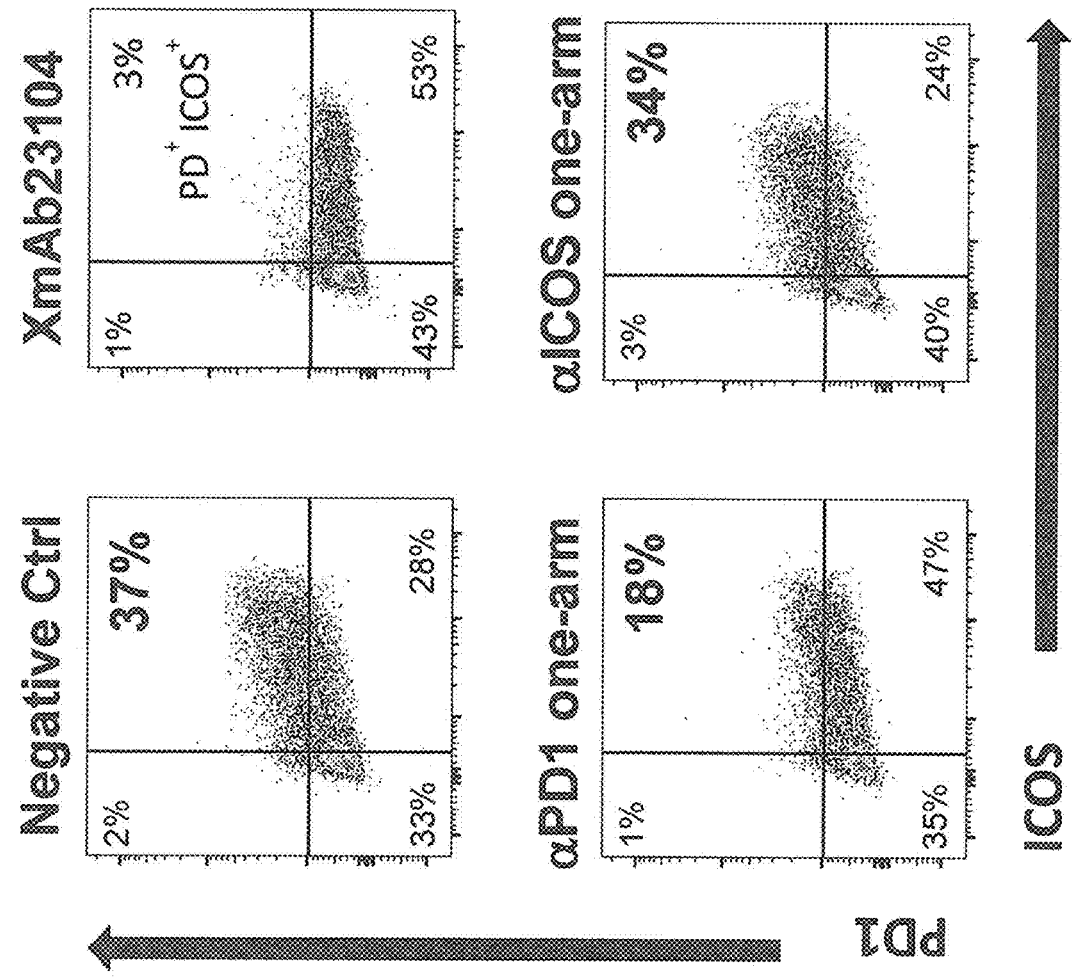
Figure 87B:
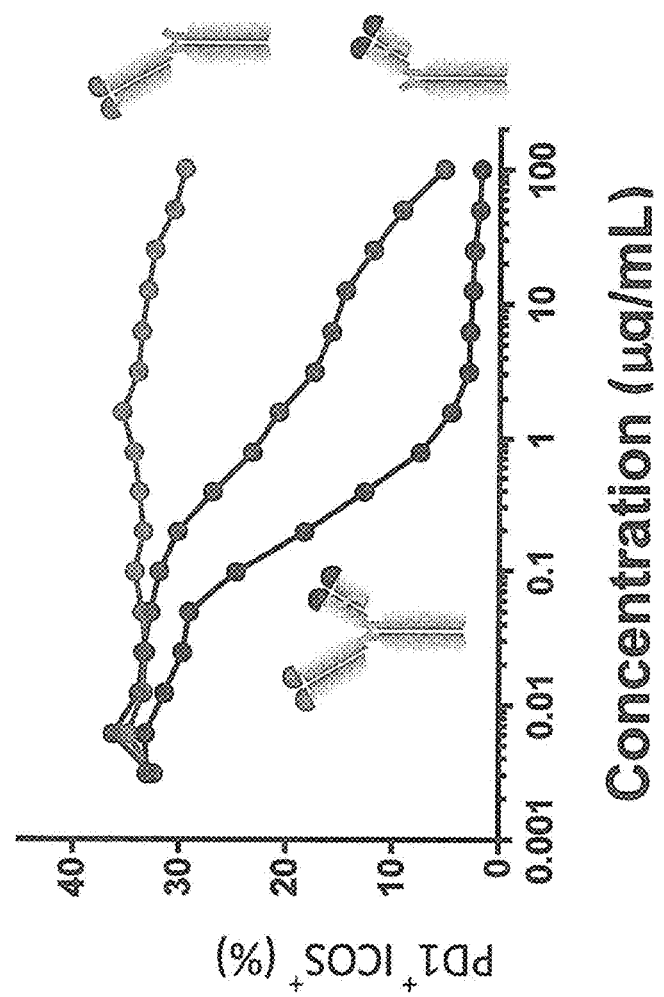

FIGS. 87A and 87B depicts that monovalent engagement of PD-1 and ICOS enables avid targeting of double positive T cells; receptor occupancy of PD1 and ICOS on human CD3+T cells stimulated with SEB. Scatterplots are shown for 3 ug/mL concentration.

Figure 88:
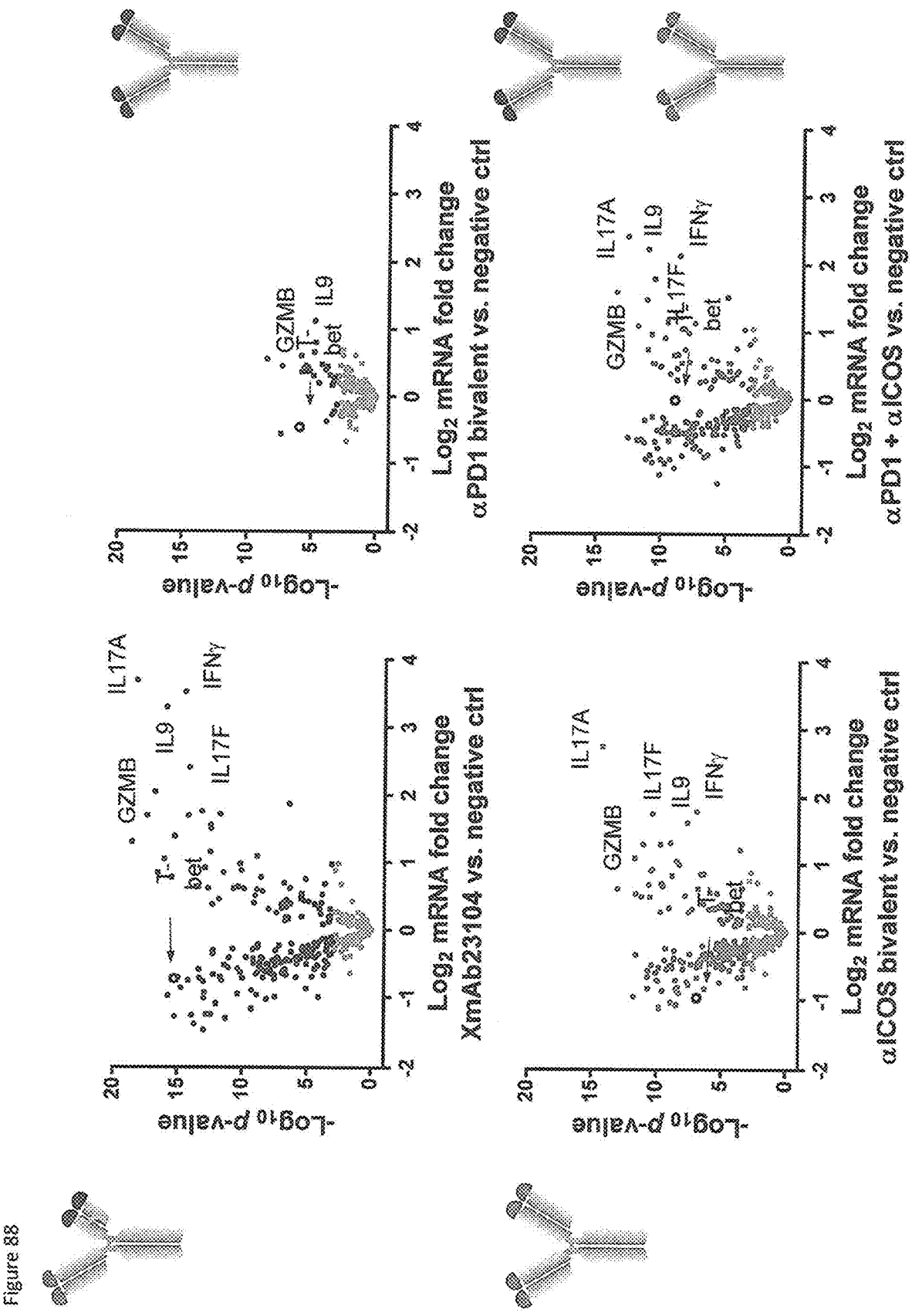

FIG. 88 depicts that XmAb23104 exhibits a multi-gene expression signature consistent with ICOS co-stimulation. SEB-stimulated human PBMCs (multiple healthy donors). RNA analyzed on a NanoString platform as described herein using the nCountrer PanCancer Immune Profiling Panel.

Figure 89:
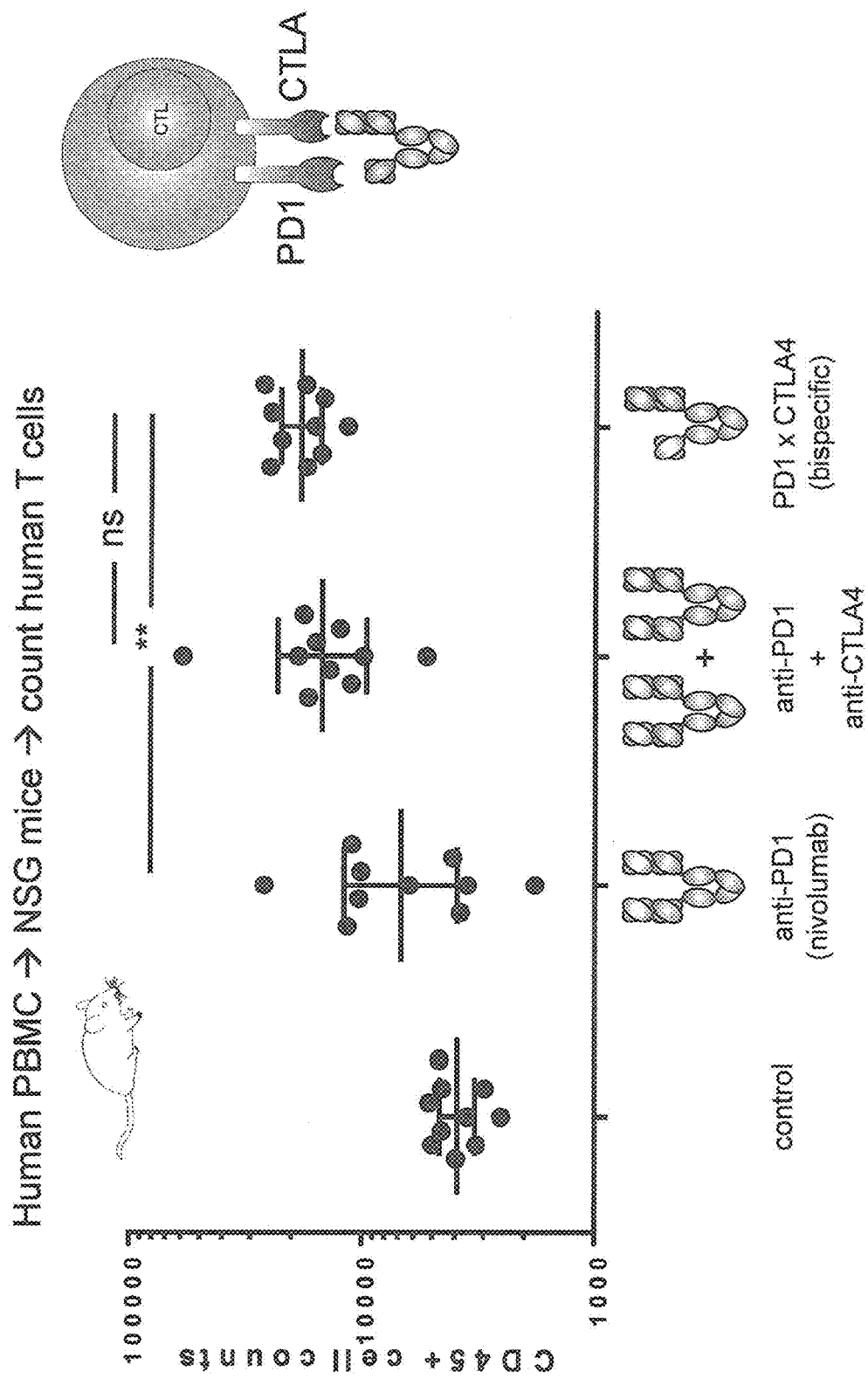

FIG. 89 shows the PD1 X CTLA4 bispecific antibody is highly active in a mouse model for checkpoint blockade.

Figure 90:
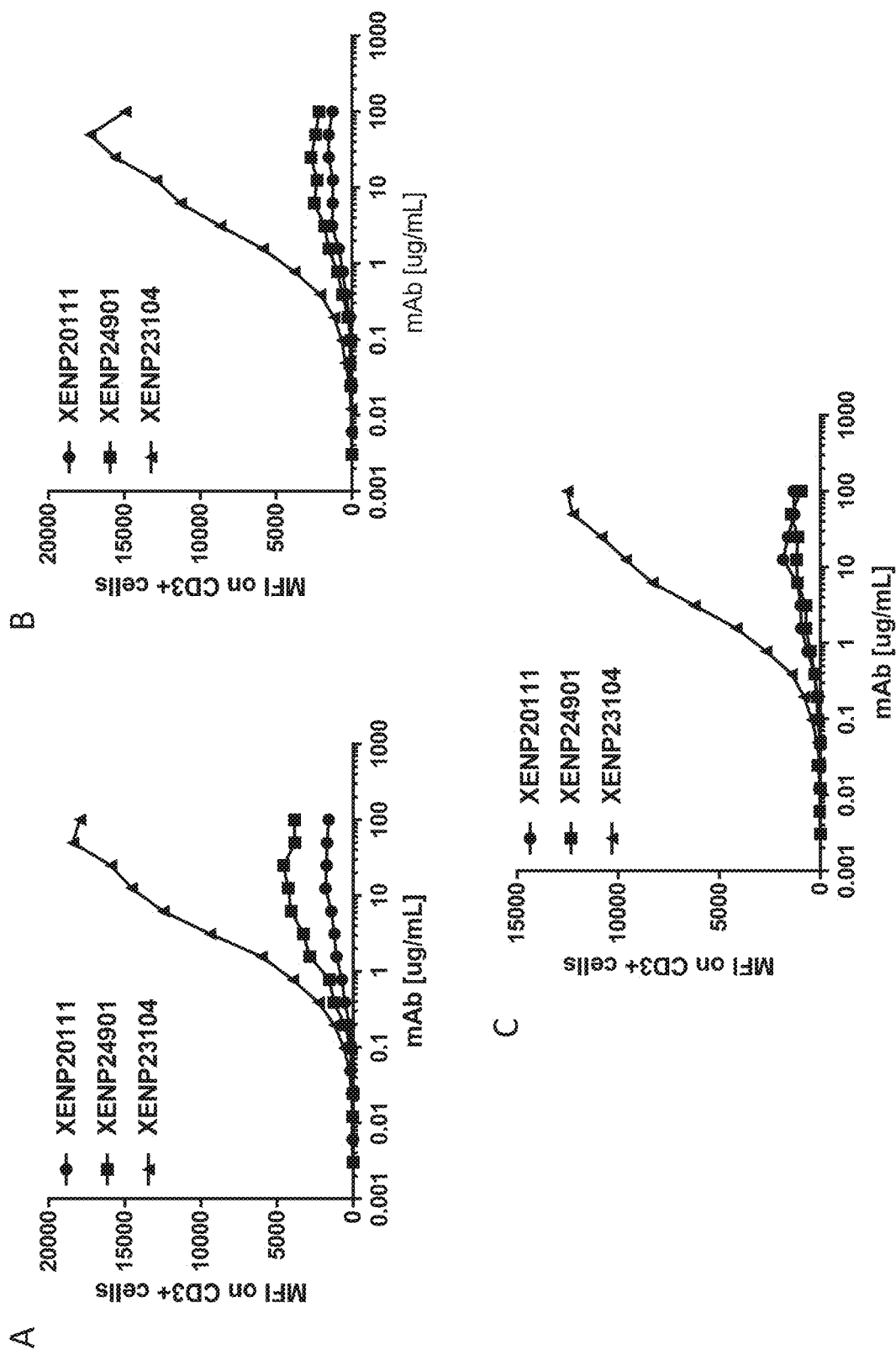

FIG. 90 depicts binding of the indicated test articles to SEB-stimulated CD3+ T cells from 3 separate PBMC donors (A-C).

Figure 91:
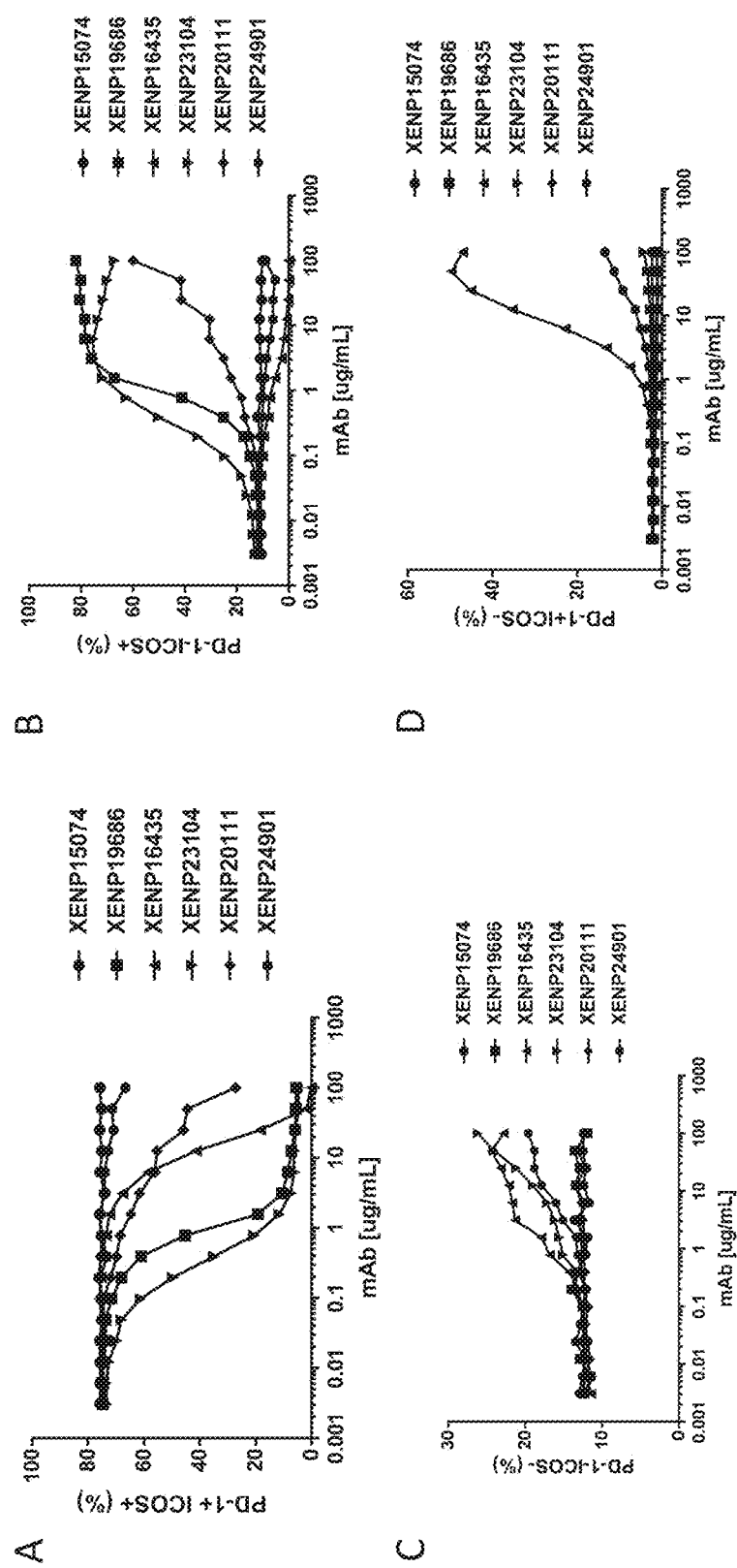

FIG. 91 depicts checkpoint receptor occupancy by the indicated test articles as indicated by percentage of populations of SEB-stimulated CD3+ T cells with unoccupied PD-1 and/or ICOS receptors as shown by staining.

Figure 92:
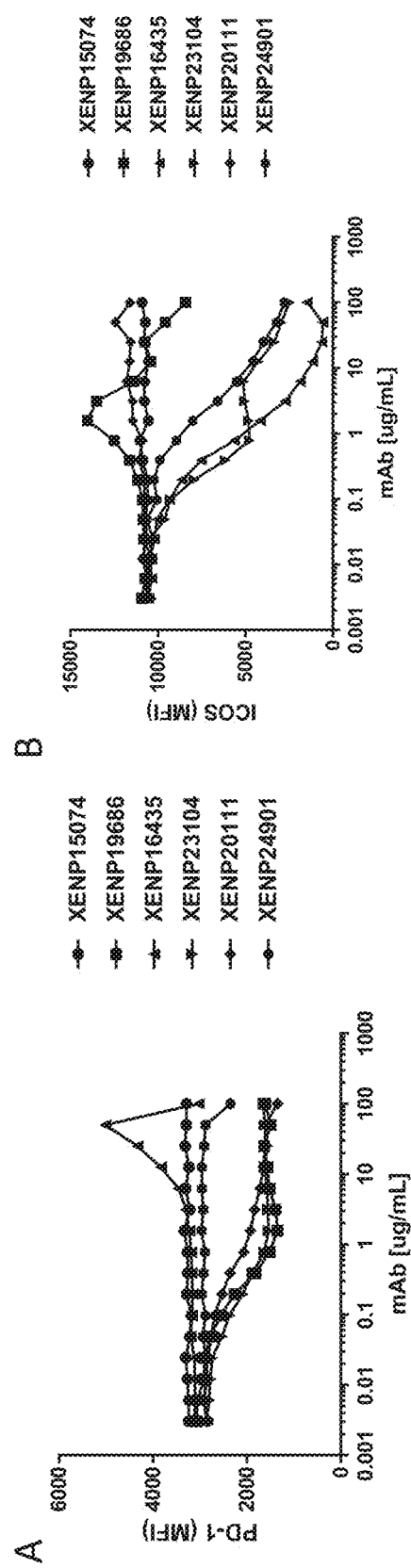

FIG. 92 shows the amount of unoccupied A) PD-1 and B) ICOS receptors on CD3+ICOS+PD-1+ SEB-stimulated T cells following treatment with the indicated test articles.

Figure 93:
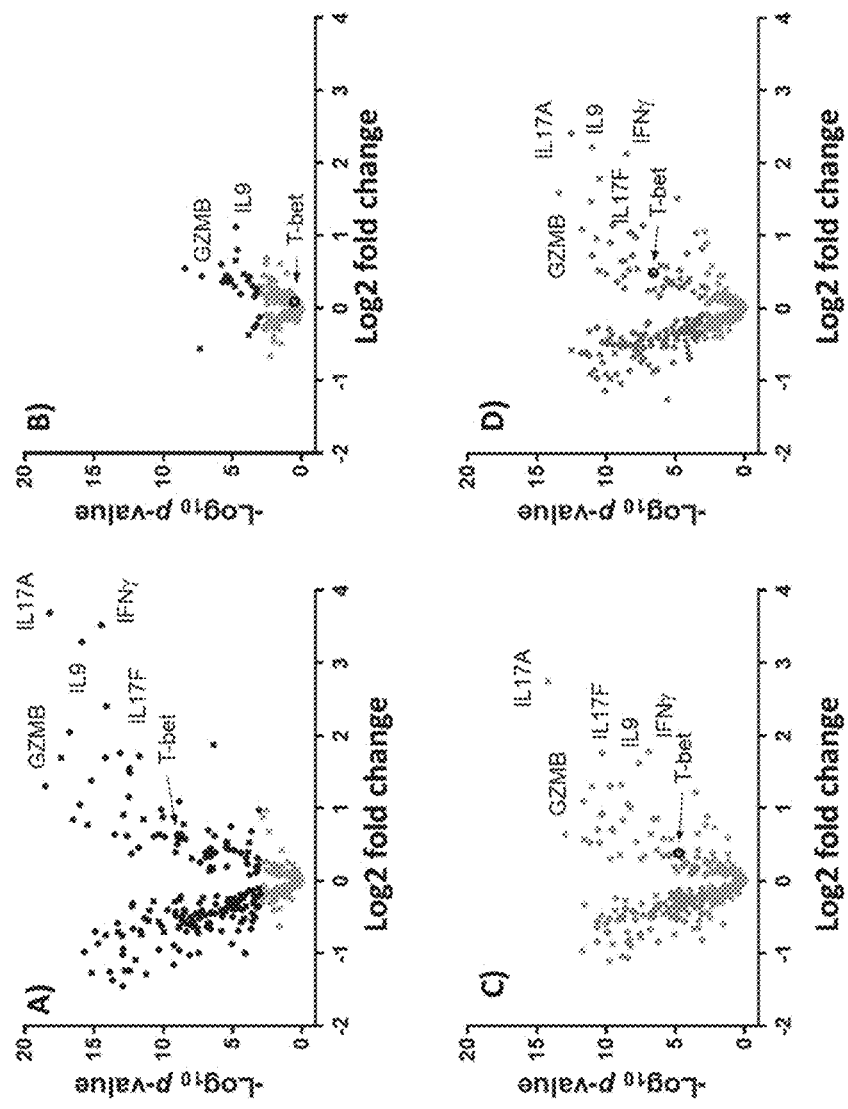

FIG. 93 depicts fold change (x-axis) in expression of immune-related genes by SEB-stimulated T cells following treatment with A) XmAb23104, B) anti-PD-1 mAb (XENP19686), C) anti-ICOS mAb (XENP16435), and D) anti-PD-1 mAb (XENP19686) in combination with anti-ICOS mAb (XENP16435) over treatment with negative control anti-RSV mAb (XENP15074).

Figure 94:
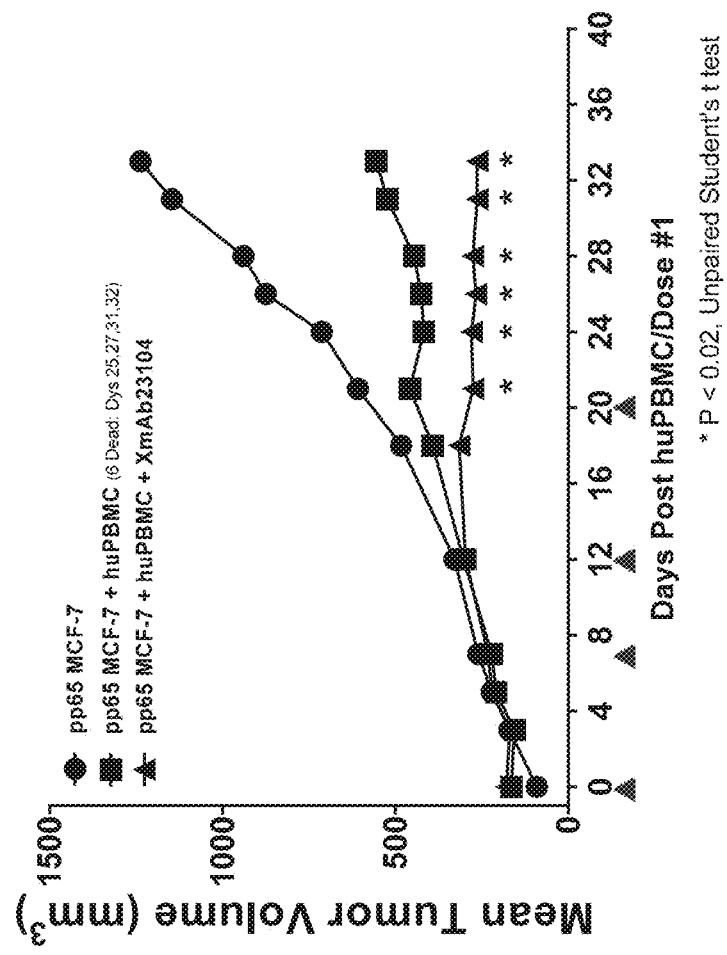

FIG. 94 depicts tumor burden (as indicated by mean tumor volume as determined by caliper measurements) in NSG mice engrafted with pp65-expressing MCF-7 cells followed by engraftment with huPBMCs following treatment with XmAb23104. Triangles below the X-axis indicate dosing days.

Figure 95:
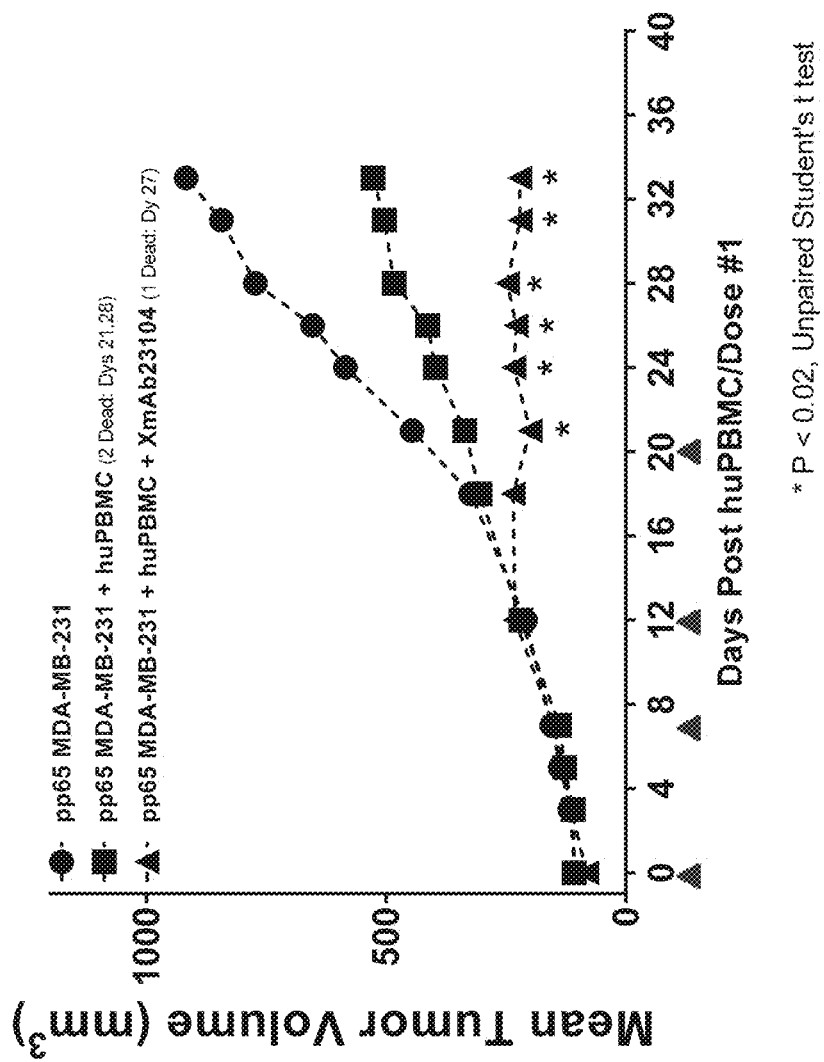

FIG. 95 depicts tumor burden (as indicated by mean tumor volume as determined by caliper measurements) in NSG mice engrafted with pp65-expressing MDA-MB-231 cells followed by engraftment with huPBMCs following treatment with XmAb23104. Triangles below the X-axis indicate dosing days.

FIG. 96 depicts the amino acid sequences of a monovalent anti-ICOS Fab-Fc fusion based on the anti-ICOS arm from XmAb23104 with M428L/N434S Xtend Fc. CDRs are underlined and slashes indicate the border(s) of the variable regions.

FIG. 97 depicts the sequences for A) human PD-L1 and B) human PD-L2 fused to murine IgG2aa Fc region. Slashes (/) indicate the border between the PD-1 ligand and the murine IgG2aa Fc-region.

Figure 98A:
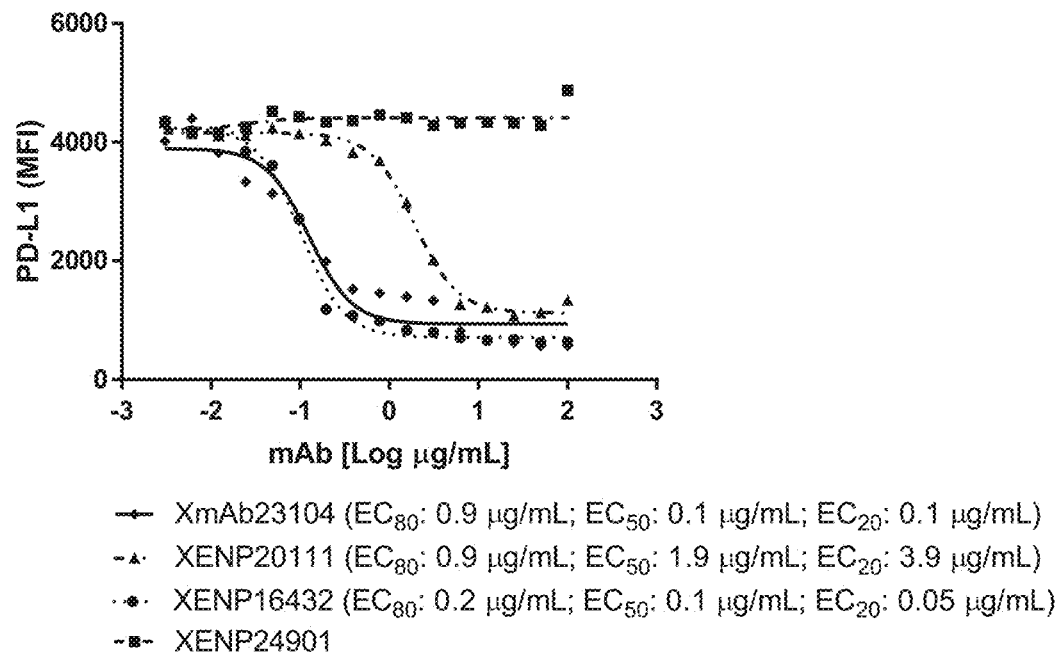
Figure 98B:
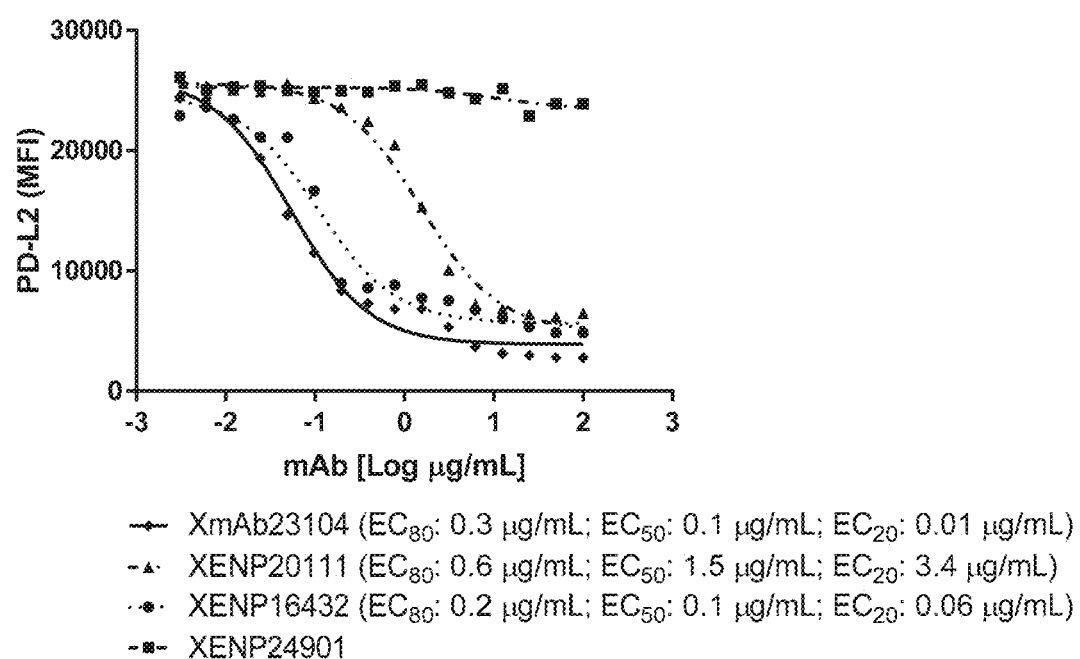
Figure 101A:
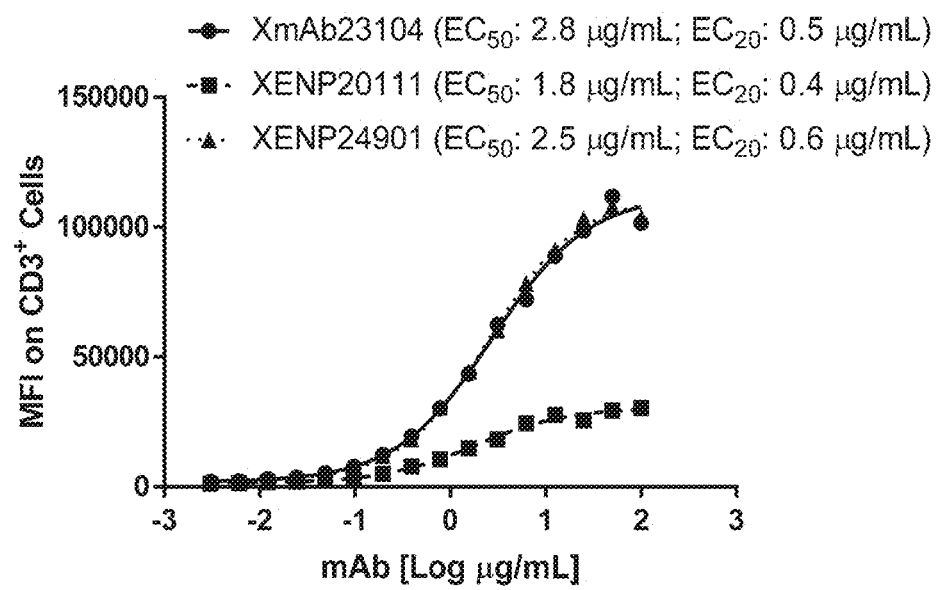
Figure 101B:
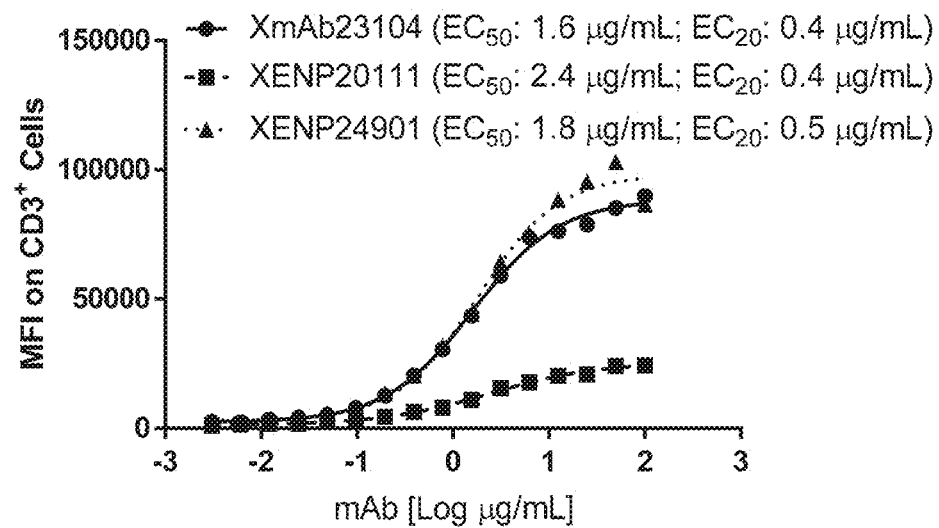
Figure 101C:
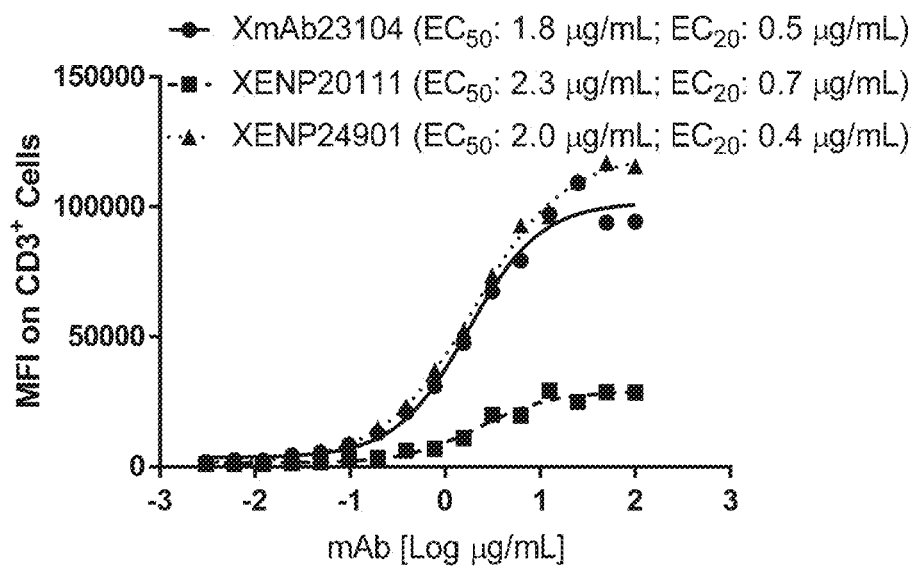
Figure 101D:
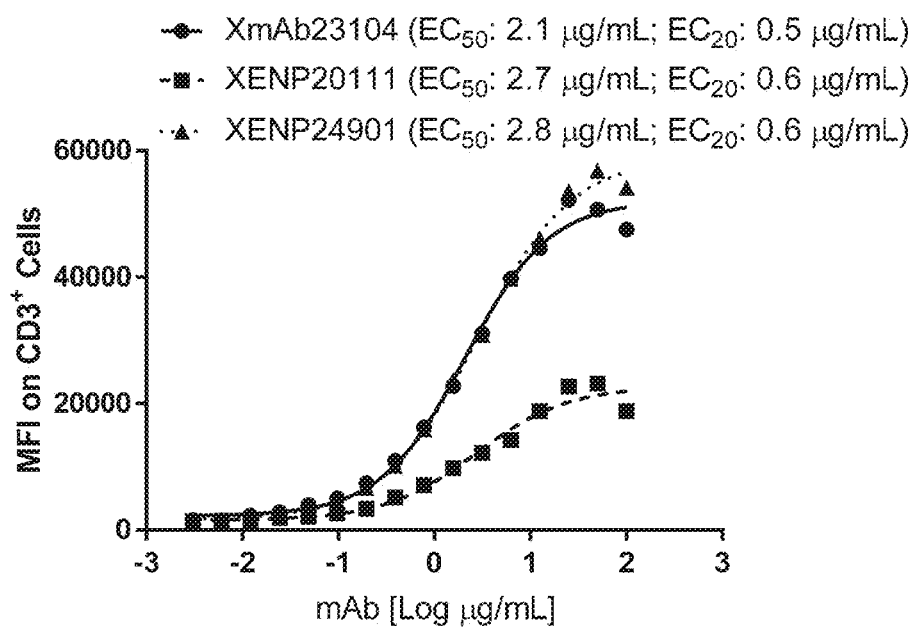

FIGS. 98A and B depicts binding of A) PD-L1 and B) PD-L2 to PD-1+ICOS+ cells following treatment with the indicated test articles.

FIG. 99 depicts the sequence for human ICOSL fused to human IgG1 Fc region with E233P/L234V/L235A/G236del/S267K substitutions. Slashes (/) indicate the border between the PD-1 ligand and the human IgG1 Fc-region.

FIG. 100 depicts binding of ICOSL to PD-1+ICOS+ cells following treatment with the indicated test articles.

FIG. 101A to 101D depicts binding of XmAb23104 to CD3+ T cells in SEB-stimulated PBMCs from 4 cynomolgus monkeys.

Figure 102A:
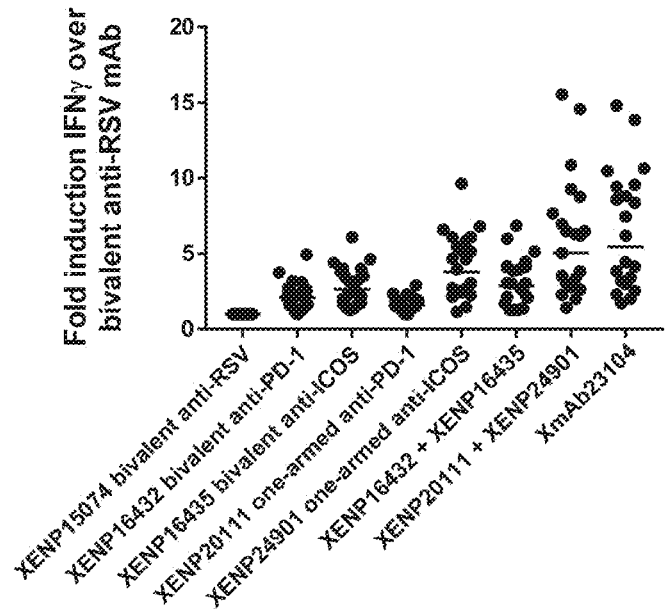
Figure 102B:
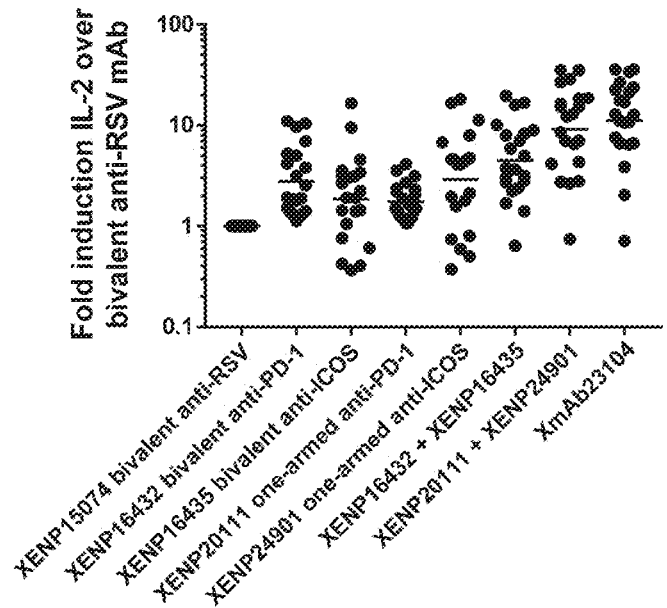

FIGS. 102A and 102B depicts fold induction of A) IFNγ and B) IL-2 over bivalent anti-RSV mAb by the indicated test articles in an SEB-stimulated PBMC assay.

Figure 103:
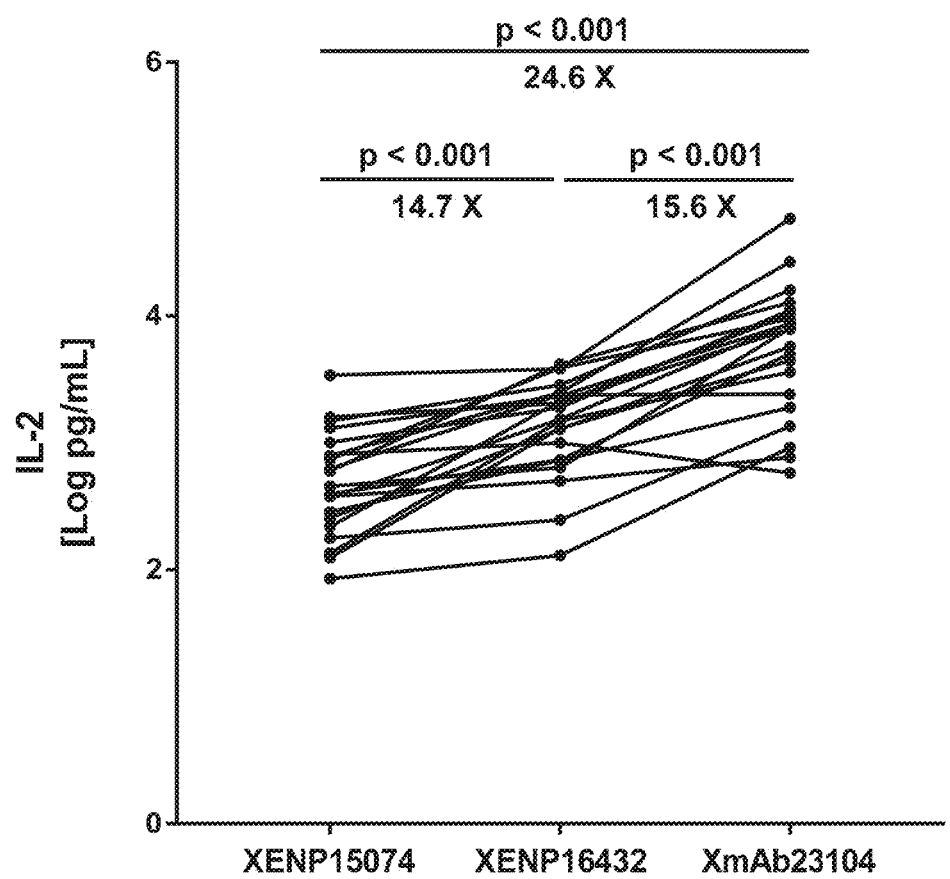

FIG. 103 depicts IL-2 induction by XENP15074, XENP16432, and XmAb23104 in an SEB-stimulated PBMC assay.

FIG. 104 depicts the amino acid sequences of a monovalent anti-PD-1 scFv-Fc fusion based on the anti-PD-1 arm from XmAb23104 with M428L/N424S Xtend Fc. CDRs are underlined and slashes indicate the border(s) of the variable regions.

FIG. 105 depicts fold induction of IFNγ over bivalent anti-RSV mAb by the indicated test articles in an MLR assay.

Figure 106A:
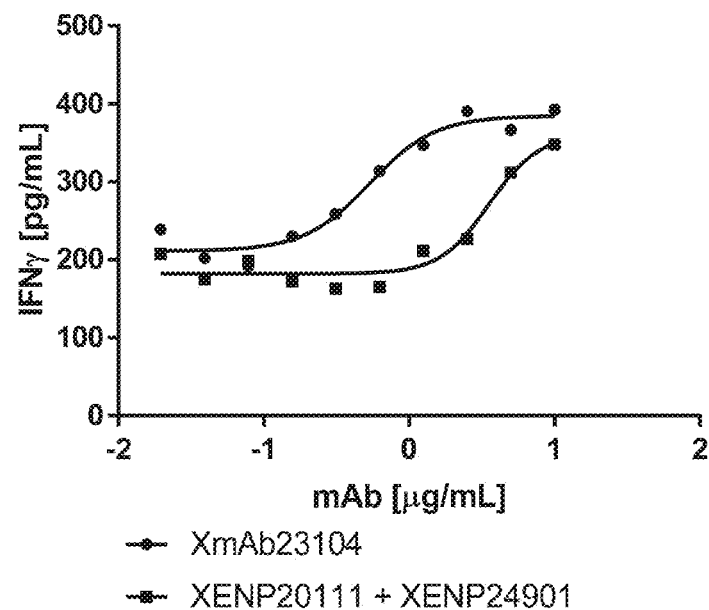
Figure 106B:
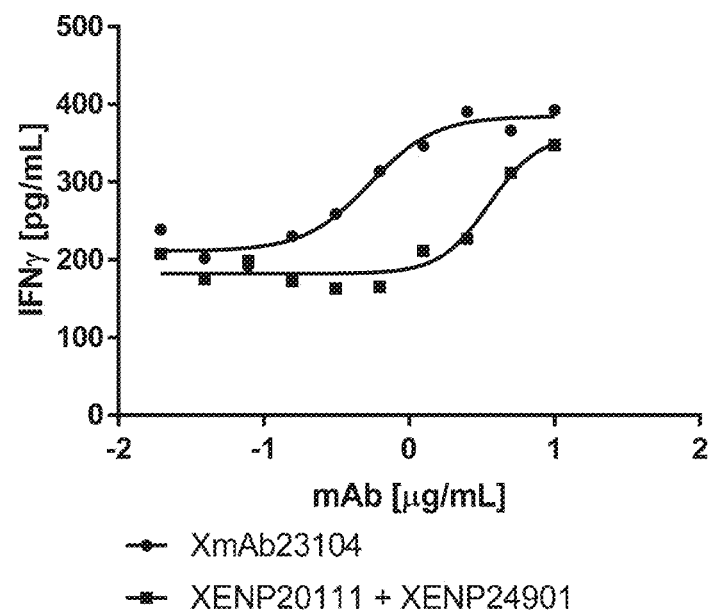

FIGS. 106A and 106B depicts IFNγ induction by XmAb23104 or a combination of XENP20111 and XENP24901 (at equimolar PD-1 and ICOS binding concentrations relative to XmAb23104) in SEB-stimulated PBMCs from 2 separate donors.

Figure 107A:
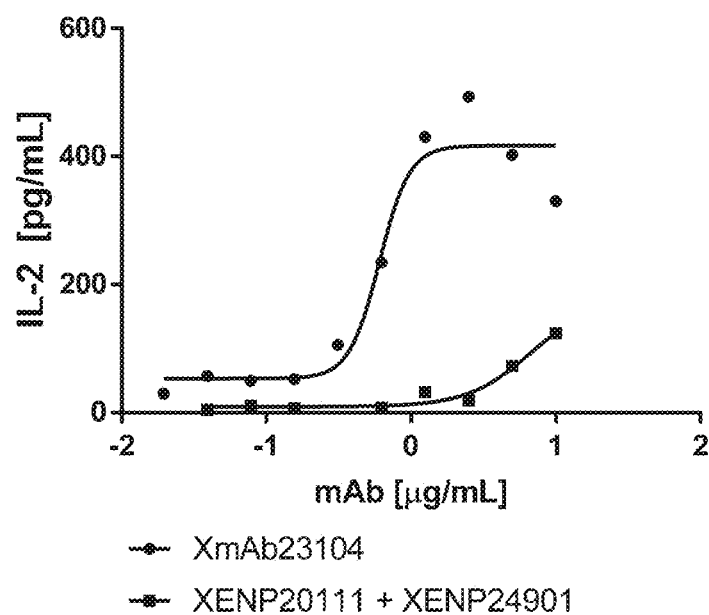
Figure 107B:
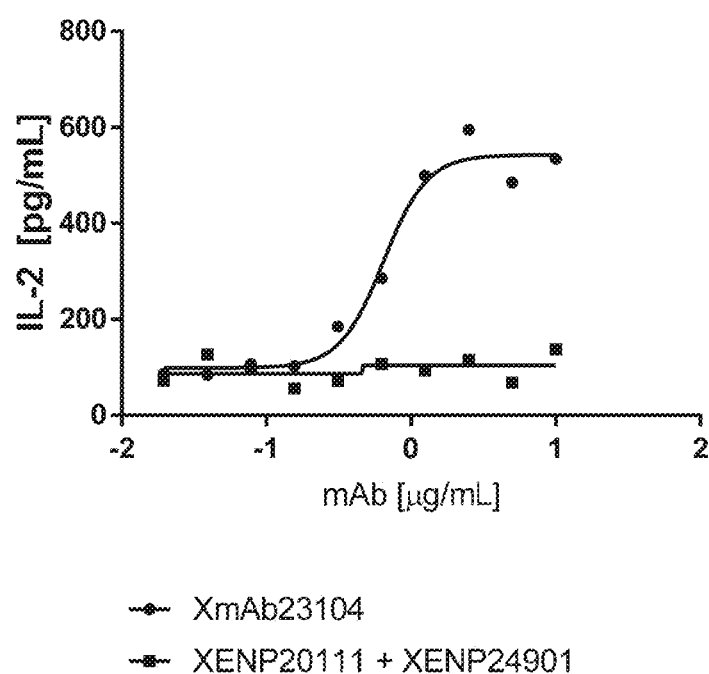

FIGS. 107A and 107B depicts IL-2 induction by XmAb23104 or a combination of XENP20111 and XENP24901 (at equimolar PD-1 and ICOS binding concentrations relative to XmAb23104) in SEB-stimulated PBMCs from 2 separate donors.

FIG. 108 depicts the amino acid sequences of a bivalent anti-CTLA-4 mAb based on ipilimumab and human IgG1 Fc region with E233P/L234V/L235A/G236del/S267K substitutions. CDRs are underlined and slashes indicate the border(s) of the variable regions.

Figure 109A:
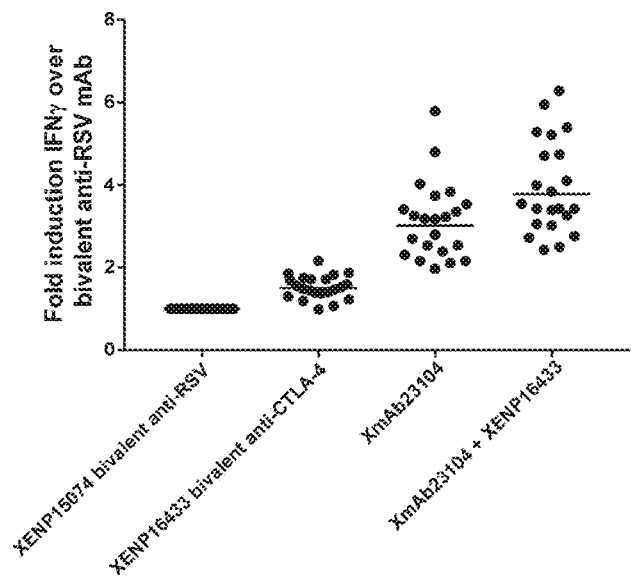
Figure 109B:
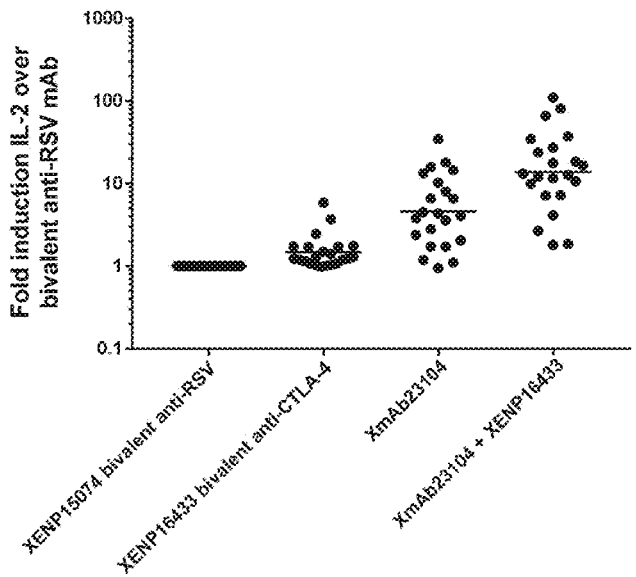

FIGS. 109A and 109B depict fold induction of A) IFNγ and B) IL-2 over bivalent anti-RSV mAb by XmAb23104 alone, XENP16433 (anti-CTLA-4 mAb based on ipilimumab), or XmAb23104 in combination with XENP16433 in an SEB-stimulated PBMC assay.

Figure 110:
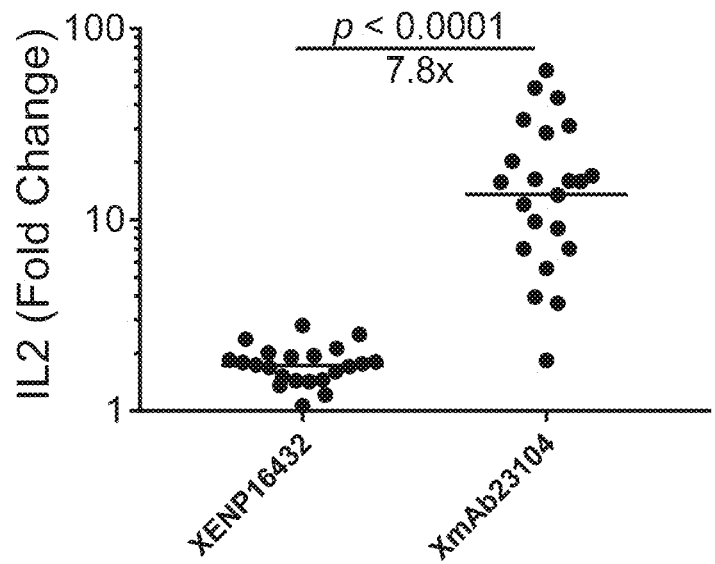

FIG. 110 depicts fold change in IL-2 secretion in MLR reactions incubated with either XENP16432 or XmAb23104 (in comparison to incubation with isotype control anti-RSV mAb).

Figure 111:
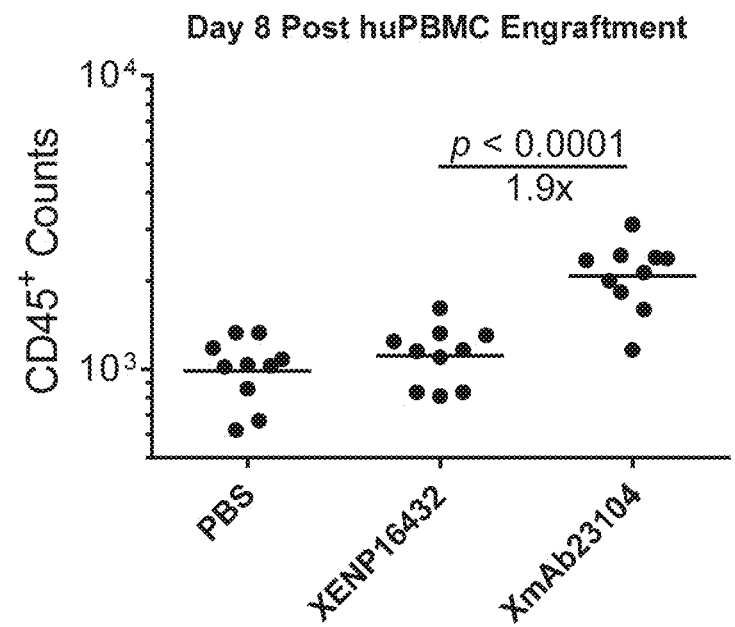

FIG. 111 depicts CD45+ cell counts on Day 8 in huPBMC-engrafted NSG mice dosed with XENP16432 or XmAb23104, and show that XmAb23104 induces greater leukocyte expansion than aPD-1 (XENP16432) alone.

Figure 112:
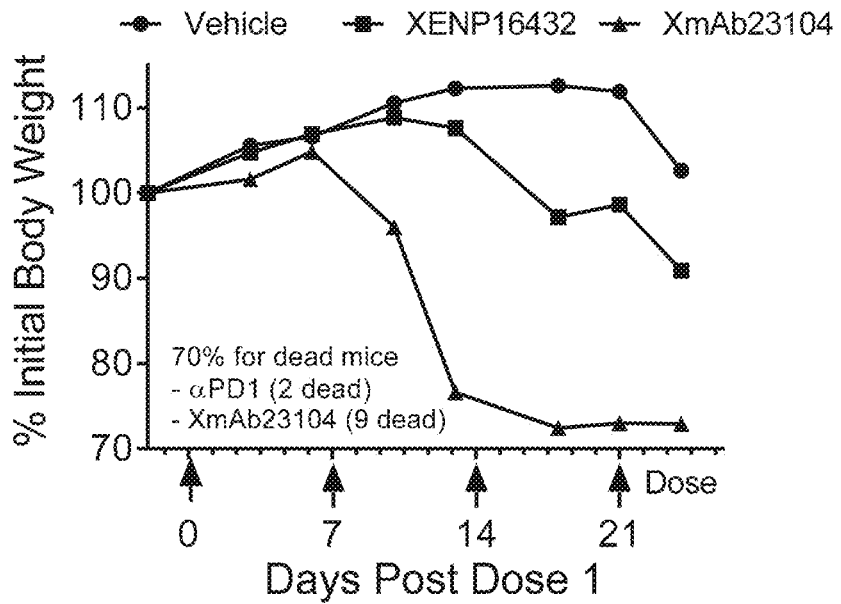

FIG. 112 depicts change in body weight over time in huPBMC-engrafted NSG mice dosed with XENP16432 or XmAb23104, and show that XmAb23104 enhanced GVHD in comparison to aPD-1 (XENP16432) alone.

Figure 113:
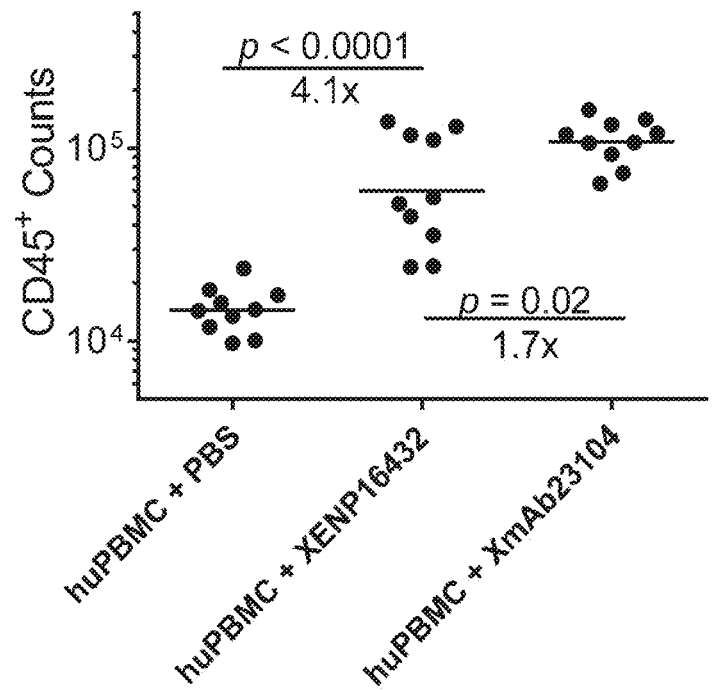

FIG. 113 depicts CD45+ cell counts on Day 21 in pp65-MCF7 and huPBMC-engrafted NSG mice dosed with XENP16432 or XmAb23104, and show that XmAb23104 induces greater leukocyte expansion than aPD-1 (XENP16432) alone.

Figure 114:
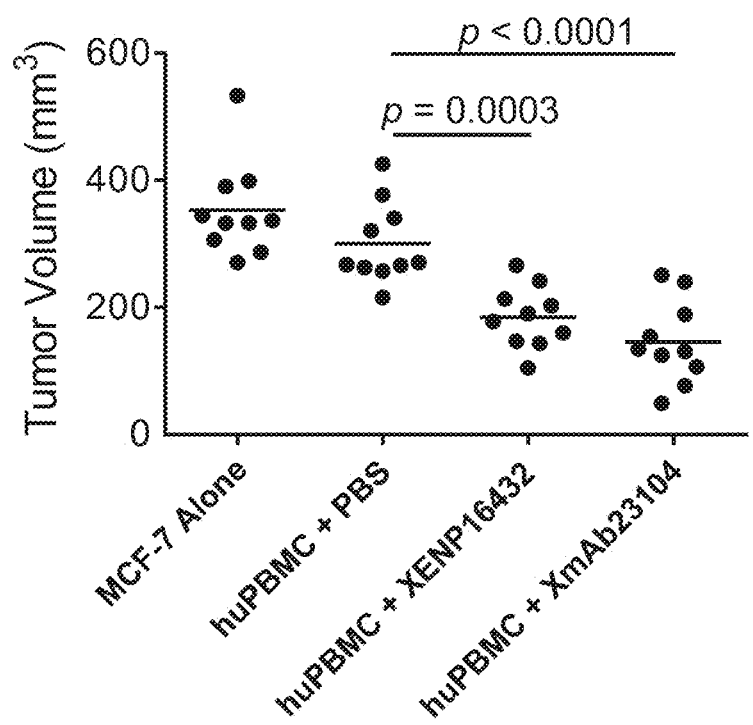

FIG. 114 depicts tumor volume on Day 21 in pp65-MCF7 and huPBMC-engrafted NSG mice dosed with XENP16432 or XmAb23104.

Figure 115:
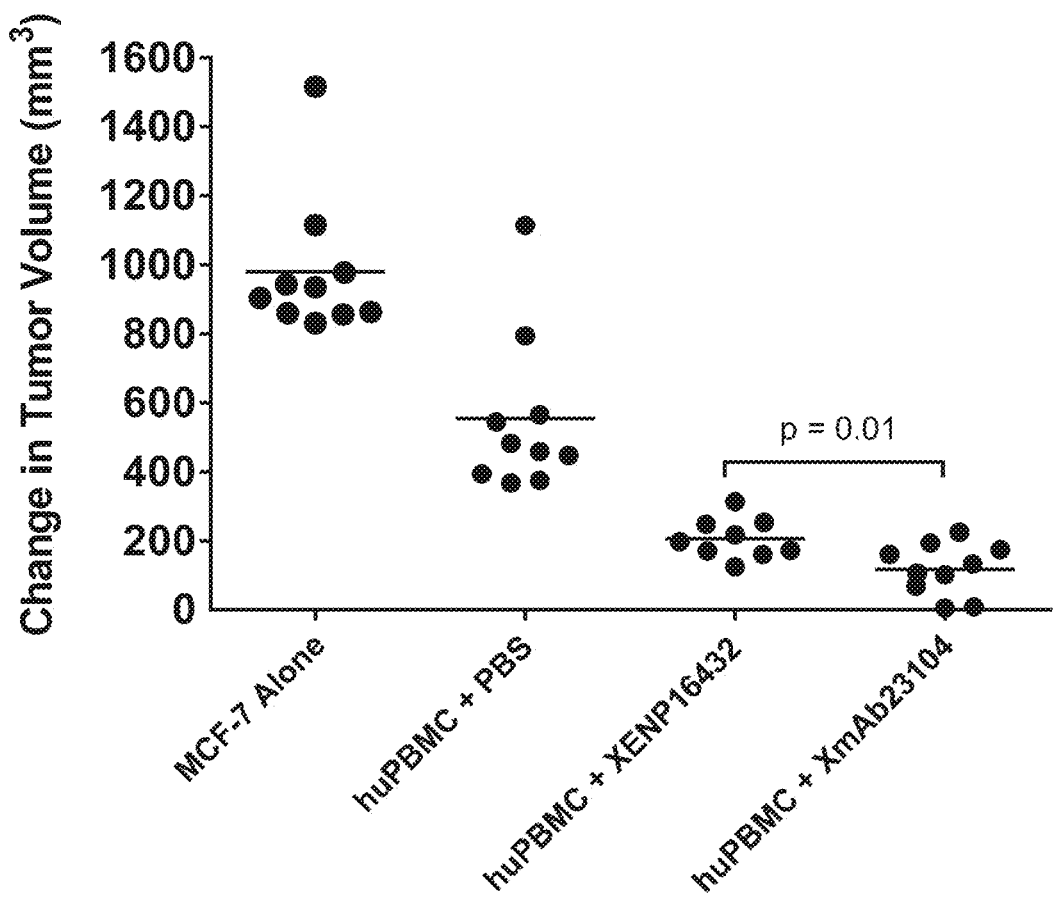

FIG. 115 depicts tumor volume on Day 38 in pp65-MCF7 and huPBMC-engrafted NSG mice dosed with XENP16432 or XmAb23104, and show that XmAb23104 enhances allogeneic anti-tumor response over aPD-1 (XENP16432) alone. p-value was determined using an unpaired t test.

Figure 116:
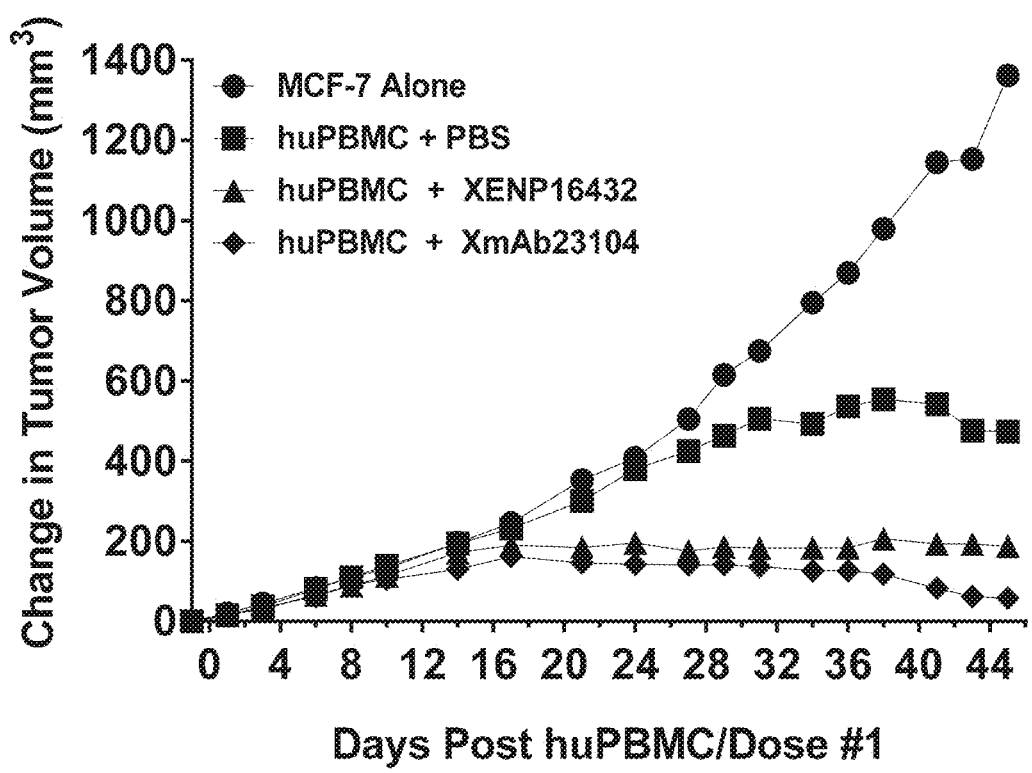

FIG. 116 depicts tumor volume over time (post-huPBMC engraftment) in pp65-MCF7 and huPBMC-engrafted NSG mice dosed with XENP16432 or XmAb23104.

FIG. 117 depicts the sequences of XENP20053, a bottle opener format with the aCTLA-4 as the Fab side (|[αCTLA-4]_H3L0.22) and the PD-1 as the scFv (1G6_L1.94_H1.279). The CDRs are underlined, the scFv linker is double underlined (in the sequences, the scFv linker is a positively charged scFv (GKPGS)4 linker (SEQ ID NO: 26209), although as will be appreciated by those in the art, this linker can be replaced by other linkers, including uncharged or negatively charged linkers, some of which are depicted in FIG. 8), and the slashes indicate the border(s) of the variable domains. As noted herein and is true for every sequence herein containing CDRs, the exact identification of the CRD locations may be slightly different depending on the numbering used as is shown in Table 1, and thus included herein are not only the CDRs that are underlined but also CDRs included within the VH and VL domains using other numbering systems.

Figure 118:
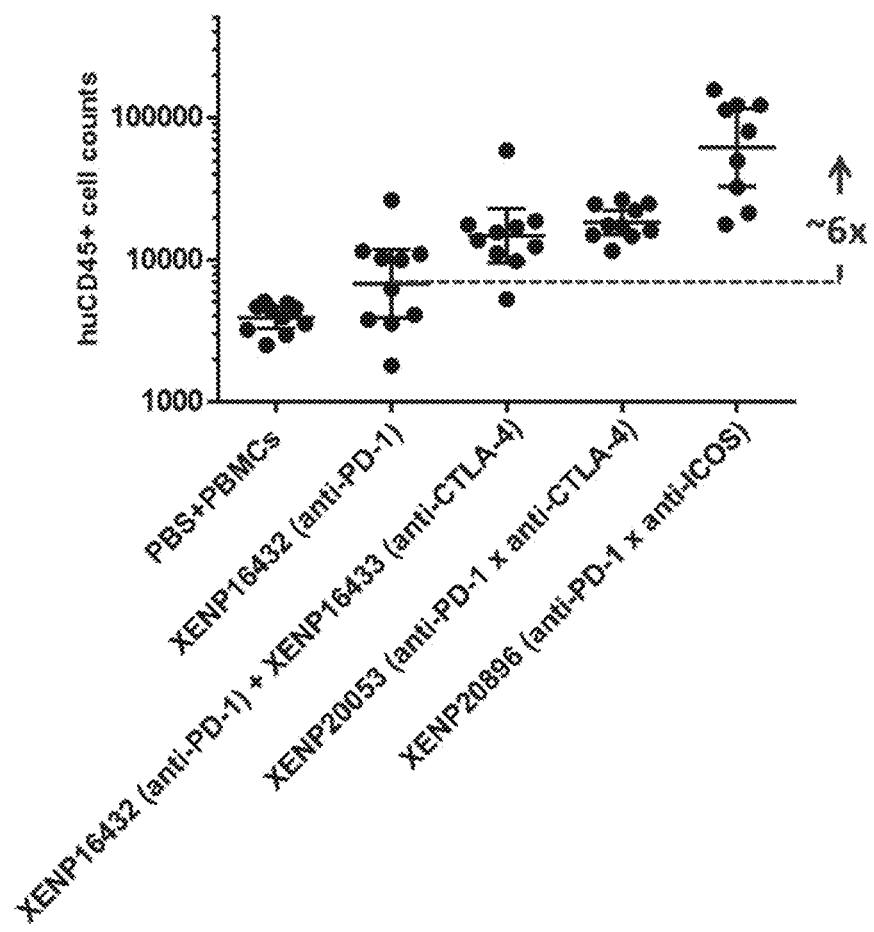
Figure 119A:
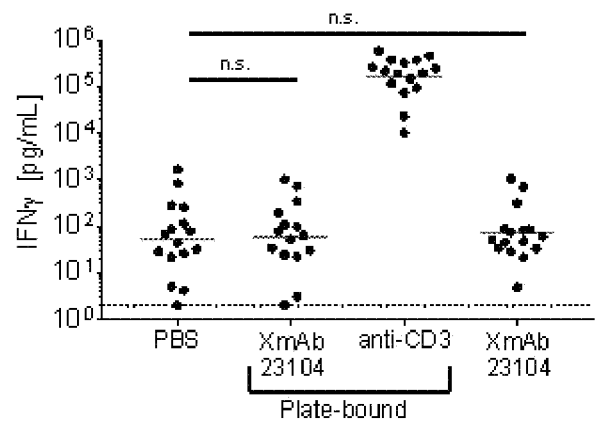
Figure 119B:
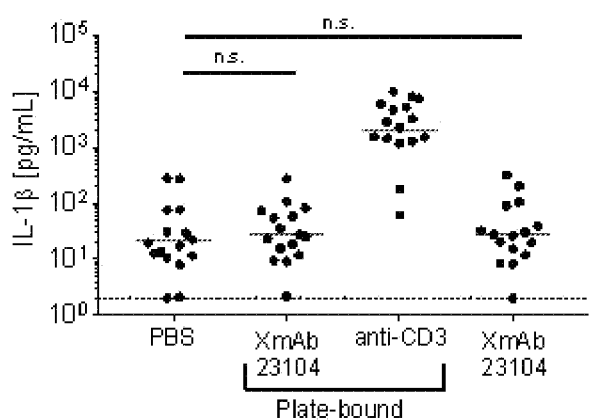
Figure 119C:
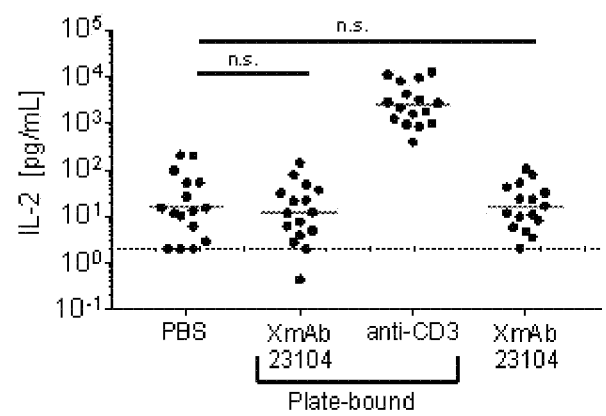
Figure 119D:
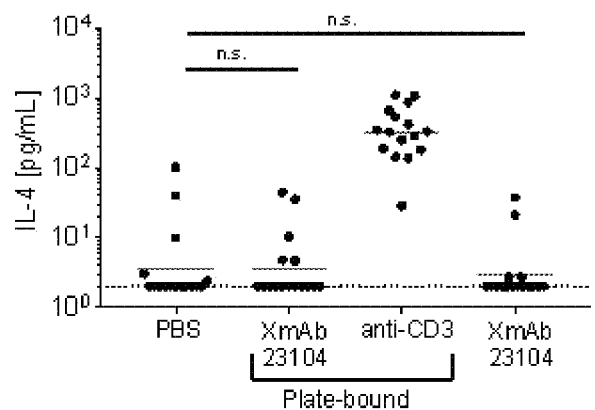
Figure 119E:
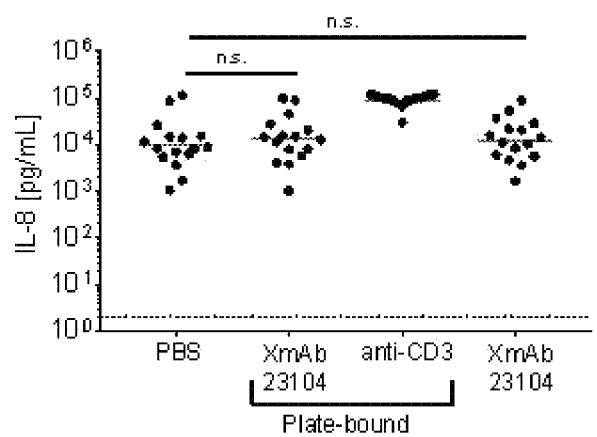
Figure 119F:
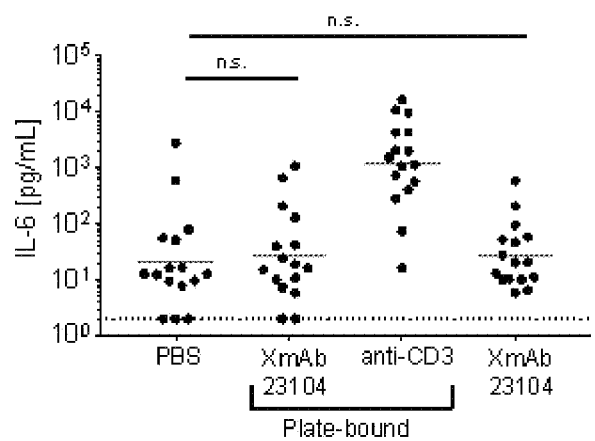
Figure 119G:
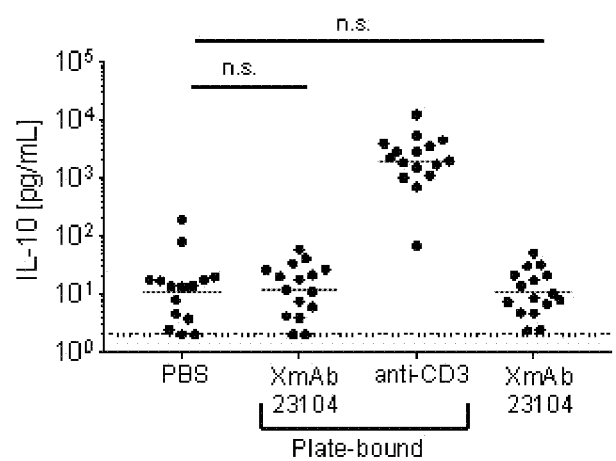
Figure 119H:
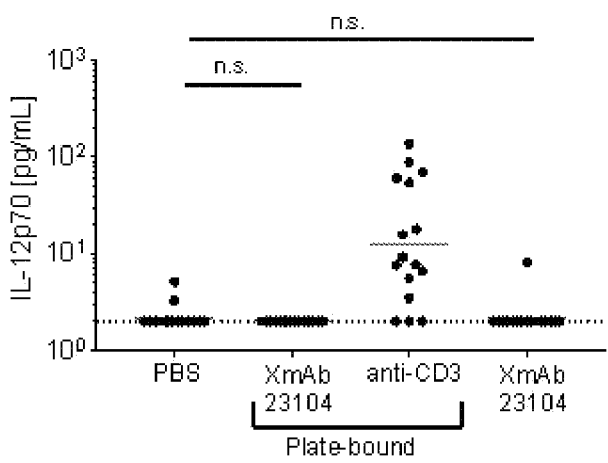
Figure 119I:
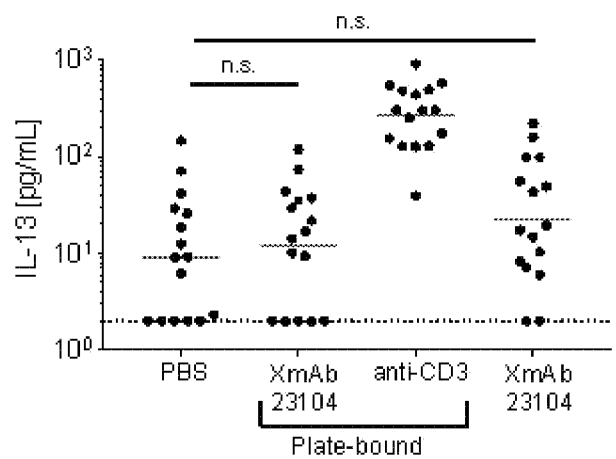
Figure 119J:
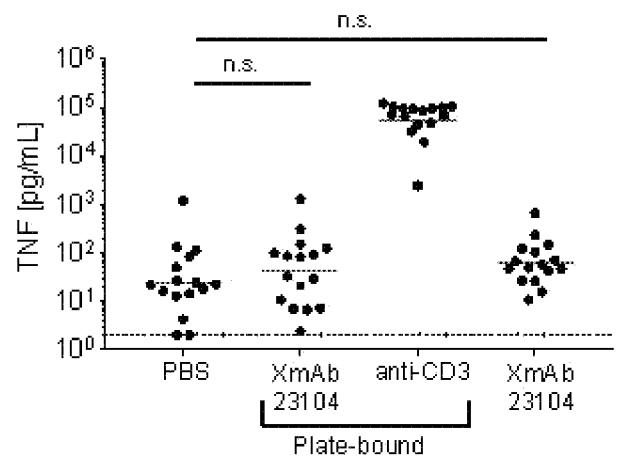
Figure 121A:
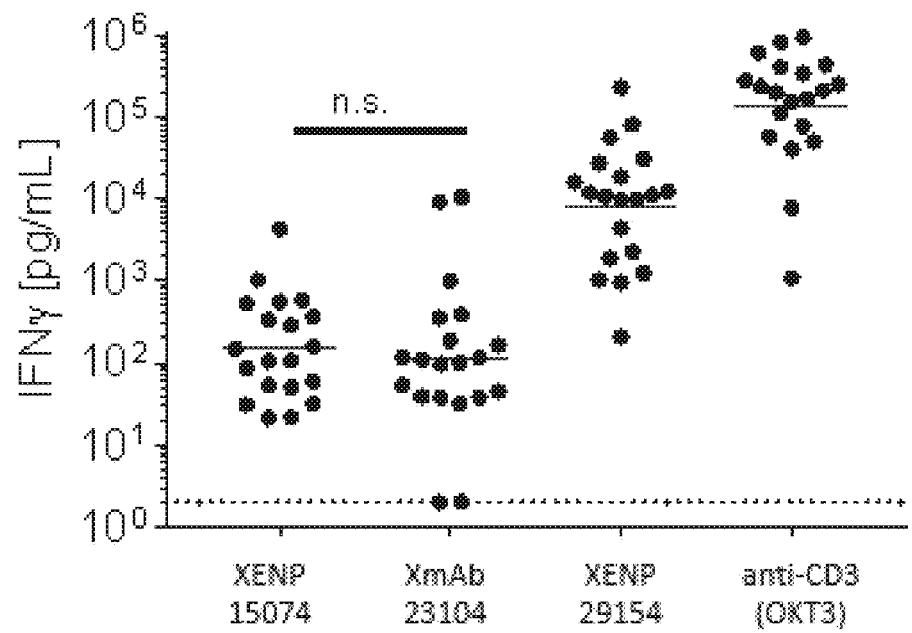
Figure 121B:
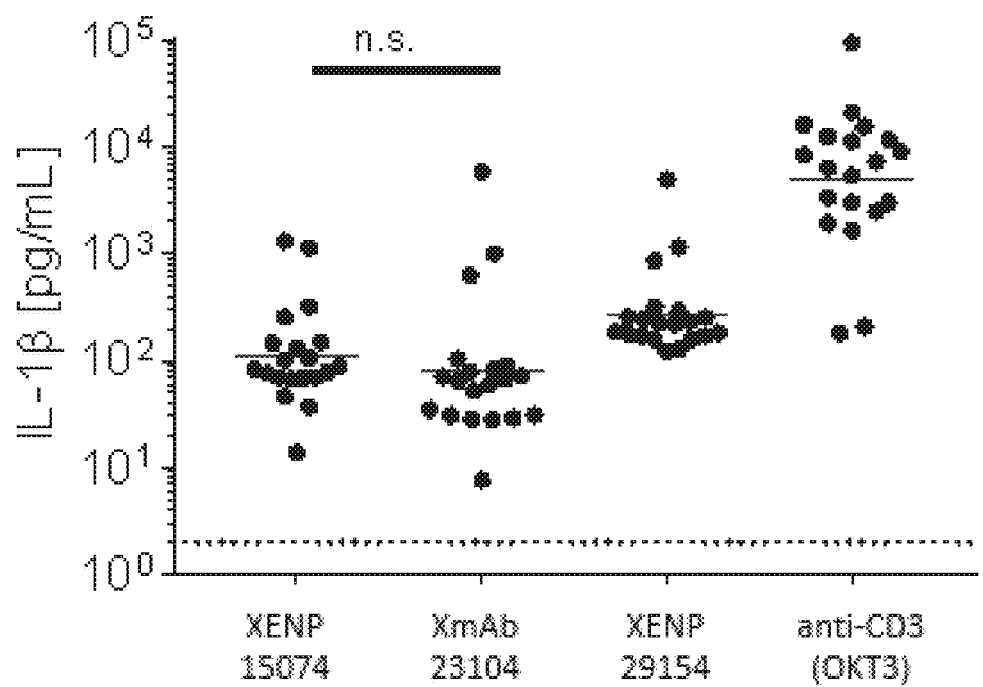
Figure 121C:
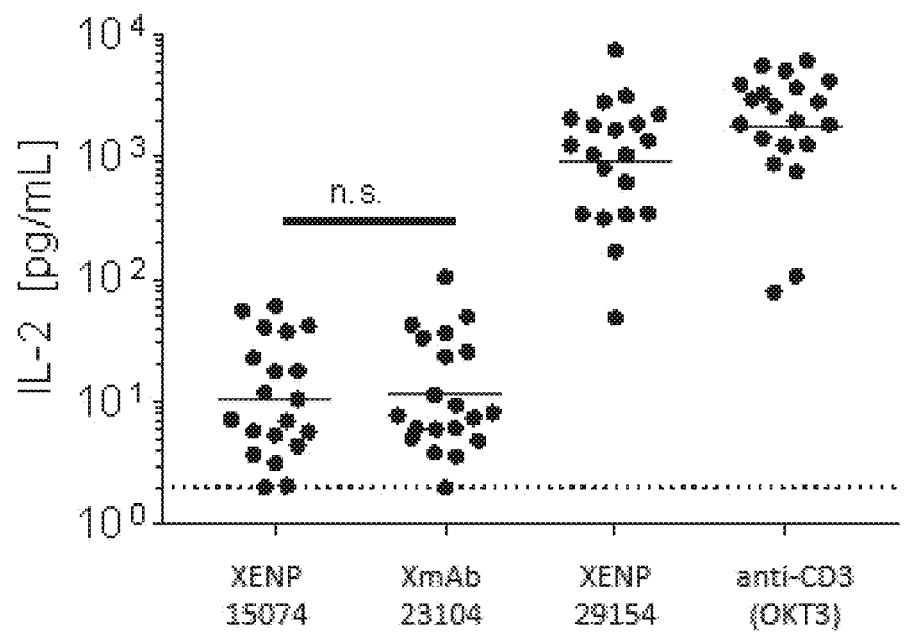
Figure 121D:
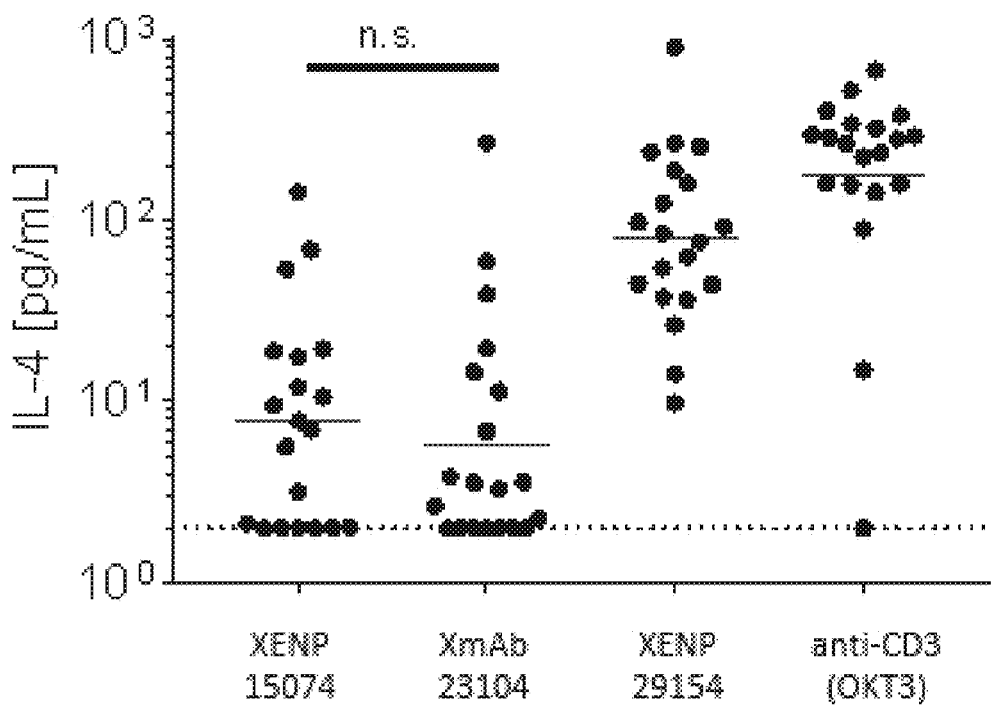
Figure 121E:
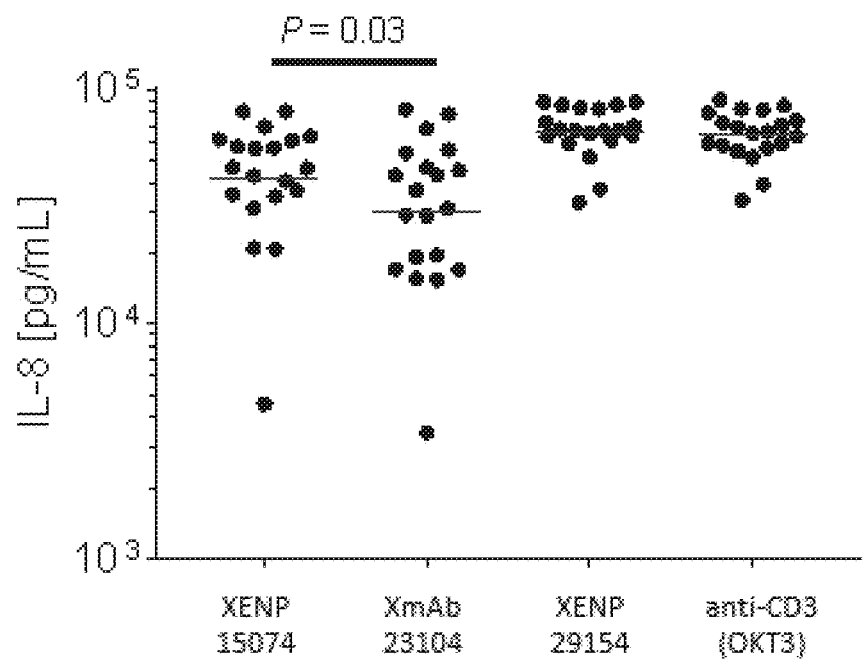
Figure 121F:
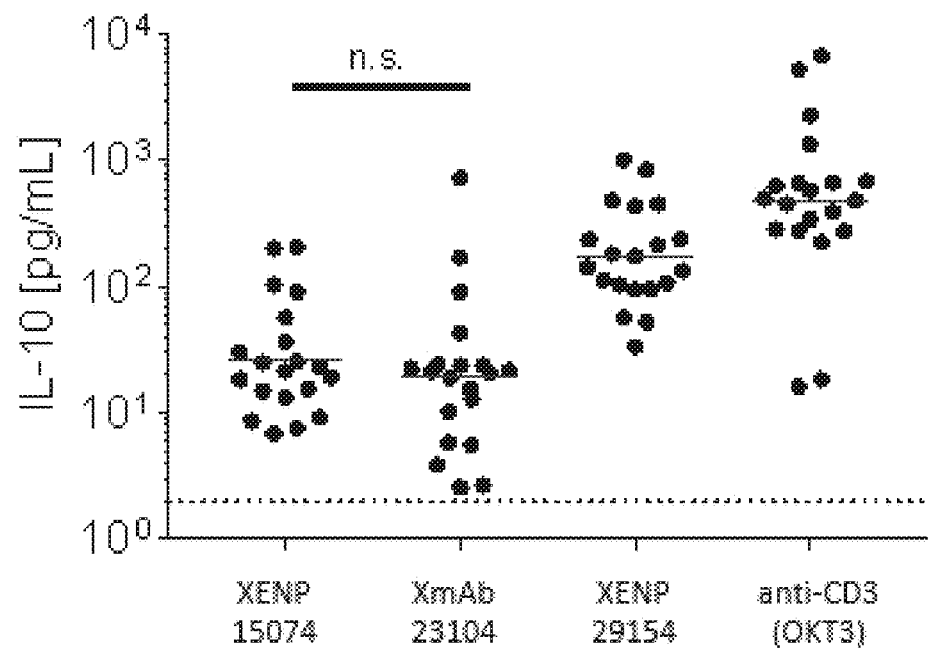
Figure 121G:
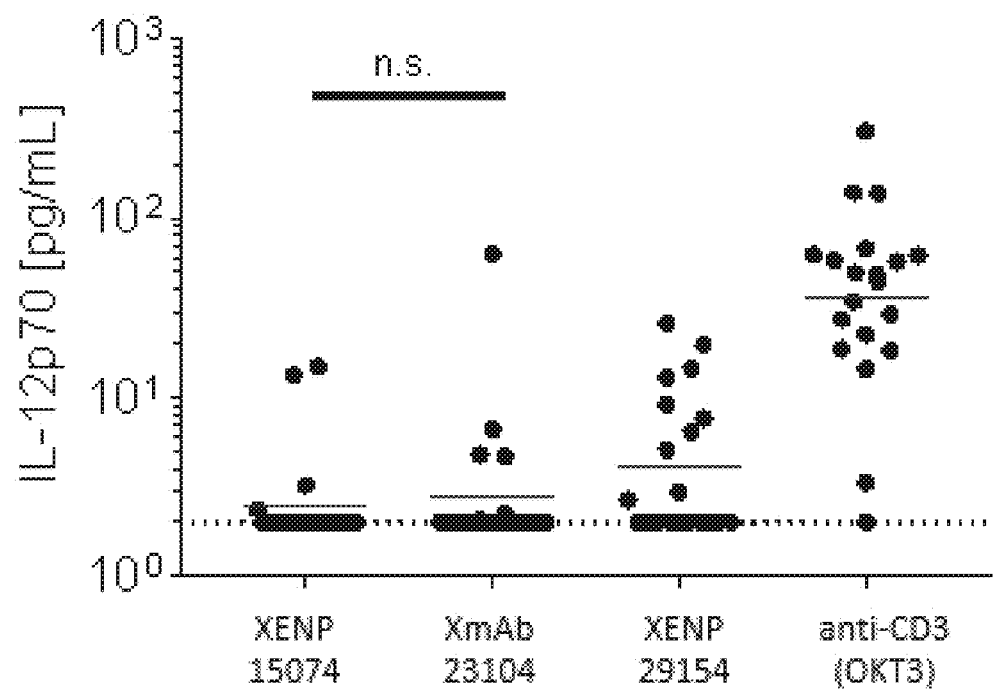
Figure 121H:
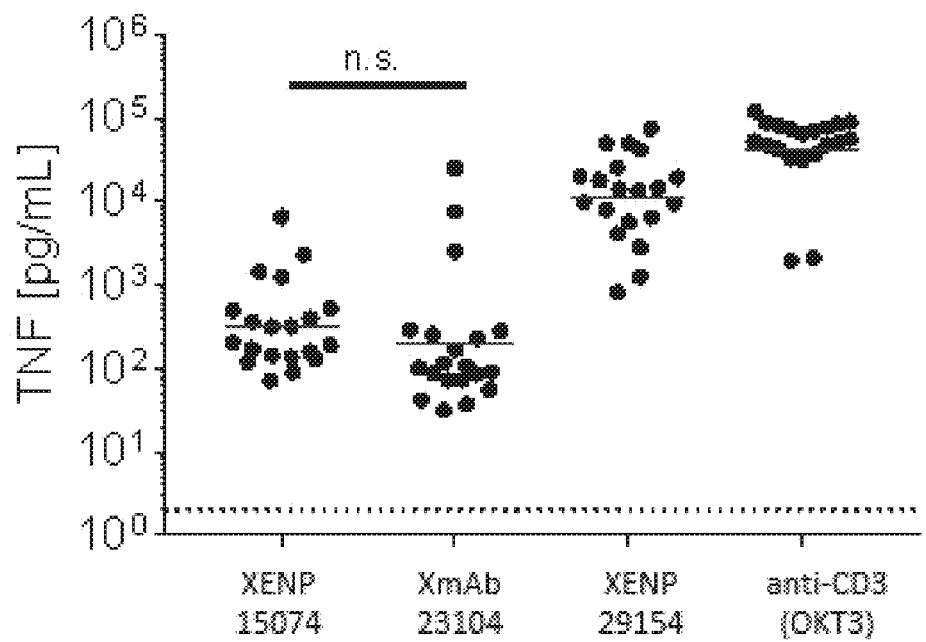
Figure 121I:
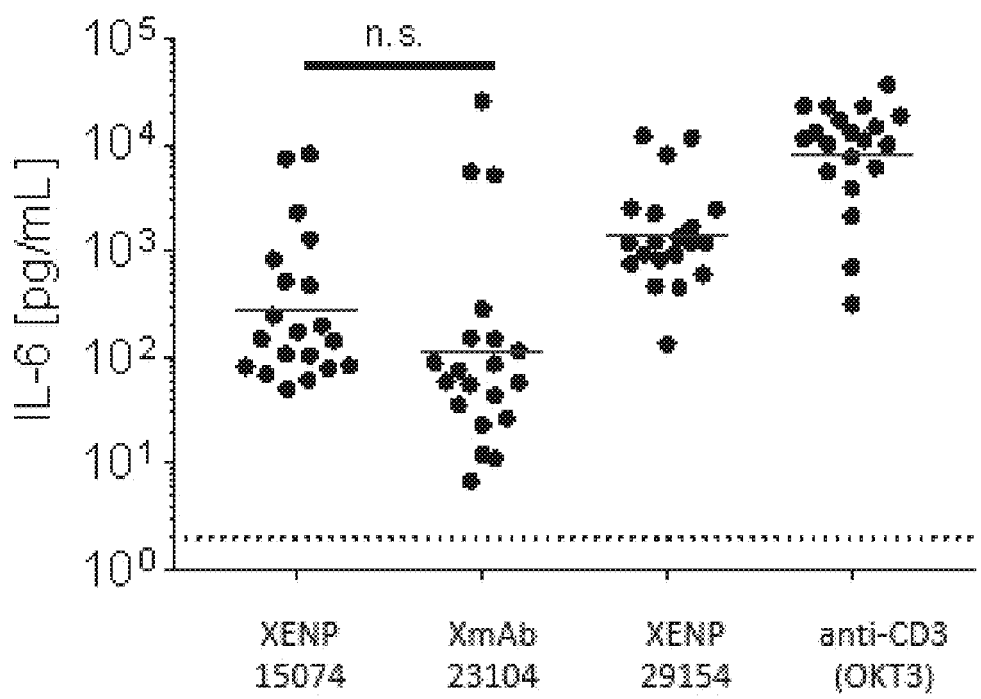
Figure 121J:
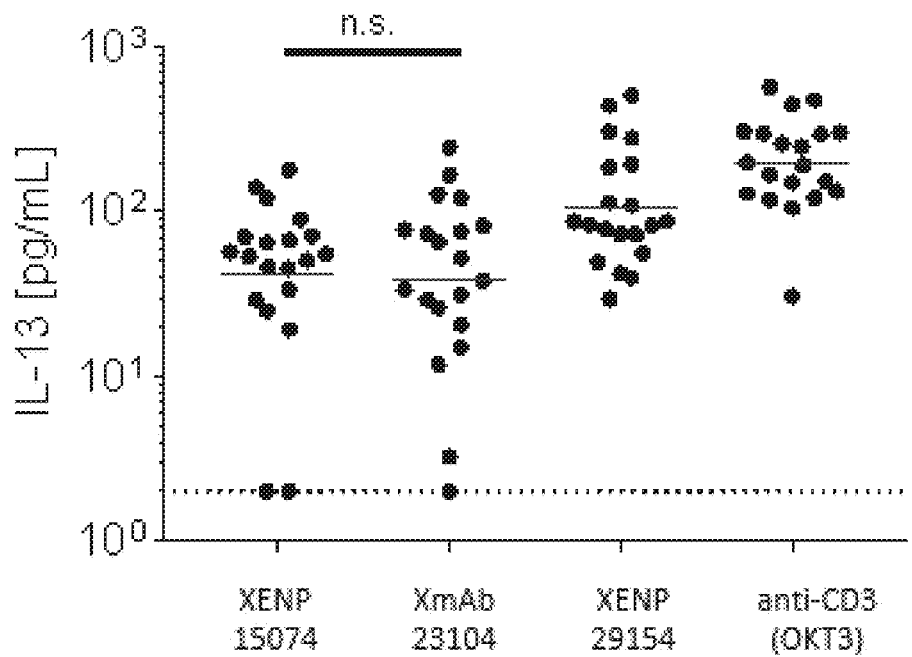

FIG. 118 depicts CD45+ cell counts in NSG mice on Day 14 after engraftment with human PBMCs and treatment with the indicated test articles.

FIG. 119A to 119J depicts the release of A) IFNγ, B) IL-1B, C) IL-2, D) IL-4, E) IL-8, F) IL-6, G) IL-10, H) IL-12p70, I) IL-13, and J) TNFα from human PBMCs treated with PBS, plate-bound XmAb23104, soluble XmAb23104, and plate-bound anti-CD3 antibody (OKT3).

FIG. 120 depicts the sequences for XENP29154, which is in-house produced TGN1412.

FIG. 121A to 121J depicts the release of A) IFNγ, B) IL-1B, C) IL-2, D) IL-4, E) IL-8, F) IL-10, G) IL-12p70, H) TNF, I) IL-6, and J) IL-13 from human PBMCs treated with air-dried XmAb23104, air-dried XENP15074 (isotype control), air-dried XENP29154 (positive control), and air-dried anti-CD3 mAb (OKT3; positive control).

Figure 122A:
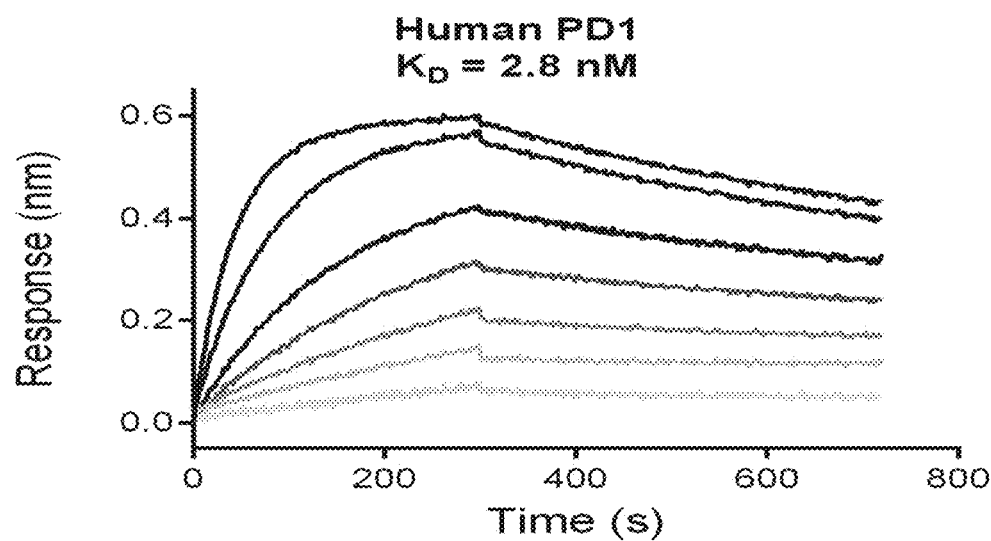
Figure 122B:
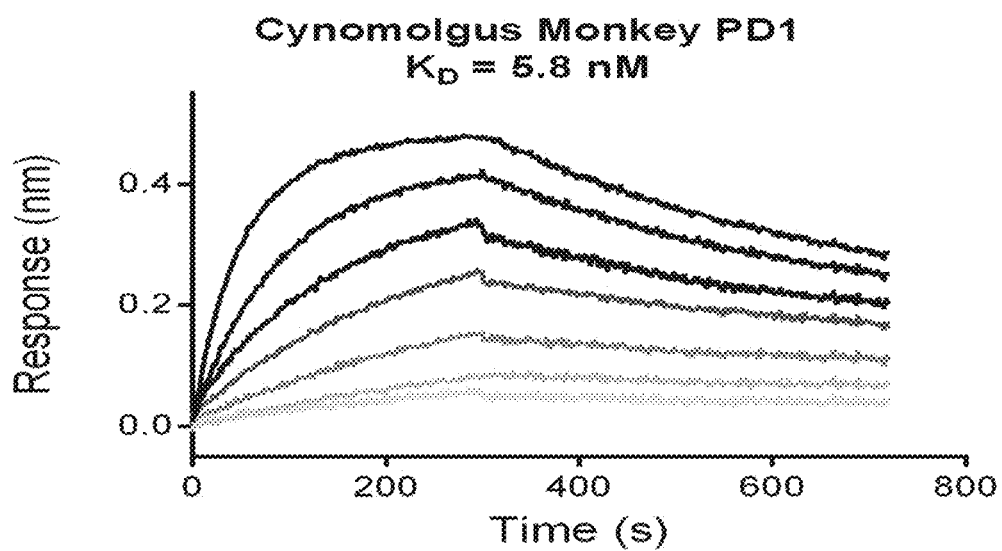

FIGS. 122A and 122B depicts sensorgrams showing binding of XmAb23104 to A) human PD-1 and B) cynomolgus PD-1.

Figure 123A:
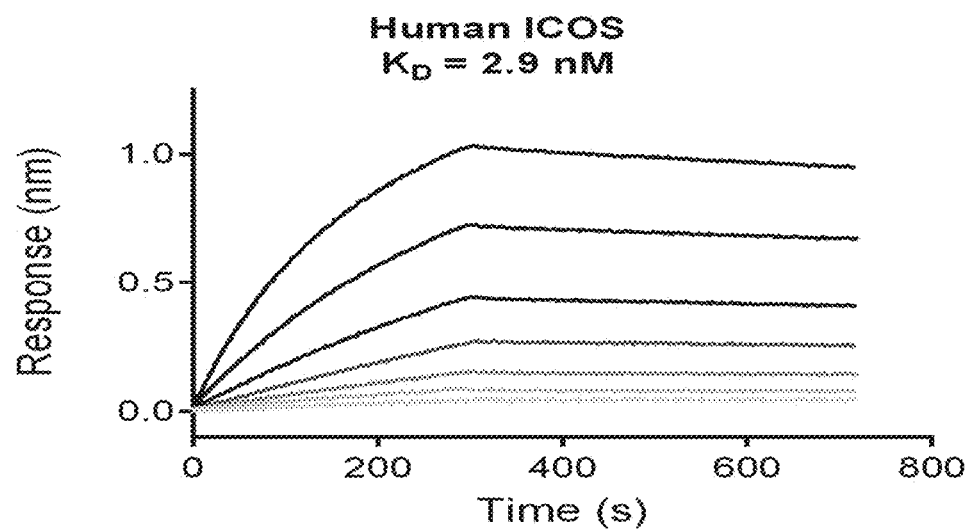
Figure 123B:
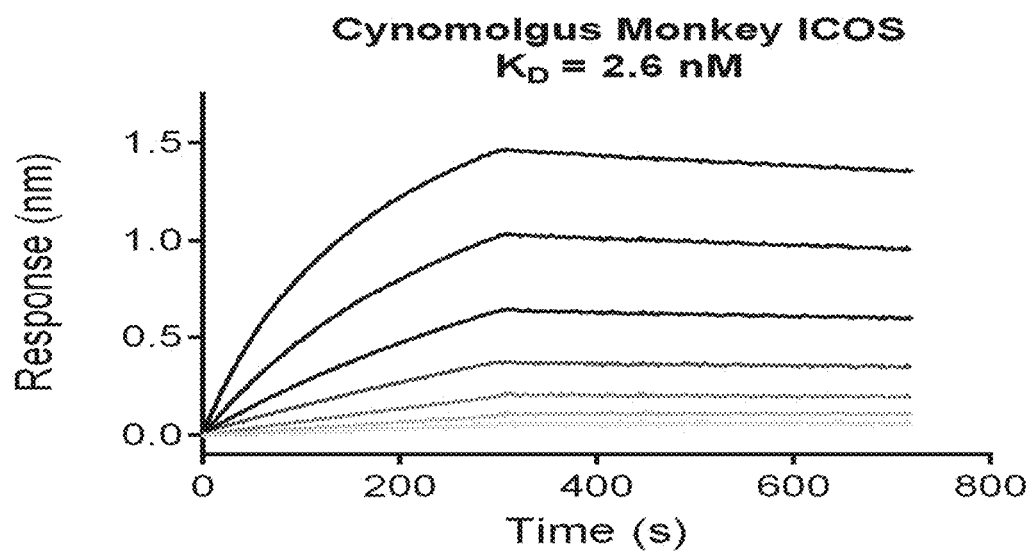

FIGS. 123A and 123B depict sensorgrams showing binding of XmAb23104 to A) human ICOS and B) cynomolgus ICOS.

FIG. 124 depicts the equilibrium dissociation constants (KD), association rates (ka), and dissociation rates (kd) for binding of XmAb23104 to human and cynomolgus PD-1 and ICOS.

Figure 125:
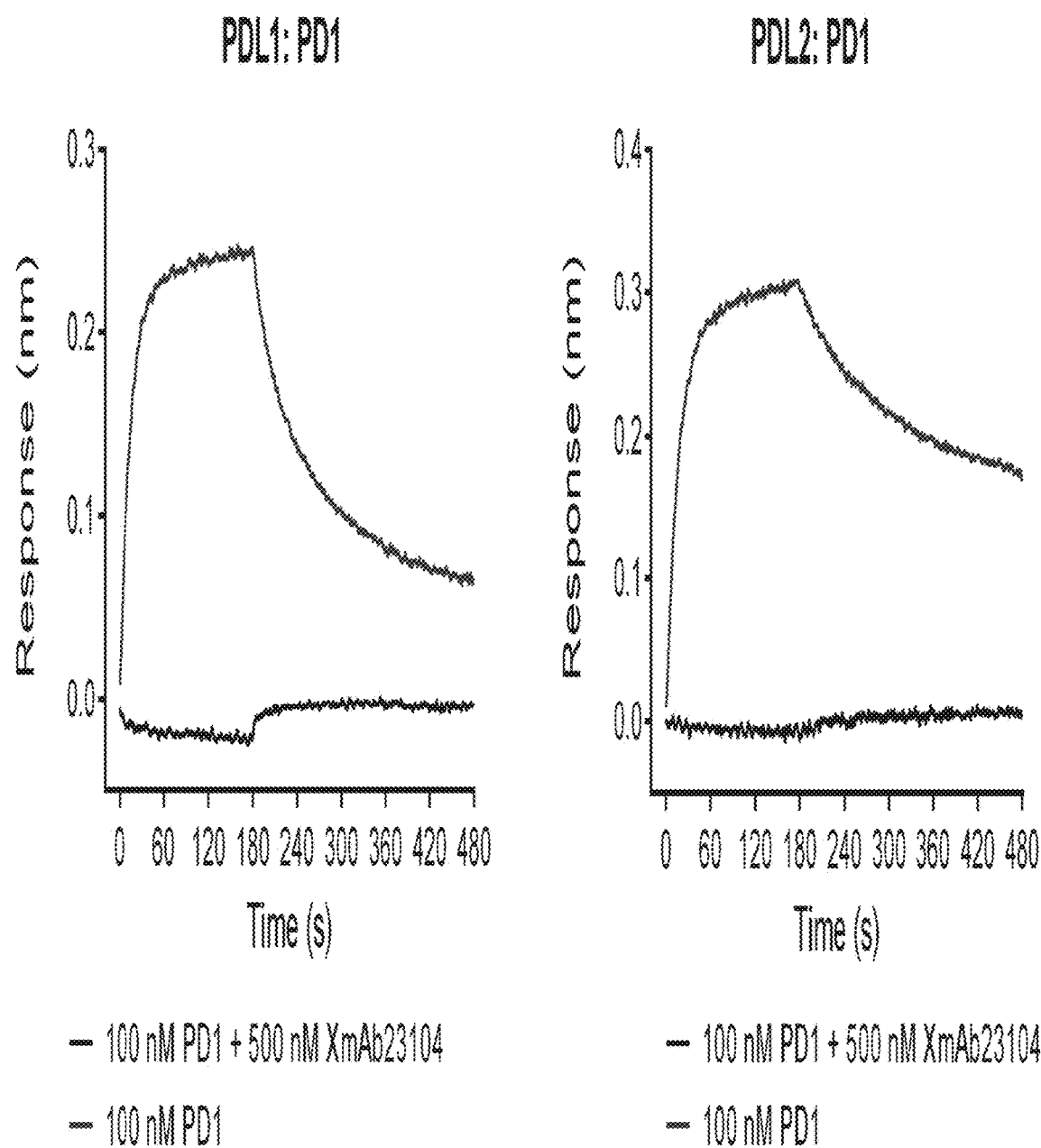

FIG. 125 depicts sensorgrams from competition binding experiments of PD-1 and ligands PD-L1 and PD-L2 with and without XmAb23104 pre-incubation.

Figure 126A:
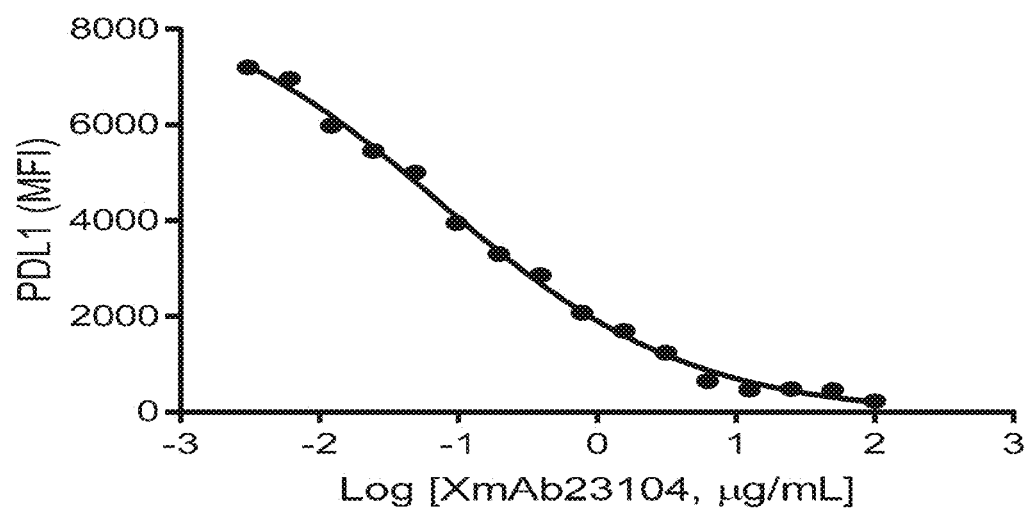
Figure 126B:
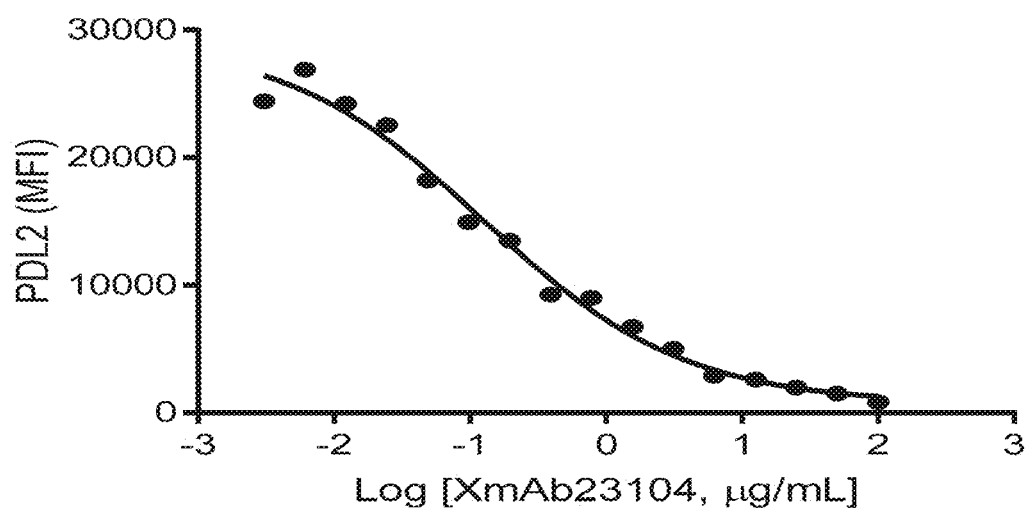
Figure 126C:
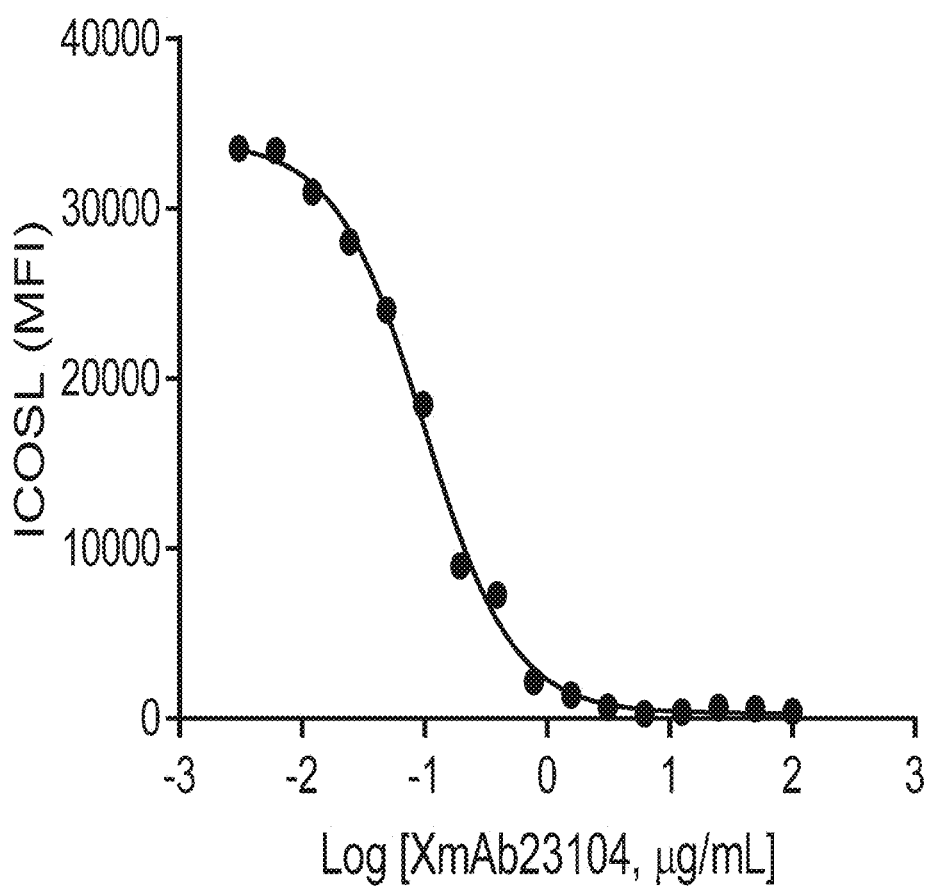

FIG. 126A to 126C depicts blocking of A) soluble PD-L1, B) soluble PD-L2, and C) soluble ICOSL to cell surface-expressed PD-1 and ICOS on PD-1+ICOS+ HEK 293T cells.

Figure 127:
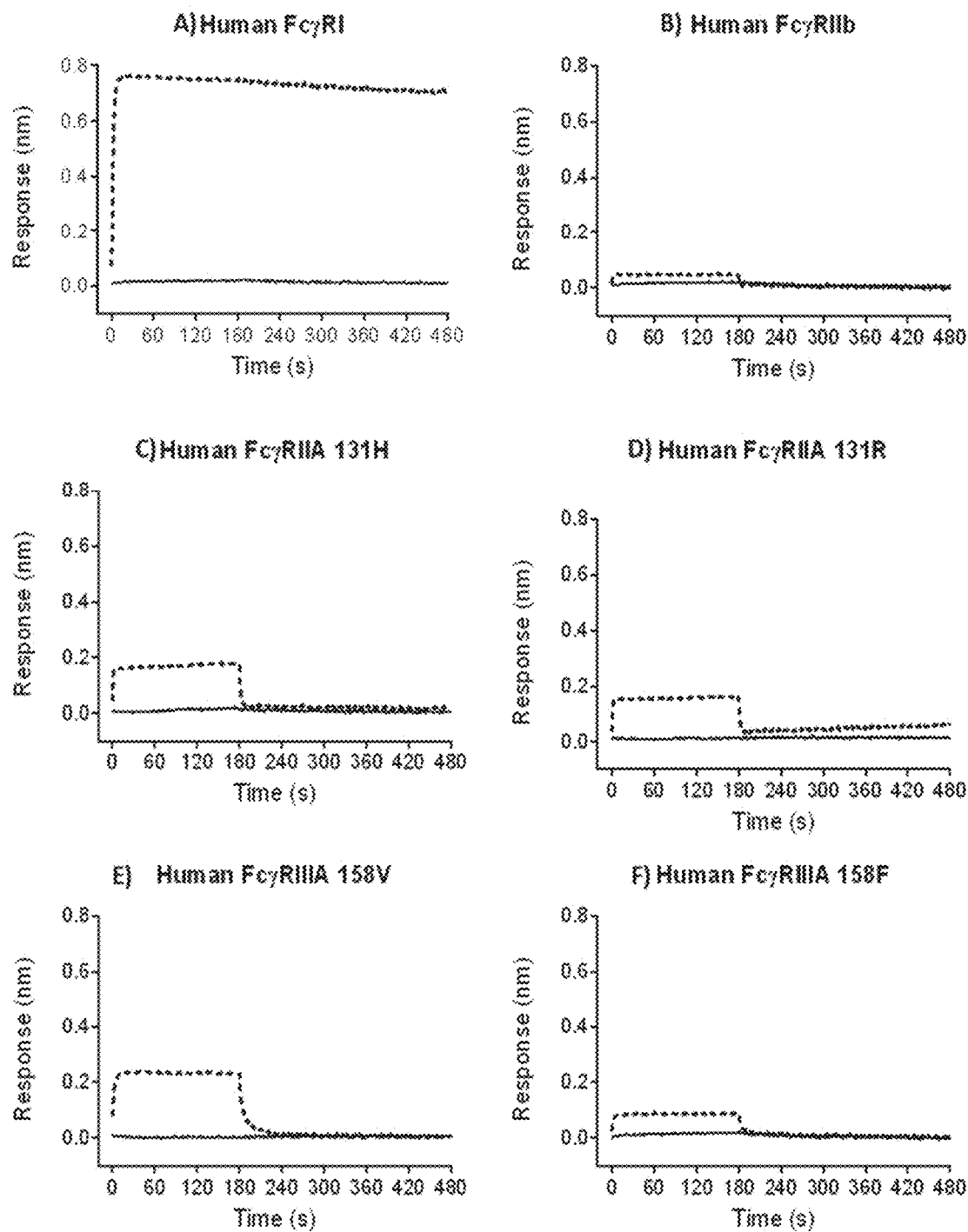

FIG. 127 depicts sensorgrams showing binding of XmAb23104 (solid line) and human IgG comparator (an anti-CD19 antibody with a native IgG1 constant region; dotted line) to A) human FcγRI, B) human FcγRIIb, C) human FcγRIIA (131H), D) human FcγRIIA (131R), E) human FcγRIIIA (158V), and F) human FcγRIIIA (158F).

Figure 128:
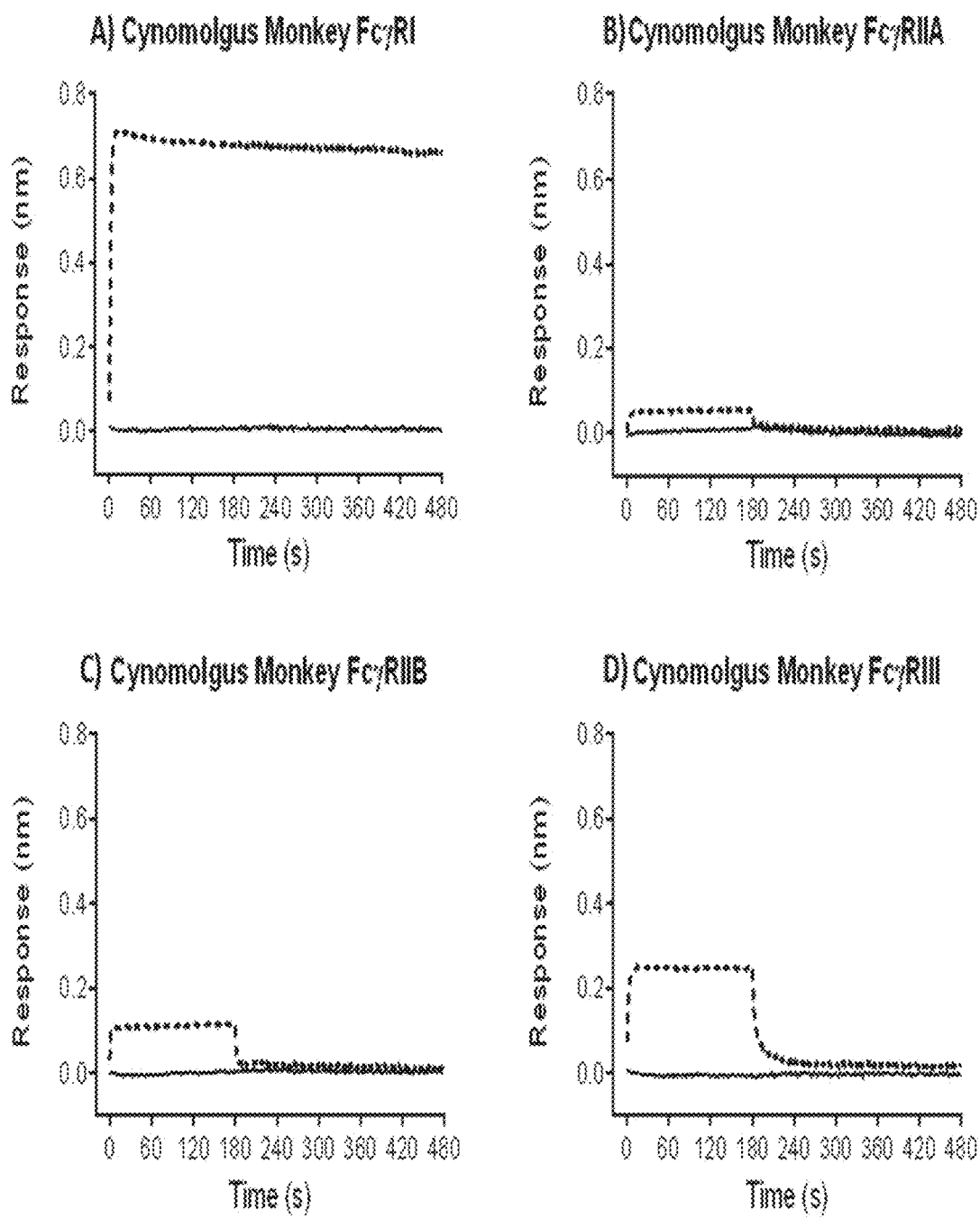

FIG. 128 depicts sensorgrams showing binding of XmAb23104 (solid line) and human IgG comparator (an anti-CD19 antibody with a native IgG1 constant region; dotted line) to A) cynomolgus FcγRI, B) cynomolgus FcγRIIA, C) cynomolgus FcγRIIb, and D) cynomolgus RcγRIIIA.

Figure 129:
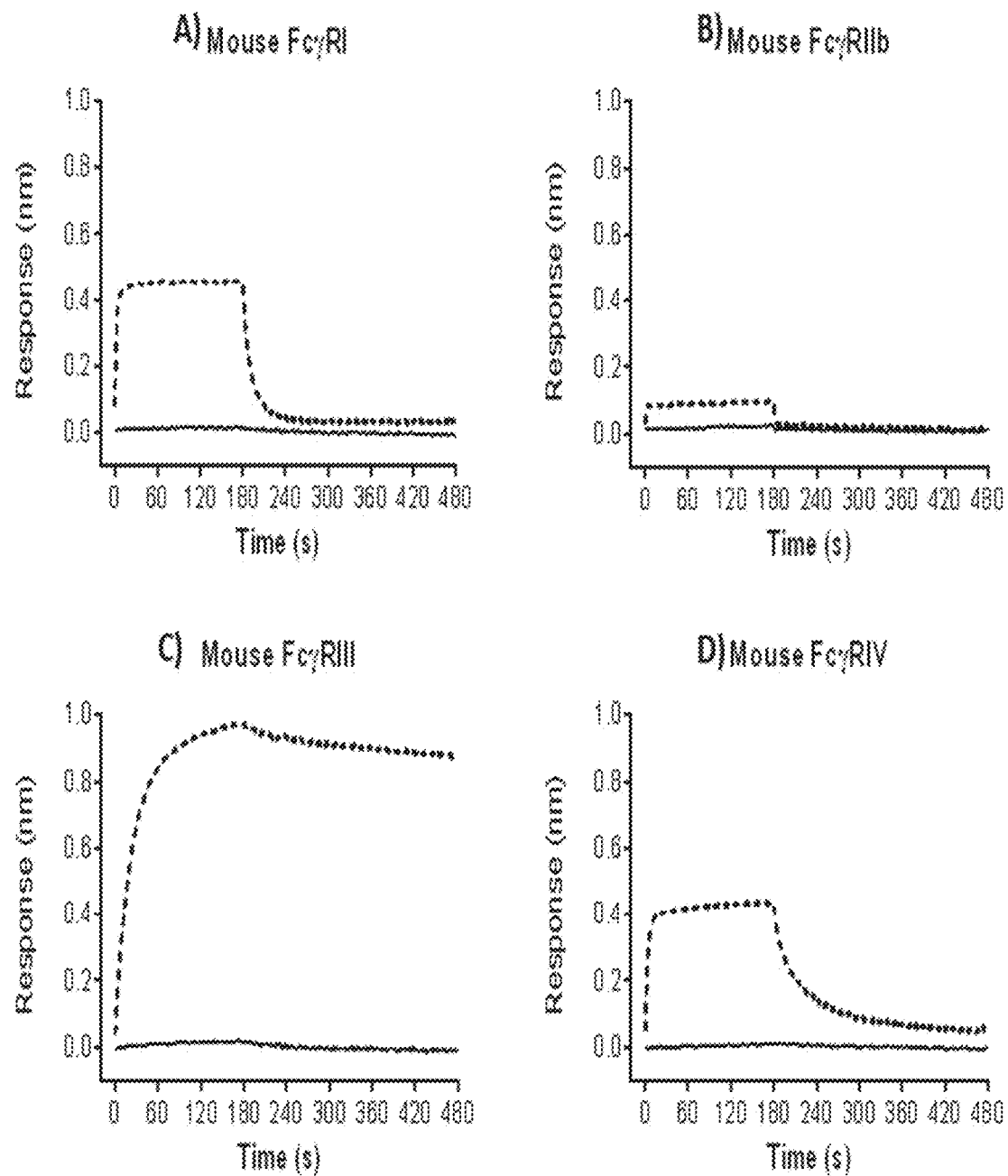

FIG. 129 depicts sensorgrams showing binding of XmAb23104 (solid line) and human IgG comparator (an anti-CD19 antibody with a native IgG1 constant region; dotted line) to A) murine FcγRI, B) murine FcγRIIb, C) murine FcγRIII, and D) murine FcγRIV.

Figures 130, 131:
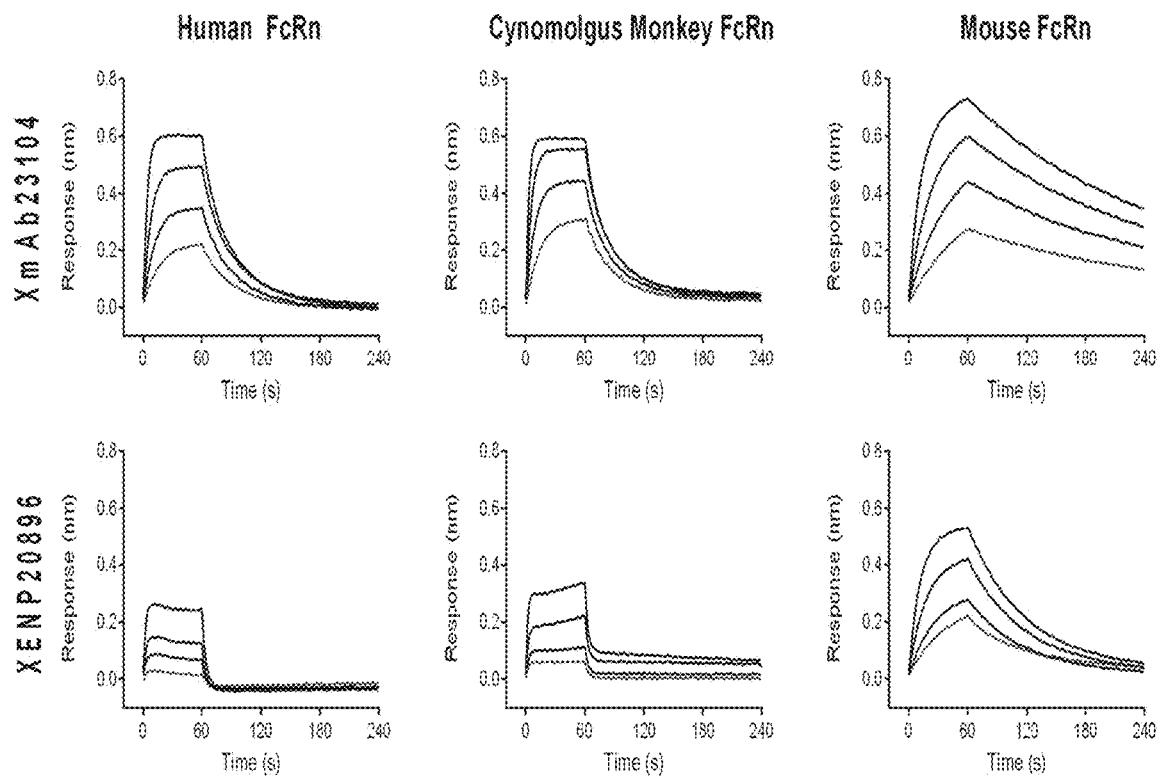

FIG. 130 depicts equilibrium dissociation constants ($K_D$) for binding of XmAb23104 and XENP20896 to human, cynomolgus, and mouse FcRn at pH 6.0.

FIG. 131 depicts sensorgrams showing binding of XmAb23104 and XENP20896 to human, cynomolgus, and mouse FcRn (1000, 500, 250, and 125 nM) at pH 6.0.

Figure 132:
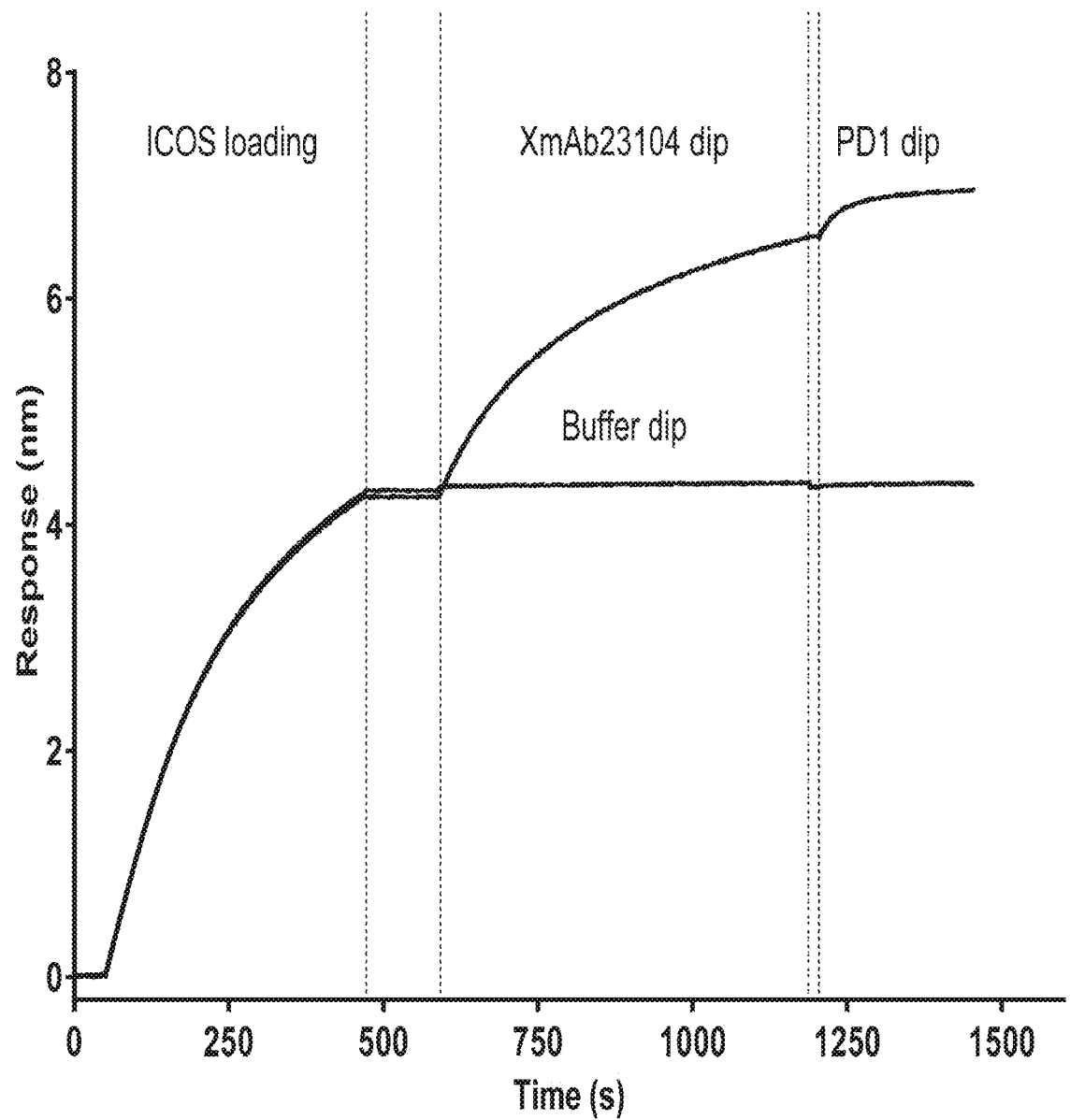

FIG. 132 depicts in-tandem BLI experiment showing biosensors loaded with ICOS and dipped into XmAb23104 or buffer followed by a final dip into PD-1 antigen.

Figure 133:
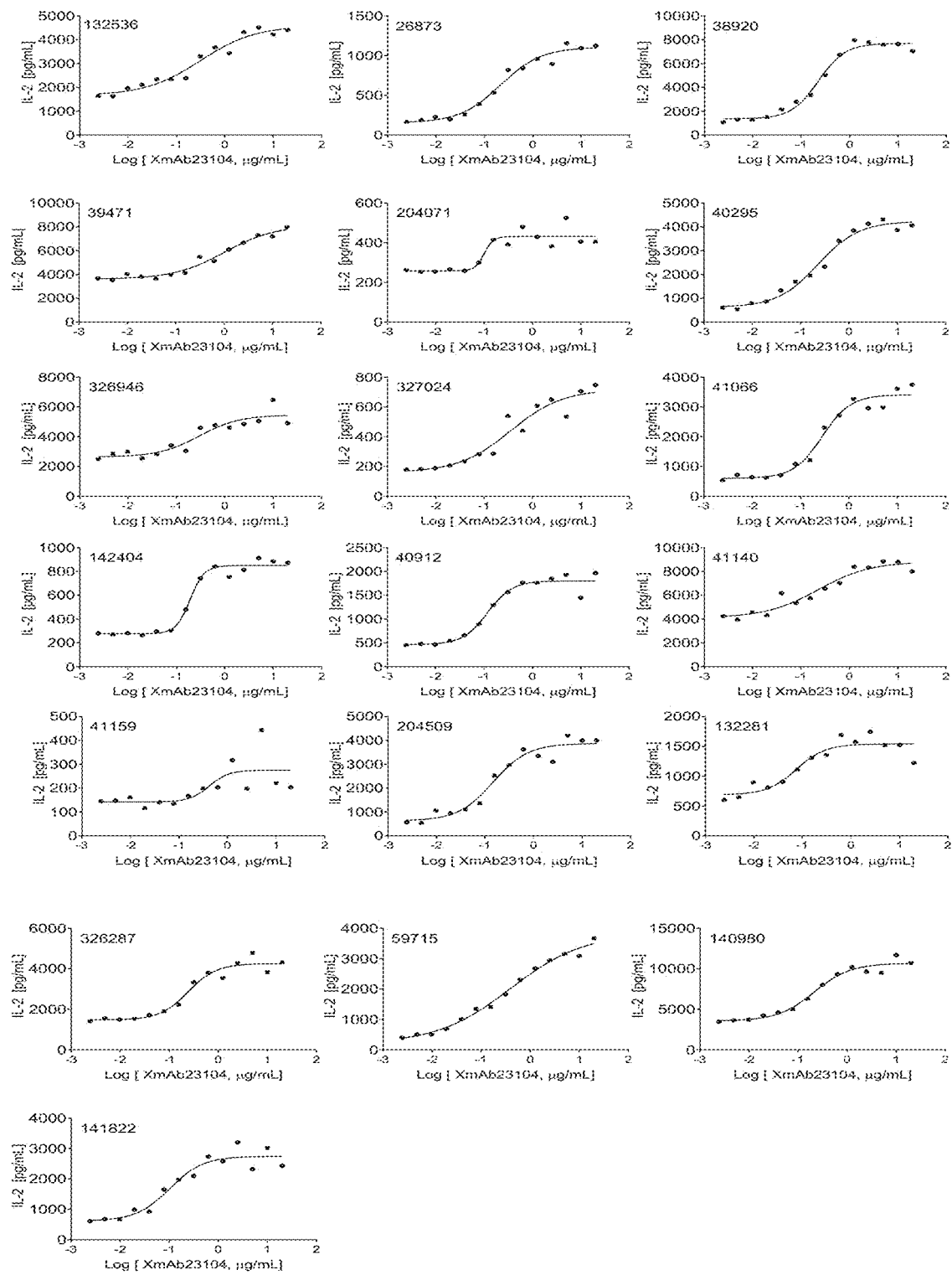

FIG. 133 depicts dose-dependent promotion of IL-2 secretion from SEB-stimulated human PBMCs (from 19 different donors) by XmAb23104.

Figure 134:
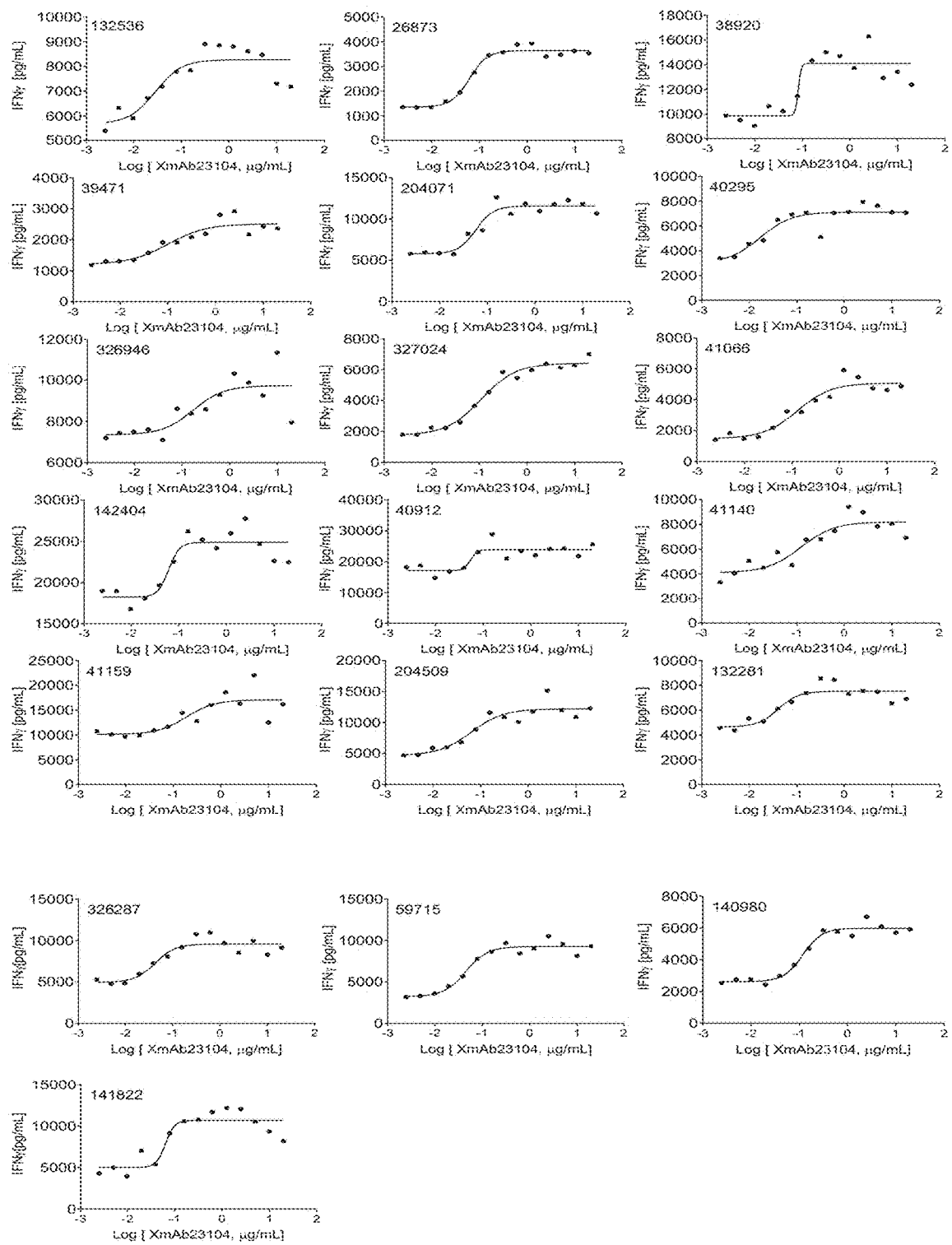

FIG. 134 depicts dose-dependent promotion of IFNγ secretion from SEB-stimulated human PBMCs (from 19 different donors) by XmAb23104.

Figure 135:
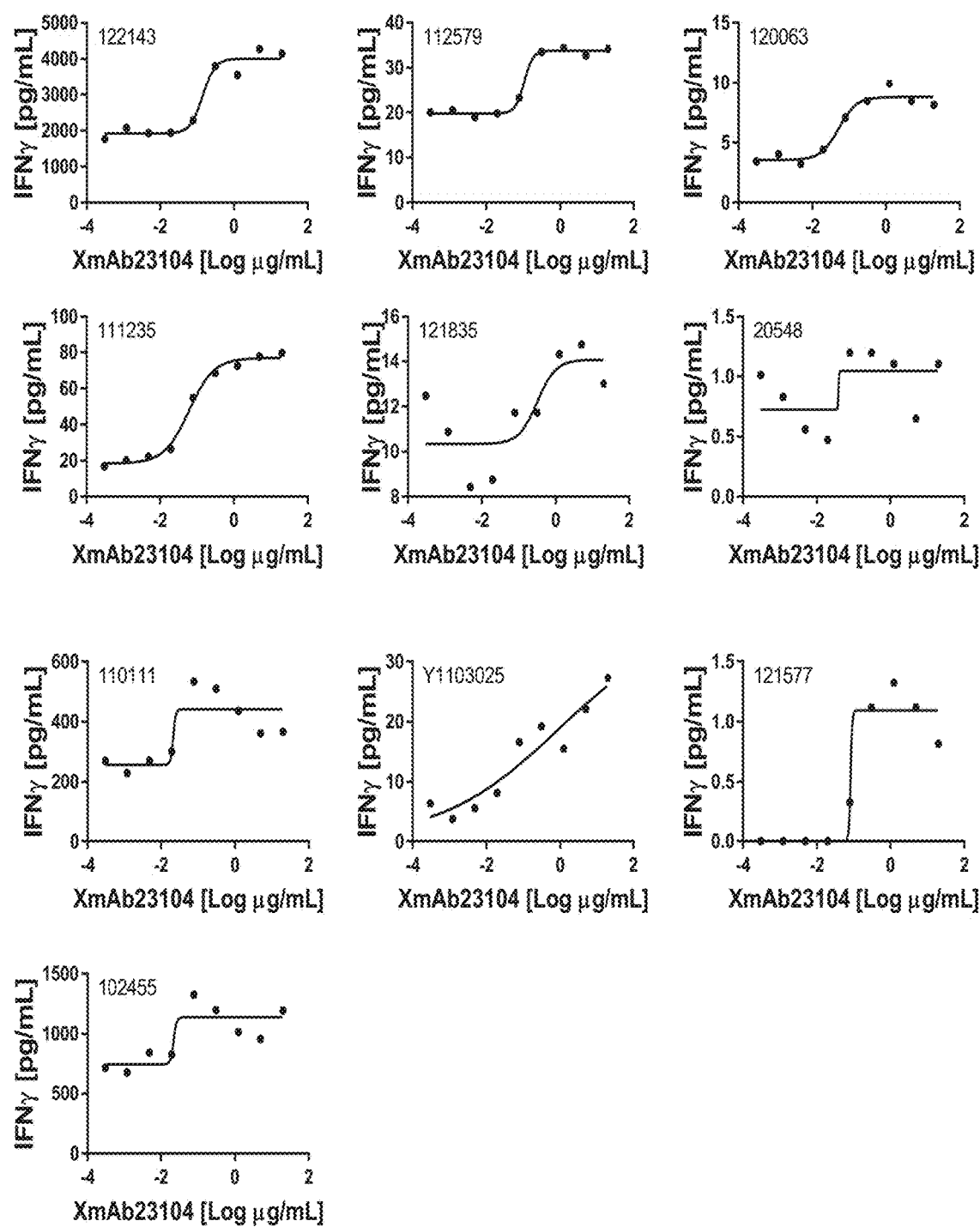

FIG. 135 depicts dose-dependent promotion of IFNγ secretion from SEB-stimulated cynomolgus PBMCs (from 10 different donors) by XmAb23104.

Figure 136:
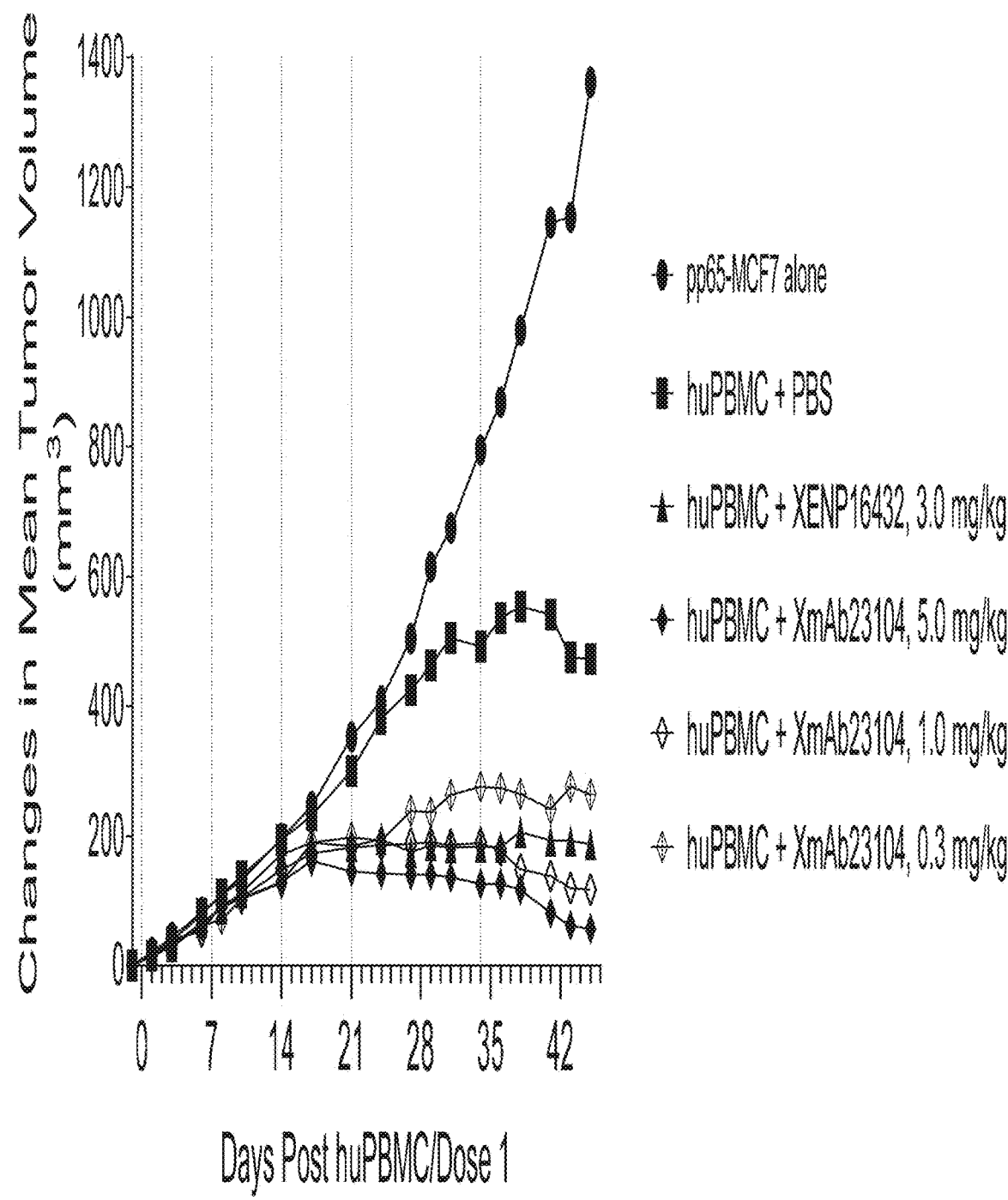

FIG. 136 depicts tumor volume over time (post-huPBMC engraftment) in pp65-MCF7 and huPBMC-engrafted NSG mice dosed with XENP16432 or indicated concentrations of XmAb23104.

Figure 137A:
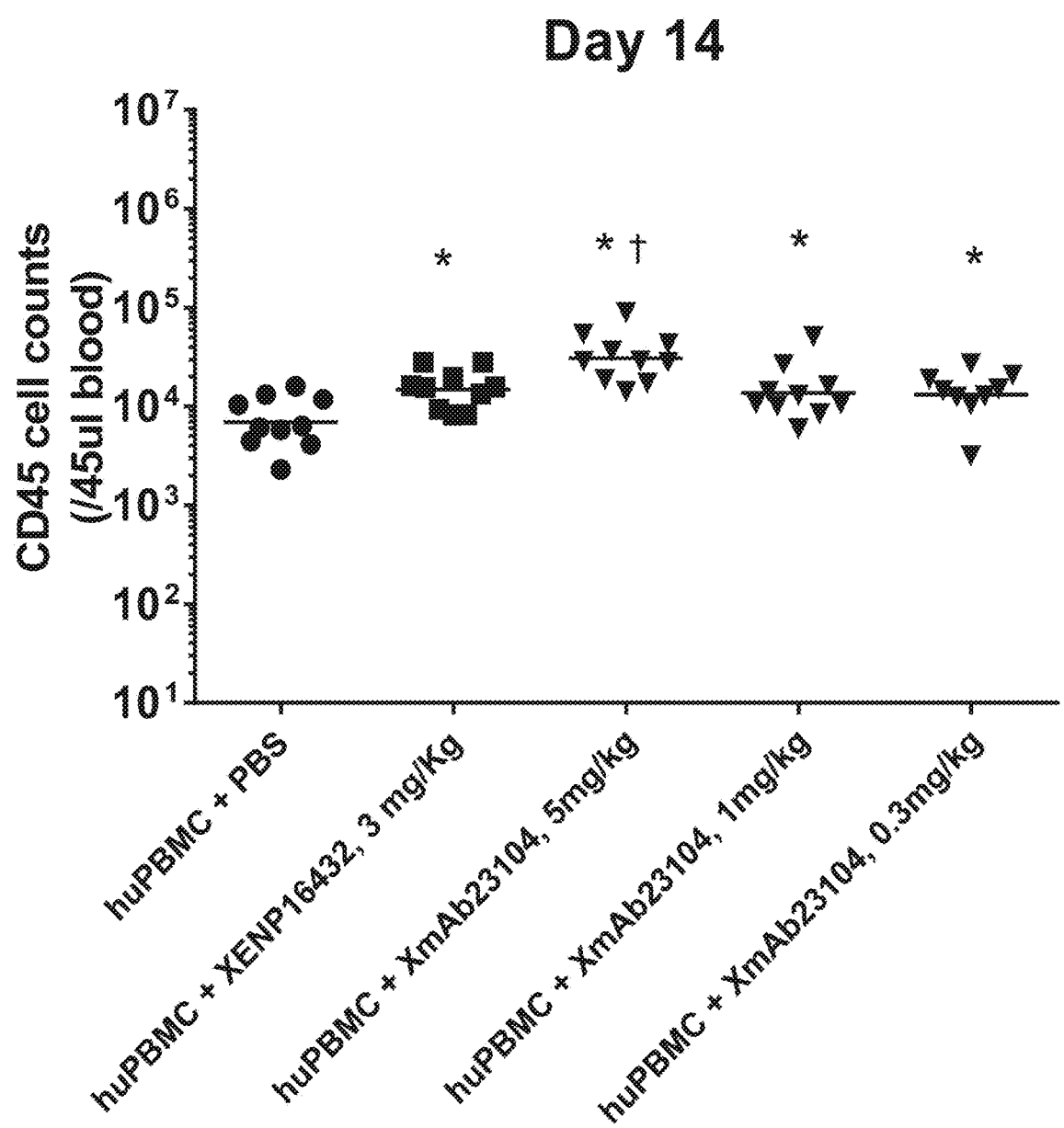
Figure 137B:
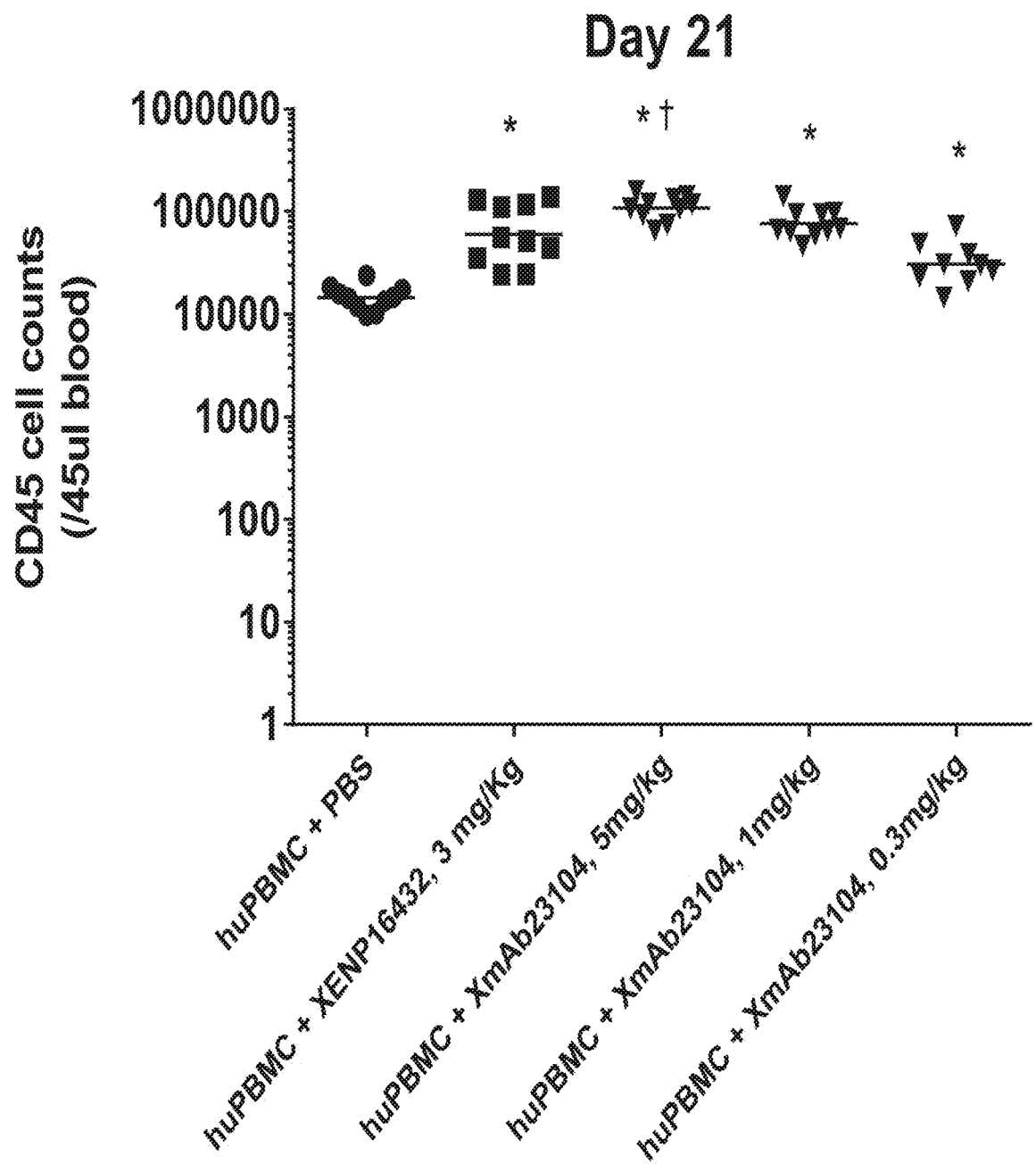
Figure 140A:
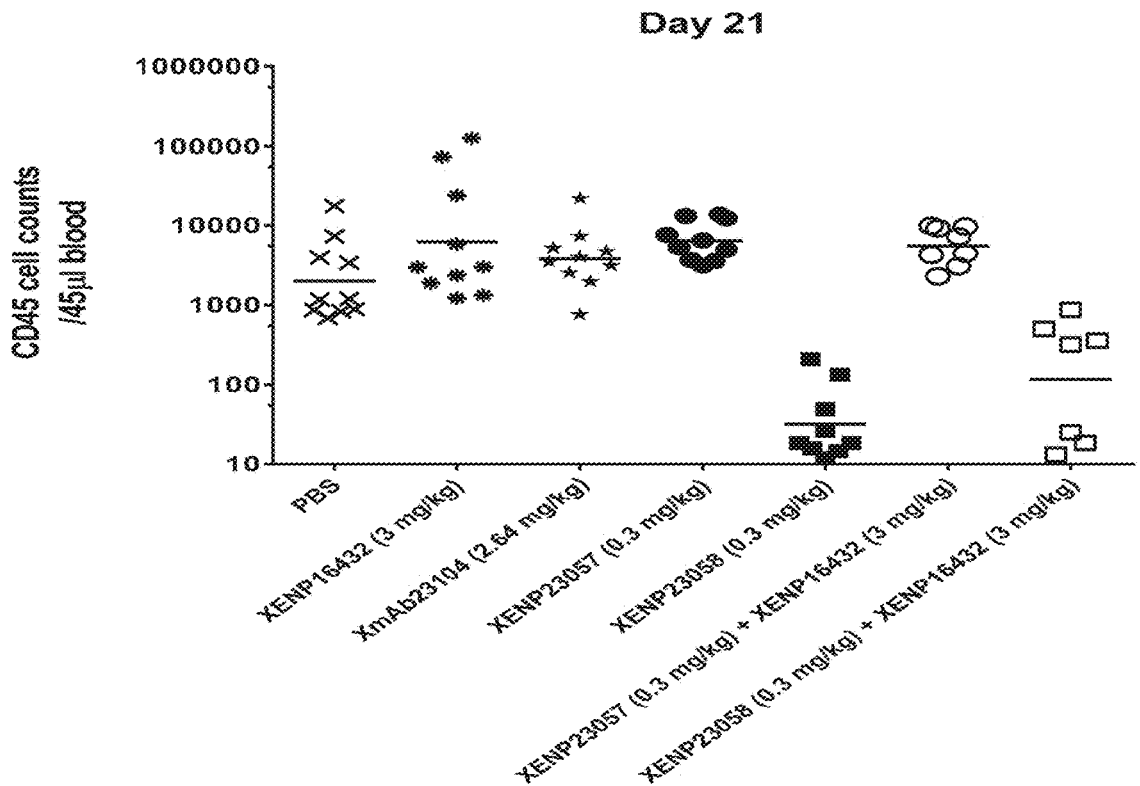
Figure 140B:
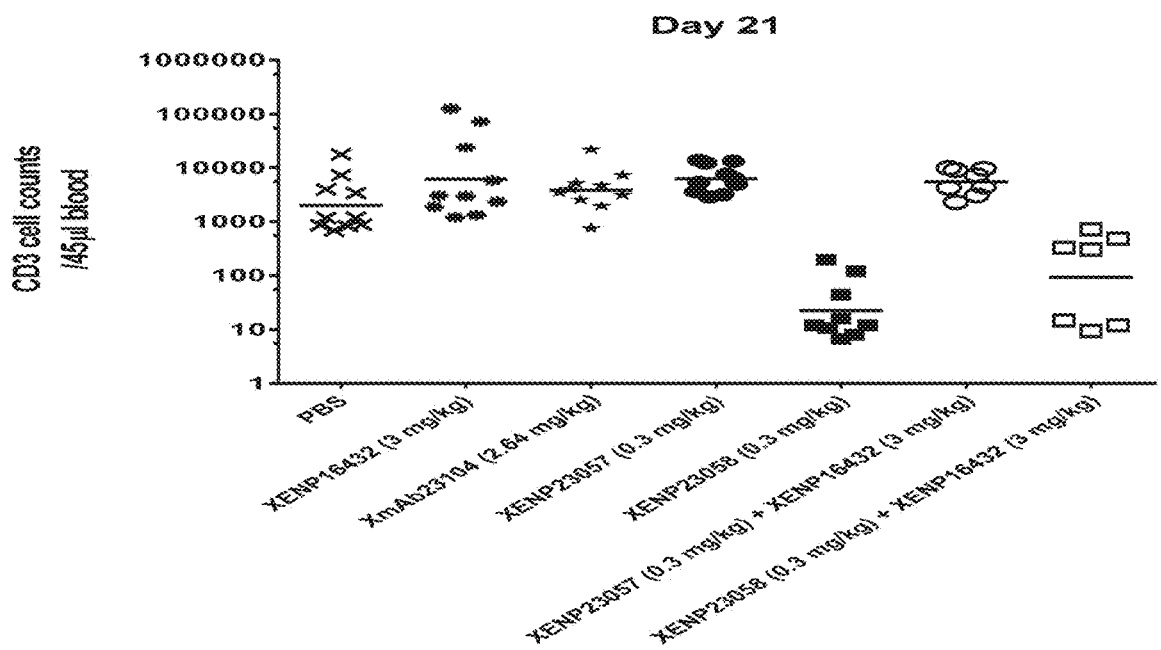
Figure 140C:
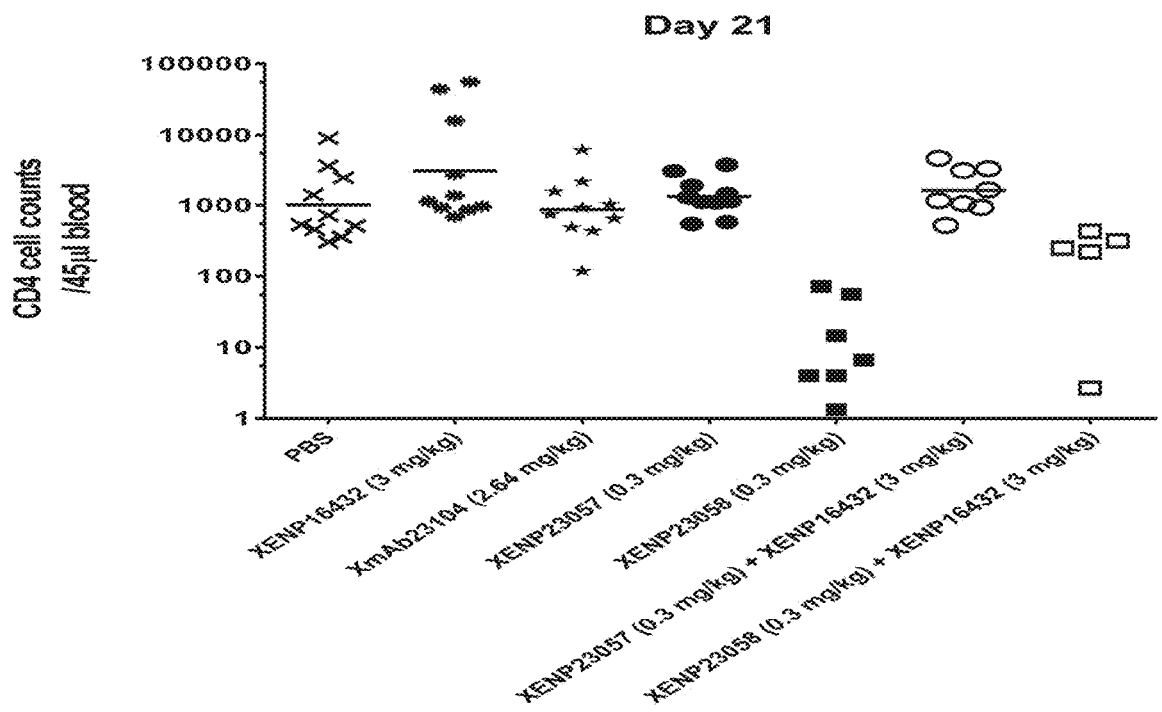
Figure 140D:
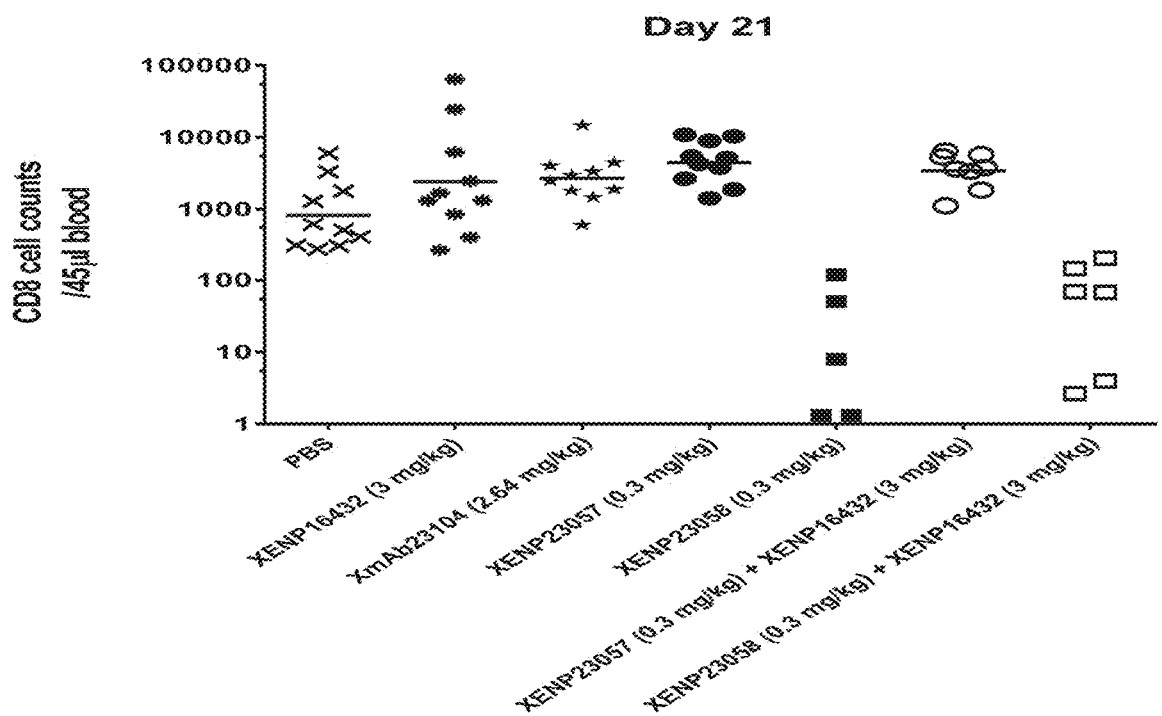

FIGS. 137A and 137B depict human CD45 cell counts on A) Day 14 and B) Day 21 in pp65-MCF7 and huPBMC-engrafted NSG mice dosed with XENP16432 or indicated concentrations of XmAb23104. *denotes P<0.05, unpaired Student t test, XmAb23104 or anti-PD-1 XENP16432-treated groups compared to PBS-treated group. † denotes P<0.05, unpaired Student t test, XmAb23104-treated groups compared to XENP16432-treated group. Data were log transformed prior to statistical analysis.

FIG. 138 depicts the sequences for JTX-2011, produced in-house as XENP23058.

FIG. 139 depicts the sequences for XENP23057, an anti-ICOS mAb based on JTX-2011 with E233P/L234V/L235A/G236del/S267K ablation variants.

FIG. 140A to 140D depicts A) human CD45+ cell, B) human CD3+ T cell, C) human CD4+ T cell, and D) human CD8+ T cell counts in huPBMC-engrafted NSG mice on Day 21 after dosing with the indicated test articles.

DETAILED DESCRIPTION OF THE INVENTION

I. Nomenclature

The bispecific antibodies of the invention are listed in several different formats. Each polypeptide is given a unique "XENP" number, although as will be appreciated in the art, a longer sequence might contain a shorter one. For example, the heavy chain of the scFv side monomer of a bottle opener format for a given sequence will have a first XENP number, while the scFv domain will have a different XENP number. Some molecules have three polypeptides, so the XENP number, with the components, is used as a name. Thus, the molecule XENP, which is in bottle opener format, comprises three sequences, generally referred to as "XENP23104-HC-Fab", XENP23104 HC-scFv" and "XENP23104 LC" or equivalents, although one of skill in the art would be able to identify these easily through sequence alignment. These XENP numbers are in the sequence listing as well as identifiers, and used in the Figures. In addition, one molecule, comprising the three components, gives rise to multiple sequence identifiers. For example, the listing of the Fab monomer has the full length sequence, the variable heavy sequence and the three CDRs of the variable heavy sequence; the light chain has a full length sequence, a variable light sequence and the three CDRs of the variable light sequence; and the scFv-Fc domain has a full length sequence, an scFv sequence, a variable light sequence, 3 light CDRs, a scFv linker, a variable heavy sequence and 3 heavy CDRs; note that all molecules herein with a scFv domain use a single charged scFv linker (+H), although others can be used. In addition, the naming nomenclature of particular variable domains uses a "Hx.xx_Ly.yy" type of format, with the numbers being unique identifiers to particular variable chain sequences. Thus, the variable domain of the scFv side of XENP23104 (which binds PD-1) is "1G6_L1.194_H1.279", which indicates that the variable heavy domain H1.279 was combined with the light domain L1.194. In the case that these sequences are used as scFvs, the designation "1G6_L1.194_H1.279", indicates that the variable heavy domain H1.279 was combined with the light domain L1.194 and is in vl-linker-vh orientation, from N- to C-terminus. This molecule with the identical sequences of the heavy and light variable domains but in the reverse order would be named "1G6_H1.279_L1.194". Similarly, different constructs may "mix and match" the heavy and light chains as will be evident from the sequence listing and the Figures.

II. Incorporation of Materials

A. Figures and Legends

Specifically incorporated by reference are the Figures, Legends and Sequences from U.S. Ser. No. 62/479,723 and the Figures, Legends and Sequences from U.S. Ser. No. 15/623,314. In addition, the claims from U.S. Ser. No. 62/479,723 are additionally specifically incorporated.

B. Sequences

Target Antigens: The sequence of human PD-1 (sp|Q15116) is SEQ ID NO: 26226. The sequence of human PD-1, extracellular domain (sp|Q15116|21-170) is SEQ ID NO: 26227. The sequence of Macaca fascicularis PD-1 (tr|B0LAJ3) is SEQ ID NO: 26228. The sequence of Macaca fascicularis PD-1, extracellular domain (predicted) (tr|B0LAJ3|21-170) is SEQ ID NO: 26229. The sequence of human CTLA-4 (sp|P16410) is SEQ ID NO: 26230. The sequence of human CTLA-4, extracellular domain (sp|P16410|36-161) is SEQ ID NO: 26231. The sequence of Macaca fascicularis CTLA-4 (tr|G7PL88) is SEQ ID NO: 26232. The sequence of Macaca fascicularis CTLA-4, extracellular domain (predicted) (tr|G7PL88) is SEQ ID NO: 26233. The sequence of human LAG-3 (sp|P18627) is SEQ ID NO: 26234. The sequence of human LAG-3, extracellular domain (sp|P18627|29-450) is SEQ ID NO: 26235. The sequence of Macaca fascicularis LAG-3 (predicted) (gi|544467815|ref|XP_005570011.1) is SEQ ID NO: 26236. The sequence of Macaca fascicularis LAG-3, extracellular domain (predicted) (gi|544467815|ref|XP_005570011.1|29-450) is SEQ ID NO: 26237. The sequence of human TIM-3 (sp|Q8TDQ0) is SEQ ID NO: 26238. The sequence of human TIM-3, extracellular domain (sp|Q8TDQ0|22-202) is SEQ ID NO: 26239. The sequence of Macaca fascicularis TIM-3 (predicted) (gi|355750365|gb|EHH54703.1) is SEQ ID NO: 26240. The sequence of Macaca fascicularis TIM-3, extracellular domain (predicted) (gi|355750365|gb|EHH54703.1|22-203) is SEQ ID NO: 26241. The sequence of human PD-L1 (sp|Q9NZQ7) is SEQ ID NO: 26242. The sequence of human PD-L1, extracellular domain (sp|Q9NZQ7|19-238) is SEQ ID NO: 26243. The sequence of Macaca fascicularis PD-L1 (predicted) (gb|XP_005581836.1) is SEQ ID NO: 26244. The sequence of Macaca fascicularis PD-L1, extracellular domain (predicted) (gb|XP_005581836.1|19-238) is SEQ ID NO: 26245. The sequence of human ICOS (sp|Q9Y6W8) is SEQ ID NO: 26246. The sequence of human ICOS, extracellular domain (sp|Q9Y6W8|21-140) is SEQ ID NO: 26247. The sequence of Macaca fascicularis ICOS (gi|544477053|ref|XP_005574075.1) is SEQ ID NO: 26248. The sequence of Macaca fascicularis ICOS, extracellular domain (predicted) (gi|544477053|ref|XP_005574075.1|21-140) is SEQ ID NO: 26249. The sequence of human GITR (sp|Q9Y5U5) is SEQ ID NO: 26250. The sequence of human GITR, extracellular domain (sp|Q9Y5U5|26-162) is SEQ ID NO: 26251. The sequence of Macaca fascicularis GITR (predicted) (ref|XP_005545180.1) is SEQ ID NO: 26252. The sequence of Macaca fascicularis GITR, extracellular domain (predicted) (ref|XP_005545180.1|26-162) is SEQ ID NO: 26253. The sequence of human OX40 (sp|P43489) is SEQ ID NO: 26254. The sequence of human OX40, extracellular domain (sp|P43489|29-214) is SEQ ID NO: 26255. The sequence of Macaca fascicularis OX40 (predicted) (ref|XP_005545179.1) is SEQ ID NO: 26256. The sequence of Macaca fascicularis OX40, extracellular domain (predicted) (ref|XP_005545179.1|29-214) is SEQ ID NO: 26257. The sequence of human 4-1BB (sp|Q07011) is SEQ ID NO: 26258. The sequence of human 4-1BB, extracellular domain (sp|Q07011|24-186) is SEQ ID NO: 26259. The sequence of Macaca fascicularis 4-1BB (predicted) (ref|XP_005544945.1) is SEQ ID NO: 26260. The sequence of Macaca fascicularis 4-1BB, extracellular domain (predicted) (ref|XP_005544945.1|24-186) is SEQ ID NO: 26261.

ICOS binding domains: In addition the sequences shown in FIG. 19, FIG. 20 and FIG. 24, SEQ ID NO:27869-28086 contain a number of ICOS Fab sequences (heavy chain VH1-CH1 and light chain VL1-CL) as indicated in the naming nomenclature. Reference for the CDRs and for the junction between the variable junctions is shown in FIG. 40 of U.S. Ser. No. 62/479,723 (hereby incorporated by reference as well as the Legend), although from the SEQ listing one of skill in the art will be able to ascertain the CDRs (see Table 1 for numbering and/or through sequence alignment) as well as for the junctions (e.g. heavy chain CH1 generally starts with the sequence "ASTK . . . " (SEQ ID NO: 30380) and light chain constant domain generally starts with "RTVA . . . " (SEQ ID NO: 30381). SEQ ID NO:28087-28269 show the three sequences for "one armed mAb" (FIG. 2N; Fab-Fc, Fc only and light chain) as shown in the naming nomenclature. Reference for the CDRs and for the junction between the variable junctions is shown in FIG. 41 of U.S. Ser. No. 62/479,723 (hereby incorporated by reference as well as the Legend), although from the SEQ listing one of skill in the art will be able to ascertain the CDRs (see Table 1 for numbering and/or through sequence alignment) as well as for the junctions (e.g. heavy chain CH1 generally starts with the sequence "ASTK . . . " (SEQ ID NO: 30380) and light chain constant domain generally starts with "RTVA . . . " (SEQ ID NO: 30381). Additional one armed ICOS molecules are shown in FIG. 68. SEQ ID NO:28549-28556 show some control antibodies (HC and LC) from which the Fvs can be used as ICOS ABDs as well; reference for the CDRs and for the junction between the variable junctions is shown in FIG. 44 of U.S. Ser. No. 62/479,723 (hereby incorporated by reference as well as the Legend), although from the SEQ listing one of skill in the art will be able to ascertain the CDRs (see Table 1 for numbering and/or through sequence alignment) as well as for the junctions (e.g. heavy chain CH1 generally starts with the sequence "ASTK . . . " (SEQ ID NO: 30380) and light chain constant domain generally starts with "RTVA . . . " (SEQ ID NO: 30381). SEQ ID NO:28557-28665 show some ICOS scFvs that find use in combination in the invention; reference for the CDRs and for the junction between the variable junctions is shown in FIG. 45 of U.S. Ser. No. 62/479,723 (hereby incorporated by reference as well as the Legend), although from the SEQ listing one of skill in the art will be able to ascertain the CDRs (see Table 1 for numbering and/or through sequence alignment) as well as for the junctions, as the scFvs utilize the charged linker (GKPGS)$_4$ between (SEQ ID NO: 26209) the vh and vl domains. Thus, suitable ICOS ABDs for use in combination with ABDs for checkpoint receptors are shown in FIG. 19, FIG. 20, FIG. 24, FIG. 68 and FIG. 77 as well as SEQ ID NO: 27869-28086, 28087-28269, 27193-27335, 28549-28556 and 28557-28665, and [ICOS]_H0.66_L0 and [ICOS]_H0_L0.

In addition, suitable ICOS X PD-1 bottle opener sequences include those in FIG. 3 as well as those in SEQ ID NO:28270-28548, which correspond to the sequences depicted in FIGS. 42 and 43 of U.S. Ser. No. 62/479,723 (both of which are hereby incorporated by reference as well as the Legends and sequences therein), again using these figures to show CDRs, junctions, etc.

III. Overview

Therapeutic antibodies directed against immune immunomodulatory inhibitors such as PD-1 are showing great promise in limited circumstances in the clinic for the treatment of cancer. Cancer can be considered as an inability of the patient to recognize and eliminate cancerous cells. In many instances, these transformed (e.g. cancerous) cells counteract immunosurveillance. There are natural control mechanisms that limit T-cell activation in the body to prevent unrestrained T-cell activity, which can be exploited by cancerous cells to evade or suppress the immune response. Restoring the capacity of immune effector cells-especially T cells—to recognize and eliminate cancer is the goal of immunotherapy. The field of immuno-oncology, sometimes referred to as "immunotherapy" is rapidly evolving, with several recent approvals of T cell checkpoint inhibitory antibodies such as Yervoy, Keytruda and Opdivo. These antibodies are generally referred to as "checkpoint inhibitors" because they block normally negative regulators of T cell immunity. It is generally understood that a variety of immunomodulatory signals, both costimulatory and coinhibitory, can be used to orchestrate an optimal antigen-specific immune response.

Checkpoint inhibitor monoclonal antibodies bind to immunomodulatory inhibitor proteins such as PD-1, which under normal circumstances prevent or suppress activation of cytotoxic T cells (CTLs). By inhibiting the immunomodulatory protein, for example through the use of antibodies that bind these proteins, an increased T cell response against tumors can be achieved. That is, these cancer immunomodulatory proteins suppress the immune response; when the proteins are blocked, for example using antibodies to the immunomodulatory protein, the immune system is activated, leading to immune stimulation, resulting in treatment of conditions such as cancer and infectious disease. Antibodies to either the PD-1 protein or its binding partner, PD-L1, leads to T cell activation.

Another area of current interest for harnessing the patient's immune system to fight disease involves the co-stimulation of T cells using agonistic antibodies that bind to co-stimulatory proteins such as ICOS (Inducible T cell Co-Stimulator, also referred to as CD278) which adds a positive signal to overcome the negative signaling of the immune checkpoint proteins on the T-cells. ICOS is a type I transmembrane protein comprising an extracellular (Ig) V-like domain, and serves as the receptor for the B7h co-stimulatory molecule.

Recent work shows that some tumor infiltrating lymphocytes (TILs) co-express PD-1 and ICOS (see Gros, J. Clinical Invest. 124(5):2246 (2014)).

Bispecific antibodies, which can bind two different targets simultaneously, offer the potential to improve the selectivity of targeting TILs vs peripheral T cells, while also reducing cost of therapy. The bivalent interaction of an antibody with two targets on a cell surface should—in some cases—lead to a higher binding avidity relative to a monovalent interaction with one target at a time. Because of this, normal bivalent antibodies tend to have high avidity for their target on a cell surface. With bispecific antibodies, the potential exists to create higher selectivity for cells that simultaneously express two different targets, utilizing the higher avidity afforded by simultaneous binding to both targets.

Accordingly, the present invention provides bispecific immunomodulatory antibodies, that bind to cells expressing the two antigens and methods of activating T cells and/or NK cells to treat diseases such as cancer and infectious diseases, and other conditions where increased immune activity results in treatment.

Thus, the invention is directed, in some instances, to solving the issue of toxicity and expense of administering multiple antibodies by providing bispecific antibodies that bind to two different immunomodulatory molecules (one a checkpoint receptor and the other a costimulatory receptor) on a single cell and advantageously requiring administration of only one therapeutic substance.

Bispecific antibodies offer the opportunity to combine immune immunomodulatory blockade with costimulation in one molecule. However, it is not obvious what combination of immune immunomodulatory plus costimulatory protein or what binding stoichiometry (monovalent+monovalent, monovalent+bivalent, etc.) would be efficacious. Here we identify bispecific antibodies that binding monovalently to a costimulatory protein (such as ICOS) and monovalent binding to a checkpoint receptor (such as PD-1) that are capable of inducing robust T cell activation.

Surprisingly, while conventional wisdom states that monovalent antibodies do not result in agonism, the present work shows the unexpected results of agonism of the ICOS receptor with the monovalent bispecific antibodies of the invention. See Merchant et al., PNAS Jul. 23, 2013 E2987-E2996, "[w]hile initial screening of bivalent antibodies produced agonists of MET, engineering them into monovalent antibodies produces antagonists instead." This positive result with only monovalent binding to ICOS is unexpected because it is thought that at least bivalent binding to a costimulatory protein is necessary to provide the required level of receptor clustering on the cell surface for triggering signaling. As shown by Fos et al., J. Immunol. 2008:1969-1977, ICOS ligation induces AKT phosphorylation. The studies here in use AKT phosphorylation as an indicator of ICOS agonism, and this effect is seen for both "one armed ICOS" (see Example 5A(a)) and for bispecific antibodies that bind ICOS monovalently. As shown in Example 7 and in FIG. 70, the one-arm XENP20266 that only binds ICOS monovalently promotes more AKT phosphorylation than XENP16435, which binds ICOS bivalently (e.g. as a traditional mAb).

Accordingly, the present invention is directed to novel constructs to provide heterodimeric, bispecific antibodies that allow binding to a checkpoint receptor as well as human ICOS.

Note that generally these bispecific antibodies are named "anti-PD-1 X anti-ICOS", or generally simplistically or for ease (and thus interchangeably) as "PD-1 X ICOS", etc. for each pair.

The heterodimeric bispecific immunomodulatory antibodies of the invention are useful to treat a variety of types of cancers. As will be appreciated by those in the art, in contrast to traditional monoclonal antibodies that bind to tumor antigens, or to the newer classes of bispecific antibodies that bind, for example, CD3 and tumor antigens (such as described in U.S. Ser. No. 15/141,350, for example), immunomodulatory antibodies are used to increase the immune response but are not generally tumor specific in their action. That is, the bispecific immunomodulatory antibodies of the invention inhibit the suppression of the immune system, generally leading to T cell activation, which in turn leads to greater immune response to cancerous cells and thus treatment.

As discussed below, there are a variety of ways that T cell activation can be measured. Functional effects of the bispecific immunomodulatory antibodies on NK and T-cells can be assessed in vitro (and in some cases in vivo, as described more fully below) by measuring changes in the following parameters: proliferation, cytokine release and cell-surface makers. For NK cells, increases in cell proliferation, cytotoxicity (ability to kill target cells as measured by increases in CD107a, granzyme, and perforin expression, or by directly measuring target cells killing), cytokine production (e.g. IFN-γ and TNF), and cell surface receptor expression (e.g. CD25) is indicative of immune modulation, e.g. enhanced killing of cancer cells. For T-cells, increases in proliferation, increases in expression of cell surface markers of activation (e.g. CD25, CD69, CD137, and PD1), cytotoxicity (ability to kill target cells), and cytokine production (e.g. IL-2, IL-4, IL-6, IFN, TNF-a, IL-10, IL-17A) are indicative of immune modulation, e.g. enhanced killing of cancer cells. Accordingly, assessment of treatment can be done using assays that evaluate one or more of the following: (i) increases in immune response, (ii) increases in activation of αβ and/or γδ T cells, (iii) increases in cytotoxic T cell activity, (iv) increases in NK and/or NKT cell activity, (v) alleviation of αβ and/or γδ T-cell suppression, (vi) increases in pro-inflammatory cytokine secretion, (vii) increases in IL-2 secretion; (viii) increases in interferon-γ production, (ix) increases in Th1 response, (x) decreases in Th2 response, (xi) decreases or eliminates cell number and/or activity of at least one of regulatory T cells, (xii) increases in IL-2 secretion.

Thus, in some embodiments the invention provides the use of bispecific immunomodulatory antibodies to perform one or more of the following in a subject in need thereof: (a) upregulating pro-inflammatory cytokines; (b) increasing T-cell proliferation and/or expansion; (c) increasing interferon-γ or TNF-α production by T-cells; (d) increasing IL-2 secretion; (e) stimulating antibody responses; (f) inhibiting cancer cell growth; (g) promoting antigenic specific T cell immunity; (h) promoting CD4+ and/or CD8+ T cell activation; (i) alleviating T-cell suppression; (j) promoting NK cell activity; (k) promoting apoptosis or lysis of cancer cells; and/or (l) cytotoxic or cytostatic effect on cancer cells.

Accordingly, the present invention provides bispecific immunomodulatory antibodies. There are a number of formats that can be used in the present invention, as generally shown in FIG. 2, many of which are heterodimeric (although not all, as DVD-Ig, for example).

The heterodimeric antibodies constructs are based on the self-assembling nature of the two Fc domains of the heavy chains of antibodies, e.g. two "monomers" that assemble into a "dimer". Heterodimeric antibodies are made by altering the amino acid sequence of each monomer as more fully discussed below. Thus, the present invention is generally directed to the creation of heterodimeric antibodies, which can co-engage two antigens in several ways, relying on amino acid variants in the constant regions that are different on each chain to promote heterodimeric formation and/or allow for ease of purification of heterodimers over the homodimers.

Thus, the present invention provides bispecific immunomodulatory antibodies. An ongoing problem in antibody technologies is the desire for "bispecific" antibodies that bind to two (or more) different antigens simultaneously, in general thus allowing the different antigens to be brought into proximity and resulting in new functionalities and new therapies. In general, these antibodies are made by including genes for each heavy and light chain into the host cells (generally, in the present invention, genes for two heavy chain monomers and a light chain as outlined herein). This generally results in the formation of the desired heterodimer (A-B), as well as the two homodimers (A-A and B-B). However, a major obstacle in the formation of bispecific antibodies is the difficulty in purifying the heterodimeric antibodies away from the homodimeric antibodies and/or biasing the formation of the heterodimer over the formation of the homodimers.

To solve this issue, there are a number of mechanisms that can be used to generate the heterodimers of the present invention. In addition, as will be appreciated by those in the art, these mechanisms can be combined to ensure high heterodimerization. Thus, amino acid variants that lead to the production of heterodimeric antibodies are referred to as "heterodimerization variants". As discussed below, heterodimerization variants can include steric variants (e.g. the "knobs and holes" or "skew" variants described below and the "charge pairs" variants described below) as well as "pI variants", which allows purification of homodimers away from heterodimers.

One mechanism is generally referred to in the art as "knobs and holes" ("KIH") or sometimes herein as "skew" variants, referring to amino acid engineering that creates steric influences to favor heterodimeric formation and disfavor homodimeric formation can also optionally be used; this is sometimes referred to as "knobs and holes", as described in Ridgway et al., Protein Engineering 9(7):617 (1996); Atwell et al., J. Mol. Biol. 1997 270:26; U.S. Pat. No. 8,216,805, US 2012/0149876, all of which are hereby incorporated by reference in their entirety. The Figures identify a number of "monomer A-monomer B" pairs that include "knobs and holes" amino acid substitutions. In addition, as described in Merchant et al., Nature Biotech. 16:677 (1998), these "knobs and hole" mutations can be combined with disulfide bonds to skew formation to heterodimerization. Of use in the present invention are T366S/L368A/Y407V paired with T366W, as well as this variant with a bridging disulfide, T366S/L368A/Y407V/Y349C paired with T366W/S354C, particularly in combination with other heterodimerization variants including pI variants as outlined below.

An additional mechanism that finds use in the generation of heterodimeric antibodies is sometimes referred to as "electrostatic steering" or "charge pairs" as described in Gunasekaran et al., J. Biol. Chem. 285(25):19637 (2010), hereby incorporated by reference in its entirety. This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". These include, but are not limited to, D221E/P228E/L368E paired with D221R/P228R/K409R (e.g. these are "monomer corresponding sets) and C220E/P228E/368E paired with C220R/E224R/P228R/K409R and others shown in the Figures.

In the present invention, in some embodiments, pI variants are used to alter the pI of one or both of the monomers and thus allowing the isoelectric purification of A-A, A-B and B-B dimeric proteins.

In the present invention, there are several basic mechanisms that can lead to ease of purifying heterodimeric proteins; one relies on the use of pI variants, such that each monomer has a different pI, thus allowing the isoelectric purification of A-A, A-B and B-B dimeric proteins. Alternatively, some scaffold formats, such as the "triple F" or "bottle opener" format, also allows separation on the basis of size. As is further outlined below, it is also possible to "skew" the formation of heterodimers over homodimers. Thus, a combination of steric heterodimerization variants and pI or charge pair variants find particular use in the invention. Additionally, as more fully outlined below, scaffolds that utilize scFv(s) such as the Triple F format can include charged scFv linkers (either positive or negative), that give a further pI boost for purification purposes. As will be appreciated by those in the art, some Triple F formats are useful with just charged scFv linkers and no additional pI adjustments, although the invention does provide the use of skew variants with charged scFv linkers as well (and combinations of Fc, FcRn and KO variants discussed herein).

In the present invention that utilizes pI as a separation mechanism to allow the purification of heterodimeric proteins, amino acid variants can be introduced into one or both of the monomer polypeptides; that is, the pI of one of the monomers (referred to herein for simplicity as "monomer A") can be engineered away from monomer B, or both monomer A and B change be changed, with the pI of monomer A increasing and the pI of monomer B decreasing. As is outlined more fully below, the pI changes of either or both monomers can be done by removing or adding a charged residue (e.g. a neutral amino acid is replaced by a positively or negatively charged amino acid residue, e.g. glycine to glutamic acid), changing a charged residue from positive or negative to the opposite charge (aspartic acid to lysine) or changing a charged residue to a neutral residue (e.g. loss of a charge; lysine to serine). A number of these variants are shown in the Figures. In addition, suitable pI variants for use in the creation of heterodimeric antibodies herein are those that are isotypic, e.g. importing pI variants from different IgG isotypes such that pI is changed without introducing significant immunogenicity; see FIG. 29 from US Publication No. 20140288275, hereby incorporated by reference in its entirety.

Accordingly, in this embodiment of the present invention provides for creating a sufficient change in pI in at least one of the monomers such that heterodimers can be separated from homodimers. As will be appreciated by those in the art, and as discussed further below, this can be done by using a "wild type" heavy chain constant region and a variant region that has been engineered to either increase or decrease its pI (wt A–+B or wt A– –B), or by increasing one region and decreasing the other region (A+–B– or A–B+).

Thus, in general, a component of some embodiments of the present invention are amino acid variants in the constant regions of antibodies that are directed to altering the isoelectric point (pI) of at least one, if not both, of the monomers of a dimeric protein to form "pI heterodimers" (when the protein is an antibody, these are referred to as "pI antibodies") by incorporating amino acid substitutions ("pI variants" or "pI substitutions") into one or both of the monomers. As shown herein, the separation of the heterodimers from the two homodimers can be accomplished if the pIs of the two monomers differ by as little as 0.1 pH unit, with 0.2, 0.3, 0.4 and 0.5 or greater all finding use in the present invention.

As will be appreciated by those in the art, the number of pI variants to be included on each or both monomer(s) to get good separation will depend in part on the starting pI of the scFv and Fab of interest. That is, to determine which monomer to engineer or in which "direction" (e.g. more positive or more negative), the Fv sequences of the two target antigens are calculated and a decision is made from there. As is known in the art, different Fvs will have different starting pIs which are exploited in the present invention. In general, as outlined herein, the pIs are engineered to result in a total pI difference of each monomer of at least about 0.1 logs, with 0.2 to 0.5 being preferred as outlined herein. Furthermore, as will be appreciated by those in the art and outlined herein, in some cases (depending on the format) heterodimers can be separated from homodimers on the basis of size (e.g. Molecular weight). For example, as shown in some embodiments of FIG. 2, some formats result in homodimers and heterodimers with different sizes (e.g. for bottle openers, one homodimer is a "dual scFv" format, one homodimer is a standard antibody, and the heterodimer has one Fab and one scFv).

In the case where pI variants are used to achieve purified heterodimers over homodimers, by using the constant region (s) of the heavy chain(s), a more modular approach to designing and purifying multispecific proteins, including antibodies, is provided. Thus, in some embodiments, heterodimerization variants (including skew and purification heterodimerization variants) are not included in the variable regions, such that each individual antibody must be engineered. In addition, in some embodiments, the possibility of immunogenicity resulting from the pI variants is significantly reduced by importing pI variants from different IgG isotypes such that pI is changed without introducing significant immunogenicity. Thus, an additional problem to be solved is the elucidation of low pI constant domains with high human sequence content, e.g. the minimization or avoidance of non-human residues at any particular position.

A side benefit that can occur with this pI engineering is also the extension of serum half-life and increased FcRn binding. That is, as described in U.S. Ser. No. 13/194,904 (incorporated by reference in its entirety), lowering the pI of antibody constant domains (including those found in antibodies and Fc fusions) can lead to longer serum retention in vivo. These pI variants for increased serum half life also facilitate pI changes for purification.

In addition, it should be noted that the pI variants of the heterodimerization variants give an additional benefit for the analytics and quality control process of bispecific antibodies, as the ability to either eliminate, minimize and distinguish when homodimers are present is significant. Similarly, the ability to reliably test the reproducibility of the heterodimeric protein production is important.

First and second antigens of the invention are herein referred to as antigen-1 and antigen-2 respectively, with one being a costimulatory receptor and one being a checkpoint receptor. One heterodimeric scaffold that finds particular use in the present invention is the "triple f" or "bottle opener" scaffold format. In this embodiment, one heavy chain of the antibody contains an single chain fv ("scfv", as defined below) and the other heavy chain is a "regular" fab format, comprising a variable heavy chain and a light chain. This structure is sometimes referred to herein as "triple f" format (scfv-fab-fc) or the "bottle-opener" format, due to a rough visual similarity to a bottle-opener (see FIG. 2). The two chains are brought together by the use of amino acid variants in the constant regions (e.g. the Fc domain and/or the hinge region) that promote the formation of heterodimeric antibodies as is described more fully below.

There are several distinct advantages to the present "triple F" format. As is known in the art, antibody analogs relying on two scFv constructs often have stability and aggregation problems, which can be alleviated in the present invention by the addition of a "regular" heavy and light chain pairing. In addition, as opposed to formats that rely on two heavy chains and two light chains, there is no issue with the incorrect pairing of heavy and light chains (e.g. heavy 1 pairing with light 2, etc.)

Furthermore, as outlined herein, additional amino acid variants may be introduced into the bispecific antibodies of the invention, to add additional functionalities. For example, amino acid changes within the Fc region can be added (either to one monomer or both) to facilitate increased ADCC or CDC (e.g. altered binding to Fcγ receptors) as well as to increase binding to FcRn and/or increase serum half-life of the resulting molecules. As is further described herein and as will be appreciated by those in the art, any and all of the variants outlined herein can be optionally and independently combined with other variants.

Similarly, another category of functional variants are "Fcγ ablation variants" or "Fc knock out (FcKO or KO) variants. In these embodiments, for some therapeutic applications, it is desirable to reduce or remove the normal binding of the Fc domain to one or more or all of the Fcγ receptors (e.g. FcγR1, FcγRIIa, FcγRIIb, FcγRIIIa, etc.) to avoid additional mechanisms of action. That is, for example, it is generally desirable to ablate FcγRIIIa binding to eliminate or significantly reduce ADCC activity. Suitable ablation variants are shown in FIG. 6.

IV. Definitions

In order that the application may be more completely understood, several definitions are set forth below. Such definitions are meant to encompass grammatical equivalents.

By "ablation" herein is meant a decrease or removal of activity. Thus for example, "ablating FcγR binding" means the Fc region amino acid variant has less than 50% starting binding as compared to an Fc region not containing the specific variant, with less than 70-80-90-95-98% loss of activity being preferred, and in general, with the activity being below the level of detectable binding in a Biacore assay. Of particular use in the ablation of FcγR binding are those shown in FIG. 6.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity. As is discussed herein, many embodiments of the invention ablate ADCC activity entirely.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "antigen binding domain" or "ABD" herein is meant a set of six Complementary Determining Regions (CDRs) that, when present as part of a polypeptide sequence, specifically binds a target antigen as discussed herein. Thus, a "immunomodulatoryantigen binding domain" binds a target immunomodulatoryantigen as outlined herein. As is known in the art, these CDRs are generally present as a first set of variable heavy CDRs (vhCDRs or $V_H$CDRs) and a second set of variable light CDRs (vlCDRs or $V_L$CDR5), each comprising three CDRs: vhCDR1, vhCDR2, vhCDR3 for the heavy chain and vlCDR1, vlCDR2 and vlCDR3 for the light. The CDRs are present in the variable heavy and variable light domains, respectively, and together form an Fv region. Thus, in some cases, the six CDRs of the antigen binding domain are contributed by a variable heavy and variable light chain. In a "Fab" format, the set of 6 CDRs are contributed by two different polypeptide sequences, the variable heavy domain (vh or $V_H$; containing the vhCDR1, vhCDR2 and vhCDR3) and the variable light domain (vl or $V_L$; containing the vlCDR1, vlCDR2 and vlCDR3), with the C-terminus of the vh domain being attached to the N-terminus of the CH1 domain of the heavy chain and the C-terminus of the vl domain being attached to the N-terminus of the constant light domain (and thus forming the light chain). In a scFv format, the vh and vl domains are covalently attached, generally through the use of a linker as outlined herein, into a single polypeptide sequence, which can be either (starting from the N-terminus) vh-linker-vl or vl-linker-vh, with the former being generally preferred (including optional domain linkers on each side, depending on the format used.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in this case an Fc variant, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, −233E or 233E designates an insertion of glutamic acid after position 233 and before position 234. Additionally, −233ADE or A233ADE designates an insertion of AlaAsp-Glu after position 233 and before position 234.

By "amino acid deletion" or "deletion" as used herein is meant the removal of an amino acid sequence at a particular position in a parent polypeptide sequence. For example, E233- or E233#, E233( ) or E233del designates a deletion of glutamic acid at position 233. Additionally, EDA233- or EDA233# designates a deletion of the sequence GluAspAla that begins at position 233.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about seventy amino acid modifications, and preferably from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4, although human sequences with variants can also serve as "parent polypeptides", for example the IgG1/2 hybrid can be included. The protein variant sequence herein will preferably possess at least about 80% identity with a parent protein sequence, and most preferably at least about 90% identity, more preferably at least about 95-98-99% identity. Variant protein can refer to the variant protein itself, compositions comprising the protein variant, or the DNA sequence that encodes it.

Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain. The Fc variants of the present invention are defined according to the amino acid modifications that compose them. Thus, for example, N434S or 434S is an Fc variant with the substitution serine at position 434 relative to the parent Fc polypeptide, wherein the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, 428L/434S is the same Fc variant as M428L/N434S, and so on. For all positions discussed in the present invention that relate to antibodies, unless otherwise noted, amino acid position numbering is according to the EU index. The EU index or EU index as in Kabat or EU numbering scheme refers to the numbering of the EU antibody (Edelman et al., 1969, Proc Natl Acad Sci USA 63:78-85, hereby entirely incorporated by reference.) The modification can be an addition, deletion, or substitution. Substitutions can include naturally occurring amino acids and, in some cases, synthetic amino acids. Examples include U.S. Pat. No. 6,586,207; WO 98/48032; WO 03/073238; US2004-0214988A1; WO 05/35727A2; WO 05/74524A2; J. W. Chin et al., (2002), Journal of the American Chemical Society 124:9026-9027; J. W. Chin, & P. G. Schultz, (2002), ChemBioChem 11:1135-1137; J. W. Chin, et al., (2002), PICAS United States of America 99:11020-11024; and, L. Wang, & P. G. Schultz, (2002), Chem. 1-10, all entirely incorporated by reference.

As used herein, "protein" herein is meant at least two covalently attached amino acids, which includes proteins, polypeptides, oligopeptides and peptides. The peptidyl group may comprise naturally occurring amino acids and peptide bonds, or synthetic peptidomimetic structures, i.e. "analogs", such as peptoids (see Simon et al., PNAS USA 89(20):9367 (1992), entirely incorporated by reference). The amino acids may either be naturally occurring or synthetic (e.g. not an amino acid that is coded for by DNA); as will be appreciated by those in the art. For example, homophenylalanine, citrulline, ornithine and noreleucine are considered synthetic amino acids for the purposes of the invention, and both D- and L-(R or S) configured amino acids may be utilized. The variants of the present invention may comprise modifications that include the use of synthetic amino acids incorporated using, for example, the technologies developed by Schultz and colleagues, including but not limited to methods described by Cropp & Shultz, 2004, Trends Genet. 20(12):625-30, Anderson et al., 2004, Proc Natl Acad Sci USA 101 (2):7566-71, Zhang et al., 2003, 303(5656):371-3, and Chin et al., 2003, Science 301(5635): 964-7, all entirely incorporated by reference. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Asparagine 297 (also referred to as Asn297 or N297) is a residue at position 297 in the human antibody IgG1.

By "Fab" or "Fab region" as used herein is meant the polypeptide that comprises the VH, CHL VL, and CL immunoglobulin domains. Fab may refer to this region in isolation, or this region in the context of a full length antibody, antibody fragment or Fab fusion protein.

By "Fv" or "Fv fragment" or "Fv region" as used herein is meant a polypeptide that comprises the VL and VH domains of a single ABD. As will be appreciated by those in the art, these generally are made up of two chains, or can be combined (generally with a linker as discussed herein) to form an scFv. In some cases, for example in the "central-Fv"

and "DVD-Ig" formats, an "extra" vh and vl domain is added that serves as a scFv but where the vh and vl domains are not linked using a scFv linker between them.

By "single chain Fv" or "scFv" herein is meant a variable heavy domain covalently attached to a variable light domain, generally using a scFv linker as discussed herein, to form a scFv or scFv domain. A scFv domain can be in either orientation from N- to C-terminus (vh-linker-vl or vl-linker-vh).

By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification.

By "non-naturally occurring modification" as used herein is meant an amino acid modification that is not isotypic. For example, because none of the IgGs comprise a serine at position 434, the substitution 434S in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "IgG Fc ligand" as used herein is meant a molecule, preferably a polypeptide, from any organism that binds to the Fc region of an IgG antibody to form an Fc/Fc ligand complex. Fc ligands include but are not limited to FcγRIs, FcγRIIs, FcγRIIIs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. A variety of FcRn variants used to increase binding to the FcRn receptor, and in some cases, to increase serum half-life, are shown in the Figure Legend of FIG. 83.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "Fc" or "Fc region" or "Fc domain" as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat. In some embodiments, as is more fully described below, amino acid modifications are made to the Fc region, for example to alter binding to one or more FcγR receptors or to the FcRn receptor.

By "heavy constant region" herein is meant the CH1-hinge-CH2-CH3 portion of an antibody.

By "Fc fusion protein" or "immunoadhesin" herein is meant a protein comprising an Fc region, generally linked (optionally through a linker moiety, as described herein) to a different protein, such as a binding moiety to a target protein, as described herein. In some cases, one monomer of the heterodimeric antibody comprises an antibody heavy chain (either including an scFv or further including a light chain) and the other monomer is a Fc fusion, comprising a variant Fc domain and a ligand. In some embodiments, these "half antibody-half fusion proteins" are referred to as "Fusionbodies".

By "position" as used herein is meant a location in the sequence of a protein. Positions may be numbered sequentially, or according to an established format, for example the EU index for antibody numbering.

By "target antigen" as used herein is meant the molecule that is bound specifically by the variable region of a given antibody. A target antigen may be a protein, carbohydrate, lipid, or other chemical compound. Suitable target antigens are described below.

By "strandedness" in the context of the monomers of the heterodimeric antibodies of the invention herein is meant that, similar to the two strands of DNA that "match", heterodimerization variants are incorporated into each monomer so as to preserve the ability to "match" to form heterodimers. For example, if some pI variants are engineered into monomer A (e.g. making the pI higher) then steric variants that are "charge pairs" that can be utilized as well do not interfere with the pI variants, e.g. the charge variants that make a pI higher are put on the same "strand" or "monomer" to preserve both functionalities. Similarly, for "skew" variants that come in pairs of a set as more fully outlined below, the skilled artisan will consider pI in deciding into which strand or monomer that incorporates one set of the pair will go, such that pI separation is maximized using the pI of the skews as well.

By "target cell" as used herein is meant a cell that expresses a target antigen.

By "variable region" as used herein is meant the region of an immunoglobulin that comprises one or more Ig domains substantially encoded by any of the V.kappa., V.lamda., and/or VH genes that make up the kappa, lambda, and heavy chain immunoglobulin genetic loci respectively.

By "wild type or WT" herein is meant an amino acid sequence or a nucleotide sequence that is found in nature, including allelic variations. A WT protein has an amino acid sequence or a nucleotide sequence that has not been intentionally modified.

The antibodies of the present invention are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities. "Recombinant" means the antibodies are generated using recombinant nucleic acid techniques in exogeneous host cells.

"Percent (%) amino acid sequence identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. One particular program is the ALIGN-2 program outlined at paragraphs 0279] to [0280] of US Pub. No. 20160244525, hereby incorporated by reference.

The degree of identity between an amino acid sequence of the present invention ("invention sequence") and the parental amino acid sequence is calculated as the number of exact matches in an alignment of the two sequences, divided by the length of the "invention sequence," or the length of the parental sequence, whichever is the shortest. The result is expressed in percent identity.

In some embodiments, two or more amino acid sequences are at least 50%, 60%, 70%, 80%, or 90% identical. In some embodiments, two or more amino acid sequences are at least 95%, 97%, 98%, 99%, or even 100% identical.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10'$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction. Binding affinity is generally measured using a Biacore assay.

V. Antibodies

The present invention relates to the generation of bispecific immunomodulatory antibodies that bind two different immunomodulatory antigens as discussed herein. As is discussed below, the term "antibody" is used generally. Antibodies that find use in the present invention can take on a number of formats as described herein.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to bispecific antibodies that generally are based on the IgG class, which has several subclasses, including, but not limited to IgG1, IgG2, IgG3, and IgG4. In general, IgG1, IgG2 and IgG4 are used more frequently than IgG3. It should be noted that IgG1 has different allotypes with polymorphisms at 356 (D or E) and 358 (L or M). The sequences depicted herein use the 356D/358M allotype, however the other allotype is included herein. That is, any sequence inclusive of an IgG1 Fc domain included herein can have 356E/358L replacing the 356D/358M allotype.

In addition, many of the sequences herein have at least one of the cysteines at position 220 replaced by a serine; generally, this is the on the "scFv monomer" side for most of the sequences depicted herein, although it can also be on the "Fab monomer" side, or both, to reduce disulfide formation. Specifically included within the sequences herein are one or both of these cysteines replaced (C220S).

Thus, "isotype" as used herein is meant any of the subclasses of immunoglobulins defined by the chemical and antigenic characteristics of their constant regions. It should be understood that therapeutic antibodies can also comprise hybrids of isotypes and/or subclasses. For example, as shown in US Publication 2009/0163699, incorporated by reference, the present invention covers pI engineering of IgG1/G2 hybrids.

The amino-terminal portion of each chain includes a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

As will be appreciated by those in the art, the exact numbering and placement of the CDRs can be different among different numbering systems. However, it should be understood that the disclosure of a variable heavy and/or variable light sequence includes the disclosure of the associated (inherent) CDRs. Accordingly, the disclosure of each variable heavy region is a disclosure of the vhCDRs (e.g. vhCDR1, vhCDR2 and vhCDR3) and the disclosure of each variable light region is a disclosure of the vhCDRs (e.g. vlCDR1, vlCDR2 and vlCDR3).

A useful comparison of CDR numbering is as below, see Lafranc et al., Dev. Comp. Immunol. 27(1):55-77 (2003):

Throughout the present specification, the Kabat numbering system is generally used when referring to a residue in the variable domain (approximately, residues 1-107 of the light chain variable region and residues 1-113 of the heavy chain variable region) and the EU numbering system for Fc regions (e.g, Kabat et al., supra (1991)).

The present invention provides a large number of different CDR sets. In this case, a "full CDR set" comprises the three variable light and three variable heavy CDRs, e.g. a vlCDR1, vlCDR2, vlCDR3, vhCDR1, vhCDR2 and vhCDR3. These can be part of a larger variable light or variable heavy domain, respectfully. In addition, as more fully outlined herein, the variable heavy and variable light domains can be on separate polypeptide chains, when a heavy and light chain is used (for example when Fabs are used), or on a single polypeptide chain in the case of scFv sequences.

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning." As outlined below, the invention not only includes the enumerated antigen binding domains and antibodies herein, but those that compete for binding with the epitopes bound by the enumerated antigen binding domains.

The carboxy-terminal portion of each chain defines a constant region primarily responsible for effector function. Kabat et al. collected numerous primary sequences of the

TABLE 1

|  | Kabat + Chothia | IMGT | Kabat | AbM | Chothia | Contact | Xencor |
|---|---|---|---|---|---|---|---|
| vhCDR1 | 26-35 | 27-38 | 31-35 | 26-35 | 26-32 | 30-35 | 27-35 |
| vhCDR2 | 50-65 | 56-65 | 50-65 | 50-58 | 52-56 | 47-58 | 54-61 |
| vhCDR3 | 95-102 | 105-117 | 95-102 | 95-102 | 95-102 | 93-101 | 103-116 |
| vlCDR1 | 24-34 | 27-38 | 24-34 | 24-34 | 24-34 | 30-36 | 27-38 |
| vlCDR2 | 50-56 | 56-65 | 50-56 | 50-56 | 50-56 | 46-55 | 56-62 |
| vlCDR3 | 89-97 | 105-117 | 89-97 | 89-97 | 89-97 | 89-96 | 97-105 | variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al., entirely incorporated by reference).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat. As shown herein and described below, the pI variants can be in one or more of the CH regions, as well as the hinge region, discussed below.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230. As noted herein, pI variants can be made in the hinge region as well.

The light chain generally comprises two domains, the variable light domain (containing the light chain CDRs and together with the variable heavy domains forming the Fv region), and a constant light chain region (often referred to as CL or Cκ).

Another region of interest for additional substitutions, outlined below, is the Fc region.

Thus, the present invention provides different antibody domains. As described herein and known in the art, the heterodimeric antibodies of the invention comprise different domains within the heavy and light chains, which can be overlapping as well. These domains include, but are not limited to, the Fc domain, the CH1 domain, the CH2 domain, the CH3 domain, the hinge domain, the heavy constant domain (CH1-hinge-Fc domain or CH1-hinge-CH2-CH3), the variable heavy domain, the variable light domain, the light constant domain, Fab domains and scFv domains.

Thus, the "Fc domain" includes the —CH2-CH3 domain, and optionally a hinge domain. In the embodiments herein, when a scFv is attached to an Fc domain, it is the C-terminus of the scFv construct that is attached to all or part of the hinge of the Fc domain; for example, it is generally attached to the sequence EPKS which is the beginning of the hinge. The heavy chain comprises a variable heavy domain and a constant domain, which includes a CH1-optional hinge-Fc domain comprising a CH2-CH3. The light chain comprises a variable light chain and the light constant domain. A scFv comprises a variable heavy chain, an scFv linker, and a variable light domain. In most of the constructs and sequences outlined herein, C-terminus of the variable light chain is attached to the N-terminus of the scFv linker, the C-terminus of which is attached to the N-terminus of a variable heavy chain (N-vh-linker-vl-C) although that can be switched (N-vl-linker-vh-C). Some embodiments of the invention comprise at least one scFv domain, which, while not naturally occurring, generally includes a variable heavy domain and a variable light domain, linked together by a scFv linker. As outlined herein, while the scFv domain is generally from N- to C-terminus oriented as vh-scFv linker-vl, this can be reversed for any of the scFv domains (or those constructed using vh and vl sequences from Fabs), to vl-scFv linker-vh, with optional linkers at one or both ends depending on the format (see generally FIG. 2).

As shown herein, there are a number of suitable scFv linkers that can be used, including traditional peptide bonds, generated by recombinant techniques. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used, with from about 5 to about 10 amino acids finding use in some embodiments. Useful linkers include glycine-serine polymers, including for example (GS)n, (GSGGS)n (SEQ ID NO: 30382), (GGGGS)n (SEQ ID NO: 30383), and (GGGS)n (SEQ ID NO: 30384), where n is an integer of at least one (and generally from 3 to 4), glycine-alanine polymers, alanine-serine polymers, and other flexible linkers. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use as linkers.

Other linker sequences may include any sequence of any length of CL/CH1 domain but not all residues of CL/CH1 domain; for example the first 5-12 amino acid residues of the CL/CH1 domains. Linkers can be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ. Linker sequences may also be derived from other proteins such as Ig-like proteins (e.g. TCR, FcR, KIR), hinge region-derived sequences, and other natural sequences from other proteins.

In some embodiments, the linker is a "domain linker", used to link any two domains as outlined herein together. While any suitable linker can be used, many embodiments utilize a glycine-serine polymer, including for example (GS)n, (GSGGS)n (SEQ ID NO: 30382), (GGGGS)n (SEQ ID NO: 30383), and (GGGS)n (SEQ ID NO: 30384), where n is an integer of at least one (and generally from 3 to 4 to 5) as well as any peptide sequence that allows for recombinant attachment of the two domains with sufficient length and flexibility to allow each domain to retain its biological function. In some cases, and with attention being paid to "strandedness", as outlined below, charged domain linkers, as used in some embodiments of scFv linkers can be used.

In some embodiments, the scFv linker is a charged scFv linker, a number of which are shown in FIG. 8. Accordingly, the present invention further provides charged scFv linkers, to facilitate the separation in pI between a first and a second monomer. That is, by incorporating a charged scFv linker, either positive or negative (or both, in the case of scaffolds that use scFvs on different monomers), this allows the monomer comprising the charged linker to alter the pI without making further changes in the Fc domains. These charged linkers can be substituted into any scFv containing standard linkers. Again, as will be appreciated by those in the art, charged scFv linkers are used on the correct "strand" or monomer, according to the desired changes in pI. For example, as discussed herein, to make triple F format heterodimeric antibody, the original pI of the Fv region for each of the desired antigen binding domains are calculated, and one is chosen to make an scFv, and depending on the pI, either positive or negative linkers are chosen.

Charged domain linkers can also be used to increase the pI separation of the monomers of the invention as well, and thus those included in FIG. 8 can be used in any embodiment herein where a linker is utilized.

In one embodiment, the antibody is an antibody fragment, as long as it contains at least one constant domain which can be engineered to produce heterodimers, such as pI engineering. Other antibody fragments that can be used include fragments that contain one or more of the CH1, CH2, CH3, hinge and CL domains of the invention that have been pI engineered. In particular, the formats depicted in FIG. 1 are antibodies, usually referred to as "heterodimeric antibodies", meaning that the protein has at least two associated Fc sequences self-assembled into a heterodimeric Fc domain and at least two Fv regions, whether as Fabs or as scFvs.

A. Chimeric and Humanized Antibodies

In some embodiments, the antibodies herein can be derived from a mixture from different species, e.g. a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference.

In certain embodiments, the antibodies of the invention comprise a heavy chain variable region from a particular germline heavy chain immunoglobulin gene and/or a light chain variable region from a particular germline light chain immunoglobulin gene. For example, such antibodies may comprise or consist of a human antibody comprising heavy or light chain variable regions that are "the product of" or "derived from" a particular germline sequence. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a humanized antibody typically is at least 90% identical in amino acids sequence to an amino acid sequence encoded by a human germline immunoglobulin gene and contains amino acid residues that identify the antibody as being derived from human sequences when compared to the germline immunoglobulin amino acid sequences of other species (e.g., murine germline sequences). In certain cases, a humanized antibody may be at least 95, 96, 97, 98 or 99%, or even at least 96%, 97%, 98%, or 99% identical in amino acid sequence to the amino acid sequence encoded by the germline immunoglobulin gene. Typically, a humanized antibody derived from a particular human germline sequence will display no more than 10-20 amino acid differences from the amino acid sequence encoded by the human germline immunoglobulin gene (prior to the introduction of any skew, pI and ablation variants herein; that is, the number of variants is generally low, prior to the introduction of the variants of the invention). In certain cases, the humanized antibody may display no more than 5, or even no more than 4, 3, 2, or 1 amino acid difference from the amino acid sequence encoded by the germline immunoglobulin gene (again, prior to the introduction of any skew, pI and ablation variants herein; that is, the number of variants is generally low, prior to the introduction of the variants of the invention).

In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J.

Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

VI. Heterodimeric Antibodies

Accordingly, in some embodiments the present invention provides heterodimeric immunomodulatory antibodies that rely on the use of two different heavy chain variant Fc sequences, that will self-assemble to form heterodimeric Fc domains and heterodimeric antibodies.

The present invention is directed to novel constructs to provide heterodimeric antibodies that allow binding to more than one immunomodulatory antigen or ligand, e.g. to allow for bispecific binding. The heterodimeric antibody constructs are based on the self-assembling nature of the two Fc domains of the heavy chains of antibodies, e.g. two "monomers" that assemble into a "dimer". Heterodimeric antibodies are made by altering the amino acid sequence of each monomer as more fully discussed below. Thus, the present invention is generally directed to the creation of heterodimeric immunomodulatory antibodies which can co-engage antigens in several ways, relying on amino acid variants in the constant regions that are different on each chain to promote heterodimeric formation and/or allow for ease of purification of heterodimers over the homodimers.

Thus, the present invention provides bispecific antibodies. An ongoing problem in antibody technologies is the desire for "bispecific" antibodies that bind to two different antigens simultaneously, in general thus allowing the different antigens to be brought into proximity and resulting in new functionalities and new therapies. In general, these antibodies are made by including genes for each heavy and light chain into the host cells. This generally results in the formation of the desired heterodimer (A-B), as well as the two homodimers (A-A and B-B (not including the light chain heterodimeric issues)). However, a major obstacle in the formation of bispecific antibodies is the difficulty in purifying the heterodimeric antibodies away from the homodimeric antibodies and/or biasing the formation of the heterodimer over the formation of the homodimers.

There are a number of mechanisms that can be used to generate the heterodimers of the present invention. In addition, as will be appreciated by those in the art, these mechanisms can be combined to ensure high heterodimerization. Thus, amino acid variants that lead to the production of heterodimers are referred to as "heterodimerization variants". As discussed below, heterodimerization variants can include steric variants (e.g. the "knobs and holes" or "skew" variants described below and the "charge pairs" variants described below) as well as "pI variants", which allows purification of homodimers away from heterodimers. As is generally described in WO2014/145806, hereby incorporated by reference in its entirety and specifically as below for the discussion of "heterodimerization variants", useful mechanisms for heterodimerization include "knobs and holes" ("KIH"; sometimes herein as "skew" variants (see discussion in WO2014/145806), "electrostatic steering" or "charge pairs" as described in WO2014/145806, pI variants as described in WO2014/145806, and general additional Fc variants as outlined in WO2014/145806 and below.

In the present invention, there are several basic mechanisms that can lead to ease of purifying heterodimeric antibodies; one relies on the use of pI variants, such that each monomer has a different pI, thus allowing the isoelectric purification of A-A, A-B and B-B dimeric proteins. Alternatively, some scaffold formats, such as the "triple F" format, also allows separation on the basis of size. As is further outlined below, it is also possible to "skew" the formation of heterodimers over homodimers. Thus, a combination of steric heterodimerization variants and pI or charge pair variants find particular use in the invention.

In general, embodiments of particular use in the present invention rely on sets of variants that include skew variants, that encourage heterodimerization formation over homodimerization formation, coupled with pI variants, which increase the pI difference between the two monomers.

Additionally, as more fully outlined below, depending on the format of the heterodimer antibody, pI variants can be either contained within the constant and/or Fc domains of a monomer, or charged linkers, either domain linkers or scFv linkers, can be used. That is, scaffolds that utilize scFv(s) such as the Triple F format can include charged scFv linkers (either positive or negative), that give a further pI boost for purification purposes. As will be appreciated by those in the art, some Triple F formats are useful with just charged scFv linkers and no additional pI adjustments, although the invention does provide pI variants that are on one or both of the monomers, and/or charged domain linkers as well. In addition, additional amino acid engineering for alternative functionalities may also confer pI changes, such as Fc, FcRn and KO variants.

In the present invention that utilizes pI as a separation mechanism to allow the purification of heterodimeric proteins, amino acid variants can be introduced into one or both of the monomer polypeptides; that is, the pI of one of the monomers (referred to herein for simplicity as "monomer A") can be engineered away from monomer B, or both monomer A and B change be changed, with the pI of monomer A increasing and the pI of monomer B decreasing. As discussed, the pI changes of either or both monomers can be done by removing or adding a charged residue (e.g. a neutral amino acid is replaced by a positively or negatively charged amino acid residue, e.g. glycine to glutamic acid), changing a charged residue from positive or negative to the opposite charge (e.g. aspartic acid to lysine) or changing a charged residue to a neutral residue (e.g. loss of a charge; lysine to serine.). A number of these variants are shown in the Figures.

Accordingly, this embodiment of the present invention provides for creating a sufficient change in pI in at least one of the monomers such that heterodimers can be separated from homodimers. As will be appreciated by those in the art, and as discussed further below, this can be done by using a "wild type" heavy chain constant region and a variant region that has been engineered to either increase or decrease its pI (wt A–+B or wt A––B), or by increasing one region and decreasing the other region (A+–B– or A–B+).

Thus, in general, a component of some embodiments of the present invention are amino acid variants in the constant regions of antibodies that are directed to altering the isoelectric point (pI) of at least one, if not both, of the monomers of a dimeric protein to form "pI antibodies" by incorporating amino acid substitutions ("pI variants" or "pI substitutions") into one or both of the monomers. As shown herein, the separation of the heterodimers from the two homodimers can be accomplished if the pIs of the two monomers differ by as little as 0.1 pH unit, with 0.2, 0.3, 0.4 and 0.5 or greater all finding use in the present invention.

As will be appreciated by those in the art, the number of pI variants to be included on each or both monomer(s) to get good separation will depend in part on the starting pI of the components, for example in the triple F format, the starting pI of the scFv and Fab of interest. That is, to determine which monomer to engineer or in which "direction" (e.g. more positive or more negative), the Fv sequences of the two target antigens are calculated and a decision is made from there. As is known in the art, different Fvs will have different starting pIs which are exploited in the present invention. In general, as outlined herein, the pIs are engineered to result in a total pI difference of each monomer of at least about 0.1 logs, with 0.2 to 0.5 being preferred as outlined herein. Furthermore, as will be appreciated by those in the art and outlined herein, in some embodiments, heterodimers can be separated from homodimers on the basis of size. As shown in FIG. 2, for example, several of the formats allow separation of heterodimers and homodimers on the basis of size.

A. Heterodimerization Variants

The present invention provides heterodimeric proteins, including heterodimeric antibodies in a variety of formats, which utilize heterodimeric variants to allow for heterodimeric formation and/or purification away from homodimers. A number of heterodimerization variants are shown in FIG. 4.

There are a number of suitable pairs of sets of heterodimerization skew variants. These variants come in "pairs" of "sets". That is, one set of the pair is incorporated into the first monomer and the other set of the pair is incorporated into the second monomer. It should be noted that these sets do not necessarily behave as "knobs in holes" variants, with a one-to-one correspondence between a residue on one monomer and a residue on the other; that is, these pairs of sets form an interface between the two monomers that encourages heterodimer formation and discourages homodimer formation, allowing the percentage of heterodimers that spontaneously form under biological conditions to be over 90%, rather than the expected 50% (25% homodimer A/A: 50% heterodimer A/B:25% homodimer B/B).

B. Steric Variants

In some embodiments, the formation of heterodimers can be facilitated by the addition of steric variants. That is, by changing amino acids in each heavy chain, different heavy chains are more likely to associate to form the heterodimeric structure than to form homodimers with the same Fc amino acid sequences. Suitable steric variants are included in in the Figures.

One mechanism is generally referred to in the art as "knobs and holes", referring to amino acid engineering that creates steric influences to favor heterodimeric formation and disfavor homodimeric formation can also optionally be used; this is sometimes referred to as "knobs and holes", as described in U.S. Ser. No. 61/596,846, Ridgway et al., Protein Engineering 9(7):617 (1996); Atwell et al., J. Mol. Biol. 1997 270:26; U.S. Pat. No. 8,216,805, all of which are hereby incorporated by reference in their entirety. The Figures identify a number of "monomer A-monomer B" pairs that rely on "knobs and holes". In addition, as described in Merchant et al., Nature Biotech. 16:677 (1998), these "knobs and hole" mutations can be combined with disulfide bonds to skew formation to heterodimerization.

An additional mechanism that finds use in the generation of heterodimers is sometimes referred to as "electrostatic steering" as described in Gunasekaran et al., J. Biol. Chem. 285(25):19637 (2010), hereby incorporated by reference in its entirety. This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". These include, but are not limited to, D221E/P228E/L368E paired with D221R/P228R/K409R (e.g. these are "monomer corresponding sets) and C220E/P228E/368E paired with C220R/E224R/P228R/K409R.

Additional monomer A and monomer B variants that can be combined with other variants, optionally and independently in any amount, such as pI variants outlined herein or other steric variants that are shown in FIG. 37 of US 2012/0149876, the figure and legend and SEQ ID NOs of which are incorporated expressly by reference herein.

In some embodiments, the steric variants outlined herein can be optionally and independently incorporated with any pI variant (or other variants such as Fc variants, FcRn variants, etc.) into one or both monomers, and can be independently and optionally included or excluded from the proteins of the invention.

A list of suitable skew variants is found in FIG. 4 showing some pairs of particular utility in many embodiments. Of particular use in many embodiments are the pairs of sets including, but not limited to, S364K/E357Q: L368D/K370S; L368D/K370S: S364K; L368E/K370S: S364K; T411T/E360E/Q362E: D401K; L368D/K370S: S364K/E357L, K370S: S364K/E357Q and T366S/L368A/Y407V: T366W (optionally including a bridging disulfide, T366S/L368A/Y407V/Y349C: T366W/S354C). In terms of nomenclature, the pair "S364K/E357Q: L368D/K370S" means that one of the monomers has the double variant set S364K/E357Q and the other has the double variant set L368D/K370S; as above, the "strandedness" of these pairs depends on the starting pI.

C. pI (Isoelectric point) Variants for Heterodimers

In general, as will be appreciated by those in the art, there are two general categories of pI variants: those that increase the pI of the protein (basic changes) and those that decrease the pI of the protein (acidic changes). As described herein, all combinations of these variants can be done: one monomer may be wild type, or a variant that does not display a significantly different pI from wild-type, and the other can be either more basic or more acidic. Alternatively, each monomer is changed, one to more basic and one to more acidic.

Preferred combinations of pI variants are shown in FIG. 5. As outlined herein and shown in the figures, these changes are shown relative to IgG1, but all isotypes can be altered this way, as well as isotype hybrids. In the case where the heavy chain constant domain is from IgG2-4, R133E and R133Q can also be used.

In one embodiment, for example in the bottle opener format, a preferred combination of pI variants has one monomer (the negative Fab side) comprising 208D/295E/384D/418E/421D variants (N208D/Q295E/N384D/Q418E/N421D when relative to human IgG1) and a second monomer (the positive scFv side) comprising a positively charged scFv linker, including (GKPGS)4 (SEQ ID NO: 26209). However, as will be appreciated by those in the art, the first monomer includes a CH1 domain, including position 208. Accordingly, in constructs that do not include a CH1 domain (for example for heterodimeric Fc fusion proteins that do not utilize a CH1 domain on one of the domains, for example in a dual scFv format), a preferred negative pI variant Fc set includes 295E/384D/418E/421D variants (Q295E/N384D/Q418E/N421D when relative to human IgG1).

Accordingly, in some embodiments, one monomer has a set of substitutions from FIG. 5 and the other monomer has a charged linker (either in the form of a charged scFv linker because that monomer comprises an scFv or a charged domain linker, as the format dictates).

1. Isotypic Variants

In addition, many embodiments of the invention rely on the "importation" of pI amino acids at particular positions from one IgG isotype into another, thus reducing or eliminating the possibility of unwanted immunogenicity being introduced into the variants. A number of these are shown in FIG. 21 of US Publ. 2014/0370013, hereby incorporated by reference. That is, IgG1 is a common isotype for therapeutic antibodies for a variety of reasons, including high effector function. However, the heavy constant region of IgG1 has a higher pI than that of IgG2 (8.10 versus 7.31). By introducing IgG2 residues at particular positions into the IgG1 backbone, the pI of the resulting monomer is lowered (or increased) and additionally exhibits longer serum half-life. For example, IgG1 has a glycine (pI 5.97) at position 137, and IgG2 has a glutamic acid (pI 3.22); importing the glutamic acid will affect the pI of the resulting protein. As is described below, a number of amino acid substitutions are generally required to significant affect the pI of the variant antibody. However, it should be noted as discussed below that even changes in IgG2 molecules allow for increased serum half-life.

In other embodiments, non-isotypic amino acid changes are made, either to reduce the overall charge state of the resulting protein (e.g. by changing a higher pI amino acid to a lower pI amino acid), or to allow accommodations in structure for stability, etc. as is more further described below.

In addition, by pI engineering both the heavy and light constant domains, significant changes in each monomer of the heterodimer can be seen. As discussed herein, having the pIs of the two monomers differ by at least 0.5 can allow separation by ion exchange chromatography or isoelectric focusing, or other methods sensitive to isoelectric point.

D. Calculating pI

The pI of each monomer can depend on the pI of the variant heavy chain constant domain and the pI of the total monomer, including the variant heavy chain constant domain and the fusion partner. Thus, in some embodiments, the change in pI is calculated on the basis of the variant heavy chain constant domain, using the chart in the FIG. 19 of US Pub. 2014/0370013. As discussed herein, which monomer to engineer is generally decided by the inherent pI of the Fv and scaffold regions. Alternatively, the pI of each monomer can be compared.

E. pI Variants that also confer better FcRn in vivo binding

In the case where the pI variant decreases the pI of the monomer, they can have the added benefit of improving serum retention in vivo.

Although still under examination, Fc regions are believed to have longer half-lives in vivo, because binding to FcRn at pH 6 in an endosome sequesters the Fc (Ghetie and Ward, 1997 Immunol Today. 18(12): 592-598, entirely incorporated by reference). The endosomal compartment then recycles the Fc to the cell surface. Once the compartment opens to the extracellular space, the higher pH, ~7.4, induces the release of Fc back into the blood. In mice, Dall' Acqua et al. showed that Fc mutants with increased FcRn binding at pH 6 and pH 7.4 actually had reduced serum concentrations and the same half life as wild-type Fc (Dall' Acqua et al. 2002, J. Immunol. 169:5171-5180, entirely incorporated by reference). The increased affinity of Fc for FcRn at pH 7.4 is thought to forbid the release of the Fc back into the blood. Therefore, the Fc mutations that will increase Fc's half-life in vivo will ideally increase FcRn binding at the lower pH while still allowing release of Fc at higher pH. The amino acid histidine changes its charge state in the pH range of 6.0 to 7.4. Therefore, it is not surprising to find His residues at important positions in the Fc/FcRn complex.

Recently it has been suggested that antibodies with variable regions that have lower isoelectric points may also have longer serum half-lives (Igawa et al., 2010 PEDS. 23(5): 385-392, entirely incorporated by reference). However, the mechanism of this is still poorly understood. Moreover, variable regions differ from antibody to antibody. Constant region variants with reduced pI and extended half-life would provide a more modular approach to improving the pharmacokinetic properties of antibodies, as described herein.

F. Additional Fc Variants for Additional Functionality

In addition to pI amino acid variants, there are a number of useful Fc amino acid modification that can be made for a variety of reasons, including, but not limited to, altering binding to one or more FcγR receptors, altered binding to FcRn receptors, etc.

Accordingly, the proteins of the invention can include amino acid modifications, including the heterodimerization variants outlined herein, which includes the pI variants and steric variants. Each set of variants can be independently and optionally included or excluded from any particular heterodimeric protein.

G. FcγR Variants

Accordingly, there are a number of useful Fc substitutions that can be made to alter binding to one or more of the FcγR receptors. Substitutions that result in increased binding as well as decreased binding can be useful. For example, it is known that increased binding to FcγRIIIa results in increased ADCC (antibody dependent cell-mediated cytotoxicity; the cell-mediated reaction wherein nonspecific cytotoxic cells that express FcγRs recognize bound antibody on a target cell and subsequently cause lysis of the target cell). Similarly, decreased binding to FcγRIIb (an inhibitory receptor) can be beneficial as well in some circumstances. Amino acid substitutions that find use in the present invention include those listed in U.S. Ser. No. 11/124,620 (particularly FIG. 41), U.S. Ser. Nos. 11/174,287, 11/396,495, 11/538,406, all of which are expressly incorporated herein by reference in their entirety and specifically for the variants disclosed therein. Particular variants that find use include, but are not limited to, 236A, 239D, 239E, 332E, 332D, 239D/332E, 267D, 267E, 328F, 267E/328F, 236A/332E, 239D/332E/330Y, 239D, 332E/330L, 243A, 243L, 264A, 264V and 299T.

In addition, there are additional Fc substitutions that find use in increased binding to the FcRn receptor and increased serum half life, as specifically disclosed in U.S. Ser. No. 12/341,769, hereby incorporated by reference in its entirety, including, but not limited to, 434S, 434A, 428L, 308F, 259I, 428L/434S, 259I/308F, 436I/428L, 436I or V/434S, 436V/428L and 259I/308F/428L.

H. Ablation Variants

Similarly, another category of functional variants are "FcγR ablation variants" or "Fc knock out (FcKO or KO)" variants. In these embodiments, for some therapeutic applications, it is desirable to reduce or remove the normal binding of the Fc domain to one or more or all of the Fcγ receptors (e.g. FcγR1, FcγRIIa, FcγRIIb, FcγRIIIa, etc.) to avoid additional mechanisms of action. That is, for example, in many embodiments, particularly in the use of bispecific immunomodulatory antibodies desirable to ablate FcγRIIIa binding to eliminate or significantly reduce ADCC activity such that one of the Fc domains comprises one or more Fcγ receptor ablation variants. These ablation variants are depicted in FIG. 6, and each can be independently and optionally included or excluded, with preferred aspects utilizing ablation variants selected from the group consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del. It should be noted that the ablation variants referenced herein ablate FcγR binding but generally not FcRn binding.

I. Combination of Heterodimeric and Fc Variants

As will be appreciated by those in the art, all of the recited heterodimerization variants (including skew and/or pI variants) can be optionally and independently combined in any way, as long as they retain their "strandedness" or "monomer partition". In addition, all of these variants can be combined into any of the heterodimerization formats.

In the case of pI variants, while embodiments finding particular use are shown in the Figures, other combinations can be generated, following the basic rule of altering the pI difference between two monomers to facilitate purification.

In addition, any of the heterodimerization variants, skew and pI, are also independently and optionally combined with Fc ablation variants, Fc variants, FcRn variants, as generally outlined herein.

VII. Useful Formats of the Invention

As will be appreciated by those in the art and discussed more fully below, the bispecific heterodimeric antibodies of the present invention can take on a wide variety of configurations, as are generally depicted in FIG. 2. Some figures depict "single ended" configurations, where there is one type of specificity on one "arm" of the molecule and a different specificity on the other "arm". Other figures depict "dual ended" configurations, where there is at least one type of specificity at the "top" of the molecule and one or more different specificities at the "bottom" of the molecule. Thus, the present invention is directed to novel immunoglobulin compositions that co-engage a different first and a second antigen.

As will be appreciated by those in the art, the heterodimeric formats (see FIG. 2) of the invention can have different valencies as well as be bispecific. That is, antibodies of the invention can be bivalent and bispecific, wherein a checkpoint target is bound by one ABD and the costimulatory target is bound by a second ABD (see for example the bottle opener format which is heterodimeric) or the bispecific mAb which is homodimeric). The heterodimeric antibodies can also be trivalent and bispecific, wherein the first antigen is bound by two ABDs and the second antigen by a second ABD (see for example the Central-scFv format and the trident format). The heterodimeric antibodies can also be bispecific and tetravalent (such as the Central scFv2 format and the DVD-Ig format).

Again, with the exception of the DVD-Ig format and the central-scFv2 format, the antibodies are generally formatted such that the co-stimulatory target is bound monovalently.

A. Bottle Opener Format

One heterodimeric scaffold that finds particular use in the present invention is the "triple F" or "bottle opener" scaffold format. In this embodiment, one heavy chain of the antibody contains a single chain Fv ("scFv", as defined below) and the other heavy chain is a "regular" Fab format, comprising a variable heavy chain and a light chain. This structure is sometimes referred to herein as "triple F" format (scFv-Fab-Fc) or the "bottle-opener" format, due to a rough visual similarity to a bottle-opener. The two chains are brought together by the use of amino acid variants in the constant regions (e.g. the Fc domain, the CH1 domain and/or the hinge region) that promote the formation of heterodimeric antibodies as is described more fully below.

There are several distinct advantages to the present "triple F" format. As is known in the art, antibody analogs relying on two scFv constructs often have stability and aggregation problems, which can be alleviated in the present invention by the addition of a "regular" heavy and light chain pairing. In addition, as opposed to formats that rely on two heavy chains and two light chains, there is no issue with the incorrect pairing of heavy and light chains (e.g. heavy 1 pairing with light 2, etc.).

Many of the embodiments outlined herein rely in general on the bottle opener format that comprises a first monomer comprising an scFv, comprising a variable heavy and a variable light domain, covalently attached using an scFv linker (charged, in many but not all instances), where the scFv is covalently attached to the N-terminus of a first Fc domain usually through a domain linker (which, as outlined herein can either be un-charged or charged and can be exogeneous or endogeneous (e.g. all or part of the native hinge domain). The second monomer of the bottle opener format is a heavy chain, and the composition further comprises a light chain.

In addition, the Fc domains of the bottle opener format generally comprise skew variants (e.g. a set of amino acid substitutions as shown in FIG. 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 6), optionally charged scFv linkers (including those shown in FIG. 8) and the heavy chain comprises pI variants (including those shown in FIG. 5).

In some embodiments, the bottle opener format includes skew variants, pI variants, and ablation variants. Accordingly, some embodiments include bottle opener formats that comprise: a) a first monomer (the "scFv monomer") that comprises a charged scFv linker (with the +H sequence of FIG. 8 being preferred in some embodiments), the skew variants S364K/E357Q, the ablation variants E233P/L234V/L235A/G236del/S267K, and an Fv that binds to one target as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, and a variable heavy domain that, with the variable light domain, makes up an Fv that binds to a second target as outlined herein; and c) a light chain. In this particular embodiment, suitable monomer Fv pairs include (Fabs listed first, scFvs second) ICOS X PD-1, ICOS X PD-L1, ICOS X CTLA-4, ICOS X LAG-3, ICOS X TIM-3, ICOS X BTLA, ICOS X TIGIT, TIGIT X ICOS, PD-1 X ICOS, PD-L1 X ICOS, CTLA-4 X ICOS, LAG-3 X ICOS, TIM-3 X ICOS, BTLA X ICOS, OX40 X TIGIT, OX40 X PD-1, OX40 X PD-L1, OX40 X CTLA-4, OX40 X LAG-3, OX40 X TIM-3, OX40 X BTLA, TIGIT X OX40, PD-1 X OX40, PD-L1 X OX40, CTLA-4 X OX40, LAG-3 X OX40, TIM-3 X OX40, BTLA X OX40, GITR X TIGIT, GITR X PD-1, GITR X PD-L1, GITR X CTLA-4, GITR X LAG-3, GITR X TIM-3, GITR X BTLA, TIGIT x GITR, PD-1 X GITR, PD-L1 X GITR, CTLA-4 X GITR, LAG-3 X GITR, TIM-3 X GITR, BTLA X GITR, 4-1BB X TIGIT, 4-1BB X PD-1, 4-1BB X PD-L1, 4-1BB X CTLA-4, 4-1BB X LAG-3, 4-1BB X TIM-3, 4-1BB X BTLA, TIGIT X 4-1BB, PD-1 X 4-1BB, PD-L1 X 4-1BB, CTLA-4 X 4-1BB, LAG-3 X 4-1BB, TIM-3 X 4-1BB and BTLA X 4-1BB.

Accordingly, some embodiments include bottle opener formats that comprise: a) a first monomer (the "scFv monomer") that comprises a charged scFv linker (with the +H sequence of FIG. 8 being preferred in some embodiments), the skew variants S364K/E357Q, the ablation variants E233P/L234V/L235A/G236del/S267K, and an Fv that binds to one target as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, and a variable heavy domain that, with the variable light domain, makes up an Fv that binds to a second target as outlined herein; and c) a light chain. In some particular embodiments with these variants in this format:

(1) the format comprises a Fab ABD binds to ICOS that has the ABD of [ICOS] H0.66_L0;

(2) the format comprises an ICOS ABD of H0.66_L0 combined with the scFv ABD comprising the ABD 1G6_L1.194_H1.279 that binds to PD-1;

(3) the format comprises an ICOS ABD of H0.66_L0 combined with the scFv comprising the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises a scFv comprising the ABD 1G6_L1.194_H1.279 that binds to PD-1 and the Fab binds to GITR;

(6) the format comprises a scFv comprising the ABD 1G6_L1.194_H1.279 that binds to PD-1 and the Fab binds to OX40;

(7) the format comprises a scFv comprising the ABD 1G6_L1.194_H1.279 that binds to PD-1 and the Fab binds to ICOS;

8) the format comprises a scFv comprising the ABD 1G6_L1.194_H1.279 that binds to PD-1 and the Fab binds to 4-1BB; and (9) the format comprises the ABD of H0.66_L0 that binds to ICOS and an ABD that binds to PD-L1.

In some embodiments, the bottle opener format includes skew variants, pI variants, ablation variants and FcRn variants. Accordingly, some embodiments include bottle opener formats that comprise: a) a first monomer (the "scFv monomer") that comprises a charged scFv linker (with the +H sequence of FIG. 8 being preferred in some embodiments), the skew variants S364K/E357Q, the ablation variants E233P/L234V/L235A/G236del/S267K, the FcRn variants M428L/N434S and an Fv that binds to a first receptor (either a costimulatory or checkpoint receptor) as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with the variable light domain, makes up an Fv that binds to a second receptor as outlined herein (the other of the costimulatory or checkpoint receptor); and c) a light chain. In some particular embodiments with these variants in this format:

(1) the format comprises a Fab ABD binds to ICOS that has the ABD of [ICOS] H0.66_L0;

(2) the format comprises an ICOS ABD of H0.66_L0 combined with the scFv ABD comprising the ABD 1G6_L1.194_H1.279 that binds to PD-1;

(3) the format comprises an ICOS ABD of H0.66_L0 combined with the scFv comprising the ABD H3.23_L0.129 that binds to CTLA-4;

(4) the format comprises an ICOS ABD of H0.66_L0 is combined with the ABD 7G8_H303_L1.34 that binds to LAG-3;

(5) the format comprises a scFv comprising the ABD 1G6_L1.194_H1.279 that binds to PD-1 and the Fab binds to GITR;

(6) the format comprises a scFv comprising the ABD 1G6_L1.194_H1.279 that binds to PD-1 and the Fab binds to OX40;

(7) the format comprises a scFv comprising the ABD 1G6_L1.194_H1.279 that binds to PD-1 and the Fab binds to ICOS;

8) the format comprises a scFv comprising the ABD 1G6_L1.194_H1.279 that binds to PD-1 and the Fab binds to 4-1BB; and (9) the format comprises the ABD of H0.66_L0 that binds to ICOS and an ABD that binds to PD-L1.

Specifically, FIG. 9 shows some bottle opener "backbone" sequences that are missing the Fv sequences that can be used in the present invention. That is, Fv sequences for the scFv portion and the Fab portion can be used from any combination of ICOS and PD-1, ICOS and CTLA-4, ICOS and LAG-3, ICOS and TIM-3, ICOS and PD-L1, ICOS and BTLA, ICOS and TIGIT, GITR and TIGIT, GITR and PD-1, GITR and CTLA-4, GITR and LAG-3, GITR and TIM-3, GITR and PD-L1, GITR and BTLA, OX40 and PD-1, OX40 and TIGIT, OX40 and CTLA-4, IC OX40 OS and LAG-3, OX40 and TIM-3, OX40 and PD-L1, OX40 and BTLA, 4-1BB and PD-1, 4-1BB and CTLA-4, 4-1BB and LAG-3, 4-1BB and TIM-3, 4-1BB and PD-L1, TIGIT and 4-1BB and 4-1BB and BTLA, in combination with any or all of backbones 1 to 10, with backbone 1 of particular use in these combinations.

For bottle opener backbone 1 from FIG. 9 (optionally including the 428L/4345 variants) specific Fv combinations of use in the present invention include ICOS and PD-1, ICOS and PD-L1 and ICOS and CTLA-4.

For bottle opener backbone 1 from FIG. 9 (optionally including the 428L/4345 variants) specific ABDs that bind human ICOS include, but are not limited to, [ICOS]_H0L0 and [ICOS]H0.66_L0 and those shown in FIG. 19, FIG. 20, FIG. 24, FIG. 68 and FIG. 77 as well as SEQ ID NO: 27869-28086, 28087-28269, 27193-27335, 28549-28556 and 28557-28665.

For bottle opener backbone 1 from FIG. 9 (optionally including the 428L/4345 variants), specific ABDs that bind human GITR include, but are not limited to, those in FIG. 18, FIG. 72 and FIG. 73 and those listed in SEQ ID NO:26282-26290.

For bottle opener backbone 1 from FIG. 9 (optionally including the 428L/4345 variants), specific ABDs that bind OX40 include, but are not limited to, FIG. 17, FIG. 72 and FIG. 73 and those listed in SEQ ID NO: 26272-26281.

For bottle opener backbone 1 from FIG. 9 (optionally including the 428L/4345 variants), specific ABDs that bind human 4-1BB include, but are not limited to, FIG. 16, FIG. 72 and FIG. 73 and SEQ ID NO: 26262-2671.

For bottle opener backbone 1 from FIG. 9 (optionally including the 428L/4345 variants), specific ABDs that bind human PD-L1 include, but are not limited to, FIG. 15, FIG. 73 and FIG. 78 and SEQ ID NO: 3961-4432.

Specific bottle opener embodiments are outlined below.

B. mAb-Fv format

One heterodimeric scaffold that finds particular use in the present invention is the mAb-Fv format. In this embodiment, the format relies on the use of a C-terminal attachment of an "extra" variable heavy domain to one monomer and the C-terminal attachment of an "extra" variable light domain to the other monomer, thus forming a third antigen binding domain (i.e. an "extra" Fv domain), wherein the Fab portions of the two monomers bind one checkpoint target and the "extra" Fv domain binds a costimulatory target.

In this embodiment, the first monomer comprises a first heavy chain, comprising a first variable heavy domain and a first constant heavy domain comprising a first Fc domain, with a first variable light domain covalently attached to the C-terminus of the first Fc domain using a domain linker (vh1-CH1-hinge-CH2-CH3-[optional linker]-vl2). The second monomer comprises a second variable heavy domain, a second constant heavy domain comprising a second Fc domain, and a third variable heavy domain covalently attached to the C-terminus of the second Fc domain using a domain linker (vh1-CH1-hinge-CH2-CH3-[optional linker]-vh2). This embodiment further utilizes a common light chain comprising a variable light domain and a constant light domain, which associates with the heavy chains to form two identical Fabs that include two identical Fvs. The two C-terminally attached variable domains make up the "extra" third Fv. As for many of the embodiments herein, these constructs include skew variants, pI variants, ablation variants, additional Fc variants, etc. as desired and described herein. In this embodiment, suitable Fv pairs include (Fabs listed first, "extra" Fv listed second) ICOS X PD-1, ICOS X PD-L1, ICOS X CTLA-4, ICOS X LAG-3, ICOS X TIM-3, ICOS X BTLA, ICOS X TIGIT, TIGIT X ICOS, PD-1 X ICOS, PD-L1 X ICOS, CTLA-4 X ICOS, LAG-3 X ICOS, TIM-3 X ICOS, BTLA X ICOS, OX40 X TIGIT, OX40 X PD-1, OX40 X PD-L1, OX40 X CTLA-4, OX40 X LAG-3, OX40 X TIM-3, OX40 X BTLA, TIGIT X OX40, PD-1 X OX40, PD-L1 X OX40, CTLA-4 X OX40, LAG-3 X OX40, TIM-3 X OX40, BTLA X OX40, GITR X TIGIT, GITR X PD-1, GITR X PD-L1, GITR X CTLA-4, GITR X LAG-3, GITR X TIM-3, GITR X BTLA, TIGIT x GITR, PD-1 X GITR, PD-L1 X GITR, CTLA-4 X GITR, LAG-3 X GITR, TIM-3 X GITR, BTLA X GITR, 4-1BB X TIGIT, 4-1BB X PD-1, 4-1BB X PD-L1, 4-1BB X CTLA-4, 4-1BB X LAG-3, 4-1BB X TIM-3, 4-1BB X BTLA, TIGIT X 4-1BB, PD-1 X 4-1BB, PD-L1 X 4-1BB, CTLA-4 X 4-1BB, LAG-3 X 4-1BB, TIM-3 X 4-1BB and BTLA X 4-1BB.

The ABD sequences for these combinations can be as disclosed in the sequence listing or as shown in the Figures.

In addition, the Fc domains of the mAb-Fv format comprise skew variants (e.g. a set of amino acid substitutions as shown in FIG. 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 6), optionally charged scFv linkers (including those shown in FIG. 8) and the heavy chain comprises pI variants (including those shown in FIG. 5).

In some embodiments, the mAb-Fv format includes skew variants, pI variants, and ablation variants. Accordingly, some embodiments include mAb-Fv formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first receptor (either a costimulatory receptor or a checkpoint receptor) as outlined herein, and a second variable light chain, that together with the second variable heavy chain forms an Fv (ABD) that binds a second receptor (e.g. the other of the costimulatory or checkpoint receptor; and c) a light chain comprising a first variable light domain and a constant light domain. Of particular use in some embodiments in this format, are (Fab-scFv order) ICOS X PD-1, PD-1 X ICOS, PD-L1 X ICOS, ICOS x PD-L1, GITR X PD-1, OX40 X PD-1 and 4-1BB X PD-1. In some particular embodiments with these variants in this format:

(1) the format comprises a Fab ABD binds to ICOS that has the ABD of [ICOS] H0.66_L0;

(2) the format comprises an ICOS ABD of H0.66_L0 combined with the scFv ABD comprising the ABD 1G6_L1.194_H1.279 that binds to PD-1;

(3) the format comprises an ICOS ABD of H0.66_L0 combined with the scFv comprising the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises a scFv comprising the ABD 1G6_L1.194_H1.279 that binds to PD-1 and the Fab binds to GITR;

(6) the format comprises a scFv comprising the ABD 1G6_L1.194_H1.279 that binds to PD-1 and the Fab binds to OX40;

(7) the format comprises a scFv comprising the ABD 1G6_L1.194_H1.279 that binds to PD-1 and the Fab binds to ICOS;

8) the format comprises a scFv comprising the ABD 1G6_L1.194_H1.279 that binds to PD-1 and the Fab binds to 4-1BB; and (9) the format comprises the ABD of H0.66_L0 that binds to ICOS and an ABD that binds to PD-L1.

In some embodiments, the mAb-Fv format includes skew variants, pI variants, ablation variants and FcRn variants. Accordingly, some embodiments include mAb-Fv formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. Of particular use in some embodiments in this format, are (Fab-scFv order) ICOS X PD-1, ICOS x PD-L1, GITR X PD-1, OX40 X PD-1 and 4-1BB X PD-1.

For mAb-Fv sequences that are similar to the mAb-scFv backbone 1 (optionally including M428L/N434S) from FIG. 75, specific ABDs that bind human ICOS are [ICOS]_H0L0 and [ICOS]_H0.66_L0, as well as those shown in FIG. 19, FIG. 20, FIG. 24, FIG. 68 and FIG. 77 as well as SEQ ID NO: 27869-28086, 28087-28269, 27193-27335, 28549-28556 and 28557-28665.

For mAb-Fv sequences that are similar to the mAb-scFv backbone 1 (optionally including M428L/N434S) from FIG. 75, specific ABDs that bind human PD-L1 are shown in FIG. 15, FIG. 73 and FIG. 78 and SEQ ID NO: 3961-4432.

For mAb-Fv sequences that are similar to the mAb-scFv backbone 1 (optionally including M428L/N434S) from FIG. 75, specific ABDs that bind human GITR are those in FIG. 18, FIG. 72 and FIG. 73 and those listed in SEQ ID NO:26282-26290.

For mAb-Fv sequences that are similar to the mAb-scFv backbone 1 (optionally including M428L/N434S) from FIG. 75, specific ABDs that bind human 4-1BB are those in FIG. 16, FIG. 72 and FIG. 73 and SEQ ID NO: 26262-2671.

For mAb-Fv sequences that are similar to the mAb-scFv backbone 1 (optionally including M428L/N434S) from FIG. 75, specific ABDs that bind human OX40 are those in FIG. 17, FIG. 72 and FIG. 73 and those listed in SEQ ID NO: 26272-26281.

For mAb-Fv sequences that are similar to the mAb-scFv backbone 1 (optionally including M428L/N434S) from FIG. 75, specific ABDs that bind human PD-L1 from FIG. 15, FIG. 73 and FIG. 78 and SEQ ID NO: 3961-4432.

C. mAb-scFv

One heterodimeric scaffold that finds particular use in the present invention is the mAb-scFv format. In this embodiment, the format relies on the use of a C-terminal attachment of an scFv to one of the monomers, thus forming a third antigen binding domain, wherein the Fab portions of the two monomers bind one receptor target and the "extra" scFv domain binds the other receptor target (generally the monovalently bound costimulatory receptor).

In this embodiment, the first monomer comprises a first heavy chain (comprising a variable heavy domain and a constant domain), with a C-terminally covalently attached scFv comprising a scFv variable light domain, an scFv linker and a scFv variable heavy domain in either orientation (vh1-CH1-hinge-CH2-CH3-[optional linker]-vh2-scFv linker-vl2 or vh1-CH1-hinge-CH2-CH3-[optional linker]-vl2-scFv linker-vh2). This embodiment further utilizes a common light chain comprising a variable light domain and a constant light domain, which associates with the heavy chains to form two identical Fabs that bind one of the target receptors. As for many of the embodiments herein, these constructs include skew variants, pI variants, ablation variants, additional Fc variants, etc. as desired and described herein. In this embodiment, suitable Fv pairs include (Fabs listed first, scFvs second) ICOS X PD-1, ICOS X PD-L1, ICOS X CTLA-4, ICOS X LAG-3, ICOS X TIM-3, ICOS X BTLA, ICOS X TIGIT, TIGIT X ICOS, PD-1 X ICOS, PD-L1 X ICOS, CTLA-4 X ICOS, LAG-3 X ICOS, TIM-3 X ICOS, BTLA X ICOS, OX40 X TIGIT, OX40 X PD-1, OX40 X PD-L1, OX40 X CTLA-4, OX40 X LAG-3, OX40 X TIM-3, OX40 X BTLA, TIGIT X OX40, PD-1 X OX40, PD-L1 X OX40, CTLA-4 X OX40, LAG-3 X OX40, TIM-3 X OX40, BTLA X OX40, GITR X TIGIT, GITR X PD-1, GITR X PD-L1, GITR X CTLA-4, GITR X LAG-3, GITR X TIM-3, GITR X BTLA, TIGIT x GITR, PD-1 X GITR, PD-L1 X GITR, CTLA-4 X GITR, LAG-3 X GITR, TIM-3 X GITR, BTLA X GITR, 4-1BB X TIGIT, 4-1BB X PD-1, 4-1BB X PD-L1, 4-1BB X CTLA-4, 4-1BB X LAG-3, 4-1BB X TIM-3, 4-1BB X BTLA, TIGIT X 4-1BB, PD-1 X 4-1BB, PD-L1 X 4-1BB, CTLA-4 X 4-1BB, LAG-3 X 4-1BB, TIM-3 X 4-1BB and BTLA X 4-1BB.

The ABD sequences for these combinations can be as disclosed in the sequence listing or as shown in the Figures.

In addition, the Fc domains of the mAb-scFv format generally comprise skew variants (e.g. a set of amino acid substitutions as shown in FIG. 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/ Y349C: T366W/S354C), optionally ablation variants (including those shown in FIG. 6), optionally charged scFv linkers (including those shown in FIG. 8) and the heavy chain comprises pI variants (including those shown in FIG. 5).

In some embodiments, the mAb-scFv format includes skew variants, pI variants, and ablation variants. Accordingly, some embodiments include bottle opener formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first receptor, and a scFv that binds to the second receptor; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first receptor as outlined herein; and c) a light chain comprising a first variable light domain and a constant light domain. In some particular embodiments with these variants in this format:

(1) the format comprises a Fab ABD binds to ICOS that has the ABD of [ICOS] H0.66_L0;

(2) the format comprises an ICOS ABD of H0.66_L0 combined with the scFv ABD comprising the ABD 1G6_L1.194_H1.279 that binds to PD-1;

(3) the format comprises an ICOS ABD of H0.66_L0 combined with the scFv comprising the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises a scFv comprising the ABD 1G6_L1.194_H1.279 that binds to PD-1 and the Fab binds to GITR;

(6) the format comprises a scFv comprising the ABD 1G6_L1.194_H1.279 that binds to PD-1 and the Fab binds to OX40;

(7) the format comprises a scFv comprising the ABD 1G6_L1.194_H1.279 that binds to PD-1 and the Fab binds to ICOS;

8) the format comprises a scFv comprising the ABD 1G6_L1.194_H1.279 that binds to PD-1 and the Fab binds to 4-1BB; and (9) the format comprises the ABD of H0.66_L0 that binds to ICOS and an ABD that binds to PD-L1.

In some embodiments, the mAb-scFv format includes skew variants, pI variants, ablation variants and FcRn variants. Accordingly, some embodiments include mAb-scFv formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first receptor, and a scFv that binds to the second receptor; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first checkpoint inhibitor as outlined herein, and c) a light chain comprising a first variable light domain and a constant light domain.

In mAb-scFv backbone 1 (optionally including M428L/N434S) from FIG. 75, specific ABDs that bind human ICOS are shown in FIG. 19, FIG. 20, FIG. 24, FIG. 68 and FIG. 77 as well as SEQ ID NO: 27869-28086, 28087-28269, 27193-27335, 28549-28556 and 28557-28665.

In mAb-scFv backbone 1 (optionally including M428L/N434S) from FIG. 75, specific ABDs that bind human GITR are those in FIG. 18, FIG. 72 and FIG. 73 and those listed in SEQ ID NO:26282-26290.

In mAb-scFv backbone 1 (optionally including M428L/N434S) from FIG. 75, specific ABDs that bind human 4-1BB include those in FIG. 16, FIG. 72 and FIG. 73 and SEQ ID NO: 26262-2671.

In mAb-scFv backbone 1 (optionally including M428L/N434S) from FIG. 75, specific ABDs that bind human OX-40 FIG. 17, FIG. 72 and FIG. 73 and those listed in SEQ ID NO: 26272-26281.

In mAb-scFv backbone 1 (optionally including M428L/N434S) from FIG. 75, specific ABDs that bind human PD-L1 include FIG. 15, FIG. 73 and FIG. 78 and SEQ ID NO: 3961-4432.

D. Central scFv

One heterodimeric scaffold that finds particular use in the present invention is the Central-scFv format. In this embodiment, the format relies on the use of an inserted scFv domain thus forming a third antigen binding domain, wherein the Fab portions of the two monomers bind one receptor target and the "extra" scFv domain binds another (again, generally the costimulatory receptor is bound monovalently). The scFv domain is inserted between the Fc domain and the CH1-Fv region of one of the monomers, thus providing a third antigen binding domain.

In this embodiment, one monomer comprises a first heavy chain comprising a first variable heavy domain, a CH1 domain (and optional hinge) and Fc domain, with a scFv comprising a scFv variable light domain, an scFv linker and a scFv variable heavy domain. The scFv is covalently attached between the C-terminus of the CH1 domain of the heavy constant domain and the N-terminus of the first Fc domain using optional domain linkers (vh1-CH1-[optional linker]-vh2-scFv linker-vl2-[optional linker including the hinge]-CH2-CH3, or the opposite orientation for the scFv, vh1-CH1-[optional linker]-vl2-scFv linker-vh2-[optional linker including the hinge]-CH2-CH3). In some embodiments, the optional linker is a hinge or fragment thereof. The other monomer is a standard Fab side (e.g. vh1-CH1-hinge-CH2-CH3). This embodiment further utilizes a common light chain comprising a variable light domain and a constant light domain, which associates with the heavy chains to form two identical Fabs that bind a checkpoint inhibitor. As for many of the embodiments herein, these constructs include skew variants, pI variants, ablation variants, additional Fc variants, etc. as desired and described herein. In this embodiment, suitable Fv pairs include (Fabs listed first, scFvs second) ICOS X PD-1, ICOS X PD-L1, ICOS X CTLA-4, ICOS X LAG-3, ICOS X TIM-3, ICOS X BTLA, ICOS X TIGIT, TIGIT X ICOS, PD-1 X ICOS, PD-L1 X ICOS, CTLA-4 X ICOS, LAG-3 X ICOS, TIM-3 X ICOS, BTLA X ICOS, OX40 X TIGIT, OX40 X PD-1, OX40 X PD-L1, OX40 X CTLA-4, OX40 X LAG-3, OX40 X TIM-3, OX40 X BTLA, TIGIT X OX40, PD-1 X OX40, PD-L1 X OX40, CTLA-4 X OX40, LAG-3 X OX40, TIM-3 X OX40, BTLA X OX40, GITR X TIGIT, GITR X PD-1, GITR X PD-L1, GITR X CTLA-4, GITR X LAG-3, GITR X TIM-3, GITR X BTLA, TIGIT x GITR, PD-1 X GITR, PD-L1 X GITR, CTLA-4 X GITR, LAG-3 X GITR, TIM-3 X GITR, BTLA X GITR, 4-1BB X TIGIT, 4-1BB X PD-1, 4-1BB X PD-L1, 4-1BB X CTLA-4, 4-1BB X LAG-3, 4-1BB X TIM-3, 4-1BB X BTLA, TIGIT X 4-1BB, PD-1 X 4-1BB, PD-L1 X 4-1BB, CTLA-4 X 4-1BB, LAG-3 X 4-1BB, TIM-3 X 4-1BB and BTLA X 4-1BB.

The ABD sequences for these combinations can be as disclosed in the sequence listing or as shown in the Figures.

In addition, the Fc domains of the central scFv format generally comprise skew variants (e.g. a set of amino acid substitutions as shown in FIG. 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 6), optionally charged scFv linkers (including those shown in FIG. 8) and the heavy chain comprises pI variants (including those shown in FIG. 5).

In some embodiments, the central scFv format includes skew variants, pI variants, and ablation variants. Accordingly, some embodiments include central scFv formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first receptor; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the second receptor as outlined herein; and c) a light chain comprising a first variable light domain and a constant light domain. In some particular embodiments with these variants in this format:

(1) the format comprises a Fab ABD binds to ICOS that has the ABD of [ICOS] H0.66_L0;

(2) the format comprises an ICOS ABD of H0.66_L0 combined with the scFv ABD comprising the ABD 1G6_L1.194_H1.279 that binds to PD-1;

(3) the format comprises an ICOS ABD of H0.66_L0 combined with the scFv comprising the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises a scFv comprising the ABD 1G6_L1.194_H1.279 that binds to PD-1 and the Fab binds to GITR;

(6) the format comprises a scFv comprising the ABD 1G6_L1.194_H1.279 that binds to PD-1 and the Fab binds to OX40;

(7) the format comprises a scFv comprising the ABD 1G6_L1.194_H1.279 that binds to PD-1 and the Fab binds to ICOS;

8) the format comprises a scFv comprising the ABD 1G6_L1.194_H1.279 that binds to PD-1 and the Fab binds to 4-1BB; and (9) the format comprises the ABD of H0.66_L0 that binds to ICOS and an ABD that binds to PD-L1.

In some embodiments, the central scFv format includes skew variants, pI variants, ablation variants and FcRn variants. Accordingly, some embodiments include central-scFv formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first receptor and an scFv domain that binds to a second receptor; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first checkpoint inhibitor as outlined herein; and c) a light chain comprising a first variable light domain and a constant light domain. In this embodiment, suitable Fv pairs include (Fabs listed first, scFvs second) ICOS X PD-1, PD-1 X ICOS, ICOS X PD-L1, PD-L1 X ICOS, ICOS X CTLA-4 and CTLA-4 X ICOS.

For central-scFv sequences that utilize the central-scFv sequences of FIGS. 55A-55D suitable Fvs that bind ICOS include, but are not limited to, shown in FIG. 19, FIG. 20, FIG. 24, FIG. 68 and FIG. 77 as well as SEQ ID NO: 27869-28086, 28087-28269, 27193-27335, 28549-28556 and 28557-28665.

For central-scFv sequences that utilize the central-scFv sequences of FIGS. 55A-55D suitable Fvs that bind PD-L1 include, but are not limited to, those shown in FIG. 15, FIG. 73 and FIG. 78 and SEQ ID NO: 3961-4432.

For central-scFv sequences that utilize the central-scFv sequences of FIGS. 55A-55D suitable Fvs that bind GITR include, but are not limited to, those in FIG. 18, FIG. 72 and FIG. 73 and those listed in SEQ ID NO:26282-26290.

For central-scFv sequences that utilize the central-scFv sequences of FIGS. 55A-55D suitable Fvs that bind OX40 include, but are not limited to, FIG. 17, FIG. 72 and FIG. 73 and those listed in SEQ ID NO: 26272-26281.

For central-scFv sequences that utilize the central-scFv sequences of FIGS. 55A-55D suitable Fvs that bind 4-1BB include, but are not limited to, FIG. 16, FIG. 72 and FIG. 73 and SEQ ID NO: 26262-2671.

E. Central-scFv2

One heterodimeric scaffold that finds particular use in the present invention is the Central-scFv2 format, which is bispecific and tetravalent. In this embodiment, the format relies on the use of two inserted scFv domains thus forming third and fourth antigen binding domains, wherein the Fab portions of the two monomers bind one receptor target and the "extra" scFv domains bind another. The scFv domain is inserted between the Fc domain and the CH1-Fv region of the monomers.

In this embodiment, both monomers comprise a first heavy chain comprising a first variable heavy domain, a CH1 domain (and optional hinge) and Fc domain, with a scFv comprising a scFv variable light domain, an scFv linker and a scFv variable heavy domain. The scFv is covalently attached between the C-terminus of the CH1 domain of the heavy constant domain and the N-terminus of the first Fc domain using optional domain linkers (vh1-CH1-[optional linker]-vh2-scFv linker-vl2-[optional linker including the hinge]-CH2-CH3, or the opposite orientation for the scFv, vh1-CH1-[optional linker]-vl2-scFv linker-vh2-[optional linker including the hinge]-CH2-CH3). In some embodiments, the optional linker is a hinge or fragment thereof. This embodiment further utilizes a common light chain comprising a variable light domain and a constant light domain, which associates with the heavy chains to form two identical Fabs that bind a receptor. As for many of the embodiments herein, these constructs include skew variants, pI variants, ablation variants, additional Fc variants, etc. as desired and described herein. In this embodiment, suitable Fv pairs include (Fabs listed first, scFvs second) ICOS X PD-1, ICOS X PD-L1, ICOS X CTLA-4, ICOS X LAG-3, ICOS X TIM-3, ICOS X BTLA, ICOS X TIGIT, TIGIT X ICOS, PD-1 X ICOS, PD-L1 X ICOS, CTLA-4 X ICOS, LAG-3 X ICOS, TIM-3 X ICOS, BTLA X ICOS, OX40 X TIGIT, OX40 X PD-1, OX40 X PD-L1, OX40 X CTLA-4, OX40 X LAG-3, OX40 X TIM-3, OX40 X BTLA, TIGIT X OX40, PD-1 X OX40, PD-L1 X OX40, CTLA-4 X OX40, LAG-3 X OX40, TIM-3 X OX40, BTLA X OX40, GITR X TIGIT, GITR X PD-1, GITR X PD-L1, GITR X CTLA-4, GITR X LAG-3, GITR X TIM-3, GITR X BTLA, TIGIT x GITR, PD-1 X GITR, PD-L1 X GITR, CTLA-4 X GITR, LAG-3 X GITR, TIM-3 X GITR, BTLA X GITR, 4-1BB X TIGIT, 4-1BB X PD-1, 4-1BB X PD-L1, 4-1BB X CTLA-4, 4-1BB X LAG-3, 4-1BB X TIM-3, 4-1BB X BTLA, TIGIT X 4-1BB, PD-1 X 4-1BB, PD-L1 X 4-1BB, CTLA-4 X 4-1BB, LAG-3 X 4-1BB, TIM-3 X 4-1BB and BTLA X 4-1BB.

The ABD sequences for these combinations can be as disclosed in the sequence listing or as shown in the Figures.

In addition, the Fc domains of the central scFv2 format generally comprise skew variants (e.g. a set of amino acid substitutions as shown in FIG. 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 6), optionally charged scFv linkers (including those shown in FIG. 8) and the heavy chain comprises pI variants (including those shown in FIG. 5).

In some embodiments, the central scFv2 format includes skew variants, pI variants, and ablation variants. Accordingly, some embodiments include central scFv formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first receptor; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the second receptor as outlined herein; and c) a light chain comprising a first variable light domain and a constant light domain. In some particular embodiments with these variants in this format:

(1) the format comprises a Fab ABD binds to ICOS that has the ABD of [ICOS] H0.66_L0;

(2) the format comprises an ICOS ABD of H0.66_L0 combined with the scFv ABD comprising the ABD 1G6_L1.194_H1.279 that binds to PD-1;

(3) the format comprises an ICOS ABD of H0.66_L0 combined with the scFv comprising the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises a scFv comprising the ABD 1G6_L1.194_H1.279 that binds to PD-1 and the Fab binds to GITR;

(6) the format comprises a scFv comprising the ABD 1G6_L1.194_H1.279 that binds to PD-1 and the Fab binds to OX40;

(7) the format comprises a scFv comprising the ABD 1G6_L1.194_H1.279 that binds to PD-1 and the Fab binds to ICOS;

8) the format comprises a scFv comprising the ABD 1G6_L1.194_H1.279 that binds to PD-1 and the Fab binds to 4-1BB; and (9) the format comprises the ABD of H0.66_L0 that binds to ICOS and an ABD that binds to PD-L1.

In some embodiments, the central scFv2 format includes skew variants, pI variants, ablation variants and FcRn variants. Accordingly, some embodiments include central-scFv formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first receptor and an scFv domain that binds to a second receptor; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first checkpoint inhibitor as outlined herein; and c) a light chain comprising a first variable light domain and a constant light domain. In this embodiment, suitable Fv pairs include (Fabs listed first, scFvs second) ICOS X PD-1, PD-1 X ICOS, ICOS X PD-L1, PD-L1 X ICOS, ICOS X CTLA-4 and CTLA-4 X ICOS.

For central-scFv2 sequences that utilize the central-scFv2 sequences of FIGS. 55A-55D suitable Fvs that bind ICOS include, but are not limited to, shown in FIG. 19, FIG. 20, FIG. 24, FIG. 68 and FIG. 77 as well as SEQ ID NO: 27869-28086, 28087-28269, 27193-27335, 28549-28556 and 28557-28665.

For central-scFv2 sequences that utilize the central-scFv2 sequences of FIGS. 55A-55D suitable Fvs that bind PD-L1 include, but are not limited to, those shown in FIG. 15, FIG. 73 and FIG. 78 and SEQ ID NO: 3961-4432.

For central-scFv2 sequences that utilize the central-scFv sequences of FIGS. 55A-55D suitable Fvs that bind GITR include, but are not limited to, those in FIG. 18, FIG. 72 and FIG. 73 and those listed in SEQ ID NO:26282-26290.

For central-scFv2 sequences that utilize the central-scFv sequences of FIGS. 55A-55D suitable Fvs that bind OX40 include, but are not limited to, FIG. 17, FIG. 72 and FIG. 73 and those listed in SEQ ID NO: 26272-26281.

For central-scFv2 sequences that utilize the central-scFv sequences of FIGS. 55A-55D suitable Fvs that bind 4-1BB include, but are not limited to, FIG. 16, FIG. 72 and FIG. 73 and SEQ ID NO: 26262-2671.

F. One Armed mAb

As noted above, surprisingly and unexpectedly, monovalent costimulatory antibodies comprising a single ABD to the target show efficacy in activating T cells.

Accordingly, in some embodiments, the invention provides monovalent, monospecific antibodies as shown in Figure FIG. 2N that comprise a heterodimeric Fc domain (for stability). In this embodiment, in this embodiment, one monomer comprises just an Fc domain, while the other monomer is a HC (VH1-CH1-hinge-CH2-CH3). This embodiment further utilizes a light chain comprising a variable light domain and a constant light domain, that associates with the heavy chain to form a Fab. As for many of the embodiments herein, these constructs include skew variants, pI variants, ablation variants, additional Fc variants, etc. as desired and described herein. In this embodiment, suitable ABDs bind a costimulatory receptor such as ICOS, GITR, OX40 or 4-1BB.

The ABD sequences for these combinations can be as disclosed in the sequence listing or as shown in the Figures.

In addition, the Fc domains of the comprise skew variants (e.g. a set of amino acid substitutions as shown in FIG. 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 6), and the heavy chain comprises pI variants (including those shown in FIG. 5).

In some embodiments, the one armed scFv-mAb format includes skew variants, pI variants, and ablation variants. Accordingly, some embodiments include formats that comprise: a) a first (Fc) monomer that comprises the skew variants S364K/E357Q, the ablation variants E233P/L234V/L235A/G236del/S267K b) a second monomer that comprises the skew variants L368D/K370S, the pI variants Q295E/N384D/Q418E/N421D, the ablation variants E233P/L234V/L235A/G236del/S267K, and a first variable heavy domain that, with the first variable light domain, makes up the Fv that binds to the costimulatory receptor as outlined herein In this format, specific ABDs that bind human ICOS include, but are not limited to, [ICOS]_H0L0 and [ICOS] H0.66_L0 and those shown in FIG. 19, FIG. 20, FIG. 24, FIG. 68 and FIG. 77 as well as SEQ ID NO: 27869-28086, 28087-28269, 27193-27335, 28549-28556 and 28557-28665.

In this format, specific ABDs that bind human GITR include, but are not limited to, those in FIG. 18, FIG. 72 and FIG. 73 and those listed in SEQ ID NO:26282-26290.

In this format, specific ABDs that bind OX40 include, but are not limited to, FIG. 17, FIG. 72 and FIG. 73 and those listed in SEQ ID NO: 26272-26281.

In this format, specific ABDs that bind human 4-1BB include, but are not limited to, FIG. 16, FIG. 72 and FIG. 73 and SEQ ID NO: 26262-2671.

In this format, specific ABDs that bind human PD-L1 include, but are not limited to, FIG. 15, FIG. 73 and FIG. 78 and SEQ ID NO: 3961-4432.

Specific "one armed mAbs" are shown in the Figures and sequence listing.

G. Bispecific mAb

One heterodimeric scaffold that finds particular use in the present invention is the bispecific mAb format, which is bispecific and tetravalent. In this embodiment, the format relies on the generation of separate homodimeric antibodies which are then recombined. In this format, there is one HC-LC pair (VH1-CH1-hinge-CH2-CH3 and VL1-LC) and a second Hc-LC pair (VH2-CH1-hinge-CH2-CH3 and VL2-LC), e.g. two different heavy chains and two different light chains. Reference is made to Example 5I(d).

In this format, suitable pairs include ICOS and PD-1, ICOS and CTLA-4, ICOS and LAG-3, ICOS and TIM-3, ICOS and PD-L1, ICOS and BTLA, ICOS and TIGIT, GITR and TIGIT, GITR and PD-1, GITR and CTLA-4, GITR and LAG-3, GITR and TIM-3, GITR and PD-L1, GITR and BTLA, OX40 and PD-1, OX40 and TIGIT, OX40 and CTLA-4, IC OX40 OS and LAG-3, OX40 and TIM-3, OX40 and PD-L1, OX40 and BTLA, 4-1BB and PD-1, 4-1BB and CTLA-4, 4-1BB and LAG-3, 4-1BB and TIM-3, 4-1BB and PD-L1, TIGIT and 4-1BB and 4-1BB and BTLA.

In some particular embodiments with these variants in this format:

(1) the format comprises a Fab ABD binds to ICOS that has the ABD of [ICOS] H0.66_L0;

(2) the format comprises an ICOS ABD of H0.66_L0 combined with the ABD comprising the ABD 1G6_L1.194_H1.279 that binds to PD-1;

(3) the format comprises an ICOS ABD of H0.66_L0 combined with the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises a scFv comprising the ABD 1G6_L1.194_H1.279 that binds to PD-1 and the Fab binds to GITR;

(6) the format comprises a scFv comprising the ABD 1G6_L1.194_H1.279 that binds to PD-1 and the Fab binds to OX40;

(7) the format comprises a scFv comprising the ABD 1G6_L1.194_H1.279 that binds to PD-1 and the Fab binds to ICOS;

8) the format comprises a scFv comprising the ABD 1G6_L1.194_H1.279 that binds to PD-1 and the Fab binds to 4-1BB; and (9) the format comprises the ABD of H0.66_L0 that binds to ICOS and an ABD that binds to PD-L1.

In this format, specific ABDs that bind human ICOS include, but are not limited to, [ICOS]_H0L0 and [ICOS] H0.66_L0 and those shown in FIG. 19, FIG. 20, FIG. 24, FIG. 68 and FIG. 77 as well as SEQ ID NO: 27869-28086, 28087-28269, 27193-27335, 28549-28556 and 28557-28665.

In this format, specific ABDs that bind human GITR include, but are not limited to, those in FIG. 18, FIG. 72 and FIG. 73 and those listed in SEQ ID NO:26282-26290.

In this format, specific ABDs that bind OX40 include, but are not limited to, FIG. 17, FIG. 72 and FIG. 73 and those listed in SEQ ID NO: 26272-26281.

In this format, specific ABDs that bind human 4-1BB include, but are not limited to, FIG. 16, FIG. 72 and FIG. 73 and SEQ ID NO: 26262-2671.

In this format, specific ABDs that bind human PD-L1 include, but are not limited to, FIG. 15, FIG. 73 and FIG. 78 and SEQ ID NO: 3961-4432.

H. Central-Fv Format

One heterodimeric scaffold that finds particular use in the present invention is the Central-Fv format shown in FIG. 2. In this embodiment, the format relies on the use of an inserted Fv domain thus forming an "extra" third antigen binding domain, wherein the Fab portions of the two monomers bind one receptor and the "extra" central-Fv domain binds another (generally the costimulatory receptor). The Fv domain is inserted between the Fc domain and the CH1-Fv region of the monomers, thus providing a third antigen binding domain, wherein each monomer contains a component of the Fv (e.g. one monomer comprises a variable heavy domain and the other a variable light domain of the "extra" central Fv domain).

In this embodiment, one monomer comprises a first heavy chain comprising a first variable heavy domain, a CH1 domain, and Fc domain and an additional variable light domain. The additional variable light domain is covalently attached between the C-terminus of the CH1 domain of the heavy constant domain and the N-terminus of the first Fc domain using domain linkers (vh1-CH1-[optional linker]-vl2-hinge-CH2-CH3). The other monomer comprises a first heavy chain comprising a first variable heavy domain, a CH1 domain and Fc domain and an additional variable heavy domain (vh1-CH1-[optional linker]-vh2-hinge-CH2-CH3). The additional variable heavy domain is covalently attached between the C-terminus of the CH1 domain of the heavy constant domain and the N-terminus of the first Fc domain using domain linkers. This embodiment utilizes a common light chain comprising a variable light domain and a constant light domain, that associates with the heavy chains to form two identical Fabs that each bind a receptor. The additional variable heavy domain and additional variable light domain form an "extra" central Fv that binds a second receptor. As for many of the embodiments herein, these constructs include skew variants, pI variants, ablation variants, additional Fc variants, etc. as desired and described herein. In this embodiment, suitable Fv pairs include (Fabs listed first, "extra" central Fv second) ICOS X PD-1, ICOS X PD-L1, ICOS X CTLA-4, ICOS X LAG-3, ICOS X TIM-3, ICOS X BTLA, ICOS X TIGIT, TIGIT X ICOS, PD-1 X ICOS, PD-L1 X ICOS, CTLA-4 X ICOS, LAG-3 X ICOS, TIM-3 X ICOS, BTLA X ICOS, OX40 X TIGIT, OX40 X PD-1, OX40 X PD-L1, OX40 X CTLA-4, OX40 X LAG-3, OX40 X TIM-3, OX40 X BTLA, TIGIT X OX40, PD-1 X OX40, PD-L1 X OX40, CTLA-4 X OX40, LAG-3 X OX40, TIM-3 X OX40, BTLA X OX40, GITR X TIGIT, GITR X PD-1, GITR X PD-L1, GITR X CTLA-4, GITR X LAG-3, GITR X TIM-3, GITR X BTLA, TIGIT x GITR, PD-1 X GITR, PD-L1 X GITR, CTLA-4 X GITR, LAG-3 X GITR, TIM-3 X GITR, BTLA X GITR, 4-1BB X TIGIT, 4-1BB X PD-1, 4-1BB X PD-L1, 4-1BB X CTLA-4, 4-1BB X LAG-3, 4-1BB X TIM-3, 4-1BB X BTLA, TIGIT X 4-1BB, PD-1 X 4-1BB, PD-L1 X 4-1BB, CTLA-4 X 4-1BB, LAG-3 X 4-1BB, TIM-3 X 4-1BB and BTLA X 4-1BB.

The ABD sequences for these combinations can be as disclosed in the sequence listing or as shown in the Figures.

In addition, the Fc domains of the central-Fv format generally comprise skew variants (e.g. a set of amino acid substitutions as shown in FIG. 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 6), optionally charged scFv linkers (including those shown in FIG. 8) and the heavy chain comprises pI variants (including those shown in FIG. 5).

In some embodiments, the central-Fv format includes skew variants, pI variants, and ablation variants. Accordingly, some embodiments include central scFv formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first receptor; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the second receptor as outlined herein; and c) a light chain comprising a first variable light domain and a constant light domain. In some particular embodiments with these variants in this format:

(1) the format comprises a Fab ABD binds to ICOS that has the ABD of [ICOS] H0.66_L0;

(2) the format comprises an ICOS ABD of H0.66_L0 combined with the scFv ABD comprising the ABD 1G6_L1.194_H1.279 that binds to PD-1;

(3) the format comprises an ICOS ABD of H0.66_L0 combined with the scFv comprising the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises a scFv comprising the ABD 1G6_L1.194_H1.279 that binds to PD-1 and the Fab binds to GITR;

(6) the format comprises a scFv comprising the ABD 1G6_L1.194_H1.279 that binds to PD-1 and the Fab binds to OX40;

(7) the format comprises a scFv comprising the ABD 1G6_L1.194_H1.279 that binds to PD-1 and the Fab binds to ICOS;

8) the format comprises a scFv comprising the ABD 1G6_L1.194_H1.279 that binds to PD-1 and the Fab binds to 4-1BB; and (9) the format comprises the ABD of H0.66_L0 that binds to ICOS and an ABD that binds to PD-L1.

In some embodiments, the central-Fv format includes skew variants, pI variants, ablation variants and FcRn variants. Accordingly, some embodiments include central-scFv formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first receptor and an scFv domain that binds to a second receptor; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first checkpoint inhibitor as outlined herein; and c) a light chain comprising a first variable light domain and a constant light domain. In this embodiment, suitable Fv pairs include (Fabs listed first, scFvs second) ICOS X PD-1, PD-1 X ICOS, ICOS X PD-L1, PD-L1 X ICOS, ICOS X CTLA-4 and CTLA-4 X ICOS.

For central-Fv formats suitable Fvs that bind ICOS include, but are not limited to, shown in FIG. 19, FIG. 20, FIG. 24, FIG. 68 and FIG. 77 as well as SEQ ID NO: 27869-28086, 28087-28269, 27193-27335, 28549-28556 and 28557-28665.

For central-Fv formats suitable Fvs that bind PD-L1 include, but are not limited to, those shown in FIG. 15, FIG. 73 and FIG. 78 and SEQ ID NO: 3961-4432.

For central-Fv formats suitable Fvs that bind GITR include, but are not limited to, those in FIG. 18, FIG. 72 and FIG. 73 and those listed in SEQ ID NO:26282-26290.

For central-Fv formats suitable Fvs that bind OX40 include, but are not limited to, FIG. 17, FIG. 72 and FIG. 73 and those listed in SEQ ID NO: 26272-26281.

For central-Fv formats suitable Fvs that bind 4-1BB include, but are not limited to, FIG. 16, FIG. 72 and FIG. 73 and SEQ ID NO: 26262-2671.

For central-FV formats suitable Fvs that bind PD-L1 include, but are not limited to, those of FIG. 15, FIG. 73 and FIG. 78 and SEQ ID NO: 3961-4432.

I. One Armed Central-scFv

One heterodimeric scaffold that finds particular use in the present invention is the one armed central-scFv format shown in FIG. 1C. In this embodiment, one monomer comprises just an Fc domain, while the other monomer includes a Fab domain (a first antigen binding domain), a scFv domain (a second antigen binding domain) and an Fc domain, where the scFv domain is inserted between the Fc domain and the Fc domain. In this format, the Fab portion binds one receptor target and the scFv binds another.

In this embodiment, one monomer comprises a first heavy chain comprising a first variable heavy domain, a CH1 domain and Fc domain, with a scFv comprising a scFv variable light domain, an scFv linker and a scFv variable heavy domain. The scFv is covalently attached between the C-terminus of the CH1 domain of the heavy constant domain and the N-terminus of the first Fc domain using domain linkers, in either orientation, VH1-CH1-[optional domain linker]-VH2-scFv linker-VL2-[optional domain linker]-CH2-CH3 or VH1-CH1-[optional domain linker]-VL2-scFv linker-VH2-[optional domain linker]-CH2-CH3. The second monomer comprises an Fc domain (CH2-CH3). This embodiment further utilizes a light chain comprising a variable light domain and a constant light domain, that associates with the heavy chain to form a Fab. As for many of the embodiments herein, these constructs include skew variants, pI variants, ablation variants, additional Fc variants, etc. as desired and described herein. In this embodiment, suitable Fv pairs include (Fabs listed first, scFvs second) ICOS X PD-1, ICOS X PD-L1, ICOS X CTLA-4, ICOS X LAG-3, ICOS X TIM-3, ICOS X BTLA, ICOS X TIGIT, TIGIT X ICOS, PD-1 X ICOS, PD-L1 X ICOS, CTLA-4 X ICOS, LAG-3 X ICOS, TIM-3 X ICOS, BTLA X ICOS, OX40 X TIGIT, OX40 X PD-1, OX40 X PD-L1, OX40 X CTLA-4, OX40 X LAG-3, OX40 X TIM-3, OX40 X BTLA, TIGIT X OX40, PD-1 X OX40, PD-L1 X OX40, CTLA-4 X OX40, LAG-3 X OX40, TIM-3 X OX40, BTLA X OX40, GITR X TIGIT, GITR X PD-1, GITR X PD-L1, GITR X CTLA-4, GITR X LAG-3, GITR X TIM-3, GITR X BTLA, TIGIT x GITR, PD-1 X GITR, PD-L1 X GITR, CTLA-4 X GITR, LAG-3 X GITR, TIM-3 X GITR, BTLA X GITR, 4-1BB X TIGIT, 4-1BB X PD-1, 4-1BB X PD-L1, 4-1BB X CTLA-4, 4-1BB X LAG-3, 4-1BB X TIM-3, 4-1BB X BTLA, TIGIT X 4-1BB, PD-1 X 4-1BB, PD-L1 X 4-1BB, CTLA-4 X 4-1BB, LAG-3 X 4-1BB, TIM-3 X 4-1BB and BTLA X 4-1BB.

The ABD sequences for these combinations can be as disclosed in the sequence listing or as shown in the Figure.

In addition, the Fc domains of the one armed central-scFv format generally comprise skew variants (e.g. a set of amino acid substitutions as shown in FIG. 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 6), optionally charged scFv linkers (including those shown in FIG. 8) and the heavy chain comprises pI variants (including those shown in FIG. 5).

In some embodiments, the one armed central-scFv format includes skew variants, pI variants, and ablation variants. Accordingly, some embodiments include formats that comprise: a) a first monomer that comprises the skew variants S364K/E357Q, the ablation variants E233P/L234V/L235A/G236del/S267K, and a variable heavy domain that, with the variable light domain of the light chain, makes up an Fv that binds to a first receptor, and a scFv that binds to the other receptor; b) a second monomer that comprises the skew variants L368D/K370S, the pI variants Q295E/N384D/Q418E/N421D, the ablation variants E233P/L234V/L235A/G236del/S267K, and c) a light chain comprising a first variable light domain and a constant light domain. In some particular embodiments with these variants in this format:

(1) the format comprises a Fab ABD binds to ICOS that has the ABD of [ICOS] H0.66_L0;

(2) the format comprises an ICOS ABD of H0.66_L0 combined with the scFv ABD comprising the ABD 1G6_L1.194_H1.279 that binds to PD-1;

(3) the format comprises an ICOS ABD of H0.66_L0 combined with the scFv comprising the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises a scFv comprising the ABD 1G6_L1.194_H1.279 that binds to PD-1 and the Fab binds to GITR;

(6) the format comprises a scFv comprising the ABD 1G6_L1.194_H1.279 that binds to PD-1 and the Fab binds to OX40;

(7) the format comprises a scFv comprising the ABD 1G6_L1.194_H1.279 that binds to PD-1 and the Fab binds to ICOS;

8) the format comprises a scFv comprising the ABD 1G6_L1.194_H1.279 that binds to PD-1 and the Fab binds to 4-1BB; and (9) the format comprises the ABD of H0.66_L0 that binds to ICOS and an ABD that binds to PD-L1.

In some embodiments, the one armed central-scFv format includes skew variants, pI variants, ablation variants and FcRn variants. Accordingly, some embodiments include formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first receptor and a scFv domain that binds to a second receptor; b) a second monomer that comprises the skew variants L368D/K370S, the pI variants Q295E/N384D/Q418E/N421D, the ablation variants E233P/L234V/L235A/G236del/S267K, the FcRn variants M428L/N434S. and c) a light chain comprising a first variable light domain and a constant light domain.

In this format, specific ABDs that bind human ICOS include, but are not limited to, [ICOS]_H0L0 and [ICOS] H0.66_L0 and those shown in FIG. 19, FIG. 20, FIG. 24, FIG. 68 and FIG. 77 as well as SEQ ID NO: 27869-28086, 28087-28269, 27193-27335, 28549-28556 and 28557-28665.

In this format, specific ABDs that bind human GITR include, but are not limited to, those in FIG. 18, FIG. 72 and FIG. 73 and those listed in SEQ ID NO:26282-26290.

In this format, specific ABDs that bind OX40 include, but are not limited to, FIG. 17, FIG. 72 and FIG. 73 and those listed in SEQ ID NO: 26272-26281.

In this format, specific ABDs that bind human 4-1BB include, but are not limited to, FIG. 16, FIG. 72 and FIG. 73 and SEQ ID NO: 26262-2671.

In this format, specific ABDs that bind human PD-L1 include, but are not limited to, FIG. 15, FIG. 73 and FIG. 78 and SEQ ID NO: 3961-4432.

J. One Armed scFv-mAb

One heterodimeric scaffold that finds particular use in the present invention is the one armed scFv-mAb format shown in FIG. 2D. In this embodiment, one monomer comprises just an Fc domain, while the other monomer uses a scFv domain attached at the N-terminus of the heavy chain, generally through the use of a linker: vh1-scFv linker-vl1-[optional domain linker]-VH2-CH1-hinge-CH2-CH3 or (in the opposite orientation) vl1-scFv linker-vh1-[optional domain linker]-VH2-CH1-hinge-CH2-CH3. In this format, either the Fab portion binds one receptor target and the scFv binds another. This embodiment further utilizes a light chain comprising a variable light domain and a constant light domain, that associates with the heavy chain to form a Fab. As for many of the embodiments herein, these constructs include skew variants, pI variants, ablation variants, additional Fc variants, etc. as desired and described herein. In this embodiment, suitable Fv pairs include (Fabs listed first, scFvs second) ICOS X PD-1, ICOS X PD-L1, ICOS X CTLA-4, ICOS X LAG-3, ICOS X TIM-3, ICOS X BTLA, ICOS X TIGIT, TIGIT X ICOS, PD-1 X ICOS, PD-L1 X ICOS, CTLA-4 X ICOS, LAG-3 X ICOS, TIM-3 X ICOS, BTLA X ICOS, OX40 X TIGIT, OX40 X PD-1, OX40 X PD-L1, OX40 X CTLA-4, OX40 X LAG-3, OX40 X TIM-3, OX40 X BTLA, TIGIT X OX40, PD-1 X OX40, PD-L1 X OX40, CTLA-4 X OX40, LAG-3 X OX40, TIM-3 X OX40, BTLA X OX40, GITR X TIGIT, GITR X PD-1, GITR X PD-L1, GITR X CTLA-4, GITR X LAG-3, GITR X TIM-3, GITR X BTLA, TIGIT x GITR, PD-1 X GITR, PD-L1 X GITR, CTLA-4 X GITR, LAG-3 X GITR, TIM-3 X GITR, BTLA X GITR, 4-1BB X TIGIT, 4-1BB X PD-1, 4-1BB X PD-L1, 4-1BB X CTLA-4, 4-1BB X LAG-3, 4-1BB X TIM-3, 4-1BB X BTLA, TIGIT X 4-1BB, PD-1 X 4-1BB, PD-L1 X 4-1BB, CTLA-4 X 4-1BB, LAG-3 X 4-1BB, TIM-3 X 4-1BB and BTLA X 4-1BB.

The ABD sequences for these combinations can be as disclosed in the sequence listing or as shown in the Figures.

In addition, the Fc domains of the comprise skew variants (e.g. a set of amino acid substitutions as shown in FIG. 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 6), optionally charged scFv linkers (including those shown in FIG. 8) and the heavy chain comprises pI variants (including those shown in FIG. 5).

In some embodiments, the one armed scFv-mAb format includes skew variants, pI variants, and ablation variants. Accordingly, some embodiments include formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. In some particular embodiments with these variants in this format:

(1) the format comprises a Fab ABD binds to ICOS that has the ABD of [ICOS] H0.66_L0;

(2) the format comprises an ICOS ABD of H0.66_L0 combined with the scFv ABD comprising the ABD 1G6_L1.194_H1.279 that binds to PD-1;

(3) the format comprises an ICOS ABD of H0.66_L0 combined with the scFv comprising the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises a scFv comprising the ABD 1G6_L1.194_H1.279 that binds to PD-1 and the Fab binds to GITR;

(6) the format comprises a scFv comprising the ABD 1G6_L1.194_H1.279 that binds to PD-1 and the Fab binds to OX40;

(7) the format comprises a scFv comprising the ABD 1G6_L1.194_H1.279 that binds to PD-1 and the Fab binds to ICOS;

8) the format comprises a scFv comprising the ABD 1G6_L1.194_H1.279 that binds to PD-1 and the Fab binds to 4-1BB; and (9) the format comprises the ABD of H0.66_L0 that binds to ICOS and an ABD that binds to PD-L1.

In some embodiments, the one armed scFv-mAb format includes skew variants, pI variants, ablation variants and FcRn variants. Accordingly, some embodiments include bottle opener formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain.

In this format, specific ABDs that bind human ICOS include, but are not limited to, [ICOS]_H0L0 and [ICOS] H0.66_L0 and those shown in FIG. 19, FIG. 20, FIG. 24, FIG. 68 and FIG. 77 as well as SEQ ID NO: 27869-28086, 28087-28269, 27193-27335, 28549-28556 and 28557-28665.

In this format, specific ABDs that bind human GITR include, but are not limited to, those in FIG. 18, FIG. 72 and FIG. 73 and those listed in SEQ ID NO:26282-26290.

In this format, specific ABDs that bind OX40 include, but are not limited to, FIG. 17, FIG. 72 and FIG. 73 and those listed in SEQ ID NO: 26272-26281.

In this format, specific ABDs that bind human 4-1BB include, but are not limited to, FIG. 16, FIG. 72 and FIG. 73 and SEQ ID NO: 26262-2671.

In this format, specific ABDs that bind human PD-L1 include, but are not limited to, FIG. 15, FIG. 73 and FIG. 78 and SEQ ID NO: 3961-4432.

K. scFv-mAb Format

One heterodimeric scaffold that finds particular use in the present invention is the mAb-scFv format shown in FIG. 2E. In this embodiment, the format relies on the use of a N-terminal attachment of a scFv to one of the monomers, thus forming a third antigen binding domain, wherein the Fab portions of the two monomers each bind one target and the "extra" scFv domain binds a different target.

In this embodiment, the first monomer comprises a first heavy chain (comprising a variable heavy domain and a constant domain), with a N-terminally covalently attached scFv comprising a scFv variable light domain, an scFv linker and a scFv variable heavy domain in either orientation ((vh1-scFv linker-vl1-[optional domain linker]-vh2-CH1-hinge-CH2-CH3) or (with the scFv in the opposite orientation) ((vl1-scFv linker-vh1-[optional domain linker]-vh2-CH1-hinge-CH2-CH3)). The second monomer comprises a heavy chain VH2OCH1-hinge-CH2-CH3. This embodiment further utilizes a common light chain comprising a variable light domain and a constant light domain, that associates with the heavy chains to form two identical Fabs that bind one of the target antigens. As for many of the embodiments herein, these constructs include skew variants, pI variants, ablation variants, additional Fc variants, etc. as desired and described herein. In this embodiment, suitable Fv pairs include (Fabs listed first, scFvs second) ICOS X PD-1, ICOS X PD-L1, ICOS X CTLA-4, ICOS X LAG-3, ICOS X TIM-3, ICOS X BTLA, ICOS X TIGIT, TIGIT X ICOS, PD-1 X ICOS, PD-L1 X ICOS, CTLA-4 X ICOS, LAG-3 X ICOS, TIM-3 X ICOS, BTLA X ICOS, OX40 X TIGIT, OX40 X PD-1, OX40 X PD-L1, OX40 X CTLA-4, OX40 X LAG-3, OX40 X TIM-3, OX40 X BTLA, TIGIT X OX40, PD-1 X OX40, PD-L1 X OX40, CTLA-4 X OX40, LAG-3 X OX40, TIM-3 X OX40, BTLA X OX40, GITR X TIGIT, GITR X PD-1, GITR X PD-L1, GITR X CTLA-4, GITR X LAG-3, GITR X TIM-3, GITR X BTLA, TIGIT x GITR, PD-1 X GITR, PD-L1 X GITR, CTLA-4 X GITR, LAG-3 X GITR, TIM-3 X GITR, BTLA X GITR, 4-1BB X TIGIT, 4-1BB X PD-1, 4-1BB X PD-L1, 4-1BB X CTLA-4, 4-1BB X LAG-3, 4-1BB X TIM-3, 4-1BB X BTLA, TIGIT X 4-1BB, PD-1 X 4-1BB, PD-L1 X 4-1BB, CTLA-4 X 4-1BB, LAG-3 X 4-1BB, TIM-3 X 4-1BB and BTLA X 4-1BB.

The ABD sequences for these combinations can be as disclosed in the sequence listing or in the Figures.

In addition, the Fc domains of the scFv-mAb format comprise skew variants (e.g. a set of amino acid substitutions as shown in FIG. 4, with particularly useful skew variants being selected from the group consisting of S364K/ E357Q: L368D/K370S; L368D/K370S: S364K; L368E/ K370S: S364K; T411T/E360E/Q362E: D401K; L368D/ K370S: S364K/E357L, K370S: S364K/E357Q, T366S/ L368A/Y407V: T366W and T366S/L368A/Y407V/Y349C: T366W/S354C), optionally ablation variants (including those shown in FIG. 6), optionally charged scFv linkers (including those shown in FIG. 8) and the heavy chain comprises pI variants (including those shown in FIG. 5).

In some embodiments, the mAb-scFv format includes skew variants, pI variants, and ablation variants. Accordingly, some embodiments include bottle opener formats that comprise: a) a first monomer that comprises the skew variants S364K/E357Q, the ablation variants E233P/L234V/ L235A/G236del/S267K, and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain. In some particular embodiments with these variants in this format:

(1) the format comprises a Fab ABD binds to ICOS that has the ABD of [ICOS] H0.66_L0;

(2) the format comprises an ICOS ABD of H0.66_L0 combined with the scFv ABD comprising the ABD 1G6_L1.194_H1.279 that binds to PD-1;

(3) the format comprises an ICOS ABD of H0.66_L0 combined with the scFv comprising the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises a scFv comprising the ABD 1G6_L1.194_H1.279 that binds to PD-1 and the Fab binds to GITR;

(6) the format comprises a scFv comprising the ABD 1G6_L1.194_H1.279 that binds to PD-1 and the Fab binds to OX40;

(7) the format comprises a scFv comprising the ABD 1G6_L1.194_H1.279 that binds to PD-1 and the Fab binds to ICOS;

8) the format comprises a scFv comprising the ABD 1G6_L1.194_H1.279 that binds to PD-1 and the Fab binds to 4-1BB; and (9) the format comprises the ABD of H0.66_L0 that binds to ICOS and an ABD that binds to PD-L1.

In some embodiments, the mAb-scFv format includes skew variants, pI variants, ablation variants and FcRn variants. Accordingly, some embodiments include bottle opener formats that comprise: a) a first monomer that comprises the skew variants S364K/E357Q, the ablation variants E233P/ L234V/L235A/G236del/S267K, the FcRn variants M428L/ N434S and a first variable heavy domain that, with the first variable light domain of the light chain, makes up an Fv that binds to a first checkpoint inhibitor, and a second variable heavy domain; b) a second monomer that comprises the skew variants L368D/K370S, the pI variants N208D/ Q295E/N384D/Q418E/N421D, the ablation variants E233P/ L234V/L235A/G236del/S267K, the FcRn variants M428L/ N434S and a first variable heavy domain that, with the first variable light domain, makes up the Fv that binds to the first checkpoint inhibitor as outlined herein, and a second variable light chain, that together with the second variable heavy chain forms an Fv (ABD) that binds a second checkpoint inhibitors; and c) a light chain comprising a first variable light domain and a constant light domain.

In this format, specific ABDs that bind human ICOS include, but are not limited to, [ICOS]_H0L0 and [ICOS] H0.66_L0 and those shown in FIG. 19, FIG. 20, FIG. 24, FIG. 68 and FIG. 77 as well as SEQ ID NO: 27869-28086, 28087-28269, 27193-27335, 28549-28556 and 28557-28665.

In this format, specific ABDs that bind human GITR include, but are not limited to, those in FIG. 18, FIG. 72 and FIG. 73 and those listed in SEQ ID NO:26282-26290.

In this format, specific ABDs that bind OX40 include, but are not limited to, FIG. 17, FIG. 72 and FIG. 73 and those listed in SEQ ID NO: 26272-26281.

In this format, specific ABDs that bind human 4-1BB include, but are not limited to, FIG. 16, FIG. 72 and FIG. 73 and SEQ ID NO: 26262-2671.

In this format, specific ABDs that bind human PD-L1 include, but are not limited to, FIG. 15, FIG. 73 and FIG. 78 and SEQ ID NO: 3961-4432.

L. Dual scFv Formats

The present invention also provides dual scFv formats as are known in the art and shown in FIG. 2B. In this embodiment, the heterodimeric bispecific antibody is made up of two scFv-Fc monomers (both in either (vh-scFv linker-vl-[optional domain linker]-CH2-CH3) format or (vl-scFv linker-vh-[optional domain linker]-CH2-CH3) format, or with one monomer in one orientation and the other in the other orientation.

In this case, all ABDs are in the scFv format, with any combination of ICOS and PD-1, ICOS and CTLA-4, ICOS and LAG-3, ICOS and TIM-3, ICOS and PD-L1, ICOS and BTLA, GITR and PD-1, GITR and CTLA-4, GITR and LAG-3, GITR and TIM-3, GITR and PD-L1, GITR and BTLA, OX40 and PD-1, OX40 and CTLA-4, OX40 and LAG-3, OX40 and TIM-3, OX40 and PD-L1, OX40 and BTLA, 4-1BB and PD-1, 4-1BB and CTLA-4, 4-1BB and LAG-3, 4-1BB and TIM-3, 4-1BB and PD-L1 and 4-1BB and BTLA being useful. The ABD sequences for these combinations can be as disclosed in the sequence listing or as shown in the Figures.

In addition, the Fc domains of the dual scFv format comprise skew variants (e.g. a set of amino acid substitutions as shown in FIG. 4, with particularly useful skew variants being selected from the group consisting of S364K/ E357Q: L368D/K370S; L368D/K370S: S364K; L368E/ K370S: S364K; T411T/E360E/Q362E: D401K; L368D/ K370S: S364K/E357L, K370S: S364K/E357Q, T366S/ L368A/Y407V: T366W and T366S/L368A/Y407V/Y349C: T366W/S354C), optionally ablation variants (including those shown in FIG. 6), optionally charged scFv linkers (including those shown in FIG. 8) and the heavy chain comprises pI variants (including those shown in FIG. 5).

In some embodiments, the dual scFv format includes skew variants, pI variants, and ablation variants. Accordingly, some embodiments include formats that comprise: a) a first monomer that comprises the skew variants S364K/ E357Q, the ablation variants E233P/L234V/L235A/ G236del/S267K, and a scFv that binds a first receptor (VH1-scFv linker-VL1-[optional domain linker]-CH2-CH3 or VL1-scFv linker-VH1-[optional domain linker]-CH2-CH3) and b) a first monomer that comprises the skew variants L368D/K370S, the ablation variants E233P/L234V/L235A/G236del/S267K, and a scFv that binds a first receptor (VH1-scFv linker-VL1-[optional domain linker]-CH2-CH3 or VL1-scFv linker-VH1-[optional domain linker]-CH2-CH3). pI variants can be as outlined herein, but most common will be charged scFv linkers of opposite charge for each monomer. FcRn variants, particularly 428L/434S, can optionally be included. In some particular embodiments with these variants in this format:

(1) the format comprises a ABD binds to ICOS that has the ABD of [ICOS] H0.66_L0;

(2) the format comprises an ICOS ABD of H0.66_L0 combined with the ABD comprising the ABD 1G6_L1.194_H1.279 that binds to PD-1;

(3) the format comprises an ICOS ABD of H0.66_L0 combined with the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises the ABD 1G6_L1.194_H1.279 that binds to PD-1 and an Fv binds to GITR;

(6) the format comprises the ABD 1G6_L1.194_H1.279 that binds to PD-1 and the Fv binds to OX40;

(7) the format comprises the ABD 1G6_L1.194_H1.279 that binds to PD-1 and the ABD binds to ICOS;

8) the format comprises the ABD 1G6_L1.194_H1.279 that binds to PD-1 and an ABD binds to 4-1BB; and (9) the format comprises the ABD of H0.66_L0 that binds to ICOS and an ABD that binds to PD-L1.

In this format, specific ABDs that bind human ICOS include, but are not limited to, [ICOS]_H0L0 and [ICOS] H0.66_L0 and those shown in FIG. 19, FIG. 20, FIG. 24, FIG. 68 and FIG. 77 as well as SEQ ID NO: 27869-28086, 28087-28269, 27193-27335, 28549-28556 and 28557-28665.

In this format, specific ABDs that bind human GITR include, but are not limited to, those in FIG. 18, FIG. 72 and FIG. 73 and those listed in SEQ ID NO:26282-26290.

In this format, specific ABDs that bind OX40 include, but are not limited to, FIG. 17, FIG. 72 and FIG. 73 and those listed in SEQ ID NO: 26272-26281.

In this format, specific ABDs that bind human 4-1BB include, but are not limited to, FIG. 16, FIG. 72 and FIG. 73 and SEQ ID NO: 26262-2671.

In this format, specific ABDs that bind human PD-L1 include, but are not limited to, FIG. 15, FIG. 73 and FIG. 78 and SEQ ID NO: 3961-4432.

M. Non-Heterodimeric Bispecific Antibodies

As will be appreciated by those in the art, the Fv sequences outlined herein can also be used in both monospecific antibodies (e.g. "traditional monoclonal antibodies") or non-heterodimeric bispecific formats (see FIGS. 2J, K and L).

In this format, specific ABDs that bind human ICOS include, but are not limited to, [ICOS]_H0L0 and [ICOS] H0.66_L0 and those shown in FIG. 19, FIG. 20, FIG. 24, FIG. 68 and FIG. 77 as well as SEQ ID NO: 27869-28086, 28087-28269, 27193-27335, 28549-28556 and 28557-28665.

In this format, specific ABDs that bind human GITR include, but are not limited to, those in FIG. 18, FIG. 72 and FIG. 73 and those listed in SEQ ID NO:26282-26290.

In this format, specific ABDs that bind OX40 include, but are not limited to, FIG. 17, FIG. 72 and FIG. 73 and those listed in SEQ ID NO: 26272-26281.

In this format, specific ABDs that bind human 4-1BB include, but are not limited to, FIG. 16, FIG. 72 and FIG. 73 and SEQ ID NO: 26262-2671.

In this format, specific ABDs that bind human PD-L1 include, but are not limited to, FIG. 15, FIG. 73 and FIG. 78 and SEQ ID NO: 3961-4432.

Suitable non-heterodimeric bispecific formats are known in the art, and include a number of different formats as generally depicted in Spiess et al., Molecular Immunology (67):95-106 (2015) and Kontermann, mAbs 4:2, 182-197 (2012), both of which are expressly incorporated by reference and in particular for the figures, legends and citations to the formats therein.

N. DVD-Ig Format

In some embodiments, the bispecific antibody is in a "Dual Variable Domain-Ig" or "DVD-Ig™" format (see FIG. 2L) such as is generally described in U.S. Pat. No. 7,612,181, hereby expressly incorporated by reference in its entirety, and in particular for the Figures and Legends therein. In the DVD-Ig format, the antibody is tetravalent and bispecific, and comprises 4 chains: two homodimeric heavy chains and two identical light chains. The heavy chains each have a VH1-(optional linker)-VH2-CH1-hinge-CH2-CH3 structure and the two light chains each have a VL1-optional linker-VL2-CL structure, with VH1 and VL1 forming a first ABD and the VH2 and VL2 forming a second ABD, where the first and second ABDs bind a costimulatory and a checkpoint receptor. In this embodiment, suitable combinations include ICOS and PD-1, ICOS and CTLA-4, ICOS and LAG-3, ICOS and TIM-3, ICOS and PD-L1, ICOS and BTLA, GITR and PD-1, GITR and CTLA-4, GITR and LAG-3, GITR and TIM-3, GITR and PD-L1, GITR and BTLA, OX40 and PD-1, OX40 and CTLA-4, OX40 and LAG-3, OX40 and TIM-3, OX40 and PD-L1, OX40 and BTLA, 4-1BB and PD-1, 4-1BB and CTLA-4, 4-1BB and LAG-3, 4-1BB and TIM-3, 4-1BB and PD-L1 and 4-1BB and BTLA.

The DVD-Ig™ and Central-scFv2 are two formats that are bispecific and tetravalent, and thus do not bind a costimulatory receptor in a monovalent fashion. Exemplary DVD-Ig™ constructs are shown in FIG. 61.

In some particular embodiments with these variants in this format:

(1) the format comprises the ABD of [ICOS] H0.66_L0;

(2) the format comprises an ICOS ABD of H0.66_L0 combined with the ABD comprising the ABD 1G6_L1.194_H1.279 that binds to PD-1;

(3) the format comprises an ICOS ABD of H0.66_L0 combined with the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises the ABD 1G6_L1.194_H1.279 that binds to PD-1 and an ABD that binds to GITR;

(6) the format comprises the ABD 1G6_L1.194_H1.279 that binds to PD-1 and ABD that binds to OX40;

(7) the format comprises the ABD 1G6_L1.194_H1.279 that binds to PD-1 and an ABD that binds to ICOS;

8) the format comprises the ABD 1G6_L1.194_H1.279 that binds to PD-1 and an ABD that binds to 4-1BB; and (9) the format comprises the ABD of H0.66_L0 that binds to ICOS and an ABD that binds to PD-L1.

In this format, specific ABDs that bind human ICOS include, but are not limited to, [ICOS]_H0L0 and [ICOS] H0.66_L0 and those shown in FIG. 19, FIG. 20, FIG. 24, FIG. 68 and FIG. 77 as well as SEQ ID NO: 27869-28086, 28087-28269, 27193-27335, 28549-28556 and 28557-28665.

In this format, specific ABDs that bind human GITR include, but are not limited to, those in FIG. 18, FIG. 72 and FIG. 73 and those listed in SEQ ID NO:26282-26290.

In this format, specific ABDs that bind OX40 include, but are not limited to, FIG. 17, FIG. 72 and FIG. 73 and those listed in SEQ ID NO: 26272-26281.

In this format, specific ABDs that bind human 4-1BB include, but are not limited to, FIG. 16, FIG. 72 and FIG. 73 and SEQ ID NO: 26262-2671.

In this format, specific ABDs that bind human PD-L1 include, but are not limited to, FIG. 15, FIG. 73 and FIG. 78 and SEQ ID NO: 3961-4432.

O. Trident Format

In some embodiments, the bispecific antibodies of the invention are in the "Trident" format as generally described in WO2015/184203, hereby expressly incorporated by reference in its entirety and in particular for the Figures, Legends, definitions and sequences of "Heterodimer-Promoting Domains" or "HPDs", including "K-coil" and "E-coil" sequences. Tridents rely on using two different HPDs that associate to form a heterodimeric structure as a component of the structure, see FIG. 2M. In this embodiment, the Trident format include a "traditional" heavy and light chain (e.g. VH1-CH1-hinge-CH2-CH3 and VL1-CL), a third chain comprising a first "diabody-type binding domain" or "DART®", VH2-(linker)-VL3-HPD1 and a fourth chain comprising a second DART®, VH3-(linker)-(linker)-VL2-HPD2. The VH1 and VL1 form a first ABD, the VH2 and VL2 form a second ABD, and the VH3 and VL3 form a third ABD. IN some cases, as is shown in FIG. 2M, the second and third ABDs bind the same antigen, in this instance generally the checkpoint receptor, e.g. bivalently, with the first ABD binding a costimulatory receptor monovalently. In this embodiment, suitable combinations include ICOS and PD-1, ICOS and CTLA-4, ICOS and LAG-3, ICOS and TIM-3, ICOS and PD-L1, ICOS and BTLA, GITR and PD-1, GITR and CTLA-4, GITR and LAG-3, GITR and TIM-3, GITR and PD-L1, GITR and BTLA, OX40 and PD-1, OX40 and CTLA-4, OX40 and LAG-3, OX40 and TIM-3, OX40 and PD-L1, OX40 and BTLA, 4-1BB and PD-1, 4-1BB and CTLA-4, 4-1BB and LAG-3, 4-1BB and TIM-3, 4-1BB and PD-L1 and 4-1BB and BTLA.

In some particular embodiments with these variants in this format:

(1) the format comprises a Fab ABD binds to ICOS that has the ABD of [ICOS] H0.66_L0;

(2) the format comprises an ICOS ABD of H0.66_L0 combined with the scFv ABD comprising the ABD 1G6_L1.194_H1.279 that binds to PD-1;

(3) the format comprises an ICOS ABD of H0.66_L0 combined with the scFv comprising the ABD H3.23_L0.129 that binds to CTLA-4;

(4) the format comprises an ICOS ABD of H0.66_L0 is combined with the ABD 7G8_H.303_L1.34 that binds to LAG-3;

(5) the format comprises a scFv comprising the ABD 1G6_L1.194_H1.279 that binds to PD-1 and the Fab binds to GITR;

(6) the format comprises a scFv comprising the ABD 1G6_L1.194_H1.279 that binds to PD-1 and the Fab binds to OX40;

(7) the format comprises a scFv comprising the ABD 1G6_L1.194_H1.279 that binds to PD-1 and the Fab binds to ICOS;

8) the format comprises a scFv comprising the ABD 1G6_L1.194_H1.279 that binds to PD-1 and the Fab binds to 4-1BB; and (9) the format comprises the ABD of H0.66_L0 that binds to ICOS and an ABD that binds to PD-L1.

In this format, specific ABDs that bind human ICOS include, but are not limited to, [ICOS]_H0L0 and [ICOS] H0.66_L0 and those shown in FIG. 19, FIG. 20, FIG. 24, FIG. 68 and FIG. 77 as well as SEQ ID NO: 27869-28086, 28087-28269, 27193-27335, 28549-28556 and 28557-28665.

In this format, specific ABDs that bind human GITR include, but are not limited to, those in FIG. 18, FIG. 72 and FIG. 73 and those listed in SEQ ID NO:26282-26290.

In this format, specific ABDs that bind OX40 include, but are not limited to, FIG. 17, FIG. 72 and FIG. 73 and those listed in SEQ ID NO: 26272-26281.

In this format, specific ABDs that bind human 4-1BB include, but are not limited to, FIG. 16, FIG. 72 and FIG. 73 and SEQ ID NO: 26262-2671.

In this format, specific ABDs that bind human PD-L1 include, but are not limited to, FIG. 15, FIG. 73 and FIG. 78 and SEQ ID NO: 3961-4432.

P. Monospecific, Monoclonal Antibodies

As will be appreciated by those in the art, the novel Fv sequences outlined herein can also be used in both monospecific antibodies (e.g. "traditional monoclonal antibodies") or non-heterodimeric bispecific formats. Accordingly, the present invention provides monoclonal (monospecific) antibodies comprising the 6 CDRs and/or the vh and vl sequences from the figures, generally with IgG1, IgG2, IgG3 or IgG4 constant regions, with IgG1, IgG2 and IgG4 (including IgG4 constant regions comprising a S228P amino acid substitution) finding particular use in some embodiments. That is, any sequence herein with a "H_L" designation can be linked to the constant region of a human IgG1 antibody.

VIII. Antigen Binding Domains (ABDs) to Target Antigens

The bispecific antibodies of the invention have two different antigen binding domains (ABDs) that bind to two different target receptor antigens ("target pairs"), in either bivalent, bispecific formats or trivalent, bispecific formats as generally shown in FIG. 2.

The bispecific antibodies bind to a first target antigen comprising a checkpoint receptor and a second target antigen comprising a costimulatory receptor. Suitable checkpoint receptors as outlined herein include PD-1, PD-L1, LAG-3, TIM-3, CTLA-4, BTLA and TIGIT. Suitable costimulatory receptors as outlined herein include ICOS, GITR, OX40 and 4-1BB. As outlined Suitable target checkpoint antigens include human (and sometimes cyno) PD-1, CTLA-4, TIM-3, LAG-3, TIGIT and BTLA (sequences in the sequence listing). Accordingly, suitable bispecific antibodies bind ICOS and PD-1, ICOS and CTLA-4, ICOS and LAG-3, ICOS and TIM-3, ICOS and PD-L1, ICOS and BTLA, ICOS and TIGIT, GITR and TIGIT, GITR and PD-1, GITR and CTLA-4, GITR and LAG-3, GITR and TIM-3, GITR and PD-L1, GITR and BTLA, OX40 and PD-1, OX40 and TIGIT, OX40 and CTLA-4, IC OX40 OS and LAG-3, OX40 and TIM-3, OX40 and PD-L1, OX40 and BTLA, 4-1BB and PD-1, 4-1BB and CTLA-4, 4-1BB and LAG-3, 4-1BB and TIM-3, 4-1BB and PD-L1, TIGIT and 4-1BB and 4-1BB and BTLA.

Note that generally these bispecific antibodies are named "anti-PD-1 X anti-CTLA-4", or generally simplistically or for ease (and thus interchangeably) as "PD-1 X CTLA-4", etc. for each pair. Note that unless specified herein, the order of the antigen list in the name does not confer structure; that is a PD-1 X CTLA-4 bottle opener antibody can have the scFv bind to PD-1 or CTLA-4, although in some cases, the order specifies structure as indicated.

As is more fully outlined herein, these combinations of ABDs can be in a variety of formats, as outlined below, generally in combinations where one ABD is in a Fab format and the other is in an scFv format. As discussed herein and shown in FIG. 2, some formats use a single Fab and a single scFv (A, C and D), and some formats use two Fabs and a single scFv (E, F, G, H and I).

A. Antigen Binding Domains

As discussed herein, the bispecific checkpoint heterodimeric antibodies of the invention include two antigen binding domains (ABDs), each of which bind to a different checkpoint protein. As outlined herein, these heterodimeric antibodies can be bispecific and bivalent (each antigen is bound by a single ABD, for example, in the format depicted in FIG. 2A), bispecific and trivalent (one antigen is bound by a single ABD and the other is bound by two ABDs, for example as depicted in FIG. 2F, G, H, I or M), or bispecific and tetravalent (both antigens are bound by two ABDs, for example as depicted in FIGS. 2J and L).

In addition, in general, one of the ABDs comprises a scFv as outlined herein, in an orientation from N- to C-terminus of vh-scFv linker-vl or vl-scFv linker-vh. One or both of the other ABDs, according to the format, generally is a Fab, comprising a vh domain on one protein chain (generally as a component of a heavy chain) and a vl on another protein chain (generally as a component of a light chain). Note that the "trident" format uses DART®s, which are similar to scFvs except the orientation is different and in general the linkers can be slightly longer.

The invention provides a number of ABDs that bind to a number of different receptor proteins, as outlined below. As will be appreciated by those in the art, any set of 6 CDRs or vh and vl domains can be in the scFv format or in the Fab format, which is then added to the heavy and light constant domains, where the heavy constant domains comprise variants (including within the CH1 domain as well as the Fc domain). The scFv sequences contained in the sequence listing utilize a particular charged linker, but as outlined herein, uncharged or other charged linkers can be used, including those depicted in FIG. 8.

In addition, as discussed above, the numbering used in the Sequence Listing for the identification of the CDRs is Kabat, however, different numbering can be used, which will change the amino acid sequences of the CDRs as shown in Table 1.

For all of the variable heavy and light domains listed herein, further variants can be made. As outlined herein, in some embodiments the set of 6 CDRs can have from 0, 1, 2, 3, 4 or 5 amino acid modifications (with amino acid substitutions finding particular use), as well as changes in the framework regions of the variable heavy and light domains, as long as the frameworks (excluding the CDRs) retain at least about 80, 85 or 90% identity to a human germline sequence selected from those listed in FIG. 1 of U.S. Pat. No. 7,657,380, which Figure and Legend is incorporated by reference in its entirety herein. Thus, for example, the identical CDRs as described herein can be combined with different framework sequences from human germline sequences, as long as the framework regions retain at least 80, 85 or 90% identity to a human germline sequence selected from those listed in FIG. 1 of U.S. Pat. No. 7,657,380. Alternatively, the CDRs can have amino acid modifications (e.g. from 1, 2, 3, 4 or 5 amino acid modifications in the set of CDRs (that is, the CDRs can be modified as long as the total number of changes in the set of 6 CDRs is less than 6 amino acid modifications, with any combination of CDRs being changed; e.g. there may be one change in vlCDR1, two in vhCDR2, none in vhCDR3, etc.)), as well as having framework region changes, as long as the framework regions retain at least 80, 85 or 90% identity to a human germline sequence selected from those listed in FIG. 1 of U.S. Pat. No. 7,657,380.

B. PD-1 Antigen Binding Domains

In some embodiments, one of the ABDs binds PD-1. Suitable sets of 6 CDRs and/or vh and vl domains, as well as scFv sequences, are depicted in FIG. 3, FIG. 10, FIG. 11, FIG. 72, FIG. 73, FIG. 74, FIG. 76 and SEQ ID NO:1-2392, 3125-3144, 4697-7594 and 4697-21810, and include those sequences in the sequence listing with the identifiers 1G6_H1.279_L1.194; 1G6_H1.280_L1.224; 1G6_L1.194_H1.279; 1G6_L1.210_H1.288; and 2E9_H1L1.

As will be appreciated by those in the art, suitable anti-PD-1 ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences of these sequences. Suitable ABDs can also include the entire vh and vl sequences as depicted in these sequences and Figures, used as scFvs or as Fabs. In many of the embodiments herein that contain an Fv to PD-1, it is the scFv monomer that binds PD-1. As discussed herein, the other of the target pair when PD-1 is one of the antigens is selected from ICOS (suitable sequences are shown in FIG. 19, FIG. 20, FIG. 24, FIG. 68 and FIG. 77 as well as SEQ ID NO: 27869-28086, 28087-28269, 27193-27335, 28549-28556 and 28557-28665 (which can be scFv sequences, CDR sequence sets or vh and vl sequences)), GITR, OX40 and 4-1BB.

Particularly useful ABDs that bind human PD-1 include, but are not limited to, 1G6_H1.279_L1.194, 1G6_H1.280_L1.224; 1G6_L1.194_H1.279, 1G6_L1.210_H1.288 and 2E9_H1L1.

Additionally useful vh and vl sequences that bind human PD-1 are shown in FIG. 76.

In addition to the parental CDR sets disclosed in the sequence listing that form an ABD to PD-1, the invention provides variant CDR sets. In one embodiment, a set of 6 CDRs can have 1, 2, 3, 4 or 5 amino acid changes from the parental CDRs, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments.

In addition to the parental variable heavy and variable light domains disclosed herein that form an ABD to PD-1, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured at least one of a Biacore, surface plasmon resonance (SPR) and/or BLI (biolayer interferometry, e.g. Octet assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments.

Specific preferred embodiments include the 1G6_L1.194_H1.279 anti-PD-1 Fv, in a scFv format, included within any of the bottle opener format backbones of FIG. 9.

Specific preferred embodiments include the 1G6_L1.194_H1.279 anti-PD-1 Fv, in a scFv format, included within any of the format backbones of FIGS. 55A-55D.

Specific preferred embodiments include the 1G6_L1.194_H1.279 anti-PD-1 Fv, in a scFv format, included within any of the mAb-scFv format backbones of FIG. 75.

Other embodiments utilize any of the anti-PD-1 vh and vl domain pairs (either as scFvs or Fabs) as shown in FIG. 76 in any format shown in FIG. 2.

C. CTLA-4 Antigen Binding Domains

In some embodiments, one of the ABDs binds CTLA-4. Suitable sets of 6 CDRs and/or vh and vl domains, as well as scFv sequences, are depicted in SEQ ID NOs: 2393-2414 and 3737-3816, as well as sequences of particular interest in some embodiments are shown in FIG. 12 and FIG. 79 and also include those sequences in the sequence listing with the identifiers [CTLA-4]_H0.25_L0; [CTLA-4]_H0.26_L0; [CTLA-4]_H0.27_L0; [CTLA-4]_H0.29_L0; [CTLA-4]_H0.38_L0; [CTLA-4]_H0.39_L0; [CTLA-4]_H0.40_L0; [CTLA-4]_H0.70_L0; [CTLA-4]_H0_L0.22; [CTLA-4]_H2_L0; [CTLA-4]_H3.21_L0.124; [CTLA-4]_H3.21_L0.129; [CTLA-4]_H3.21_L0.132; [CTLA-4]_H3.23_L0.124; [CTLA-4]_H3.23_L0.129; [CTLA-4]_H3.23_L0.132; [CTLA-4]_H3.25_L0.124; [CTLA-4]_H3.25_L0.129; [CTLA-4]_H3.25_L0.132; [CTLA-4]_H3.4_L0.118; [CTLA-4]_H3.4_L0.119; [CTLA-4]_H3.4_L0.12; [CTLA-4]_H3.4_L0.121; [CTLA-4]_H3.4_L0.122; [CTLA-4]_H3.4_L0.123; [CTLA-4]_H3.4_L0.124; [CTLA-4]_H3.4_L0.125; [CTLA-4]_H3.4_L0.126; [CTLA-4]_H3.4_L0.127; [CTLA-4]_H3.4_L0.128; [CTLA-4]_H3.4_L0.129; [CTLA-4]_H3.4_L0.130; [CTLA-4]_H3.4_L0.131; [CTLA-4]_H3.4_L0.132; [CTLA-4]_H3.5_L2.1; [CTLA-4]_H3.5_L2.2; [CTLA-4]_H3.5_L2.3; [CTLA-4]_H3_L0; [CTLA-4]_H3_L0.22; [CTLA-4]_H3_L0.44; [CTLA-4]_H3_L0.67; and [CTLA-4]_H3_L0.74.

As will be appreciated by those in the art, suitable anti-CTLA-4 ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences outlined herein. Suitable ABDs can also include the entire vh and vl sequences as depicted in these sequences and Figures, used as scFvs or as Fabs. In many of the embodiments herein that contain an Fv to CTLA-4, it is the scFv monomer that binds CTLA-4.

As discussed herein, the other of the target pair when CTLA-4 is one of the antigens is selected from ICOS (suitable sequences are shown in FIG. 19, FIG. 20, FIG. 24, FIG. 68 and FIG. 77 as well as SEQ ID NO: 27869-28086, 28087-28269, 27193-27335, 28549-28556 and 28557-28665, and those with the identifiers [ICOS]_H0.66_L0 and [ICOS]_H0L0), GITR, OX40 and 4-1BB.

In addition to the parental CDR sets disclosed in the sequence listing that form an ABD to CTLA-4, the invention provides variant CDR sets. In one embodiment, a set of 6 CDRs can have 1, 2, 3, 4 or 5 amino acid changes from the parental CDRs, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments.

In addition to the parental variable heavy and variable light domains disclosed herein that form an ABD to CTLA-4, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments.

D. TIM-3 Antigen Binding Domains

In some embodiments, one of the ABDs binds TIM-3. Suitable sets of 6 CDRs and/or vh and vl domains, as well as scFv sequences, are depicted in FIG. 14 and FIG. 81 and SEQ ID NO: 3345-3704, 4585-4696. ABD sequences of particular interest in some embodiments include those sequences in the sequence listing with the identifiers 1D10_H0L0; 1D12_H0L0; 3H3_H1_L2.1; 6C8_H0L0; 6D9_H0_1D12_L0; 7A9_H0L0; 7B11_H0L0; 7B11var_H0L0; and 7C2_H0L0.

As will be appreciated by those in the art, suitable anti-TIM-3 ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences of those depicted herein. Suitable ABDs can also include the entire vh and vl sequences as depicted in these sequences and Figures, used as scFvs or as Fabs. In many of the embodiments herein that contain an Fv to TIM-3, it is the Fab monomer that binds TIM-3. As discussed herein, the other of the target pair when TIM-3 is one of the antigens is selected ICOS (suitable sequences are shown in FIG. 19, FIG. 20, FIG. 24, FIG. 68 and FIG. 77 as well as SEQ ID NO: 27869-28086, 28087-28269, 27193-27335, 28549-28556 and 28557-28665, and those with the identifiers [ICOS]_H0.66_L0 and [ICOS]_H0L0), GITR, OX40 and 4-1BB.

In addition to the parental CDR sets disclosed in the sequence listing that form an ABD to TIM-3, the invention provides variant CDR sets. In one embodiment, a set of 6 CDRs can have 1, 2, 3, 4 or 5 amino acid changes from the parental CDRs, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments.

In addition to the parental variable heavy and variable light domains disclosed herein that form an ABD to TIM-3, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured at least one of a Biacore, surface plasmon resonance (SPR) and/or BLI (biolayer interferometry, e.g. Octet assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments.

LAG-3 Antigen Binding Domains

In some embodiments, one of the ABDs binds LAG-3. Suitable sets of 6 CDRs and/or vh and vl domains, as well as scFv sequences, are depicted in FIG. 13, FIG. 80 and in SEQ ID NO: 2415-2604, 3817-3960 also include those sequences in the sequence listing with the identifiers 2A11_H0L0; 2A11_H1.125_L2.113; 2A11_H1.144_L2.142; 2A11_H1_L2.122; 2A11_H1_L2.123; 2A11_H1_L2.124; 2A11_H1_L2.25; 2A11_H1_L2.47; 2A11_H1_L2.50; 2A11_H1_L2.91; 2A11_H1_L2.93; 2A11_H1_L2.97; 2A11_H1L1; 2A11_H1L2; 2A11_H2L2; 2A11_H3L1; 2A11_H3L2; 2A11_H4L1; 2A11_H4L2; 7G8_H0L0; 7G8_H1L1, 7G8_H3.18_L1.11, 7G8_H3.23_L1.11; 7G8_H3.28_L1; 7G8_H3.28_L1.11; 7G8_H3.28_L1.13; 7G8_H3.30_L1.34; 7G8_H3.30_L1.34; and 7G8_H3L1.

As will be appreciated by those in the art, suitable anti-LAG-3 ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences of the sequences herein. Suitable ABDs can also include the entire vh and vl sequences as depicted in these sequences and Figures, used as scFvs or as Fabs. In many of the embodiments herein that contain an Fv to LAG-3, it is the Fab monomer that binds LAG-3. As discussed herein, the other of the target pair when LAG-3 is one of the antigens is selected from ICOS (suitable sequences are shown in FIG. 19, FIG. 20, FIG. 24, FIG. 68 and FIG. 77 as well as SEQ ID NO: 27869-28086, 28087-28269, 27193-27335, 28549-28556 and 28557-28665, and those with the identifiers [ICOS]_H0.66_L0 and [ICOS]_H0L0), GITR, OX40 and 4-1BB.

In addition to the parental CDR sets disclosed in the sequence listing that form an ABD to LAG-3, the invention provides variant CDR sets. In one embodiment, a set of 6 CDRs can have 1, 2, 3, 4 or 5 amino acid changes from the parental CDRs, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments.

In addition to the parental variable heavy and variable light domains disclosed herein that form an ABD to LAG-3, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments.

E. BTLA Antigen Binding Domains

In some embodiments, one of the ABDs binds BTLA. Suitable sets of 6 CDRs and/or vh and vl domains, as well as scFv sequences, are depicted in FIG. 82, FIG. 84 and SEQ ID NO:3705-3736, and also include those sequences in the sequence listing with the identifiers 9C6_H0L0; 9C6_H1.1_L1; and 9C6_H1.11_L1.

As will be appreciated by those in the art, suitable anti-BTLA ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences depicted herein. Suitable ABDs can also include the entire vh and vl sequences as depicted in these sequences and Figures, used as scFvs or as Fabs. In many of the embodiments herein that contain an Fv to BTLA, it is the Fab monomer that binds BTLA. As discussed herein, the other of the target pair when BTLA is one of the antigens is selected from ICOS (suitable sequences are shown in FIG. 19, FIG. 20, FIG. 24, FIG. 68 and FIG. 77 as well as SEQ ID NO: 27869-28086, 28087-28269, 27193-27335, 28549-28556 and 28557-28665, and those with the identifiers [ICOS]_H0.66_L0 and [ICOS]_H0L0), GITR, OX40 and 4-1BB.

In addition to the parental CDR sets disclosed in the sequence listing that form an ABD to BTLA, the invention provides variant CDR sets. In one embodiment, a set of 6 CDRs can have 1, 2, 3, 4 or 5 amino acid changes from the parental CDRs, as long as the ABD is still able to bind to the target antigen, as measured at least one of a Biacore, surface plasmon resonance (SPR) and/or BLI (biolayer interferometry, e.g. Octet assay) assay, with the latter finding particular use in many embodiments.

In addition to the parental variable heavy and variable light domains disclosed herein that form an ABD to BTLA, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a Biacore, surface plasmon

F. TIGIT Antigen Binding Domains

In some embodiments, one of the ABDs binds TIGIT. Suitable sets of 6 CDRs and/or vh and vl domains, as well as scFv sequences, are depicted in FIG. 8? And in SEQ ID NO:4433-4585.

As will be appreciated by those in the art, suitable anti-TIGIT ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences depicted herein. Suitable ABDs can also include the entire vh and vl sequences as depicted in these sequences and Figures, used as scFvs or as Fabs. In many of the embodiments herein that contain an Fv to TIGIT, it is the Fab monomer that binds TIGIT. As discussed herein, the other of the target pair when TIGIT is one of the antigens is selected ICOS (suitable sequences are shown in FIG. 19, FIG. 20, FIG. 24, FIG. 68 and FIG. 77 as well as SEQ ID NO: 27869-28086, 28087-28269, 27193-27335, 28549-28556 and 28557-28665, and those with the identifiers [ICOS]_H0.66_L0 and [ICOS]_H0L0), GITR, OX40 and 4-1BB.

G. PD-L1 Antigen Binding Domains

In some embodiments, one of the ABDs binds PD-L1. Suitable sets of 6 CDRs and/or vh and vl domains, as well as scFv sequences, are depicted in FIG. 15, FIG. 73 and FIG. 78, and in SEQ ID NO:3961-4432.

As will be appreciated by those in the art, suitable anti-TIGIT ABDs can comprise a set of 6 CDRs as depicted in these sequences and Figures, either as they are underlined or, in the case where a different numbering scheme is used as described herein and as shown in Table 1, as the CDRs that are identified using other alignments within the vh and vl sequences depicted herein. Suitable ABDs can also include the entire vh and vl sequences as depicted in these sequences and Figures, used as scFvs or as Fabs. In many of the embodiments herein that contain an Fv to TIGIT, it is the Fab monomer that binds TIGIT. As discussed herein, the other of the target pair when TIGIT is one of the antigens is selected ICOS (suitable sequences are shown in FIG. 19, FIG. 20, FIG. 24, FIG. 68 and FIG. 77 as well as SEQ ID NO: 27869-28086, 28087-28269, 27193-27335, 28549-28556 and 28557-28665, and those with the identifiers [ICOS]_H0.66_L0 and [ICOS]_H0L0), GITR, OX40 and 4-1BB.

H. ICOS Antigen Binding Domains

In some embodiments, one of the ABDs binds ICOS. Suitable sets of 6 CDRs and/or vh and vl domains, as well as scFv sequences ICOS (suitable sequences are shown in FIG. 19, FIG. 20, FIG. 24, FIG. 68 and FIG. 77 as well as SEQ ID NO: 27869-28086, 28087-28269, 27193-27335, 28549-28556 and 28557-28665, and those with the identifiers [ICOS]_H0.66_L0 and [ICOS]_H0L0.

As will be appreciated by those in the art, suitable anti-ICOS ABDs can comprise a set of 6 CDRs as depicted in these sequences and Figures, either as they are underlined or, in the case where a different numbering scheme is used as described herein and as shown in Table 1, as the CDRs that are identified using other alignments within the sequences disclosed herein. Suitable ABDs can also include the entire vh and vl sequences as depicted in these sequences and Figures, used as scFvs or as Fabs. In many of the embodiments herein that contain an Fv to ICOS, it is the Fab monomer that binds ICOS. As discussed herein, the other of the target pair when ICOS is one of the antigens is selected from PD-1 are depicted in FIG. 3, FIG. 10, FIG. 11, FIG. 72, FIG. 73, FIG. 74, FIG. 76 and SEQ ID NO:1-2392, 3125-3144, 4697-7594 and 4697-21810, and include those sequences in the sequence listing with the identifiers 1G6_H1.279_L1.194; 1G6_H1.280_L1.224; 1G6_L1.194_H1.279; 1G6_L1.210_H1.288; and 2E9_H1L1 (which can be scFv sequences, CDR sequence sets or vh and vl sequences)), CTLA-4 (suitable sequences are depicted in FIGS. 12, 72 and 79, as well as SEQ ID NO:2393-2414 and 3737-3816 (which can be scFv sequences, CDR sequence sets or vh and vl sequences)), TIM-3 (suitable sequences are depicted in FIG. 14, FIG. 81 and SEQ ID NO: 3345-3704, 4585-4696 (which can be scFv sequences, CDR sequence sets or vh and vl sequences)), LAG-3 (suitable sequences are depicted in FIG. 13, FIG. 80 and SEQ ID NO:2415-2604, 3817-3960 (which can be scFv sequences, CDR sequence sets or vh and vl sequences)), BTLA (suitable sequences are depicted in FIGS. 82 and 84 and SEQ ID NO?3705-3736 (which can be scFv sequences, CDR sequence sets or vh and vl sequences)), and TIGIT (suitable sequences are depicted in Figure XX and SEQ ID NO:4433-4585 (which can be scFv sequences, CDR sequence sets or vh and vl sequences)).

In addition to the parental CDR sets disclosed in the sequence listing that form an ABD to ICOS, the invention provides variant CDR sets. In one embodiment, a set of 6 CDRs can have 1, 2, 3, 4 or 5 amino acid changes from the parental CDRs, as long as the ABD is still able to bind to the target antigen, as measured at least one of a Biacore, surface plasmon resonance (SPR) and/or BLI (biolayer interferometry, e.g. Octet assay) assay, with the latter finding particular use in many embodiments.

In addition to the parental variable heavy and variable light domains disclosed herein that form an ABD to ICOS, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments.

Specific preferred embodiments include the [ICOS]_H0.66_L0 anti-ICOS Fv, in a Fab format, included within any of the bottle opener format backbones of FIG. 9.

Specific preferred embodiments include the [ICOS]_H0_L0 anti-ICOS Fv, in a scFv format, included within any of the bottle opener format backbones of FIG. 9.

Specific preferred embodiments include the [ICOS]_H0.66_L0 anti-ICOS Fv, in a scFv format, included within any of the mAb-scFv format backbones of FIG. 75.

Specific preferred embodiments include the [ICOS]_H0.66_L0 anti-ICOS Fv, in a Fab format, included within any of the mAb-scFv format backbones of FIG. 75.

Specific preferred embodiments include the [ICOS]_H0.66_L0 anti-ICOS Fv, in a Fab format, included within any of the format backbones of FIGS. 55A-55D.

I. GITR Antigen Binding Domains

In some embodiments, one of the ABDs binds GITR. Suitable sets of 6 CDRs and/or vh and vl domains, as well as scFv sequences FITR (suitable sequences are shown in FIG. 18, FIG. 72 and FIG. 73, and in SEQ ID NO: 26282-26290.

As will be appreciated by those in the art, suitable anti-GITR ABDs can comprise a set of 6 CDRs as depicted in these sequences and Figures, either as they are underlined or, in the case where a different numbering scheme is used as described herein and as shown in Table 1, as the CDRs that are identified using other alignments within the sequences disclosed herein. Suitable ABDs can also include the entire vh and vl sequences as depicted in these sequences and Figures, used as scFvs or as Fabs. In many of the embodiments herein that contain an Fv to GITR, it is the Fab monomer that binds GITR. As discussed herein, the other of the target pair when GITR is one of the antigens is selected from PD-1 are depicted in FIG. 3, FIG. 10, FIG. 11, FIG. 72, FIG. 73, FIG. 74, FIG. 76 and SEQ ID NO:1-2392, 3125-3144, 4697-7594 and 4697-21810, and include those sequences in the sequence listing with the identifiers 1G6_H1.279_L1.194; 1G6_H1.280_L1.224; 1G6_L1.194_H1.279; 1G6_L1.210_H1.288; and 2E9_H1L1 (which can be scFv sequences, CDR sequence sets or vh and vl sequences)), CTLA-4 (suitable sequences are depicted in FIGS. 12, 72 and 79, as well as SEQ ID NO:2393-2414 and 3737-3816 (which can be scFv sequences, CDR sequence sets or vh and vl sequences)), TIM-3 (suitable sequences are depicted in FIG. 14, FIG. 81 and SEQ ID NO: 3345-3704, 4585-4696 (which can be scFv sequences, CDR sequence sets or vh and vl sequences)), LAG-3 (suitable sequences are depicted in FIG. 13, FIG. 80 and SEQ ID NO:2415-2604, 3817-3960 (which can be scFv sequences, CDR sequence sets or vh and vl sequences)), BTLA (suitable sequences are depicted in FIGS. 82 and 84 and SEQ ID NO?3705-3736 (which can be scFv sequences, CDR sequence sets or vh and vl sequences)), and TIGIT (suitable sequences are depicted in Figure XX and SEQ ID NO:4433-4585 (which can be scFv sequences, CDR sequence sets or vh and vl sequences)).

In addition to the parental CDR sets disclosed in the sequence listing that form an ABD to GITR, the invention provides variant CDR sets. In one embodiment, a set of 6 CDRs can have 1, 2, 3, 4 or 5 amino acid changes from the parental CDRs, as long as the ABD is still able to bind to the target antigen, as measured at least one of a Biacore, surface plasmon resonance (SPR) and/or BLI (biolayer interferometry, e.g. Octet assay) assay, with the latter finding particular use in many embodiments.

In addition to the parental variable heavy and variable light domains disclosed herein that form an ABD to GITR, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments.

J. OX40 Antigen Binding Domains

In some embodiments, one of the ABDs binds OX40. Suitable sets of 6 CDRs and/or vh and vl domains, as well as scFv sequences for OX40 are provided (suitable sequences are shown in FIG. 17, FIG. 72 and FIG. 73, and in SEQ ID NO: 26272-26281.

As will be appreciated by those in the art, suitable anti-OX40 ABDs can comprise a set of 6 CDRs as depicted in these sequences and Figures, either as they are underlined or, in the case where a different numbering scheme is used as described herein and as shown in Table 1, as the CDRs that are identified using other alignments within the sequences disclosed herein. Suitable ABDs can also include the entire vh and vl sequences as depicted in these sequences and Figures, used as scFvs or as Fabs. In many of the embodiments herein that contain an Fv to OX40, it is the Fab monomer that binds GITR. As discussed herein, the other of the target pair when OX40 is one of the antigens is selected from PD-1 are depicted in FIG. 3, FIG. 10, FIG. 11, FIG. 72, FIG. 73, FIG. 74, FIG. 76 and SEQ ID NO:1-2392, 3125-3144, 4697-7594 and 4697-21810, and include those sequences in the sequence listing with the identifiers 1G6_H1.279_L1.194; 1G6_H1.280_L1.224; 1G6_L1.194_H1.279; 1G6_L1.210_H1.288; and 2E9_H1L1 (which can be scFv sequences, CDR sequence sets or vh and vl sequences)), CTLA-4 (suitable sequences are depicted in FIGS. 12, 72 and 79, as well as SEQ ID NO:2393-2414 and 3737-3816 (which can be scFv sequences, CDR sequence sets or vh and vl sequences)), TIM-3 (suitable sequences are depicted in FIG. 14, FIG. 81 and SEQ ID NO: 3345-3704, 4585-4696 (which can be scFv sequences, CDR sequence sets or vh and vl sequences)), LAG-3 (suitable sequences are depicted in FIG. 13, FIG. 80 and SEQ ID NO:2415-2604, 3817-3960 (which can be scFv sequences, CDR sequence sets or vh and vl sequences)), BTLA (suitable sequences are depicted in FIGS. 82 and 84 and SEQ ID NO?3705-3736 (which can be scFv sequences, CDR sequence sets or vh and vl sequences)), and TIGIT (suitable sequences are depicted in Figure XX and SEQ ID NO:4433-4585 (which can be scFv sequences, CDR sequence sets or vh and vl sequences)).

In addition to the parental CDR sets disclosed in the sequence listing that form an ABD to OX40, the invention provides variant CDR sets. In one embodiment, a set of 6 CDRs can have 1, 2, 3, 4 or 5 amino acid changes from the parental CDRs, as long as the ABD is still able to bind to the target antigen, as measured at least one of a Biacore, surface plasmon resonance (SPR) and/or BLI (biolayer interferometry, e.g. Octet assay) assay, with the latter finding particular use in many embodiments.

In addition to the parental variable heavy and variable light domains disclosed herein that form an ABD to OX40, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments.

K. 4-1BB Antigen Binding Domains

In some embodiments, one of the ABDs binds 4-1BB. Suitable sets of 6 CDRs and/or vh and vl domains, as well as scFv sequences 4-1BB (suitable sequences are shown in FIG. 16, FIG. 72 and FIG. 73, and in SEQ ID NO:26262-2671.

As will be appreciated by those in the art, suitable anti-4-1BB ABDs can comprise a set of 6 CDRs as depicted in these sequences and Figures, either as they are underlined or, in the case where a different numbering scheme is used as described herein and as shown in Table 1, as the CDRs that are identified using other alignments within the sequences disclosed herein. Suitable ABDs can also include the entire vh and vl sequences as depicted in these sequences and Figures, used as scFvs or as Fabs. In many of the embodiments herein that contain an Fv to 4-1BB, it is the Fab monomer that binds 4-1BB. As discussed herein, the other of the target pair when ICOS is one of the antigens is selected from PD-1 are depicted in FIG. 3, FIG. 10, FIG. 11, FIG. 72, FIG. 73, FIG. 74, FIG. 76 and SEQ ID NO:1-2392, 3125-3144, 4697-7594 and 4697-21810, and include those sequences in the sequence listing with the identifiers 1G6_H1.279_L1.194; 1G6_H1.280_L1.224; 1G6_L1.194_H1.279; 1G6_L1.210_H1.288; and 2E9_H1L1 (which can be scFv sequences, CDR sequence sets or vh and vl sequences)), CTLA-4 (suitable sequences are depicted in FIGS. 12, 72 and 79, as well as SEQ ID NO:2393-2414 and 3737-3816 (which can be scFv sequences, CDR sequence sets or vh and vl sequences)), TIM-3 (suitable sequences are depicted in FIG. 14, FIG. 81 and SEQ ID NO: 3345-3704, 4585-4696 (which can be scFv sequences, CDR sequence sets or vh and vl sequences)), LAG-3 (suitable sequences are depicted in FIG. 13, FIG. 80 and SEQ ID NO:2415-2604, 3817-3960 (which can be scFv sequences, CDR sequence sets or vh and vl sequences)), BTLA (suitable sequences are depicted in FIGS. 82 and 84 and SEQ ID NO?3705-3736 (which can be scFv sequences, CDR sequence sets or vh and vl sequences)), and TIGIT (suitable sequences are depicted in Figure XX and SEQ ID NO:4433-4585 (which can be scFv sequences, CDR sequence sets or vh and vl sequences)).

In addition to the parental CDR sets disclosed in the sequence listing that form an ABD to 4-1BB, the invention provides variant CDR sets. In one embodiment, a set of 6 CDRs can have 1, 2, 3, 4 or 5 amino acid changes from the parental CDRs, as long as the ABD is still able to bind to the target antigen, as measured at least one of a Biacore, surface plasmon resonance (SPR) and/or BLI (biolayer interferometry, e.g. Octet assay) assay, with the latter finding particular use in many embodiments.

In addition to the parental variable heavy and variable light domains disclosed herein that form an ABD to 4-1BB, the invention provides variant vh and vl domains. In one embodiment, the variant vh and vl domains each can have from 1, 2, 3, 4, 5, 6, 7, 8, 9 or 10 amino acid changes from the parental vh and vl domain, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments. In another embodiment, the variant vh and vl are at least 90, 95, 97, 98 or 99% identical to the respective parental vh or vl, as long as the ABD is still able to bind to the target antigen, as measured by at least one of a Biacore, surface plasmon resonance (SPR) and/or BLI (biolayer interferometry, e.g. Octet assay) assay, with the latter finding particular use in many embodiments.

L. Specific Bispecific Embodiments

The invention provides a number of particular bispecific antibodies as outlined below.

1. ICOS X PD-1

The invention provides bispecific heterodimeric antibodies that bind ICOS and PD-1 each monovalently, and in some cases as outlined herein, both bivalently.

In one embodiment, the PD-1 ABD is 1G6_L1.194_H1.279 and the ICOS ABD is selected from sequences shown in FIG. 19, FIG. 20, FIG. 24, FIG. 68 and FIG. 77 as well as SEQ ID NO: 27869-28086, 28087-28269, 27193-27335, 28549-28556 and 28557-28665, and those with the identifiers [ICOS]_H0.66_L0 and [ICOS]_H0L0.

In one embodiment, the ICOS X PD-1 bispecific antibody is selected from XENP numbers 20261, 20730, 20896, 22432-22438, 22731-22748, 22878-22894, 22931-22932, 22950-22961, 23090-23093, 23295-23296, 23301, 23405, 23408, 23410 (all without 428L/4345, although they can have those substitutions); XENP numbers 22730, 22917-22928, 22935-22937, 22974-22979, 22995-22996, 23001, 23103, 23104 (all with 428L/4345, although they can not have those); XENP numbers 23411, 21828, 21829, 21830, 21831, 22348, 23059 (using prior art ICOS sequences); XENP numbers 18920, 24125, 24130 (additional bottle openers); XENP 23406, 23407, 24128 (ICOS x PD-1 central-scFv), XENP24123 (ICOS x PD-1 central-scFv2); XENP24134 (ICOS x PD-1 bispecific mAb) 24122 (ICOS x PD-1 DVD-Ig), XENP 24132, 24133 (ICOS x PD-1 Trident).

2. ICOS X PD-L1

In this embodiment, the ICOS ABD is selected from sequences shown in FIG. 19, FIG. 20, FIG. 24, FIG. 68 and FIG. 77 as well as SEQ ID NO: 27869-28086, 28087-28269, 27193-27335, 28549-28556 and 28557-28665, and those with the identifiers [ICOS]_H0.66_L0 and [ICOS]_H0L0.

3. ICOS X CTLA-4

In this embodiment, the ICOS ABD is selected from sequences shown in FIG. 19, FIG. 20, FIG. 24, FIG. 68 and FIG. 77 as well as SEQ ID NO: 27869-28086, 28087-28269, 27193-27335, 28549-28556 and 28557-28665, and those with the identifiers [ICOS]_H0.66_L0 and [ICOS]_H0L0.

In one embodiment, a bottle opener format with a Fab ICOS ABD of [ICOS]H0.66_L0 is paired with a scFv CTLA-4 ABD of [CTLA-4]_H3.32_L0.129, particularly in bottle opener backbone 1 from FIG. 9.

4. ICOS X LAG-3

In this embodiment, the ICOS ABD is selected from sequences shown in FIG. 19, FIG. 20, FIG. 24, FIG. 68 and FIG. 77 as well as SEQ ID NO: 27869-28086, 28087-28269, 27193-27335, 28549-28556 and 28557-28665, and those with the identifiers [ICOS]_H0.66_L0 and [ICOS]_H0L0.

5. ICOS X TIM-3

I this embodiment, the ICOS ABD is selected from sequences shown in FIG. 19, FIG. 20, FIG. 24, FIG. 68 and FIG. 77 as well as SEQ ID NO: 27869-28086, 28087-28269, 27193-27335, 28549-28556 and 28557-28665, and those with the identifiers [ICOS]_H0.66_L0 and [ICOS]_H0L0.

M. Homologous Antibodies

The invention further provides antibodies that share amino acid sequence identity with the antibodies outlined herein.

In one embodiment, bispecific antibodies are made that have amino acid variants in one or more of the CDRs of the Vh and V1 sequences outlined herein and in the Figures. In one embodiment, antibodies are provided that have 1, 2, 3, 4 or 5 amino acid differences in one or more of the CDRs of the vh and vl chains outlined herein. These amino acid variants can be in one CDR or spread out between more than one CDR. These amino acid variants can also be in one or both of the Fvs of the bispecific antibody; e.g. there can be 2 amino acid variants in CDRs on the ICOS Fv side (generally a Fab but can be a scFv as outlined herein) and one on the PD-1 side, etc.

Similarly, the invention provides for antibodies that have at least 95, 96, 97 98 or 99% amino acid identity to the sequences outlined herein, and particularly in the variable heavy and/or variable light domains. This sequence identity can also be on one Fv or both Fv of the bispecific antibodies. That is, bispecific antibodies are provided that are 95-99% identical to the variable heavy and/or variable light domains outlined in the figures.

IX. Nucleic Acids of the Invention

The invention further provides nucleic acid compositions encoding the bispecific antibodies of the invention (or, in the case of "monospecific" antibodies, nucleic acids encoding those as well).

As will be appreciated by those in the art, the nucleic acid compositions will depend on the format and scaffold of the heterodimeric protein. Thus, for example, when the format requires three amino acid sequences, three nucleic acid sequences can be incorporated into one or more expression vectors for expression. Similarly, some formats (e.g. dual scFv formats such as disclosed in FIG. 2) only two nucleic acids are needed; again, they can be put into one or two expression vectors. Some formats need 4 amino acids (bispecific mAbs).

As is known in the art, the nucleic acids encoding the components of the invention can be incorporated into expression vectors as is known in the art, and depending on the host cells used to produce the heterodimeric antibodies of the invention. Generally, the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with mammalian cells (e.g. CHO cells), finding use in many embodiments.

In some embodiments, nucleic acids encoding each monomer and the optional nucleic acid encoding a light chain, as applicable depending on the format, are each contained within a single expression vector, generally under different or the same promoter controls. In embodiments of particular use in the present invention, each of these two or three nucleic acids are contained on a different expression vector. As shown herein and in 62/025,931, hereby incorporated by reference, different vector ratios can be used to drive heterodimer formation. That is, surprisingly, while the proteins comprise first monomer:second monomer:light chains (in the case of many of the embodiments herein that have three polypeptides comprising the heterodimeric antibody) in a 1:1:2 ratio, these are not the ratios that give the best results.

The heterodimeric antibodies of the invention are made by culturing host cells comprising the expression vector(s) as is well known in the art. Once produced, traditional antibody purification steps are done, including an ion exchange chromotography step. As discussed herein, having the pIs of the two monomers differ by at least 0.5 can allow separation by ion exchange chromatography or isoelectric focusing, or other methods sensitive to isoelectric point. That is, the inclusion of pI substitutions that alter the isoelectric point (pI) of each monomer so that such that each monomer has a different pI and the heterodimer also has a distinct pI, thus facilitating isoelectric purification of the "triple F" heterodimer (e.g., anionic exchange columns, cationic exchange columns). These substitutions also aid in the determination and monitoring of any contaminating dual scFv-Fc and mAb homodimers post-purification (e.g., IEF gels, cIEF, and analytical IEX columns).

X. Biological and Biochemical Functionality of the Heterodimeric Immunomodulatory Antibodies Generally the bispecific immunomodulatory antibodies of the invention are administered to patients with cancer, and efficacy is assessed, in a number of ways as described herein. Thus, while standard assays of efficacy can be run, such as cancer load, size of tumor, evaluation of presence or extent of metastasis, etc., immuno-oncology treatments can be assessed on the basis of immune status evaluations as well. This can be done in a number of ways, including both in vitro and in vivo assays. For example, evaluation of changes in immune status (e.g. presence of ICOS+CD4+ T cells following ipi treatment) along with "old fashioned" measurements such as tumor burden, size, invasiveness, LN involvement, metastasis, etc. can be done. Thus, any or all of the following can be evaluated: the inhibitory effects of PVRIG on CD4$^+$ T cell activation or proliferation, CD8$^+$ T (CTL) cell activation or proliferation, CD8$^+$ T cell-mediated cytotoxic activity and/or CTL mediated cell depletion, NK cell activity and NK mediated cell depletion, the potentiating effects of PVRIG on Treg cell differentiation and proliferation and Treg- or myeloid derived suppressor cell (MDSC)-mediated immunosuppression or immune tolerance, and/or the effects of PVRIG on proinflammatory cytokine production by immune cells, e.g., IL-2, IFN-γ or TNF-α production by T or other immune cells.

In some embodiments, assessment of treatment is done by evaluating immune cell proliferation, using for example, CFSE dilution method, Ki67 intracellular staining of immune effector cells, and 3H-Thymidine incorporation method, In some embodiments, assessment of treatment is done by evaluating the increase in gene expression or increased protein levels of activation-associated markers, including one or more of: CD25, CD69, CD137, ICOS, PD1, GITR, OX40, and cell degranulation measured by surface expression of CD107A.

In general, gene expression assays are done as is known in the art.

In general, protein expression measurements are also similarly done as is known in the art.

In some embodiments, assessment of treatment is done by assessing cytotoxic activity measured by target cell viability detection via estimating numerous cell parameters such as enzyme activity (including protease activity), cell membrane permeability, cell adherence, ATP production, co-enzyme production, and nucleotide uptake activity. Specific examples of these assays include, but are not limited to, Trypan Blue or PI staining, $^{51}$Cr or $^{35}$S release method, LDH activity, MTT and/or WST assays, Calcein-AM assay, Luminescent based assay, and others.

In some embodiments, assessment of treatment is done by assessing T cell activity measured by cytokine production, measure either intracellularly in culture supernatant using cytokines including, but not limited to, IFNγ, TNFα, GM-CSF, IL2, IL6, IL4, IL5, IL10, IL13 using well known techniques.

Accordingly, assessment of treatment can be done using assays that evaluate one or more of the following: (i) increases in immune response, (ii) increases in activation of αβ and/or γδ T cells, (iii) increases in cytotoxic T cell activity, (iv) increases in NK and/or NKT cell activity, (v) alleviation of αβ and/or γδ T-cell suppression, (vi) increases in pro-inflammatory cytokine secretion, (vii) increases in IL-2 secretion; (viii) increases in interferon-γ production, (ix) increases in Th1 response, (x) decreases in Th2 response, (xi) decreases or eliminates cell number and/or activity of at least one of regulatory T cells (Tregs.

Assays to Measure Efficacy

In some embodiments, T cell activation is assessed using a Mixed Lymphocyte Reaction (MLR) assay as is known in the art. An increase in activity indicates immunostimulatory activity. Appropriate increases in activity are outlined below.

In one embodiment, the signaling pathway assay measures increases or decreases in immune response as measured for an example by phosphorylation or de-phosphorylation of different factors, or by measuring other post translational modifications. An increase in activity indicates immunostimulatory activity. Appropriate increases in activity are outlined below.

In one embodiment, the signaling pathway assay measures increases or decreases in activation of αβ and/or γδ T cells as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in cytotoxic T cell activity as measured for an example by direct killing of target cells like for an example cancer cells or by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in NK and/or NKT cell activity as measured for an example by direct killing of target cells like for an example cancer cells or by cytokine secretion or by changes in expression of activation markers like for an example CD107a, etc. An increase in activity indicates immunostimulatory activity. Appropriate increases in activity are outlined below.

In one embodiment, the signaling pathway assay measures increases or decreases in αβ and/or γδ T-cell suppression, as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in pro-inflammatory cytokine secretion as measured for example by ELISA or by Luminex or by Multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in IL-2 secretion as measured for example by ELISA or by Luminex or by Multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in interferon-γ production as measured for example by ELISA or by Luminex or by Multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in Th1 response as measured for an example by cytokine secretion or by changes in expression of activation markers. An increase in activity indicates immunostimulatory activity. Appropriate increases in activity are outlined below.

In one embodiment, the signaling pathway assay measures increases or decreases in Th2 response as measured for an example by cytokine secretion or by changes in expression of activation markers. An increase in activity indicates immunostimulatory activity. Appropriate increases in activity are outlined below.

In one embodiment, the signaling pathway assay measures increases or decreases cell number and/or activity of at least one of regulatory T cells (Tregs), as measured for example by flow cytometry or by IHC. A decrease in response indicates immunostimulatory activity. Appropriate decreases are the same as for increases, outlined below.

In one embodiment, the signaling pathway assay measures increases or decreases in M2 macrophages cell numbers, as measured for example by flow cytometry or by IHC. A decrease in response indicates immunostimulatory activity. Appropriate decreases are the same as for increases, outlined below.

In one embodiment, the signaling pathway assay measures increases or decreases in M2 macrophage pro-tumorigenic activity, as measured for an example by cytokine secretion or by changes in expression of activation markers. A decrease in response indicates immunostimulatory activity. Appropriate decreases are the same as for increases, outlined below.

In one embodiment, the signaling pathway assay measures increases or decreases in N2 neutrophils increase, as measured for example by flow cytometry or by IHC. A decrease in response indicates immunostimulatory activity. Appropriate decreases are the same as for increases, outlined below.

In one embodiment, the signaling pathway assay measures increases or decreases in N2 neutrophils pro-tumorigenic activity, as measured for an example by cytokine secretion or by changes in expression of activation markers. A decrease in response indicates immunostimulatory activity. Appropriate decreases are the same as for increases, outlined below.

In one embodiment, the signaling pathway assay measures increases or decreases in inhibition of T cell activation, as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in inhibition of CTL activation as measured for an example by direct killing of target cells like for an example cancer cells or by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in $\alpha\beta$ and/or $\gamma\delta$ T cell exhaustion as measured for an example by changes in expression of activation markers. A decrease in response indicates immunostimulatory activity. Appropriate decreases are the same as for increases, outlined below.

In one embodiment, the signaling pathway assay measures increases or decreases $\alpha\beta$ and/or $\gamma\delta$ T cell response as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in stimulation of antigen-specific memory responses as measured for an example by cytokine secretion or by proliferation or by changes in expression of activation markers like for an example CD45RA, CCR7 etc. An increase in activity indicates immunostimulatory activity. Appropriate increases in activity are outlined below.

In one embodiment, the signaling pathway assay measures increases or decreases in apoptosis or lysis of cancer cells as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases in stimulation of cytotoxic or cytostatic effect on cancer cells. as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases direct killing of cancer cells as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases Th17 activity as measured for an example by cytokine secretion or by proliferation or by changes in expression of activation markers. An increase in activity indicates immunostimulatory activity. Appropriate increases in activity are outlined below.

In one embodiment, the signaling pathway assay measures increases or decreases in induction of complement dependent cytotoxicity and/or antibody dependent cell-mediated cytotoxicity, as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, T cell activation is measured for an example by direct killing of target cells like for an example cancer cells or by cytokine secretion or by proliferation or by changes in expression of activation markers like for an example CD137, CD107a, PD1, etc. For T-cells, increases in proliferation, cell surface markers of activation (e.g. CD25, CD69, CD137, PD1), cytotoxicity (ability to kill target cells), and cytokine production (e.g. IL-2, IL-4, IL-6, IFN$\gamma$, TNF-a, IL-10, IL-17A) would be indicative of immune modulation that would be consistent with enhanced killing of cancer cells.

In one embodiment, NK cell activation is measured for example by direct killing of target cells like for an example cancer cells or by cytokine secretion or by changes in expression of activation markers like for an example CD107a, etc. For NK cells, increases in proliferation, cytotoxicity (ability to kill target cells and increases CD107a, granzyme, and perforin expression), cytokine production (e.g. IFN$\gamma$ and TNF), and cell surface receptor expression (e.g. CD25) would be indicative of immune modulation that would be consistent with enhanced killing of cancer cells.

In one embodiment, $\gamma\delta$ T cell activation is measured for example by cytokine secretion or by proliferation or by changes in expression of activation markers.

In one embodiment, Th1 cell activation is measured for example by cytokine secretion or by changes in expression of activation markers.

Appropriate increases in activity or response (or decreases, as appropriate as outlined above), are increases of 10%, 20%, 30%, 40%, 50%, 60%, 70%, 80%, 90%, 95% or 98 to 99% percent over the signal in either a reference sample or in control samples, for example test samples that do not contain an anti-PVRIG antibody of the invention. Similarly, increases of at least one-, two-, three-, four- or five-fold as compared to reference or control samples show efficacy.

XI. Treatments

Once made, the compositions of the invention find use in a number of oncology applications, by treating cancer, generally by inhibiting the suppression of T cell activation (e.g. T cells are no longer suppressed) with the binding of the bispecific immunomodulatory antibodies of the invention.

Accordingly, the heterodimeric compositions of the invention find use in the treatment of these cancers.

XII. Antibody Compositions for In Vivo Administration

Formulations of the antibodies used in accordance with the present invention are prepared for storage by mixing an antibody having the desired degree of purity with optional pharmaceutically acceptable carriers, excipients or stabilizers (as generally outlined in Remington's Pharmaceutical Sciences 16th edition, Osol, A. Ed. [1980]), in the form of lyophilized formulations or aqueous solutions. Acceptable carriers, buffers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Administrative Modalities

The antibodies and chemotherapeutic agents of the invention are administered to a subject, in accord with known methods, such as intravenous administration as a bolus or by continuous infusion over a period of time.

Treatment Modalities

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the bispecific antibodies used in the present invention depend on the disease or condition to be treated and may be determined by the persons skilled in the art.

An exemplary, non-limiting range for a therapeutically effective amount of an bispecific antibody used in the present invention is about 0.1-100 mg/kg.

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

XIII. Examples

Examples are provided below to illustrate the present invention. These examples are not meant to constrain the present invention to any particular application or theory of operation. For all constant region positions discussed in the present invention, numbering is according to the EU index as in Kabat (Kabat et al., 1991, Sequences of Proteins of Immunological Interest, 5th Ed., United States Public Health Service, National Institutes of Health, Bethesda, entirely incorporated by reference). Those skilled in the art of antibodies will appreciate that this convention consists of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

General and specific scientific techniques are outlined in US Publications 2015/0307629, 2014/0288275 and WO2014/145806, all of which are expressly incorporated by reference in their entirety and particularly for the techniques outlined therein.

A. Example 1: TILs from Multiple Cancer Types Co-Express PD-1 and T Cell Costimulatory Receptors To investigate potential associations between PD-1 and various T cell costimulatory receptors, RNA sequencing data from The Cancer Genome Atlas project (TCGA) were used for analysis. V2 RSEM data were downloaded from FireBrowse (http://firebrowse.org/). Analysis was performed using R with custom routines. The correlation between the expression of PD-1 and eight costimulatory receptors is depicted in FIG. 1, along with calculated R2 values (square of the Pearson correlation coefficient). The data show that PD-1 and several costimulatory receptors were co-expressed in cancers including bladder, breast, colon, head & neck, kidney, lung-adeno, lung squamous, ovarian, pancreatic, prostate, and melanoma cancer. Notably, expression of ICOS on TILs correlates better with that of PD-1 than several other costims.

B. Example 2: Immune Checkpoint Antigen Binding Domains 1. 2A: anti-PD-1 ABDs Examples of antibodies which bind PD-1 were generated in bivalent IgG1 format with E233P/L234V/L235A/G236del/S267K substitutions, illustrative sequences for which are depicted in FIG. 10. DNA encoding the variable regions was generated by gene synthesis and was inserted into the mammalian expression vector pTT5 by the Gibson Assembly method. Heavy chain VH genes were inserted via Gibson Assembly into pTT5 encoding the human IgG1 constant region with the substitutions mentioned above. Light chains VL genes were inserted into pTT5 encoding the human C? constant region. DNA was transfected into HEK293E cells for expression. Additional PD-1 ABDs (including those derived from the above antibodies) were formatted as Fabs and scFvs for use in costim/checkpoint bispecific antibodies, illustrative sequences for which are depicted respectively in FIG. 11 and in the sequence listing.

2. 2B: anti-CTLA-4 ABDs

Antibodies which bind CTLA-4 were generated in bivalent IgG1 format with E233P/L234V/L235A/G236del/S267K substitutions. DNA encoding the variable regions was generated by gene synthesis and was inserted into the mammalian expression vector pTT5 by the Gibson Assembly method. Heavy chain VH genes were inserted via Gibson Assembly into pTT5 encoding the human IgG1 constant region with the substitutions mentioned above. Light chains VL genes were inserted into pTT5 encoding the human C? constant region. DNA was transfected into HEK293E cells for expression. Additional CTLA-4 ABDs (including those derived from the above antibodies) were formatted as scFvs for use in costim/checkpoint bispecific antibodies, illustrative sequences for which are depicted in FIG. 12 and in the sequence listing.

3. 2C: anti-LAG-3 ABDs

Examples of antibodies which bind LAG-3 were generated in bivalent IgG1 format with E233P/L234V/L235A/G236del/S267K substitutions. DNA encoding the variable regions was generated by gene synthesis and was inserted into the mammalian expression vector pTT5 by the Gibson Assembly method. Heavy chain VH genes were inserted via Gibson Assembly into pTT5 encoding the human IgG1 constant region with the substitutions mentioned above. Light chains VL genes were inserted into pTT5 encoding the human C? constant region. DNA was transfected into HEK293E cells for expression. Additional LAG-3 ABDs (including those derived from the above antibodies) were formatted as Fabs for use in costim/checkpoint bispecific antibodies, illustrative sequences for which are depicted in FIG. 13 and in the sequence listing.

4. 2D: anti-TIM-3 ABDs

Examples of antibodies which bind TIM-3 were generated in bivalent IgG1 format with E233P/L234V/L235A/G236del/S267K substitutions, exemplary sequences for which are depicted in FIG. 14. DNA encoding the variable regions was generated by gene synthesis and was inserted into the mammalian expression vector pTT5 by the Gibson Assembly method. Heavy chain VH genes were inserted via Gibson Assembly into pTT5 encoding the human IgG1 constant region with the substitutions mentioned above. Light chains VL genes were inserted into pTT5 encoding the human C? constant region. DNA was transfected into HEK293E cells for expression. The above antibodies were formatted as Fabs for use in costim/checkpoint bispecific antibodies.

5. 2E: anti-PD-L1 ABDs

Prototype antibodies which bind PD-L1 were generated in bivalent IgG1 format with E233P/L234V/L235A/G236del/S267K substitutions, exemplary sequences for which are depicted in FIG. 15. DNA encoding the variable regions was generated by gene synthesis and was inserted into the mammalian expression vector pTT5 by the Gibson Assembly method. Heavy chain VH genes were inserted via Gibson Assembly into pTT5 encoding the human IgG1 constant region with the substitutions mentioned above. Light chains VL genes were inserted into pTT5 encoding the human C? constant region. DNA was transfected into HEK293E cells for expression. The above antibodies were formatted as Fabs and scFvs for use in costim/checkpoint bispecific antibodies.

C. Example 3: Costimulatory Receptor Antigen Binding Domains

Prototype costimulatory receptor antibodies which bind ICOS, GITR, OX40, and 4-1BB were generated in bivalent IgG1 format with E233P/L234V/L235A/G236del/S267K substitutions, sequences for which are depicted in FIGS. 16-19. DNA encoding the variable regions was generated by gene synthesis and was inserted into the mammalian expression vector pTT5 by the Gibson Assembly method. Heavy chain VH genes were inserted via Gibson Assembly into pTT5 encoding the human IgG1 constant region with the substitutions mentioned above. Light chains VL genes were inserted into pTT5 encoding the human C? constant region. DNA was transfected into HEK293E cells for expression. The above antibodies were formatted as Fabs or scFvs for use in costim/checkpoint bispecific antibodies.

D. Example 4: Engineering Anti-ICOS ABD for Stability and Affinity

The parental variable region of an anti-ICOS antibody (XENP16435; depicted in FIG. 19) was engineered for use as a component in an ICOS x checkpoint bispecific antibody. A library of Fv variants engineered to have optimal affinity and stability was constructed by site-directed mutagenesis (QuikChange, Stratagene, Cedar Creek, Tx.) or additional gene synthesis and subcloning in Fab-His and scFv-His formats and produced as described below.

1. 4A: anti-ICOS Fabs

Amino acid sequences for variant anti-ICOS Fabs are listed in FIG. 20 (the polyhistidine (His6 (SEQ ID NO: 28666)) tags have been removed from the C-terminal of the Fab heavy chains). DNA encoding the two chains needed for Fab expression were generated by gene synthesis and were subcloned using standard molecular biology techniques into the expression vector pTT5. The Fab heavy chain included a C-terminal polyhistidine tag. DNA was transfected into HEK293E cells for expression and resulting proteins were purified from the supernatant using Ni-NTA chromatography. The resultant anti-ICOS Fabs were characterized for stability and affinity.

Differential Scanning Fluorimetry (DSF) experiments were performed using a Bio-Rad CFX Connect Real-Time PCR Detection System. Proteins were mixed with SYPRO Orange fluorescent dye and diluted to 0.2 mg/mL in PBS. The final concentration of SYPRO Orange was 10×. After an initial 10 minute incubation period at 25° C., proteins were heated from 25 to 95° C. using a heating rate of 1° C./min. A fluorescence measurement was taken every 30 seconds. Melting temperatures (Tm) were calculated using the instrument software. The results are shown in FIG. 21.

A series of affinity screens of the anti-ICOS Fabs to human ICOS were performed using Octet, a BioLayer Interferometry (BLI)-based method. Experimental steps for Octet generally included the following: Immobilization (capture of ligand or test article onto a biosensor); Association (dipping of ligand- or test article-coated biosensors into wells containing serial dilutions of the corresponding test article or ligand); and Dissociation (returning of biosensors to well containing buffer) in order to determine the monovalent affinity of the test articles. Specifically, anti-mouse Fc (AMC) biosensors were used to capture mouse IgG2a Fc fusion of ICOS and dipped into multiple concentrations of the test articles. The resulting equilibrium dissociation constants (KD), association rates (ka), and dissociation rates (kd) are presented in Figures FIG. 22 and FIG. 23. Binding affinities and kinetic rate constants were obtained by analyzing the processed data using a 1:1 binding model using ForteBio Octet Data Analysis software (ForteBio). The data from a two separate experiments are depicted in FIG. 22A-B. In a further experiment, streptavidin (SA) biosensors were used to capture ICOS-TEV-Fc-Avi and dipped into the test articles. The data are depicted in FIG. 23. A number of variant anti-ICOS Fabs including XENP22780, XENP22782, XENP22783, and XENP22784 had improved stability while maintaining affinity characteristics similar to a Fab comprising the parental variable regions (XENP22050).

2. 4B: anti-ICOS scFvs

Amino acid sequences for anti-ICOS scFvs are listed in FIG. 24 (the polyhistidine (His6 (SEQ ID NO: 28666)) tags have been removed from the C-terminal of the scFvs). DNA encoding the scFv was generated by gene synthesis and were subcloned using standard molecular biology techniques into the expression vector pTT5. The scFv included a C-terminal polyhistidine tag. DNA was transfected into HEK293E cells for expression and resulting proteins were purified from the supernatant using Ni-NTA chromatography. The resultant anti-ICOS scFvs were characterized for stability in DSF experiments as described above. The data is depicted in FIG. 25.

E. Example 5: Anti-ICOS x Anti-PD-1 Bispecific Antibodies 1. 5A: Prototype Costim/Checkpoint Bottle-Openers Schematics for costim/checkpoint bispecific antibody in the bottle-opener format are depicted as FIG. 2A. Prototype bottle-openers with costimulatory receptor binding Fab arms based on prototype anti-GITR mAb (XENP16438), anti-OX40 mAb (XENP16437), anti-4-1BB mAb (XENP14410) and anti-ICOS mAb (XENP16435) and exemplary anti-PD-1 scFv (XENP19692) arm were produced to investigate their effect on cytokine secretion in an SEB-stimulated PBMC assay. Sequences are depicted in FIG. 26. DNA encoding the three chains needed for bottle-opener expression were generated by gene synthesis and were subcloned using standard molecular biology techniques into the expression vector pTT5. DNA transfected into HEK293E cells for expression and resulting proteins were purified using standard techniques.

a. 5A(a): Prototype Anti-ICOS x Anti-PD-1 Bottle-Opener Enhances Cytokine Secretion Staphylococcal Enterotoxin B (SEB) is a superantigen that causes T cell activation and proliferation in a manner similar to that achieved by activation via the T cell receptor (TCR). Stimulating human PBMC with SEB is a common method for assaying T cell activation and proliferation. PBMCs were simulated with 100 ng/mL SEB for 2 days. Cells were washed twice and restimulated with 100 ng/mL SEB in combination with 20 µg/mL of the indicated test articles. A first bivalent anti-PD-1 antibody based on nivolumab (XENP16432), a second bivalent anti-PD-1 mAb (XENP19686), and a bivalent anti-RSV mAb (XENP15074) were used as controls. 24 hours after treatment, supernatants were assayed for IL-2. The data depicted in FIG. 27 show that each of the costim/checkpoint bottle-openers enhanced cytokine secretion in comparison to the bivalent anti-RSV antibody. Surprisingly, induction of cytokine secretion by XENP22730 is vastly superior to cytokine secretion by bivalent anti-PD-1 antibody alone as well as the other prototype costim/checkpoint bottle-openers, indicating that addition of ICOS binding enhances cytokine production and that ICOS is a better PD-1 partner than other costimulatory receptors for a bispecific antibody.

In another experiment, PBMCs were stimulated with 0.01 µg/mL SEB for 3 days with 20 µg/mL of indicated test articles. As control, test articles were also incubated with naive (non-SEB stimulated) PBMCs. 3 days after treatment, supernatant was assessed for IL-2 secretion as an indicator of T cell activation (depicted in FIG. 28). The data show that neither the anti-PD-1 bivalent antibody nor the anti-ICOS x anti-PD-1 bottle-opener stimulate IL-2 secretion in naive cells. Further, the data show again that XENP20896 enhances IL-2 secretion more than the bivalent anti-PD-1 antibody alone does and that XENP20896 enhances IL-2 secretion more than combination of bivalents (XENP16432 and XENP16435) as well as combination of one-arms (XENP20111 and XENP20266) do.

Costimulatory receptors such as ICOS have previously been found to induce cytokine production only following crosslinking by bivalent antibodies or multimerized ligands (Viera et al. 2004; Sanmamed et al. 2015). In view of the crosslinking mechanisms, it is surprising that monovalent ICOS binding by a single arm in a costim x checkpoint blockade bispecific antibody was able to enhance cytokine production. Further, it is notable that the bispecific antibody was able to enhance cytokine secretion more than bivalent anti-PD-1 mAb in combination with bivalent anti-ICOS mAb (XENP16432+ XENP16435).

b. 5A(b): PD-1 and ICOS Double-Positive Cells are Selectively Occupied by Prototype Anti-ICOS x Anti-PD-1 Bottle-Opener Selective targeting of tumor-reactive TILs co-expressing immune checkpoint receptors (e.g. PD-1) and costimulatory receptors as shown in Example 1 over non-tumor reactive T cells expressing immune checkpoint receptors or costimulatory receptors alone could enhance anti-tumor activity while avoiding peripheral toxicity (as depicted in FIG. 29).

An SEB-stimulated PBMC assay was used to investigate binding of anti-ICOS x anti-PD-1 bottle-opener to T cells. PBMCs were stimulated with 100 ng/mL SEB (staphylococcal enterotoxin B) for 3 days, after which the PBMCs were treated with the indicated test articles for 30 minutes at 4° C. PBMCs were then incubated with APC-labeled one-arm anti-ICOS antibody and FITC-labeled one-arm anti-PD-1 antibody for 30 minutes at 4° C. FIG. 30 and FIG. 31 shows receptor occupancy of a prototype anti-ICOS x anti-PD-1 bottle-opener (XENP20896), one-arm anti-ICOS antibody (XENP20266) and one-arm anti-PD-1 antibody (XENP20111).

The data show that double-positive cells (expressing both PD-1 and ICOS) are selectively occupied by the anti-ICOS x anti-PD-1 bottle-opener (XENP20896) as depicted in FIG. 30, indicating that monovalent ICOS and PD-1 binding is useful for selective targeting. Further, anti-ICOS x anti-PD-1 bottle-opener (e.g. XENP20896) binds more potently to double-positive cells than monovalent, monospecific one-arm anti-PD-1 and anti-ICOS as shown in FIG. 31A.

c. 5A(c): Prototype Anti-ICOS x Anti-PD-1 Bottle-Opener Enhance Engraftment in a GVHD Mouse Study The prototype anti-ICOS x anti-PD-1 bottle-opener was evaluated in a Graft-versus-Host Disease (GVHD) model conducted in NSG (NOD-SCID-gamma) immunodeficient mice. The mice were engrafted with human PBMCs. When NSG mice are injected with human PBMCs, they develop an autoimmune response against the human PBMCs. Treatment of NSG mice injected with human PBMCs with immune checkpoint antibodies (e.g. anti-PD-1) enhance engraftment. Thus, increased engraftment shows efficacy of the antibodies.

10 million human PBMCs were engrafted into NSG mice via IV-OSP on Day 0 followed by dosing with the indicated test articles on Day 1, 8, 15, and 22. Human CD45+ cell counts were measured on Day 14 as an indicator of disease.

The data depicted in Figure A show that the anti-ICOS x anti-PD-1 bottle-opener enhance proliferation of CD45+ cells in human PBMC-engrafted NSG mice as compared to controls (PBS and PBS+PBMC). Further, enhancement is greater using antibodies of the invention than that seen with bivalent anti-PD-1 antibody.

2. 5B: Production of Variant Anti-ICOS x Anti-PD-1 Bottle-Openers with Optimized Anti-ICOS Fab Arms Variant anti-ICOS x anti-PD-1 bottle-openers comprising anti-ICOS Fabs engineered as described in Example 4A were produced as generally described above. Amino acid sequences for variant anti-ICOS x anti-PD-1 bottle-openers are listed in FIG. 32. Amino acid sequences for variant anti-ICOS x anti-PD-1 with FcRn pH 6.0 affinity enhancing substitutions are listed in FIG. 33.

The resultant anti-ICOS x anti-PD-1 bispecific antibodies were characterized for affinity to human and cynomolgus ICOS using Octet as generally described above. In a first set of experiments, AMC biosensors were used to capture mouse IgG2a Fc fusion of ICOS and dipped into multiple concentrations of the test articles (data depicted in FIG. 34). In further experiments, streptavidin (SA or SAX) biosensors were used to capture biotinylated human and cynomolgus IgG1 Fc fusions of human and cynomolgus ICOS and dipped into multiple concentrations of the test articles (data depicted in FIG. 35).

3. 5C: T Cell Surface Binding of Variant Anti-ICOS x Anti-PD-1 Bottle-Openers

Binding of anti-ICOS x anti-PD-1 bispecifics to T cells was measured in an SEB-stimulated PBMC assay. Human PBMCs were stimulated with 100 ng/mL SEB for 3 days. PBMCs were then treated with the indicated test articles and incubated at 4° C. for 30 minutes. After treatment, cells were incubated with FITC-labeled anti-CD3 antibody and APC-labeled anti-human IgG Fc secondary antibody. MFI on CD3+ cells are depicted in FIG. 36A-B.

4. 5D: Receptor Occupancy of Variant Anti-ICOS x Anti-PD-1 Bottle-Openers on T Cells Receptor occupancy of variant anti-ICOS x anti-PD-1 bottle-openers on T cells was measured in an SEB-stimulated PBMC assay. PBMCs were stimulated with 100 ng/mL SEB (staphylococcal enterotoxin B) for 3 days, after which the PBMCs were treated with the indicated test articles for 30 minutes at 4° C. PBMCs were then incubated with APC-labeled one-arm anti-ICOS antibody and FITC-labeled one-arm anti-PD-1 antibody for 30 minutes at 4° C. FIG. 37 depicts the receptor occupancy of variant anti-ICOS x anti-PD-1 bispecific antibodies, corresponding one-arm anti-ICOS antibodies and one-arm anti-PD-1 antibody (XENP20111) on PD-1 and ICOS double-positive T cells. Consistent with the prototype antibodies investigated in Example 1A, each of the bottle-openers binds more potently to double-positive cells than monovalent, monospecific one-arm anti-PD-1 and one-arm anti-ICOS antibodies.

5. 5E: In Vitro Activity of Variant Anti-ICOS x Anti-PD-1 Bottle-Openers in a Cytokine Release Assay Human PBMCs were stimulated with 100 ng/mL SEB for 2 days. Cells were washed and stimulated again with 100 ng/mL SEB in combination with 20 µg/mL of indicated test articles. 24 hours after treatment, cells were assayed for IL-2 (FIG. 38A) and IFN? (FIG. 38B). The data show that anti-ICOS x anti-PD-1 bottle-openers stimulated significantly more cytokine release than bivalent anti-PD-1 antibody (XENP16432) alone, bivalent anti-ICOS antibody (XENP16435) alone, or bivalent anti-PD-1 antibody plus bivalent anti-ICOS antibody in combination.

In a further experiment, human PBMCs were stimulated with 100 ng/mL SEB for 2 days. Cells were washed and stimulated again with 100 ng/mL SEB in combination with 20 µg/mL of indicated test articles. 24 hours after treatment, cells were assayed for IL-2 (FIG. 39A) and IFN? (FIG. 39B).

6. 5F: In Vivo Activity of Variant Anti-ICOS x Anti-PD-1 Bottle Openers in a GVHD Mouse Study In a first study, 10 million human PBMCs were engrafted into NSG mice via IV-OSP on Day 0 followed by dosing with the indicated test articles on Day 1. IFN? levels and human CD45+, CD8+ T cell and CD4+ T cell counts were measured on Day 7, 11 and 14. FIGS. 40A-B respectively depicts IFN? levels on Day 7 and 11. FIGS. 41A-B respectively depict CD45+ cell counts on Day 11 and 14. FIGS. 42A-B respectively depict CD8+ T cell and CD4+ T cell counts on Day 14. FIG. 43 depicts the change in body weight in the mice by Day 14 resulting from exacerbation of GVHD due to T cell expansion and IFN? production.

In a further study with additional variant anti-ICOS x anti-PD-1 bottle-openers, 10 million human PBMCs were engrafted into NSG mice via IV-OSP on Day 0 followed by dosing with the indicated test articles at indicated concentrations on Day 1. IFNγ levels and human CD45+, CD8+ T cell and CD4+ T cell counts were measured on Day 7 and 14. FIG. 44A-B respectively depicts IFN? levels on Day 7 and 14. FIG. 45 depicts CD45+ cell count on Day 14. FIG. 46A-C respectively depict CD8+ T cell count, CD4+ T cell counts and CD8+/CD4+ ratio on Day 14. Body weight of mice were also measured on Day 12 and 15 and depicted respectively in FIG. 47A-B as percentage of initial body weight.

The Figures show that the anti-ICOS x anti-PD-1 bottle-openers enhance engraftment (as indicated by the proliferation of CD45+ cells, CD8+ T cells and CD4+ T cells and decrease in body weight of mice). The observed activity is correlated to the in vitro potency of each variant. Further, a number of the bottle-openers including XENP20896, XENP22744, XENP23092, XENP22730, XENP23104, XENP22974, and XENP23411 enhance engraftment much more than the control bivalent anti-PD-1 antibody (XENP16432) does.

7. 5G: Additional Anti-ICOS ABDs Work in Anti-ICOS x Anti-PD-1 Bottle Opener

Additional anti-ICOS x anti-PD-1 bottle-openers were produced comprising anti-ICOS Fabs based on other anti-ICOS ABDs described in Example 3 as generally described above. Sequences for the additional bottle-openers are depicted in FIG. 48.

In a first experiment, PBMCs were stimulated with 100 ng/mL SEB for 2 days. Cells were washed twice and restimulated with 100 ng/mL SEB in combination with 20 µg/mL of indicated test articles (PBS as control). 24 hours after treatment, supernatants were assayed for IL-2 concentration as depicted in FIG. 49. In a second experiment, PBMCs were stimulated with 10 ng/mL SEB and treated with 20 µg/mL of indicated test articles for 3 days (bivalent anti-PD-1 XENP16432 as control). Supernatants were collected and assays for IL-2. FIG. 50 depicts the fold induction in IL-2 over bivalent anti-RSV mAb.

Consistent with the data in Example 5A(a), XENP20896 stimulated secretion of IL-2. Notably, the additional bottle-openers comprising alternative anti-ICOS ABDs were also able to stimulate secretion of IL-2 demonstrating that the enhancement of cytokine secretion by an anti-ICOS x anti-PD-1 bottle-opener is not unique to ABDs derived from the parental anti-ICOS ABD described in Example 4.

8. 5H: Clear ICOS Signature is Exhibited by Anti-ICOS x Anti-PD-1 Bottle-Openers a. 5H(a): Anti-ICOS x Anti-PD-1 Bispecific Antibodies Induce AKT Phosphorylation ICOS ligation induces AKT phosphorylation in activated T cells (Fos, C et al. 2008), and as such, AKT phosphorylation would be an indicator of ICOS agonism by anti-ICOS x anti-PD-1 bispecific antibodies of the invention.

Human PBMCs were stimulated with 100 ng/mL SEB for 2 days. Following stimulation, CD3+ cells were isolated by negative selection using EasySep™ Human T Cell Enrichment Kit (STEMCELL Technologies, Vancouver, Canada) and then treated with indicated test articles in combination with plate bound anti-CD3 antibody (OKT3; 500 ng/mL). Cells were lysed 30 minutes after treatment and assayed for total AKT and phosphorylated AKT (Ser473) by a multiplexed phosphoprotein assay on MULTI-SPOT 384-Well Spot plates (Meso Scale Discovery, Rockville, Md.). The data are depicted in FIG. 51 as percentage of AKT phosphorylated following treatment.

The data shows no increase in AKT phosphorylation following treatment with negative control bivalent anti-PD-1 mAb (XENP16432). Both bivalent anti-ICOS mAb alone (XENP16435) and XENP16435 in combination with XENP16432 increase AKT phosphorylation demonstrating ICOS ligation and agonism by XENP16435. Surprisingly, despite only monovalent engagement of ICOS, treatment with the anti-ICOS x anti-PD-1 bispecific antibodies induces more AKT phosphorylation than treatment with XENP16435 alone and XENP16435 in combination with XENP16432. The positive AKT phosphorylation data demonstrate a clear signature of ICOS activity with the bispecific antibodies despite monovalent engagement of ICOS.

b. 5H(b): Activated T Helper Cell-Associated Genes Upregulated by Anti-ICOS x Anti-PD-1 Bottle-Openers Guedan et al. (2014) describes gene expression profiles for activated T helper cells (i.e. Th1, Th2, and Th17) and regulatory T cells (Tregs) following activation of ICOS signaling domain-based CAR-Ts. They found that genes related to activated T helper cells such as IL-17A, IL22, IFN?, TNF, and IL-13 were upregulated, while Treg-related genes such as TGFβ1, SMAD3 and FOXP3 were either unchanged or downregulated.

To investigate if engagement of T cells with anti-ICOS x anti-PD-1 bispecific antibodies of the invention led to a similar signature, we used Nanostring technology. PBMCs were stimulated with 100 ng/mL SEB for 2 days. Cells were washed 2 times and restimulated with 100 ng/mL SEB and treated with indicated test articles for 24 hours. RNA was extracted from cells and assayed by nCounter® PanCancer Immune Profiling Panel (NanoString Technologies, Seattle, Wash.) which assays 770 target genes covering immune response. FIG. 52 depicts mean fold induction in expression of a number of Th-related and Treg-related genes over bivalent anti-RSV antibody. FIGS. 53A-F respectively depict fold induction of IL-17A, IL-17F, IL-22, IL-10, IL-9 and IFN? gene expression by the indicated test articles over induction by bivalent anti-RSV mAb.

As depicted in FIGS. 52-53 and consistent with the observation by Gueden et al., Th-related genes associated with ICOS signaling such as IL-17A, IL-17F, IL-22, IL-9, and IFN? are upregulated following treatment with bivalent anti-ICOS mAb and combination of anti-ICOS and anti-PD-1 mAbs. Notably, expression of Th-related genes associated with ICOS signaling are further upregulated following treatment with an anti-ICOS x anti-PD-1 antibody, again indicating a clear ICOS costimulatory signature and dramatic synergy of anti-ICOS and anti-PD-1 engagement by a bispecific antibody.

9. 5I: Alternative Format Anti-ICOS x Anti-PD-1 Bispecific Antibodies

Alternative format costim/checkpoint bispecific antibodies were produced to investigate whether the effect of anti-ICOS x anti-PD-1 bottle-openers was unique to the bottle-opener format or broadly applicable to anti-ICOS x anti-PD-1 bispecific antibodies.

a. 5I(a): Anti-PD-1 x Anti-ICOS Bottle-Opener

Anti-PD-1 x anti-ICOS bottle-openers with an anti-PD-1 Fab generated using DNA encoding anti-PD-1 mAbs (e.g. XENP16432 and XENP29120) as described in Example 2A and anti-ICOS scFvs as described in Example 4B. Bottle-openers were produced as generally described in Example 5A. Sequences for exemplary anti-PD-1 x anti-ICOS bottle-openers are depicted in FIG. 56.

b. 5I(b): Central-scFv

Schematics for the central-scFv format are depicted as FIGS. 55A-55B. DNA encoding anti-ICOS Fab-Fc heavy chains was generated using DNA encoding anti-ICOS Fabs described in Example 4A by standard subcloning into the expression vector pTTS. DNA encoding anti-ICOS-anti-PD-1 Fab-scFv-Fc heavy chains was generated using DNA encoding anti-ICOS Fabs described in Example 4A and anti-PD-1 scFv described in Example 2A by a combination of gene synthesis and standard subcloning into the expression vector pTTS. DNA was transfected into HEK293E cells for expression. Sequences for exemplary anti-ICOS x anti-PD-1 central-scFv antibodies are depicted in FIG. 57.

c. 5I(c): Central-scFv2

A schematic for the central-scFv2 format is depicted as FIG. 55C. DNA encoding anti-ICOS-anti-PD-1 Fab-scFv-Fc heavy chains was generated using DNA encoding anti-ICOS Fabs described in Example 4A and anti-PD-1 scFv described in Example 2A by a combination of gene synthesis and standard subcloning into the expression vector pTT5. DNA was transfected into HEK293E cells for expression. Sequences for exemplary anti-ICOS x anti-PD-1 central-scFv2 antibodies are depicted in FIG. 58.

d. 5I(d): Bispecific mAb

A schematic for the bispecific mAb format is depicted as FIG. 2K. DNA encoding the anti-ICOS heavy and light chains were generated based on the DNA encoding the anti-ICOS Fabs described in Example, and DNA encoding anti-PD-1 heavy and light chains were generated based on the DNA encoding the anti-PD-1 mAbs described in Example 2A. Heavy chain VH genes were inserted via Gibson assembly into pTT5 encoding the human IgG1 constant region with E233P/L234V/L235A/G236del/S267K substitutions. Light chain VL genes were inserted into pTT5 encoding the human C? constant region.

DNA was transfected into HEK293E cells for expression as 2 separate antibodies which are separately expressed and purified by Protein A affinity (GE Healthcare). These antibodies contain heterodimerization-skewing substitutions in the CH3:CH3 interface. 2-Mercaptoethylamine-HCl (2-MEA) was used to induce controlled reduction of interchain disulfide bonds in the two parental IgGs. 2-MEA was then removed allowing the reoxidation of interchain disulfide bonds to occur enabling recombination of the HC-LC pairs (driven by the heterodimerization mutations). Finally, the trispecific antibodies were purified by cation exchange chromatography. Such methods are common in the art (see, for instance, Labrijn (2013) PNAS 110(13):5145-50 or Strop et al. (2012) J Mol Biol 420(3):204-19). Other methods of design and purification known in the art may be used facilitate bispecific mAb production, for instance, common light chain antibodies (Merchant (1998) Nat Biotechnol 16(7):677-81) or heterodimeric Fab domains (Lewis et al. (2014) Nat Biotechnol 32(2):191-8). Sequence for an exemplary anti-PD-1 x anti-ICOS bispecific mAb is depicted in FIG. 59.

e. 5I(e): DVD-IgG

A schematic for the DVD-IgG format is depicted as FIGS. 55A-55D. DNA encoding anti-PD-1-anti-ICOS VH-VH-CH1-Fc heavy chains and VL-VL-C? light chains was generated using DNA encoding anti-ICOS Fabs described in Example 4A and anti-PD-1 scFv described in Example 2A by a combination of gene synthesis and standard subcloning into the expression vector pTT5. DNA was transfected into HEK293E cells for expression. Sequences for exemplary anti-ICOS x anti-PD-1 DVD-IgGs are depicted in FIG. 60.

f. 5I(f): Trident

A schematic for the Trident format is depicted as FIGS. 55A-55D. DNA encoding anti-PD-1 VL-VH-Fc heavy chains and VL-VH light chains was generated using DNA encoding anti-ICOS Fabs described in Example 4A and anti-PD-1 scFv described in Example 2A by a combination of gene synthesis and standard subcloning into the expression vector pTTS. DNA was transfected into HEK293E cells for expression. Sequences for exemplary anti-ICOS x anti-PD-1 Tridents are depicted in FIG. 61.

g. 5I(g): Alternative Format Anti-ICOS x Anti-PD-1 Bispecific Antibodies Enhance Cytokine Secretion Human PBMCs were stimulated with 200 ng/mL SEB for 2 days. Cells were washed twice then re-stimulated with 100 ng/mL SEB and treated with the indicated concentrations of the indicated test articles. 24 hours after treatment, supernatants were assayed for IL-2. The data are depicted in FIG. 62 and show that each of the alternative format bispecific antibodies enhances IL-2 secretion in comparison to bivalent anti-RSV (XENP15074) control. Notably, the majority of these alternative format antibodies enhance IL-2 secretion in comparison to a bivalent anti-PD-1 antibody.

F. Example 6: Costim/Checkpoint Bispecific Antibodies Targeting Different Immune Checkpoint Antigens 1. 6A: Anti-CTLA-4 x Anti-ICOS Anti-CTLA-4 x anti-ICOS bottle-openers were generated with an anti-ICOS Fab derived from XENP16435 and anti-CTLA-4 scFvs derived from ABDs described in Example 2B. Sequence for an exemplary anti-ICOS x anti-CTLA-4 bottle-opener is depicted in FIG. 63. Bispecific mAbs were produced as generally described in Example 5I(c).

2. 6B: Anti-LAG-3 x Anti-ICOS

Anti-LAG-3 x anti-ICOS bispecific antibodies were generated with anti-LAG-3 Fabs derived from ABDs described in Example 2C and an anti-ICOS Fab derived from XENP16435. Sequences for exemplary anti-LAG-3 x anti-ICOS bispecific antibodies are depicted in FIG. 64. Bispecific mAbs were produced as generally described in Example 5I(c).

3. 6C: anti-TIM-3 x anti-ICOS

Anti-TIM-3 x anti-ICOS bispecific antibodies were generated with anti-TIM-3 Fabs derived from ABDs described in Example 2D and an anti-ICOS Fab derived from XENP16435. Sequence for an exemplary anti-TIM-3 x anti-ICOS bispecific antibody is depicted in FIG. 65. Bispecific mAbs were produced as generally described in Example 5I(c).

4. 6D: Anti-PD-L1 x Anti-ICOS

Anti-PD-L1 x anti-ICOS bottle-openers were generated with anti-PD-L1 Fabs derived from ABDs described in Example 2E and anti-ICOS scFvs as described in Example 4B. Sequences for exemplary anti-PD-L1 x anti-ICOS bispecific antibodies are depicted in FIG. 66. The bottle-openers were produced as generally described in Example 5A.

5. 6E: Additional Costim x Checkpoint Blockade Bispecific Antibodies Function to Enhance Cytokine Secretion Human PBMCs were stimulated with 200 ng/mL SEB for 2 days. Cells were washed twice then restimulated with 100 ng/mL SEB and treated with the indicated concentrations of the indicated test articles (as described above). 24 hours after treatment, supernatants were assayed for IL-2. The data are depicted in FIG. 67 and show that each of the additional costim x checkpoint blockade bispecific antibodies enhance IL-2 secretion in comparison to bivalent anti-RSV (XENP15074) control. Notably, the majority of these alternative checkpoint blockade antibodies (but not all, e.g. TIM-3 blockade) enhance IL-2 secretion in comparison to a bivalent anti-PD-1 antibody (XENP16432).

G. Example 7: Monovalent Ligation of ICOS is Superior to Bivalent Crosslinking In Example 5A(a), it was surprisingly found that anti-ICOS x anti-PD-1 antibody worked to enhance cytokine secretion despite monovalent binding of ICOS which is contrary to the crosslinking of costimulatory receptors such as ICOS which was thought to be necessary for stimulation of cytokine production. In Example 5H(a), it was surprisingly found that anti-ICOS x anti-PD-1 antibodies enhanced AKT phosphorylation (a signature of ICOS agonism) over bivalent anti-ICOS mAbs. In this section, we further examine this trend in which monovalent binding of ICOS appears to be superior to bivalent binding of ICOS.

1. 7A: Production of One-Arm Anti-ICOS Fab-Fc Antibodies

Amino acid sequences for illustrative one-arm anti-ICOS Fab-Fc antibodies are listed in FIG. 68. DNA encoding the three chains needed for antibody expression were generated by gene synthesis and were subcloned using standard molecular biology techniques into the expression vector pTT5. DNA was transfected into HEK293E cells for expression and resulting proteins were purified using standard techniques.

The resultant one-arm anti-ICOS Fab-Fc antibodies were characterized for affinity to human ICOS using Octet. Anti-mouse Fc (AMC) biosensors were used to capture mouse IgG2a Fc fusion of ICOS and dipped into multiple concentrations of the test articles. The resulting equilibrium dissociation constants (KD), association rates (ka), and dissociation rates (kd) are presented in FIG. 69. Binding affinities and kinetic rate constants were obtained by analyzing the processed data using a 1:1 binding model using ForteBio Octet Data Analysis software (ForteBio).

2. 7B: Monovalent One-Arm Anti-ICOS Fab-Fc Antibodies Promote Greater AKT Activation in PBMCs than Bivalent Anti-ICOS Antibody PBMCs were stimulated with 100 ng/mL SEB for 2 days. Following stimulation, CD3+ T cells were isolated by negative selection using EasySep™ Human T Cell Enrichment Kit (STEMCELL Technologies, Vancouver, Canada) and then treated with indicated test articles in combination with plate bound anti-CD3 antibody (OKT3; 500 ng/mL). Cells were lysed 30 minutes after treatment and assayed for total AKT and phosphorylated AKT (Ser473) by a multiplexed phosphoprotein assay on MULTI-SPOT 384-Well Spot plates (Meso Scale Discovery, Rockville, Md.). The data are depicted in FIG. 70 as percentage of AKT phosphorylated following treatment.

Consistent with Example X, the anti-ICOS x anti-PD-1 bispecific antibodies promoted significantly greater AKT activation than bivalent anti-ICOS antibody. Surprisingly, monovalent one-arm anti-ICOS Fab-Fc antibodies enhanced also promoted significantly greater AKT activation than bivalent anti-ICOS antibody to a level comparable to the bispecific antibodies.

3. 7C: Monovalent Agonism of ICOS Works with Multiple Anti-ICOS ABDs

CD3+ T cells were isolated by negative selection using EasySep™ Human T Cell Enrichment Kit (STEMCELL Technologies, Vancouver, Canada) and then treated with indicated test articles in combination with plate bound anti-CD3 antibody (OKT3; 500 ng/mL). Cells were lysed 30 minutes after treatment and assayed for total AKT and phosphorylated AKT (Ser473) by a multiplexed phosphoprotein assay on MULTI-SPOT 384-Well Spot plates (Meso Scale Discovery, Rockville, Md.). The data is depicted in FIG. 74 and show that monovalent anti-ICOS Fab-Fc antibodies comprising various anti-ICOS ABDs were able to induce AKT phosphorylation.

H. Example 8: Investigating In Vitro Binding by XmAb23104

1. XmAb23104 Binding to SEB-Stimulated T Cells

Staphylococcal Enterotoxin B (SEB) is a superantigen that causes T cell activation and proliferation in a manner similar to that achieved by activation via the T cell receptor (TCR), including expression of checkpoint receptors such as PD-1. Accordingly, human PBMCs from 3 separate donors were stimulated with 100 ng/mL SEB for 3 days. Cells were then treated with the following test articles at the indicated concentrations for 30 minutes: XmAb23104; XENP20111, a one-armed scFv-Fc based on the anti-PD-1 arm from XmAb23104; and XENP24901, a one-armed Fab-Fc based on the anti-ICOS arm from XmAb23104. Following incubation, cells were washed and stained with anti-human-Fc-A647 and anti-CD3-FITC. Cells were washed two more times and assayed by FACS. MFI on CD3+ T cells indicating binding of the test articles are depicted in FIGS. 90A-D, respectively for each donor.

The data show that, in PBMCs from each of the donors, XmAb23104 binds more avidly to CD3+ T cells compared to one-armed controls XENP20111 and XENP24901, demonstrating that binding to human T cells is significantly better by bispecific antibody XmAb23104, where each arm monovalently binds a different antigen, than by monovalent, monospecific antibodies.

2. Occupancy of PD-1 and ICOS on SEB-Stimulated T Cells by XmAb23104

Receptor occupancy by XmAb23104 was measured in an SEB-stimulated PBMC assay. Human PBMCs were stimulated with 500 ng/mL SEB for 3 days. Cells were then treated with the following test articles at indicated concentrations for 30 minutes: XmAb23104; XENP20111; XENP24901; XENP19686, a bivalent mAb based on the anti-PD-1 arm from XmAb23104; XENP16435, a bivalent mAb based on the parental clone from which the anti-ICOS arm of XmAb23104 was generated; and XENP15074, a bivalent anti-RSV mAb used as a control. Following incubations, cells were pelleted and stained with A488-conjugated XENP20111, A647-conjugated XENP24901, and BV510-conjugated anti-CD3 mAb. Cells were then washed two times and assayed by FACS. FIGS. 91A-D show receptor occupancy following treatment with the various test articles as depicted by percentage of various populations of $CD3^+$ T cells with unoccupied PD-1 and/or ICOS receptors as indicated by staining. For example, occupancy of PD-1 receptors decreases the percentage of $ICOS^+PD-1^+$ and $ICOS^-PD-1^+$ populations and increases the percentage of $ICOS^+PD-1^-$ and $ICOS^-PD-1^-$ populations. FIGS. 92A-B respectively show the amount of unoccupied of PD-1 and ICOS receptors on $ICOS^+PD-1^+CD3^+$ T cells following treatment with test articles as indicated by XENP20111 and XENP24901 binding.

I. Example 9: XmAb23104 Exhibits a Multi-Gene Expression Signature Consistent with ICOS Costimulation FIG. 93 depicts the fold change in expression of additional genes (as determined by Nanostring nCounter® in the experiment described in Example 5H(b)) between XmAb23104, anti-PD-1 mAb (XENP19686), anti-ICOS mAb (XENP16435), anti-PD-1 mAb (XENP19686) in combination with anti-ICOS mab (XENP16435), and negative control anti-RSV mAb (XENP15074).

J. Example 10: XmAb23104 Enhances Anti-Tumor Responses in Mice

NOD SCID gamma (NSG) mice were engrafted intradermally with either $3 \times 10^6$ pp65-expressing MCF-7 cells or $2 \times 10^6$ pp65-expressing MDA-MB-231 cells in the rear flank on Day −14. On Day 0, mice were engrafted intraperitoneally with $5 \times 10^6$ human PBMCs from a $CMV^+$ donor that screened positive for T cell pp65 reactivity. Mice were treated weekly with XmAb23104 (control mice were dosed with PBS) for 4 weeks (or 4 total doses). Tumor volumes were monitored by caliper measurements and data are shown (days post 1st dose) in FIGS. 94 and 95.

K. Example 11: Further In Vitro Characterization of XmAb23104

1. 11A: XmAb23104 Blocks PD-1 Binding by PD-L1 and PD-L2

HEK293T cells stably expressing ICOS (Crown Bioscience, Santa Clara, Calif.) were stably transfected with a pCMV6-AC-GFP vector encoding PD-1 (OriGene, Rockville, Md.). Cells were treated with the following test articles for 30 minutes at 4° C.: XmAb23104, XENP16432 (a bivalent anti-PD-1 mAb based on nivolumab), XENP20111 (a monovalent anti-PD-1 scFv-Fc fusion based on the anti-PD-1 arm from XmAb23104), and XENP24901 (a monovalent anti-ICOS Fab-Fc fusion based on the anti-ICOS arm from XmAb23104 with M428L/N434S Xtend Fc; sequence depicted in FIG. 1). Cells were washed and incubated with A647-conjugated PD-L1-Fc (1 µg/mL; sequence depicted in FIG. 2A) or A647-conjugated PD-L2-Fc (0.1 µg/mL; sequence depicted in FIG. 2B) for 30 minutes at 4° C. Cells were washed twice more and analyzed by flow cytometry. PD-L1 and PD-L2 binding (as indicated by A647 MFI on GFP+ cells) following treatment with the indicated test articles are depicted respectively in FIGS. 3A-B. The data show that XmAb23104, XENP16432, and XENP20111 blocked PD-L1 and PD-L2 binding to PD-1$^+$ICOS$^+$ cells in a dose dependent manner, while XENP24901 did not block PD-L1 and PD-L2 binding.

2. 11B: XmAb23104 Blocks ICOS Binding by ICOSL

HEK293T cells stably expressing ICOS (Crown Bioscience, Santa Clara, Calif.) were stably transfected with a pCMV6-AC-GFP vector encoding PD-1 (OriGene, Rockville, Md.). Cells were treated with the following test articles for 30 minutes at 4° C.: XmAb23104, XENP20111, and XENP24901. Cells were washed and incubated with A647-conjugated ICOSL-Fc (0.5 µg/mL; sequence depicted in FIG. 4) for 30 minutes at 4° C. Cells were washed twice more and analyzed by flow cytometry. ICOSL binding (as indicated by A647 MFI on GFP+ cells) following treatment with the indicated test articles is depicted in FIG. 5. The data show that XmAb23104 and XENP24901 blocked ICOSL binding to PD-1$^+$ICOS$^+$ cells in a dose dependent manner, while XENP20111 did not block ICOSL binding.

3. 11C: XmAb23104 Binds Cynomolgus T Cells

Towards preclinical studies, it is helpful to have antibodies that are cross-reactive for human and cynomolgus monkeys. Accordingly, we confirmed whether XmAb23104 (and its component arms) could bind cynomolgus T cells. PBMCs collected from 4 cynomolgus monkeys were stimulated with 100 ng/mL SEB for 3 days. Cells were then treated with the following test articles at the indicated concentrations: XmAb23104, XENP20111, and XENP24901. Following incubation, cells were washed and stained with anti-human-Fc-A647 and anti-CD3-FITC. Cells were washed two more times and assayed by FACS. MFI on CD3$^+$ T cells indicating binding of the test articles are depicted in FIGS. 6A-D respectively for each animal. The data show that XmAb23104, as well as its component Fab and scFv arms as Fc-fusions, bound to CD3$^+$ cells from cynomolgus monkeys.

4. 11D: XmAb23104 Enhances IFNγ and IL-2 Secretion in an SEB-Stimulated PBMC Assay Human PBMCs from 21 donors were stimulated with 100 ng/mL SEB for 2 days. Cells were washed two times and re-stimulated with 100 ng/mL SEB and 20 µg/mL of the following test articles for 24 hours: XENP16432, XENP16435 (a bivalent mAb based on the parental clone from which the anti-ICOS arm of XmAb23104 was generated), XENP20111, XENP24901, XENP16432 in combination with XENP16435, XENP20111 in combination with XENP24901, and XmAb23104 (as well as XENP15074 as control). Following incubation with the test articles, cell supernatants were collected and assayed for IFNγ and IL-2. Data depicting IFNγ secretion are depicted in FIG. 7A, and data depicting IL-2 secretion are depicted in FIGS. 7B and 8. The data show that XmAb23104 is superior at induction of IFNγ and IL-2 secretion in comparison to a bivalent anti-PD-1 mAb based on nivolumab.

5. 11E: XmAb23104 Enhances IFNγ Secretion in an MLR Assay

The ability of XmAb23104 to enhance IFNγ secretion was investigated in a mixed-lymphocyte reaction (also known as a mixed-lymphocyte reaction or MLR). Mixing lymphocytes from unique donors induces allogeneic T cell activation and proliferation, and subsequently upregulation of checkpoint receptors such as PD-1. Human PBMCs from 11 unique donors were mixed to generate 22 unique MLR mixes (400,000 cells/donor in a total volume of 100 µL) and treated with 20 µg/mL of the following test articles for 5 days: XENP16432, XENP19686 (a bivalent anti-PD-1 mAb based on the anti-PD-1 arm from XmAb23104), XENP16435, XENP21622 (a monovalent anti-PD-1 scFv-Fc fusion based on the anti-PD-1 arm from XmAb23104 with M428L/N424S Xtend Fc; sequence depicted in FIG. 9), XENP20266 (a monovalent anti-ICOS Fab-Fc fusion based on the parental clone from which the anti-ICOS arm of XmAb23104 was generated), XENP16432 in combination with XENP16435, XENP21622 in combination with XENP20266, or XmAb23104 (and XENP15074 as control). Following incubation, cell supernatants were collected and assayed for IFNγ. Data depicting induction of IFNγ by indicated test articles over control anti-RSV mAb (XENP15074) are shown in FIG. 10. Consistent with Example 1D, the data show that XmAb23104 is superior at induction of IFNγ secretion in comparison to a bivalent anti-PD-1 mAb based on nivolumab.

6. 11F: XmAb23104 Enhanced Cytokine Secretion is Dose-Dependent Manner

Human PBMCs from 2 donors were stimulated with 100 ng/mL SEB for 2 days. Cells were then washed two times and re-stimulated with 100 ng/mL SEB in combination with XmAb23104 or a combination of XENP20111 and XENP24901 (at equimolar PD-1 and ICOS binding concentrations relative to XmAb23104). 24 hours after treatment, cell supernatant was collected and assayed for IFNγ and IL-2, as depicted respectively in FIGS. 11-12.

L. Example 12: XmAb23104 in Combination with Anti-CTLA-4 mAb

Next we investigated the effect of combining XmAb23104 with an additional checkpoint inhibitor. Human PBMCs from 22 donors were stimulated with 100 ng/mL SEB for 2 days. Cells were washed two times, and re-stimulated with 100 ng/mL SEB in combination with 20 μg/mL XmAb23104 alone, XENP16433 (a bivalent anti-CTLA-4 mAb based on ipilimumab; sequence depicted in FIG. 13), or XmAb23104 in combination with XENP16433 (and XENP15074 as a control). Cell supernatant was then collected and assayed for IFNγ and IL-2, as depicted respectively in FIGS. 14A-B. The data show that the combination of XmAb23104 with XENP16433 induced greater cytokine secretion than each antibody alone.

M. Example 13: XmAb23104 Enhances Greater T Cell Activation In Vitro than αPD-1 Alone as Indicated by IL-2 Secretion 21 unique MLR reactions were treated with 20 μg/mL of XmAb23104, XENP16432 (a bivalent mAb based on nivolumab with ablated effector function), or XENP15074 (a bivalent anti-RSV mAb as isotype control) for 6 days. Cell supernatants were collected and assayed on MULTI-SPOT 384-Well Spot plates (Meso Scale Discovery, Rockville, Md.) for IL-2 concentration. Data showing fold change in IL-2 secretion are depicted in FIG. 310, and show that XmAb23104 enhances greater T cell activation than anti-PD-1 mAb alone.

N. Example 14: XmAb23104 Induces Greater Human Leukocyte Expansion and GVHD in huPBMC-Engrafted NSG Mice than αPD-1 Alone NSG mice (10 per group) were engrafted via IV-OSP with $10 \times 10^6$ human PBMCs on Day −1. On Days 0, 7, 14, and 21, mice were dosed with XmAb23104 or XENP16432. Mice were weighted on Days −2, 3, 6, 10, 13, 18, 21, 24, and 27, and blood was drawn on Days 8, 14, 21 and 28 to count leukocyte populations. and $CD45^+$ cell counts on Day 8 are depicted in FIG. 111, and changes in body weight over time (as a percentage of initial body weight on Day −2) are depicted in FIG. 112. The data show that XmAb23104 induced greater leukocyte expansion and enhanced GVHD in huPBMC-engrafted NSG mice in comparison to αPD-1 alone.

O. Example 15: XmAb23104 Enhances Allogeneic Anti-Tumor Response in NSG Mice NSG mice (10 per group) were intradermally inoculated with 3×106 pp65-transduced MCF-7 cells on Day −14. Mice were then intraperitoneally injected with 5×106 pp65-reactive human PBMCs (or PBS for control) and treated with the indicated test articles on Day 0, and further treated with the indicated test articles on Days 7, 14, and 21. CD45+ cell counts on Day 21 post-huPBMC engraftment are depicted in FIG. 113. Tumor volume on Days 21 and 38 post-huPBMC engraftment are depicted in FIGS. 114 and 115. Tumor volume as a time course over the duration of the study are depicted in FIG. 116. The data show that XmAb23104 enhances allogeneic anti-tumor response in NSG mice. Notably, treatment with anti-PD-1 x anti-ICOS bispecific XmAb23104 is more efficacious than PD-1 blockade alone (using a bivalent anti-PD-1 mAb).

P. Example 16: Costim x Checkpoint Blockade Bispecific Antibodies are Highly Active In Vivo Here we show an earlier GVHD study investigating prototype anti-PD-1 x anti-ICOS XENP20896 and prototype dual checkpoint inhibitor bispecific antibody XENP20053 (blocking PD-1 and CTLA-4 checkpoint receptors; sequences for which are depicted in FIG. 117) in a GVHD study.

NSG mice (10 per group) were injected with PBMC on Day 0, and then treated with anti-PD-1 mAb, anti-PD-1 mAb in combination with anti-CTLA-4 mAb, anti-PD-1 x anti-CTLA-4 bispecific XENP20053, or anti-PD-1 x anti-ICOS bispecific XENP20896 on Days 1, 8, 15, 22, and 29. CD45+ cell counts on Day 14 post-huPBMC engraftment are depicted in FIG. 118. The data show that anti-PD-1 x anti-ICOS bispecific XENP20896 is highly active in vivo, and enhances engraftment in comparison to anti-PD-1 blockade alone with an anti-PD-1 antibody, dual checkpoint blockade with anti-PD-1 and anti-CTLA-4 antibodies, as well as dual checkpoint blockade with an illustrative anti-PD-1 x anti-CTLA-4 bispecific antibody.

Q. Example 17: XmAb23104 Does Not Induce Cytokine Release in Naive T Cells and is Not Superagonistic PBMCs were thawed overnight and treated with 20 μg/mL of indicated soluble or plate bound test articles for 24 hours. Anti-CD3 antibody was clone OKT3. Cell supernatants were then collected and assayed with V-PLEX Proinflammatory Panel 1 Human Kit (Meso Scale, Rockville, Md.). Each point represents a unique human donor tested in technical singlet. Paired t tests were used to determine statistical significance (n.s. signifies a p-value>0.05). The data depicted in FIG. 119 show that XmAb23104 does not induce cytokine release (A: IFNγ; B: IL-1ß; C: IL-2; D: IL-4; E: IL-8; F: IL-6; G: IL-10; H: IL-12p70; I: IL-13; J: TNFα) in naive T cells.

Superagonstic properties of XmAb23104 was also assessed by air-drying per the Stebbings protocol (Stebbings R. et al. 2007). Air-drying of test articles was achieved by drying in a SpeedVac™ for 2 hours at room temperature. Human PBMCs were treated for 24 hours with 10 μg of air-dried XmAb23104, and activity was compared to 10 μg of air-dried XENP15074 (anti-RSV negative isotype control), the superagonist TGN1412 (XENP29154; sequences for which are depicted in FIG. 120, or anti-CD3 (OKT3). TGN1412 did not possess any activity when bound to the assay plate using an aqueous adsorption method; however, air-dried TGN1412 (as well as anti-CD3 mAb) promoted IFNγ, IL-1β, IL-2, IL-4, IL-6, IL-8, IL-10, IL-12p70, IL-13, and TNF cytokine secretion from unstimulated human PBMC. In comparison, the cytokine levels in PBMCs R. Example 18: Further Characterization of Binding by XmAb23104 treated with air-dried XmAb23104 remained similar to the negative control of air-dried XENP15074 (data shown in FIG. 121).

1. A: XmAb23104 Binds Human and Cynomolgus PD-1 and ICOS

Binding of XmAb23104 to human and cynomolgus PD-1 and ICOS was characterized using Octet, a BioLayer Interferometry (BLI)-based method. Binding affinities were obtained by analyzing the processed data globally using a 1:1 binding model. Octet sensorgrams are shown in FIG. 128 and FIG. 129. The resulting equilibrium dissociation constants ($K_D$), association rate constants ($k_a$), and dissociation constants ($k_d$) are presented in FIG. 130. Affinities for both human and cynomolgus PD-1 were measured at approximately 2.8 and 5.8 nM respectively. Binding affinities for human and cyno ICOS were 2.9 and 2.6 nM respectively.

2. B: XmAb23104 Competes for Binding with Ligands of PD-1 and ICOS

Binding of PD-L1 and PD-L2 to PD-1 with and without XmAb23104 was characterized using Octet, a BioLayer Interferometry (BLI)-based method. Octet sensorgrams are shown in FIG. 132. In both cases, 100 nM PD-1 show a binding signal with their ligands (PDL1/PDL2). In the presence of excess XmAb23104, pre-incubated with PD-1 at room temperature for 1 hour prior to the experiment, there is no binding signal observed to any ligands due to the competition of XmAb23104 with PD-1 for its ligands PD-L1 and PD-L2.

In another experiment to investigate the competition of XmAb23104 with ICOS ligand (ICOSL) and well as with PD-1 ligands (PD-L1 and PD-L2), HEK 293T cells expressing PD-1 and ICOS were incubated with various concentrations of XmAb23104 for 30 minutes at 4° C. Following incubation, 1 µg/mL PD-L1-mFc-Alexa647, 0.1 µg/mL PD-L1-mFc-Alexa647, or 0.5 µg/mL ICOSL-mFc-Alex647 was added and incubated for 30 minutes at 4° C. Binding of soluble ligands was visualized with flow cytometry. Data are depicted in FIG. 119, and show that XmAb23104 blocked binding of soluble PD-L1 ($EC_{10}$ 1 ng/mL and $EC_{90}$ 7100 ng/mL) and PDL2 ($EC_{10}$ 3 ng/mL and $EC_{90}$ 5300 ng/mL) antigen binding to cell surface-expressed PD1 receptor antigen in a dose-dependent fashion, as well as binding of soluble ICOSL ($EC_{10}$ 20 ng/mL, $EC_{90}$ 600 ng/mL) to cell surface-expressed ICOS receptor in a dose-dependent fashion.

3. C: XmAb23104 does not bind FcγR

Binding of XmAb23104 to human, cynomolgus, and mouse FcγRs was characterized using Octet, a BioLayer Interferometry (BLI)-based method. A comparator antibody was also tested using similar methods: anti-CD19 antibody with a native IgG1 constant region. Octet sensorgrams are shown in the FIG. 127 to FIG. 129. While the expected binding patterns for a native human IgG1 antibody were observed for the comparator antibody, no binding for any of the FcγRs was detected for XmAb23104.

4. D: XmAb23104 Binds Human, Cynomolgus, and Mouse FcRn at pH 6.0

Binding of XmAb23104 to human, cynomolgus, and mouse FcRn at pH 6.0 was characterized using Octet, a BioLayer Interferometry (BLI)-based method. A comparator antibody was also tested using similar methods: XENP20896, an anti-PD1×anti-ICOS bispecific antibody containing the same variable regions and engineered constant regions as XmAb23104 but lacking the amino acid substitutions XmAb23104 contains for enhancing FcRn binding. Binding affinities were obtained by analyzing the processed data globally using a 1:1 Langmuir model. Octet sensorgrams are shown in FIG. 131. The resulting equilibrium dissociation constants (KD) are presented Figure. Affinities measured for XmAb23104 are tighter than those measured for the comparator, indicating that the Fc substitutions contained in XmAb23104 improve the affinity for FcRn at pH 6.0, the physiologically relevant pH for endosome trafficking.

5. E: XmAb23104 Simultaneously Binds PD-1 and ICOS

Binding of XmAb23104 to both ICOS and PD1 antigens was tested using an in-tandem dip approach using BLI technology on the Octet HTX instrument. First, biosensors were loaded with ICOS, then dipped into either XmAb23104 or buffer as a control, and finally, into PD-1. FIG. 132 shows the binding sensorgrams which indicate that XmAb23104 binds to both antigens simultaneously. The XmAb23104 sensorgram continues to increase in signal during the final PD-1 antigen dip while the control sensorgram with no XmAb23104 loaded remains flat.

S. Example 19: Further In Vitro Characterization of XmAb23104

1. A: XmAb23104 Dose-Dependently Promoted IL-2 and IFNγ Secretion from SEB-Stimulated Human PBMC IL-2 and IFNγ production was assessed in SEB-stimulated PBMC treated with soluble XmAb23104. Human PBMC (100,000) were cultured in RPMI1640 with 10% FBS and stimulated with 100 ng/mL SEB (48 hours or 96 hours; 37° C.). Logistical considerations necessitated two sets of pre-stimulation conditions; of note, 96 hours of pre-stimulation abrogates detection of IL-2. Following stimulation, cells were washed two times in warm culture medium and then cultured in medium containing the indicated amount of XmAb23104 plus 100 ng/mL SEB (18 hours; 37° C.). To evaluate cytokine release, culture supernatant was collected 18 hours after treatment, then assayed for IL-2 and IFNγ secretion by ELISA (MSD® format) per the manufacturer's instructions. Samples were assayed in technical singlet.

Soluble XmAb23104 promoted a dose-dependent increase in IL-2 and IFNγ in all 19 donors tested with variable maximum amounts of cytokine expression induced between donors varying approximately between 1 ng/mL to 10 ng/mL for IL-2 (FIG. 133) and from 5 ng/mL to 25 ng/mL for IFNγ (FIG. 134). The potency was derived from curve fits, with least-squares methods all providing acceptable curve fits from which the EC values were derived. The average potency of XmAb23104 to induce IL-2 release from SEB-stimulated PBMC is: $EC_{10}$ 44 ng/mL, $EC_{20}$ 79 ng/mL, $EC_{30}$ 125 ng/mL, $EC_{50}$ 273 ng/mL, $EC_{80}$ 1201 ng/mL, and $EC_{90}$ 3215 ng/mL. The average potency of XmAb23104 in stimulating IFNγ release from human SEB-stimulated PBMC is: $EC_{10}$ 21 ng/mL, $EC_{20}$ 34 ng/mL, $EC_{30}$ 48 ng/mL, $EC_{50}$ 81 ng/mL, $EC_{80}$ 206 ng/mL, and $EC_{90}$ 384 ng/mL.

2. B: XmAb23104 Dose-Dependently Promotes IFNγ Secretion from SEB-Stimulated Cynomolgus PBMC Because IFNγ release was the most sensitive cytokine induced by XmAb23104 in human PBMC, we also quantified IFNγ secretion from SEB-stimulated PBMC from 10 cynomolgus monkeys. Cynomolgus PBMC (400,000) were cultured in RPMI1640 with 10% FBS and stimulated with 100 ng/mL SEB. Following stimulation, cells were washed two times in warm culture medium and then cultured in medium containing the indicated amount of XmAb23104 plus 100 ng/mL SEB (18 hours; 37° C.). To evaluate cytokine release, culture supernatant was collected 18 hours after treatment and assayed for IFNγ secretion by ELISA (MSD® format) per the manufacturer's instructions. Samples were assayed in technical singlet, data for which are depicted in FIG. 135.

The potency of XmAb23104 was derived from the five out of 10 monkey PBMC that generated data that could be fit to a sigmoidal dose response curve. XmAb23104 stimulated IFNγ release from monkey PBMC with the following average effective potencies: EC10 32 ng/mL, EC20 45 ng/mL, EC30 56 ng/mL, EC50 81 ng/mL, EC80 155 ng/mL, and EC90 233 ng/mL. For comparison, the EC50 for IFNγ release from SEB stimulated human PBMC was 81 ng/mL, which has similar potency to the monkey SEB stimulated PBMC.

T. Example 20: XmAb23104 Anti-Tumor Response is Dose-Dependent

In the study described in Example 15 investigating the enhancement of allogeneic anti-tumor response in NSG mice by XmAb23104, treatment with additional concentrations of XmAb23104 was investigated. The data depicted in FIGS. 114-116 show treatment with 5.0 mg/kg of XmAb23104. In FIG. 136 and FIG. 137, we depict data additionally showing treatment with 0.3 mg/kg and 1.0 mg/kg of Xmab23104.

U. Example 21: XmAb23104 Enhances Induction of Leukocyte Expansion in huPBMC-Engrafted NSG Mice in Comparison to Comparator Anti-ICOS mAb Since JTX-2011 is being administered to patients in combination with nivolumab, the leukocyte expanding activity of XmAb23104 was compared to the activity of JTX-2011 alone (in-house produced as XENP23058; sequences depicted in FIG. 138) and in combination with XENP16432 (anti-PD-1 mAb based on nivolumab with E233P/L234V/L235A/G236del/S267K ablation variants) in a mouse GVHD study. We also investigated the leukocyte expanding activity of XENP23057 (anti-ICOS mAb based on JTX-2011 with E233P/L234V/L235A/G236del/S267K ablation variants; sequences depicted in FIG. 139) alone and in combination with XENP16432. NSG mice were engrafted with $5\times10^6$ huPBMCs on Day −1, followed by dosing with the indicated test articles at indicated concentrations on Days 0, 7, 14, and 21. Mice were bled and whole blood analyzed to investigate the expansion of various human lymphocyte populations, data for which are depicted in FIG. 140 for Day 21.

Notably, the data show that JTX-2011 (XENP23058), alone and in combination with XENP16432, decreased human leukocytes in comparison to induction of leukocyte expansion by XENP16432 and XmAb23104. We reasoned that this is due to the WT IgG1 backbone of XENP23058 which induced depletion of ICOS positive cells by ADCC or CDC through binding of activating FcγR. Consistent with this reasoning, XENP23057 which has ablated FcγR binding, alone and in combination with XENP16432, induced expansion of human leukocytes.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10981992B2). An electronic copy of the "Sequence Listing" will also be available from the USPTO upon request and payment of the fee set forth in 37 CFR 1.19(b)(3).

The invention claimed is:

1. A composition comprising an ICOS binding domain, the ICOS binding domain comprising:
   a) a variable heavy domain having the amino acid sequence of SEQ ID NO: 29562; and
   b) a variable light domain having the amino acid sequence of SEQ ID NO: 29567.

2. A nucleic acid composition comprising:
   a) a first nucleic acid encoding the variable heavy domain of claim 1; and
   b) a second nucleic acid encoding the variable light domain of claim 1.

3. An expression vector comprising the first nucleic acid and second nucleic acid of claim 2.

4. An expression vector composition comprising:
   a) a first expression vector comprising the first nucleic acid of claim 2; and
   b) a second expression vector comprising the second nucleic acid of claim 2.

5. A host cell comprising the expression vector of claim 3 or the expression vector composition of claim 4.

6. A method of making an ICOS binding domain comprising culturing the host cell of claim 5 under conditions wherein the ICOS binding domain is expressed, and recovering the ICOS binding domain.

* * * * *